US008722662B2

(12) United States Patent
Ishichi et al.

(10) Patent No.: US 8,722,662 B2
(45) Date of Patent: May 13, 2014

(54) HETEROCYCLIC COMPOUNDS

(75) Inventors: Yuji Ishichi, Kanagawa (JP); Masami Yamada, San Diego, CA (US); Taku Kamei, Kanagawa (JP); Ikuo Fujimori, San Diego, CA (US); Yoshihisa Nakada, Kanagawa (JP); Tomoya Yukawa, Kanagawa (JP); Nobuki Sakauchi, Kanagawa (JP); Yusuke Ohba, Kanagawa (JP); Tetsuya Tsukamoto, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 191 days.

(21) Appl. No.: 13/253,293

(22) Filed: Oct. 5, 2011

(65) Prior Publication Data
US 2012/0088748 A1    Apr. 12, 2012

(30) Foreign Application Priority Data

Oct. 7, 2010  (JP) .................. 2010-227864
Aug. 10, 2011 (JP) .................. 2011-175336

(51) Int. Cl.
| | | |
|---|---|---|
| *A61K 31/55* | (2006.01) | |
| *C07D 267/10* | (2006.01) | |
| *C07D 413/04* | (2006.01) | |
| *C07D 413/06* | (2006.01) | |
| *C07D 413/10* | (2006.01) | |
| *C07D 413/12* | (2006.01) | |
| *C07D 413/14* | (2006.01) | |
| *C07D 417/06* | (2006.01) | |
| *C07D 417/14* | (2006.01) | |

(52) U.S. Cl.
USPC ................. 514/211.01; 540/544

(58) Field of Classification Search
USPC .................. 514/211.01; 540/544
See application file for complete search history.

(56) References Cited

U.S. PATENT DOCUMENTS

| | | | |
|---|---|---|---|
| 3,018,222 A | 1/1962 | Konstanz et al. | |
| 4,010,166 A | 3/1977 | Bowman | |
| 4,499,087 A | 2/1985 | Treiber et al. | |
| 6,288,079 B1 | 9/2001 | Scheel-Kruger et al. | |
| 2002/0010169 A1 | 1/2002 | Drewe et al. | |

FOREIGN PATENT DOCUMENTS

| | | |
|---|---|---|
| EP | 0 109 622 | 5/1984 |
| WO | 97/30997 | 8/1997 |
| WO | 2007/104933 | 9/2007 |
| WO | 2007/137953 | 12/2007 |
| WO | 2009/056520 | 5/2009 |
| WO | 2009/119528 | 10/2009 |
| WO | 2010/016554 | 2/2010 |

OTHER PUBLICATIONS

CAPLUS printout of Aparicio et al., Chemodivergent Synthesis of 7-Aryl/Alkyl-6-hydroxy-1,4-oxazepan-5-ones and 2-[Aryl/alkyl(hydroxy)methyl'morpholin-3-ones from a Common Epoxyamide Precursor, Synthesis, vol. 14, pp. 2310-2320, 2011.*
C. W. Becker et al., "Synthesis of Single-Enantiomer 6-Hydroxy-7-Phenyl-1,4-Oxazepan-5-Ones", Synthesis, No. 15, pp. 2549-2561, 2005.
J. Nonnenmacher et al., "Synthesis of Enantiopure 2-Aryl(Alkyl)-2-Trifluoromethyl-Substituted Morpholines and Oxazepanes", European Journal of Organic Chemistry, vol. 22, pp. 3762-3731, 2009.
Chemical Abstracts, Registry Nos. 933743-37-4 (2007); 933743-35-2 (2007); 933706-10-6 (2007) and 374704-51-5 (2001).
Partial International Search Report issued Feb. 2, 2012 in International (PCT) Application No. PCT/JP2011/073745.
I. Rozas et al., "Improving Antidepressant Drugs: Update on Recently Patented Compounds", Expert Opin. Ther. Patents, vol. 19, No. 6, pp. 827-845, 2009.
International Search Report and Written Opinion issued Mar. 16, 2012 in International (PCT) Application No. PCT/JP2011/073745.
C. G. Wermuth, "Molecular Variations Based on Isosteric Replacements", The Practice of Medicinal Chemistry, pp. 203-237, Jan. 1, 1996.
Notice of Opposition issued May 7, 2013 in corresponding Costa Rican Patent Application No. 2013-0158, with English translation.

* cited by examiner

*Primary Examiner* — Brenda Coleman
(74) *Attorney, Agent, or Firm* — Wenderoth, Lind & Ponack, L.L.P.

(57) ABSTRACT

Provided is a compound having a monoamine reuptake inhibitory activity, which is represented by the formula (I)

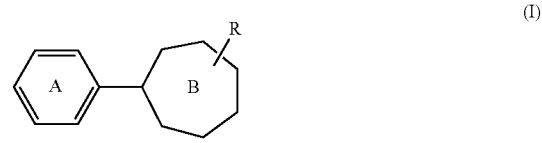

wherein ring A is an optionally substituted 6-membered aromatic ring, ring B is

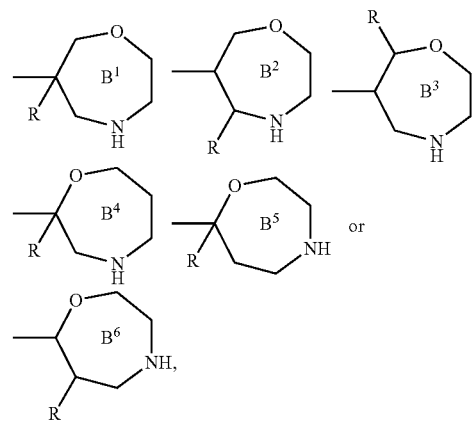

the substituents on ring A are optionally bonded to form, together with ring A, an optionally substituted 9- or 10-membered aromatic fused ring, and other symbols are as defined in the specification, or a salt thereof.

14 Claims, No Drawings

HETEROCYCLIC COMPOUNDS

TECHNICAL FIELD OF THE INVENTION

The present invention relates to heterocyclic compounds having a superior monoamine reuptake inhibitory activity, and useful as prophylactic or therapeutic drugs for depression, anxiety, attention deficit hyperactivity disorder, climacteric disorder, pain, stress urinary incontinence, mixed urinary incontinence and the like.

BACKGROUND OF THE INVENTION

Serotonin (5-HT), norepinephrine (NE) and dopamine (DA), which are monoamine neurotransmitters, are widely present in the brain, and have various functions such as neurotransmission via receptors thereof and the like. These monoamines are released from the nerve terminal, and rapidly reuptaken from nerve gap by respective transporters (serotonin transporter: SERT, norepinephrine transporter: NET and dopamine transporter: DAT), which terminates the neurotransmission. Compounds showing a monoamine reuptake inhibitory activity are known to be effective for various diseases including psychoneurotic diseases such as depression and the like, and widely used as therapeutic drugs. Compounds that inhibit reuptake of 3 kinds of serotonin, norepinephrine and dopamine are called Triple Reuptake Inhibitors, and expected to provide therapeutic drugs for psychoneurotic diseases and the like.

As a therapeutic drug for depression, tricyclic antidepressant (TCA) represented by imipramine, selective serotonin reuptake inhibitor (SSRI) represented by fluoxetine, selective serotonin-norepinephrine reuptake inhibitor (SNRI) represented by venlafaxine, norepinephrine-dopamine reuptake inhibitors such as bupropion and the like, monoamine oxidase inhibitor and the like have been used. However, they are not entirely highly sufficient since they require several weeks before expression of the effect, and in terms of effectiveness, improving rate, side effects and the like (see non-patent documents 1, 2).

Moreover, TCA, SSRI and SNRI have been reported to be useful for improving the symptoms of psychoneurotic diseases such as depression as well as anxiety, attention deficit hyperactivity disorder and the like, and neurodegenerative diseases such as Alzheimer's disease and the like; pain treatment of diabetic pain, muscle fibrosis and the like; or as therapeutic drugs for digestive tract diseases such as irritable bowel syndrome and the like.

In addition, it has been reported that monoamine reuptake inhibitor is also effective as a therapeutic drug for lower urinary tract diseases such as overactive bladder, stress urinary incontinence and the like, particularly, stress urinary incontinence. Stress urinary incontinence is a disease characterized by a symptom of urine leakage when intravesical pressure rises when the abdominal pressure rises transiently as a result of coughing, sneezing or light exercise. This disease is often found in female, and considered to be developed because pelvic floor muscles are weakened due to childbirth and aging, and the urethral resistance decreases (see non-patent document 3). On the other hand, it has been clarified that a urethral continence reflex mechanism exists in which when intravesical pressure rises due to a transient increase in the abdominal pressure, the pelvic floor muscles and the urethral sphincter muscle actively contract via a series of neural reflexes to maintain urethral continence (see non-patent documents 4-7). In recent years, it has been shown that serotonin and norepinephrine, which are monoamine neurotransmitters, are involved in the urethral continence reflex (see non-patent documents 6-8). Furthermore, it has been clarified that Duloxetine, which is a serotonin and norepinephrine reuptake inhibitor, Esreboxetine, which is a norepinephrine reuptake inhibitor, or the like can be used to provide a prophylactic or therapeutic effect on stress urinary incontinence, since they inhibit one of or both transporters and potentiate neurotransmission (see non-patent documents 9-11).

Patent document 1 (WO2009/056520) describes, as azabicyclo[3.2.1]octane derivatives having a monoamine reuptake inhibitory action and useful as an antidepressant, a compound represented by the formula:

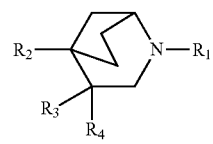

wherein $R_2$ is

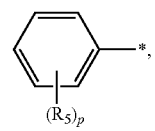

$R_3$ is

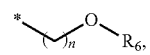

and
other symbols are as defined in patent document 1, and the following compound:

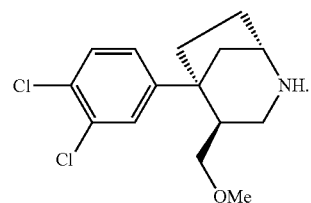 [SMILES: COC[C@@H]1CN[C@H]2CC[C@]1(c1ccc(Cl)c(Cl)c1)C2]

Patent document 2 (WO97/30997) describes, as tropane derivatives having a monoamine reuptake inhibitory action and useful as therapeutic drugs for obesity and Parkinson's disease, a compound represented by the formula:

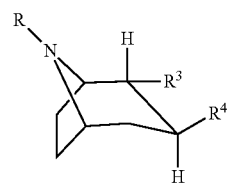

wherein each symbol is as defined in patent document 2, and the following compound:

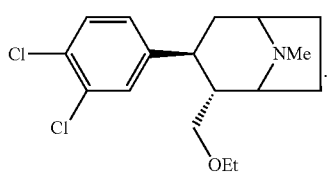 [SMILES: CCOC[C@H]1C2CCC(C[C@@H]1c1ccc(Cl)c(Cl)c1)N2C]

Patent document 3 (U.S. Pat. No. 3,018,222) describes, as an oxazepine derivative useful as a central nervous system stimulant or anorectic agent, the following compound:

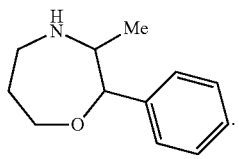 [SMILES: CC1NCCCOC1c1ccccc1]

Patent document 4 (U.S. Pat. No. 4,010,166) describes, as 1,4-oxazepine derivatives useful as antidepressants, a compound represented by the formula:

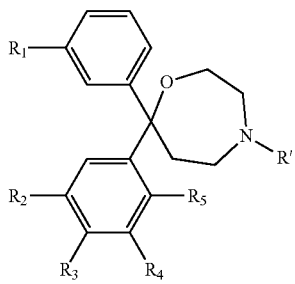

wherein each symbol is as defined in patent document 4, and the following compound:

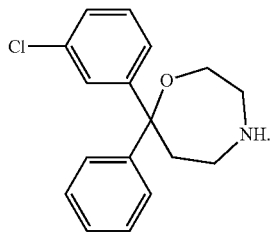 [SMILES: Clc1cccc(C2(c3ccccc3)CCNCCO2)c1]

Patent document 5 (WO2009/119528) describes, as a homopiperazinone derivative having a monoamine reuptake inhibitory action and useful as an antidepressant, a compound represented by the formula:

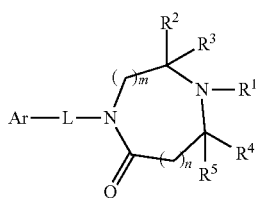

wherein each symbol is as defined in patent document 5.

Patent document 6 (WO2010/016554) describes, as a piperidine derivative having a monoamine reuptake inhibitory action, a compound represented by the formula:

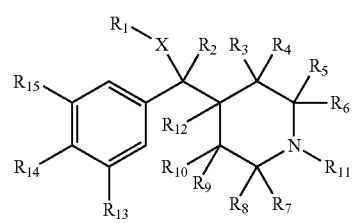

(I)

wherein each symbol is as defined in patent document 6.

In addition, as oxazepine compounds, patent document 7 (EP109622A1) describes the following compounds:

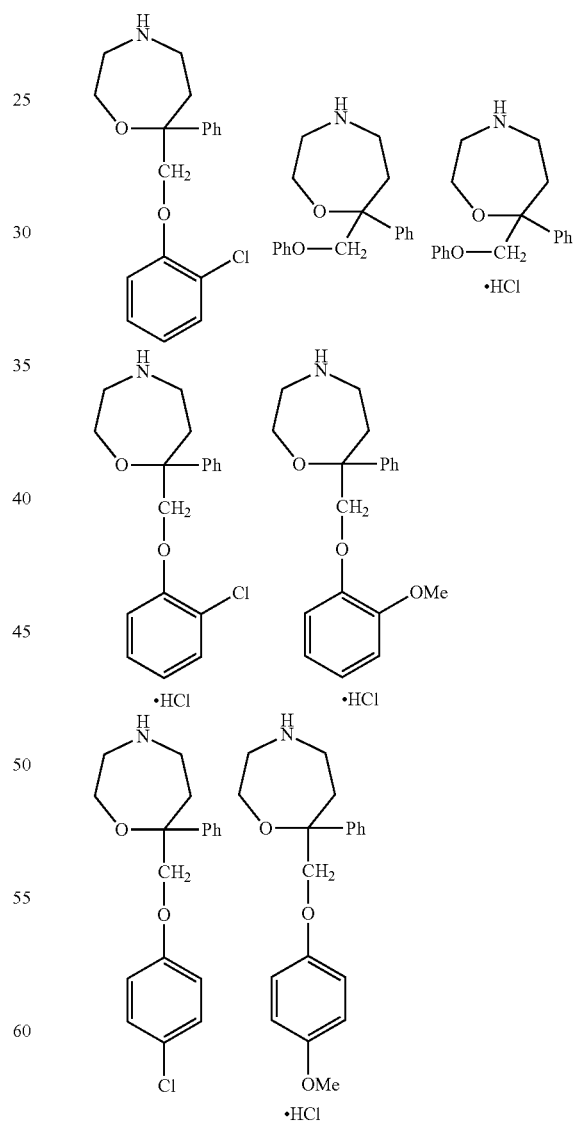

As an oxazepine compound, moreover, non-patent document 12 describes the following compound:

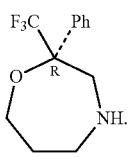

As oxazepine compounds, the following compounds are known:

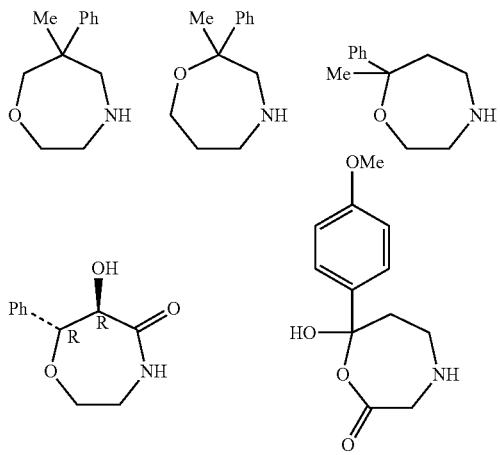

DOCUMENT LIST

Patent Documents patent document 1: WO2009/056520
patent document 2: WO97/30997
patent document 3: U.S. Pat. No. 3,018,222
patent document 4: U.S. Pat. No. 4,010,166
patent document 5: WO2009/119528
patent document 6: WO2010/016554
patent document 7: EP109622A1

Non-Patent Documents non-patent document 1: Annual Reports in Medicinal Chemistry, 2007, vol. 42, p. 13-26
non-patent document 2: The Annals of Pharmacotherapy, 2002, vol. 36, No. 10, p. 1577-1589
non-patent document 3: The Journal of Family Practice, 1982, vol. 14, p. 935-936
non-patent document 4: American Journal of Physiology-Regulatory, Integrative and Comparative Physiology, 2003, vol. 285, p. R356-R365
non-patent document 5: American Journal of Physiology-Renal Physiology, 2004, vol. 287, p. F434-F441
non-patent document 6: American Journal of Physiology-Renal Physiology, 2007, vol. 293, p. F920-F926
non-patent document 7: International Journal of Gynecology and Obstetrics, 2004, vol. 86, p. S38-S52
non-patent document 8: American Journal of Physiology-Renal Physiology, 2007, vol. 292, p. F639-F646
non-patent document 9: BJU International, 2004, vol. 93, p. 311-318
non-patent document 10: BJU International, 2008, vol. 102, p. 214-218
non-patent document 11: Annual Meeting of American Urological Association, 2008, Abst 1667
non-patent document 12: European Journal of Organic Chemistry, 2009, No. 22, p. 3726-3731

SUMMARY OF THE INVENTION

Problems to be Solved by the Invention

It has been desired to develop a compound having a monoamine (serotonin, norepinephrine, dopamine etc.) reuptake inhibitory activity, useful as a prophylactic or therapeutic drug for depression, anxiety, attention deficit hyperactivity disorder, climacteric disorder, pain, stress urinary incontinence, mixed urinary incontinence and the like, and having superior properties in the efficacy, duration of action, specificity, lower toxicity and the like.

The present invention aims to provide a compound having a chemical structure different from the structures of known compounds including the aforementioned compounds, as well as a monoamine reuptake inhibitory activity and the like, and a novel prophylactic or therapeutic drug for depression, anxiety, attention deficit hyperactivity disorder, climacteric disorder, pain, stress urinary incontinence, mixed urinary incontinence and the like.

Means of Solving the Problems

The present inventors have conducted intensive studies in an attempt to solve the aforementioned problems and found that a compound represented by the following formula (I) has a superior monoamine (serotonin, norepinephrine, dopamine etc.) reuptake inhibitory activity, which resulted in the completion of the present invention.

Accordingly, the present invention relates to:
[1] a compound represented by the formula (I)

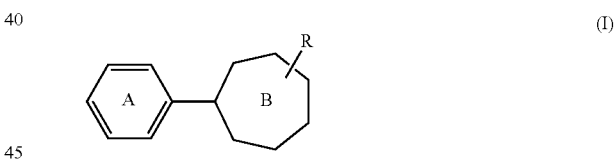

wherein
ring A is an optionally substituted 6-membered aromatic ring, and a group represented by

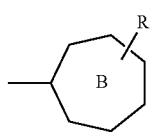

is

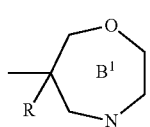

-continued

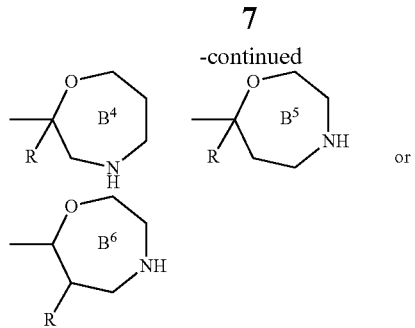

wherein rings $B^1$-$B^6$ are optionally further substituted, provided a hydrogen atom bonded to a nitrogen atom constituting rings $B^1$-$B^6$ is not substituted, and R is a hydroxy group, a cyano group, an optionally substituted carboxy group, an optionally substituted amino group, an optionally substituted $C_{1-6}$ alkyl group, an optionally substituted $C_{1-6}$ alkoxy group, an optionally substituted $C_{1-6}$ alkyl-carbonyl group, an optionally substituted carbamoyl group, an optionally substituted $C_{6-12}$ aryloxy group, an optionally substituted aromatic heterocyclyl-oxy group, an optionally substituted aromatic heterocyclic group, or an optionally substituted nonaromatic heterocyclic group, wherein substituents on ring A are optionally bonded to form, together with ring A, optionally substituted 9- or 10-membered aromatic fused ring,
provided that
(1) a compound, wherein a partial structure of the formula (I):

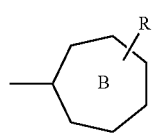

is

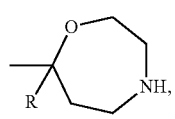

ring A is a benzene ring, and
R is $R^x$—$CH_2$— ($R^x$ is a phenoxy group optionally substituted by substituent(s) selected from a halogen atom and a methoxy group),
(2) 2-methyl-2-phenyl-1,4-oxazepane,
(3) 6-methyl-6-phenyl-1,4-oxazepane,
(4) (2R)-2-phenyl-2-(trifluoromethyl)-1,4-oxazepane,
(5) 7-methyl-7-phenyl-1,4-oxazepane,
(6) (6R,7R)-6-hydroxy-7-phenyl-1,4-oxazepan-5-one, and
(7) 7-hydroxy-7-(4-methoxyphenyl)-1,4-oxazepan-2-one
are excluded, or a salt thereof,
[2] a compound represented by the formula (I')

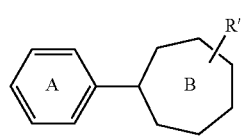
(I')

wherein
ring A is an optionally substituted 6-membered aromatic ring, and
a group represented by

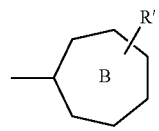

is

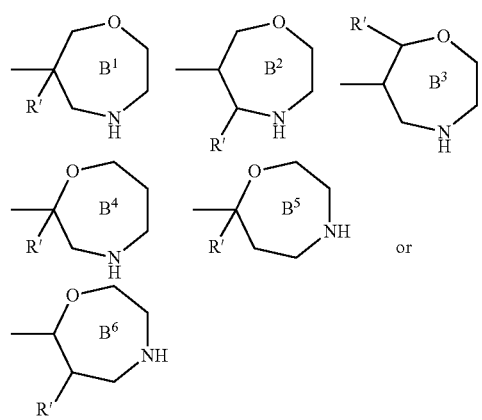

wherein rings $B^1$-$B^6$ are optionally further substituted, provided a hydrogen atom bonded to a nitrogen atom constituting rings $B^1$-$B^6$ is not substituted, and R' is a hydroxy group, a cyano group, an optionally substituted carboxy group, an optionally substituted amino group, an optionally substituted $C_{1-6}$ alkyl group, an optionally substituted $C_{1-6}$ alkoxy group, or an optionally substituted carbamoyl group,
wherein substituents on ring A are optionally bonded to form, together with ring A, optionally substituted 9- or 10-membered aromatic fused ring,
provided that
(1) a compound, wherein a partial structure of the formula (I):

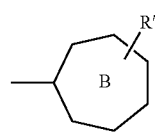

is

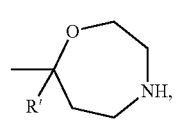

ring A is a benzene ring, and
R' is $R^x$—$CH_2$— ($R^x$ is a phenoxy group optionally substituted by substituent(s) selected from a halogen atom and a methoxy group),
(2) 2-methyl-2-phenyl-1,4-oxazepane,
(3) 6-methyl-6-phenyl-1,4-oxazepane,
(4) (2R)-2-phenyl-2-(trifluoromethyl)-1,4-oxazepane, (5) 7-methyl-7-phenyl-1,4-oxazepane,
(6) (6R,7R)-6-hydroxy-7-phenyl-1,4-oxazepan-5-one, and
(7) 7-hydroxy-7-(4-methoxyphenyl)-1,4-oxazepan-2-one
are excluded, or a salt thereof,

[3] the compound of [2], wherein ring A is an optionally substituted benzene ring, or a salt thereof,

[4] the compound of [2] or [3], wherein R' is
(1) a mono- or di-($C_{1-6}$ alkyl-carbonyl)amino group,
(2) a sulfamoylamino group, or
(3) a $C_{1-6}$ alkyl group optionally substituted by 1 to 3 substituents selected from
  (a) a hydroxy group,
  (b) a mono- or di-($C_{1-6}$ alkyl-carbonyl)amino group,
  (c) a sulfamoylamino group,
  (d) a $C_{1-6}$ alkoxy-$C_{1-6}$ alkyl-carbonylamino group,
  (e) a $C_{1-6}$ alkylsulfonylamino group, and
  (f) 2-oxopyridin-1(2H)-yl optionally substituted by 1 to 3 substituents selected from a carboxy group and 5-oxo-4,5-dihydro-1,2,4-oxadiazolyl.
or a salt thereof,

[5] the compound of any of [2] to [4], wherein the group represented by

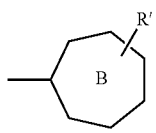

is

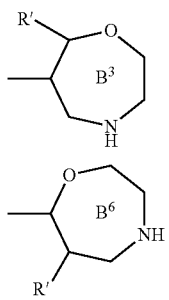

wherein each symbol is as defined in [2],
or a salt thereof,

[6] the compound of [2], wherein the ring A is a benzene ring substituted by 2 substituents selected from a fluorine atom and a chlorine atom, the group represented by

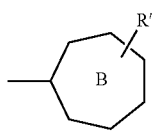

is

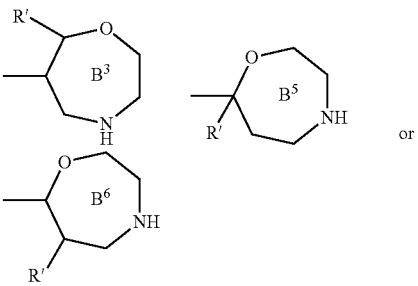

wherein
R' is
(1) a mono- or di-($C_{1-6}$ alkyl-carbonyl)amino group,
(2) a sulfamoylamino group, or
(3) a $C_{1-6}$ alkyl group optionally substituted by 1 to 3 substituents selected from
  (a) a hydroxy group,
  (b) a mono- or di-($C_{1-6}$ alkyl-carbonyl)amino group,
  (c) a sulfamoylamino group,
  (d) a $C_{1-6}$ alkoxy-$C_{1-6}$ alkyl-carbonylamino group,
  (e) a $C_{1-6}$ alkylsulfonylamino group, and
  (f) 2-oxopyridin-1(2H)-yl optionally substituted by 1 to 3 substituents selected from a carboxy group and 5-oxo-4,5-dihydro-1,2,4-oxadiazolyl,
and other symbols are as defined in [2], or a salt thereof,

[7] N-{[(6S,7R)-7-(3,4-dichlorophenyl)-1,4-oxazepan-6-yl]methyl}-2-methoxyacetamide, or a salt thereof,

[8] N-[(6R,7S)-7-(3,4-dichlorophenyl)-1,4-oxazepan-6-yl]acetamide, or a salt thereof,

[9] N-{[(6S,7R)-7-(4-chloro-3-fluorophenyl)-1,4-oxazepan-6-yl]methyl}-2-[($^2H_3$)methyloxy]acetamide, or a salt thereof,

[10] 1-{[(6S,7R)-7-(4-chloro-3-fluorophenyl)-1,4-oxazepan-6-yl]methyl}-2-oxo-1,2-dihydropyridine-3-carboxylic acid, or a salt thereof,

[11] (1S)-1-[(6R,7R)-6-(3,4-dichlorophenyl)-1,4-oxazepan-7-yl]ethane-1,2-diol, or a salt thereof,

[12] [(7S)-7-(3,4-dichlorophenyl)-1,4-oxazepan-7-yl]methanol, or a salt thereof,

[13] a medicament comprising the compound of [1] or [2] or a salt thereof,

[14] the medicament of [13], which is a monoamine reuptake inhibitor,

[15] the medicament of [13], which is a prophylactic or therapeutic drug for depression, anxiety, attention deficit hyperactivity disorder, climacteric disorder, pain, stress urinary incontinence or mixed urinary incontinence,

[16] a method for the prophylaxis or treatment of depression, anxiety, attention deficit hyperactivity disorder, climacteric disorder, pain, stress urinary incontinence or mixed urinary incontinence in a mammal, comprising administering an effective amount of the compound of [1] or [2] or a salt thereof to said mammal,

[17] use of the compound of [1] or [2] or a salt thereof for the production of a prophylactic or therapeutic drug for depression, anxiety, attention deficit hyperactivity disorder, climacteric disorder, pain, stress urinary incontinence or mixed urinary incontinence,

[18] the compound of [1] or [2] or a salt thereof for the prophylaxis or treatment of depression, anxiety, attention deficit hyperactivity disorder, climacteric disorder, pain, stress urinary incontinence or mixed urinary incontinence, and the like.

Effect of the Invention

Since the compound of the present invention has a superior monoamine (serotonin, norepinephrine, dopamine etc.) reuptake inhibitory activity, it is useful as a prophylactic or therapeutic drug for, for example, depression, anxiety, attention deficit hyperactivity disorder, climacteric disorder, pain, stress urinary incontinence, mixed urinary incontinence and the like.

DESCRIPTION OF EMBODIMENTS

Detailed Description of the Invention

The present invention is explained in detail in the following.

In the present specification, examples of the "halogen atom" include a fluorine atom, a chlorine atom, a bromine atom, and an iodine atom.

In the present specification, examples of the "$C_{1-6}$ alkyl group" and "$C_{1-6}$ alkyl" in a substituent include a linear or branched chain $C_{1-6}$ alkyl group, for example, methyl, ethyl, propyl, isopropyl, butyl, isobutyl, sec-butyl, tert-butyl, 1-methylpropyl, pentyl, isopentyl, neopentyl, tert-pentyl, 1,2-dimethylpropyl, hexyl, 2-methylpentyl, 3-methylpentyl, 1,2-dimethylbutyl, 1,2,2-trimethylpropyl and the like.

In the present specification, examples of the "$C_{1-6}$ alkoxy group" and "$C_{1-6}$ alkoxy" in a substituent include linear or branched chain $C_{1-6}$ alkoxy group, for example, methoxy, ethoxy, propoxy, isopropoxy, butoxy, isobutoxy, sec-butoxy, tert-butoxy, 1-methylpropoxy, pentyloxy, isopentyloxy, neopentyloxy, tert-pentyloxy, 1,2-dimethylpropoxy, hexyloxy, 2-methylpentyloxy, 3-methylpentyloxy, 1,2-dimethylbutoxy, 1,2,2-trimethylpropoxy and the like.

In the present specification, examples of the "$C_{3-6}$ cycloalkyl group" and "$C_{3-6}$ cycloalkyl" in a substituent include cyclopropyl, cyclobutyl, cyclopentyl, cyclohexyl and the like.

In the present specification, examples of the "$C_{3-6}$ cycloalkyloxy group" include cyclopropyloxy, cyclobutyloxy, cyclopentyloxy, cyclohexyloxy and the like.

In the present specification, examples of the "$C_{6-12}$ aryl group" and "$C_{6-12}$ aryl" in a substituent include phenyl, naphthyl (1-naphthyl, 2-naphthyl) and the like.

In the present specification, examples of the "$C_{7-12}$ aralkyl group" and "$C_{7-12}$ aralkyl" in a substituent include benzyl, 2-phenylethyl, 1-phenylethyl, 3-phenylpropyl, 4-phenylbutyl, 1-naphthylmethyl, 2-naphthylmethyl and the like.

In the present specification, examples of the "aromatic heterocyclic group" and "aromatic heterocyclyl-" in a substituent include a 4- to 7-membered (preferably 5- or 6-membered) monocyclic aromatic heterocyclic group containing, as a ring constituting atom besides carbon atom, 1-4 hetero atoms selected from an oxygen atom, a sulfur atom (said sulfur atom is optionally oxidized) and a nitrogen atom, and a condensed aromatic heterocyclic group. Examples of the condensed aromatic heterocyclic group include groups wherein these 4- to 7-membered monocyclic aromatic heterocyclic groups are condensed with 1 or 2 selected from a 5- or 6-membered aromatic heterocycle (e.g., pyrrole, imidazole, pyrazole, pyrazine, pyridine, pyrimidine) containing 1 or 2 nitrogen atoms, a 5-membered aromatic heterocycle (e.g., thiophene) containing one sulfur atom, and a benzene ring and the like, and the like.

Preferable examples of the "aromatic heterocyclic group" and "aromatic heterocyclyl-" in a substituent include monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,5-oxadiazol-3-yl, 1,3,4-oxadiazol-2-yl, 1,2,4-oxadiazol-3-yl), thiadiazolyl (e.g., 1,2,3-thiadiazol-4-yl, 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-3-yl, 1,2,4-triazin-5-yl, 1,2,4-triazin-6-yl) and the like; condensed aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl, 4-benzofuranyl, 5-benzofuranyl, 6-benzofuranyl, 7-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl, 6-benzothiazolyl), benzimidazolyl (e.g., benzimidazol-1-yl, benzimidazol-2-yl, benzimidazol-5-yl), benzotriazolyl (e.g., 1H-1,2,3-benzotriazol-1-yl, 1H-1,2,3-benzotriazol-5-yl), indolyl (e.g., indol-1-yl, indol-2-yl, indol-3-yl, indol-5-yl), indazolyl (e.g., 2H-indazol-3-yl, 1H-indazol-1-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazopyrazinyl (e.g., 1H-imidazo[4,5-b]pyrazin-2-yl), pyrazolopyridinyl (e.g., 1H-pyrazolo[4,3-c]pyridin-3-yl), thienopyrazolyl (e.g., 1H-thieno[2,3-c]pyrazol-5-yl), pyrazolotriazinyl (e.g., pyrazolo[5,1-c][1,2,4]triazin-3-yl), triazolopyrimidinyl (e.g., [1,2,4]triazolo[1,5-a]pyrimidin-2-yl), phthalazinyl and the like;
and the like.

In the present specification, examples of the "nonaromatic heterocyclic group" and "nonaromatic heterocyclyl-" in a substituent include a 4- to 7-membered (preferably 5- or 6-membered) monocyclic nonaromatic heterocyclic group containing, as a ring constituting atom besides carbon atom, 1-4 hetero atoms selected from an oxygen atom, a sulfur atom (said sulfur atom is optionally oxidized) and a nitrogen atom, and a condensed nonaromatic heterocyclic group. Examples of the condensed nonaromatic heterocyclic group include groups wherein these 4- to 7-membered monocyclic nonaromatic heterocyclic groups are condensed with 1 or 2 selected from a 5- or 6-membered aromatic or nonaromatic heterocycle (e.g., pyrrole, imidazole, pyrazole, pyrazine, pyridine, pyrimidine) containing 1 or 2 nitrogen atoms, a 5-membered aromatic or nonaromatic heterocycle (e.g., thiophene) containing one sulfur atom, and a benzene ring and the like, and the like. The monocyclic nonaromatic heterocyclic group and condensed nonaromatic heterocyclic group may be crosslinked.

Preferable examples of the "nonaromatic heterocyclic group" and "nonaromatic heterocyclyl-" in a substituent include,
monocyclic nonaromatic heterocyclic groups such as azetidinyl (e.g., 2-azetidinyl), pyrrolidinyl (e.g., 2-pyrrolidinyl, 3-pyrrolidinyl), piperidyl (e.g., 2-piperidyl, 3-piperidyl, 4-piperidyl), homopiperidinyl (e.g., 2-homopiperidyl, 3-homopiperidyl, 4-homopiperidyl), tetrahydropyridyl (e.g., 1,2,3,6-tetrahydropyridin-2-yl), dihydropyridyl (e.g., 2,3-dihydropyridin-4-yl, 1,2-dihydropyridin-1-yl, 1,2-dihydropyridin-3-yl), morpholinyl (e.g., 2-morpholinyl), thiomorpholinyl (e.g., 2-thiomorpholinyl), 1,1-dioxide-thiomorpholinyl (e.g., 1,1-dioxide-thiomorpholin-2-yl), piperazinyl (e.g., 2-piperazinyl), hexamethyleneiminyl (e.g., 2-hexamethyleneiminyl), oxazolidinyl (e.g., 2-oxazolidinyl), thiazolidinyl (e.g., 2-thiazolidinyl), imidazolidinyl (e.g., 2-imidazolidinyl), oxazolinyl (e.g., 2-oxazolinyl), thiazolinyl (e.g., 2-thiazolinyl), imidazolinyl (e.g., 2-imidazolinyl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl, 2,3-dihydro-1,3,4-oxadiazol-5-yl), pyranyl (e.g., 2-pyranyl, 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxide-tetrahydrothiopyranyl (e.g., 1-oxide-tetrahydrothiopyran-4-yl), 1,1-dioxide-tetrahydrothiopyranyl (e.g., 1,1-dioxide-tetrahydrothiopyran-4-yl), tetrahydrofuryl (e.g., tetrahydrofuran-3-yl, tetrahydrofuran-2-yl), pyrazolidinyl (e.g., 3-pyrazolidinyl), pyrazolinyl (e.g., 3-pyrazolinyl), tetrahydropyrimidinyl (e.g., 2-tetrahydropyrimidinyl), hexahydropyrimidinyl (e.g., 2-hexahydropyrimidinyl), dihydrotriazolyl (e.g., 2,3-dihydro-1H-1,2,3-triazol-4-yl, 4,5-dihydro-1H-1,2,4-triazol-3-yl), tetrahydrotriazolyl (e.g., 2,3,4,5-tetrahydro-1H-1,2,3-triazol-4-yl), thiazinyl (e.g., 1,4-thiazin-2-yl), 1,1-dioxide-thiazinanyl (e.g., 1,1-dioxide-1,2-thiazinan-3-yl), dihydropyridazinyl (e.g., 1,6-dihydropyridazin-3-yl, 2,3-dihydropyridazin-3-yl), tetrahydropyridazinyl (e.g., 1,4,5,6-tetrahydropyridazin-3-yl), dihydrothioxazinyl (e.g., 2,3-dihydro-1,4-thioxazin-3-yl), dihydrothiazinyl (e.g., 3,4-dihydro-2H-1,4-thiazin-5-yl), dioxanyl (e.g., 1,4-dioxan-2-yl) and the like;
condensed nonaromatic heterocyclic groups such as dihydroindolyl (e.g., 2,3-dihydro-1H-indol-2-yl), dihydroisoindolyl (e.g., 2,3-dihydro-1H-isoindol-1-yl, 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepin-7-yl), tetrahydrobenzofuranyl (e.g., 4,5,6,7-tetrahydro-1-benzofuran-3-yl), chromenyl (e.g., 4H-chromen-2-yl, 2H-chromen-3-yl, 2H-chromen-7-yl), dihydroquinolinyl (e.g., 1,2-dihydroquinolin-4-yl, 3,4-dihydroquinolin-2(1H)-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl, 1,2,3,4-tetrahydroisoquinolin-1-yl), dihydrophthalazinyl (e.g., 3,4-dihydrophthalazin-1-yl, 1,4-dihydrophthalazin-4-yl), tetrahydrobenzoazepinyl (e.g., 2,3,4,5-tetrahydro-1H-benzo[c]azepin-1-yl), benzodioxolyl (e.g., 1,3-benzodioxol-5-yl), benzothiazine (e.g., 3,4-dihydro-2H-1,4-benzothiazin-2-yl) and the like;
and the like.

In the present specification, examples of the "cyclic amino" of the "cyclic amino group" and substituent include cyclic amino groups such as 1-azetidinyl, 1-pyrrolidinyl, piperidino, homopiperidino, thiomorpholino, 1,1-dioxide-thiomorpholino, morpholino, 1-piperazinyl, 1-imidazolidinyl, 1-pyrrolyl, 1-imidazolyl, 1-dihydropyridinyl (e.g., 2,3-dihydropyridazin-2-yl), 1-hexahydropyrimidinyl, tetrahydropyridyl (e.g., 1,2,3,6-tetrahydropyridin-1-yl), 1-hexamethyleneiminyl, 3-oxazolidinyl, 3-thiazolidinyl, 1-imidazolinyl, 1-pyrazolidinyl, 1-pyrazolinyl, 1-tetrahydropyrimidinyl, dihydrotriazolyl (e.g., 2,3-dihydro-1H-1,2,3-triazol-1-yl, 4,5-dihydro-1H-1,2,4-triazol-1-yl), tetrahydrotriazolyl (e.g., 2,3,4,5-tetrahydro-1H-1,2,3-triazol-1-yl), 1,1-dioxide-thiazinanyl (e.g., 1,1-dioxide-1,2-thiazinan-2-yl), dihydropyridazinyl (e.g., 1,6-dihydropyridazin-1-yl, 2,3-dihydropyridazin-2-yl), 1-dihydroindolyl (e.g., 2,3-dihydro-1H-indol-1-yl), 1-dihydroquinolinyl (e.g., 1,2-dihydroquinolin-1-yl, 3,4-dihydroquinolin-1(2H)-yl), 1-tetrahydroquinolinyl (e.g., 1,2,3,4-tetrahydroquinolin-1-yl), 2-dihydroisoquinolinyl (e.g., 1,2-dihydroisoquinolin-2-yl), 2-tetrahydroisoquinolinyl (e.g., 1,2,3,4-tetrahydroisoquinolin-2-yl), 2-dihydroisoindolyl (e.g., 1,3-dihydro-2H-isoindol-2-yl), 3-dihydroquinazolinyl (e.g., 3,4-dihydroquinazolin-3-yl), 3-tetrahydroquinazolinyl (e.g., 1,2,3,4-tetrahydroquinazolin-3-yl), 3-tetrahydropyrido[3,2-d]pyrimidinyl (e.g., 1,2,3,4-tetrahydropyrido[3,2-d]pyrimidin-3-yl), 3-tetrahydropteridinyl (e.g., 1,2,3,4-tetrahydropteridin-3-yl), 8-oxa-3-azabicyclo[3.2.1]octan-3-yl and the like.

Examples of the "6-membered aromatic ring" of the "optionally substituted 6-membered aromatic ring" for ring A include benzene ring, 6-membered aromatic heterocycle containing 1 to 3 nitrogen atoms (e.g., pyridine, pyrazine, pyrimidine, pyridazine, triazine) and the like.

Examples of the substituent that the "6-membered aromatic ring" optionally has include substituents selected from
(1) a halogen atom (e.g., a fluorine atom, a chlorine atom, a bromine atom, an iodine atom),
(2) a cyano group,
(3) a hydroxy group,
(4) a $C_{1-6}$ alkyl group optionally substituted by 1 to 3 halogen atoms,
(5) a $C_{1-6}$ alkoxy group optionally substituted by 1 to 3 halogen atoms. The number of the substituents is 1 to 5, preferably 1 to 3, more preferably 1 or 2.

Examples of the "9 or 10-membered aromatic fused ring" of the "optionally substituted 9 or 10-membered aromatic fused ring" formed, together with ring A, by the substituents on ring A bonded to each other include naphthalene, benzofuran, indazole and the like. Examples of the substituent that the "9 or 10-membered aromatic fused ring" optionally has include those similar to the substituents that the 6-membered aromatic ring for ring A optionally has. The number of the substituents is 1 to 5, preferably 1 to 3, more preferably 1 or 2.

Ring A is preferably an optionally substituted benzene ring. As the "optionally substituted benzene ring", a benzene ring substituted by 1 to 3 (preferably 2) substituents selected from a halogen atom, a $C_{1-6}$ alkyl group and a $C_{1-6}$ alkoxy group is preferable, and a benzene ring substituted by 2 halogen atoms is particularly preferable.

In another embodiment, ring A is preferably an optionally substituted benzene ring, more preferably, a benzene ring optionally substituted 1 to 3 (preferably 2) substituents selected from a halogen atom, a $C_{1-6}$ alkyl group and a $C_{1-6}$ alkoxy group, more preferably, a benzene ring optionally substituted 1 to 3 (preferably 1 or 2) halogen atoms (preferably, a fluorine atom, a chlorine atom).

In another embodiment, ring A is preferably an optionally substituted benzene ring, more preferably, a benzene ring optionally substituted by 1 to 3 (preferably 2) substituents selected from a halogen atom (preferably, a fluorine atom, a chlorine atom) and a $C_{1-6}$ alkyl group (preferably, methyl), more preferably, a benzene ring substituted by 2 substituents selected from a fluorine atom and a chlorine atom.

Preferable examples of ring A include

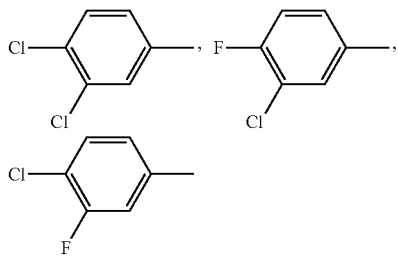

and the like. Particularly preferred is

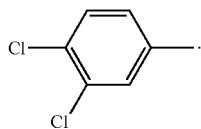

In another embodiment, preferable specific examples of ring A include,

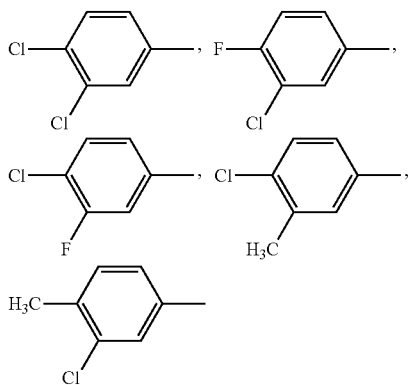

and the like.
A group represented by

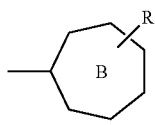

is preferably

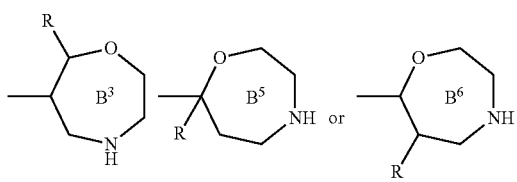

wherein each symbol is as defined above.

Rings $B^1$-$B^6$ are optionally further substituted. However, a hydrogen atom bonded to a nitrogen atom constituting rings $B^1$-$B^6$ is not substituted. Examples of the substituents that rings $B^1$-$B^6$ optionally further have include substituents selected from
(1) a halogen atom (e.g., a fluorine atom, a chlorine atom, a bromine atom, an iodine atom),
(2) a cyano group,
(3) a hydroxy group,
(4) a $C_{1-6}$ alkyl group optionally substituted by 1 to 3 halogen atoms,
(5) a $C_{1-6}$ alkoxy group optionally substituted by 1 to 3 halogen atoms,
(6) an oxo group and the like. The number of the substituents is 1 to 5, preferably 1 to 3, more preferably 1 or 2.

The substituents that rings $B^1$-$B^6$ optionally further have are preferably a hydroxy group and a $C_{1-6}$ alkoxy group (preferably, methoxy).

The embodiment of rings $B^1$-$B^6$ is preferably one wherein they are substituted by a hydroxy group or a $C_{1-6}$ alkoxy group (preferably, methoxy) besides ring A and R or one wherein they do not have substituent other than ring A and R, more preferably one wherein they do not have substituent other than ring A and R.

In another embodiment, rings $B^1$-$B^6$ are more preferably substituted by a hydroxy group or a $C_{1-6}$ alkoxy group (preferably, methoxy) besides ring A and R.

In another embodiment, a group represented by

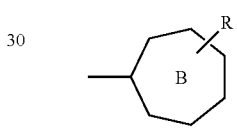

is preferably

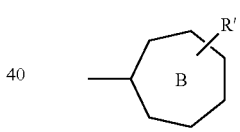

wherein each symbol is as defined above, more preferably,

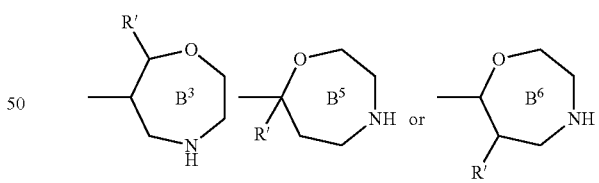

wherein each symbol is as defined above.
Here, rings $B^1$-$B^6$ preferably do not have substituent other than ring A and R'.

Examples of the "optionally substituted carboxy group" for R include
(1) a carboxy group,
(2) a $C_{1-6}$ alkoxy-carbonyl group,
(3) a $C_{6-12}$ aryloxy-carbonyl group,
(4) a $C_{7-12}$ aralkyloxy-carbonyl group
and the like.

The "optionally substituted carboxy group" for R is preferably a carboxy group or a $C_{1-6}$ alkoxy-carbonyl group (preferably, ethoxycarbonyl).

Examples of the "optionally substituted amino group" for R include
(1) an amino group,
(2) a mono- or di-$C_{1-6}$ alkylamino group,
(3) a mono- or di-$C_{3-6}$ cycloalkylamino group,
(4) a mono- or di-$C_{6-12}$ arylamino group,
(5) a mono- or di-$C_{7-12}$ aralkylamino group,
(6) a hydrazino group,
(7) a mono- or di-($C_{1-6}$ alkylsulfonyl)amino group,
(8) a mono- or di-($C_{3-6}$ cycloalkylsulfonyl)amino group,
(9) a mono- or di-($C_{6-12}$ arylsulfonyl)amino group,
(10) a mono- or di-(aromatic heterocyclyl-sulfonyl)amino group,
(11) —$NR^A$—CO—$R^B$
  wherein
  $R^A$ is
    (a) a hydrogen atom,
    (b) a $C_{1-6}$ alkyl group, or
    (c) a $C_{1-6}$ alkyl-carbonyl group, and
  $R^B$ is
    (a) a $C_{1-6}$ alkyl group optionally substituted by 1 to 3 substituents selected from
      (i) a halogen atom,
      (ii) a hydroxy group,
      (iii) a $C_{1-6}$ alkoxy group,
      (iv) an aromatic heterocyclic group, and
      (v) a nonaromatic heterocyclic group optionally substituted by an oxo group,
    (b) a $C_{1-6}$ alkoxy group,
    (c) a $C_{3-6}$ cycloalkyl group,
    (d) a $C_{1-6}$ alkyl-carbonyl group,
    (e) an amino group,
    (f) a mono- or di-$C_{1-6}$ alkylamino group,
    (g) a cyclic amino group,
    (h) a $C_{6-12}$ aryl group optionally substituted by 1 to 3 substituents selected from
      (i) a cyano group,
      (ii) a carboxy group,
      (iii) a $C_{1-6}$ alkoxy-carbonyl group,
      (iv) a $C_{1-6}$ alkylsulfonylamino group, and
      (v) a nonaromatic heterocyclic group optionally substituted by an oxo group,
    (i) a $C_{7-12}$ aralkyl group optionally substituted by a heterocyclic group optionally substituted by an oxo group, or
    (j) an aromatic heterocyclic group,
(12) —$NR^C$—$SO_2$—$N(R^D)(R^E)$
  wherein
  $R^C$ is
    (a) a hydrogen atom, or
    (b) a $C_{1-6}$ alkyl group, and
  $R^D$ and $R^E$ are each independently,
    (a) a hydrogen atom,
    (b) a $C_{1-6}$ alkyl group, or
    (c) a $C_{3-6}$ cycloalkyl group,
(13) an optionally substituted cyclic amino group
and the like.
Here, examples of the substituent that the "cyclic amino group" of the "optionally substituted cyclic amino group" optionally has include substituents selected from
(1) an oxo group,
(2) a halogen atom,
(3) a cyano group,
(4) a hydroxy group,
(5) a nitro group,
(6) a formyl group,
(7) an amino group,
(8) a mono- or di-$C_{1-6}$ alkylamino group,
(9) a $C_{1-6}$ alkyl-carbonylamino group,
(10) a $C_{1-6}$ alkoxy-carbonylamino group,
(11) a $C_{1-6}$ alkoxy group optionally substituted by 1 to 3 halogen atoms,
(12) a $C_{7-12}$ aralkyloxy group,
(13) a $C_{6-12}$ aryloxy group,
(14) a $C_{1-6}$ alkyl-carbonyloxy group,
(15) a carboxy group,
(16) a $C_{1-6}$ alkoxy-carbonyl group,
(17) a $C_{7-12}$ aralkyloxy-carbonyl group,
(18) a $C_{6-12}$ aryloxy-carbonyl group,
(19) a $C_{1-6}$ alkyl-carbonyl group,
(20) a $C_{3-6}$ cycloalkyl-carbonyl group,
(21) a $C_{7-12}$ aralkyl-carbonyl group,
(22) a $C_{6-12}$ aryl-carbonyl group,
(23) a carbamoyl group,
(24) a thiocarbamoyl group,
(25) a mono- or di-($C_{1-6}$ alkyl)carbamoyl group,
(26) a mono- or di-($C_{7-12}$ aralkyl)carbamoyl group,
(27) a thiol group,
(28) a $C_{1-6}$ alkylthio group,
(29) a $C_{7-12}$ aralkylthio group,
(30) a $C_{1-6}$ alkylsulfonyl group,
(31) a $C_{3-6}$ cycloalkylsulfonyl group,
(32) a $C_{6-12}$ arylsulfonyl group,
(33) a $C_{7-12}$ aralkylsulfonyl group,
(34) an ureido group,
(35) a mono- or di-($C_{1-6}$ alkyl)ureido group,
(36) a mono- or di-($C_{6-12}$ aryl)ureido group,
(37) a sulfamoyl group,
(38) a $C_{1-6}$ alkylsulfonylamino group,
(39) a sulfamoylamino group,
(40) a mono- or di-($C_{1-6}$ alkyl)sulfamoylamino group,
(41) a nonaromatic heterocyclic group optionally substituted by 1 to 3 substituents selected from
    (a) a nonaromatic heterocyclic group optionally substituted by an oxo group,
    (b) a carboxy group, and
    (c) an oxo group
and the like. The number of the substituents is 1 to 4, preferably 1 to 3.

The "optionally substituted amino group" for R is preferably
(1) an amino group,
(2) a mono- or di-$C_{1-6}$ alkylamino group (preferably, dimethylamino),
(3) a mono- or di-$C_{7-12}$ aralkylamino group (preferably, benzylamino),
(4) a mono- or di-($C_{1-6}$ alkylsulfonyl)amino group (preferably, methylsulfonylamino, ethylsulfonylamino),
(5) a mono- or di-($C_{3-6}$ cycloalkylsulfonyl)amino group (preferably, cyclopropylsulfonylamino),
(6) a mono- or di-($C_{6-12}$ arylsulfonyl)amino group (preferably, phenylsulfonylamino),
(7) a mono- or di-(aromatic heterocyclyl-sulfonyl)amino group (preferably, pyridylsulfonylamino (preferably, pyridin-3-ylsulfonylamino)),
(8) —$NR^A$—CO—$R^B$
  wherein
  $R^A$ is
    (a) a hydrogen atom, or
    (b) a $C_{1-6}$ alkyl group (preferably, methyl), and
  $R^B$ is
    (a) a $C_{1-6}$ alkyl group (preferably, methyl, ethyl) optionally substituted by 1 to 3 (preferably, 1 or 2) substituents selected from (i) a halogen atom (preferably, fluorine atom),
(ii) a hydroxy group,
(iii) a $C_{1-6}$ alkoxy group (preferably, methoxy),
(iv) an aromatic heterocyclic group (preferably, triazolyl (preferably, 1,2,4-triazol-1-yl)), and
(v) a heterocyclic group (preferably, dihydrooxadiazolyl (preferably, 4,5-dihydro-1,2,4-oxadiazol-3-yl)) optionally substituted by an oxo group,
(b) a $C_{3-6}$ cycloalkyl group (preferably, cyclopropyl),
(c) a $C_{1-6}$ alkyl-carbonyl group (preferably, acetyl),
(d) an amino group,
(e) a mono- or di-$C_{1-6}$ alkylamino group (preferably, methylamino),
(f) a cyclic amino group (preferably, morpholino),
(g) a $C_{6-12}$ aryl group (preferably, phenyl) optionally substituted by 1 to 3 (preferably, 1) substituents selected from
(i) a cyano group,
(ii) a carboxy group,
(iii) a $C_{1-6}$ alkoxy-carbonyl group (preferably, ethoxycarbonyl),
(iv) a $C_{1-6}$ alkylsulfonylamino group (preferably, methylsulfonylamino), and
(v) a nonaromatic heterocyclic group (preferably, dihydrooxadiazolyl (preferably, 4,5-dihydro-1,2,4-oxadiazol-3-yl)) optionally substituted by an oxo group,
(h) a $C_{7-12}$ aralkyl group (preferably, benzyl) optionally substituted by a nonaromatic heterocyclic group (preferably, dihydrooxadiazolyl (preferably, 4,5-dihydro-1,2,4-oxadiazol-3-yl)) optionally substituted by an oxo group, or
(i) an aromatic heterocyclic group (preferably, oxazolyl (preferably, oxazol-5-yl)),
(9) —NR$^C$—SO$_2$—N(R$^D$)(R$^E$)
wherein
R$^C$ is
(a) a hydrogen atom, or
(b) a $C_{1-6}$ alkyl group (preferably, methyl), and
R$^D$ and R$^E$ are each independently,
(a) a hydrogen atom,
(b) a $C_{1-6}$ alkyl group (preferably, methyl, ethyl), or
(c) a $C_{3-6}$ cycloalkyl group (preferably, cyclopropyl), or
(10) an optionally substituted cyclic amino group (preferably, a cyclic amino group (preferably, 1-imidazolidinyl) optionally substituted by 1 or 2 oxo groups).

In another embodiment, the "optionally substituted amino group" for R is preferably
(1) a mono- or di-($C_{1-6}$ alkyl-carbonyl)amino group (preferably, acetylamino), or
(2) a sulfamoylamino group.

The "$C_{1-6}$ alkyl group" of the "optionally substituted $C_{1-6}$ alkyl group" for R is preferably methyl, ethyl, propyl or isopropyl.

Examples of the substituent that the "$C_{1-6}$ alkyl group" optionally has include
(1) a halogen atom,
(2) a cyano group,
(3) a hydroxy group,
(4) a carboxy group,
(5) an amino group,
(6) a carbamoyl group,
(7) a mono- or di-($C_{1-6}$ alkyl)carbamoyl group (said $C_{1-6}$ alkyl is optionally substituted by a hydroxy group or a carboxy group),
(8) a mono- or di-($C_{6-12}$ aryl)carbamoyl group (said $C_{6-12}$ aryl is optionally substituted by a carboxy group),
(9) a $C_{1-6}$ alkoxy group optionally substituted by 1 to 3 (preferably, 1 or 2) substituents selected from
(i) a hydroxy group,
(ii) a carboxy group,
(iii) a carbamoyl group,
(iv) a mono- or di-($C_{1-6}$ alkyl-carbonyl)amino group,
(v) a mono- or di-($C_{1-6}$ alkylsulfonyl)amino group,
(vi) a $C_{1-6}$ alkoxy-carbonyl group, and
(vii) a cyclic amino-carbonyl group optionally substituted by a hydroxy group,
(10) a $C_{1-6}$ alkyl-carbonyloxy group,
(11) a $C_{1-6}$ alkylsulfonyloxy group,
(12) a $C_{1-6}$ alkoxy-carbonyl group,
(13) a $C_{6-12}$ aryloxy group optionally substituted by 1 to 3 substituents selected from
(i) a halogen atom,
(ii) a cyano group,
(iii) a carboxy group,
(iv) a $C_{1-6}$ alkoxy group,
(v) a $C_{1-6}$ alkoxy-carbonyl group,
(vi) a $C_{1-6}$ alkylsulfonyl group,
(vii) a mono- or di-($C_{1-6}$ alkylsulfonyl)carbamoyl group,
(viii) a nonaromatic heterocyclic group (preferably, dihydrooxadiazolyl) optionally substituted by an oxo group or a thioxo group, and
(ix) a cyclic amino-carbonyl group optionally substituted by a hydroxy group,
(14) a $C_{7-12}$ aralkyloxy group optionally substituted by a nonaromatic heterocyclic group optionally substituted by an oxo group,
(15) an aromatic heterocyclyl-oxy group optionally substituted by 1 to 3 substituents selected from
(i) a carboxy group,
(ii) a $C_{1-6}$ alkoxy-carbonyl group, and
(iii) a nonaromatic heterocyclic group optionally substituted by an oxo group,
(16) a $C_{1-6}$ alkylthio group,
(17) a $C_{6-12}$ arylthio group optionally substituted by a carboxy group,
(18) a $C_{1-6}$ alkylsulfinyl group,
(19) a $C_{2-6}$ alkylsulfonyl group,
(20) a $C_{6-12}$ arylsulfonyl group optionally substituted by 1 to 3 substituents selected from
(i) a carboxy group, and
(ii) a nonaromatic heterocyclic group optionally substituted by an oxo group,
(21) a mono- or di-$C_{1-6}$ alkylsulfamoyl group,
(22) an aromatic heterocyclyl-amino group optionally substituted by 1 to 3 substituents selected from
(i) a carboxy group, and
(ii) a nonaromatic heterocyclic group optionally substituted by an oxo group,
(23) —NR$^F$—CO—R$^G$
wherein
R$^F$ is
(i) a hydrogen atom,
(ii) a $C_{1-6}$ alkyl group optionally substituted by a hydroxy group, or
(iii) a $C_{1-6}$ alkyl-carbonyl group, and
R$^G$ is
(i) a $C_{1-6}$ alkyl group optionally substituted by 1 to 3 substituents selected from
(1) a halogen atom,
(2) a cyano group,
(3) a hydroxy group, (4) a $C_{1-6}$ alkoxy group optionally substituted by 1 to 3 substituents selected from a halogen atom and a $C_{3-6}$ cycloalkyl group,
(5) a $C_{3-6}$ cycloalkyloxy group,
(6) an aromatic heterocyclyl-oxy group optionally substituted by 1 to 3 substituents selected from a halogen atom, a cyano group and a carboxy group,
(7) a mono- or di-$C_{1-6}$ alkylamino group,
(8) an N—($C_{1-6}$ alkyl-carbonyl)-N—($C_{1-6}$ alkyl) amino group,
(9) a mono- or di-($C_{6-12}$ aryl-carbonyl)amino group,
(10) a mono- or di-(aromatic heterocyclyl-carbonyl) amino group,
(11) an N-(aromatic heterocyclyl-carbonyl)-N—($C_{1-6}$ alkyl)amino group,
(12) a mono- or di-($C_{6-12}$ arylsulfonyl)amino group,
(13) a $C_{1-6}$ alkylthio group,
(14) a $C_{1-6}$ alkylsulfonyl group,
(15) a $C_{1-6}$ alkyl-carbonyloxy group,
(16) a $C_{6-12}$ aryloxy group optionally substituted by 1 to 3 substituents selected from a nonaromatic heterocyclic group optionally substituted by an oxo group, and a carboxy group,
(17) an aromatic heterocyclic group optionally substituted by 1 to 3 substituents selected from a carboxy group and a $C_{1-6}$ alkyl group,
(18) a cyclic amino group optionally substituted by 1 to 3 substituents selected from a halogen atom and an oxo group, and
(19) a nonaromatic heterocyclic group optionally substituted by an oxo group,
(ii) a $C_{1-6}$ alkoxy group,
(iii) a $C_{3-6}$ cycloalkyl group,
(iv) a $C_{6-12}$ aryl group optionally substituted by 1 to 3 substituents selected from
  (1) a halogen atom,
  (2) a cyano group,
  (3) a hydroxy group,
  (4) a carboxy group,
  (5) a $C_{1-6}$ alkyl group optionally substituted by a nonaromatic heterocyclic group optionally substituted by an oxo group,
  (6) a $C_{1-6}$ alkoxy group,
  (7) a $C_{1-6}$ alkylsulfonyl group,
  (8) a mono- or di-($C_{1-6}$ alkylsulfonyl)amino group,
  (9) a $C_{6-12}$ aryl group,
  (10) an aromatic heterocyclic group optionally substituted by a $C_{1-6}$ alkyl group,
  (11) a cyclic amino group optionally substituted by an oxo group, and
  (12) a nonaromatic heterocyclic group optionally substituted by an oxo group,
(v) a $C_{7-12}$ aralkyl group optionally substituted by a nonaromatic heterocyclic group optionally substituted by an oxo group,
(vi) an aromatic heterocyclic group optionally substituted by 1 to 3 substituents selected from
  (1) a $C_{1-6}$ alkyl group,
  (2) a mono- or di-($C_{1-6}$ alkylsulfonyl)amino group, and
  (3) a nonaromatic heterocyclic group substituted by an oxo group,
(vii) a cyclic amino group optionally substituted by 1 or 2 oxo groups,
(viii) a nonaromatic heterocyclic group optionally substituted by 1 or 2 oxo groups,
(ix) a $C_{1-6}$ alkyl-carbonyl group, or
(x) a cyclic amino-carbonyl group,
(24) —$NR^H$—$SO_2$—$R^I$
  wherein
  $R^H$ is
    (i) a hydrogen atom,
    (ii) a $C_{1-6}$ alkyl group, or
    (iii) a $C_{7-12}$ aralkyl group optionally substituted by a $C_{1-6}$ alkoxy group, and
  $R^I$ is
    (i) a $C_{1-6}$ alkyl group optionally substituted by 1 to 3 substituents selected from
      (1) a halogen atom,
      (2) a $C_{1-6}$ alkoxy group, and
      (3) a cyclic amino group,
    (ii) a $C_{6-12}$ aryl group optionally substituted by 1 to 3 substituents selected from
      (1) a carboxy group, and
      (2) a nonaromatic heterocyclic group optionally substituted by an oxo group, or
    (iii) an aromatic heterocyclic group optionally substituted by 1 to 3 substituents selected from
      (1) a carboxy group, and
      (2) a nonaromatic heterocyclic group optionally substituted by an oxo group,
(25) —$NR^J$—CO—$NR^K R^L$
  wherein
  $R^J$ is
    (i) a hydrogen atom, or
    (ii) a $C_{1-6}$ alkyl group optionally substituted by a hydroxy group, and
  $R^K$ and $R^L$ are each independently,
    (i) a hydrogen atom,
    (ii) a $C_{1-6}$ alkyl group optionally substituted by 1 to 3 substituents selected from a hydroxy group and a $C_{1-6}$ alkoxy group, or
    (iii) a $C_{1-6}$ alkoxy group,
(26) —$NR^M$—$SO_2$—$NR^N R^O$
  wherein
  $R^M$ is
    (i) a hydrogen atom, or
    (ii) a $C_{1-6}$ alkyl group, and
  $R^N$ and $R^O$ are each independently,
    (i) a hydrogen atom,
    (ii) a $C_{1-6}$ alkyl group, or
    (iii) a $C_{1-6}$ alkoxy group,
(27) an aromatic heterocyclic group optionally substituted by 1 to 3 substituents selected from
  (i) a carboxy group,
  (ii) a $C_{1-6}$ alkyl group optionally substituted by 1 to 3 substituents selected from a halogen atom, a hydroxy group and a carboxy group,
  (iii) a $C_{1-6}$ alkoxy group optionally substituted by a $C_{1-6}$ alkoxy group,
  (iv) a $C_{3-6}$ cycloalkyl group, and
  (v) a nonaromatic heterocyclic group optionally substituted by an oxo group,
(28) a cyclic amino group optionally substituted by 1 to 4 substituents selected from
  (i) a halogen atom,
  (ii) a cyano group,
  (iii) a carboxy group,
  (iv) a carbamoyl group,
  (v) a $C_{1-6}$ alkyl group,
  (vi) a $C_{1-6}$ alkoxy-carbonyl group,
  (vii) a mono- or di-($C_{1-6}$ alkyl-carbonyl)amino group, (viii) an aromatic heterocyclic group optionally substituted by a $C_{1-6}$ alkyl group,
(ix) a nonaromatic heterocyclic group optionally substituted by an oxo group, and
(x) an oxo group,
(29) a nonaromatic heterocyclic group optionally substituted by an oxo group
and the like. The number of the substituents is 1 to 4, preferably 1 to 3.

The "optionally substituted $C_{1-6}$ alkyl group" for R is preferably a $C_{1-6}$ alkyl group (preferably, methyl, ethyl, propyl, isopropyl) optionally substituted by 1 to 4 (preferably 1 to 3, more preferably 1 or 2) substituents selected from
(1) a halogen atom (preferably, a fluorine atom),
(2) a cyano group,
(3) a hydroxy group,
(4) a carboxy group,
(5) an amino group,
(6) a carbamoyl group,
(7) a mono- or di-($C_{1-6}$ alkyl)carbamoyl group (preferably, isopropylcarbamoyl) (said $C_{1-6}$ alkyl is optionally substituted by a carboxy group),
(8) a mono- or di-($C_{6-12}$ aryl)carbamoyl group (preferably, phenylcarbamoyl) (said $C_{6-12}$ aryl is optionally substituted by a carboxy group),
(9) a $C_{1-6}$ alkoxy group (preferably, methoxy, ethoxy, propoxy) optionally substituted by 1 to 3 (preferably, 1 or 2) substituents selected from
  (i) a hydroxy group,
  (ii) a carboxy group,
  (iii) a carbamoyl group,
  (iv) a mono- or di-($C_{1-6}$ alkyl-carbonyl)amino group (preferably, acetylamino),
  (v) a mono- or di-($C_{1-6}$ alkylsulfonyl)amino group (preferably, methylsulfonylamino),
  (vi) a $C_{1-6}$ alkoxy-carbonyl group (preferably, ethoxycarbonyl), and
  (vii) a cyclic amino-carbonyl group (preferably, azetidin-1-ylcarbonyl, 1,1-dioxide-thiomorpholinocarbonyl) optionally substituted by a hydroxy group,
(10) a $C_{1-6}$ alkyl-carbonyloxy group (preferably, acetyloxy),
(11) a $C_{1-6}$ alkylsulfonyloxy group (preferably, methylsulfonyloxy),
(12) a $C_{6-12}$ aryloxy group (preferably, phenoxy) optionally substituted by 1 to 3 (preferably, 1 or 2) substituents selected from
  (i) a halogen atom (preferably, a fluorine atom, a chlorine atom),
  (ii) a cyano group,
  (iii) a carboxy group,
  (iv) a $C_{1-6}$ alkoxy group (preferably, methoxy),
  (v) a $C_{1-6}$ alkoxy-carbonyl group (preferably, methoxycarbonyl),
  (vi) a $C_{1-6}$ alkylsulfonyl group (preferably, methylsulfonyl),
  (vii) a mono- or di-($C_{1-6}$ alkylsulfonyl)carbamoyl group (preferably, methylsulfonylcarbamoyl),
  (viii) a nonaromatic heterocyclic group (preferably, dihydrooxadiazolyl (preferably, 4,5-dihydro-1,2,4-oxadiazol-3-yl)) optionally substituted by an oxo group or a thioxo group, and
  (ix) a cyclic amino-carbonyl group (preferably, azetidin-1-ylcarbonyl) optionally substituted by a hydroxy group,
(13) a $C_{7-12}$ aralkyloxy group (preferably, benzyloxy) optionally substituted by a nonaromatic heterocyclic group (preferably, dihydrooxadiazolyl (preferably, 4,5-dihydro-1,2,4-oxadiazol-3-yl)) optionally substituted by an oxo group,
(14) an aromatic heterocyclyl-oxy group (preferably, pyridyloxy (preferably, pyridin-2-yloxy)) optionally substituted by 1 to 3 (preferably, 1) substituents selected from
  (i) a carboxy group,
  (ii) a $C_{1-6}$ alkoxy-carbonyl group (preferably, methoxycarbonyl), and
  (iii) a nonaromatic heterocyclic group (preferably, dihydrooxadiazolyl (preferably, 4,5-dihydro-1,2,4-oxadiazol-3-yl, 2,3-dihydro-1,3,4-oxadiazol-5-yl)) optionally substituted by an oxo group,
(15) a $C_{1-6}$ alkylthio group (preferably, methylthio),
(16) a $C_{6-12}$ arylthio group (preferably, phenylthio) optionally substituted by a carboxy group,
(17) a $C_{1-6}$ alkylsulfinyl group (preferably, methylsulfinyl),
(18) a $C_{1-6}$ alkylsulfonyl group (preferably, methylsulfonyl),
(19) a $C_{6-12}$ arylsulfonyl group (preferably, phenylsulfonyl) optionally substituted by 1 to 3 (preferably, 1) substituents selected from
  (i) a carboxy group, and
  (ii) a nonaromatic heterocyclic group (preferably, dihydrooxadiazolyl (preferably, 4,5-dihydro-1,2,4-oxadiazol-3-yl)) optionally substituted by an oxo group,
(20) a mono- or di-$C_{1-6}$ alkylsulfamoyl group (preferably, isopropylsulfamoyl),
(21) an aromatic heterocyclyl-amino group (preferably, pyridylamino (preferably, pyridin-2-ylamino), pyrimidinylamino (preferably, pyrimidin-2-ylamino), benzooxazolylamino (preferably, benzooxazol-2-ylamino)) optionally substituted by 1 to 3 (preferably, 1) substituents selected from
  (i) a carboxy group, and
  (ii) a nonaromatic heterocyclic group (preferably, dihydrooxadiazolyl (preferably, 4,5-dihydro-1,2,4-oxadiazol-3-yl)) optionally substituted by an oxo group,
(22) —$NR^F$—CO—$R^G$
wherein
$R^F$ is
  (i) a hydrogen atom, or
  (ii) a $C_{1-6}$ alkyl group (preferably, methyl, ethyl) optionally substituted by a hydroxy group, and
$R^G$ is
  (i) a $C_{1-6}$ alkyl group (preferably, methyl, ethyl, propyl, isopropyl) optionally substituted by 1 to 3 substituents selected from
    (1) a halogen atom (preferably, a fluorine atom),
    (2) a cyano group,
    (3) a hydroxy group,
    (4) a $C_{1-6}$ alkoxy group (preferably, methoxy, ethoxy, isopropoxy, isobutoxy) optionally substituted by 1 to 3 substituents selected from a halogen atom (preferably, a fluorine atom) and a $C_{3-6}$ cycloalkyl group (preferably, cyclopropyl),
    (5) a $C_{3-6}$ cycloalkyloxy group (preferably, cyclopropyloxy),
    (6) an aromatic heterocyclyl-oxy group (preferably, pyridyloxy (preferably, pyridin-2-yloxy), pyrimidinyloxy (preferably, pyrimidin-2-yloxy)) optionally substituted by 1 to 3 (preferably, 1) substituents selected from a halogen atom (preferably, a fluorine atom, a chlorine atom), a cyano group and a carboxy group,
    (7) a mono- or di-$C_{1-6}$ alkylamino group (preferably, methylamino, dimethylamino),
    (8) an N—($C_{1-6}$ alkyl-carbonyl)-N—($C_{1-6}$ alkyl) amino group (preferably, N-acetyl-N-methylamino),
    (9) a mono- or di-($C_{6-12}$ aryl-carbonyl)amino group (preferably, benzoylamino),

(10) a mono- or di-(aromatic heterocyclyl-carbonyl) amino group (preferably, pyridylcarbonylamino (preferably, pyridin-2-ylcarbonylamino)),

(11) an N-(aromatic heterocyclyl-carbonyl)-N—($C_{1-5}$ alkylamino group (preferably, N-(pyridylcarbonyl)-N-methylamino (preferably, N-(pyridin-2-ylcarbonyl)-N-methylamino)),

(12) a mono- or di-($C_{6-12}$ arylsulfonyl)amino group (preferably, phenylsulfonylamino),

(13) a $C_{1-6}$ alkylthio group (preferably, methylthio),

(14) a $C_{1-6}$ alkylsulfonyl group (preferably, methylsulfonyl),

(15) a $C_{1-6}$ alkyl-carbonyloxy group (preferably, acetyloxy),

(16) a $C_{6-12}$ aryloxy group (preferably, phenoxy) optionally substituted by 1 to 3 (preferably, 1) substituents selected from a nonaromatic heterocyclic group (preferably, dihydrooxadiazolyl (preferably, 4,5-dihydro-1,2,4-oxadiazol-3-yl)) optionally substituted by an oxo group, and a carboxy group,

(17) an aromatic heterocyclic group (preferably, pyridyl (preferably, pyridin-2-yl), pyrazolyl (preferably, pyrazol-1-yl), isoxazolyl (preferably, isoxazol-5-yl), triazolyl (preferably, 1H-1,2,4-triazol-1-yl), tetrazolyl (preferably, tetrazol-1-yl)) optionally substituted by 1 to 3 (preferably, 1 or 2) substituents selected from a carboxy group and a $C_{1-6}$ alkyl group (preferably, methyl),

(18) a cyclic amino group (preferably, 1-pyrrolidinyl, piperidino, 1-imidazolidinyl, morpholino, 8-oxa-3-azabicyclo[3.2.1]octan-3-yl) optionally substituted by 1 to 3 (preferably, 1 or 2) substituents selected from a halogen atom (preferably, a fluorine atom, a chlorine atom) and an oxo group, and

(19) a nonaromatic heterocyclic group (preferably, dihydropyridyl (preferably, 1,2-dihydropyridin-1-yl), dihydrooxadiazolyl (preferably, 4,5-dihydro-1,2,4-oxadiazol-3-yl)) optionally substituted by 1 to 3 (preferably, 1 or 2) substituents selected from a halogen atom (preferably, a chlorine atom) and an oxo group, (ii) a $C_{1-6}$ alkoxy group (preferably, methoxy, isopropoxy), (iii) a $C_{3-6}$ cycloalkyl group (preferably, cyclopropyl), (iv) a $C_{6-12}$ aryl group (preferably, phenyl) optionally substituted by 1 to 3 substituents selected from
(1) a halogen atom (preferably, a fluorine atom, a chlorine atom),
(2) a cyano group,
(3) a hydroxy group,
(4) a carboxy group,
(5) a $C_{1-6}$ alkyl group (preferably, methyl, tert-butyl) optionally substituted by a nonaromatic heterocyclic group (preferably, dihydrooxadiazolyl (preferably, 4,5-dihydro-1,2,4-oxadiazol-3-yl)) optionally substituted by an oxo group,
(6) a $C_{1-6}$ alkoxy group (preferably, methoxy, ethoxy),
(7) a $C_{1-6}$ alkylsulfonyl group (preferably, methylsulfonyl),
(8) a mono- or di-($C_{1-6}$ alkylsulfonyl)amino group (preferably, methylsulfonylamino),
(9) a $C_{6-12}$ aryl group (preferably, phenyl), and
(10) an aromatic heterocyclic group (preferably, oxadiazolyl (preferably, 1,2,4-oxadiazol-3-yl), tetrazolyl (preferably, tetrazol-5-yl)) optionally substituted by a $C_{1-6}$ alkyl group (preferably, methyl),

(11) a cyclic amino group (preferably, 1-pyrrolidinyl) optionally substituted by an oxo group, and
(12) a nonaromatic heterocyclic group (preferably, dihydrooxadiazolyl (preferably, 4,5-dihydro-1,2,4-oxadiazol-3-yl)) optionally substituted by an oxo group, (v) a $C_{7-12}$ aralkyl group (preferably, benzyl) optionally substituted by a nonaromatic heterocyclic group (preferably, dihydrooxadiazolyl (preferably, 4,5-dihydro-1,2,4-oxadiazol-3-yl)) optionally substituted by an oxo group, (vi) an aromatic heterocyclic group (preferably, pyridyl (preferably, pyridin-2-yl, pyridin-3-yl), thiazolyl (preferably, thiazol-5-yl)) optionally substituted by 1 to 3 (preferably, 1) substituents selected from
(1) a $C_{1-6}$ alkyl group (preferably, methyl),
(2) a mono- or di-($C_{1-6}$ alkylsulfonyl)amino group (preferably, methylsulfonylamino), and
(3) a nonaromatic heterocyclic group (preferably, dihydrooxadiazolyl (preferably, 4,5-dihydro-1,2,4-oxadiazol-3-yl)) optionally substituted by an oxo group, (vii) a cyclic amino group (preferably, 1-pyrrolidinyl, morpholino, 1,1-dioxide-thiomorpholino) optionally substituted by 1 or 2 oxo groups, (viii) a nonaromatic heterocyclic group (preferably, dihydropyridyl (preferably, 1,2-dihydropyridin-3-yl), tetrahydrofuryl (preferably, tetrahydrofuran-2-yl, tetrahydrofuran-3-yl), tetrahydropyranyl (preferably, tetrahydropyran-2-yl, tetrahydropyran-4-yl), dioxanyl (preferably, 1,4-dioxan-2-yl)) optionally substituted by 1 or 2 oxo groups, (ix) a $C_{1-6}$ alkyl-carbonyl group (preferably, acetyl, ethylcarbonyl), or (x) a cyclic amino-carbonyl group (preferably, pyrrolidin-1-ylcarbonyl),

(23) —$NR^H$—$SO_2$—$R^I$ wherein $R^H$ is
(i) a hydrogen atom,
(ii) a $C_{1-6}$ alkyl group (preferably, methyl), or
(iii) a $C_{7-12}$ aralkyl group (preferably, benzyl) optionally substituted by a $C_{1-6}$ alkoxy group (preferably, methoxy), and $R^I$ is
(i) a $C_{1-6}$ alkyl group (preferably, methyl, ethyl, isopropyl) optionally substituted by 1 to 3 substituents selected from
(1) a halogen atom (preferably, a fluorine atom),
(2) a $C_{1-6}$ alkoxy group (preferably, methoxy), and
(3) a cyclic amino group (preferably, morpholino),
(ii) a $C_{6-12}$ aryl group (preferably, phenyl) optionally substituted by 1 to 3 (preferably, 1) substituents selected from
(1) a carboxy group, and
(2) a nonaromatic heterocyclic group (preferably, dihydrooxadiazolyl (preferably, 4,5-dihydro-1,2,4-oxadiazol-3-yl)) optionally substituted by an oxo group, or
(iii) an aromatic heterocyclic group (preferably, pyridyl (preferably, pyridin-2-yl, pyridin-3-yl), furyl (preferably, furan-2-yl)) optionally substituted by 1 to 3 (preferably, 1) substituents selected from (1) a carboxy group, and
(2) a nonaromatic heterocyclic group (preferably, dihydrooxadiazolyl (preferably, 4,5-dihydro-1,2,4-oxadiazol-3-yl)) optionally substituted by an oxo group,

(24) —NR$^J$—CO—NR$^K$R$^L$
wherein
R$^J$ is
  (i) a hydrogen atom, or
  (ii) a $C_{1-6}$ alkyl group (preferably, methyl, ethyl) optionally substituted by a hydroxy group, and
R$^K$ and R$^L$ are each independently,
  (i) a hydrogen atom,
  (ii) a $C_{1-6}$ alkyl group (preferably, methyl, ethyl, tert-butyl) optionally substituted by 1 to 3 (preferably, 1) substituents selected from a hydroxy group and a $C_{1-6}$ alkoxy group (preferably, methoxy), or
  (iii) a $C_{1-6}$ alkoxy group (preferably, methoxy),

(25) —NR$^M$—SO$_2$—NR$^N$R$^O$
wherein
R$^M$ is
  (i) a hydrogen atom, or
  (ii) a $C_{1-6}$ alkyl group (preferably, methyl), and
R$^N$ and R$^O$ are each independently,
  (i) a hydrogen atom,
  (ii) a $C_{1-6}$ alkyl group (preferably, methyl), or
  (iii) a $C_{1-6}$ alkoxy group (preferably, methoxy),

(26) an aromatic heterocyclic group (preferably, pyrazolyl (preferably, pyrazol-1-yl, pyrazol-3-yl), oxadiazolyl (preferably, 1,2,4-oxadiazol-3-yl), thiazolyl (preferably, thiazol-2-yl, thiazol-4-yl), triazolyl (preferably, 1H-1,2,3-triazol-1-yl, 1H-1,2,4-triazol-3-yl), indazolyl (preferably, 1H-indazol-1-yl), benzimidazolyl (preferably, 1H-benzimidazol-2-yl)) optionally substituted by 1 to 3 (preferably, 1 or 2) substituents selected from
  (i) a carboxy group,
  (ii) a $C_{1-6}$ alkyl group (preferably, methyl) optionally substituted by 1 to 3 substituents selected from a halogen atom (preferably, a fluorine atom), a hydroxy group and a carboxy group,
  (iii) a $C_{1-6}$ alkoxy group (preferably, ethoxy, tert-butoxy) optionally substituted by a $C_{1-6}$ alkoxy group (preferably, methoxy),
  (iv) a $C_{3-6}$ cycloalkyl group (preferably, cyclopropyl), and
  (v) a nonaromatic heterocyclic group (preferably, dihydrooxadiazolyl (preferably, 4,5-dihydro-1,2,4-oxadiazol-3-yl)) optionally substituted by an oxo group,

(27) a cyclic amino group (preferably, 1-azetidinyl, 1-pyrrolidinyl, piperidino, 1-imidazolidinyl, 1-dihydropyridazinyl (preferably, 2,3-dihydropyridazin-2-yl), 1-hexahydropyrimidinyl, 2-dihydroisoindolyl (preferably, 1,3-dihydro-2H-isoindol-2-yl), 3-dihydroquinazolinyl (preferably, 3,4-dihydroquinazolin-3-yl), 3-tetrahydroquinazolinyl (preferably, 1,2,3,4-tetrahydroquinazolin-3-yl), 3-tetrahydropyrido[3,2-d]pyrimidinyl (preferably, 1,2,3,4-tetrahydropyrido[3,2-d]pyrimidin-3-yl), 3-tetrahydropteridinyl (preferably, 1,2,3,4-tetrahydropteridin-3-yl)) optionally substituted by 1 to 4 substituents selected from
  (i) a cyano group,
  (ii) a carboxy group,
  (iii) a $C_{1-6}$ alkyl group (preferably, methyl),
  (iv) a $C_{1-6}$ alkoxy-carbonyl group (preferably, ethoxycarbonyl),
  (v) a mono- or di-($C_{1-6}$ alkyl-carbonyl)amino group (preferably, acetylamino),
  (vi) a nonaromatic heterocyclic group (preferably, dihydrooxadiazolyl (preferably, 4,5-dihydro-1,2,4-oxadiazol-3-yl)) optionally substituted by an oxo group, and
  (vii) an oxo group, or

(28) a nonaromatic heterocyclic group (preferably, 1-dihydropyridyl (preferably, 1,2-dihydropyridin-1-yl), dihydrooxadiazolyl (preferably, 4,5-dihydro-1,2,4-oxadiazol-3-yl)) optionally substituted by 1 to 3 substituents selected from
  (i) a halogen atom (preferably, a chlorine atom),
  (ii) a cyano group,
  (iii) a carboxy group,
  (iv) a carbamoyl group,
  (v) a $C_{1-6}$ alkoxy-carbonyl group (preferably, methoxycarbonyl),
  (vi) an aromatic heterocyclic group (preferably, triazolyl (preferably, 1,2,4-triazol-3-yl), tetrazolyl (preferably, tetrazol-5-yl)) optionally substituted by a $C_{1-6}$ alkyl group (preferably, methyl),
  (vii) a nonaromatic heterocyclic group (preferably, dihydrooxadiazolyl (preferably, 4,5-dihydro-1,2,4-oxadiazol-3-yl, 4,5-dihydro-1,3,4-oxadiazol-2-yl), dihydrotriazolyl (preferably, 4,5-dihydrotriazol-3-yl)) optionally substituted by an oxo group, and
  (viii) an oxo group.

In another embodiment, the "optionally substituted $C_{1-6}$ alkyl group" for R is preferably a $C_{1-6}$ alkyl group (preferably, methyl, ethyl, propyl, isopropyl) optionally substituted by 1 to 3 substituents selected from
(1) a hydroxyl group,
(2) a mono- or di-($C_{1-6}$ alkyl-carbonyl)amino group (preferably, acetyl),
(3) a sulfamoylamino group,
(4) a $C_{1-6}$ alkoxy-$C_{1-6}$ alkyl-carbonylamino group (preferably, (2-methoxyacetyl)amino, (2-ethoxyacetyl)amino, (2-isopropoxyacetyl)amino),
(5) a $C_{1-6}$ alkylsulfonylamino group (preferably, methylsulfonylamino), and
(6) a 2-oxo-1,2-dihydropyridin-1-yl optionally substituted by 1 to 3 substituents selected from a carboxy group and 5-oxo-4,5-dihydro-1,2,4-oxadiazolyl.

Here, the "$C_{1-6}$ alkoxy-$C_{1-6}$ alkyl-carbonylamino group" means a $C_{1-6}$ alkyl-carbonylamino group substituted by a $C_{1-6}$ alkoxy group.

The "$C_{1-6}$ alkoxy group" of the "optionally substituted $C_{1-6}$ alkoxy group" for R is preferably methoxy or ethoxy.

Examples of the substituent that the "$C_{1-6}$ alkoxy group" optionally has include those similar to the substituents that the "$C_{1-6}$ alkyl group" of the aforementioned "optionally substituted $C_{1-6}$ alkyl group" optionally has. The number of the substituents is 1 to 4, preferably 1 to 3, more preferably 1.

In another embodiment, the number of the substituents that the "$C_{1-6}$ alkoxy group" optionally has is preferably 1 or 2.

The "optionally substituted $C_{1-6}$ alkoxy group" for R is preferably a $C_{1-6}$ alkoxy group, more preferably, methoxy or ethoxy.

The "$C_{1-6}$ alkyl-carbonyl group" of the "optionally, substituted $C_{1-6}$ alkyl-carbonyl group" for R is preferably acetyl.

Examples of the substituent that the "$C_{1-6}$ alkyl-carbonyl group" optionally has include those similar to the substituents that the "$C_{1-6}$ alkyl group" of the aforementioned "optionally substituted $C_{1-6}$ alkyl group" optionally has. The number of the substituents is 1 to 4, preferably 1 to 3, more preferably 1.

In another embodiment, the number of the substituents that the "$C_{1-6}$ alkyl-carbonyl group" optionally has is preferably 1 or 2.

The "optionally substituted $C_{1-6}$ alkyl-carbonyl group" for R is preferably a $C_{1-6}$ alkyl-carbonyl group, more preferably, acetyl.

The "optionally substituted carbamoyl group" for R is —CO—NR$^P$R$^Q$
wherein
R$^P$ and R$^Q$ are each independently,
(a) a hydrogen atom,
(b) a $C_{1-6}$ alkyl group optionally substituted by 1 to 3 substituents selected from
　(i) a hydroxy group,
　(ii) a $C_{1-6}$ alkylsulfonyl group, and
　(iii) a $C_{1-6}$ alkoxy group,
(c) a $C_{1-6}$ alkoxy group,
(d) a $C_{6-12}$ aryl group optionally substituted by a carboxy group,
(e) a $C_{7-12}$ aralkyl group,
(f) a $C_{1-6}$ alkylsulfonyl group, or
(g) a $C_{6-12}$ arylsulfonyl group optionally substituted by 1 to 3 substituents selected from
　(i) a $C_{1-6}$ alkyl group optionally substituted by 1 to 3 halogen atoms, and
　(ii) a $C_{1-6}$ alkoxy group optionally substituted by 1 to 3 halogen atoms
and the like.

The "optionally substituted carbamoyl group" for R is preferably —CO—NR$^P$R$^Q$
wherein
R$^P$ and R$^Q$ are each independently,
(a) a hydrogen atom,
(b) a $C_{1-6}$ alkyl group (preferably, methyl, ethyl, isobutyl) optionally substituted by 1 to 3 (preferably 1 or 2, more preferably 1) substituents selected from
　(i) a hydroxy group,
　(ii) a $C_{1-6}$ alkylsulfonyl group (preferably, methylsulfonyl), and
　(iii) a $C_{1-6}$ alkoxy group (preferably, methoxy),
(c) a $C_{1-6}$ alkoxy group (preferably, methoxy),
(d) a $C_{6-12}$ aryl group (preferably, phenyl) optionally substituted by a carboxy group,
(e) a $C_{1-6}$ alkylsulfonyl group (preferably, methylsulfonyl), or
(f) a $C_{6-12}$ arylsulfonyl group (preferably, phenylsulfonyl) optionally substituted by 1 to 3 (preferably, 1) substituents selected from
　(i) a $C_{1-6}$ alkyl group (preferably, methyl) optionally substituted by 1 to 3 halogen atoms (preferably, a fluorine atom), and
　(ii) a $C_{1-6}$ alkoxy group (preferably, methoxy) optionally substituted by 1 to 3 (preferably, 1 or 2) halogen atoms (preferably, a fluorine atom).

The "$C_{6-12}$ aryloxy group" of the "optionally substituted $C_{6-12}$ aryloxy group" for R is preferably phenoxy.

Examples of the substituent that the "$C_{6-12}$ aryloxy group" optionally has include those similar to the substituents that the "$C_{1-6}$ alkyl group" of the aforementioned "optionally substituted $C_{1-6}$ alkyl group" optionally has. The number of the substituents is 1 to 4, preferably 1 to 3, more preferably 1.

The "optionally substituted $C_{6-12}$ aryloxy group" for R is preferably a $C_{6-12}$ aryloxy group (preferably, phenoxy) optionally substituted by a nonaromatic heterocyclic group (preferably, dihydrooxadiazolyl (preferably, 4,5-dihydro-1,2,4-oxadiazol-3-yl)) optionally substituted by an oxo group.

The "aromatic heterocyclyl-oxy group" of the "optionally substituted aromatic heterocyclyl-oxy group" for R is preferably pyridyloxy (preferably, pyridin-3-yloxy, pyridin-4-yloxy).

Examples of the substituent that the "aromatic heterocyclyl-oxy group" optionally has include those similar to the substituents that the "$C_{1-6}$ alkyl group" of the aforementioned "optionally substituted $C_{1-6}$ alkyl group" optionally has. The number of the substituents is 1 to 4, preferably 1 to 3, more preferably 1.

The "optionally substituted aromatic heterocyclyl-oxy group" for R is preferably an aromatic heterocyclyl-oxy group (preferably, pyridyloxy (preferably, pyridin-3-yloxy, pyridin-4-yloxy)) optionally substituted by 1 to 3 (preferably, 1) substituents selected from
(a) a cyano group,
(b) a carboxy group,
(c) a $C_{1-6}$ alkoxy-carbonyl group (preferably, methoxycarbonyl),
(d) a carbamoyl group,
(e) a mono- or di-$C_{1-6}$ alkylcarbamoyl group (preferably, methyl carbamoyl, ethylcarbamoyl)
　(said $C_{1-6}$ alkyl is optionally substituted by a hydroxy group),
(f) an aromatic heterocyclic group (preferably, triazolyl (preferably, 1H-1,2,4-triazol-3-yl), tetrazolyl (preferably, tetrazol-5-yl)) optionally substituted by a $C_{1-6}$ alkyl group (preferably, methyl), and
(g) a nonaromatic heterocyclic group (preferably, dihydrooxadiazolyl (preferably, 4,5-dihydro-1,2,4-oxadiazol-3-yl), dihydrotriazolyl (preferably, 4,5-dihydro-1H-1,2,4-triazol-3-yl)) optionally substituted by an oxo group.

The "aromatic heterocyclic group" of the "optionally substituted aromatic heterocyclic group" for R is preferably thiazolyl (preferably, thiazol-2-yl).

Examples of the substituent that the "aromatic heterocyclic group" optionally has include those similar to the substituents that the "$C_{1-6}$ alkyl group" of the aforementioned "optionally substituted $C_{1-6}$ alkyl group" optionally has. The number of the substituents is 1 to 4, preferably 1 to 3, more preferably 1.

The "optionally substituted aromatic heterocyclic group" for R is preferably an aromatic heterocyclic group (preferably, thiazolyl (preferably, thiazol-2-yl)) optionally substituted by a carboxy group.

The "nonaromatic heterocyclic group" of the "optionally substituted nonaromatic heterocyclic group" for R is preferably dihydropyridyl (preferably, 1,2-dihydropyridin-1-yl), dihydrooxadiazolyl (preferably, 4,5-dihydro-1,2,4-oxadiazol-3-yl).

Examples of the substituent that the "nonaromatic heterocyclic group" optionally has include those similar to the substituents that the "$C_{1-6}$ alkyl group" of the aforementioned "optionally substituted $C_{1-6}$ alkyl group" optionally has. The number of the substituents is 1 to 4, preferably 1 to 3, more preferably 1.

The "optionally substituted nonaromatic heterocyclic group" for R is preferably a nonaromatic heterocyclic group (preferably, dihydropyridyl (preferably, 1,2-dihydropyridin-1-yl), dihydrooxadiazolyl (preferably, 4,5-dihydro-1,2,4-oxadiazol-3-yl)) optionally substituted by 1 to 3 (preferably, 1 or 2) substituents selected from
(a) a nonaromatic heterocyclic group (preferably, dihydrooxadiazolyl (preferably, 4,5-dihydro-1,2,4-oxadiazol-3-yl)), and
(b) an oxo group.

R is preferably
(1) a hydroxy group,
(2) a cyano group,
(3) a carboxy group,
(4) a $C_{1-6}$ alkoxy-carbonyl group (preferably, ethoxycarbonyl), (5) an amino group,
(6) a mono- or di-$C_{1-6}$ alkylamino group (preferably, dimethylamino),
(7) a mono- or di-$C_{7-12}$ aralkylamino group (preferably, benzylamino),
(8) a mono- or di-($C_{1-6}$ alkylsulfonyl)amino group (preferably, methylsulfonylamino, ethylsulfonylamino),
(9) a mono- or di-($C_{3-6}$ cycloalkylsulfonyl)amino group (preferably, cyclopropylsulfonylamino),
(10) a mono- or di-($C_{6-12}$ arylsulfonyl)amino group (preferably, phenylsulfonylamino),
(11) a mono- or di-(aromatic heterocyclyl-sulfonyl)amino group (preferably, pyridylsulfonylamino (preferably, pyridin-3-ylsulfonylamino)),
(12) —$NR^A$—CO—$R^B$
wherein
$R^A$ is
   (a) a hydrogen atom, or
   (b) a $C_{1-6}$ alkyl group (preferably, methyl), and
$R^B$ is
   (a) a $C_{1-6}$ alkyl group (preferably, methyl, ethyl) optionally substituted by 1 to 3 (preferably, 1 or 2) substituents selected from
     (i) a halogen atom (preferably, fluorine atom),
     (ii) a hydroxy group,
     (iii) a $C_{1-6}$ alkoxy group (preferably, methoxy),
     (iv) an aromatic heterocyclic group (preferably, triazolyl (preferably, 1,2,4-triazol-1-yl)), and
     (v) a nonaromatic heterocyclic group (preferably, dihydrooxadiazolyl (preferably, 4,5-dihydro-1,2,4-oxadiazol-3-yl)) optionally substituted by an oxo group,
   (b) a $C_{3-6}$ cycloalkyl group (preferably, cyclopropyl),
   (c) a $C_{1-6}$ alkyl-carbonyl group (preferably, acetyl),
   (d) an amino group,
   (e) a mono- or di-$C_{1-6}$ alkylamino group (preferably, methylamino),
   (f) a cyclic amino group (preferably, morpholino),
   (g) a $C_{6-12}$ aryl group (preferably, phenyl) optionally substituted by 1 to 3 (preferably, 1) substituents selected from
     (i) a cyano group,
     (ii) a carboxy group,
     (iii) a $C_{1-6}$ alkoxy-carbonyl group (preferably, ethoxycarbonyl),
     (iv) a $C_{1-6}$ alkylsulfonylamino group (preferably, methylsulfonylamino), and
     (v) a nonaromatic heterocyclic group (preferably, dihydrooxadiazolyl (preferably, 4,5-dihydro-1,2,4-oxadiazol-3-yl)) optionally substituted by an oxo group,
   (h) a $C_{7-12}$ aralkyl group (preferably, benzyl) optionally substituted by a nonaromatic heterocyclic group (preferably, dihydrooxadiazolyl (preferably, 4,5-dihydro-1,2,4-oxadiazol-3-yl)) optionally substituted by an oxo group, or
   (i) an aromatic heterocyclic group (preferably, oxazolyl (preferably, oxazol-5-yl)),
(13) —$NR^C$—$SO_2$—$N(R^D)(R^E)$
wherein
$R^C$ is
   (a) a hydrogen atom, or
   (b) a $C_{1-6}$ alkyl group (preferably, methyl), and
$R^D$ and $R^E$ are each independently,
   (a) a hydrogen atom,
   (b) a $C_{1-6}$ alkyl group (preferably, methyl, ethyl), or
   (c) a $C_{3-6}$ cycloalkyl group (preferably, cyclopropyl), or
(14) an optionally substituted cyclic amino group (preferably, a cyclic amino group (preferably, imidazolidinyl (preferably, imidazolidin-1-yl)) optionally substituted by 1 or 2 oxo groups, and
   (b) an oxo group,
(15) a $C_{1-6}$ alkyl group (preferably, methyl, ethyl, propyl, isopropyl) optionally substituted by 1 to 4 (preferably 1 to 3, more preferably 1 or 2) substituents selected from
   (a) a halogen atom (preferably, a fluorine atom),
   (b) a cyano group,
   (c) a hydroxy group,
   (d) a carboxy group,
   (e) an amino group,
   (f) a carbamoyl group,
   (g) a mono- or di-($C_{1-6}$ alkyl)carbamoyl group (preferably, isopropylcarbamoyl) (said $C_{1-6}$ alkyl is optionally substituted by a carboxy group),
   (h) a mono- or di-($C_{6-12}$ aryl)carbamoyl group (preferably, phenylcarbamoyl) (said $C_{6-12}$ aryl is optionally substituted by a carboxy group),
   (i) a $C_{1-6}$ alkoxy group (preferably, methoxy, ethoxy, propoxy) optionally substituted by 1 to 3 (preferably, 1 or 2) substituents selected from
     (i) a hydroxy group,
     (ii) a carboxy group,
     (iii) a carbamoyl group,
     (iv) a mono- or di-($C_{1-6}$ alkyl-carbonyl)amino group (preferably, acetylamino),
     (v) a mono- or di-($C_{1-6}$ alkylsulfonyl)amino group (preferably, methylsulfonylamino),
     (vi) a $C_{1-6}$ alkoxy-carbonyl group (preferably, ethoxycarbonyl), and
     (vii) a cyclic amino-carbonyl group (preferably, azetidin-1-ylcarbonyl, 1,1-dioxide-thiomorpholinocarbonyl) optionally substituted by a hydroxy group,
   (j) a $C_{1-6}$ alkyl-carbonyloxy group (preferably, acetyloxy),
   (k) a $C_{1-6}$ alkylsulfonyloxy group (preferably, methylsulfonyloxy),
   (l) a $C_{6-12}$ aryloxy group (preferably, phenoxy) optionally substituted by 1 to 3 (preferably, 1 or 2) substituents selected from
     (i) a halogen atom (preferably, a fluorine atom, a chlorine atom),
     (ii) a cyano group,
     (iii) a carboxy group,
     (iv) a $C_{1-6}$ alkoxy group (preferably, methoxy),
     (v) a $C_{1-6}$ alkoxy-carbonyl group (preferably, methoxycarbonyl),
     (vi) a $C_{1-6}$ alkylsulfonyl group (preferably, methylsulfonyl),
     (vii) a mono- or di-($C_{1-6}$ alkylsulfonyl)carbamoyl group (preferably, methylsulfonylcarbamoyl),
     (viii) a nonaromatic heterocyclic group (preferably, dihydrooxadiazolyl (preferably, 4,5-dihydro-1,2,4-oxadiazol-3-yl)) optionally substituted by an oxo group or a thioxo group, and
     (ix) a cyclic amino-carbonyl group (preferably, azetidin-1-ylcarbonyl) optionally substituted by a hydroxy group,
   (m) a $C_{7-12}$ aralkyloxy group (preferably, benzyloxy) optionally substituted by a nonaromatic heterocyclic group (preferably, dihydrooxadiazolyl (preferably, 4,5-dihydro-1,2,4-oxadiazol-3-yl)) optionally substituted by an oxo group, (n) an aromatic heterocyclyl-oxy group (preferably, pyridyloxy (preferably, pyridin-2-yloxy)) optionally substituted by 1 to 3 (preferably, 1) substituents selected from
  (i) a carboxy group,
  (ii) a $C_{1-6}$ alkoxy-carbonyl group (preferably, methoxycarbonyl), and
  (iii) a nonaromatic heterocyclic group (preferably, dihydrooxadiazolyl (preferably, 4,5-dihydro-1,2,4-oxadiazol-3-yl, 2,3-dihydro-1,3,4-oxadiazol-5-yl)) optionally substituted by an oxo group,
(o) a $C_{1-6}$ alkylthio group (preferably, methylthio),
(p) a $C_{6-12}$ arylthio group (preferably, phenylthio) optionally substituted by a carboxy group,
(q) a $C_{1-6}$ alkylsulfinyl group (preferably, methylsulfinyl),
(r) a $C_{1-6}$ alkylsulfonyl group (preferably, methylsulfonyl),
(s) a $C_{6-12}$ arylsulfonyl group (preferably, phenylsulfonyl) optionally substituted by 1 to 3 (preferably, 1) substituents selected from
  (i) a carboxy group, and
  (ii) a nonaromatic heterocyclic group (preferably, dihydrooxadiazolyl (preferably, 4,5-dihydro-1,2,4-oxadiazol-3-yl)) optionally substituted by an oxo group,
(t) a mono- or di-$C_{1-6}$ alkylsulfamoyl group (preferably, isopropylsulfamoyl),
(u) an aromatic heterocyclyl-amino group (preferably, pyridylamino (preferably, pyridin-2-ylamino), pyrimidinylamino (preferably, pyrimidin-2-ylamino), benzooxazolylamino (preferably, benzooxazol-2-ylamino)) optionally substituted by 1 to 3 (preferably, 1) substituents selected from
  (i) a carboxy group, and
  (ii) a nonaromatic heterocyclic group (preferably, dihydrooxadiazolyl (preferably, 4,5-dihydro-1,2,4-oxadiazol-3-yl)) optionally substituted by an oxo group,
(v) —NR$^F$—CO—R$^G$
  wherein
  R$^F$ is
    (i) a hydrogen atom, or
    (ii) a $C_{1-6}$ alkyl group (preferably, methyl, ethyl) optionally substituted by a hydroxy group, and
  R$^G$ is
    (i) a $C_{1-6}$ alkyl group (preferably, methyl, ethyl, propyl, isopropyl) optionally substituted by 1 to 3 substituents selected from
      (1) a halogen atom (preferably, a fluorine atom),
      (2) a cyano group,
      (3) a hydroxy group,
      (4) a $C_{1-6}$ alkoxy group (preferably, methoxy, ethoxy, isopropoxy, isobutoxy) optionally substituted by 1 to 3 substituents selected from a halogen atom (preferably, a fluorine atom) and a $C_{3-6}$ cycloalkyl group (preferably, cyclopropyl),
      (5) a $C_{3-6}$ cycloalkyloxy group (preferably, cyclopropyloxy),
      (6) an aromatic heterocyclyl-oxy group (preferably, pyridyloxy (preferably, pyridin-2-yloxy), pyrimidinyloxy (preferably, pyrimidin-2-yloxy)) optionally substituted by 1 to 3 (preferably, 1) substituents selected from a halogen atom (preferably, a fluorine atom, a chlorine atom), a cyano group and a carboxy group,
      (7) a mono- or di-$C_{1-6}$ alkylamino group (preferably, methylamino, dimethylamino),
      (8) an N—($C_{1-6}$ alkyl-carbonyl)-N—($C_{1-6}$ alkyl) amino group (preferably, N-acetyl-N-methylamino),
      (9) a mono- or di-($C_{6-12}$ aryl-carbonyl)amino group (preferably, benzoylamino),
      (10) a mono- or di-(aromatic heterocyclyl-carbonyl)amino group (preferably, pyridylcarbonylamino (preferably, pyridin-2-ylcarbonylamino)),
      (11) an N-(aromatic heterocyclyl-carbonyl)-N—($C_{1-6}$ alkylamino group (preferably, N-(pyridylcarbonyl)-N-methylamino (preferably, N-(pyridin-2-ylcarbonyl)-N-methylamino)),
      (12) a mono- or di-($C_{6-12}$ arylsulfonyl)amino group (preferably, phenylsulfonylamino),
      (13) a $C_{1-6}$ alkylthio group (preferably, methylthio),
      (14) a $C_{1-6}$ alkylsulfonyl group (preferably, methylsulfonyl),
      (15) a $C_{1-6}$ alkyl-carbonyloxy group (preferably, acetyloxy),
      (16) a $C_{6-12}$ aryloxy group (preferably, phenoxy) optionally substituted by 1 to 3 (preferably, 1) substituents selected from a nonaromatic heterocyclic group (preferably, dihydrooxadiazolyl (preferably, 4,5-dihydro-1,2,4-oxadiazol-3-yl)) optionally substituted by an oxo group, and a carboxy group,
      (17) an aromatic heterocyclic group (preferably, pyridyl (preferably, pyridin-2-yl), pyrazolyl (preferably, pyrazol-1-yl), isoxazolyl (preferably, isoxazol-5-yl), triazolyl (preferably, 1H-1,2,4-triazol-1-yl), tetrazolyl (preferably, tetrazol-1-yl)) optionally substituted by 1 to 3 (preferably, 1 or 2) substituents selected from a carboxy group and a $C_{1-6}$ alkyl group (preferably, methyl),
      (18) a cyclic amino group (preferably, 1-pyrrolidinyl, piperidino, 1-imidazolidinyl, morpholino, 8-oxa-3-azabicyclo[3.2.1]octan-3-yl) optionally substituted by 1 to 3 (preferably, 1 or 2) substituents selected from a halogen atom (preferably, a fluorine atom, a chlorine atom) and an oxo group, and
      (19) a nonaromatic heterocyclic group (preferably, dihydrooxadiazolyl (preferably, 1-dihydropyridyl (preferably, 1,2-dihydropyridin-1-yl), 4,5-dihydro-1,2,4-oxadiazol-3-yl)) optionally substituted by 1 to 3 (preferably, 1 or 2) substituents selected from a halogen atom (preferably, a chlorine atom) and an oxo group,
    (ii) a $C_{1-6}$ alkoxy group (preferably, methoxy, isopropoxy),
    (iii) a $C_{3-6}$ cycloalkyl group (preferably, cyclopropyl),
    (iv) a $C_{6-12}$ aryl group (preferably, phenyl) optionally substituted by 1 to 3 substituents selected from
      (1) a halogen atom (preferably, a fluorine atom, a chlorine atom),
      (2) a cyano group,
      (3) a hydroxy group,
      (4) a carboxy group,
      (5) a $C_{1-6}$ alkyl group (preferably, methyl, tert-butyl) optionally substituted by a nonaromatic heterocyclic group (preferably, dihydrooxadiazolyl (preferably, 4,5-dihydro-1,2,4-oxadiazol-3-yl)) optionally substituted by an oxo group,
      (6) a $C_{1-6}$ alkoxy group (preferably, methoxy, ethoxy),
      (7) a $C_{1-6}$ alkylsulfonyl group (preferably, methylsulfonyl), (8) a mono- or di-($C_{1-6}$ alkylsulfonyl)amino group (preferably, methylsulfonylamino),
(9) a $C_{6-12}$ aryl group (preferably, phenyl), and
(10) an aromatic heterocyclic group (preferably, oxadiazolyl (preferably, 1,2,4-oxadiazol-3-yl), tetrazolyl (preferably, tetrazol-5-yl)) optionally substituted by a $C_{1-6}$ alkyl group (preferably, methyl),
(11) a cyclic amino group (preferably, 1-pyrrolidinyl) optionally substituted by an oxo group, and
(12) a nonaromatic heterocyclic group (preferably, dihydrooxadiazolyl (preferably, 4,5-dihydro-1,2,4-oxadiazol-3-yl)) optionally substituted by an oxo group,
(v) a $C_{7-12}$ aralkyl group (preferably, benzyl) optionally substituted by a nonaromatic heterocyclic group (preferably, dihydrooxadiazolyl (preferably, 4,5-dihydro-1,2,4-oxadiazol-3-yl)) optionally substituted by an oxo group,
(vi) an aromatic heterocyclic group (preferably, pyridyl (preferably, pyridin-2-yl, pyridin-3-yl), thiazolyl (preferably, thiazol-5-yl)) optionally substituted by 1 to 3 (preferably, 1) substituents selected from
(1) a $C_{1-6}$ alkyl group (preferably, methyl),
(2) a mono- or di-($C_{1-6}$ alkylsulfonyl)amino group (preferably, methylsulfonylamino), and
(3) a nonaromatic heterocyclic group (preferably, dihydrooxadiazolyl (preferably, 4,5-dihydro-1,2,4-oxadiazol-3-yl)) optionally substituted by an oxo group,
(vii) a cyclic amino group (preferably, 1-pyrrolidinyl, morpholino, 1,1-dioxide-thiomorpholino) optionally substituted by 1 or 2 oxo groups,
(viii) a nonaromatic heterocyclic group (preferably, dihydropyridyl (preferably, 1,2-dihydropyridin-3-yl), tetrahydrofuryl (preferably, tetrahydrofuran-2-yl, tetrahydrofuran-3-yl), tetrahydropyranyl (preferably, tetrahydropyran-2-yl, tetrahydropyran-4-yl), dioxanyl (preferably, 1,4-dioxan-2-yl)) optionally substituted by 1 or 2 oxo group,
(ix) a $C_{1-6}$ alkyl-carbonyl group (preferably, acetyl, ethylcarbonyl), or
(x) a cyclic amino-carbonyl group (preferably, pyrrolidin-1-ylcarbonyl),
(w) —$NR^H$—$SO_2$—$R^I$
wherein
$R^H$ is
(i) a hydrogen atom,
(ii) a $C_{1-6}$ alkyl group (preferably, methyl), or
(iii) a $C_{7-12}$ aralkyl group (preferably, benzyl) optionally substituted by a $C_{1-6}$ alkoxy group (preferably, methoxy), and
$R^I$ is
(i) a $C_{1-6}$ alkyl group (preferably, methyl, ethyl, isopropyl) optionally substituted by 1 to 3 substituents selected from
(1) a halogen atom (preferably, a fluorine atom),
(2) a $C_{1-6}$ alkoxy group (preferably, methoxy), and
(3) a cyclic amino group (preferably, morpholino),
(ii) a $C_{6-12}$ aryl group (preferably, phenyl) optionally substituted by 1 to 3 (preferably, 1) substituents selected from
(1) a carboxy group, and
(2) a nonaromatic heterocyclic group (preferably, dihydrooxadiazolyl (preferably, 4,5-dihydro-1,2,4-oxadiazol-3-yl)) optionally substituted by an oxo group, or
(iii) an aromatic heterocyclic group (preferably, pyridyl (preferably, pyridin-2-yl, pyridin-3-yl), furyl (preferably, furan-2-yl)) optionally substituted by 1 to 3 (preferably, 1) substituents selected from
(1) a carboxy group, and
(2) a nonaromatic heterocyclic group (preferably, dihydrooxadiazolyl (preferably, 4,5-dihydro-1,2,4-oxadiazol-3-yl)) optionally substituted by an oxo group,
(x) —$NR^J$—CO—$NR^K R^L$
wherein
$R^J$ is
(i) a hydrogen atom, or
(ii) a $C_{1-6}$ alkyl group (preferably, methyl, ethyl) optionally substituted by a hydroxy group, and
$R^K$ and $R^L$ are each independently,
(i) a hydrogen atom,
(ii) a $C_{1-6}$ alkyl group (preferably, methyl, ethyl, tert-butyl) optionally substituted by 1 to 3 (preferably, 1) substituents selected from a hydroxy group and a $C_{1-6}$ alkoxy group (preferably, methoxy), or
(iii) a $C_{1-6}$ alkoxy group (preferably, methoxy),
(y) —$NR^M$—$SO_2$—$NR^N R^O$
wherein
$R^M$ is
(i) a hydrogen atom, or
(ii) a $C_{1-6}$ alkyl group (preferably, methyl),
$R^N$ and $R^O$ are each independently,
(i) a hydrogen atom,
(ii) a $C_{1-6}$ alkyl group (preferably, methyl), or
(iii) a $C_{1-6}$ alkoxy group (preferably, methoxy),
(z) an aromatic heterocyclic group (preferably, pyrazolyl (preferably, pyrazol-1-yl, pyrazol-3-yl), oxadiazolyl (preferably, 1,2,4-oxadiazol-3-yl), thiazolyl (preferably, thiazol-2-yl, thiazol-4-yl), triazolyl (preferably, 1H-1,2,3-triazol-1-yl, 1H-1,2,4-triazol-3-yl), indazolyl (preferably, 1H-indazol-1-yl), benzimidazolyl (preferably, 1H-benzimidazol-2-yl)) optionally substituted by 1 to 3 (preferably, 1 or 2) substituents selected from
(i) a carboxy group,
(ii) a $C_{1-6}$ alkyl group (preferably, methyl) optionally substituted by 1 to 3 substituents selected from a halogen atom (preferably, a fluorine atom), a hydroxy group and a carboxy group,
(iii) a $C_{1-6}$ alkoxy group (preferably, ethoxy, tert-butoxy) optionally substituted by a $C_{1-6}$ alkoxy group (preferably, methoxy),
(iv) a $C_{3-6}$ cycloalkyl group (preferably, cyclopropyl), and
(v) a nonaromatic heterocyclic group (preferably, dihydrooxadiazolyl (preferably, 4,5-dihydro-1,2,4-oxadiazol-3-yl)) optionally substituted by an oxo group,
(aa) a cyclic amino group (preferably, 1-azetidinyl, 1-pyrrolidinyl, piperidino, 1-imidazolidinyl, 1-dihydropyridazinyl (preferably, 2,3-dihydropyridazin-2-yl), 1-hexahydropyrimidinyl, 2-dihydroisoindolyl (preferably, 1,3-dihydro-2H-isoindol-2-yl), 3-dihydroquinazolinyl (preferably, 3,4-dihydroquinazolin-3-yl), 3-tetrahydroquinazolinyl (preferably, 1,2,3,4-tetrahydroquinazolin-3-yl), 3-tetrahydropyrido[3,2-d]pyrimidinyl (preferably, 1,2,3,4-tetrahydropyrido[3,2-d]pyrimidin-3-yl), 3-tetrahydropteridinyl (preferably, 1,2,3,4-tetrahydropteridin-3-yl)) optionally substituted by 1 to 4 substituents selected from
(i) a cyano group,
(ii) a carboxy group,
(iii) a $C_{1-6}$ alkyl group (preferably, methyl),
(iv) a $C_{1-6}$ alkoxy-carbonyl group (preferably, ethoxycarbonyl),
(v) a mono- or di-($C_{1-5}$ alkyl-carbonyl)amino group (preferably, acetylamino),
(vi) a nonaromatic heterocyclic group (preferably, dihydrooxadiazolyl (preferably, 4,5-dihydro-1,2,4-oxadiazol-3-yl)) optionally substituted by an oxo group, and
(vii) an oxo group, and
(bb) a nonaromatic heterocyclic group (preferably, dihydrooxadiazolyl (preferably, 1-dihydropyridyl (preferably, 1,2-dihydropyridin-1-yl), dihydrooxadiazolyl (preferably, 4,5-dihydro-1,2,4-oxadiazol-3-yl) optionally substituted by 1 to 3 substituents selected from
(i) a halogen atom (preferably, a chlorine atom),
(ii) a cyano group,
(iii) a carboxy group,
(iv) a carbamoyl group,
(v) a $C_{1-6}$ alkoxy-carbonyl group (preferably, methoxycarbonyl),
(vi) an aromatic heterocyclic group (preferably, triazolyl (preferably, 1,2,4-triazol-3-yl), tetrazolyl (preferably, tetrazol-5-yl)) optionally substituted by a $C_{1-6}$ alkyl group (preferably, methyl),
(vii) a nonaromatic heterocyclic group (preferably, dihydrooxadiazolyl (preferably, 4,5-dihydro-1,2,4-oxadiazol-3-yl, 4,5-dihydro-1,3,4-oxadiazol-2-yl), dihydrotriazolyl (preferably, 4,5-dihydrotriazol-3-yl)) optionally substituted by an oxo group,
(16) a $C_{1-6}$ alkoxy group (preferably, methoxy, ethoxy),
(17) a $C_{1-6}$ alkyl-carbonyl group (preferably, acetyl),
(18) —CO—NR$^P$R$^Q$
wherein
R$^P$ and R$^Q$ are each independently,
(a) a hydrogen atom,
(b) a $C_{1-6}$ alkyl group (preferably, methyl, ethyl, isobutyl) optionally substituted by 1 to 3 (preferably, 1) substituents selected from
(i) a hydroxy group,
(ii) a $C_{1-6}$ alkylsulfonyl group (preferably, methylsulfonyl), and
(iii) a $C_{1-6}$ alkoxy group (preferably, methoxy),
(c) a $C_{1-6}$ alkoxy group (preferably, methoxy),
(d) a $C_{6-12}$ aryl group (preferably, phenyl) optionally substituted by a carboxy group,
(e) a $C_{1-6}$ alkylsulfonyl group (preferably, methylsulfonyl), or
(f) a $C_{6-12}$ arylsulfonyl group (preferably, phenylsulfonyl) optionally substituted by 1 to 3 (preferably, 1) substituents selected from
(i) a $C_{1-6}$ alkyl group (preferably, methyl) optionally substituted by 1 to 3 halogen atoms (preferably, a fluorine atom), and
(ii) a $C_{1-6}$ alkoxy group (preferably, methoxy) optionally substituted by 1 to 3 (preferably, 1 or 2) halogen atoms (preferably, a fluorine atom),
(19) a $C_{6-12}$ aryloxy group (preferably, phenoxy) optionally substituted by a nonaromatic heterocyclic group (preferably, dihydrooxadiazolyl (preferably, 4,5-dihydro-1,2,4-oxadiazol-3-yl)) optionally substituted by an oxo group,

(20) an aromatic heterocyclyl-oxy group (preferably, pyridyloxy (preferably, pyridin-3-yloxy, pyridin-4-yloxy)) optionally substituted by 1 to 3 (preferably, 1) substituents selected from
(a) a cyano group,
(b) a carboxy group,
(c) a $C_{1-6}$ alkoxy-carbonyl group (preferably, methoxycarbonyl),
(d) a carbamoyl group,
(e) a mono- or di-$C_{1-6}$ alkylcarbamoyl group (preferably, methylcarbamoyl, ethylcarbamoyl)
(said $C_{1-6}$ alkyl is optionally substituted by a hydroxy group),
(f) an aromatic heterocyclic group (preferably, triazolyl (preferably, 1H-1,2,4-triazol-3-yl), tetrazolyl (preferably, tetrazol-5-yl)) optionally substituted by a $C_{1-6}$ alkyl group (preferably, methyl), and
(g) a nonaromatic heterocyclic group (preferably, dihydrooxadiazolyl (preferably, 4,5-dihydro-1,2,4-oxadiazol-3-yl), dihydrotriazolyl (preferably, 4,5-dihydro-1H-1,2,4-triazol-3-yl)) optionally substituted by an oxo group,
(21) an aromatic heterocyclic group (preferably, thiazolyl (preferably, thiazol-2-yl)) optionally substituted by a carboxy group, or
(22) a nonaromatic heterocyclic group (preferably, dihydropyridyl (preferably, 1,2-dihydropyridin-1-yl), dihydrooxadiazolyl (preferably, 4,5-dihydro-1,2,4-oxadiazol-3-yl)) optionally substituted by
(a) a nonaromatic heterocyclic group (preferably, dihydrooxadiazolyl (preferably, 4,5-dihydro-1,2,4-oxadiazol-3-yl)) optionally substituted by an oxo group, and
(b) an oxo group.
In another embodiment, R is preferably
(1) a mono- or di-($C_{1-6}$ alkyl-carbonyl)amino group (preferably, acetyl),
(2) a sulfamoylamino group,
(3) a $C_{1-6}$ alkyl group (preferably, methyl, ethyl, propyl, isopropyl) optionally substituted by 1 to 3 substituents selected from
(a) a hydroxy group,
(b) a mono- or di-($C_{1-6}$ alkyl-carbonyl)amino group (preferably, acetyl),
(c) a sulfamoylamino group,
(d) a $C_{1-6}$ alkoxy-$C_{1-6}$ alkyl-carbonylamino group (preferably, (2-methoxyacetyl)amino, (2-ethoxyacetyl)amino, (2-isopropoxyacetyl)amino),
(e) a $C_{1-6}$ alkylsulfonylamino group (preferably, methylsulfonylamino), and
(f) 2-oxopyridin-1(2H)-yl optionally substituted by 1 to 3 substituents selected from a carboxy group and 5-oxo-4,5-dihydro-1,2,4-oxadiazolyl.
In another embodiment, R is preferably R'.
Examples of the substituent that the "$C_{1-6}$ alkyl group" of the "optionally substituted $C_{1-6}$ alkyl group" for R' optionally has include substituents selected from
(1) a halogen atom (e.g., a fluorine atom, a chlorine atom, a bromine atom, an iodine atom),
(2) a cyano group,
(3) a hydroxy group,
(4) a nitro group,
(5) a formyl group,
(6) an amino group,
(7) a mono- or di-$C_{1-6}$ alkylamino group (e.g., methylamino, ethylamino, propylamino, dimethylamino, diethylamino, dipropylamino, ethylmethylamino etc.), (8) a $C_{1-6}$ alkyl-carbonylamino group (e.g., acetylamino, ethylcarbonylamino etc.),
(9) a $C_{1-6}$ alkoxy-carbonylamino group (e.g., methoxycarbonylamino, ethoxycarbonylamino, propoxycarbonylamino, tert-butoxycarbonylamino etc.),
(10) a $C_{1-6}$ alkoxy group (e.g., methoxy, ethoxy, propoxy, isopropoxy, butoxy, isobutoxy, sec-butoxy, tert-butoxy etc.) optionally substituted by 1 to 3 halogen atoms (e.g., a fluorine atom, a chlorine atom, a bromine atom, an iodine atom),
(11) a $C_{7-12}$ aralkyloxy group (e.g., benzyloxy etc.),
(12) a $C_{6-12}$ aryloxy group (e.g., phenoxy etc.),
(13) a $C_{1-6}$ alkyl-carbonyloxy group (e.g., acetyloxy etc.),
(14) a carboxy group,
(15) a $C_{1-6}$ alkoxy-carbonyl group (e.g., methoxycarbonyl, ethoxycarbonyl, propoxycarbonyl, isopropoxycarbonyl, tert-butoxycarbonyl etc.),
(16) a $C_{7-12}$ aralkyloxy-carbonyl group (e.g., benzyloxycarbonyl etc.),
(17) a $C_{6-12}$ aryloxy-carbonyl group (e.g., phenyloxycarbonyl etc.),
(18) a $C_{1-6}$ alkyl-carbonyl group (e.g., acetyl, ethylcarbonyl, propylcarbonyl, isopropylcarbonyl, 2,2-dimethylpropylcarbonyl etc.),
(19) a $C_{3-6}$ cycloalkyl-carbonyl group (e.g., cyclopropylcarbonyl, cyclobutylcarbonyl, cyclopentylcarbonyl, cyclohexylcarbonyl),
(20) a $C_{7-12}$ aralkyl-carbonyl group (e.g., benzylcarbonyl etc.),
(21) a $C_{6-12}$ aryl-carbonyl group (e.g., benzoyl etc.),
(22) a carbamoyl group,
(23) a thiocarbamoyl group,
(24) a mono- or di-($C_{1-6}$ alkyl)carbamoyl group (e.g., methylcarbamoyl, ethylcarbamoyl, propylcarbamoyl, isopropylcarbamoyl, dimethylcarbamoyl, diethylcarbamoyl, dipropylcarbamoyl etc.),
(25) a mono- or di-($C_{7-12}$ aralkyl)carbamoyl group (e.g., benzylcarbamoyl, dibenzylcarbamoyl etc.),
(26) a thiol group,
(27) a $C_{1-6}$ alkylthio group (e.g., methylthio, ethylthio, propylthio etc.),
(28) a $C_{7-12}$ aralkylthio group (e.g., benzylthio etc.),
(29) a $C_{1-6}$ alkylsulfonyl group (e.g., methylsulfonyl, ethylsulfonyl, propylsulfonyl, isopropylsulfonyl etc.),
(30) a $C_{3-6}$ cycloalkylsulfonyl group (e.g., cyclopropylsulfonyl, cyclobutylsulfonyl, cyclopentylsulfonyl etc.),
(31) a $C_{6-12}$ arylsulfonyl group (e.g., phenylsulfonyl, 1-naphthylsulfonyl, 2-naphthylsulfonyl etc.),
(32) a $C_{7-12}$ aralkylsulfonyl group (e.g., benzylsulfonyl etc.),
(33) an ureido group,
(34) a mono- or di-($C_{1-6}$ alkyl)ureido group (e.g., methylureido, ethylureido, propylureido etc.),
(35) a mono- or di-($C_{6-12}$ aryl)ureido group (e.g., phenylureido, 1-naphthylureido, 2-naphthylureido etc.),
(36) a sulfamoyl group,
(37) a $C_{1-6}$ alkylsulfonylamino group (e.g., methylsulfonylamino, ethylsulfonylamino etc.),
(38) a sulfamoylamino group,
(39) a mono- or di-($C_{1-6}$ alkyl)sulfamoylamino group (e.g., methylsulfamoylamino, ethylsulfamoylamino, dimethylsulfamoylamino)
(40) a nonaromatic heterocyclic group optionally substituted by 1 to 3 substituents selected from (a) a nonaromatic heterocyclic group optionally substituted by oxo group, (b) a carboxy group and (c) an oxo group and the like. The number of the substituents is 1 to 4, preferably 1 to 3, more preferably 1.

Examples of the substituent that the "$C_{1-6}$ alkoxy group" of the "optionally substituted $C_{1-6}$ alkoxy group" for R' optionally has include those similar to the substituents that the "$C_{1-6}$ alkyl group" of the aforementioned "optionally substituted $C_{1-6}$ alkyl group" optionally has. The number of the substituents is 1 to 4, preferably 1 to 3, more preferably 1.

Examples of the "optionally substituted carboxy group" for R' include
(1) a carboxy group,
(2) a $C_{1-6}$ alkoxy-carbonyl group (e.g., methoxycarbonyl, ethoxycarbonyl, propoxycarbonyl, butoxycarbonyl, tert-butoxycarbonyl etc.),
(3) a $C_{6-12}$ aryloxy-carbonyl group (e.g., phenoxycarbonyl, naphthoxycarbonyl etc.),
(4) a $C_{7-12}$ aralkyloxy-carbonyl group (e.g., benzyloxycarbonyl, 2-phenylethyloxycarbonyl etc.)
and the like.

Examples of the "optionally substituted amino group" for R' include
(1) an amino group,
(2) a mono- or di-$C_{1-6}$ alkylamino group (e.g., methylamino, ethylamino, propylamino, dimethylamino, diethylamino, dipropylamino, ethylmethylamino etc.),
(3) a $C_{3-6}$ cycloalkylamino group (e.g., cyclopropylamino, cyclobutylamino, cyclopentylamino, cyclohexylamino),
(4) a $C_{6-12}$ arylamino group (e.g., phenylamino, 1-naphthylamino, 2-naphthylamino etc.),
(5) a $C_{7-12}$ aralkylamino group (e.g., benzylamino, 2-phenylethylamino, 1-phenylethylamino etc.)
(6) a hydrazino group,
(7) a mono- or di-($C_{1-6}$ alkylsulfonyl)amino group (e.g., methylsulfonylamino etc.),
(8) a mono- or di-($C_{1-6}$ alkyl-carbonyl)amino group (e.g., acetylamino etc.),
(9) a mono- or di-($C_{1-6}$ alkoxy-carbonyl)amino group (e.g., methoxycarbonylamino, ethoxycarbonylamino, propoxycarbonylamino, tert-butoxycarbonylamino etc.),
(10) a sulfamoylamino group,
(11) an optionally substituted cyclic amino group
and the like.

Here, examples of the substituent that the "cyclic amino group" of the "optionally substituted cyclic amino group" optionally has include substituents selected from
(a) an oxo group, and
(b) the substituent that the "$C_{1-6}$ alkyl group" of the aforementioned "optionally substituted $C_{1-6}$ alkyl group" for R' optionally has. The number of the substituents is 1 to 4, preferably 1 to 3.

Examples of the "optionally substituted carbamoyl group" for R' include
(1) a carbamoyl group,
(2) a mono- or di-($C_{1-6}$ alkyl)carbamoyl group (e.g., methyl carbamoyl, ethyl carbamoyl, propylcarbamoyl, isopropylcarbamoyl, dimethylcarbamoyl, diethylcarbamoyl, dipropylcarbamoyl etc.),
(3) a mono- or di-($C_{6-12}$ aryl)carbamoyl group (e.g., phenylcarbamoyl, naphthylcarbamoyl, diphenylcarbamoyl, dinaphthylcarbamoyl etc.),
(4) a mono- or di-($C_{7-12}$ aralkyl)carbamoyl group (e.g., benzylcarbamoyl, dibenzylcarbamoyl etc.)
and the like.

Preferable examples of the "optionally substituted $C_{1-6}$ alkyl group" for R' include a $C_{1-6}$ alkyl group substituted by 1 to 4 (preferably 1 to 3, more preferably 1) substituents selected from
(a) a halogen atom,
(b) a hydroxy group, (c) a $C_{1-6}$ alkoxy group,
(d) —S—$R^{1a}$,
(e) —$SO_2$—$R^{1a}$,
(f) —N($R^{1b}$)($R^{1c}$),
(g) —NH—CO—$R^{1a}$,
(h) —NH—CO—N($R^{1b}$)($R^{1c}$),
(i) —NH—$SO_2$—$R^{1a}$, and
(j) —NH—$SO_2$—N($R^{1b}$)($R^{1c}$)
wherein $R^{1a}$ is a $C_{1-6}$ alkyl group, and $R^{1b}$ and $R^{1c}$ are each independently a hydrogen atom or a $C_{1-6}$ alkyl group.

In another embodiment, preferable examples of the "optionally substituted $C_{1-6}$ alkyl group" for R' include a $C_{1-6}$ alkyl group (preferably, methyl, ethyl) optionally substituted by 1 to 4 (preferably 1 to 3, more preferably 1 or 2) substituents selected from
(a) a halogen atom,
(b) a hydroxy group,
(c) a $C_{1-6}$ alkoxy group (preferably, methoxy),
(d) —S—$R^{1a}$,
(e) —$SO_2$—$R^{1a}$,
(f) —N($R^{1b}$)($R^{1c}$),
(g) —NH—CO—$R^{1a}$,
(h) —NH—CO—N($R^{1b}$)($R^{1c}$),
(i) —NH—$SO_2$—$R^{1a}$,
(j) —NH—$SO_2$—N($R^{1b}$)($R^{1c}$)
wherein
$R^{1a}$ is a $C_{1-6}$ alkyl group (preferably, methyl) optionally substituted by 1 to 3 (preferably, 1) $C_{1-6}$ alkoxy groups (preferably, methoxy, ethoxy, isopropoxy), and
$R^{1b}$ and $R^{1c}$ are each independently a hydrogen atom or a $C_{1-6}$ alkyl group (preferably, a hydrogen atom), and
(k) a nonaromatic heterocyclic group (preferably, dihydropyridyl (preferably, 1,2-dihydropyridin-1-yl)) optionally substituted by 1 to 3 (preferably, 1 or 2) substituents selected from
  (i) a nonaromatic heterocyclic group (preferably, dihydrooxadiazolyl (preferably, 4,5-dihydro-1,2,4-oxadiazol-3-yl)) optionally substituted by an oxo group,
  (ii) a carboxy group, and
  (iii) an oxo group.

More preferred are
a $C_{1-6}$ alkyl group (preferably, methyl, ethyl) optionally substituted by 1 to 4 (preferably 1 to 3, more preferably 1 or 2) substituents selected from
(a) a hydroxy group,
(b) a $C_{1-6}$ alkoxy group (preferably, methoxy),
(c) —$SO_2$—$R^{1a}$,
(d) —NH—CO—$R^{1a}$,
(e) —NH—CO—N($R^{1b}$)($R^{1c}$)
(f) —NH—$SO_2$—$R^{1a}$,
(g) —NH—$SO_2$—N($R^{1b}$)($R^{1c}$)
wherein
$R^{1a}$ is a $C_{1-6}$ alkyl group (preferably, methyl) optionally substituted by 1 to 3 (preferably, 1) $C_{1-6}$ alkoxy groups (preferably, methoxy, ethoxy, isopropoxy), and
$R^{1b}$ and $R^{1c}$ are each independently a hydrogen atom or a $C_{1-6}$ alkyl group (preferably, a hydrogen atom), and
(h) a nonaromatic heterocyclic group (preferably, dihydropyridyl (preferably, 1,2-dihydropyridin-1-yl)) optionally substituted by 1 to 3 (preferably, 1 or 2) substituents selected from
  (i) a nonaromatic heterocyclic group (preferably, dihydrooxadiazolyl (preferably, 4,5-dihydro-1,2,4-oxadiazol-3-yl)) optionally substituted by an oxo group,
  (ii) a carboxy group, and
  (iii) an oxo group.

In another embodiment, preferable examples of the "optionally substituted $C_{1-6}$ alkyl group" for R' include a $C_{1-6}$ alkyl group (preferably, methyl, ethyl, propyl, isopropyl) optionally substituted by 1 to 3 substituents selected from
(1) a hydroxyl group,
(2) a mono- or di-($C_{1-6}$ alkyl-carbonyl)amino group (preferably, acetyl),
(3) a sulfamoylamino group,
(4) a $C_{1-6}$ alkoxy-$C_{1-6}$ alkyl-carbonylamino group (preferably, (2-methoxyacetyl)amino, (2-ethoxyacetyl)amino, (2-isopropoxyacetyl)amino),
(5) a $C_{1-6}$ alkylsulfonylamino group (preferably, methylsulfonylamino), and
(6) 2-oxopyridin-1(2H)-yl optionally substituted by 1 to 3 substituents selected from a carboxy group and 5-oxo-4,5-dihydro-1,2,4-oxadiazolyl.

Preferable examples of the "optionally substituted $C_{1-6}$ alkoxy group" for R' include a $C_{1-6}$ alkoxy group (preferably, methoxy, ethoxy).

Preferable examples of the "optionally substituted carboxy group" for R' include
(1) a carboxy group,
(2) a $C_{1-6}$ alkoxy-carbonyl group (e.g., methoxycarbonyl, ethoxycarbonyl, propoxycarbonyl, butoxycarbonyl, tert-butoxycarbonyl etc.)
and the like.

Preferable examples of the "optionally substituted amino group" for R' include
(1) a mono- or di-($C_{1-6}$ alkyl-carbonyl)amino group (preferably, acetylamino),
(2) a sulfamoylamino group
and the like.

Preferable examples of R' include
(1) a hydroxy group,
(2) a $C_{1-6}$ alkoxy-carbonyl group,
(3) a $C_{1-6}$ alkoxy group, or
(4) a $C_{1-6}$ alkyl group optionally substituted by one substituent selected from
  (a) a halogen atom,
  (b) a hydroxy group,
  (c) a $C_{1-6}$ alkoxy group,
  (d) —S—$R^{1a}$,
  (e) —$SO_2$—$R^{1a}$,
  (f) —N($R^{1b}$)($R^{1c}$),
  (g) —NH—CO—$R^{1a}$,
  (h) —NH—CO—N($R^{1b}$)($R^{1c}$),
  (i) —NH—$SO_2$—$R^{1a}$, and
  (j) —NH—$SO_2$—N($R^{1b}$)($R^{1c}$)
wherein $R^{1a}$ is a $C_{1-6}$ alkyl group, and $R^{1b}$ and $R^{1c}$ are each independently a hydrogen atom or a $C_{1-6}$ alkyl group.

In another embodiment, preferable examples of R' include
(1) a hydroxy group,
(2) a mono- or di-($C_{1-6}$ alkyl-carbonyl)amino group (preferably, acetylamino),
(3) a sulfamoylamino group,
(4) a $C_{1-6}$ alkoxy group (preferably, methoxy, ethoxy), or
(5) a $C_{1-6}$ alkyl group (preferably, methyl, ethyl) optionally substituted by 1 to 4 (preferably 1 to 3, more preferably 1 or 2) substituents selected from
  (a) a halogen atom,
  (b) a hydroxy group,
  (c) a $C_{1-6}$ alkoxy group (preferably, methoxy),
  (d) —S—$R^{1a}$,
  (e) —$SO_2$—$R^{1a}$,
  (f) —N($R^{1b}$)($R^{1c}$),
  (g) —NH—CO—$R^{1a}$,
  (h) —NH—CO—N($R^{1b}$)($R^{1c}$), (i) —NH—SO$_2$—R$^{1a}$,
(j) —NH—SO$_2$—N(R$^{1b}$)(R$^{1c}$)
wherein
R$^{1a}$ is a C$_{1-6}$ alkyl group (preferably, methyl) optionally substituted by 1 to 3 (preferably, 1) C$_{1-6}$ alkoxy groups (preferably, methoxy, ethoxy, isopropoxy), and
R$^{1b}$ and R$^{1c}$ are each independently a hydrogen atom or a C$_{1-6}$ alkyl group (preferably, a hydrogen atom), and
  (k) a nonaromatic heterocyclic group (preferably, dihydropyridyl (preferably, 1,2-dihydropyridin-1-yl)) optionally substituted by 1 to 3 (preferably, 1 or 2) substituents selected from
    (i) a nonaromatic heterocyclic group (preferably, dihydrooxadiazolyl (preferably, 4,5-dihydro-1,2,4-oxadiazol-3-yl)) optionally substituted by an oxo group,
    (ii) a carboxy group, and
    (iii) an oxo group.
More preferred are
(1) a hydroxy group,
(2) a mono- or di-(C$_{1-6}$ alkyl-carbonyl)amino group (preferably, acetylamino),
(3) a sulfamoylamino group,
(4) a C$_{1-6}$ alkoxy group (preferably, methoxy, ethoxy), or
(5) a C$_{1-6}$ alkyl group (preferably, methyl, ethyl) optionally is substituted by 1 to 4 (preferably 1 to 3, more preferably 1 or 2) substituents selected from
  (a) a hydroxy group,
  (b) a C$_{1-6}$ alkoxy group (preferably, methoxy),
  (c) —SO$_2$—R$^{1a}$,
  (d) —NH—CO—R$^{1a}$,
  (e) —NH—CO—N(R$^{1b}$)(R$^{1c}$)
  (f) —NH—SO$_2$—R$^{1a}$,
  (g) —NH—SO$_2$—N(R$^{1b}$)(R$^{1c}$)
wherein
R$^{1a}$ is a C$_{1-6}$ alkyl group (preferably, methyl) optionally substituted by 1 to 3 (preferably, 1) C$_{1-6}$ alkoxy groups (preferably, methoxy, ethoxy, isopropoxy), and
R$^{1b}$ and R$^{1c}$ are each independently a hydrogen atom or a C$_{1-6}$ alkyl group (preferably, a hydrogen atom), and
  (h) a nonaromatic heterocyclic group (preferably, dihydropyridyl (preferably, 1,2-dihydropyridin-1-yl)) optionally substituted by 1 to 3 (preferably, 1 or 2) substituents selected from
    (i) a nonaromatic heterocyclic group (preferably, dihydrooxadiazolyl (preferably, 4,5-dihydro-1,2,4-oxadiazol-3-yl)) optionally substituted by an oxo group,
    (ii) a carboxy group, and
    (iii) an oxo group.
In another embodiment, preferable examples of R' include
(1) a mono- or di-(C$_{1-6}$ alkyl-carbonyl)amino group (preferably, acetylamino),
(2) a sulfamoylamino group,
(3) a C$_{1-6}$ alkyl group (preferably, methyl, ethyl, propyl, isopropyl) optionally substituted by 1 to 3 substituents selected from
  (a) a hydroxy group,
  (b) a mono- or di-(C$_{1-6}$ alkyl-carbonyl)amino group (preferably, acetyl),
  (c) a sulfamoylamino group,
  (d) a C$_{1-6}$ alkoxy-C$_{1-6}$ alkyl-carbonylamino group (preferably, (2-methoxyacetyl)amino, (2-ethoxyacetyl)amino, (2-isopropoxyacetyl)amino),
  (e) a C$_{1-6}$ alkylsulfonylamino group (preferably, methylsulfonylamino), and
  (f) 2-oxopyridin-1(2H)-yl optionally substituted by 1 to 3 substituents selected from a carboxy group and 5-oxo-4,5-dihydro-1,2,4-oxadiazolyl.

Preferable examples of a compound represented by the formula (I) or a salt thereof (hereinafter to be referred to as compound (I)) include the following compounds.
[Compound (I)-1]
Compound (I) wherein ring A is an optionally substituted benzene ring [preferably, a benzene ring optionally substituted by 1 to 3 (preferably 2) substituents selected from a halogen atom (preferably, a fluorine atom, a chlorine atom) and a C$_{1-6}$ alkyl group (preferably, methyl)],
R is
(1) a hydroxy group,
(2) a cyano group,
(3) a carboxy group,
(4) a C$_{1-6}$ alkoxy-carbonyl group (preferably, ethoxycarbonyl),
(5) an amino group,
(6) a mono- or di-C$_{1-6}$ alkylamino group (preferably, dimethylamino),
(7) a mono- or di-C$_{7-12}$ aralkylamino group (preferably, benzylamino),
(8) a mono- or di-(C$_{1-6}$ alkylsulfonyl)amino group (preferably, methylsulfonylamino, ethylsulfonylamino),
(9) a mono- or di-(C$_{3-6}$ cycloalkylsulfonyl)amino group (preferably, cyclopropylsulfonylamino),
(10) a mono- or di-(C$_{6-12}$ arylsulfonyl)amino group (preferably, phenylsulfonylamino),
(11) a mono- or di-(aromatic heterocyclyl-sulfonyl)amino group (preferably, pyridylsulfonylamino (preferably, pyridin-3-ylsulfonylamino)),
(12) —NR$^A$—CO—R$^B$
  wherein
  R$^A$ is
    (a) a hydrogen atom, or
    (b) a C$_{1-6}$ alkyl group (preferably, methyl), and
  R$^B$ is
    (a) a C$_{1-6}$ alkyl group (preferably, methyl, ethyl) optionally substituted by 1 to 3 (preferably, 1 or 2) substituents selected from
      (i) a halogen atom (preferably, a fluorine atom),
      (ii) a hydroxy group,
      (iii) a C$_{1-6}$ alkoxy group (preferably, methoxy),
      (iv) an aromatic heterocyclic group (preferably, triazolyl (preferably, 1,2,4-triazol-1-yl)), and
      (v) a nonaromatic heterocyclic group (preferably, dihydrooxadiazolyl (preferably, 4,5-dihydro-1,2,4-oxadiazol-3-yl)) optionally substituted by an oxo group,
    (b) a C$_{3-6}$ cycloalkyl group (preferably, cyclopropyl),
    (c) a C$_{1-6}$ alkyl-carbonyl group (preferably, acetyl),
    (d) an amino group,
    (e) a mono- or di-C$_{1-6}$ alkylamino group (preferably, methylamino),
    (f) a cyclic amino group (preferably, morpholino),
    (g) a C$_{6-12}$ aryl group (preferably, phenyl) optionally substituted by 1 to 3 (preferably, 1) substituents selected from
      (i) a cyano group,
      (ii) a carboxy group,
      (iii) a C$_{1-6}$ alkoxy-carbonyl group (preferably, ethoxycarbonyl),
      (iv) a C$_{1-6}$ alkylsulfonylamino group (preferably, methylsulfonylamino), and
      (v) a nonaromatic heterocyclic group (preferably, dihydrooxadiazolyl (preferably, 4,5-dihydro-1,2,4-oxadiazol-3-yl)) optionally substituted by an oxo group, (h) a $C_{7-12}$ aralkyl group (preferably, benzyl) optionally substituted by a nonaromatic heterocyclic group (preferably, dihydrooxadiazolyl (preferably, 4,5-dihydro-1,2,4-oxadiazol-3-yl)) optionally substituted by an oxo group, or
(i) an aromatic heterocyclic group (preferably, oxazolyl (preferably, oxazol-5-yl)),
(13) —NR$^C$—SO$_2$—N(R$^D$)(R$^E$)
wherein
R$^C$ is
(a) a hydrogen atom, or
(b) a $C_{1-6}$ alkyl group (preferably, methyl), and
R$^D$ and R$^E$ are each independently,
(a) a hydrogen atom,
(b) a $C_{1-6}$ alkyl group (preferably, methyl, ethyl), or
(c) a $C_{3-6}$ cycloalkyl group (preferably, cyclopropyl),
(14) an optionally substituted cyclic amino group (preferably, a cyclic amino group (preferably, 1-imidazolidinyl) optionally substituted by 1 to 3 (preferably, 1 or 2) substituents selected from
(a) a nonaromatic heterocyclic group (preferably, dihydrooxadiazolyl (preferably, 4,5-dihydro-1,2,4-oxadiazol-3-yl)) optionally substituted by an oxo group, and
(b) an oxo group,
(15) a $C_{1-6}$ alkyl group (preferably, methyl, ethyl, propyl, isopropyl) optionally substituted by 1 to 4 (preferably 1 to 3, more preferably 1 or 2) substituents selected from
(a) a halogen atom (preferably, a fluorine atom),
(b) a cyano group,
(c) a hydroxy group,
(d) a carboxy group,
(e) an amino group,
(f) a carbamoyl group,
(g) a mono- or di-($C_{1-6}$ alkyl)carbamoyl group (preferably, isopropylcarbamoyl) (said $C_{1-6}$ alkyl is optionally substituted by a carboxy group),
(h) a mono- or di-($C_{6-12}$ aryl)carbamoyl group (preferably, phenylcarbamoyl) (said $C_{6-12}$ aryl is optionally substituted by a carboxy group),
(i) a $C_{1-6}$ alkoxy group (preferably, methoxy, ethoxy, propoxy) optionally substituted by 1 to 3 (preferably, 1 or 2) substituents selected from
 (i) a hydroxy group,
 (ii) a carboxy group,
 (iii) a carbamoyl group,
 (iv) a mono- or di-($C_{1-6}$ alkyl-carbonyl)amino group (preferably, acetylamino),
 (v) a mono- or di-($C_{1-6}$ alkylsulfonyl)amino group (preferably, methylsulfonylamino),
 (vi) a $C_{1-6}$ alkoxy-carbonyl group (preferably, ethoxycarbonyl), and
 (vii) a cyclic amino-carbonyl group (preferably, azetidin-1-ylcarbonyl, 1,1-dioxide-thiomorpholinocarbonyl) optionally substituted by a hydroxy group,
(j) a $C_{1-6}$ alkyl-carbonyloxy group (preferably, acetyloxy),
(k) a $C_{1-6}$ alkylsulfonyloxy group (preferably, methylsulfonyloxy),
(l) a $C_{6-12}$ aryloxy group (preferably, phenoxy) optionally substituted by 1 to 3 (preferably, 1 or 2) substituents selected from
 (i) a halogen atom (preferably, a fluorine atom, a chlorine atom),
 (ii) a cyano group,
 (iii) a carboxy group,
 (iv) a $C_{1-6}$ alkoxy group (preferably, methoxy),
 (v) a $C_{1-6}$ alkoxy-carbonyl group (preferably, methoxycarbonyl),
 (vi) a $C_{1-6}$ alkylsulfonyl group (preferably, methylsulfonyl),
 (vii) a mono- or di-($C_{1-6}$ alkylsulfonyl)carbamoyl group (preferably, methylsulfonylcarbamoyl),
 (viii) a nonaromatic heterocyclic group (preferably, dihydrooxadiazolyl (preferably, 4,5-dihydro-1,2,4-oxadiazol-3-yl)) optionally substituted by an oxo group or a thioxo group, and
 (ix) a cyclic amino-carbonyl group (preferably, azetidin-1-ylcarbonyl) optionally substituted by a hydroxy group,
(m) a $C_{7-12}$ aralkyloxy group (preferably, benzyloxy) optionally substituted by a nonaromatic heterocyclic group (preferably, dihydrooxadiazolyl (preferably, 4,5-dihydro-1,2,4-oxadiazol-3-yl)) optionally substituted by an oxo group,
(n) an aromatic heterocyclyl-oxy group (preferably, pyridyloxy (preferably, pyridin-2-yloxy)) optionally substituted by 1 to 3 (preferably, 1) substituents selected from
 (i) a carboxy group,
 (ii) a $C_{1-6}$ alkoxy-carbonyl group (preferably, methoxycarbonyl), and
 (iii) a nonaromatic heterocyclic group (preferably, dihydrooxadiazolyl (preferably, 4,5-dihydro-1,2,4-oxadiazol-3-yl, 2,3-dihydro-1,3,4-oxadiazol-5-yl)) optionally substituted by an oxo group,
(o) a $C_{1-6}$ alkylthio group (preferably, methylthio),
(p) a $C_{6-12}$ arylthio group (preferably, phenylthio) optionally substituted by a carboxy group,
(q) a $C_{1-6}$ alkylsulfinyl group (preferably, methylsulfinyl),
(r) a $C_{1-6}$ alkylsulfonyl group (preferably, methylsulfonyl),
(s) a $C_{6-12}$ arylsulfonyl group (preferably, phenylsulfonyl) optionally substituted by 1 to 3 (preferably, 1) substituents selected from
 (i) a carboxy group, and
 (ii) a nonaromatic heterocyclic group (preferably, dihydrooxadiazolyl (preferably, 4,5-dihydro-1,2,4-oxadiazol-3-yl)) optionally substituted by an oxo group,
(t) a mono- or di-$C_{1-6}$ alkylsulfamoyl group (preferably, isopropylsulfamoyl),
(u) an aromatic heterocyclyl-amino group (preferably, pyridylamino (preferably, pyridin-2-ylamino), pyrimidinylamino (preferably, pyrimidin-2-ylamino), benzooxazolylamino (preferably, benzooxazol-2-ylamino)) optionally substituted by 1 to 3 (preferably, 1) substituents selected from
 (i) a carboxy group, and
 (ii) a nonaromatic heterocyclic group (preferably, dihydrooxadiazolyl (preferably, 4,5-dihydro-1,2,4-oxadiazol-3-yl)) optionally substituted by an oxo group,
(v) —NR$^F$—CO—R$^G$
wherein
R$^F$ is
 (i) a hydrogen atom, or
 (ii) a $C_{1-6}$ alkyl group (preferably, methyl, ethyl) optionally substituted by a hydroxy group, and
R$^G$ is
 (i) a $C_{1-6}$ alkyl group (preferably, methyl, ethyl, propyl, isopropyl) optionally substituted by 1 to 3 substituents selected from
  (1) a halogen atom (preferably, a fluorine atom),
  (2) a cyano group,
  (3) a hydroxy group,
  (4) a $C_{1-6}$ alkoxy group (preferably, methoxy, ethoxy, isopropoxy, isobutoxy) optionally substituted by 1 to 3 substituents selected from a halogen atom (preferably, a fluorine atom) and a $C_{3-6}$ cycloalkyl group (preferably, cyclopropyl),
(5) a $C_{3-6}$ cycloalkyloxy group (preferably, cyclopropyloxy),
(6) an aromatic heterocyclyl-oxy group (preferably, pyridyloxy (preferably, pyridin-2-yloxy), pyrimidinyloxy (preferably, pyrimidin-2-yloxy)) optionally substituted by 1 to 3 (preferably, 1) substituents selected from a halogen atom (preferably, a fluorine atom, a chlorine atom), a cyano group and a carboxy group,
(7) a mono- or di-$C_{1-6}$ alkylamino group (preferably, methylamino, dimethylamino),
(8) an N—($C_{1-6}$ alkyl-carbonyl)-N—($C_{1-6}$ alkyl) amino group (preferably, N-acetyl-N-methylamino),
(9) a mono- or di-($C_{6-12}$ aryl-carbonyl)amino group (preferably, benzoylamino),
(10) a mono- or di-(aromatic heterocyclyl-carbonyl)amino group (preferably, pyridylcarbonylamino (preferably, pyridin-2-ylcarbonylamino)),
(11) an N-(aromatic heterocyclyl-carbonyl)-N—($C_{1-6}$ alkyl)amino group (preferably, N-(pyridylcarbonyl)-N-methylamino (preferably, N-(pyridin-2-ylcarbonyl)-N-methylamino)),
(12) a mono- or di-($C_{6-12}$ arylsulfonyl)amino group (preferably, phenylsulfonylamino),
(13) a $C_{1-6}$ alkylthio group (preferably, methylthio),
(14) a $C_{1-6}$ alkylsulfonyl group (preferably, methylsulfonyl),
(15) a $C_{1-6}$ alkyl-carbonyloxy group (preferably, acetyloxy),
(16) a $C_{6-12}$ aryloxy group (preferably, phenoxy) optionally substituted by 1 to 3 (preferably, 1) substituents selected from a nonaromatic heterocyclic group (preferably, dihydrooxadiazolyl (preferably, 4,5-dihydro-1,2,4-oxadiazol-3-yl)) optionally substituted by an oxo group, and a carboxy group,
(17) an aromatic heterocyclic group (preferably, pyridyl (preferably, pyridin-2-yl), pyrazolyl (preferably, pyrazol-1-yl), isoxazolyl (preferably, isoxazol-5-yl), triazolyl (preferably, 1H-1,2,4-triazol-1-yl), tetrazolyl (preferably, tetrazol-1-yl)) optionally substituted by 1 to 3 (preferably, 1 or 2) substituents selected from a carboxy group and a $C_{1-6}$ alkyl group (preferably, methyl),
(18) a cyclic amino group (preferably, 1-pyrrolidinyl, piperidino, 1-imidazolidinyl, morpholino, 8-oxa-3-azabicyclo[3.2.1]octan-3-yl) optionally substituted by 1 to 3 (preferably, 1 or 2) substituents selected from a halogen atom (preferably, a fluorine atom, a chlorine atom) and an oxo group, and
(19) a nonaromatic heterocyclic group (preferably, dihydropyridyl (preferably, 1,2-dihydropyridin-1-yl), dihydrooxadiazolyl (preferably, 4,5-dihydro-1,2,4-oxadiazol-3-yl)) optionally substituted by 1 to 3 (preferably, 1 or 2) substituents selected from a halogen atom (preferably, a chlorine atom) and an oxo group,
(ii) a $C_{1-6}$ alkoxy group (preferably, methoxy, isopropoxy),
(iii) a $C_{3-6}$ cycloalkyl group (preferably, cyclopropyl),
(iv) a $C_{6-12}$ aryl group (preferably, phenyl) optionally substituted by 1 to 3 substituents selected from
  (1) a halogen atom (preferably, a fluorine atom, a chlorine atom),
  (2) a cyano group,
  (3) a hydroxy group,
  (4) a carboxy group,
  (5) a $C_{1-6}$ alkyl group (preferably, methyl, tert-butyl) optionally substituted by a nonaromatic heterocyclic group (preferably, dihydrooxadiazolyl (preferably, 4,5-dihydro-1,2,4-oxadiazol-3-yl)) optionally substituted by an oxo group,
  (6) a $C_{1-6}$ alkoxy group (preferably, methoxy, ethoxy),
  (7) a $C_{1-6}$ alkylsulfonyl group (preferably, methylsulfonyl),
  (8) a mono- or di-($C_{1-6}$ alkylsulfonyl)amino group (preferably, methylsulfonylamino),
  (9) a $C_{6-12}$ aryl group (preferably, phenyl),
  (10) an aromatic heterocyclic group (preferably, oxadiazolyl (preferably, 1,2,4-oxadiazol-3-yl), tetrazolyl (preferably, tetrazol-5-yl)) optionally substituted by a $C_{1-6}$ alkyl group (preferably, methyl),
  (11) a cyclic amino group (preferably, 1-pyrrolidinyl) optionally substituted by an oxo group, and
  (12) a nonaromatic heterocyclic group (preferably, dihydrooxadiazolyl (preferably, 4,5-dihydro-1,2,4-oxadiazol-3-yl)) optionally substituted by an oxo group,
(v) a $C_{7-12}$ aralkyl group (preferably, benzyl) optionally substituted by a nonaromatic heterocyclic group (preferably, dihydrooxadiazolyl (preferably, 4,5-dihydro-1,2,4-oxadiazol-3-yl)) optionally substituted by an oxo group,
(vi) an aromatic heterocyclic group (preferably, pyridyl (preferably, pyridin-2-yl, pyridin-3-yl), thiazolyl (preferably, thiazol-5-yl)) optionally substituted by 1 to 3 (preferably, 1) substituents selected from
  (1) a $C_{1-6}$ alkyl group (preferably, methyl),
  (2) a mono- or di-($C_{1-6}$ alkylsulfonyl)amino group (preferably, methylsulfonylamino), and
  (3) a nonaromatic heterocyclic group (preferably, dihydrooxadiazolyl (preferably, 4,5-dihydro-1,2,4-oxadiazol-3-yl)) optionally substituted by an oxo group,
(vii) a cyclic amino group (preferably, 1-pyrrolidinyl, morpholino, 1,1-dioxide-thiomorpholino) optionally substituted by 1 or 2 oxo groups,
(viii) a nonaromatic heterocyclic group (preferably, dihydropyridyl (preferably, 1,2-dihydropyridin-3-yl), tetrahydrofuryl (preferably, tetrahydrofuran-2-yl, tetrahydrofuran-3-yl), tetrahydropyranyl (preferably, tetrahydropyran-2-yl, tetrahydropyran-4-yl), dioxanyl (preferably, 1,4-dioxan-2-yl)) optionally substituted by 1 or 2 oxo groups,
(ix) a $C_{1-6}$ alkyl-carbonyl group (preferably, acetyl, ethylcarbonyl), or
(x) a cyclic amino-carbonyl group (preferably, pyrrolidin-1-ylcarbonyl),
(w) —NR$^H$—SO$_2$—R$^I$
wherein
R$^H$ is
  (i) a hydrogen atom,
  (ii) a $C_{1-6}$ alkyl group (preferably, methyl), or (iii) a $C_{7-12}$ aralkyl group (preferably, benzyl) optionally substituted by a $C_{1-6}$ alkoxy group (preferably, methoxy), and $R^I$ is
- (i) a $C_{1-6}$ alkyl group (preferably, methyl, ethyl, isopropyl) optionally substituted by 1 to 3 substituents selected from
  - (1) a halogen atom (preferably, a fluorine atom),
  - (2) a $C_{1-6}$ alkoxy group (preferably, methoxy), and
  - (3) a cyclic amino group (preferably, morpholino),
- (ii) a $C_{6-12}$ aryl group (preferably, phenyl) optionally substituted by 1 to 3 (preferably, 1) substituents selected from
  - (1) a carboxy group, and
  - (2) a nonaromatic heterocyclic group (preferably, dihydrooxadiazolyl (preferably, 4,5-dihydro-1,2,4-oxadiazol-3-yl)) optionally substituted by an oxo group, or
- (iii) an aromatic heterocyclic group (preferably, pyridyl (preferably, pyridin-2-yl, pyridin-3-yl), furyl (preferably, furan-2-yl)) optionally substituted by 1 to 3 (preferably, 1) substituents selected from
  - (1) a carboxy group, and
  - (2) a nonaromatic heterocyclic group (preferably, dihydrooxadiazolyl (preferably, 4,5-dihydro-1,2,4-oxadiazol-3-yl)) optionally substituted by an oxo group, (x) —$NR^J$—CO—$NR^K R^L$ wherein $R^J$ is
- (i) a hydrogen atom, or
- (ii) a $C_{1-6}$ alkyl group (preferably, methyl, ethyl) optionally substituted by a hydroxy group, and $R^K$ and $R^L$ are each independently,
- (i) a hydrogen atom,
- (ii) a $C_{1-6}$ alkyl group (preferably, methyl, ethyl, tert-butyl) optionally substituted by 1 to 3 (preferably, 1) substituents selected from a hydroxy group and a $C_{1-6}$ alkoxy group (preferably, methoxy), or
- (iii) a $C_{1-6}$ alkoxy group (preferably, methoxy), (y) —$NR^M$—$SO_2$—$NR^N R^O$ wherein $R^M$ is
- (i) a hydrogen atom, or
- (ii) a $C_{1-6}$ alkyl group (preferably, methyl), and $R^N$ and $R^O$ are each independently,
- (i) a hydrogen atom,
- (ii) a $C_{1-6}$ alkyl group (preferably, methyl), or
- (iii) a $C_{1-6}$ alkoxy group (preferably, methoxy), (z) an aromatic heterocyclic group (preferably, pyrazolyl (preferably, pyrazol-1-yl, pyrazol-3-yl), oxadiazolyl (preferably, 1,2,4-oxadiazol-3-yl), thiazolyl (preferably, thiazol-2-yl, thiazol-4-yl), triazolyl (preferably, 1H-1,2,3-triazol-1-yl, 1H-1,2,4-triazol-3-yl), indazolyl (preferably, 1H-indazol-1-yl), benzimidazolyl (preferably, 1H-benzimidazol-2-yl)) optionally substituted by 1 to 3 (preferably, 1 or 2) substituents selected from
- (i) a carboxy group,
- (ii) a $C_{1-6}$ alkyl group (preferably, methyl) optionally substituted by 1 to 3 substituents selected from a halogen atom (preferably, a fluorine atom), a hydroxy group and a carboxy group,
- (iii) a $C_{1-6}$ alkoxy group (preferably, ethoxy, tert-butoxy) optionally substituted by a $C_{1-6}$ alkoxy group (preferably, methoxy),
- (iv) a $C_{3-6}$ cycloalkyl group (preferably, cyclopropyl), and
- (v) a nonaromatic heterocyclic group (preferably, dihydrooxadiazolyl (preferably, 4,5-dihydro-1,2,4-oxadiazol-3-yl)) optionally substituted by an oxo group, (aa) a cyclic amino group (preferably, 1-azetidinyl, 1-pyrrolidinyl, piperidino, 1-imidazolidinyl, 1-dihydropyridazinyl (preferably, 2,3-dihydropyridazin-2-yl), 1-hexahydropyrimidinyl, 2-dihydroisoindolyl (preferably, 1,3-dihydro-2H-isoindol-2-yl), 3-dihydroquinazolinyl (preferably, 3,4-dihydroquinazolin-3-yl), 3-tetrahydroquinazolinyl (preferably, 1,2,3,4-tetrahydroquinazolin-3-yl), 3-tetrahydropyrido[3,2-d]pyrimidinyl (preferably, 1,2,3,4-tetrahydropyrido[3,2-d]pyrimidin-3-yl), 3-tetrahydropteridinyl (preferably, 1,2,3,4-tetrahydropteridin-3-yl)) optionally substituted by 1 to 4 substituents selected from
- (i) a cyano group,
- (ii) a carboxy group,
- (iii) a $C_{1-6}$ alkyl group (preferably, methyl),
- (iv) a $C_{1-6}$ alkoxy-carbonyl group (preferably, ethoxycarbonyl),
- (v) a mono- or di-($C_{1-6}$ alkyl-carbonyl)amino group (preferably, acetylamino),
- (vi) a nonaromatic heterocyclic group (preferably, dihydrooxadiazolyl (preferably, 4,5-dihydro-1,2,4-oxadiazol-3-yl)) optionally substituted by an oxo group, and
- (vii) an oxo group, and (bb) a nonaromatic heterocyclic group (preferably, dihydrooxadiazolyl (preferably, 1-dihydropyridyl (preferably, 1,2-dihydropyridin-1-yl), dihydrooxadiazolyl (preferably, 4,5-dihydro-1,2,4-oxadiazol-3-yl) optionally substituted by 1 to 3 substituents selected from
- (i) a halogen atom (preferably, a chlorine atom),
- (ii) a cyano group,
- (iii) a carboxy group,
- (iv) a carbamoyl group,
- (v) a $C_{1-6}$ alkoxy-carbonyl group (preferably, methoxycarbonyl),
- (vi) an aromatic heterocyclic group (preferably, triazolyl (preferably, 1,2,4-triazol-3-yl), tetrazolyl (preferably, tetrazol-5-yl)) optionally substituted by a $C_{1-6}$ alkyl group (preferably, methyl),
- (vii) a nonaromatic heterocyclic group (preferably, dihydrooxadiazolyl (preferably, 4,5-dihydro-1,2,4-oxadiazol-3-yl, 4,5-dihydro-1,3,4-oxadiazol-2-yl), dihydrotriazolyl (preferably, 4,5-dihydrotriazol-3-yl)) optionally substituted by an oxo group,

(16) a $C_{1-6}$ alkoxy group (preferably, methoxy, ethoxy),
(17) a $C_{1-6}$ alkyl-carbonyl group (preferably, acetyl),
(18) —CO—$NR^P R^Q$ wherein $R^P$ and $R^Q$ are each independently,
- (a) a hydrogen atom,
- (b) a $C_{1-6}$ alkyl group (preferably, methyl, ethyl, isobutyl) optionally substituted by 1 to 3 (preferably, 1) substituents selected from
  - (i) a hydroxy group,
  - (ii) a $C_{1-6}$ alkylsulfonyl group (preferably, methylsulfonyl), and
  - (iii) a $C_{1-6}$ alkoxy group (preferably, methoxy),
- (c) a $C_{1-6}$ alkoxy group (preferably, methoxy),
- (d) a $C_{6-12}$ aryl group (preferably, phenyl) optionally substituted by a carboxy group, (e) a $C_{1-6}$ alkylsulfonyl group (preferably, methylsulfonyl), or
(f) a $C_{6-12}$ arylsulfonyl group (preferably, phenylsulfonyl) optionally substituted by 1 to 3 (preferably, 1) substituents selected from
   (i) a $C_{1-6}$ alkyl group (preferably, methyl) optionally substituted by 1 to 3 halogen atoms (preferably, fluorine atom), and
   (ii) a $C_{1-6}$ alkoxy group (preferably, methoxy) optionally substituted by 1 to 3 (preferably, 1 or 2) halogen atoms (preferably, a fluorine atom),
(19) a $C_{6-12}$ aryloxy group (preferably, phenoxy) optionally substituted by a nonaromatic heterocyclic group (preferably, dihydrooxadiazolyl (preferably, 4,5-dihydro-1,2,4-oxadiazol-3-yl)) optionally substituted by an oxo group,
(20) an aromatic heterocyclyl-oxy group (preferably, pyridyloxy (preferably, pyridin-3-yloxy, pyridin-4-yloxy)) optionally substituted by 1 to 3 (preferably, 1) substituents selected from
   (a) a cyano group,
   (b) a carboxy group,
   (c) a $C_{1-6}$ alkoxy-carbonyl group (preferably, methoxycarbonyl),
   (d) a carbamoyl group,
   (e) a mono- or di-$C_{1-6}$ alkylcarbamoyl group (preferably, methylcarbamoyl, ethylcarbamoyl)
      (said $C_{1-6}$ alkyl is optionally substituted by a hydroxy group),
   (f) an aromatic heterocyclic group (preferably, triazolyl (preferably, 1H-1,2,4-triazol-3-yl), tetrazolyl (preferably, tetrazol-5-yl)) optionally substituted by a $C_{1-6}$ alkyl group (preferably, methyl), and
   (g) a nonaromatic heterocyclic group (preferably, dihydrooxadiazolyl (preferably, 4,5-dihydro-1,2,4-oxadiazol-3-yl), dihydrotriazolyl (preferably, 4,5-dihydro-1H-1,2,4-triazol-3-yl)) optionally substituted by an oxo group,
(21) an aromatic heterocyclic group (preferably, thiazolyl (preferably, thiazol-2-yl)) optionally substituted by a carboxy group, or
(22) a nonaromatic heterocyclic group (preferably, dihydropyridyl (preferably, 1,2-dihydropyridin-1-yl), dihydrooxadiazolyl (preferably, 4,5-dihydro-1,2,4-oxadiazol-3-yl)) optionally substituted by 1 to 3 (preferably, 1 or 2) substituents selected from
   (a) a nonaromatic heterocyclic group (preferably, dihydrooxadiazolyl (preferably, 4,5-dihydro-1,2,4-oxadiazol-3-yl)) optionally substituted by an oxo group, and
   (b) an oxo group, and
rings $B^1$-$B^6$ are optionally substituted by a hydroxy group or a $C_{1-6}$ alkoxy group (preferably, methoxy) besides ring A and R.

[Compound (I)-1']
Compound (I) wherein rings $B^1$-$B^6$ are free of a substituent other than ring A and R.

[Compound (I)-1"]
Compound (I) wherein rings $B^1$-$B^6$ are substituted by a hydroxy group or a $C_{1-6}$ alkoxy group (preferably, methoxy) besides ring A and R.

[Compound (I)-2]
Compound (I) wherein ring A is an optionally substituted benzene ring.

[Compound (I)-3]
Compound (I)-2 wherein
R is
(1) a mono- or di-($C_{1-6}$ alkyl-carbonyl)amino group,
(2) a sulfamoylamino group, or
(3) a $C_{1-6}$ alkyl group optionally substituted by 1 to 3 substituents selected from
   (a) a hydroxy group,
   (b) a mono- or di-($C_{1-6}$ alkyl-carbonyl)amino group,
   (c) a sulfamoylamino group,
   (d) a $C_{1-6}$ alkoxy-$C_{1-6}$ alkyl-carbonylamino group,
   (e) a $C_{1-6}$ alkylsulfonylamino group, and
   (f) 2-oxopyridin-1(2H)-yl optionally substituted by 1 to 3 substituents selected from a carboxy group and 5-oxo-4,5-dihydro-1,2,4-oxadiazoly.

[Compound (I)-4]
Compound (I)-2 or (I)-3 wherein the group represented by

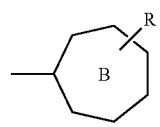

is

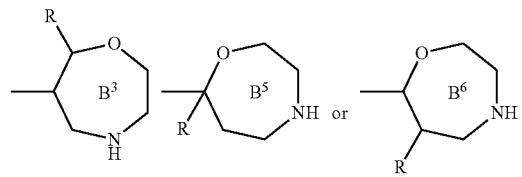

wherein each symbol is as defined above.

[Compound (I)-5]
Compound (I) wherein
ring A is a benzene ring substituted by 2 substituents selected from a fluorine atom and a chlorine atom,
the group represented by

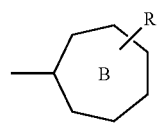

is

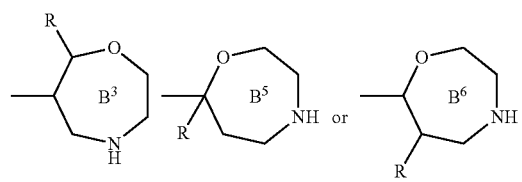

wherein
R is
(1) a mono- or di-($C_{1-6}$ alkyl-carbonyl)amino group,
(2) a sulfamoylamino group, or
(3) a $C_{1-6}$ alkyl group optionally substituted by 1 to 3 substituents selected from
   (a) a hydroxy group,
   (b) a mono- or di-($C_{1-6}$ alkyl-carbonyl)amino group,
   (c) a sulfamoylamino group,
   (d) a $C_{1-6}$ alkoxy-$C_{1-6}$ alkyl-carbonylamino group,
   (e) a $C_{1-6}$ alkylsulfonylamino group, and (f) 2-oxopyridin-1(2H)-yl optionally substituted by 1 to 3 substituents selected from a carboxy group and 5-oxo-4,5-dihydro-1,2,4-oxadiazolyl, and other symbols are as defined above.

In another embodiment, compound (I) is preferably a compound represented by the formula (I') or a salt thereof (hereinafter to be referred to as compound (I')).

Preferable examples of compound (I') are the following compounds.

[Compound (I')-1]

Compound (I') wherein ring A is a benzene ring substituted by two halogen atoms, R' is (1) a hydroxy group,
(2) a $C_{1-6}$ alkoxy-carbonyl group,
(3) a $C_{1-6}$ alkoxy group, or
(4) a $C_{1-6}$ alkyl group optionally substituted by 1 substituent selected from
  (a) a halogen atom,
  (b) a hydroxy group,
  (c) a $C_{1-6}$ alkoxy group,
  (d) —S—$R^{1a}$,
  (e) —$SO_2$—$R^{1a}$,
  (f) —N($R^{1b}$)($R^{1c}$),
  (e) —$SO_2$—$R^{1a}$,
  (g) —NH—CO—$R^{1a}$,
  (h) —NH—CO—N($R^{1b}$)($R^{1c}$),
  (i) —NH—$SO_2$—$R^{1a}$, and
  (j) —NH—$SO_2$—N($R^{1b}$)($R^{1c}$)

wherein $R^{1a}$ is a $C_{1-6}$ alkyl group, and $R^{1b}$ and $R^{1c}$ are each independently a hydrogen atom or a $C_{1-6}$ alkyl group, and rings $B^1$-$B^6$ are free of a substituent other than ring A and R'.

[Compound (I')-1']

Compound (I') wherein ring A is a benzene ring substituted by two halogen atoms, R' is (1) a hydroxy group,
(2) a $C_{1-6}$ alkoxy-carbonyl group,
(3) a $C_{1-6}$ alkoxy group, or
(4) a $C_{1-6}$ alkyl group optionally substituted by 1 substituent selected from
  (a) a halogen atom,
  (b) a hydroxy group,
  (c) a $C_{1-6}$ alkoxy group,
  (d) —S—$R^{1a}$,
  (e) —$SO_2$—$R^{1a}$,
  (f) —N($R^{1b}$)($R^{1c}$),
  (g) —NH—CO—$R^{1a}$,
  (h) —NH—CO—N($R^{1b}$)($R^{1c}$),
  (i) —NH—$SO_2$—$R^{1a}$, and
  (j) —NH—$SO_2$—N($R^{1b}$)($R^{1c}$)

wherein $R^{1a}$ is a $C_{1-6}$ alkyl group, and $R^{1b}$ and $R^{1c}$ are each independently a hydrogen atom or a $C_{1-6}$ alkyl group, and rings $B^1$-$B^6$ are substituted by a hydroxy group or a $C_{1-6}$ alkoxy group (preferably, methoxy) besides ring A and R'.

[Compound (I')-2]

Compound (I') wherein ring A is an optionally substituted benzene ring [preferably, a benzene ring optionally substituted by 1 to 3 (preferably 1 or 2) halogen atoms (preferably, a fluorine atom, a chlorine atom)], R' is (1) a hydroxy group,
(2) a mono- or di-($C_{1-6}$ alkyl-carbonyl)amino group (preferably, acetylamino),
(3) a sulfamoylamino group,
(4) a $C_{1-6}$ alkoxy group (preferably, methoxy, ethoxy), or
(5) a $C_{1-6}$ alkyl group (preferably, methyl, ethyl) optionally substituted by 1 to 4 (preferably 1 to 3, more preferably 1 or 2) substituents selected from
  (a) a hydroxy group,
  (b) a $C_{1-6}$ alkoxy group (preferably, methoxy),
  (c) —$SO_2$—$R^{1a}$,
  (d) —NH—CO—$R^{1a}$,
  (e) —NH—CO—N($R^{1b}$)($R^{1c}$),
  (f) —NH—$SO_2$—$R^{1a}$,
  (g) —NH—$SO_2$—N($R^{1b}$)($R^{1c}$)

wherein $R^{1a}$ is a $C_{1-6}$ alkyl group (preferably, methyl) optionally substituted by 1 to 3 (preferably, 1) $C_{1-6}$ alkoxy groups (preferably, methoxy, ethoxy, isopropoxy), and $R^{1b}$ and $R^{1c}$ are each independently a hydrogen atom or a $C_{1-6}$ alkyl group (preferably, a hydrogen atom), and (h) a nonaromatic heterocyclic group (preferably, dihydropyridyl (preferably, 1,2-dihydropyridin-1-yl)) optionally substituted by 1 to 3 (preferably, 1 or 2) substituents selected from
    (i) a nonaromatic heterocyclic group (preferably, dihydrooxadiazolyl (preferably, 4,5-dihydro-1,2,4-oxadiazol-3-yl)) optionally substituted by an oxo group,
    (ii) a carboxy group, and
    (iii) an oxo group, and rings $B^1$-$B^6$ are free of a substituent other than ring A and R'.

[Compound (I')-2']

Compound (I') wherein ring A is an optionally substituted benzene ring [preferably, a benzene ring optionally substituted by 1 to 3 (preferably 1 or 2) halogen atoms (preferably, a fluorine atom, a chlorine atom)], R' is (1) a hydroxy group,
(2) a mono- or di-($C_{1-6}$ alkyl-carbonyl)amino group (preferably, acetylamino),
(3) a sulfamoylamino group,
(4) a $C_{1-6}$ alkoxy group (preferably, methoxy, ethoxy), or
(5) a $C_{1-6}$ alkyl group (preferably, methyl, ethyl) optionally substituted by 1 to 4 (preferably 1 to 3, more preferably 1 or 2) substituents selected from
  (a) a hydroxy group,
  (b) a $C_{1-6}$ alkoxy group (preferably, methoxy),
  (c) —$SO_2$—$R^{1a}$,
  (d) —NH—CO—$R^{1a}$,
  (e) —NH—CO—N($R^{1b}$)($R^{1c}$),
  (f) —NH—$SO_2$—$R^{1a}$,
  (g) —NH—$SO_2$—N($R^{1b}$)($R^{1c}$)

wherein $R^{1a}$ is a $C_{1-6}$ alkyl group (preferably, methyl) optionally substituted by 1 to 3 (preferably, 1) $C_{1-6}$ alkoxy groups (preferably, methoxy, ethoxy, isopropoxy), and $R^{1b}$ and $R^{1c}$ are each independently a hydrogen atom or a $C_{1-6}$ alkyl group (preferably, a hydrogen atom), and (h) a nonaromatic heterocyclic group (preferably, dihydropyridyl (preferably, 1,2-dihydropyridin-1-yl)) optionally substituted by 1 to 3 (preferably, 1 or 2) substituents selected from
    (i) a nonaromatic heterocyclic group (preferably, dihydrooxadiazolyl (preferably, 4,5-dihydro-1,2,4-oxadiazol-3-yl)) optionally substituted by an oxo group,
    (ii) a carboxy group, and
    (iii) an oxo group, and rings $B^1$-$B^6$ are substituted by a hydroxy group or a $C_{1-6}$ alkoxy group (preferably, methoxy) besides ring A and R'.
[Compound (I')-3]
Compound (I') wherein
ring A is a benzene ring substituted by 2 substituents selected from a fluorine atom and a chlorine atom,
the group represented by

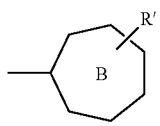

is

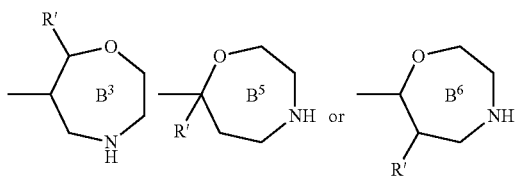

wherein
R' is
(1) a mono- or di-($C_{1-6}$ alkyl-carbonyl)amino group,
(2) a sulfamoylamino group, or
(3) a $C_{1-6}$ alkyl group optionally substituted by 1 to 3 substituents selected from
  (a) a hydroxy group,
  (b) a mono- or di-($C_{1-6}$ alkyl-carbonyl)amino group,
  (c) a sulfamoylamino group,
  (d) a $C_{1-6}$ alkoxy-$C_{1-6}$ alkyl-carbonylamino group,
  (e) a $C_{1-6}$ alkylsulfonylamino group, and
  (f) 2-oxopyridin-1(2H)-yl optionally substituted by 1 to 3 substituents selected from a carboxy group and 5-oxo-4,5-dihydro-1,2,4-oxadiazolyl, and
other symbols are as defined above.

When compound (I) is a salt, examples of the salt include salt with inorganic base, ammonium salt, salt with organic base, salt with inorganic acid, salt with organic acid, salt with basic or acidic amino acid and the like.

Preferable examples of the salt with inorganic base include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Of these salts, pharmaceutically acceptable salts are preferable. When the compound has a basic functional group, preferable examples of the pharmaceutically acceptable salt include salts with inorganic acids such as hydrochloric acid, hydrobromic acid, nitric acid, sulfuric acid, phosphoric acid and the like salts with inorganic acids, or organic acids such as acetic acid, phthalic acid, fumaric acid, oxalic acid, tartaric acid, maleic acid, citric acid, succinic acid, methanesulfonic acid, p-toluenesulfonic acid and the like. When the compound has an acidic functional group, preferable examples of the pharmaceutically acceptable salt include inorganic salts such as alkali metal salts (e.g., sodium salt, potassium salt etc.), alkaline earth metal salts (e.g., calcium salt, magnesium salt, barium salt etc.) and the like, ammonium salt and the like.

Compound (I) encompasses solvates (e.g., hydrate) and non-solvates. In addition, compound (I) may be labeled with an isotope (e.g., $^3$H, $^{11}$C, $^{14}$C, $^{18}$F, $^{35}$S, $^{125}$I and the like) and the like. Furthermore, a deuterium converter wherein $^1$H is converted to $^2$H(D) is also encompassed in compound (I).

When compound (I) of the present invention has an asymmetric center, isomers such as enantiomer, diastereomer and the like may be present. Such isomers and a mixture thereof are all encompassed in the scope of the present invention. When an isomer due to conformation or tautomerism is present, such isomer and a mixture thereof are also encompassed in compound (I) of the present invention.

Next, the preparation of compound (I) is explained.

Compound (I) is constituted by the following compounds (Ia)-(If) based on the positions of ring A and substituent R. Hereinafter, the preparation of compounds (Ia)-(If) are explained in the following. The compound used for preparation of compounds (Ia)-(If) may be in the form of a salt, and examples of the salt include those similar to the salts of compound (I).

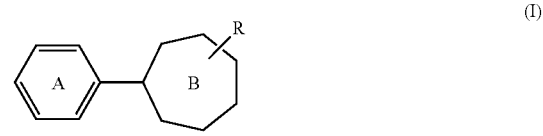

(I)

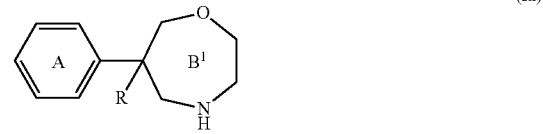

(Ia)

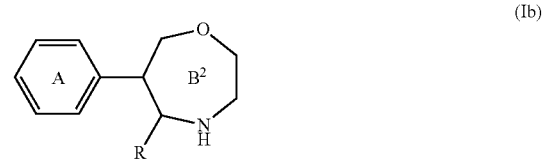

(Ib)

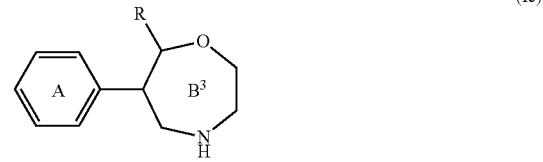

(Ic)

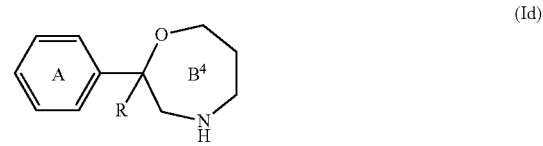

(Id)

(Ie)

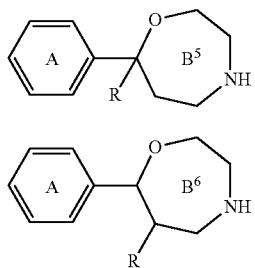

(If)

[Preparation of Compound (Ia)]

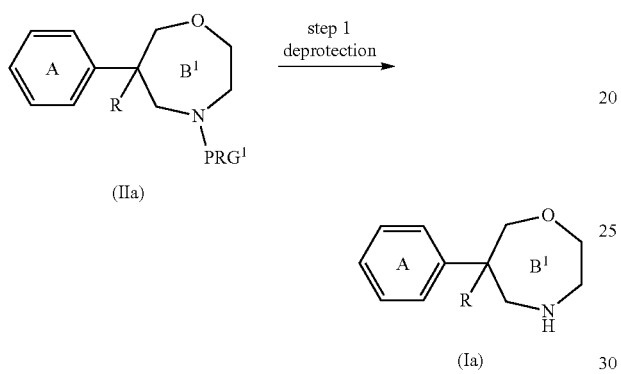

wherein PRG¹ is a protecting group, and other symbols are each as defined above.

In Step 1, compound (Ia) can be prepared, for example, by deprotecting compound (IIa). Examples of the "protecting group" for PRG¹ include those described in Greene's protective groups in organic synthesis 4$^{th}$ edition (Wiley-International Publication). Preferred are carbamate protecting groups such as tert-butoxycarbonyl (Boc) group, benzyloxycarbonyl (Cbz) group, 9-fluorenylmethyloxycarbonyl (Fmoc) group and the like; amide protecting groups such as acetyl (Ac) group, trifluoroacetyl group and the like; and alkyl protecting groups such as benzyl (Bzl) group, methyl group and the like. The deprotection of Step 1 is performed, for example, according to the method described in the above-mentioned Greene's protective groups in organic synthesis 4$^{th}$ edition. For example, a treatment with an acid such as hydrochloric acid, trifluoroacetic acid and the like, and the like is preferably employed for a tert-butoxycarbonyl group, and a catalytic reduction using a metal catalyst such as palladium and the like, or a method using an alkyl chloroformate and the like is preferably employed for a benzyl group. When protecting group is a tert-butoxycarbonyl group, the "acid" used for the acid treatment is preferably an organic solvent solution containing hydrogen chloride, hydrochloric acid or is trifluoroacetic acid. The "organic solvent" is preferably, for example, an alcohol solvent such as ethanol, methanol and the like, or an ester solvent such as ethyl acetate and the like. The amount of the "acid" to be used is generally 1 equivalent to a solvent amount, preferably 1 equivalent to 100 equivalents, relative to compound (IIa). The reaction solvent is preferably, for example, an alcohol solvent such as ethanol, methanol and the like, or an ester solvent such as ethyl acetate and the like. The reaction temperature is generally −78° C. to 200° C., preferably 0° C. to 50° C. The reaction time is generally 1 min to 48 hr, preferably 5 min to 24 hr.

Compound (IIa¹) (R is —OH) and compound (IIa²) (R is —O-Alkyl¹) which are encompassed in compound (IIa) can be prepared, for example, according to the following method.

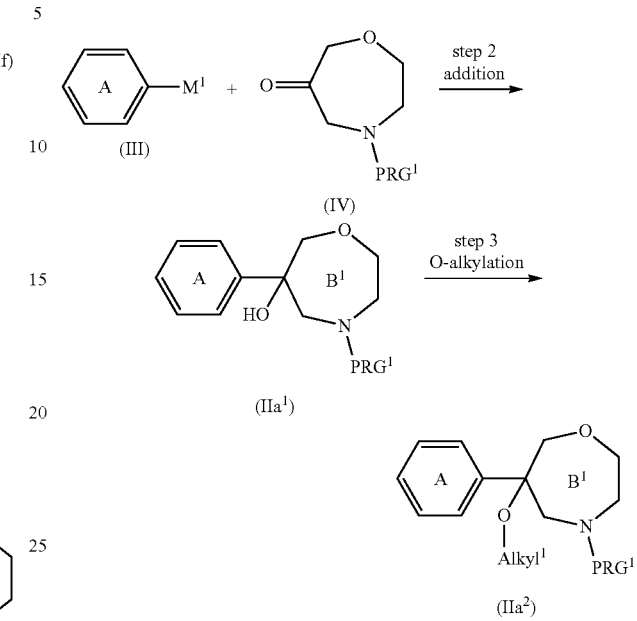

wherein M¹ is a metal or a salt thereof, Alkyl¹ is a $C_{1-6}$ alkyl group optionally having substituent(s), and other symbols are each as defined above.

In Step 2, compound (IIa¹) (R is —OH) can be prepared, for example, by subjecting compound (IV) (PRG¹ is -Boc) described in WO 2004/074291 to an addition reaction with compound (III). "M¹" of compound (III) is preferable an alkali metal, an alkaline earth metal or a salt thereof, more preferable lithium or a halogenated magnesium.

In Step 3, the obtained compound (IIa¹) can be converted to compound (IIa²) (R is —O-Alkyl¹) by introduction of an alkyl group. The "O-alkylation" can be performed, for example, according to the method described in Tetrahedron Lett., 30, 641 (1989).

[Preparation of Compound (Ib)]

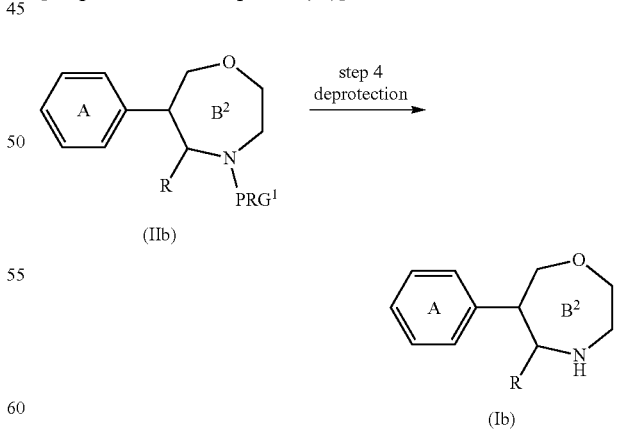

wherein each symbol is as defined above.

In Step 4, compound (Ib) can be prepared, for example, by deprotecting compound (IIb). Examples of the "protecting group" for PRG¹ include those similar to the protecting group exemplified in Step 1. Among them, tert-butoxycarbonyl (Boc) group and the like are preferable. Step 4 can be performed under the same reaction conditions as in Step 1 or reaction conditions similar thereto.
Compound (IIb¹) (R is —CO₂Alkyl²) encompassed in compound (IIb) can be prepared, for example, according to the following method.
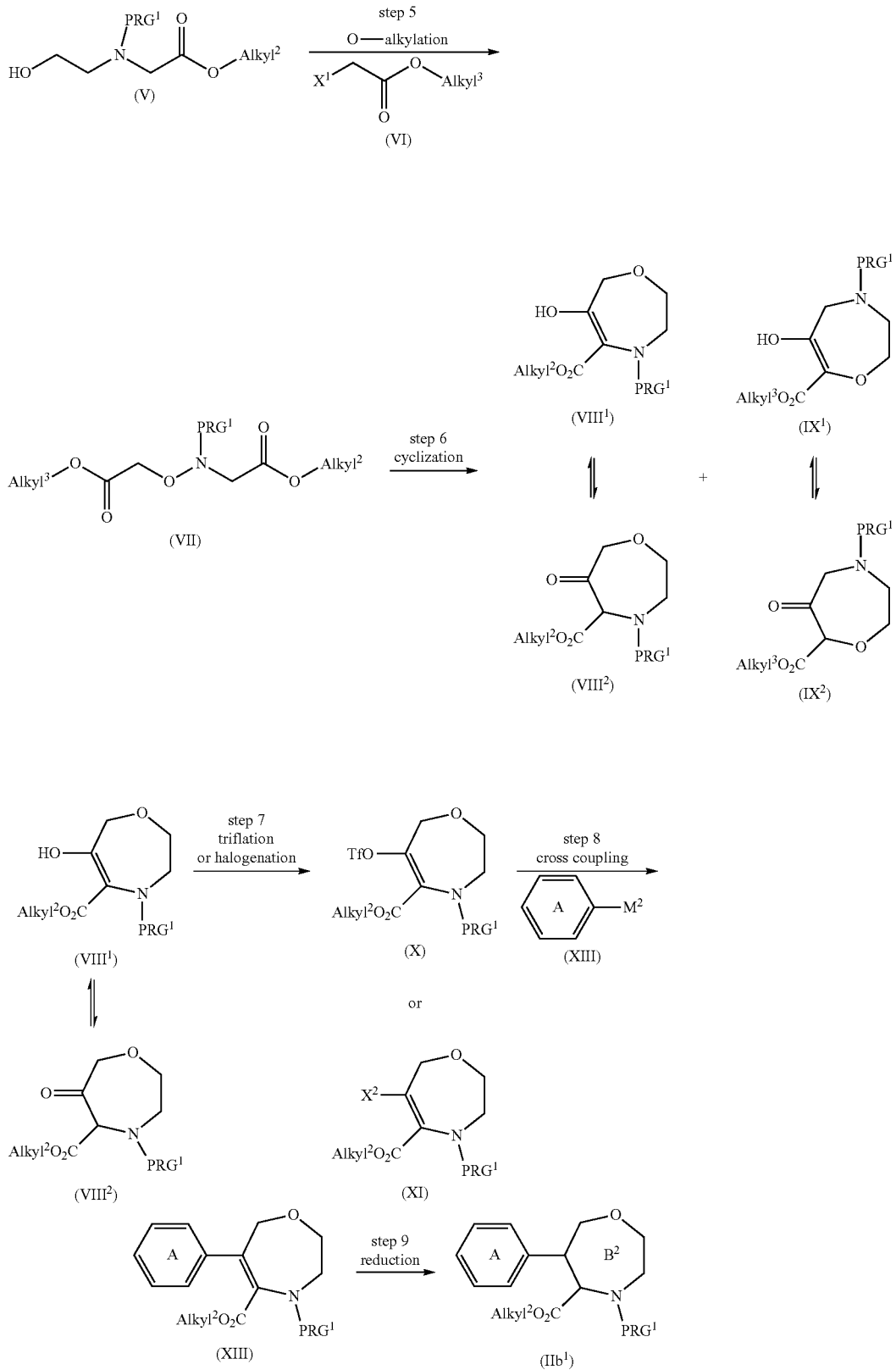

wherein Alkyl² and Alkyl³ are each a $C_{1-6}$ alkyl group, $X^1$ and $X^2$ are each a halogen atom, Tf is a trifluoromethanesulfonyl group, $M^2$ is a metal or a derivative thereof, and other symbols are each as defined above.

In Step 5, compound (VII) can be prepared by alkylating the hydroxyl group of compound (V) with compound (VI). The step may be performed in the presence of a base. Examples of the "base" include
1) strong bases such as hydrides of an alkali metal or alkaline earth metal (e.g., lithium hydride, sodium hydride, potassium hydride, calcium hydride and the like), amides of an alkali metal or alkaline earth metal (e.g., lithium amide, sodium amide, lithium diisopropylamide, lithium dicyclohexylamide, lithium hexamethyldisilazide, sodium hexamethyldisilazide, potassium hexamethyldisilazide and the like), $C_{1-6}$ alkoxides of an alkali metal or alkaline earth metal (e.g., sodium methoxide, sodium ethoxide, potassium tert-butoxide, sodium tert-butoxide and the like) and the like;
2) inorganic bases such as hydroxides of an alkali metal or alkaline earth metal (e.g., sodium hydroxide, potassium hydroxide, lithium hydroxide, barium hydroxide and the like), carbonates of an alkali metal or alkaline earth metal (e.g., sodium carbonate, potassium carbonate, cesium carbonate and the like), hydrogencarbonates of an alkali metal or alkaline earth metal (e.g., sodium hydrogencarbonate, potassium hydrogencarbonate and the like) and the like; and
3) organic bases such as amines such as triethylamine, diisopropylethylamine, N-methylmorpholine and the like; amidines such as DBU (1,8-diazabicyclo[5.4.0]undec-7-ene), DBN (1,5-diazabicyclo[4.3.0]non-5-ene) and the like; basic heterocyclic compounds such as pyridine, dimethylaminopyridine, imidazole, 2,6-lutidine and the like, and the like and the like. Among them, a hydride of an alkali metal or alkaline earth metal (e.g. sodium hydride and the like) is preferable.

In Step 6, compounds (VIII¹) and (VIII²) can be prepared by subjecting compound (VII) to cyclization. Compounds (VIII¹) and (VIII²) are in the keto-enol tautomer relationship, and are present in the form of a mixture thereof or isomer of either of them. The step can be performed by a general Dieckmann condensation, for example, the method described in Helvetica Chimica Acta, 90, 1006-1027 (2007). While byproducts (IX¹) and (IX²) (which are also keto-enol tautomers, like the above) may be prepared in this step, they can be removed by a purification method such as silica gel column chromatography, recrystallization and the like.

In Step 7, compound (X) or (XI) can be prepared by triflating or halogenating compounds (VIII¹) and (VIII²). The "triflation" can be performed, for example, according to the method described in Comprehensive Organic Functional Group Transformations II (Elsevier Pergamon), vol. 2, 633-634. The "halogenation" can be performed, for example, according to the method described in Journal of the American Chemical Society, 65, 2208 (1943). The "halogen" of the "halogenation" is preferably chlorine, bromine or iodine.

In Step 8, compound (XIII) can be prepared by subjecting compound (X) or (XI) to cross coupling with compound (XII). The step can be performed, for example, according to the Suzuki-Miyaura coupling reaction described in Tetrahedron, 58, 9633-9695 (2002), the Stille coupling reaction described in for example, Organic Reactions, 50, 1-652 (1997), and the like. Compound (XII) is an organic boronic acid compound ($M^2$=—$B(OH)_2$ or an ester thereof) when employing the Suzuki-Miyaura coupling reaction, or an organotin compound ($M^2$=trialkylstannyl) when employing the Stille coupling reaction. The step is preferably performed by the Suzuki-Miyaura coupling reaction.

In Step 9, compound (IIb¹) can be prepared by reducing compound (XIII). The "reduction" can be performed, for example, according to a method using a metal hydride such as sodium borohydride, lithium borohydride, zinc borohydride, sodium cyanoborohydride, sodium triacetoxyborohydride, cyanolithium borohydride, dibutylaluminum hydride, aluminum hydride, lithium aluminum hydride, borane complex (borane-THF complex etc.), catecholborane and the like; a catalytic reduction using a transition metal catalyst such as palladium, platinum, rhodium, Raney-nickel and the like; or a method using a metal such as magnesium and the like. Among them, a method using sodium borohydride is preferable. The product obtained in this step may be a diastereomer mixture due to stereoisomerism, and it can be separated and purified by silica gel column chromatography, recrystallization and the like, as necessary.

Compounds (IIb²) (R is —$CH_2OH$), (IIb³) (R is —$CH_2L^1$), (IIb⁴) (R is —$CH_2S$-Alkyl⁴) and (IIb⁵) (R is —$CH_2SO_2$-Alkyl⁴) which are encompassed in compound (IIb) can be prepared, for example, from compound (IIb¹) as shown in the following method.

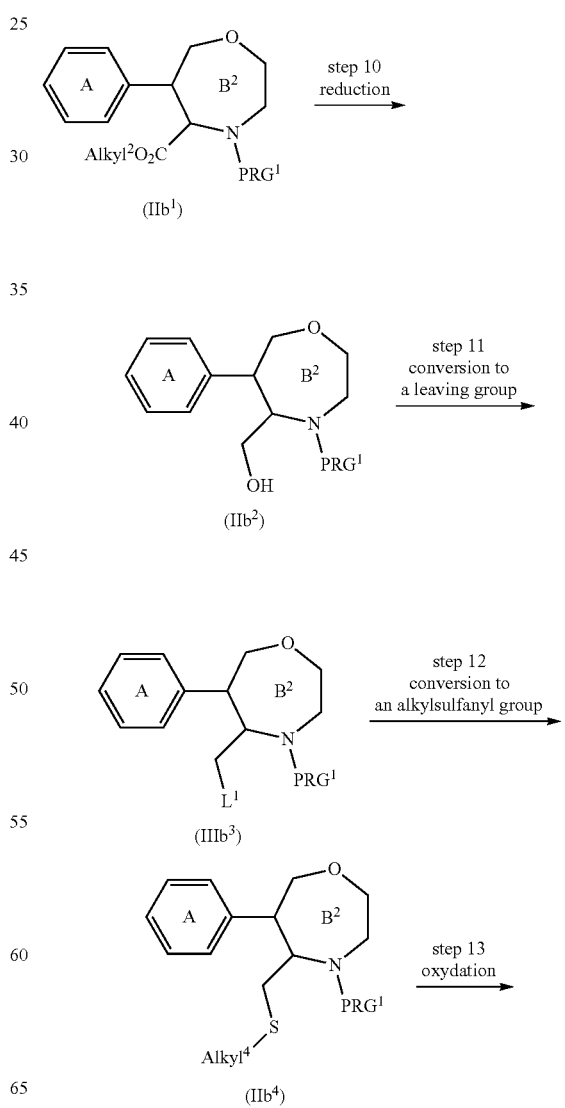

-continued

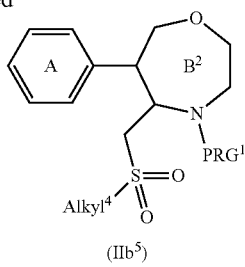

(IIb⁵)

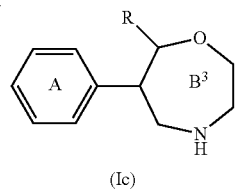

(Ic)

wherein each symbol is as defined above.

In Step 14, compound (Ic) can be prepared, for example, by deprotecting compound (IIc). Examples of the "protecting group" for PRG¹ include those similar to the "protecting group" exemplified in Step 1. Among them, tert-butoxycarbonyl (Boc) group, benzyl (Bzl) group and the like are preferable. Step 14 can be performed under the same reaction conditions as in Step 1 or reaction conditions similar thereto.

Compound (IIc¹) (R is —CH₂OPRG², and PRG¹ is Bzl) and (IIc²) (R is —CH₂OH, and PRG¹ is Bzl) which are encompassed in compound (IIc) can be prepared, for example, according to the following method.

wherein L¹ is a leaving group, Alkyl⁴ is a C₁₋₆ alkyl group optionally having substituent(s), and other symbols are each as defined above.

In Step 10, compound (IIb²) can be prepared by reducing compound (IIb¹). The "reduction" can be performed in the same manner as in Step 9. Among them, a method using a metal hydride such as sodium borohydride, lithium borohydride, lithium aluminum hydride and the like is preferable.

In Step 11, compound (IIb³) can be prepared by converting the hydroxyl group of compound (IIb²) to the leaving group L¹. Examples of the leaving group L¹ include a halogen atom (e.g., a chlorine atom, a bromine atom, an iodine atom), C₁₋₆ alkylsulfonyloxy optionally substituted by halogen atom(s) (e.g., methanesulfonyloxy, ethanesulfonyloxy, trifluoromethanesulfonyloxy), C₆₋₁₀ arylsulfonyloxy optionally substituted by C₁₋₆ alkyl (e.g., benzenesulfonyloxy, p-toluenesulfonyloxy) and the like. Among them, a halogen atom and methanesulfonyloxy are preferable. For example, this step is performed according to the method described in Journal of the American Chemical Society, 107, 3950 (1985) when the leaving group L¹ is a halogen atom, and this step is performed according to the method described in Synthesis, 6, 627-629 (1995) when the leaving group L¹ is methanesulfonyloxy.

In Step 12, compound (IIb⁴) can be prepared by converting the leaving group L¹ of compound (IIb³) into the alkylsulfanyl group using the corresponding thiol. The step may be performed using a base. Examples of the "base" include those similar to the "base" exemplified in Step 5. Among them, an alkali metal hydride such as sodium hydride and the like is preferable. In addition, an alkali metal salt of the thiol may be used instead of the thiol.

In Step 13, compound (IIb⁵) can be prepared by oxidizing compound (IIb⁴). The "oxidation" can be performed, for example, using an oxidant such as 3-chlorophenylperbenzoic acid, sodium periodate, aqueous hydrogen peroxide, peracetic acid, Oxone (registered trade mark) and the like. Among them, 3-chlorophenylperbenzoic acid and the like are preferable. The step can be performed, for example, according to the method described in Journal of Organic Chemistry, 68, 5075-5083 (2003).

[Preparation of Compound (Ic)]

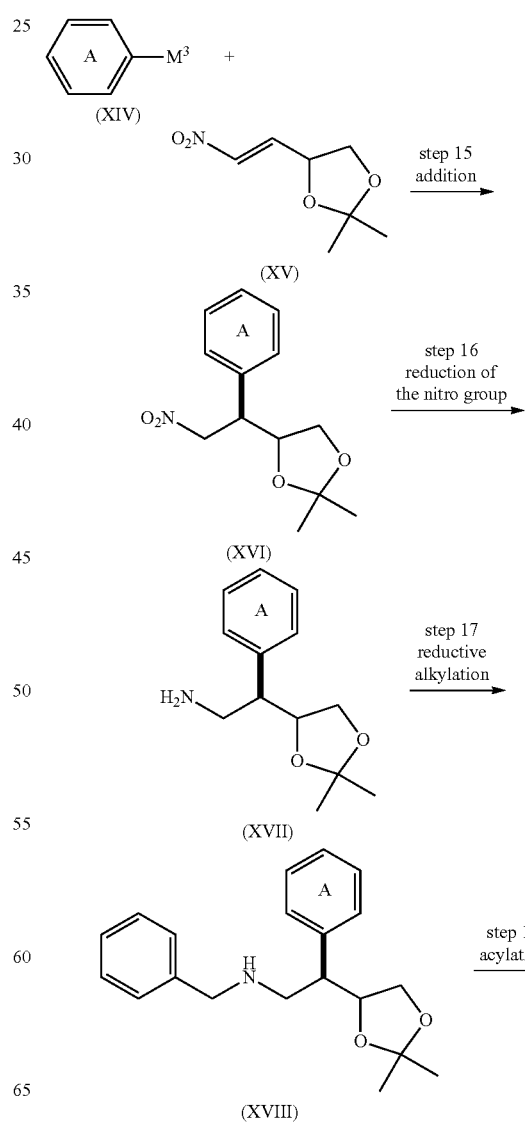

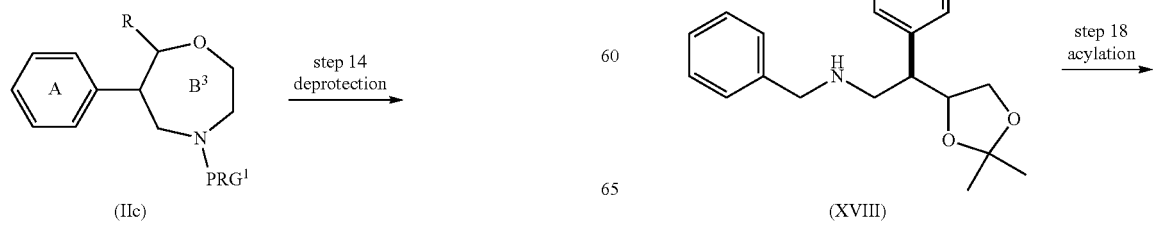

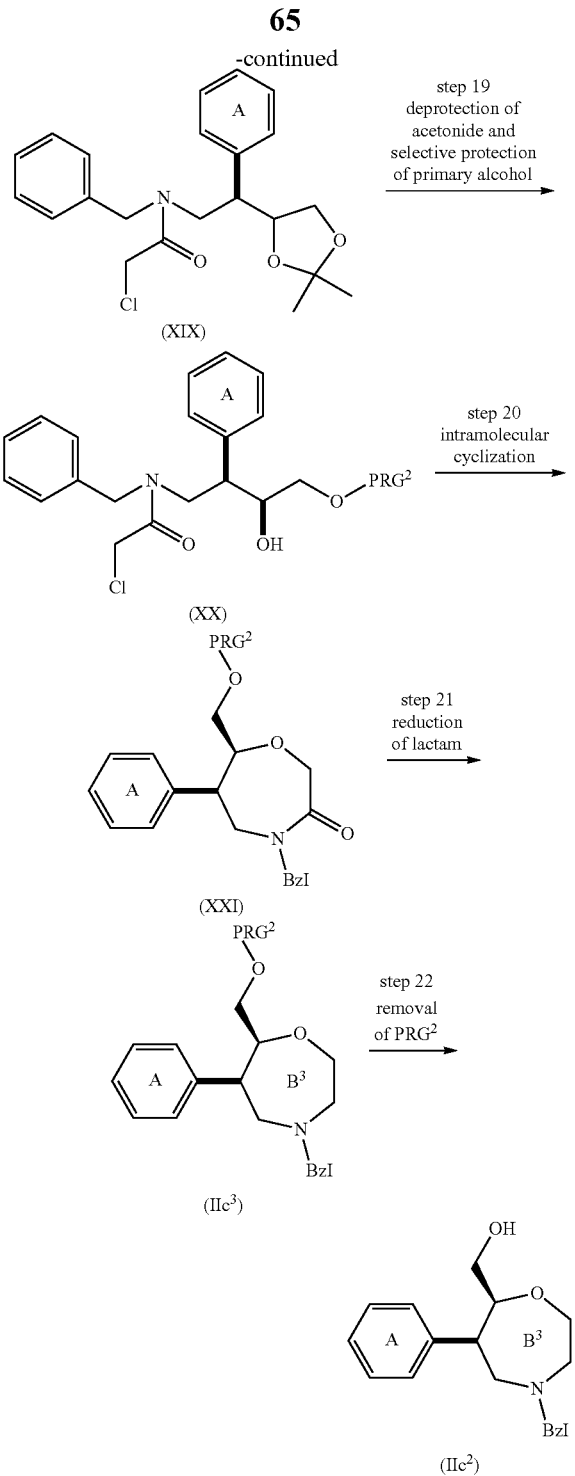

obtained in this step may be a diastereomer mixture due to stereoisomerism, and it can be separated and purified by silica gel column chromatography, recrystallization and the like, as necessary.

In Step 16, compound (XVII) can be prepared by reducing the nitro group of compound (XVI). The "reduction of the nitro group" can be performed, for example, according to a catalytic reduction reaction using a transition metal catalyst such as palladium, platinum, rhodium, Raney-nickel and the like; a method using a metal hydride such as lithium aluminum hydride, sodium borohydride in the presence of divalent nickel chloride and the like; a method using a powder of a metal such as zinc, iron, tin and the like under acidic conditions; and the like. Among them, catalytic reduction is preferable. The step can be performed, for example, according to the method described in Synthesis, 19, 3245-3252 (2005) when using Raney-nickel.

In Step 17, compound (XVIII) can be prepared by subjecting compound (XVII) to a reductive alkylation with benzaldehyde. The "reductive alkylation" can be performed, for example, according to the method described in Organic Reactions, 59, 1-714 (2001).

In Step 18, compound (XIX) can be prepared by acylating compound (XVIII). The step can be generally performed in the presence of the "base" exemplified in Step 5. The "base" is preferably triethylamine or diisopropylethylamine.

In Step 19, compound (XX) can be prepared by deprotecting the acetonide compound (XIX), and then selectively protecting the resulting primary alcohol. The "deprotection of the acetonide" can be performed, for example, according to the method described in Greene's protective groups in organic synthesis 4$^{th}$ edition (Wiley-International Publication). For example, a method using diluted hydrochloric acid, and the like are preferably employed. The "deprotection of the acetonide" can be performed, for example, according to the conditions described in Tetrahedron, 46, 1767-1782 (1990). The "selective protection of the primary alcohol" can be generally performed, for example, by introducing a bulky protecting group such as pivaloyl (Piv) group, tert-butyldimethylsilyl (TBDMS) group, tert-butyldiphenylsilyl (TBDPS) group and the like. tert-Butyldimethylsilyl group is preferably used. The "selective protection of the primary alcohol" can be performed, for example, according to the conditions described in Tetrahedron, 49, 8211-8222 (1993) when using tert-butyldimethylsilyl group as a protecting group. The "deprotection of the acetonide" and "selective protection of the primary alcohol" may be performed successively without via an isolation and purification operation.

In Step 20, compound (XXI) can be prepared by subjecting compound (XX) to an intramolecular cyclization reaction. The "intramolecular cyclization reaction" can be generally performed in the presence of a base. Examples of the "base" include those similar to the "base" exemplified in Step 5. Among them, sodium tert-butoxide is preferable.

In Step 21, compound (IIc$^1$) can be prepared by reducing the lactam compound (XXI). The "reduction of the lactam" can be performed, for example, using the "reducing agent" exemplified in Step 9. Among them, borane complex (borane-THF complex etc.), catecholborane, aluminum hydride, lithium aluminum hydride and the like are preferable.

In Step 22, compound (IIc$^2$) can be prepared by removing the protecting group "PRG$^2$" of compound (IIc$^1$). The removal can be performed, for example, according to the method selected from the methods described in Greene's protective groups in organic synthesis 4$^{th}$ edition (Wiley-International Publication), depending on the protecting group wherein M$^3$ is a metal or a derivative thereof, PRG$^2$ is a protecting group, Bzl is a benzyl group, and other symbols are each as defined above.

In Step 15, compound (XVI) can be prepared by subjecting compound (XV) to addition with compound (XIV). Examples of the "M$^3$" of compound (XIV) include an alkali metal, an alkaline earth metal, zinc, copper, boron, silicon, a derivative thereof and the like. Among them, lithium and halogenated magnesium are preferable. The step can be performed, for example, according to the method described in Tetrahedron Letters, 37, 3055-3058 (1996). The product "PRG². When the removal of "PRG²" proceeds simultaneously in Step 20 or Step 21, this step may be omitted.

Compound (IIc³) (R is —CH₂OPRG², and RPG¹ is Boc), (IIc⁴) (R is —CH₂OH, and RPG¹ is Boc), (IIc⁵) (R is —CH₂SO₂-Alkyl⁵, and RPG¹ is Boc), (IIc⁶) (R is —CH₂L², and RPG¹ is Boc), (IIc⁷) (R is —CH₂N₃, and RPG¹ is Boc), (IIc⁸) (R is —CH₂Phthalimide, and RPG¹ is Boc), (IIc⁹) (R is —CH₂NH₂, and RPG¹ is Boc), (IIc¹⁰) (R is —CH₂NHCOAlkyl⁶, and RPG¹ is Boc), (IIc¹¹) (R is —CH₂NHCON(Alkyl⁷)(Alkyl⁸), and RPG¹ is Boc), (IIc¹²) (R is —CH₂NHSO₂Alkyl⁹, and RPG¹ is Boc) and (IIc¹³) (R is —CH₂NHSO₂N(Alkyl¹⁰)(Alkyl¹¹), and RPG¹ is Boc) which are encompassed in compound (IIc) can be prepared, for example, from compound (IIc¹) according to the following method.

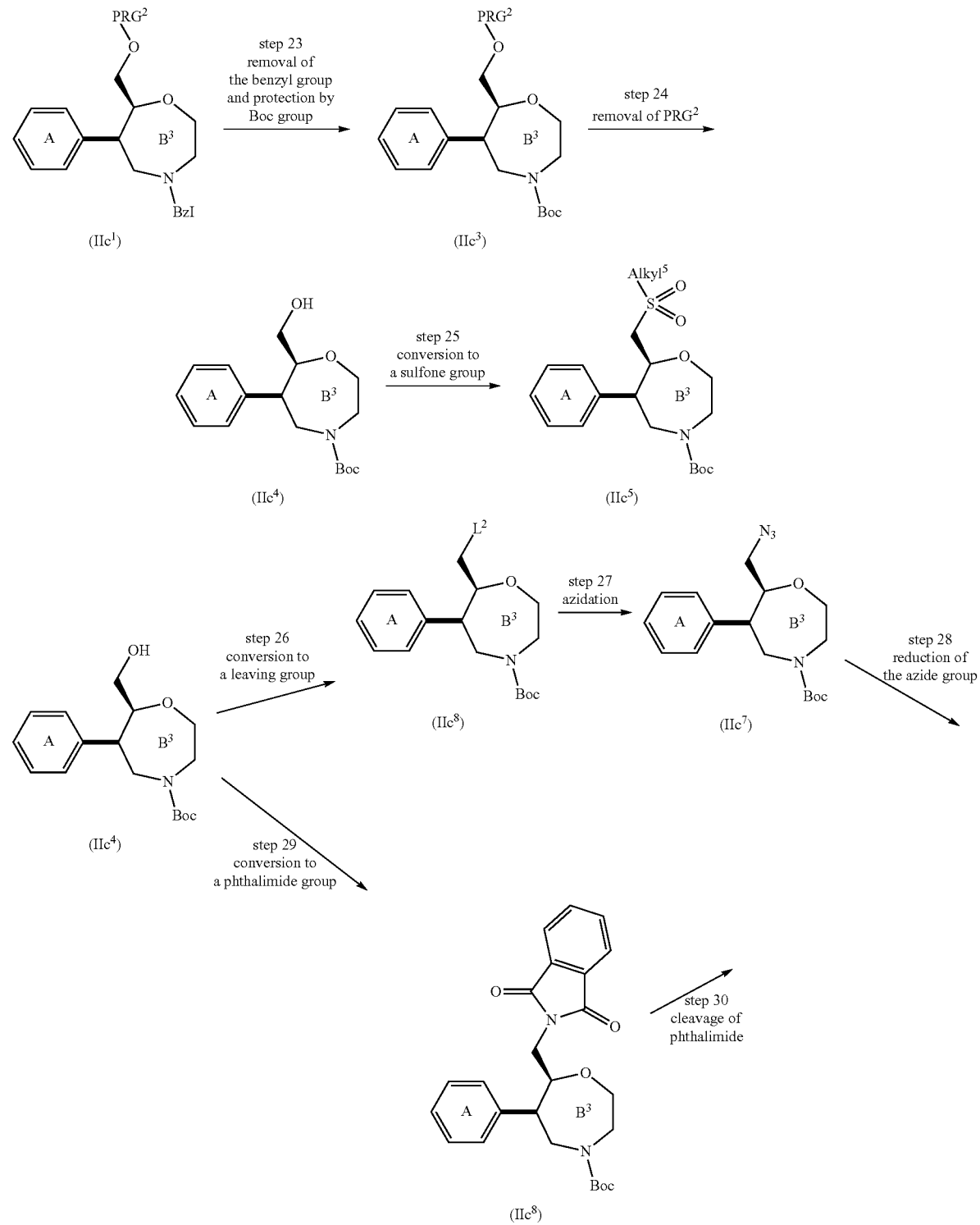

-continued

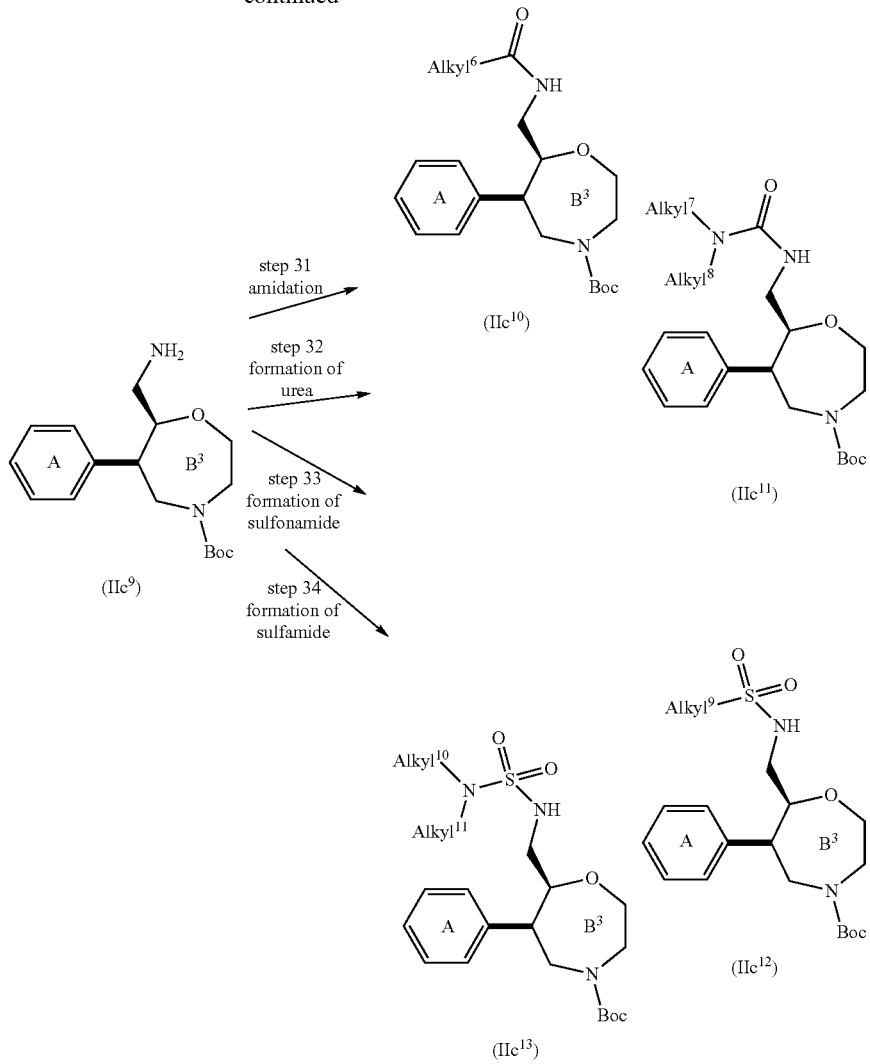

wherein L² is a leaving group, Alkyl⁵, Alkyl⁶ and Alkyl⁹ are each a $C_{1-6}$ alkyl group optionally having substituent(s), Alkyl⁷, Alkyl⁸, Alkyl¹⁰ and Alkyl¹¹ are each a hydrogen atom or a $C_{1-6}$ alkyl group optionally having substituent(s), and other symbols are each as defined above.

In Step 23, compound (IIc³) can be prepared by removing the N-benzyl group of compound (IIc¹), and then subjecting the resulting compound to protection by Boc group. The "removal of the benzyl group" and "protection by Boc group" can be performed, for example, according to the method selected from the methods described in Greene's protective groups in organic synthesis 4th edition (Wiley-International Publication).

In Step 24, compound (IIc⁴) can be prepared by removing PRG² of compound (IIc³). The "removal of PRG²" can be performed, for example, according to the method selected from the methods described in the aforementioned "Greene's protective groups in organic synthesis 4th edition". When the removal of "PRG²" proceeds simultaneously in Step 23, this step may be omitted.

In Step 25, compound (IIc⁵) can be prepared by converting the hydroxyl group presented in the side chain of compound (IIc⁴) to a sulfone group. The "conversion to the sulfone group" can be performed, for example, in the same manner as in the aforementioned Steps 11-13.

Compound (IIc⁹) can be prepared, for example, from the azide derivative (IIc⁷) or the phthalimide derivative (IIc⁸).

The "azide derivative (IIc⁷)" can be prepared by, in Step 26, converting the hydroxyl group presented in the side chain of compound (IIc⁴) to a leaving group L², and then, in Step 27, subjecting the resulting compound to azidation. Examples of the leaving group L² include those similar to the aforementioned L¹, and a methanesulfonyloxy group, a chlorine atom and the like are preferable. The "azidation" is performed using an azidating agent such as sodium azide, trimethylsilylazide and the like.

In Step 29, the "phthalimide derivative (IIc⁸)" can be prepared, for example, according to the Mitsunobu reaction described in Bioorganic and Medicinal Chemistry Letters, 19 (8), 2244-2248 (2009). The "phthalimide derivative (IIc⁸)" can also be prepared, for example, by reacting compound (IIc⁶) with potassium phthalimide.

In Step 28, Compound (IIc⁹) can be prepared by reducing the azide group of the azide derivative (IIc⁷). The "reduction of the azide group" can be performed, for example, in the same reaction conditions as in Step 9, or according to the Staudinger reaction described in Tetrahedron, 48, 1353-1406 (1992). In Step 30, compound (IIc$^9$) can also be prepared by subjecting the phthalimide derivative (IIc$^8$) to cleavage. The step can be performed, for example, according to the method described in Journal of Organic Chemistry, 43, 2320 (1978).

In Step 31, compound) (IIc$^{10}$) can be prepared by subjecting compound (IIc$^9$) to amidation. The "amidation" can be performed according to a method known per se, for example, a method using a reactive derivative such as an acid halide, an acid azide, an acid anhydride and the like; condensation of a carboxylic acid in the presence of a condensing agent such as dicyclohexylcarbodiimide, 1-ethyl-3-(3-dimethylaminopropyl)carbodiimide, carbonyldiimidazole and the like, and the like.

In Step 32, compound (IIc$^{11}$) can be prepared by subjecting compound (IIc$^9$) to formation of urea. The "formation of urea" can be performed according to a method known per se, for example, a reaction with an alkylisocyanate; the method via a phenylcarbamate, which is described in Journal of Medicinal Chemistry, 36, 2984-2997, (1993); and the like. Among them, for the preparation of a terminal-unsubstituted urea, trimethylsilyl isocyanate is preferably used.

In Step 33, compound (IIc$^{12}$) can be prepared by subjecting compound (IIc$^9$) to formation of sulfonamide. The "formation of sulfonamide" can be performed according to a method known per se, for example, the reaction with sulfonyl chloride in the presence of a base. Examples of the "base" include those similar to the base exemplified in Step 5. Among them, a tertiary amine such as triethylamine and the like is preferable.

In Step 34, compound (IIc$^{13}$) can be prepared by subjecting compound (IIc$^9$) to formation of sulfamide. The "formation of sulfamide" can be performed, for example, according to the condensation with sulfamoyl chloride, which is described in WO 2007/049041; the method using N-(tert-butoxycarbonyl)-N-[4-(dimethylazaniumylidene)-1,4-dihydropyridin-1-ylsulfonyl]azanide, which is described in Organic Letters, 3 (14), 2241-2243 (2001); and the like.

[Preparation of Compound (Id)]

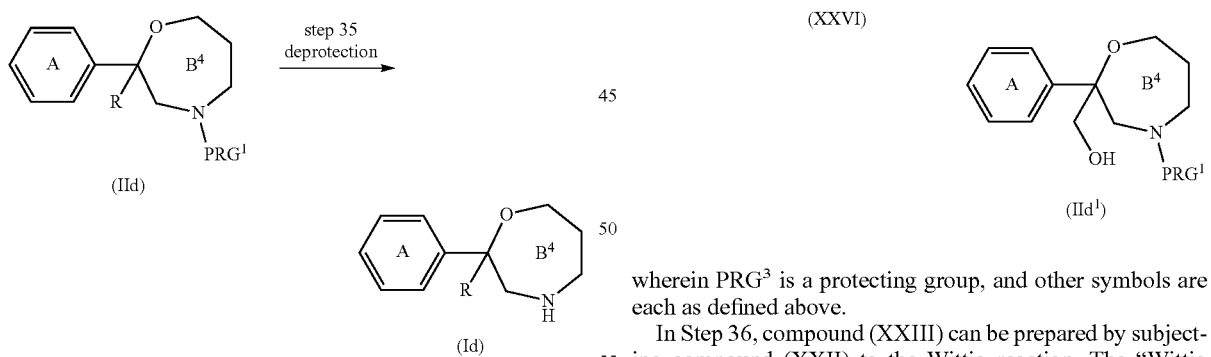

wherein each symbol is as defined above.

In Step 35, compound (1d) can be prepared, for example, by deprotecting compound (IId). Examples of the "protecting group" for PRG$^1$ include those similar to the protecting group exemplified in Step 1. Among them, tert-butoxycarbonyl (Boc) group and the like are preferable. Step 35 can be performed under the same reaction conditions as in Step 1 or reaction conditions similar thereto.

Compound (IId$^1$) (R is —CH$_2$OH) which is encompassed in compound (IId) can be prepared, for example, according to the following method.

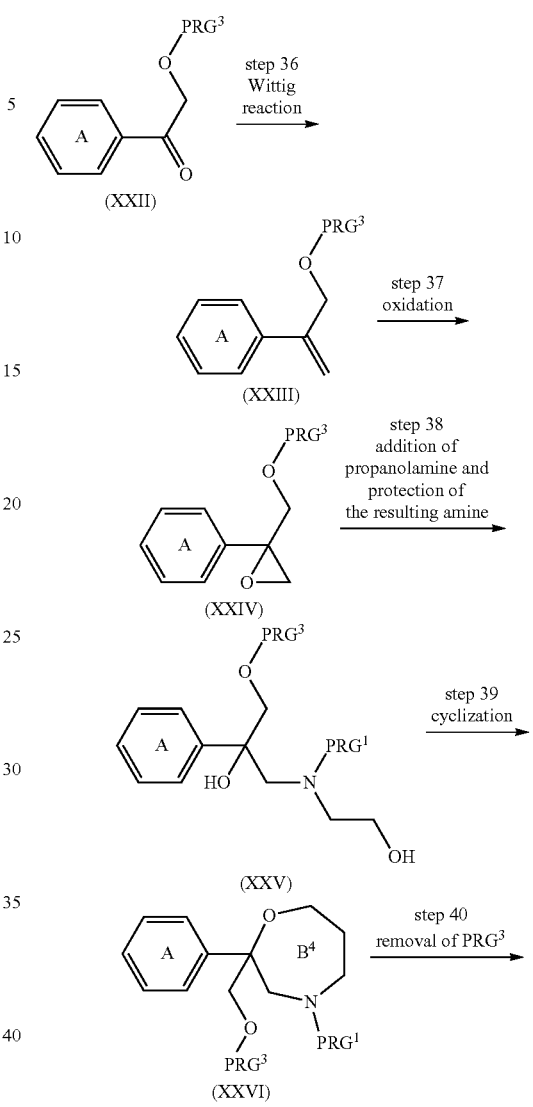

wherein PRG$^3$ is a protecting group, and other symbols are each as defined above.

In Step 36, compound (XXIII) can be prepared by subjecting compound (XXII) to the Wittig reaction. The "Wittig reaction" can be performed according to a method known per se, for example, the method described in Tetrahedron, 62 (17), 4120-4127 (2006).

In Step 37, compound (XXIV) can be prepared by oxidizing compound (XXIII). The "oxidation" can be performed using a known oxidant, for example, an organic peroxide such as aqueous hydrogen peroxide, tert-butylhydroperoxide and the like, a peracid such as peracetic acid, m-chloroperbenzoic acid and the like, and the like. For example, when m-chloroperbenzoic acid is used, the "oxidation" can be performed according to the conditions described in European Journal of Organic Chemistry, 2, 489-497 (2006).

In Step 38, compound (XXV) can be prepared by subjecting compound (XXIV) to addition of propanolamine, and then protecting the resulting amine. The "addition of propanolamine" can be performed, for example, according to the conditions described in Tetrahedron: Asymmetry, 16, 2249-2256 (2005). Examples of the protecting group and introduction method used for the "protection of the resulting amine" include those exemplified in Step 1.

In Step 39, compound (XXVI) can be prepared by subjecting compound (XXV) to an intramolecular cyclization reaction. This reaction is generally performed under dehydrating conditions. Examples of the conditions include a condition in the presence of a mineral acid such as sulfuric acid, phosphoric acid and the like; a condition in the presence of a dehydrating reagent such as thionyl chloride, phosphorus oxychloride and the like; or the condition employed in the Mitsunobu reaction. Among them, the condition employed in the Mitsunobu reaction is preferable. The "Mitsunobu reaction" can be performed, for example, according to the method described in Organic Reactions, 42, 335-656 (1992). Examples of the reagent to be used include those described in the aforementioned "Organic Reactions". Among them, cyanomethylenetributylphosphorane, which is known as the Tsunoda reagent, is preferable.

In Step 40, compound (IId$^1$) can be prepared by removing "PRG$^3$" of compound (XXVI). Examples of "PRG$^3$" and deprotection thereof include the hydroxyl-protecting group and deprotection thereof, which are described in Greene's protective groups in organic synthesis 4$^{th}$ edition (Wiley-International Publication). Preferred is deprotection that does not adversely influence the co-presenting "PRG$^1$". For example, when "PRG$^1$" is a Boc group, and "PRG$^3$" is a p-methoxyphenyl group or a p-methoxybenzyl group, "PRG$^3$" can be removed using a reagent such as cerium ammonium nitrate, and the reagent does not adversely influence the "Boc group" that is co-present.

Compounds (IId$^2$) (R is —CH$_2$Phthalimide), (IId$^3$) (R is —CH$_2$NH$_2$) and (IId$^4$) (R is —CH$_2$NHSO$_2$Alkyl$^{12}$) which are encompassed in compound (IId) can be prepared, for example, from compound (IId$^1$) according to the following method.

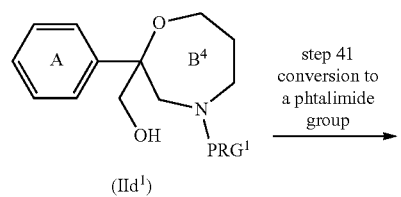

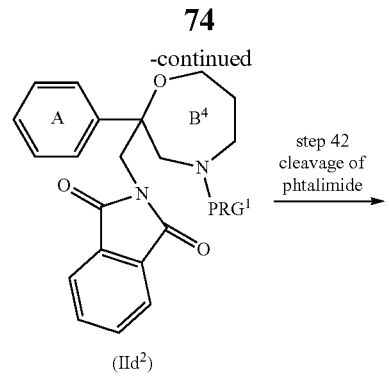

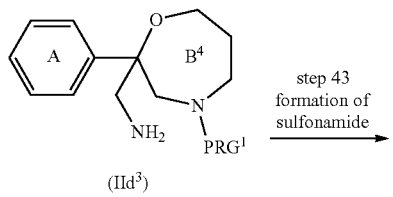

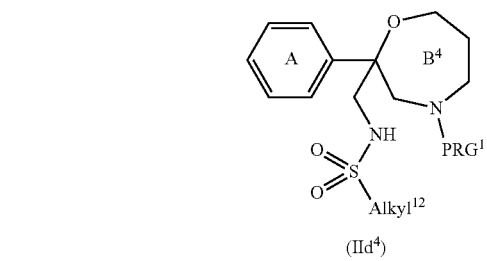

wherein Alkyl$^{12}$ is a C$_{1-6}$ alkyl group optionally having substituent(s), and other symbols are each as defined above.

In Step 41, compound (IId$^2$) can be prepared by converting the hydroxyl group of compound (IId$^1$) to a phthalimide group. The step can be performed, for example, in the same manner as in the aforementioned Step 29.

In Step 42, compound (IId$^3$) can be prepared by subjecting the phthalimide of compound (IId$^2$) to cleavage. The step can be performed, for example, in the same manner as in the aforementioned Step 30.

In Step 43, compound (IId$^4$) can be prepared by subjecting compound (IId$^3$) to formation of sulfonamide. The step can be performed, for example, in the same manner as in the aforementioned Step 33.

[Preparation of Compound (Ie)]

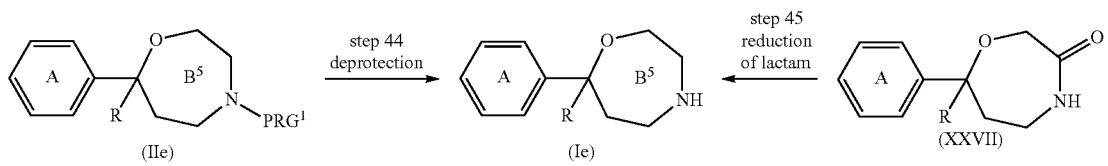

wherein each symbol is as defined above.

In Step 44, compound (Ie) can be prepared, for example, by deprotecting compound (IIe). Examples of the "protecting group" for PRG¹ include those similar to the protecting group exemplified in Step 1. Among them, tert-butoxycarbonyl (Boc) group and the like are preferable. Step 44 can be performed under the same reaction conditions as in Step 1 or reaction conditions similar thereto.

In Step 45, compound (Ie) can also be prepared, for example, by reducing the lactam compound (XXVII). The "reduction of the lactam" can be performed, for example, using a reducing agent exemplified in the aforementioned Step 9. Among them, the method using a borane complex (borane-THF complex etc.), catecholborane, aluminum hydride, lithium aluminum hydride or the like is preferable. For example, the "reduction of the lactam" can be performed, for example, according to the conditions described in Journal of Medicinal Chemistry, 39, 3539-3546 (1996) when borane-THF complex is used.

Compounds (IIe¹) (R is —CH₂OPRG⁴) and (IIe²) (R is —CH₂OH) which are encompassed in compound (IIe) can be prepared according to the method described in U.S. Pat. No. 4,499,087, for example, according to the following method.

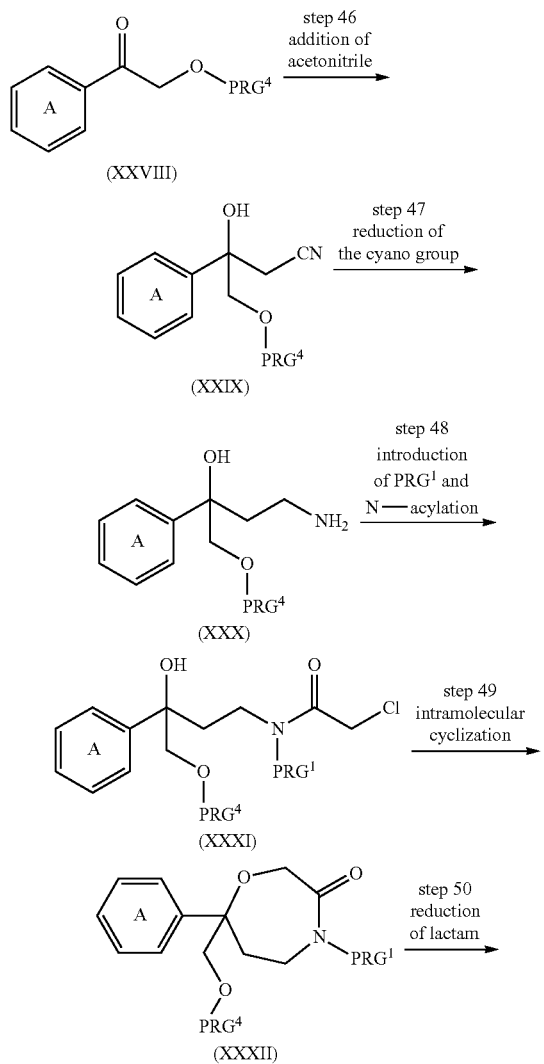

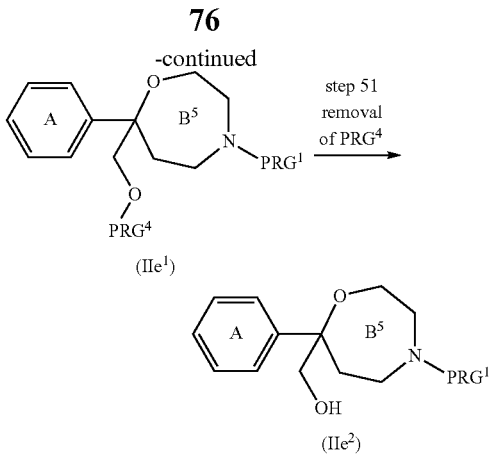

wherein PRG⁴ is a protecting group, and other symbols are each as defined above.

In Step 46, compound (XXIX) can be prepared, for example, by subjecting compound (XXVIII) to addition with acetonitrile. The step can be performed according to the method described in the aforementioned U.S. Pat. No. 4,499,087. Examples of "PRG⁴" include the hydroxyl-protecting group described in Greene's protective groups in organic synthesis 4$^{th}$ edition (Wiley-International Publication). Among them, an optionally substituted benzyl group, an optionally substituted phenyl group, silicon protecting groups such as a tert-butyldimethylsilyl group and the like, a methyl group, and the like are preferable.

In Step 47, compound (XXX) can be prepared, for example, by reducing the cyano group of compound (XXIX). The step can be performed according to a method known per se, for example, using the reducing agent exemplified in the aforementioned Step 9. Among them, the method using a borane complex (borane-THF complex etc.), catecholborane, aluminum hydride, lithium aluminum hydride, Raney-nickel or the like is preferable.

In Step 48, compound (XXXI) can be prepared, for example, by subjecting compound (XXX) to introduction of PRG¹ and N-acylation. Examples of "PRG¹" include those similar to the protecting group exemplified in Step 1. Among them, preferred is a protecting group that maintains basicity of the nitrogen atom after protection. To be specific, a benzyl group, a methyl group and the like are preferable. The "introduction of PRG¹" can be performed according to a method known per se. For example, when PRG¹ is a benzyl group, the "introduction of PRG¹" can be performed by subjecting compound (XXX) to reductive alkylation with benzaldehyde, or subjecting compound (XXX) to benzoylation and the reduction of the aminobenzoyl group. The "N-acylation" can be performed, for example, by subjecting the amine after the introduction of PRG¹ to condensation with chloroacetyl chloride. The step can be performed in the presence of a "base" exemplified in the aforementioned Step 5. The "base" is preferably an organic tertiary amine such as triethylamine and the like.

In Step 49, compound (XXXII) can be prepared, for example, by subjecting compound (XXXI) to intramolecular cyclization. The step can be performed, for example, in the same manner as in the aforementioned Step 20.

In Step 50, compound (IIe¹) can be prepared, for example, by reducing the lactam compound (XXXII). The step can be performed in the same manner as in the aforementioned Step 45, for example, by using the reducing agent exemplified in the aforementioned Step 9. Among them, the method using a borane complex (borane-THF complex etc.), catecholborane, aluminum hydride, lithium aluminum hydride or the like is preferable.

In Step 51, compound (IIe$^2$) can be prepared, for example, by removing the protecting group PRG$^4$ of compound (IIe$^1$). The step can be performed, for example, according to the method selected from the methods described in the aforementioned "Greene's protective groups in organic synthesis 4$^{th}$ edition". For example, when PRG$^4$ is a p-methoxyphenyl group, PRG$^4$ can be removed, for example, using cerium ammonium nitrate. The step can be performed, for example, according to the conditions described in Journal of Medicinal Chemistry, 46, 2790-2793 (2003).

Compounds (IIe$^5$) (R is —CH$_2$NHSO$_2$Alkyl$^{13}$) and (IIe$^6$) (R is —CH$_2$NHSO$_2$N(Alkyl$^{14}$)(Alkyl$^{15}$)) which are encompassed in compound (IIe) can be prepared, for example, from compound (IIe$^2$) according to the following method.

wherein Alkyl$^{13}$ is a C$_{1-6}$ alkyl group optionally having substituent(s), Alkyl$^{14}$ and Alkyl$^{15}$ are each a hydrogen atom or a C$_{1-6}$ alkyl group optionally having substituent(s), and other symbols are each as defined above.

Compound (IIe$^5$) can be prepared, for example, from compound (IIe$^2$) via compounds (IIe$^3$) and (IIe$^4$) according to Steps 52, 53 and 54 successively in this order. The "Steps 52, 53 and 54" can be performed in the same manner as in the aforementioned Steps 29, 30 and 33.

In Step 55, compound (IIe$^6$) can be prepared, for example, by subjecting compound (IIe$^4$) to formation of sulfamide. The step can be performed in the same manner as in the aforementioned Step 34.

[Preparation of Compound (If)]

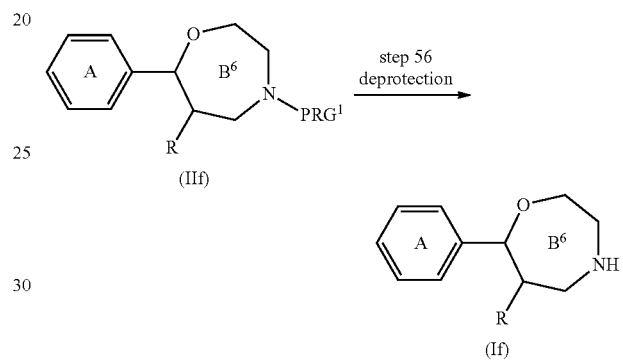

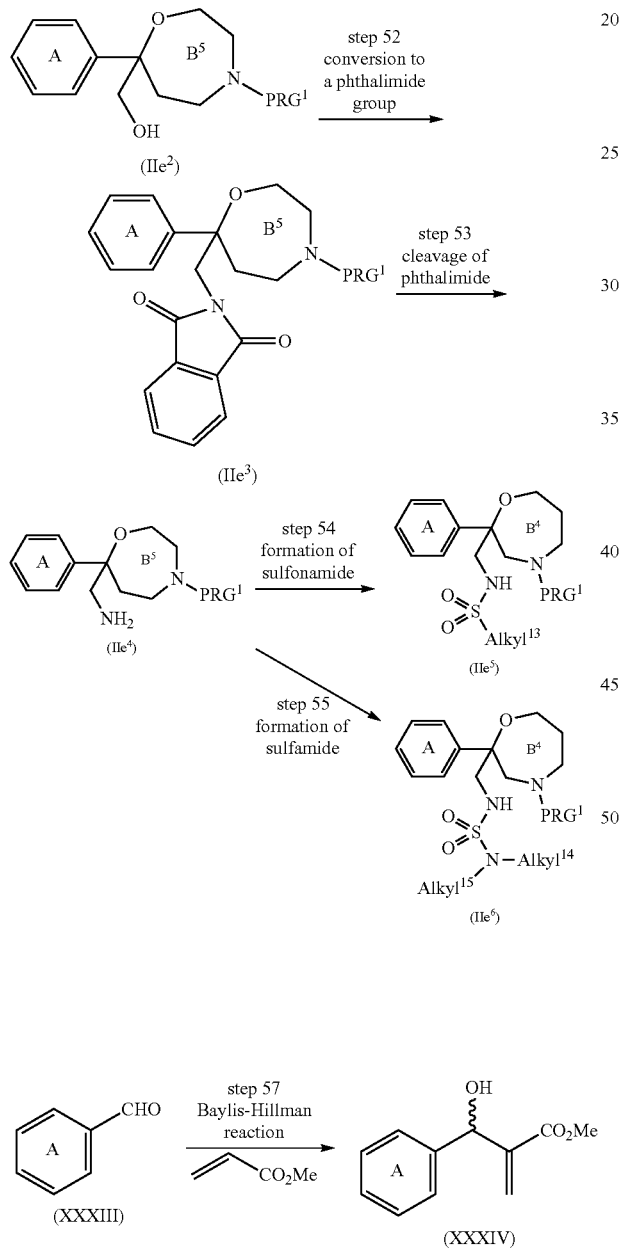

wherein each symbol is as defined above.

In Step 56, compound (If) can be prepared, for example, by deprotecting compound (IIf). Examples of the "protecting group" for PRG$^1$ include those similar to the protecting group exemplified in Step 1. Among them, a tert-butoxycarbonyl (Boc) group and the like are preferable. Step 56 can be performed under the same reaction conditions as in Step 1 or reaction conditions similar thereto.

Compounds (IIf$^1$) (PRG$^1$ is Bzl, and R is —CH$_2$OPRG$^6$), (IIf$^2$) (R is —CH$_2$OPRG$^6$), (IIf$^3$) (PRG$^1$ is Bzl, and R is —CH$_2$OH) and (IIf$^4$) (R is —CH$_2$OH) which are encompassed in compound (IIf) can be prepared, for example, according to the following method.

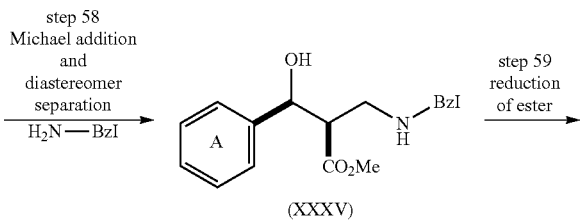

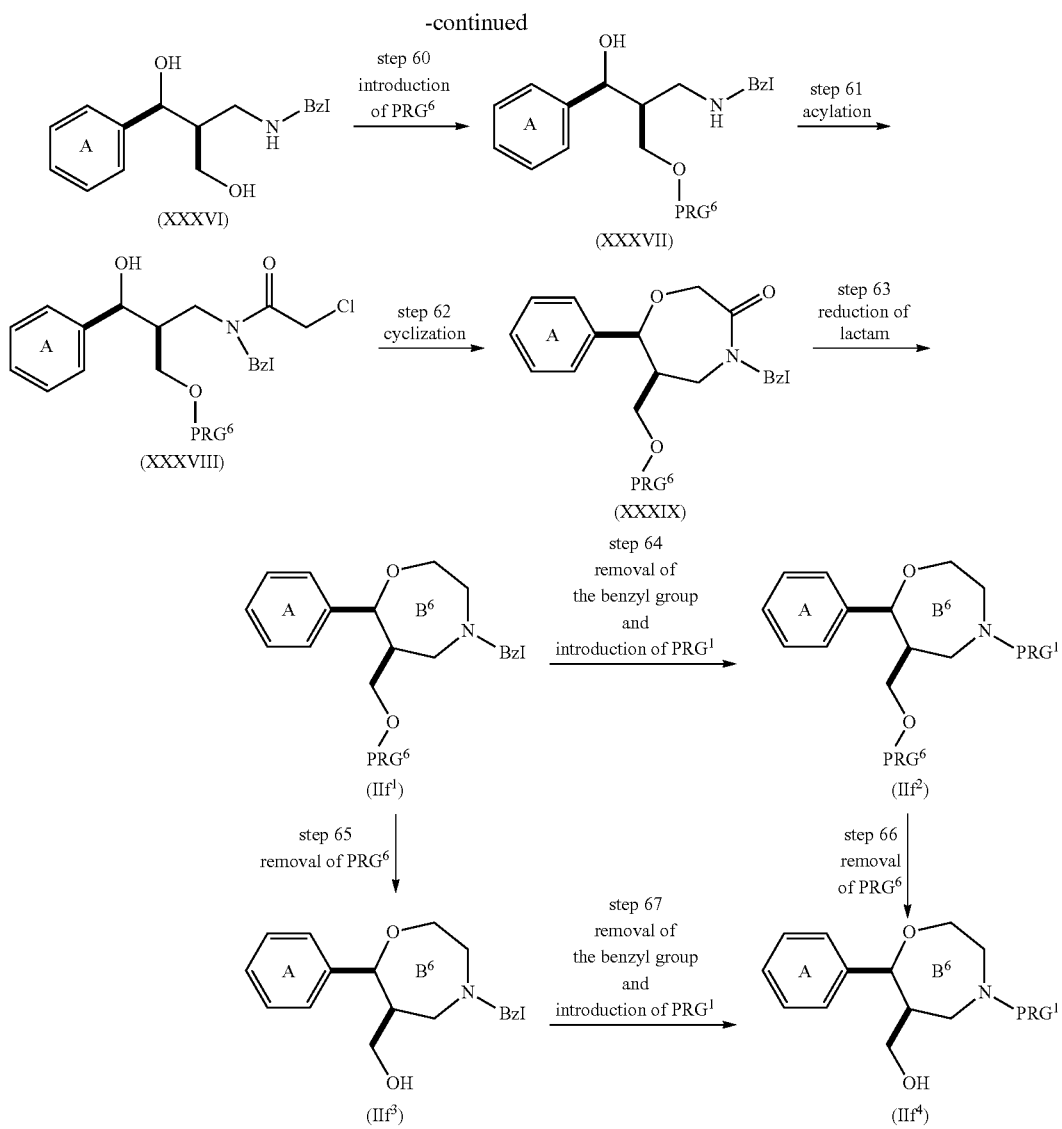

wherein PRG⁶ is a protecting group, and other symbols are each as defined above.

In Step 57, compound (XXXIV) can be prepared, for example, by subjecting compound (XXXIII) to the Baylis-Hillman reaction. The step can be performed, for example, according to the method described in Organic Reactions, 51, 201-350 (1997).

In Step 58, compound (XXXV) can be prepared, for example, by subjecting compound (XXXIV) to the Michael addition with benzylamine, and then subjecting the resulting compound to diastereomer separation. The "Michael addition with benzylamine" can be performed, for example, according to the method described in Synthesis, 6, 911-917 (2007) and the like. Other primary amine (capable of removing the alkyl moiety in the later step, for example, methylamine, (diphenylmethyl)amine, dibenzosuberylamine etc.) can also be used instead of benzylamine. The compound obtained in this step may be in the form of a mixture with the below-mentioned compound (XL). These are in the diastereomer relationship, and can be separated by an appropriate method. The "diastereomer separation" can be performed, for example, by purification method such as silica gel column chromatography and the like, recrystallization and the like. The "diastereomer separation" may be performed not only in this step but also in the below-mentioned Steps 59-67.

In Step 59, compound (XXXVI) can be prepared, for example, by reducing the ester moiety of compound (XXXV). The step can be performed, for example, using the reducing agent exemplified in Step 9. Among them, the method using a reducing agent such as lithium aluminum hydride, lithium borohydride or the like is preferable.

In Step 60, compound (XXXVII) can be prepared, for example, by introducing the protecting group PRG⁶ into the hydroxyl group of compound (XXXVI). Examples of "PRG⁶" include the hydroxyl-protecting group described in Greene's protective groups in organic synthesis 4$^{th}$ edition (Wiley-International Publication). Among them, an optionally substituted benzyl group, an optionally substituted phenyl group, silicon protecting groups such as a tert-butyldimethylsilyl group and the like, a methyl group and the like are preferable. The introduction of a protecting group can be performed according to the method selected from the methods described in the above-mentioned "Greene's protective groups in organic synthesis 4$^{th}$ edition". For example, when "PRG⁶" is a tert-butyldimethylsilyl group, the introduction can be performed, for example, according to the method described in Journal of Organic Chemistry, 71, 9628-9636 (2006).

In Step 61, compound (XXXVIII) can be prepared by subjecting compound (XXXVII) to acylation. The step can be generally performed in the presence of a "base" exemplified in Step 5, according to a method known per se. Among them, triethylamine and diisopropylethylamine are preferable.

In Step 62, compound (XXXIX) can be prepared by subjecting compound (XXXVIII) to cyclization. The step can be generally performed in the same manner as in the aforementioned Step 20, and also performed in the presence of a "base" exemplified in Step 5. As the "base", among them, sodium tert-butoxide, sodium hydride, sodium hydroxide and the like are preferable.

In Step 63, compound (IIf$^1$) can be prepared, for example, by reducing the lactam compound (XXXIX). The step can be performed, for example, using a reducing agent exemplified in the aforementioned Step 9. Among them, the method using a borane complex (borane-THF complex etc.), catecholborane, aluminum hydride, lithium aluminum hydride or the like is preferable.

In Step 64, compound (IIf$^2$) can be prepared, for example, by removing the benzyl group of compound (IIf$^1$), and then introducing the protecting group PRG$^1$. The "removal of the benzyl group" can be performed, for example, by hydrogenation using a transition metal catalyst, which is described in Journal of Medicinal Chemistry, 51, 875-896 (2008) and the like; or the method using a chlorocarbonate described in Chemical and Pharmaceutical Bulletin, 54 (11), 1535-1544 (2006) and the like, and the like. The "introduction of the protecting group PRG$^1$" can be performed according to the method selected from the methods described in the aforementioned "Greene's protective groups in organic synthesis 4$^{th}$ edition". For example, when "PRG$^1$" is a tert-butoxycarbonyl (Boc) group, the introduction can be performed according to the method described in Journal of Medicinal Chemistry, 48, 2100-2107 (2005) and the like.

In Step 65, compound (IIf$^3$) can be prepared, for example, by removing the protecting group PRG$^6$ of compound (IIf$^1$). The "removal of the protecting group PRG$^6$" can be performed according to the method selected from the methods described in the aforementioned "Greene's protective groups in organic synthesis 4$^{th}$ edition". For example, when "PRG$^6$" is a tert-butyldimethylsilyl group, the removal can be performed according to the method described in Journal of Organic Chemistry, 71, 9628-9636 (2006).

In Step 66, compound (IIf$^4$) can be prepared, for example, by removing the protecting group PRG$^6$ of compound (IIf$^2$). The step can be performed in the same manner as in the aforementioned Step 65.

In Step 67, compound (IIf$^4$) can also be prepared, for example, by removing the benzyl group of compound (IIf$^3$), and then introducing the protecting group PRG$^1$. The step can be performed in the same manner as in the aforementioned Step 64.

Compounds (IIf$^5$) (R is —CH$_2$OAlkyl$^{16}$), (IIf$^6$) (R is —CH$_2$L$^3$), (IIf$^7$) (R is —CH$_2$N$_3$), (IIf$^8$) (R is —CH$_2$NH$_2$), (IIf$^9$) (R is —CH$_2$Phthalimide) and (IIf$^{10}$) (R is —CH$_2$NHCON(Alkyl$^{17}$)(Alkyl$^{18}$)) which are encompassed in compound (IIf) can be prepared, for example, from compound (IIf$^4$) according to the following method.

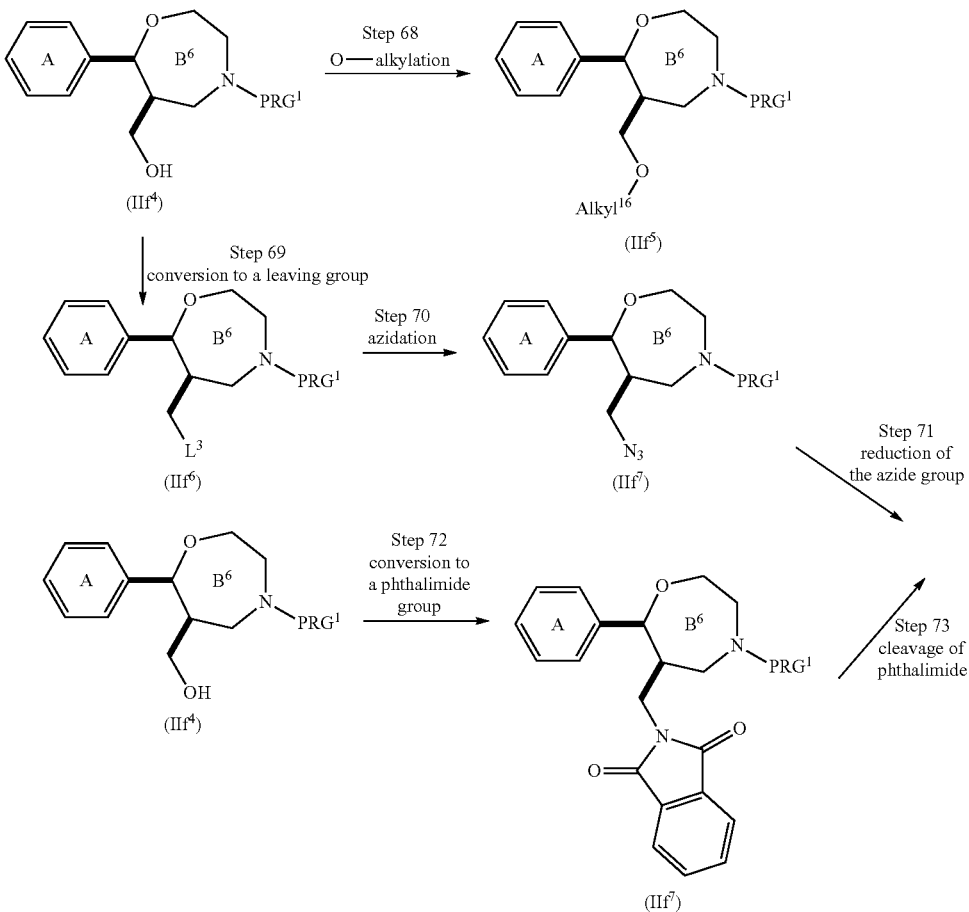

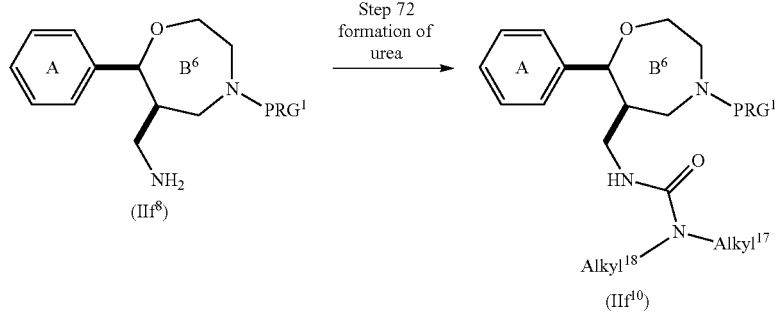

wherein Alkyl$^{16}$ is a C$_{1-6}$ alkyl group optionally having substituent(s), Alkyl$^{17}$ and Alkyl$^{18}$ are each a hydrogen atom or a C$_{1-6}$ alkyl group optionally having substituent(s), L$^3$ is a leaving group, and other symbols are each as defined above.

Steps 68, 69, 70, 71, 72, 73 and 74 shown here can be performed in the same manner as in the aforementioned Steps 3, 26, 27, 28, 29, 30 and 32.

Compounds (IIf$^{11}$) (PRG$^1$ is Bzl, and R is —CH$_2$OPRG$^6$), (IIf$^{12}$) (R is —CH$_2$OPRG$^6$), (IIf$^{13}$) (PRG$^1$ is Bzl, and R is —CH$_2$OH) and (IIf$^{14}$) (R is —CH$_2$OH) which are encompassed in compound (IIf) can be prepared, for example, according to the following method.

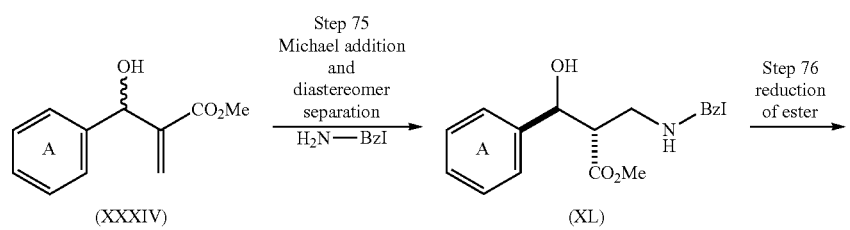

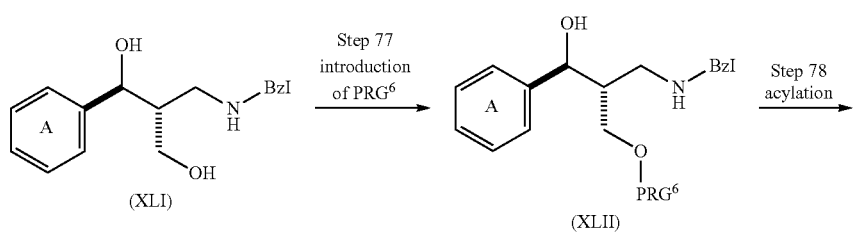

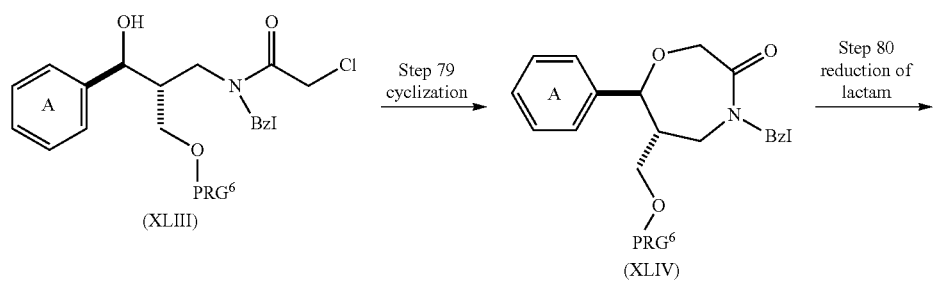

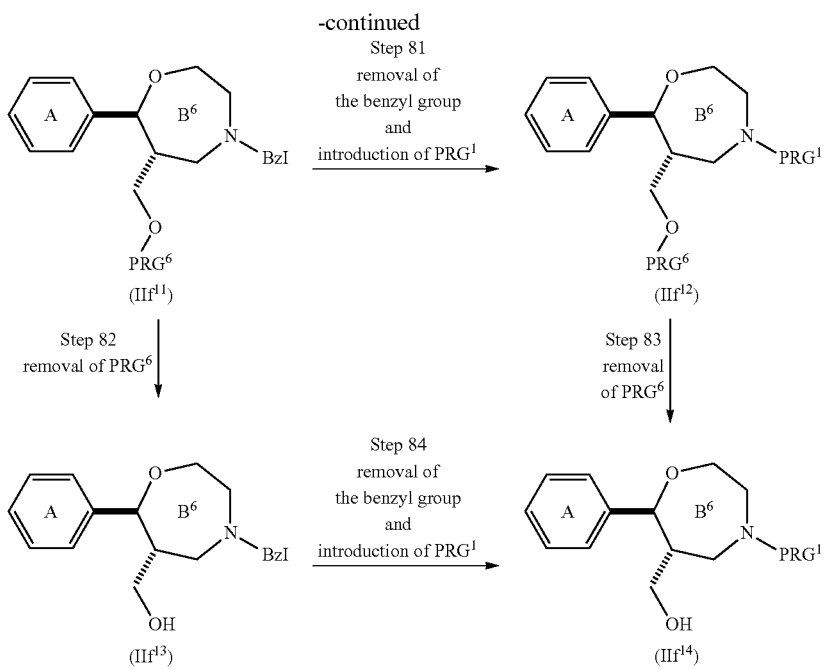

wherein each symbol is as defined above.

Steps 75, 76, 77, 78, 79, 80, 81, 82, 83 and 84 shown here can be performed in the same manner as in the aforementioned Steps 58, 59, 60, 61, 62, 63, 64, 65, 66 and 67. The compound obtained in Step 75 may be in the form of a mixture with the aforementioned compound (XXXV). These are in the diastereomer relationship, and can be separated by an appropriate method. The "diastereomer separation" may be performed not only in step 75 but also in the below-mentioned Steps 76-84.

Compounds (IIf$^{15}$) (R is —CH$_2$L$^4$), (IIf$^{16}$) (R is —CH$_2$S-Alkyl$^{19}$), (IIf$^{17}$) (R is —CH$_2$SO$_2$-Alkyl$^{19}$), (IIf$^{18}$) (R is —CH$_2$N$_3$), (IIf$^{19}$) (R is —CH$_2$NH$_2$), (IIf$^{20}$) (R is —CH$_2$Phthalimide), (IIf$^{21}$) (R is —CH$_2$NHCO(Alkyl$^{20}$)) (IIf$^{22}$) (R is —CH$_2$NHCON(Alkyl$^{21}$)(Alkyl$^{22}$)), (IIf$^{23}$) (R is —CH$_2$NHSO$_2$(Alkyl$^{23}$)) and (IIf$^{24}$) (R is —CH$_2$NHSO$_2$N(Alkyl$^{24}$)(Alkyl$^{25}$)) which are encompassed in compound (IIf) can be prepared, for example, from compound (IIf$^{14}$) according to the following method.

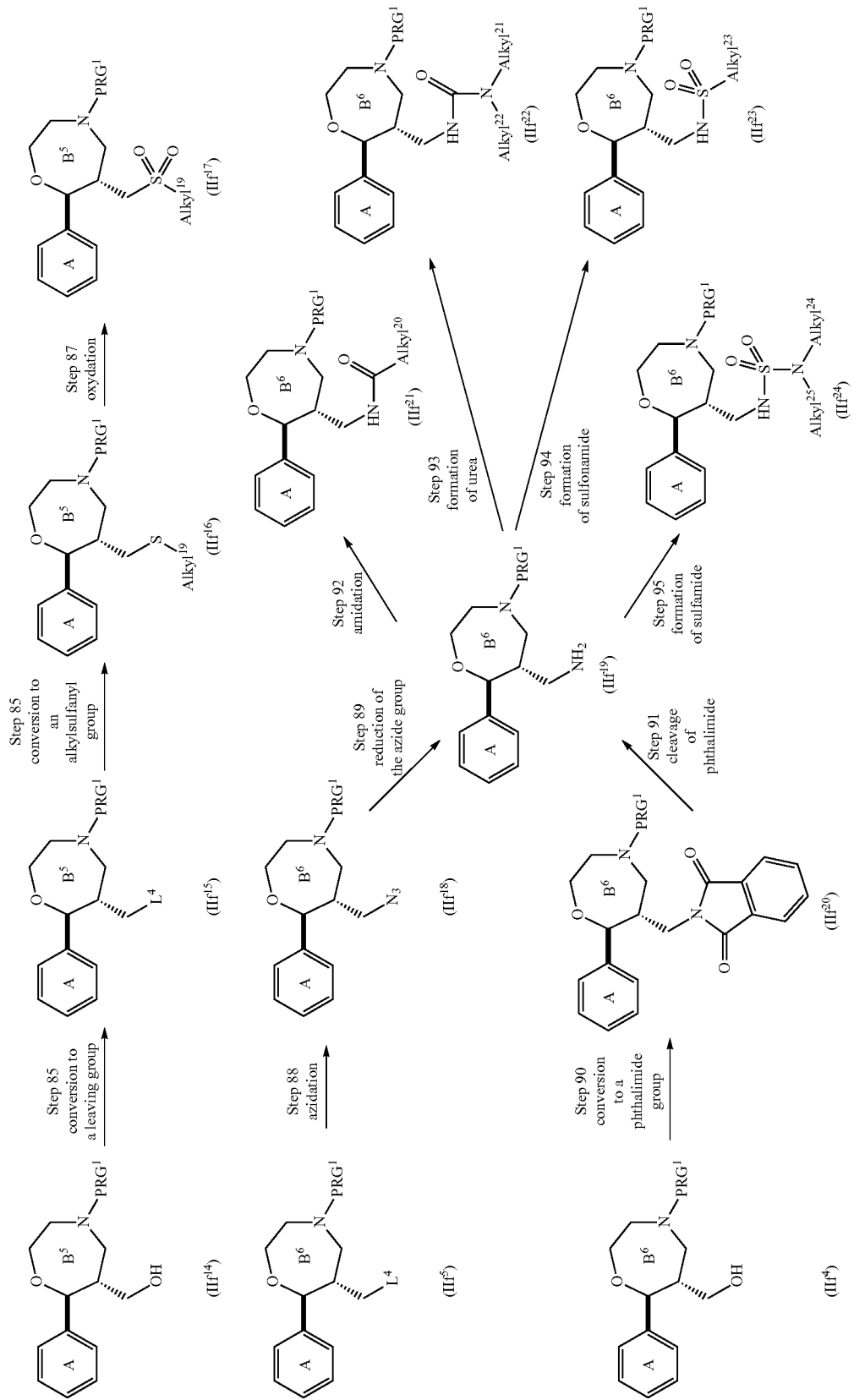

wherein Alkyl[19], Alkyl[20] and Alkyl[23] are each a $C_{1-6}$ alkyl group optionally having substituent(s), Alkyl[21], Alkyl[22], Alkyl[24] and Alkyl[25] are each a hydrogen atom or a $C_{1-6}$ alkyl group optionally having substituent(s), $L^4$ is a leaving group, and other symbols are each as defined above.

Steps 85, 86, 87, 88, 89, 90, 91, 92, 93, 94 and 95 shown here can be performed in the same manner as in the aforementioned Steps 26, 12, 13, 27, 28, 29, 30, 31, 32, 33 and 34.

[Alternative Preparation Method of Compound (XVII)]

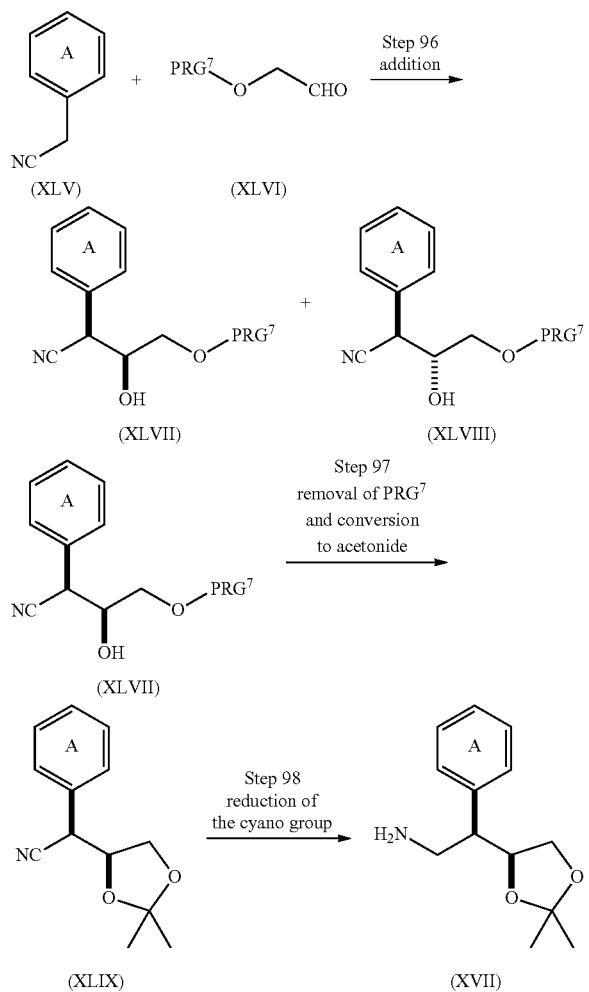

wherein PRG[7] is a protecting group, and other symbols are each as defined above.

Compound (XVII) can also be prepared, for example, according to Steps 96, 97 and 98 instead of Steps 15 and 16. Examples of the "protecting group" for PRG[7] include those similar to the protecting group exemplified in Step 1. Among them, a tert-butyldimethylsilyl (TBDMS) group, tert-butyldiphenylsilyl (TBDPS) group and the like are preferable.

In Step 96, compound (XLVII) can be prepared, for example, according to the method described in Journal of Organic Chemistry, 59, 4053-4055 (1994). The "addition" can be performed in the presence of a base. Examples of the "base" include those similar to the "base" exemplified in Step 5, and, for example, an alkali metal alkylate or alkaline earth metal alkylate (e.g., n-butyllithium, isopropylmagnesium bromide and the like) and an alkali metal arylate or alkaline earth metal arylate (e.g., phenyllithium, phenylmagnesium bromide and the like). The base to be used in Step 96 is preferably lithium diisopropylamide, lithium hexamethyldisilazide, n-butyllithium or the like. In the step, the corresponding diastereomer compound (XLVIII) may be prepared besides compound (XLVII), and it can be separated and purified by column chromatography or crystallization. Compound (XLVIII) obtained in the step can be used for the below-mentioned Step 99. The "separation and purification of the diastereomer" may be performed in Step 17, 18, 19, 20, 21 or 22, or the below-mentioned Step 97 or 98 instead of this step.

In Step 97, compound (XLIX) can be prepared by removing PRG[7] and then converting the resulting compound to the corresponding acetonide. The "removal of PRG[7]" can be performed according to the method described in Greene's protective groups in organic synthesis 4th edition (Wiley-International Publication). For example, the removal is preferably performed in the presence of p-toluenesulfonic acid, boron trifluoride, tetrabutylammonium fluoride or the like. The "conversion to the acetonide" can be performed according to the method described in the above-mentioned Greene's protective groups in organic synthesis 4th edition (Wiley-International Publication). As a reagent, for example, acetone, 2,2-dimethoxypropane, 2-methoxy-1-propene and the like are preferably used. The "removal of PRG[7]" and "conversion to the acetonide" may be performed successively in stepwisely or simultaneously in a single system.

In Step 98, compound (XVII) can be prepared by reducing the cyano group of compound (XLIX). The step can be performed in the same manner as in the aforementioned Step 47. The reagent to be used is preferably, for example, diisobutylaluminum hydride (DIBAL-H) or borane-THF complex.

[Preparation of Compounds (IIc[14]) and (IIc[15]), and Derivative Thereof]

Compound (IIc[14]) (R is —CH$_2$OPRG$^2$, and PRG[1] is Bzl) and compound (IIc[15]) (R is —CH$_2$OH, and PRG[1] is Bzl) which are encompassed in compound (IIc) can be prepared, for example, according to the following method.

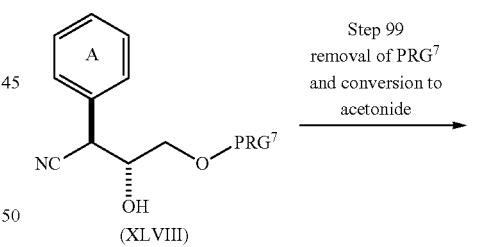

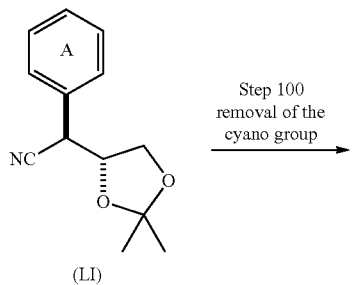

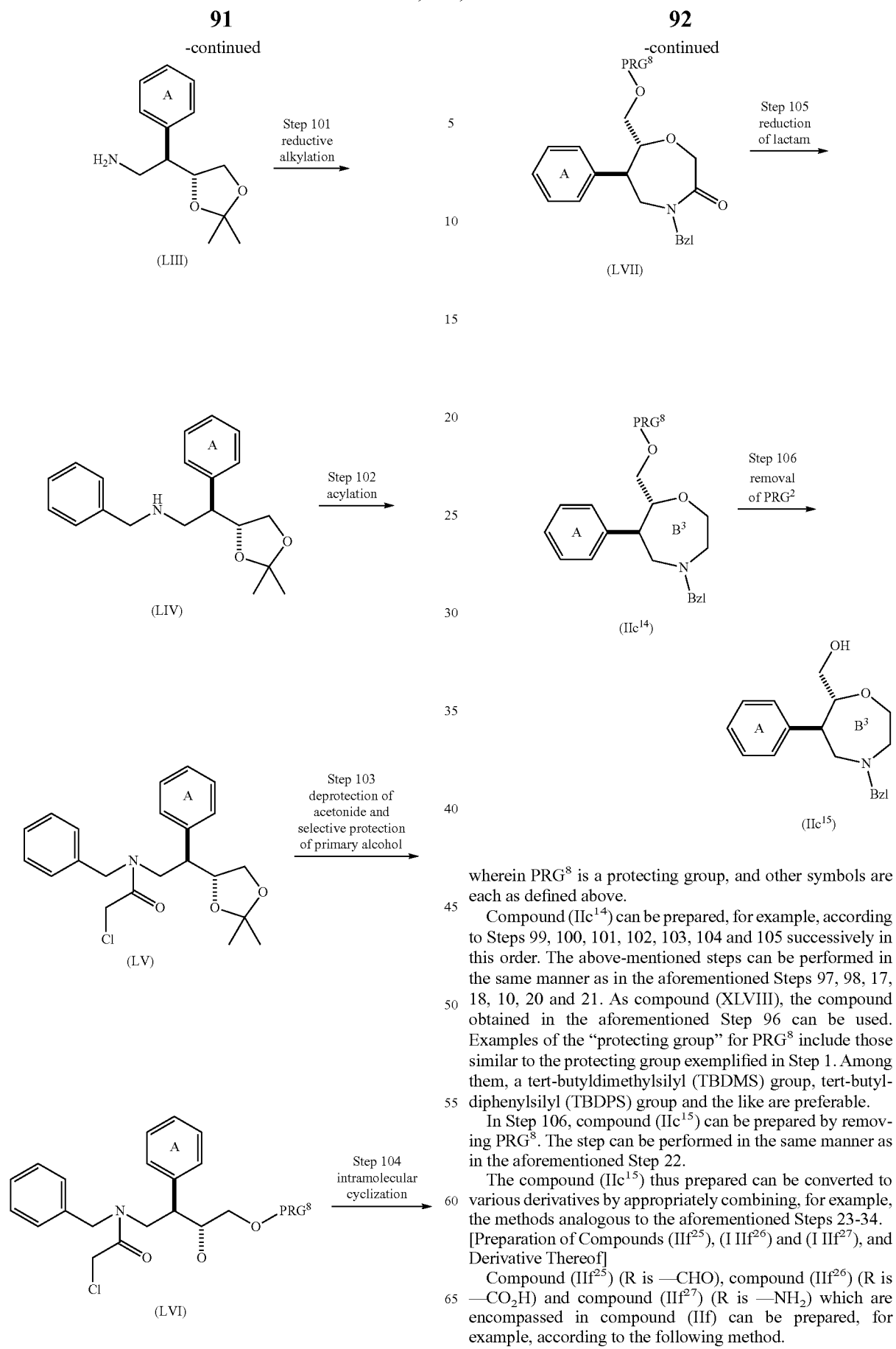

wherein PRG⁸ is a protecting group, and other symbols are each as defined above.

Compound (IIc$^{14}$) can be prepared, for example, according to Steps 99, 100, 101, 102, 103, 104 and 105 successively in this order. The above-mentioned steps can be performed in the same manner as in the aforementioned Steps 97, 98, 17, 18, 10, 20 and 21. As compound (XLVIII), the compound obtained in the aforementioned Step 96 can be used. Examples of the "protecting group" for PRG$^8$ include those similar to the protecting group exemplified in Step 1. Among them, a tert-butyldimethylsilyl (TBDMS) group, tert-butyldiphenylsilyl (TBDPS) group and the like are preferable.

In Step 106, compound (IIc$^{15}$) can be prepared by removing PRG$^8$. The step can be performed in the same manner as in the aforementioned Step 22.

The compound (IIc$^{15}$) thus prepared can be converted to various derivatives by appropriately combining, for example, the methods analogous to the aforementioned Steps 23-34.

[Preparation of Compounds (IIf$^{25}$), (I IIf$^{26}$) and (I IIf$^{27}$), and Derivative Thereof]

Compound (IIf$^{25}$) (R is —CHO), compound (IIf$^{26}$) (R is —CO$_2$H) and compound (IIf$^{27}$) (R is —NH$_2$) which are encompassed in compound (IIf) can be prepared, for example, according to the following method.

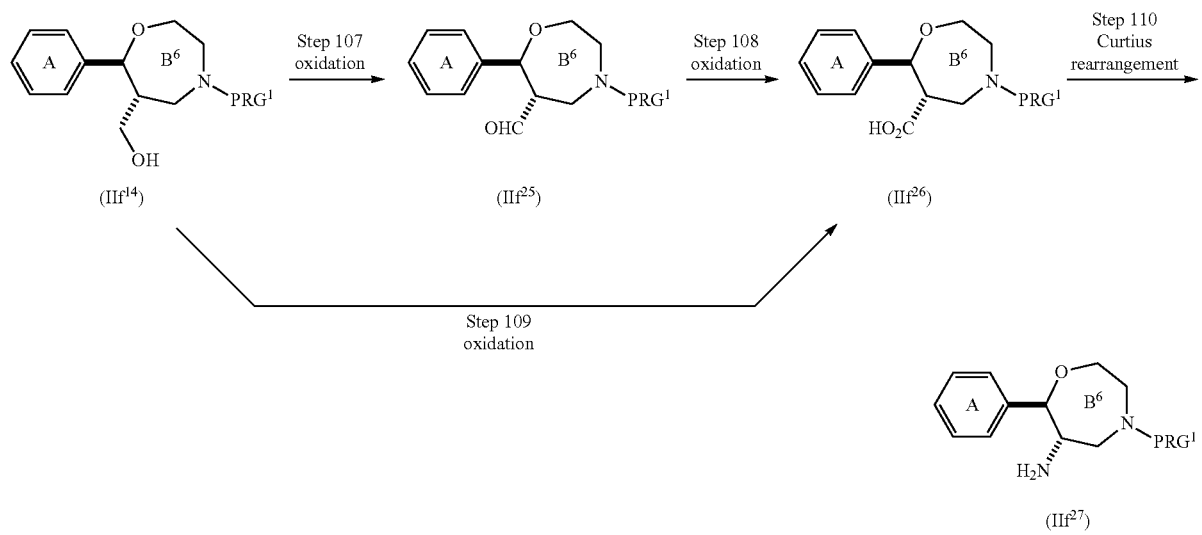

wherein each symbol is as defined above.

In Step 107, compound (IIf$^{25}$) can be prepared by oxidizing compound (IIf$^{14}$). The step can be performed, for example, according to the DMSO oxidation described in Tetrahedron, 34, 1651-1660 (1978) or the Dess-Martin oxidation described in Synthesis, 1271-1287 (1999).

In Step 108, compound (IIf$^{26}$) can be prepared by oxidizing compound (IIf$^{25}$). The step can be performed, for example, according to the method described in Journal of Medicinal Chemistry, 35, 3135-3141 (1992).

In Step 109, compound (IIf$^{26}$) can also be prepared by directly oxidizing compound (IIf$^{14}$) without via compound (IIf$^{25}$). The step can be performed, for example, according to the method using ruthenium oxide, which is described in Tetrahedron, 40, 2365-2380 (1948); or the method using chromic acid, which is described in Comprehensive Organic Synthesis, 7, 251-289 (Pergamon Press, 1991).

In Step 110, compound (IIf$^{27}$) can be prepared by subjecting compound (IIf$^{26}$) to the Curtius rearrangement. The step can be performed, for example, according to the method described in Organic Reactions, 337-349 (1946), Journal of Organic Chemistry, 69, 6184-6201 (2004), or Chemical Communication, 514 (1979).

Compound (IIf$^{27}$) obtained in the step can be subjected to amidation, or formation of urea, sulfonamide or sulfamide in the same manner as in Steps 31, 32, 33 or 34.

[Preparation of Compounds (IIf$^{28}$), (IIf$^{29}$), (IIf$^{30}$), (IIf$^{31}$), (IIf$^{32}$) and (IIf$^{33}$), and Derivative Thereof]

Compound (IIf$^{28}$) (R is —OH, and PRG$^1$ is Bzl), compound (IIf$^{29}$) (R is —OPRG$^9$, and PRG$^1$ is Bzl), compound (IIf$^{30}$) (R is —OPRG$^9$), compound (IIf$^{31}$) (R is —OH), compound (IIf$^{32}$) (R is -L$^5$) and compound (IIf$^{33}$) (R is —N$_3$) which are encompassed in compound (IIf) can be prepared, for example, according to the following method.

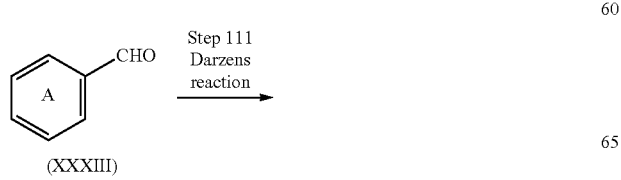

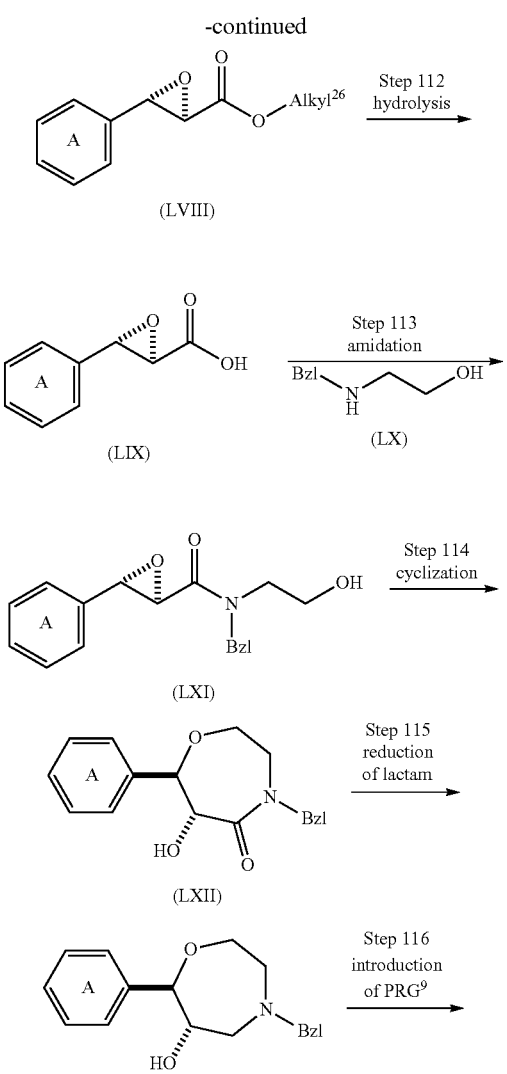

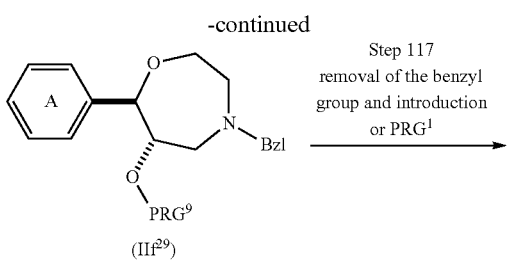

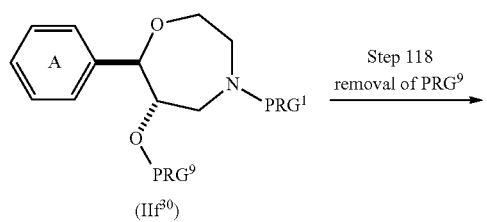

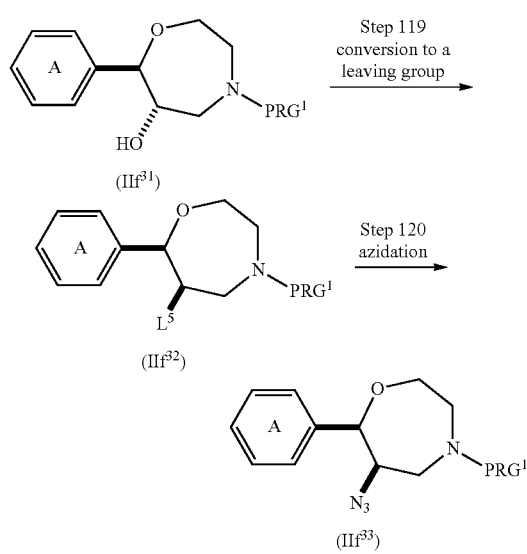

wherein Alkyl$^{26}$ is a C$_{1-6}$ alkyl group, PRG$^9$ is a protecting group, L$^5$ is a leaving group, and other symbols are each as defined above.

Compound (LXII) can be produce, for example, from compound (XXXIII) via compounds (LVIII), (LIX) and (LXI) according to Steps 111, 112, 113 and 114 successively in this order. These steps can be performed, for example, according to the method described in Synthesis, 15, 2549-2561 (2005).

Amidation in Step 113 can be also performed, for example, according to the method described in [Fundamentals and Experiments of Peptide Synthesis] (Nobuo Izumiya et al.; Maruzen Co., Ltd.). As a condensation agent to be used in the step, 4-(4,6-dimethoxy-1,3,5-triazin-2-yl)-4-methylmorpholinium chloride (DMT-MM) described in Tetrahedron, 57, 1551 (2001) can be used.

In Step 115, compound (IIf$^{28}$) can be prepared by reducing the lactam compound (LXII). The step can be performed in the same manner as in the aforementioned Step 21.

In Step 116, compound (IIf$^{29}$) can be prepared by introducing the protecting group PRG$^9$. Examples of the "protecting group" for PRG$^9$ include those similar to the protecting group exemplified in Step 1. Among them, a tert-butyldimethylsilyl (TBDMS) group, tert-butyldiphenylsilyl (TBDPS) group and the like are preferable. The step can be performed in the same manner as in the aforementioned Step 60.

In Step 117, compound (IIf$^{30}$) can be prepared by removing the benzyl group, and then introducing PRG$^1$. The step can be performed in the same manner as in the aforementioned Step 64.

In Step 118, compound (IIf$^{31}$) can be prepared by removing PRG$^9$. The step can be performed in the same manner as in the aforementioned Step 65. Compound (IIf$^{31}$) obtained in the step can be subjected to inversion of configuration on the carbon atom which the hydroxyl group is bonded to, according to the method described in Organic Reactions, 42, 335-656 (1992), and the resulting inverted compound may be used for Step 120. Compound (IIf$^{31}$) and the resulting inverted compound thereof can also be, for example, converted to the corresponding ether in the same manner as in the aforementioned Step 3.

In Step 119, compound (IIf$^{32}$) can be prepared by converting the hydroxy group of compound (IIf$^{31}$) to a leaving group. The step can be performed in the same manner as in the aforementioned Step 11.

In Step 120, compound (IIf$^{33}$) can be prepared by subjecting compound (IIf$^{32}$) to azidation. The step can be performed in the same manner as in the aforementioned Step 27. In the step, the configuration on the reaction center is known to be generally inverted due to the substitution of the azide group. Compound (IIf$^{33}$) obtained in the step can also be converted to the corresponding amine, amide, urea, sulfonamide or sulfamide in the same manner as in the aforementioned Steps 28, 31, 32, 33 or 34.

[Preparation of Compounds (IIf$^{34}$), (IIf$^{35}$) and Derivative Thereof]

Compound (IIf$^{34}$) (R is —CH$_2$OH, ring B$^6$ further has a hydroxy group on the 6-position), and compound (IIf$^{35}$) (R is —CH$_2$N$_3$, and ring B$^6$ further has a hydroxy group on the 6-position) which are encompassed in compound (IIf) can be prepared, for example, according to the following method.

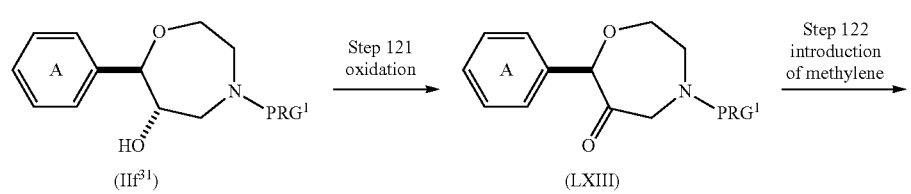

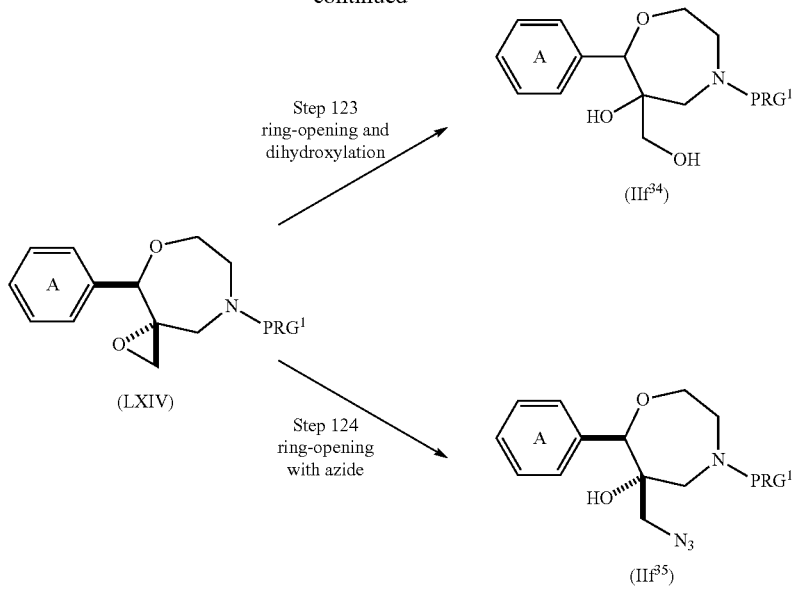

wherein each symbol is as defined above.

In Step 121, compound (LXIII) can be prepared by oxidizing the hydroxyl group of compound (IIf$^{31}$). The step can be performed in the same manner as in the aforementioned Step 107.

In Step 122, compound (LXIV) can be prepared by introducing methylene into the carbonyl group of compound (LXIII). The step can be performed, for example, according to the method described in Tetrahedron, 57, 8983-8988 (2001) or Chemical Reviews, 97, 2341-2372 (1997).

In Step 123, compound (IIf$^{34}$) can be prepared by subjecting the epoxy group of compound (LXIV) to a ring-opening reaction and dihydroxylation. The step can be performed, for example, according to the method described in Angewandte Chemie International Edition, 44, 734-737 (2005).

In Step 124, compound (IIf$^{35}$) can be prepared by subjecting the epoxy group of compound (LXIV) to a ring-opening reaction with an azide. The step can be performed, for example, according to the method described in Synthesis, 19, 3108-3120 (2008). Compound (IIf$^{35}$) obtained in the step can be converted to the corresponding amine, amide, urea, sulfonamide or sulfamide in the same manner as in the aforementioned Step 28, 31, 32, 33 or 34.

[Conversion of R Group in Compound (Ia), (Ib), (Ic), (Id), (Ie) and (If) to Alcohol, Amine, Azide, Ether, Thioether, Sulfone, Amide, Urea, Sulfonamide, Sulfamide, Ester or Carboxylic Acid]

The construction method of each R group shown in the preparation of the above-mentioned compounds (IIa)-(IIf) can also be applied to construction of any R group of compounds (IIa)-(IIf), as long as it is chemically acceptable. That is, the method of conversion of each R group shown in the preparation of the above-mentioned compounds (IIa)-(IIf) to the corresponding alcohol, amine, azide, ether, thioether, sulfone, amide, urea, sulfonamide, sulfamide, ester or carboxylic acid can be used for any of the preparation of compounds (IIa)-(IIf).

After obtaining the corresponding compounds (IIa)-(IIf), the object compounds (Ia)-(If) can be prepared, respectively, according to the aforementioned Steps 1, 4, 14, 35, 44 and 56.

[Addition of One Carbon to R Group in Compounds (Ia), (Ib), (Ic), (Id), (Ie) and (If)]

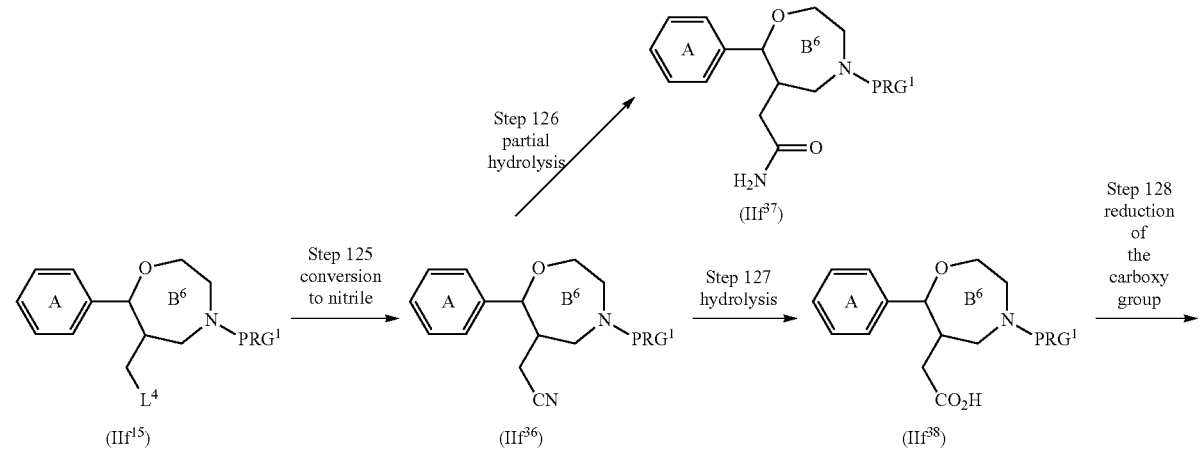

-continued

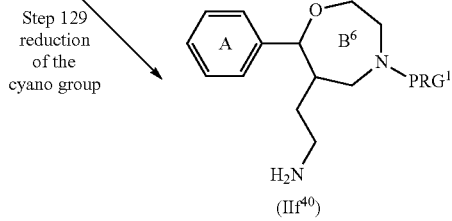

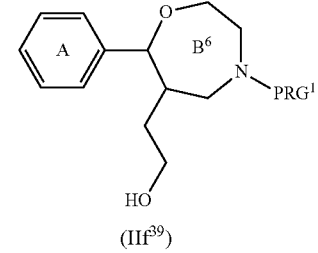

wherein each symbol is as defined above.

In Step 125, addition of one carbon to R group can be performed, for example, by converting compound (IIf$^{15}$) to the corresponding nitrile. The step can be performed, for example, according to the method described in Journal of Organic Chemistry, 25, 257 (1960).

In Step 126, the obtained compound (IIf$^{36}$) can be converted to the amide compound (IIf$^{37}$) by partial hydrolysis of the cyano group of compound (IIf$^{36}$). The step can be performed, for example, according to the method described in Journal of Organic Chemistry, 57, 4441-4444 (1992).

In Step 127, compound (IIf$^{36}$) can be converted to the carboxylic acid compound (IIf$^{38}$) by hydrolysis of the cyano group of compound (IIf$^{36}$). The step can be performed, for example, according to the method described in Journal of the American Chemical Society, 107, 7967 (1985).

In Step 128, compound (IIf$^{38}$) can be converted to the alcohol compound (IIf$^{39}$) by reduction of the carboxy group of compound (IIf$^{38}$). The step can be performed, for example, according to the method described in Organic Synthesis, 64, 104 (1985) or Organic Reactions, 6, 469 (1951).

In Step 129, compound (IIf$^{36}$) can be converted to the amine compound (IIf$^{40}$) by reduction of the cyano group of compound (IIf$^{36}$). The step can be performed in the same manner as in the aforementioned Step 9. Among them, the method described in Journal of Organic Chemistry, 51, 4856 (1986) or Journal of the American Chemical Society, 72, 876 (1950) is preferable.

The obtained carboxylic acid compound (IIf$^{38}$), alcohol compound (IIf$^{39}$), amine compound (IIf$^{40}$) can be converted according to the method described in the present specification.

The above-mentioned addition of one carbon to R group can be applied not only to compound (IIf) but also to any of compounds (IIa)-(IIe), as long as it is chemically acceptable.

After obtaining the corresponding compounds (IIa)-(IIf), the object compounds (Ia)-(If) can be prepared, respectively, according to the aforementioned Steps 1, 4, 14, 35, 44 and 56.

[Addition of Two Carbons to R Group in Compounds (Ia), (Ib), (Ic), (Id), (Ie) and (If)]

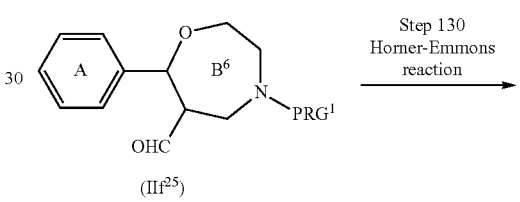

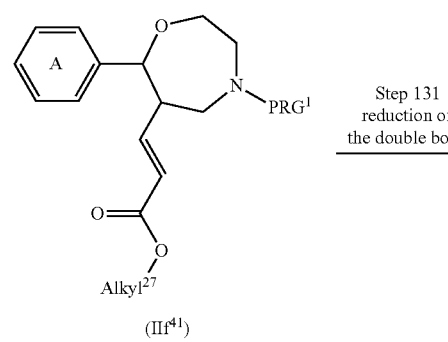

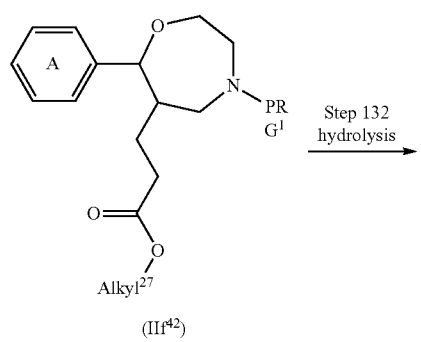

-continued

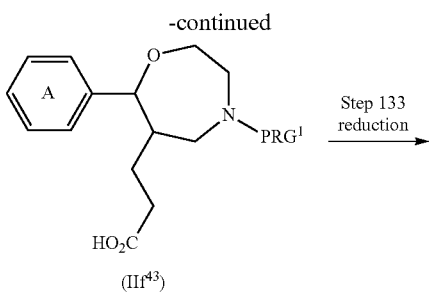

(IIf⁴³)

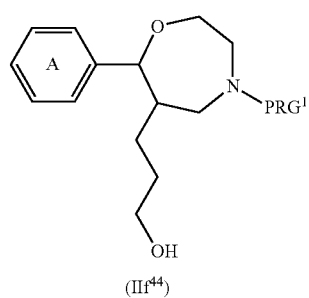

(IIf⁴⁴)

wherein Alkyl²⁷ is a $C_{1-6}$ alkyl group, and other symbols are each as defined above.

In Step 130, addition of two carbons to R group can be performed, for example, by subjecting compound (IIf²⁵) to the Horner-Emmons reaction. The step can be performed, for example, according to the method described in Chemical Reviews, 89, 863-927 (1989).

In Step 131, the obtained compound (IIf⁴¹) can be converted to the ester compound (IIf⁴²) by reduction of the double bond of compound (IIf⁴¹). The step can be performed, for example, according to the method described in Journal of Medicinal Chemistry, 35, 3135-3141 (1992) or Journal of Medicinal Chemistry, 50, 2651-2966 (2007).

In Step 132, compound (IIf⁴²) can be converted to the carboxylic acid compound (IIf⁴³) by hydrolysis. The step can be performed, for example, according to the method described in Journal of Organic Chemistry, 50, 2128 (1985).

In Step 133, compound (IIf⁴³) can be converted to the alcohol compound (IIf⁴⁴) by reduction. The step can be performed in the same manner as in the aforementioned Step 128.

Compound (IIf⁴²) can also be directly converted to the alcohol compound (IIf⁴⁴) by reduction without via compound (IIf⁴³). The "reduction of the ester" can be performed in the same manner as in the aforementioned Step 9.

The obtained carboxylic acid compound (IIf⁴³) and alcohol compound (IIf⁴⁴) can be converted according to the method described in the present specification.

The above-mentioned addition of two carbons to R group can be applied not only to compound (IIf) but also to any of compounds (IIa)-(IIe), as long as it is chemically acceptable.

After obtaining the corresponding compounds (IIa)-(IIf), the object compounds (Ia)-(If) can be prepared, respectively, according to the aforementioned Steps 1, 4, 14, 35, 44 and 56.

[Various Modification Method of R Group in Compounds (Ia), (Ib), (Ic), (Id), (Ie) and (If)]

(1) Conversion to 2-oxopyridin-1(2H)-yl, 2-oxopyridazin-2(3H)-yl, 1H-pyrazol-1-yl or 1H-indazol-1-yl

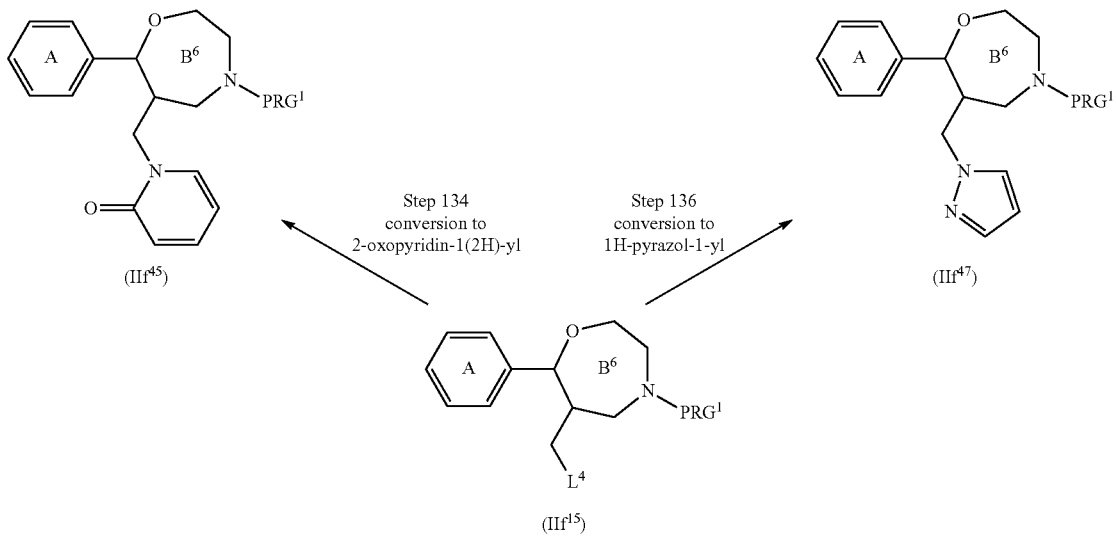

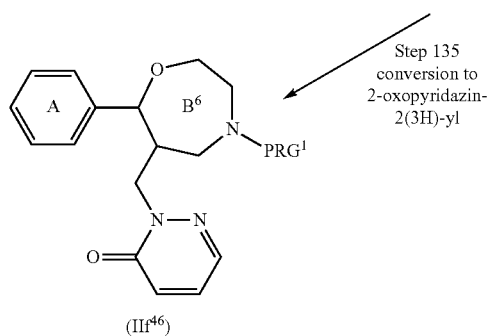

(IIf⁴⁶)

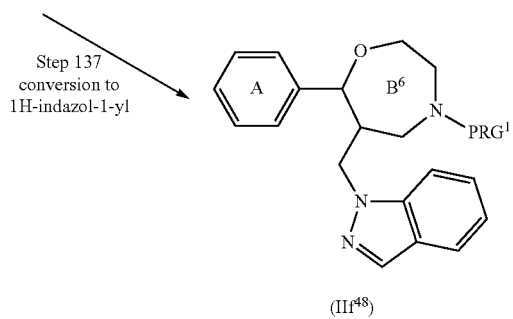

(IIf⁴⁸)

wherein each symbol is as defined above.

In Step 134, compound (IIf⁴⁵) can be prepared by converting the leaving group of compound (IIf¹⁵) to 2-oxopyridin-1(2H)-yl. The "2-oxopyridin-1(2H)-yl" optionally has additional substituent(s). The step can be performed, for example, according to the method described in Journal of Organic Chemistry, 64, 950-953 (1999), Tetrahedron, 57, 607-616 (2001). In addition, Step 134 can be performed, for example, according to the Mitsunobu reaction described in Organic Reactions, 42, 335-656 (1992).

In Step 135, compound (IIf⁴⁶) can be prepared by converting the leaving group of compound (IIf¹⁵) to 2-oxopyridazin-2(3H)-yl. The "2-oxopyridazin-2(3H)-yl" optionally has additional substituent(s). The step can be performed in the same manner as in the aforementioned Step 134.

In Step 136, compound (IIf⁴⁷) can be prepared by converting the leaving group of compound (IIf¹⁵) to 1H-pyrazol-1-yl. The "1H-pyrazol-1-yl" optionally has additional substituent(s). The step can be performed in the same manner as in the aforementioned Step 134.

In Step 137, compound (IIf⁴⁸) can be prepared by converting the leaving group of compound (IIf¹⁵) to 1H-indazol-1-yl. The "1H-indazol-1-yl" optionally has additional substituent(s). The step can be performed in the same manner as in the aforementioned Step 134.

(2) Construction of 1,2,4-oxadiazol-3-yl, 5-oxo-4,5-dihydro-1,2,4-oxadiazol-3-yl or tetrazol-5-yl

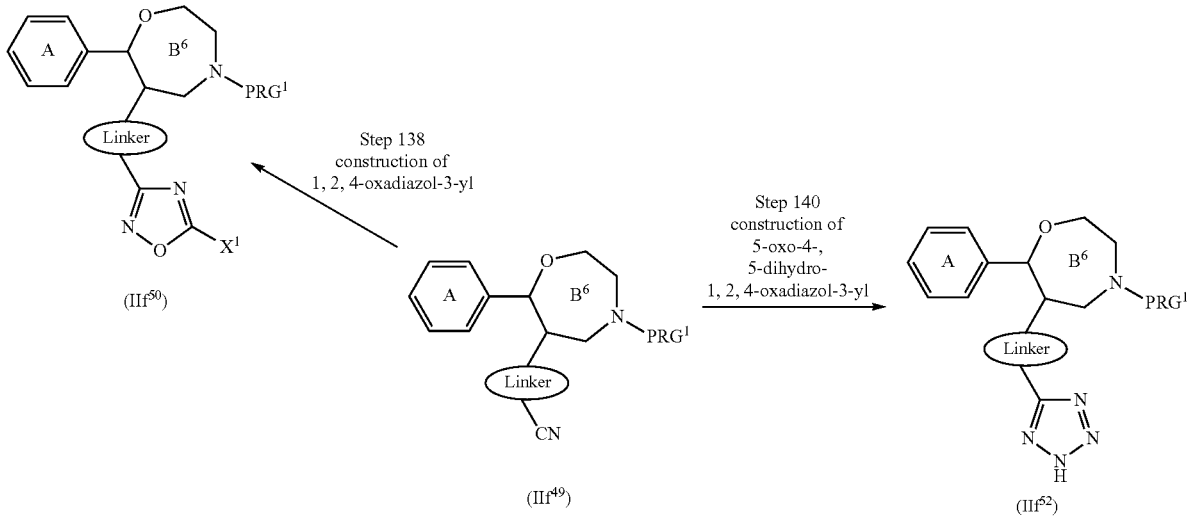

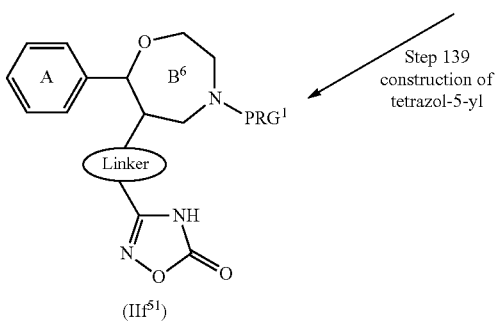

(IIf⁵¹)

wherein Linker is not particularly limited as long as

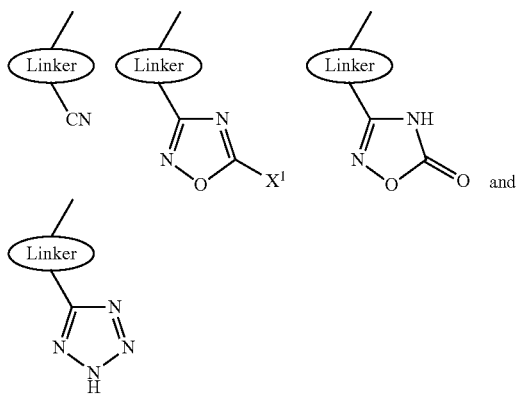

are encompassed in R, $X^1$ is a hydrogen atom, a $C_{1-6}$ alkyl group optionally having substituent(s), an aryl group optionally having substituent(s), an amide group or a carboxyl group, and other symbols are each as defined above.

In Step 138, compound ($IIIf^{50}$) can be prepared by converting the cyano group of compound ($IIIf^{49}$) to 1,2,4-oxadiazol-3-yl having $X^1$ on the 5-position. The step can be performed, for example, according to the method described in Bioorganic and Medicinal Chemistry, 12, 2815-2824 (2004).

In Step 139, compound ($IIIf^{51}$) can be prepared by converting the cyano group of compound ($IIIf^{49}$) to 5-oxo-4,5-dihydro-1,2,4-oxadiazol-3-yl. The step can be performed, for example, according to the method described in WO 2008-62905.

In Step 140, compound ($IIIf^{52}$) can be prepared by converting the cyano group of compound ($IIIf^{49}$) to tetrazol-5-yl. The step can be performed, for example, according to the method described in Advances in Heterocyclic Chemistry, 21, 323-435 (1977).

(3) Construction of 1,3-thiazol-2-yl, 4H-1,2,4-triazol-3-yl or 3-oxo-2,4-dihydro-3H-1,2,4-triazol-5-yl

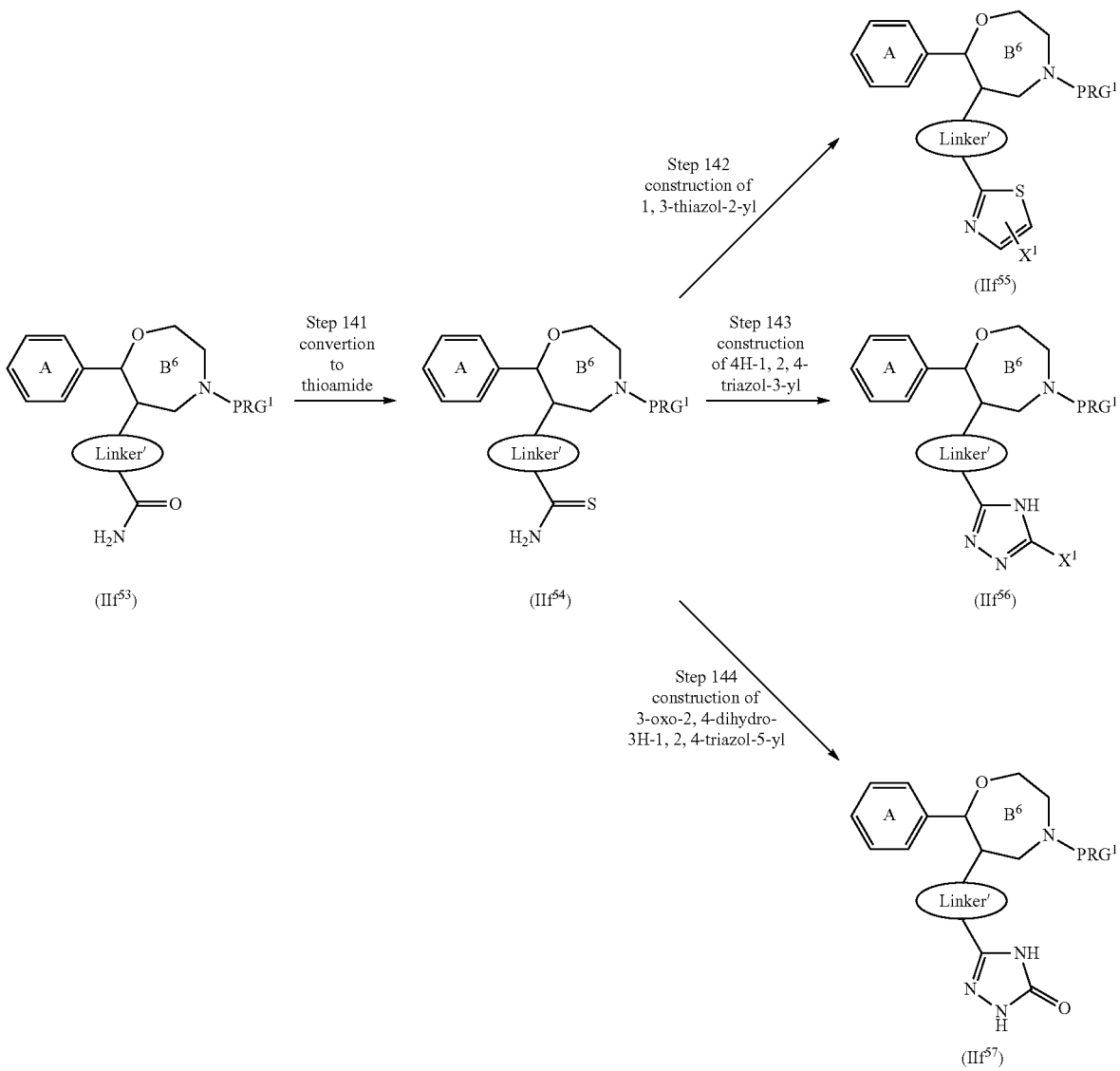

wherein Linker' is not particularly limited as long as

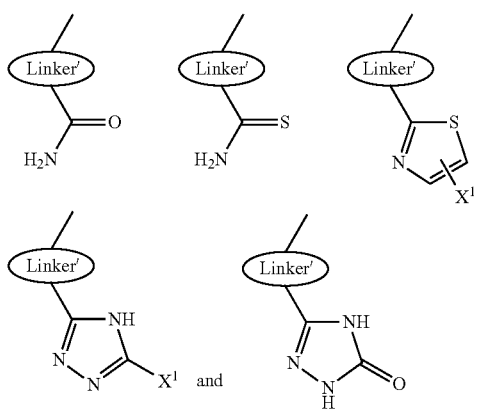

are encompassed in R, and other symbols are each as defined above.

Both 1,3-thiazol-2-yl, 4H-1,2,4-triazol-3-yl and 3-oxo-2,4-dihydro-3H-1,2,4-triazol-5-yl can be induced from thioamide.

In Step 141, compound (IIf$^{54}$) can be prepared by converting the amide group of compound (IIf$^{53}$) to a thioamide group. The step can be performed, for example, according to the method described in Journal of Organic Chemistry, 66, 3459-3466 (2001).

In Step 142, compound (IIf$^{55}$) can be prepared by converting the thioamide group of compound (IIf$^{54}$) to 1,3-thiazol-2-yl. The step can be performed, for example, according to the method described in Bioorganic and Medicinal Chemistry, 15, 6574-6595 (2007).

In Step 143, compound (IIf$^{56}$) can be prepared by converting the thioamide group of compound (IIf$^{54}$) to 4H-1,2,4-triazol-3-yl. The step can be performed, for example, according to the method described in Bioorganic and Medicinal Chemistry Letters, 14, 817-821 (2004).

In Step 144, compound (IIf$^{57}$) can be prepared by converting the thioamide group of compound (IIf$^{54}$) to 3-oxo-2,4-dihydro-3H-1,2,4-triazol-5-yl. The step can be performed, for example, according to the method described in Journal of Heterocyclic Chemistry, 18, 79-83 (1981).

(4) Construction of 2-oxo-2,3-dihydro-1,3,4-oxadiazol-5-yl

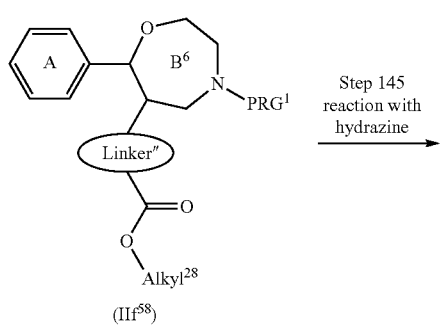

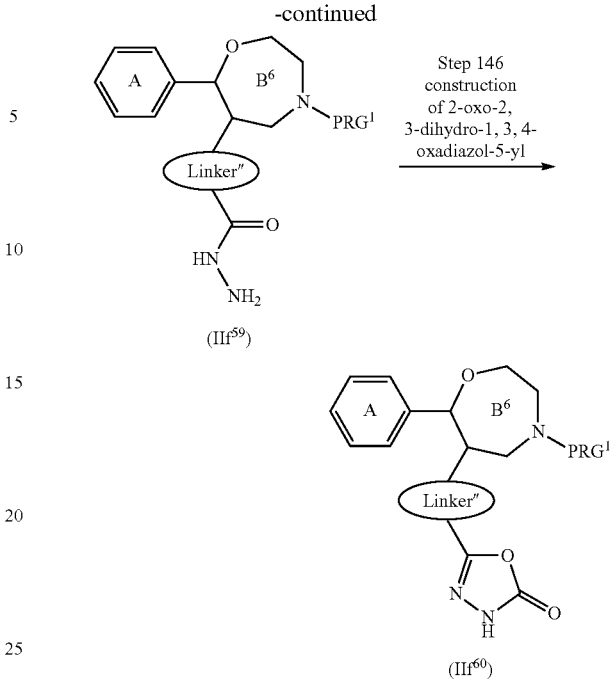

wherein Linker" is not particularly limited as long as

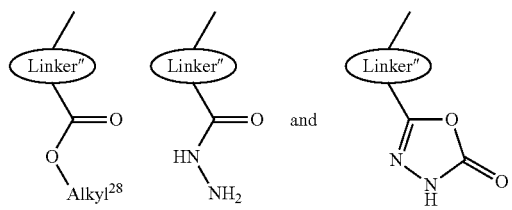

are encompassed in R, Alkyl$^{28}$ is a $C_{1-6}$ alkyl group, and other symbols are each as defined above.

In Step 145, compound (IIf$^{59}$) can be prepared by reacting compound (IIf$^{58}$) with hydrazine. The step can be performed, for example, according to the method described in Bioorganic and Medicinal Chemistry, 18, 5007-5015 (2010).

In Step 146, compound (IIf$^{60}$) can be prepared by subjecting compound (IIf$^{59}$) to cyclization. The step can be performed, for example, according to the method described in Organic Letters, 10, 1755-1758 (2008).

(5) Construction of Lactam Ring

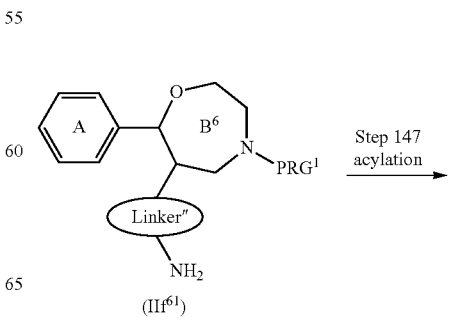

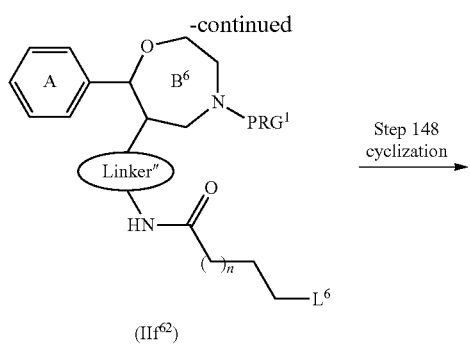

(IIf⁶²)

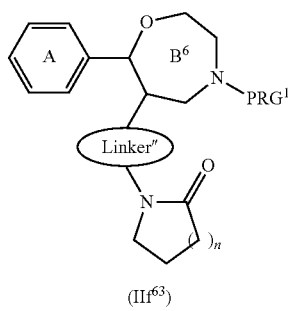

(IIf⁶³)

wherein Linker''' is not particularly limited as long as

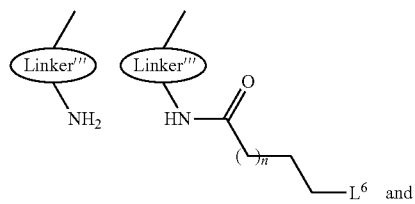

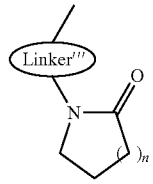

are encompassed in R, $L^6$ is a leaving group, n is any integer of 1 to 5, and other symbols are each as defined above.

In Step 147, compound (IIf⁶²) can be prepared by subjecting compound (IIf⁶¹) to acylation. The step can be performed in the same manner as in the aforementioned Step 18. For the "acylation", an acyl group having a leaving group $L^6$ at the terminal is selected. Examples of the "leaving group $L^6$" include those similar to the leaving group exemplified in the aforementioned Step 11. Among them, a chlorine atom and a bromine atom are preferable.

In Step 148, compound (IIf⁶³) can be prepared by subjecting compound (IIf⁶²) to cyclization. The step can be generally performed in the presence of a base. Examples of the "base" include those similar to the base exemplified in the aforementioned Step 5. Among them, sodium hydride, sodium tert-butoxide and sodium hydroxide are preferable.

(6) Conversion to 1,2-diol

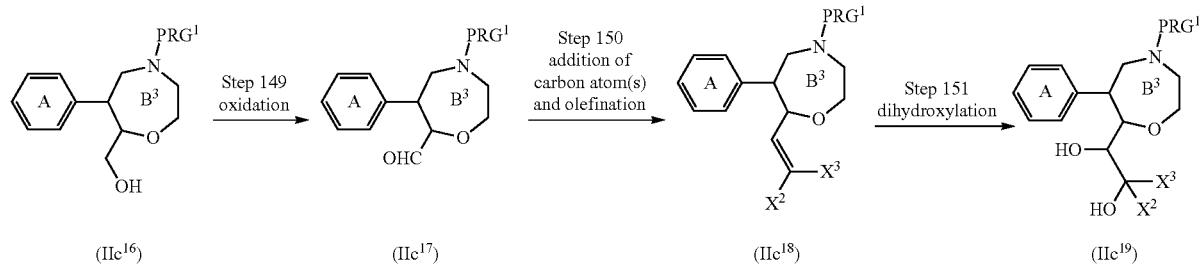

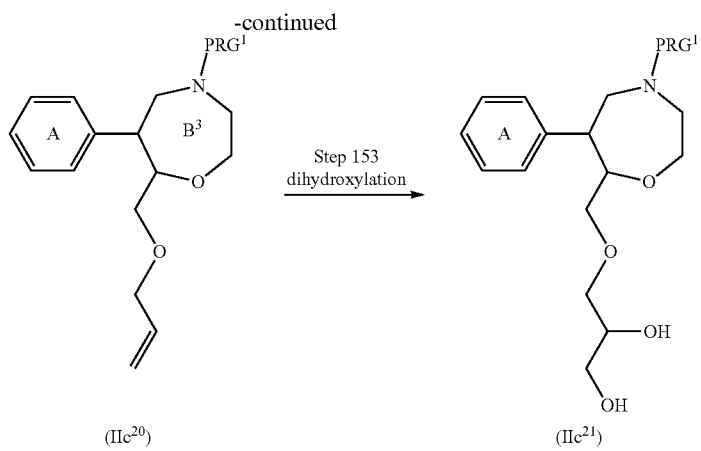

wherein $X^2$ and $X^3$ are each a hydrogen atom, a $C_{1-6}$ alkyl group optionally having substituent(s), an aryl group, a 5-membered or 6-membered aromatic heterocyclic group, and other symbols are each as defined above.

In Step 149, compound ($IIc^{17}$) can be prepared by oxidizing the hydroxyl group of compound ($IIc^{16}$). The step can be performed, for example, by DMSO oxidation such as the Swern oxidation, the Moffat oxidation, the Corey-Kim oxidation and the like, the Ley oxidation using tetrapropylammonium perruthenate (TPAP), or the oxidation using Dess-Martin reagent, and the like. The step can be performed, for example, according to the method described in Organic Reactions, 39, 297-572 (1990) for the Swern oxidation, Aldrichimica Acta, 23, 13-19 (1990) for the Ley oxidation, Journal of the American Chemical Society, 126, 320-328 (2004) for the Dess-Martin oxidation, and the like.

In Step 150, compound ($IIc^{18}$) can be prepared by subjecting compound ($IIc^{17}$) to addition of carbon(s) and olefination. The step can be performed, for example, according to the Wittig reaction, Horner-Emmons reaction, Peterson reaction and the like. The Wittig reaction can be performed, for example, according to the method described in Organic Reactions, 14, 270-490 (1965) and the like.

In Step 151, compound ($IIc^{19}$) can be prepared by subjecting compound ($IIc^{18}$) to dihydroxylation. The step can be performed, for example, according to the method using osmium tetraoxide, which is described in the Chemical Reviews, 80, 187-213 (1980). Osmium tetraoxide supported by a polymer which is described in Synthesis 45 (1989) and the like may be used as a catalyst. In addition, the asymmetric dihydroxylation described in Tetrahedron: Asymmetry 3, 1317-1349 (1992) and the like may be performed.

In Step 152, compound ($IIc^{20}$) can be prepared by subjecting compound ($IIc^{16}$) to allylation. The step can be performed, for example, according to the method described in Tetrahedron, 53, 17501-17512 (1997).

In Step 153, compound ($IIc^{21}$) can be prepared by subjecting compound ($IIc^{20}$) to dihydroxylation. The step can be performed in the same manner as in the aforementioned Step 151.

(7) Conversion to 1,2,3-Triol

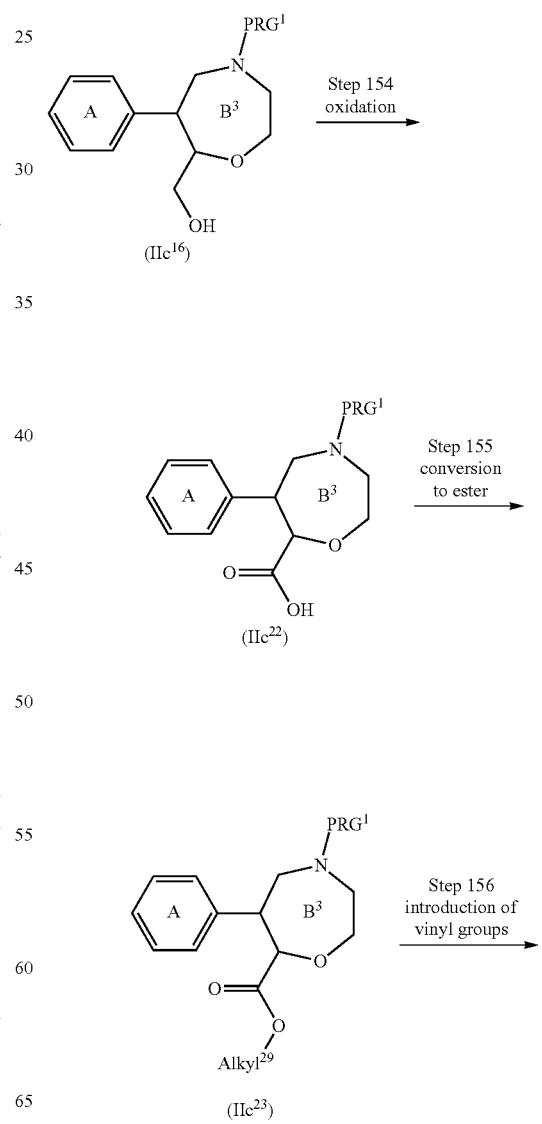

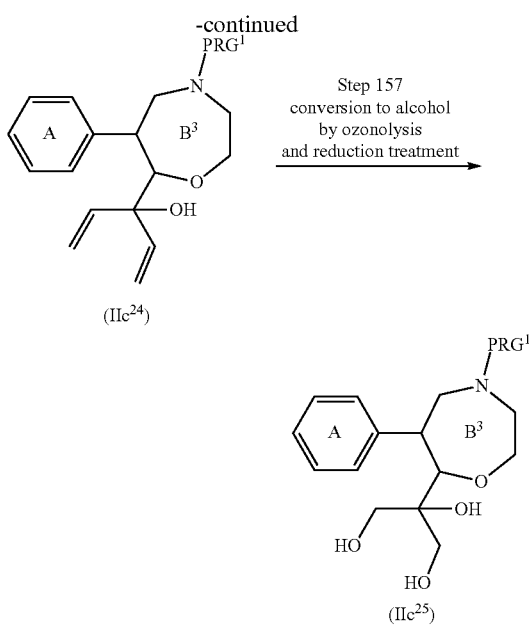

wherein Alkyl[29] is a $C_{1-6}$ alkyl group, and other symbols are each as defined above.

In Step 154, compound (IIc[22]) can be prepared by oxidizing compound (II[16]). The step can be performed, for example, according to a conventional oxidation of carboxylic acid, such as Jones oxidation and the like. Among them, the method using ruthenium catalyst, which is described in Tetrahedron Letters 33, 2307-2310 (1992) or the like is preferable. The step can be performed in the same manner as in the aforementioned Steps 107-108.

In Step 155, compound (IIc[23]) can be prepared by converting the carboxylic acid moiety of compound (II[22]) to an ester moiety. The step can be performed, for example, according to the Fischer esterification reaction described in Organic Synthesis Collective Volume 1, 241 (1941) and the like, the alkylation using an alkyl halide which is described in the Journal of Organic Chemistry, 50, 2668 (1985) and the like, or the methylation using diazomethane which is described in Journal of Organic Chemistry, 50, 2323 (1985).

In Step 156, compound (IIc[24]) can be prepared by introducing two vinyl groups into the ester group of compound (II[23]). The step can be performed by adding reacting 2 or more equivalents of a vinyl metal compound to compound (II[23]). The vinyl metal compound to be used is preferably a Grignard reagent such as vinylmagnesium bromide and the like, or vinyllithium. The step can be performed, for example, according to the method described in Journal of Organic Chemistry, 65, 5817-5822 (2000) and the like. The reaction may be performed in the presence of cerium(III) chloride which is described in Organic Letters, 3, 671-674 (2001).

In Step 157, compound (IIc[25]) can be prepared by subjecting compound (II[24]) to ozonolysis, and then treating the resulting compound with a reducing agent. The step may be performed by isolating the aldehyde intermediate produced by the ozonolysis, and then reducing the aldehyde intermediate. However, the step is preferably performed by reducing the aldehyde intermediate without isolation in the same system. Examples of the "reducing agent" include those similar to the reducing agent exemplified in Step 9. Among them, sodium borohydride is preferable. The step can be performed, for example, according to the method described in Journal of Organic Chemistry, 61, 3999-4006 (1996).

The various modification methods of R group shown in the above-mentioned (1)-(7) can also be applied to the modification of R group in each of the compounds (IIa), (IIb), (IIc), (IId), (IIe) and (IIf).

After obtaining the corresponding compounds (IIa)-(IIf), the object compounds (Ia)-(If) can be prepared, respectively, according to the aforementioned Steps 1, 4, 14, 35, 44 and 56.

When compound (I) is obtained as a free compound, it can be converted to the object salt by a method known per se or a method analogous thereto. When it is obtained as a salt, it can be converted to the object other salt by a method known per se or a method analogous thereto.

Compound (I) prepared by such method can be isolated and purified by a conventional separation means such as recrystallization, distillation, chromatography and the like.

When compound (I) contains an optical isomer, a stereoisomer, a positional isomer or a rotamer, these are also encompassed in compound (I), and each of them can be obtained as a single produce by a synthesis method and a separation method (e.g., concentration, solvent extraction, column chromatography, recrystallization etc.) known per se. For example, when compound (I) contains an optical isomer, the optical isomer resolved from the compound is also encompassed in compound (I).

The optical isomer can be prepared by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation method (e.g., a fractional recrystallization method, a chromatography method, etc.) and the like, and is subjected to a chemical treatment such as hydrolysis and the like to separate an optically active reagent moiety, whereby an optical isomer is obtained. For example, when compound (I) contains hydroxy, or primary or secondary amino in a molecule, the compound and an optically active organic acid (e.g., MTPA [α-methoxy-α-(trifluoromethyl)

phenylacetic acid], (−)-menthoxyacetic acid, etc.) and the like are subjected to condensation reaction to give diastereomers in the ester form or in the amide form, respectively. When compound (I) has a carboxylic acid group, this compound and an optically active amine or alcohol reagent are subjected to condensation reaction to give diastereomers in the amide form or in the ester form, respectively. The separated diastereomer is converted to an optical isomer of the original compound by acid hydrolysis or base hydrolysis.

The compound (I) may be a crystal. The compound (I) may be a single crystal, or a mixture of plural crystal forms. Moreover, compound (I) may be a cocrystal.

The crystal of the compound (I) can be prepared by crystallization of compound (I) according to crystallization methods known per se.

Examples of the crystallization method include a method of crystallization from a solution, a method of crystallization from vapor, a method of crystallization from the melts and the like.

The "crystallization from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, isopropyl alcohol, etc.), water and the like. These solvents are used alone or in a combination of two or more at a suitable ratio (e.g., 1:1 to 1:100 (a volume ratio)). Where necessary, a seed crystal can be used.

Examples of the "crystallization from vapor" include a vaporization method (a sealed tube method, a gas stream method), a gas phase reaction method, a chemical transportation method and the like.

Examples of the "crystallization from the melts" include a normal freezing method (a Czockralski method, a temperature gradient method and a Bridgman method, etc.), a zone melting method (a zone leveling method and a floating zone method, etc.), a special growth method (a VLS method and a liquid phase epitaxy method, etc.) and the like.

Preferable examples of the crystallization method include a method of dissolving compound (I) in a suitable solvent (e.g., alcohols such as methanol, ethanol, etc., and the like) at a temperature of 20 to 120° C., and cooling the resulting solution to a temperature not higher than the temperature of dissolution (e.g., 0 to 50° C., preferably 0 to 20° C.) and the like.

The thus obtained crystals of compound (I) can be isolated, for example, by filtration and the like.

An analysis method of the obtained crystal is generally a method of crystal analysis by powder X-ray diffraction. As a method of determining crystal orientation, a mechanical method or an optical method and the like can also be used.

The compound (I) may be a pharmaceutically acceptable cocrystal or cocrystalline salt. Here, the cocrystal or cocrystalline salt means a crystalline substance constituted by two or more kinds of specific solids at room temperature, each of which has different physical properties (e.g., structure, melting point, melting heat, hygroscopicity, solubility, stability etc.). The cocrystal or cocrystalline salt can be prepared by a cocrystallization method known per se.

The crystal of compound (I) obtained by the above-mentioned preparation has high purity, high quality, and low hygroscopicity, is not denatured even after a long-term preservation under general conditions, and is extremely superior in the stability. In addition, it is also superior in the biological properties (e.g., pharmacokinetics (absorption, distribution, metabolism, excretion), efficacy expression etc.) and is extremely useful as a pharmaceutical agent.

In the present specification, the specific rotation ($[\alpha]_D$) means, for example, a specific rotation measured using a polarimeter (JASCO, P-1030 polarimeter (No. AP-2)) and the like.

In the present specification, the melting point means a melting point measured using, for example, a micro melting point apparatus (YANACO, MP-500D), a DSC (differential scanning calorimetry) apparatus (SEIKO, EXSTAR6000) and the like.

A prodrug of compound (I) means a compound which is converted to compound (I) with a reaction due to an enzyme, an gastric acid, etc. under the physiological condition in the living body, that is, a compound which is converted to compound (I) with oxidation, reduction, hydrolysis, etc. according to an enzyme; and a compound which is converted to compound (I) by hydrolysis etc. due to gastric acid, etc. A prodrug for compound (I) may be a compound obtained by subjecting an amino group in compound (I) to an acylation, alkylation or phosphorylation [e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.]; a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation, etc.); a compound obtained by subjecting a carboxy group in compound (I) to an esterification or amidation [e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.] and the like. These compounds can be prepared from compound (I) by a method known per se.

A prodrug for compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

The compound (I) of the present invention or a salt thereof or a prodrug thereof (hereinafter sometimes to be abbreviated as the compound of the present invention) has a superior monoamine (serotonin, norepinephrine, dopamine etc.) reuptake inhibitory activity.

In addition, the compound of the present invention is low toxic and safe. Particularly, it is useful since it does not show phototoxicity.

Compound (I) or a salt thereof can also be used as a tracer in positron emission tomography (PET) once it is labeled with a positron-emitting radionuclide such as $^{11}$C, $^{18}$F, $^{15}$O, $^{13}$N and the like.

Therefore, the compound of the present invention acts as a substance having an monoamine neurotransmitter (serotonin, norepinephrine, dopamine etc.) reuptake inhibitory activity in a mammal (e.g., mouse, rat, hamster, rabbit, cat, dog, bovine, sheep, monkey, human and the like), inhibits reuptake of monoamine neurotransmitter, and improves the symptoms of psychoneurotic diseases such as depression, anxiety and the like.

In addition, the compound of the present invention acts as a substance having a monoamine (serotonin, norepinephrine, dopamine etc.) reuptake inhibitory activity in a mammal (e.g., mouse, rat, hamster, rabbit, cat, dog, bovine, sheep, monkey, human and the like), inhibits reuptake of monoamines, and improves the symptoms of lower urinary tract symptoms such as stress urinary incontinence and the like.

Since the compound of the present invention has superior properties as a pharmaceutical product, such as low toxicity, a few side effects and the like, it is useful for, for example, the prophylaxis or treatment of the following diseases.

(1) Central Neurological Diseases (a) psychoneurotic diseases [e.g., depression (e.g., major depression, cerebrovascular disease depression, seasonal depression, depression caused by medicament, HIV depression etc.), anxiety (e.g., generalized anxiety disorder, social anxiety disorder, obsessive-compulsive disorder, panic disorder, posttraumatic stress disorder etc.), attention deficit hyperactivity disorder (ADHD), bipolar disorder, mania, repetitive depression, sustained mood affective disorders (e.g., cyclothymia, dysthymia etc.), depressive neurosis, sleep disorder, circadian rhythm disorder, eating disorder, drug addiction, premenstrual syndrome, autism, mood disorder due to menopause, senile dementia, mild cognitive dysfunction, narcolepsy, psychophysiologic disorder, manic depression, posttraumatic stress disorder (PTSD), schizophrenia, anxiety neurosis, obsessive neurosis, mood disorder and movement disorder associated with cerebral apoplexy or cerebrovascular disorder etc.]

(b) neurodegenerative diseases (e.g., muscle fibrosis, Alzheimer's disease, Parkinson's disease, mood disorder associated with neurodegenerative disease etc.)

(2) various pains (e.g., neuropathic pain, inflammatory pain, fibromyalgia etc.)

(3) lower urinary tract symptoms (e.g., overactive bladder, stress urinary incontinence, mixed urinary incontinence, pelvic organ pain, urination disorders such as lower urinary tract symptom associated with interstitial cystitis and the like, male lower urinary tract symptom etc.)

(4) pelvic organ prolapse (anterior vaginal wall prolapse, posterior vaginal wall prolapse, uterine prolapse, apical vaginal prolapse, rectal prolapse (rectocele), enterocele, cystocele, urethrocele etc.)

(5) other diseases [for example, climacteric disorder, diabetes, obesity, irritable bowel syndrome (IBS), restless legs syndrome (RLS), chronic fatigue syndrome, premenstrual syndrome (PMS), functional dyspepsia (FD), fecal incontinence, digestive system disease, smoking cessation, various dependences]

The compound of the present invention is useful as a monoamine reuptake inhibitor, and particularly useful as a prophylactic or therapeutic drug for depression, anxiety, attention deficit hyperactivity disorder, stress urinary incontinence or mixed urinary incontinence. Since the compound of the present invention has a reuptake inhibitory activity against serotonin, norepinephrine and dopamine, it is useful as a triple reuptake inhibitor. Since the compound (I') of the present invention has a norepinephrine reuptake inhibitory activity, it is useful as a norepinephrine reuptake inhibitor.

In the present invention, the "monoamine reuptake inhibitor" means a reuptake inhibitor of at least one monoamine selected from serotonin, norepinephrine and dopamine, which are neurotransmitters. Examples of the "monoamine reuptake inhibitor" include serotonin reuptake inhibitor, norepinephrine reuptake inhibitor, dopamine reuptake inhibitor, serotonin-norepinephrine reuptake inhibitor, norepinephrine-dopamine reuptake inhibitor, serotonin-dopamine reuptake inhibitor, and serotonin-norepinephrine-dopamine reuptake inhibitor.

A medicament containing the compound of the present invention can be used singly or in the form of a pharmaceutical composition prepared according to a method known per se as a production method of pharmaceutical preparations (e.g., the method described in the Japanese Pharmacopoeia etc.) by mixing the compound and pharmacologically acceptable carriers to give, for example, tablet (including sugar-coated tablet, film-coated tablet, sublingual tablet, orally disintegrable tablet, buccal tablet and the like), pill, powder, granule, capsule (including soft capsule, microcapsule), troche, syrup, liquid, emulsion, suspension, controlled release preparation (e.g., immediate-release preparation, sustained-release preparation, sustained-release microcapsule), aerosol, film (e.g., orally disintegrable film, oral mucosal adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like. A sustained-release preparation can be produced according to the method described in JP-A-H9-263545.

The medicament containing the compound of the present invention can be safely administered orally or parenterally (e.g., intravenous, intramuscular, subcutaneous, intraorgan, intranasal, intradermal, instillation, intracerebral, rectal, vaginal, intraperitoneal, intratumor, tumor proximal administration, direct administration to a lesion and the like).

In the preparations of the present invention, the content of the compound of the present invention varies depending on the forms of the preparations, but is generally in the order of 0.01 to 100% by weight, preferably 0.1 to 50% by weight, more preferably 0.5 to 20% by weight, as the content of the compound of the present invention relative to the total weight of each preparation.

While the dose varies depending on the kind of the compound of the present invention, administration route, symptom, age of patients and the like, it is, for example, about 0.005-50 mg, preferably about 0.05-10 mg, more preferably about 0.2-4 mg, as the compound of the present invention per 1 kg body weight per day for oral administration to an adult patient with depression, anxiety, attention deficit hyperactivity disorder, climacteric disorder, pain, stress urinary incontinence or mixed urinary incontinence, which may be administered in 1 to 3 divided portions.

When the pharmaceutical composition of the present invention is a sustained-release preparation, the dose thereof varies depending on the kind and content of the compound of the present invention, dosage form, sustained duration of drug release, administration subject animal (e.g., mammals such as human, rat, mouse, cat, dog, rabbit, bovine, swine and the like), and administration object. For application by parenteral administration, for example, about 0.1-about 100 mg of the compound of the present invention only needs to be released from the administered preparation in one week.

Examples of the aforementioned pharmacologically acceptable carrier include excipients (e.g., starch, lactose, sucrose, calcium carbonate, calcium phosphate and the like), binders (e.g., starch, gum arabic, carboxymethylcellulose, hydroxypropylcellulose, crystalline cellulose, alginic acid, gelatin, polyvinylpyrrolidone and the like), lubricants (e.g., stearic acid, magnesium stearate, calcium stearate, talc and the like), disintegrants (e.g., calcium carboxymethylcellulose, talc and the like), diluents (e.g., water for injection, saline and the like), additives (e.g., stabilizer, preservative, colorant, flavor, dissolution aid, emulsifier, buffering agent, isotonicity agent and the like) and the like.

For formulation into an injection, for example, the compound of the present invention is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give an injection to be actually used. In addition, an oily suspension can be obtained by dispersing the compound of the present invention together with vegetable oil such as sesame oil, corn oil and the like or a mixture thereof with a phospholipid such as lecithin and the like, or medium-chain triglyceride (e.g., miglyol 812 etc.) to give an injection to be actually used.

The prophylactic or therapeutic drug of the present invention can also be used together with other medicament.

Examples of the drug that can be blended or used with the compound of the present invention (hereinafter to be abbreviated as concomitant drug) include the following.

(1) Prophylactic or Therapeutic Drug for Other Central Neurological Diseases

Therapeutic drugs for depression, therapeutic drugs for anxiety (e.g., benzodiazepines such as chlordiazepoxide, diazepam, potassium clorazepate, lorazepam, clonazepam, alprazolam and the like), mood-stabilizing drugs (e.g., lithium carbonate etc.), 5-HT2 antagonists (e.g., nefazodone etc.), 5-HT1A agonists (e.g., tandospirone, buspirone, gepiron etc.), CRF antagonists (e.g., pexacerfont etc.), β3 agonists (e.g., amibegron etc.), melatonin agonists (e.g., ramelteon, agomelatine etc.), α2 antagonists (e.g., mirtazapine, setiptiline etc.), NK2 antagonists (e.g., saredutant etc.), GR antagonists (e.g., mifepristone etc.), NK-1 antagonists (e.g., casopitant, orvepitant etc.), therapeutic drugs for schizophrenia (e.g., chlorpromazine, haloperidol, sulpiride, clozapine, aripiprazole, quetiapine, olanzapine, risperidone etc.), acetylcholinesterase inhibitors (e.g., donepezil, rivastigmine, galanthamine, zanapezil etc.), NMDA antagonists (e.g., memantine etc.), inhibitors of production, secretion, accumulation, coagulation and/or deposition of β amyloid protein [β secretase inhibitor, γ secretase inhibitory action agent, inhibitory action agents of β amyloid protein coagulation (e.g., PTI-00703, ALZHEMED (NC-531), PPI-368 (JP-A-H11-514333), PPI-558 (JP-A-2001-500852), SKF-74652 (Biochem. J. (1999), 340(1), 283-289)), β amyloid vaccine, β amyloid degrading enzyme etc.], activation drugs of brain function (e.g., aniracetam, nicergoline etc.), therapeutic drugs for Parkinson's disease [e.g., dopamine receptor agonists (e.g., L-DOPA, bromocriptine, pergolide, talipexole, pramipexole, cabergoline, amantadine etc.), COMT inhibitors (e.g., entacapone etc.)], therapeutic drugs for attention deficit hyperactivity disorder (e.g., modafinil etc.), therapeutic drugs for amyotrophic lateral sclerosis (e.g., riluzole, neurotrophic factor etc.), therapeutic drugs for insomnia (e.g., etizolam, zopiclone, triazolam, zolpidem, indiplon etc.), therapeutic drugs for narcolepsy (e.g., modafinil etc.), anti-cytokine drugs (TNF inhibitor, MAP kinase inhibitor etc.), steroid drugs (e.g., dexamethasone, hexestrol, cortisone acetate etc.) and the like.

(2) Prophylactic or Therapeutic Drug for Other Stress Urinary Incontinence

Adrenaline α1 receptor agonists (e.g., ephedrine hydrochloride, midodrine hydrochloride etc.), adrenaline β2 receptor agonists (e.g., clenbuterol etc.), norepinephrine reuptake inhibitory substance, norepinephrine and serotonin reuptake inhibitory substances (e.g., duloxetine etc.), tricyclic antidepressants (e.g., imipramine hydrochloride etc.), anticholinergic drugs or stimulants of smooth muscle (e.g., oxybutynin hydrochloride, propiverine hydrochloride, celimeverine hydrochloride etc.), female sex hormone drugs (e.g., conjugated estrogen (premarin), estriol etc.) etc.

(3) Agent for Treating Diabetes

Insulin preparations [e.g., animal insulin preparations extracted from the bovine or swine pancreas; human insulin preparations synthesized by a genetic engineering technique using *Escherichia coli* or a yeast; insulin zinc; protamine zinc insulin; a fragment or a derivative of insulin (e.g., INS-1, etc.)], insulin sensitizers (e.g., pioglitazone hydrochloride, troglitazone, rosiglitazone or its maleate, JTT-501, MCC-555, YM-440, GI-262570, KRP-297, FK-614, CS-011, etc.), α-glucosidase inhibitors (e.g., voglibose, acarbose, miglitol, emiglitate, etc.), biguanides (e.g., phenformin, metformin, buformin, etc.), sulfonylureas (e.g., tolbutamide, glibenclamide, gliclazide, chlorpropamide, tolazamide, acetohexamide, glyclopyramide, glimepiride, etc.) and other insulin secretagogues (e.g., repaglinide, senaglinide, mitiglinide or its calcium salt hydrate, GLP-1, nateglinide, etc.), dipeptidylpeptidase IV inhibitors (e.g., vildagliptin, sitagliptin, saxagliptin, alogliptin, NVP-DPP-728, PT-100, P32/98, etc.), β3 agonists (e.g., CL-316243, SR-58611-A, UL-TG-307, AJ-9677, AZ40140, etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), SGLT (sodium-glucose cotransporter) inhibitors (e.g., T-1095, etc.) and the like.

(4) Agent for Treating Diabetic Complications

Aldose reductase inhibitors (e.g., tolrestat, epalrestat, zenarestat, zopolrestat, fidarestat (SNK-860), minalrestat (ARI-509), CT-112, etc.), neurotrophic factors (e.g., NGF, NT-3, etc.), AGE inhibitors (e.g., ALT-945, pimagedine, pyratoxathine, N-phenacylthiazolium bromide (ALT-766), EXO-226, etc.), active oxygen scavengers (e.g., thioctic acid, etc.), cerebral vasodilators (e.g., tiapride, etc.) and the like.

(5) Antihyperlipidemic Agent

Statin compounds inhibiting cholesterol synthesis (e.g., pravastatin, simvastatin, lovastatin, atorvastatin, fluvastatin, cerivastatin or their salt (e.g., sodium salt, etc.), etc.), squalene synthase inhibitors or fibrate compounds having triglyceride lowering action (e.g., bezafibrate, clofibrate, simfibrate, clinofibrate, etc.) and the like.

(6) Hypotensive Agent

Angiotensin converting enzyme inhibitors (e.g., captopril, enalapril, delapril, etc.), angiotensin II antagonists (e.g., losartan, candesartan cilexetil, etc.), calcium antagonists (e.g., manidipine, nifedipine, amlodipine, efonidipine, nicardipine, etc.), clonidine, and the like.

(7) Antiobesity Agent

Antiobesity drugs acting on the central nervous system (e.g. dexfenfluramine, fenfluramine, phentermine, sibutramine, amfepramone, dexamphetamine, mazindol, phenylpropanolamine, clobenzorex, etc.), pancreatic lipase inhibitors (e.g. orlistat, etc.), β3 agonists (e.g. CL-316243, SR-58611-A, UL-TG-307, AJ-9677, AZ40140, etc.), anorectic peptides (e.g. leptin, CNTF (ciliary neurotrophic factor), etc.), cholecystokinin agonists (e.g. lintitript, FPL-15849, etc.), and the like.

(8) Diuretic Agent

Xanthine derivatives (e.g., theobromine sodium salicylate, theobromine calcium salicylate, etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide, etc.), antialdosterone preparations (e.g., spironolactone, triamterene, etc.), carbonic anhydrase inhibitors (e.g., acetazolamide, etc.), chlorobenzenesulfonamide preparations (e.g., chlorthalidone, mefruside, indapamide, etc.), azosemide, isosorbide, ethacrynic acid, piretanide, bumetanide, furosemide, etc.

(9) Chemotherapeutic Agent

Alkylating agents (e.g., cyclophosphamide, ifosamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, taxol, etc.), cisplatin, carboplatin, etoposide, etc. Among these, 5-fluorouracil derivatives such as furtulon and neo-furtulon are preferred.

(10) Immunotherapeutic Agent

Microorganism- or bacterium-derived components (e.g., muramyl dipeptide derivatives, picibanil, etc.), immunopotentiator polysaccharides (e.g., lentinan, schizophyllan, krestin, etc.), genetically engineered cytokines (e.g., interferons, interleukins (IL), etc.), colony stimulating factors (e.g., granulocyte colony stimulating factor, erythropoietin, etc.) and the like. Among these, IL-1, IL-2, IL-12, etc. are preferred.

(11) Therapeutic Agent Recognized to Ameliorate Cachexia in Animal Models or Clinical Practice Progesterone derivatives (e.g., megestrol acetate) [Journal of Clinical Oncology, vol. 12, pp. 213-225, 1994], metoclopramide pharmaceuticals, tetrahydrocannabinol pharmaceuticals (the above references are applied to both), fat metabolism ameliorating agents (e.g., eicosapentaenoic acid) [British Journal of Cancer, vol. 68, pp. 314-318, 1993], growth hormones, IGF-1, and antibodies to the cachexia-inducing factors such as TNF-α, LIF, IL-6 and oncostatin M.

(12) Antiinflammatory Agent

Steroids (e.g., dexamethasone, etc.), sodium hyaluronate, cyclooxygenase inhibitors (e.g., indomethacin, ketoprofen, loxoprofen, meloxicam, ampiroxicam, celecoxib, rofecoxib, etc.) and the like.

(13) Miscellaneous

Glycosylation inhibitors (e.g., ALT-711, etc.), nerve regeneration promoting drugs (e.g., Y-128, VX853, prosaptide, etc.), drugs acting on the central nervous system (e.g., antidepressants such as desipramine, amitriptyline, imipramine, fluoxetine, paroxetine, doxepin, etc.), anticonvulsants (e.g., lamotrigine, carbamazepine), antiarrhythmic drugs (e.g., mexiletine), acetylcholine receptor ligands (e.g., ABT-594), endothelin receptor antagonists (e.g., ABT-627), monoamine reuptake inhibitors (e.g., tramadol), indoleamine reuptake inhibitors (e.g., fluoxetine, paroxetine), narcotic analgesics (e.g., morphine), GABA receptor agonists (e.g., gabapentin), GABA reuptake inhibitors (e.g., tiagabine), $\alpha_2$ receptor agonists (e.g., clonidine), local analgesics (e.g., capsaicin), protein kinase C inhibitors (e.g., LY-333531), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatriptan), serotonin receptor antagonists (e.g., cyproheptadine hydrochloride, ondansetron), serotonin reuptake inhibitors (e.g., fluvoxamine maleate, fluoxetine, paroxetine), hypnotics (e.g., triazolam, zolpidem), anticholinergic agents, $\alpha_1$ receptor blocking agents (e.g., tamsulosin, silodosin, naftopidil), muscle relaxants (e.g., baclofen), potassium channel openers (e.g., nicorandil), calcium channel blocking agents (e.g., nifedipine), agents for preventing and/or treating Alzheimer's disease (e.g., donepezil, rivastigmine, galanthamine), agents for treating Parkinson's disease (e.g., L-dopa), agents for preventing and/or treating multiple sclerosis (e.g., interferon β-1a), histamine $H_1$ receptor inhibitors (e.g., promethazine hydrochloride), proton pump inhibitors (e.g., lansoprazole, omeprazole), antithrombotic agents (e.g., aspirin, cilostazol), NK-2 receptor antagonists, agents of treating HIV infection (saquinavir, zidovudine, lamivudine, nevirapine), agents of treating chronic obstructive pulmonary diseases (salmeterol, thiotropium bromide, cilomilast), etc.

Anticholinergic agents include, for example, atropine, scopolamine, homatropine, tropicamide, cyclopentolate, butylscopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrogen bromide, homatropine hydrogen bromide, cyclopentolate hydrochloride, flavoxate hydrochloride, pirenzepine hydrochloride, trihexyphenidyl hydrochloride, oxybutynin hydrochloride, tolterodine tartrate, etc.), preferably, oxybutynin, propiverine, darifenacin, tolterodine, temiverine, trospium chloride or a salt thereof (e.g., oxybutynin hydrochloride, tolterodine tartrate, etc.). In addition, acetylcholinesterase inhibitors (e.g., distigmine, etc.) and the like can be used.

NK-2 receptor antagonists include, for example, piperidine derivatives such as GR159897, GR149861, SR48968 (saredutant), SR144190, YM35375, YM38336, ZD7944, L-743986, MDL105212A, ZD6021, MDL105172A, SCH205528, SCH62373, R-113281, etc., perhydroisoindole derivatives such as RPR-106145, etc., quinoline derivatives such as SB-414240, etc., pyrrolopyrimidine derivatives such as ZM-253270, etc., pseudopeptide derivatives such as MEN11420 (nepadutant), SCH217048, L-659877, PD-147714 (CAM-2291), MEN10376, S16474, etc., and others such as GR100679, DNK333, GR94800, UK-224671, MEN10376, MEN10627, or a salt thereof, and the like.

In combination of the compound of the present invention and the concomitant drug, the administration time of the compound of the present invention and the concomitant drug is not restricted, and the compound of the present invention or a pharmaceutical composition thereof and the concomitant drug or a pharmaceutical composition thereof can be administered to the administration subject simultaneously, or may be administered at different times. The dosage of the concomitant drug may be determined according to the administration amount clinically used, and can be appropriately selected depending on the administration subject, administration route, disease, combination and the like.

The concomitant administration mode is not particularly restricted, and it is sufficient that the compound of the present invention and the concomitant drug are combined in administration. Examples of such administration mode include the following methods:
(1) The compound of the present invention or a pharmaceutical composition thereof and the concomitant drug are simultaneously produced to give a single preparation which is administered. (2) The compound of the present invention or a pharmaceutical composition thereof and the concomitant drug or a pharmaceutical composition thereof are separately produced to give two kinds of preparations which are administered simultaneously by the same administration route. (3) The compound of the present invention or a pharmaceutical composition thereof and the concomitant drug or a pharmaceutical composition thereof are separately produced to give two kinds of preparations which are administered by the same administration route only at the different times. (4) The compound of the present invention or a pharmaceutical composition thereof and the concomitant drug or a pharmaceutical composition thereof are separately produced to give two kinds of preparations which are administered simultaneously by different administration routes. (5) The compound of the present invention or a pharmaceutical composition thereof and the concomitant drug or a pharmaceutical composition thereof are separately produced to give two kinds of preparations which are administered by different administration routes at different times (for example, the compound of the present invention or a pharmaceutical composition thereof; and the concomitant drug or a pharmaceutical composition thereof are administered in this order, or in the reverse order).

The mixing ratio of the compound of the present invention and a concomitant drug in the combination drug of the present invention can be appropriately determined according to the subject of administration, administration route, disease and the like.

For example, while the content of the compound of the present invention in the combination drug of the present invention varies depending on the form of the preparation, it is generally about 0.01 to about 100 wt %, preferably about 0.1 to about 50 wt %, more preferably about 0.5 to about 20 wt %, relative to the whole preparation.

While the content of the concomitant drug in the combination drug of the present invention varies depending on the form of the preparation, it is generally about 0.01 to about 100 wt %, preferably about 0.1 to about 50 wt %, more preferably about 0.5 to about 20 wt %, relative to the whole preparation.

While the content of the additive such as a carrier and the like in the combination drug of the present invention varies depending on the form of the preparation, it is generally about 1 to about 99.99 wt %, preferably about 10 to about 90 wt %, relative to the whole preparation.

Similar contents can be employed when the compound of the present invention and the concomitant drug are independently formulated.

The dose of the concomitant drug may be set within the range such that it causes no problems of side effects. The daily dose as the concomitant drug varies depending on severity of symptoms, age, sex, weight and sensitivity of the subject to be administered, time and interval of administration, property, formulation and kinds of pharmaceutical preparation, kinds of active ingredients, etc., and is not particularly limited. In the case of oral administration, a daily dosage in terms of drugs is usually in the order of about 0.001 to 2000 mg, preferably about 0.01 to 500 mg, and more preferably about 0.1 to 100 mg, per 1 kg body weight of mammals, which may be administered once a day or in two to four divided portions a day.

In administering the combination drug of the present invention, it may be administered at the same time or, the concomitant drug may be administered before administering the compound of the present invention, and vice versa. In case of staggered administration, the time interval varies depending on the active ingredients to be administered, a formulation and an administration route. For example, if the concomitant drug is administered first, the compound of the present invention may be administered 1 minute to 3 days, preferably 10 minutes to 1 day, more preferably 15 minutes to 1 hour after administering the concomitant drug. If the compound of the present invention is administered first, the concomitant drug may be administered 1 minute to 1 day, preferably 10 minutes to 6 hours, more preferably 15 minutes to 1 hour after administering the compound of the present invention.

The pharmaceutical composition of the present invention shows low toxicity and can be used safely. Particularly, since the Example compounds shown below are superior in the absorption by oral administration, they can be advantageously used for oral preparations. In addition, the composition is also superior in that it does not show phototoxicity.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. The ratios of elution solvents are volume mixing ratios, unless otherwise specified.

In the following Examples, the following abbreviations are used.

THF: tetrahydrofuran, DMF: dimethylformamide, $CDCl_3$: deuterated chloroform, DMSO: dimethyl sulfoxide, CDI: carbonyldiimidazole, $AcONH_4$: ammonium acetate, EtOH: ethanol, mCPBA: methachloroperbenzoic acid, WSC: 1-ethyl-3-(3-dimethylaminopropyl)carbodiimide hydrochloride, HOBt: 1-hydroxybenzotriazole $^1$H NMR (proton nuclear magnetic resonance spectrum) was measured by Fourier-transform type NMR. For the analysis, ACD/SpecManager (trade name) and the like were used. Peaks with very mild protons such as hydroxyl group, amino group and the like are note described.

MS (mass spectrum) was measured by LC/MS (liquid chromatography mass spectrometer). As the ionization method, ESI (ElectroSpray Ionization) method, or APCI (Atmospheric Pressure Chemical Ionization) method was used. The data indicates those found. Generally, a molecular ion peak is observed. In the case of a compound having a tert-butoxycarbonyl group (-Boc), a peak after elimination of a tert-butoxycarbonyl group or tert-butyl group may be observed as a fragment ion. In the case of a compound having a hydroxyl group (—OH), a peak after elimination of $H_2O$ may be observed as a fragment ion. In the case of a salt, a molecular ion peak or fragment ion peak of free form is generally observed.

Example 1

[(6RS,7RS)-7-(3,4-dichlorophenyl)-1,4-oxazepan-6-yl]methanol monohydrochloride

A) methyl 2-[(3,4-dichlorophenyl)(hydroxy)methyl]prop-2-enoate

To a solution of 3,4-dichlorobenzaldehyde (17.5 g) and methyl acrylate (8.6 mL) in acetonitrile (100 ml) was added 1,4-diazabicyclo[2.2.2]octane (3.36 g), and the mixture was stirred at room temperature for 2 days. The reaction mixture was concentrated under reduced pressure, and the residue was purified by silica gel chromatography (hexane/ethyl acetate) to give the title compound (18.7 g).
$^1$H NMR (300 MHz, CDCl$_3$) δ 3.17 (1H, d, J=6.0 Hz), 3.75 (3H, s), 5.50 (1H, d, J=5.7 Hz), 5.85 (1H, s), 6.37 (1H, s), 7.22 (1H, dd, J=8.3, 1.9 Hz), 7.41 (1H, d, J=8.3 Hz), 7.48 (1H, d, J=1.9 Hz).

B) methyl (2RS,3RS)-2-[(benzylamino)methyl]-3-(3,4-dichlorophenyl)-3-hydroxypropanoate To a solution of methyl 2-[(3,4-dichlorophenyl)(hydroxy)methyl]prop-2-enoate (13.6 g) and triethylamine (8.74 mL) in methanol (100 mL) was added benzylamine (6.84 mL), and the mixture was stirred at room temperature for 3 days. The reaction mixture was concentrated under reduced pressure, and the residue was purified by silica gel chromatography (hexane/ethyl acetate) to give the title compound (4.17 g).
$^1$H NMR (300 MHz, CDCl$_3$) δ 2.85-2.98 (2H, m), 3.01-3.12 (1H, m), 3.58 (3H, s), 3.71-3.86 (2H, m), 5.12 (1H, d, J=3.8 Hz), 7.09 (1H, dd, J=8.3, 1.9 Hz), 7.26-7.45 (7H, m), 2H not detected.

C) (1RS,2RS)-2-[(benzylamino)methyl]-1-(3,4-dichlorophenyl)propane-1,3-diol

To a solution of lithium aluminum hydride (644 mg) in THF (40 mL) was added dropwise a solution of (6RS,7RS)-4-benzyl-6-({[tert-butyl(dimethyl)silyl]oxy}methyl)-7-(3,4-dichlorophenyl)-1,4-oxazepan-3-one (4.17 g) in THF (20 mL) under ice-cooling, and the mixture was stirred at room temperature for 3 hr. The reaction mixture was cooled to −78° C., a solution of methyl (2R,3S)-2-[(benzylamino)methyl]-3-(3,4-dichlorophenyl)-3-hydroxypropanoate (10.8 g) in THF (80 mL) was added dropwise, and the mixture was stirred at 0° C. for 3 hr. The reaction mixture was poured into ice water, and the mixture was stirred for 30 min, and filtered through celite. The filtrate was extracted twice with ethyl acetate. The organic layer was washed with brine, and dried over anhydrous sodium sulfate. The solvent was evaporated under reduced pressure to give the title compound (3.44 g).
MS (ESI+): [M+H]$^+$ 340.1.

D) (1RS,2RS)-3-(benzylamino)-2-({[tert-butyl(dimethyl)silyl]oxy}methyl)-1-(3,4-dichlorophenyl)propan-1-ol To a solution of (1RS,2RS)-2-[(benzylamino)methyl]-1-(3,4-dichlorophenyl)propane-1,3-diol (3.44 g) in DMF (30 ml) were added tert-butylchlorodimethylsilane (1.68 g) and imidazole (1.03 g) under ice-cooling, and the mixture was stirred at room temperature for 2 hr. The reaction mixture was concentrated under reduced pressure, and the residue was diluted with ethyl acetate. The diluted solution was washed with distilled water, saturated aqueous sodium hydrogen carbonate and brine, and dried over anhydrous sodium sulfate. The solvent was evaporated under reduced pressure. The residue was purified by silica gel chromatography (hexane/ethyl acetate) to give the title compound (2.98 g).
MS (ESI+): [M+H]$^+$ 454.1.

E) N-benzyl-N-[(2RS,3RS)-2-({[tert-butyl(dimethyl)silyl]oxy}methyl)-3-(3,4-dichlorophenyl)-3-hydroxypropyl]-2-chloroacetamide To a solution of (1RS,2RS)-3-(benzylamino)-2-({[tert-butyl(dimethyl)silyl]oxy}methyl)-1-(3,4-dichlorophenyl)propan-1-ol (2.98 g) and triethylamine (1.10 mL) in THF (30 mL) was added chloroacetyl chloride (0.526 mL) under ice-cooling, and the mixture was stirred at 0° C. for 4 hr. The reaction mixture was concentrated under reduced pressure, and the residue was diluted with ethyl acetate. The diluted solution was washed with distilled water and brine, and dried over anhydrous magnesium sulfate. The solvent was evaporated under reduced pressure. The residue was purified by silica gel chromatography (hexane/ethyl acetate) to give the title compound (2.95 g).
MS (ESI+): [M-OH+H]$^+$ 514.1.

F) (6RS,7RS)-4-benzyl-6-({[tert-butyl(dimethyl)silyl]oxy}methyl)-7-(3,4-dichlorophenyl)-1,4-oxazepan-3-one To a solution of N-benzyl-N-[(2RS,3RS)-2-({[tert-butyl(dimethyl)silyl]oxy}methyl)-3-(3,4-dichlorophenyl)-3-hydroxypropyl]-2-chloroacetamide (2.72 g) in THF (100 ml) was added sodium tert-butoxide (621 mg) under ice-cooling, and the mixture was stirred at room temperature for 2 hr. The reaction mixture was concentrated under reduced pressure, and the residue was diluted with ethyl acetate. The diluted solution was washed with distilled water and brine, dried over anhydrous magnesium sulfate and concentrated under reduced pressure to give the title compound (2.51 g).
MS (ESI+): [M+H]$^+$ 494.2.

G) (6RS,7RS)-4-benzyl-6-({[tert-butyl(dimethyl)silyl]oxy}methyl)-7-(3,4-dichlorophenyl)-1,4-oxazepane To a solution of lithium aluminum hydride (347 mg) in diethyl ether (30 mL) was added, under a nitrogen stream, aluminum(III) chloride (406 mg) at room temperature, and the mixture was stirred at room temperature for 30 min. The reaction mixture was cooled to −78° C., a solution of (6RS,7RS)-4-benzyl-6-({[tert-butyl(dimethyl)silyl]oxy}methyl)-7-(3,4-dichlorophenyl)-1,4-oxazepan-3-one (2.51 g) in THF (20 mL) was added dropwise, and the mixture was stirred at 0° C. for 3 hr. To the reaction mixture was added 1 N aqueous sodium hydroxide solution (5 mL) at −78° C., and the mixture was stirred at room temperature for 2 hr, and filtered through celite. The filtrate was concentrated under reduced pressure to give the title compound (2.42 g).
$^1$H NMR (300 MHz, CDCl$_3$) δ −0.16--0.06 (6H, m), 0.79 (9H, s), 2.35-2.50 (1H, m), 2.56-2.74 (2H, m), 2.74-2.85 (2H, m), 3.18-3.27 (1H, m), 3.31-3.40 (1H, m), 3.62-3.73 (2H, m), 3.73-3.78 (1H, m), 3.84-3.96 (1H, m), 4.96-5.02 (1H, m), 7.18 (1H, dd, J=8.3, 1.5 Hz), 7.24-7.42 (6H, m), 7.49 (1H, d, J=1.9 Hz).

H) tert-butyl (6RS,7RS)-7-(3,4-dichlorophenyl)-6-(hydroxymethyl)-1,4-oxazepane-4-carboxylate To a solution of (6RS,7RS)-4-benzyl-6-({[tert-butyl(dimethyl)silyl]oxy}methyl)-7-(3,4-dichlorophenyl)-1,4-oxazepane (2.42 g) in acetonitrile (25 ml) was added 1-chloroethyl chloroformate (0.652 ml), and the mixture was stirred at room temperature for 20 min. The reaction mixture was concentrated under reduced pressure, the residue was diluted with methanol (25 mL), and 2 N hydrogen chloride-ethanol solution (3 ml) was added. The reaction mixture was stirred at 80° C. for 1 hr, and ice-cooled, and triethylamine (1.05 mL) and di-tert-butyl dicarbonate (1.16 mL) were added. The reaction mixture was stirred at room temperature for 18 hr, and concentrated under reduced pressure, and the residue was diluted with ethyl acetate. The diluted solution was washed with distilled water and brine, dried over anhydrous magnesium sulfate and concentrated under reduced pressure. The residue was purified by silica gel chromatography (hexane/ethyl acetate) to give the title compound (997 mg).

$^1$H NMR (300 MHz, CDCl$_3$) δ 1.43-1.56 (9H, m), 2.21-2.40 (1H, m), 3.15 (1H, td, J=11.2, 3.8 Hz), 3.24-3.56 (3H, m), 3.57-3.78 (2H, m), 3.77-3.95 (1H, m), 4.02-4.34 (2H, m), 4.64 (1H, d, J=2.7 Hz), 7.10 (1H, dd, J=8.3, 1.5 Hz), 7.39 (1H, d, J=8.3 Hz), 7.42 (1H, d, J=1.5 Hz).

I) [(6RS,7RS)-7-(3,4-dichlorophenyl)-1,4-oxazepan-6-yl]methanol monohydrochloride To a solution of tert-butyl (6RS,7RS)-7-(3,4-dichlorophenyl)-6-(hydroxymethyl)-1,4-oxazepane-4-carboxylate (100 mg) in ethanol (0.5 mL) was added 2 N hydrogen chloride-ethanol solution (2.0 ml), and the mixture was stirred at room temperature for 24 hr. The crystals obtained by concentration under reduced pressure were recrystallized from ethyl acetate-ethanol to give the title compound (56.3 mg).

$^1$H NMR (300 MHz, DMSO-d$_6$) δ2.63 (1H, brs), 2.95-3.06 (1H, m), 3.08-3.17 (1H, m), 3.18-3.27 (1H, m), 3.28-3.40 (3H, m), 3.85-3.97 (1H, m), 3.99-4.11 (1H, m), 4.81 (1H, brs), 5.01 (1H, J=4.5 Hz), 7.35 (1H, dd, J=8.5, 1.9 Hz), 7.61 (1H, d, J=6.4 Hz), 7.63 (1H, s), 9.21 (2H, brs).

Example 2

(6RS,7RS)-7-(3,4-dichlorophenyl)-6-(methoxymethyl)-1,4-oxazepane monohydrochloride A) tert-butyl (6RS,7RS)-7-(3,4-dichlorophenyl)-6-(methoxymethyl)-1,4-oxazepane-4-carboxylate To a solution of sodium hydride (10.5 mg) in THF (1 mL) was added a solution of tert-butyl (6RS,7RS)-7-(3,4-dichlorophenyl)-6-(hydroxymethyl)-1,4-oxazepane-4-carboxylate (65.7 mg) in THF (1 ml), and the mixture was stirred at room temperature for 30 min. To the reaction mixture was added methyl iodide (49.7 mg), and the mixture was stirred at room temperature for 2 hr. The reaction mixture was concentrated under reduced pressure, and the residue was diluted with ethyl acetate. The diluted solution was washed with distilled water and brine, and dried over anhydrous sodium sulfate. The solvent was evaporated under reduced pressure. The residue was purified by silica gel chromatography (hexane/ethyl acetate) to give the title compound (58.4 mg).

$^1$H NMR (300 MHz, CDCl$_3$) δ 1.50 (9H, d, J=6.8 Hz), 2.37-2.67 (1H, m), 2.96-3.45 (7H, m), 3.46-3.76 (1H, m), 3.76-4.16 (3H, m), 4.57 (1H, brs), 7.10 (1H, t, J=7.6 Hz), 7.28-7.52 (2H, m).

B) (6RS,7RS)-7-(3,4-dichlorophenyl)-6-(methoxymethyl)-1,4-oxazepane monohydrochloride To a solution of tert-butyl (6RS,7RS)-7-(3,4-dichlorophenyl)-6-(methoxymethyl)-1,4-oxazepane-4-carboxylate (58 mg) in ethyl acetate (2 mL) was added 4 N hydrogen chloride-ethyl acetate solution (3.0 mL), and the mixture was stirred at room temperature for 2 hr. The crystals obtained by concentration under reduced pressure were recrystallized from ethanol to give the title compound (26.7 mg).

$^1$H NMR (300 MHz, DMSO-d$_6$) δ 2.77-2.91 (1H, m), 2.91-3.04 (2H, m), 3.10 (3H, s), 3.14-3.24 (1H, m), 3.27 (1H, d, J=6.4 Hz), 3.85-3.98 (1H, m), 3.99-4.12 (1H, m), 5.02 (1H, d, J=4.5 Hz), 7.35 (1H, dd, J=8.5, 2.1 Hz), 7.56-7.68 (2H, m), 9.26 (2H, brs).

Example 3

1-{[(6RS,7RS)-7-(3,4-dichlorophenyl)-1,4-oxazepan-6-yl]methyl}urea monohydrochloride A) tert-butyl (6RS,7RS)-7-(3,4-dichlorophenyl)-6-{[(methylsulfonyl)oxy]methyl}-1,4-oxazepane-4-carboxylate To tert-butyl (6RS,7RS)-7-(3,4-dichlorophenyl)-6-(hydroxymethyl)-1,4-oxazepane-4-carboxylate (896 mg) were added triethylamine (0.50 mL) and methanesulfonyl chloride (0.26 mL) under ice-cooling, and the mixture was stirred for 1 hr. The reaction mixture was concentrated under reduced pressure, and the residue was diluted with ethyl acetate. The diluted solution was washed with 1 N hydrochloric acid, distilled water and brine, and dried over anhydrous magnesium sulfate, and the solvent was evaporated under reduced pressure to give the title compound (1.07 g).

$^1$H NMR (300 MHz, CDCl$_3$) δ 1.46-1.56 (9H, m), 2.62-2.78 (1H, m), 2.78-3.00 (3H, m), 3.23-3.85 (4H, m), 3.85-4.13 (4H, m), 4.66 (1H, brs), 7.12 (1H, d, J=8.3 Hz), 7.42 (2H, d, J=8.3 Hz).

B) tert-butyl (6RS,7RS)-6-(azidomethyl)-7-(3,4-dichlorophenyl)-1,4-oxazepane-4-carboxylate To a solution of tert-butyl (6RS,7RS)-7-(3,4-dichlorophenyl)-6-{[(methylsulfonyl)oxy]methyl}-1,4-oxazepane-4-carboxylate (830 mg) in DMF (10 mL) was added sodium azide (178 mg), and the mixture was stirred at 70° C. for 18 hr. The reaction mixture was concentrated under reduced pressure, and the residue was diluted with ethyl acetate. The diluted solution was washed with distilled water and brine, and dried over anhydrous magnesium sulfate. The solvent was evaporated under reduced pressure. The residue was purified by silica gel chromatography (hexane/ethyl acetate) to give the title compound (723 mg).

$^1$H NMR (300 MHz, CDCl$_3$) δ 1.51 (9H, d), 2.29-2.59 (1H, m), 3.01-3.18 (2H, m), 3.29-3.52 (2H, m), 3.52-3.70 (1H, m), 3.72-3.97 (2H, m), 4.03-4.12 (1H, m), 4.62 (1H, d, J=6.4 Hz), 7.10 (1H, t, J=6.4 Hz), 7.42 (2H, d, J=8.7 Hz).

C) tert-butyl (6RS,7SR)-6-(aminomethyl)-7-(3,4-dichlorophenyl)-1,4-oxazepane-4-carboxylate To a solution of tert-butyl (6RS,7RS)-6-(azidomethyl)-7-(3,4-dichlorophenyl)-1,4-oxazepane-4-carboxylate (723 mg) in THF (7.5 mL) were added triphenylphosphine (567 mg) and water (1.5 mL), and the mixture was stirred at room temperature for 36 hr. The reaction mixture was concentrated under reduced pressure, and the residue was diluted with ethyl acetate. The diluted solution was washed with distilled water and brine, and dried over anhydrous magnesium sulfate. The solvent was evaporated under reduced pressure. The D) tert-butyl (6RS,7SR)-6-[(carbamoylamino)methyl]-7-(3,4-dichlorophenyl)-1,4-oxazepane-4-carboxylate To a solution of tert-butyl (6RS,7SR)-6-(aminomethyl)-7-(3,4-dichlorophenyl)-1,4-oxazepane-4-carboxylate (125 mg) in THF (1.5 mL) was added trimethylsilyl isocyanate (57.7 mg), and the mixture was stirred at room temperature for 1.5 hr. The reaction mixture was concentrated under reduced pressure, and the residue was diluted with ethyl acetate. The diluted solution was washed with distilled water and brine, and dried over anhydrous magnesium sulfate. The solvent was evaporated under reduced pressure. The residue was purified by silica gel chromatography (hexane/ethyl acetate) to give the title compound (160 mg).
$^1$H NMR (300 MHz, CDCl$_3$) δ 1.48 (9H, s), 2.39 (1H, dt, J=10.4, 3.3 Hz), 2.66 (1H, ddd, J=14.0, 10.6, 4.2 Hz), 3.12-3.25 (1H, m), 3.30 (1H, dd, J=15.0, 2.5 Hz), 3.40 (1H, dt, J=14.2, 4.4 Hz), 3.66-3.88 (2H, m), 4.12-4.19 (2H, m), 4.19-4.30 (2H, m), 4.65 (1H, d, J=2.7 Hz), 5.70 (1H, d, J=4.9 Hz), 7.17 (1H, dd, J=8.3, 1.9 Hz), 7.41 (1H, d, J=8.3 Hz), 7.51 (1H, d, J=1.5 Hz).

E) 1-{[(6RS,7RS)-7-(3,4-dichlorophenyl)-1,4-oxazepan-6-yl]methyl}urea monohydrochloride To a solution of tert-butyl (6RS,7SR)-6-[(carbamoylamino)methyl]-7-(3,4-dichlorophenyl)-1,4-oxazepane-4-carboxylate (160 mg) in ethanol (0.5 mL) was added 4 N hydrogen chloride-ethyl acetate solution (3.0 mL), and the mixture was stirred at room temperature for 2 hr. The crystals obtained by concentration under reduced pressure were recrystallized from ethanol-water to give the title compound (102 mg).
$^1$H NMR (300 MHz, DMSO-d$_6$) δ 2.53 (1H, brs), 2.59-2.72 (1H, m), 2.77-2.92 (1H, m), 3.18-3.43 (4H, m), 3.92 (1H, ddd, J=13.4, 7.7, 3.8 Hz), 4.09 (1H, dt, J=13.6, 4.3 Hz), 4.98 (1H, d, J=3.0 Hz), 5.78 (2H, s), 6.18 (1H, t, J=5.9 Hz), 7.35 (1H, dd, J=8.5, 1.9 Hz), 7.57-7.69 (2H, m), 9.34 (2H, brs).

Example 4

[(6RS,7SR)-7-(3,4-dichlorophenyl)-1,4-oxazepan-6-yl]methanol monohydrochloride

A) methyl (2RS,3RS)-2-[(benzylamino)methyl]-3-(3,4-dichlorophenyl)-3-hydroxypropanoate To a solution of methyl 2-[(3,4-dichlorophenyl)(hydroxy)methyl]prop-2-enoate (13.6 g) and triethylamine (8.74 ml) in methanol (100 mL) was added benzylamine (6.84 mL), and the mixture was stirred at room temperature for 3 days. The reaction mixture was concentrated under reduced pressure, and the residue was purified by silica gel chromatography (hexane/ethyl acetate) to give the title compound (12.7 g).
$^1$H NMR (300 MHz, CDCl$_3$) δ 2.66-2.76 (2H, m), 3.11-3.23 (1H, m), 3.66-3.79 (5H, m), 5.27 (1H, d, J=4.9 Hz), 7.10 (1H, dd, J=8.3, 1.5 Hz), 7.26-7.40 (6H, m), 7.45 (1H, d, J=1.9 Hz), 2H not detected.

B) (1RS,2SR)-2-[(benzylamino)methyl]-1-(3,4-dichlorophenyl)propane-1,3-diol

To a suspension of calcium chloride (5.74 g) in THF (80 mL) and ethanol (50 mL) was added sodium borohydride (2.61 g), and the mixture was stirred at room temperature for 30 min. To the reaction mixture was added a solution of methyl (2RS,3RS)-2-[(benzylamino)methyl]-3-(3,4-dichlorophenyl)-3-hydroxypropanoate (12.7 g) in THF (20 mL) and ethanol (20 mL) under ice-cooling, and the mixture was stirred at room temperature for 2 hr. To the reaction mixture was added 1 N aqueous hydrochloric acid solution (15 mL), the mixture was stirred for 30 min, and neutralized with 1 N aqueous sodium hydroxide solution (15 mL), and the mixture was filtered through celite. The obtained oil was diluted with ethyl acetate, and the mixture was washed with distilled water and brine, dried over anhydrous magnesium sulfate and concentrated under reduced pressure to give the title compound (11.6 g).
MS (ESI+): [M+H]$^+$ 340.1.

C) (1RS,2SR)-3-(benzylamino)-2-({[tert-butyl(dimethyl)silyl]oxy}methyl)-1-(3,4-dichlorophenyl)propan-1-ol To a solution of (1RS,2SR)-2-[(benzylamino)methyl]-1-(3,4-dichlorophenyl)propane-1,3-diol (11.6 g) in THF (100 mL) were added tert-butylchlorodimethylsilane (5.63 g) and imidazole (2.55 g) under ice-cooling, and the mixture was stirred at room temperature for 2 hr. The reaction mixture was concentrated under reduced pressure, and the residue was diluted with ethyl acetate. The diluted solution was washed with distilled water, saturated aqueous sodium hydrogen carbonate and brine, and dried over anhydrous sodium sulfate. The solvent was evaporated under reduced pressure. The residue was purified by silica gel chromatography (hexane/ethyl acetate) to give the title compound (10.9 g).
MS (ESI+): [M+H]$^+$ 454.1.

D) N-benzyl-N-[(2RS,3SR)-2-({[tert-butyl(dimethyl)silyl]oxy}methyl)-3-(3,4-dichlorophenyl)-3-hydroxypropyl]-2-chloroacetamide To a solution of (1RS,2SR)-3-(benzylamino)-2-({[tert-butyl(dimethyl)silyl]oxy}methyl)-1-(3,4-dichlorophenyl)propan-1-ol (10.9 g) and triethylamine (4.00 mL) in THF (100 mL) was added chloroacetyl chloride (1.91 mL) under ice-cooling, and the mixture was stirred at 0° C. for 1.5 hr. The reaction mixture was concentrated under reduced pressure, and the residue was diluted with ethyl acetate. The diluted solution was washed with distilled water and brine, dried over anhydrous magnesium sulfate and concentrated under reduced pressure to give the title compound (12.5 g).
MS (ESI+): [M-OH+H]$^+$ 514.1.

E) (6RS,7SR)-4-benzyl-6-({[tert-butyl(dimethyl)silyl]oxy}methyl)-7-(3,4-dichlorophenyl)-1,4-oxazepan-3-one To a solution of N-benzyl-N-[(2RS,3SR)-2-({[tert-butyl(dimethyl)silyl]oxy}methyl)-3-(3,4-dichlorophenyl)-3-hydroxypropyl]-2-chloroacetamide (12.5 g) in THF (470 ml) was added sodium tert-butoxide (2.71 g) under ice-cooling, and the mixture was stirred at room temperature for 2 hr. The reaction mixture was concentrated under reduced pressure, and the residue was diluted with ethyl acetate. The diluted solution was washed with distilled water and brine, dried over anhydrous magnesium sulfate and concentrated under reduced pressure to give the title compound (11.3 g).
MS (ESI+): [M+H]$^+$ 494.0.

F) (6RS,7SR)-4-benzyl-6-({[tert-butyl(dimethyl) silyl]oxy}methyl)-7-(3,4-dichlorophenyl)-1,4-oxazepane To a solution of lithium aluminum hydride (1.49 g) in diethyl ether (120 mL) was added, under a nitrogen stream, aluminum(III) chloride (1.74 g) under ice-cooling, and the mixture was stirred at room temperature for 40 min. The reaction mixture was cooled to −78° C., a solution of (6RS,7SR)-4-benzyl-6-({[tert-butyl(dimethyl)silyl]oxy}methyl)-7-(3,4-dichlorophenyl)-1,4-oxazepan-3-one (10.8 g) in THF (80 mL) was added dropwise, and the mixture was stirred at 0° C. for 3 hr. To the reaction mixture was added 1 N aqueous sodium hydroxide solution (22 mL) at −78° C., and the mixture was stirred at room temperature for 2 hr, and filtered through celite. The filtrate was concentrated under reduced pressure to give the title compound (9.77 g).
$^1$H NMR (300 MHz, CDCl$_3$) δ −0.05 (6H, d), 0.83 (9H, s), 2.07-2.23 (1H, m), 2.57-2.77 (2H, m), 2.88 (2H, d, J=3.8 Hz), 3.39-3.49 (1H, m), 3.51-3.64 (2H, m), 3.65 (2H, s), 3.93-4.04 (1H, m), 4.42 (1H, d, J=8.3 Hz), 7.22 (1H, dd, J=8.3, 2.3 Hz), 7.24-7.42 (6H, m), 7.49 (1H, d, J=2.3 Hz).

G) tert-butyl (6RS,7SR)-7-(3,4-dichlorophenyl)-6-(hydroxymethyl)-1,4-oxazepane-4-carboxylate To a solution of (6RS,7SR)-4-benzyl-6-({[tert-butyl(dimethyl)silyl]oxy}methyl)-7-(3,4-dichlorophenyl)-1,4-oxazepane (9.77 g) in acetonitrile (100 ml) was added 1-chloroethyl chloroformate (2.63 mL), and the mixture was stirred at room temperature for 15 min. The reaction mixture was concentrated under reduced pressure, methanol (100 mL) was added, and the mixture was heated at 80° C. 1 N Hydrochloric acid (1.00 mL) was added. The reaction mixture was stirred at 80° C. for 18 hr, and ice-cooled, and triethylamine (3.40 mL) and di-tert-butyl dicarbonate (4.90 mL) were added. The reaction mixture was stirred at room temperature for 2 hr, and concentrated under reduced pressure, and the residue was diluted with ethyl acetate. The diluted solution was washed with distilled water and brine, dried over anhydrous magnesium sulfate and concentrated under reduced pressure. The residue was purified by silica gel chromatography (hexane/ethyl acetate) to give the title compound (7.10 g).
$^1$H NMR (300 MHz, CDCl$_3$) δ 1.51 (9H, s), 2.06-2.19 (1H, m), 3.05-3.30 (2H, m), 3.43 (1H, dd, J=14.7, 6.4 Hz), 3.49-3.67 (2H, m), 4.04-4.12 (3H, m), 4.21 (1H, dd, J=10.0, 4.7 Hz), 4.33 (1H, d, J=9.8 Hz), 7.19 (1H, dd, J=8.3, 1.9 Hz), 7.40 (1H, d, J=8.3 Hz), 7.48 (1H, d, J=1.9 Hz).

H) [(6RS,7SR)-7-(3,4-dichlorophenyl)-1,4-oxazepan-6-yl]methanol monohydrochloride To a solution of tert-butyl (6RS,7SR)-7-(3,4-dichlorophenyl)-6-(hydroxymethyl)-1,4-oxazepane-4-carboxylate (150 mg) in ethanol (2 mL) was added 2 N hydrogen chloride-ethanol solution (3.0 mL), and the mixture was stirred at room temperature for 14 hr. The oil obtained by concentration under reduced pressure was crystallized from ethyl acetate-ethanol, and the crystals were recrystallized from ethyl acetate-ethanol to give the title compound (86.5 mg).
$^1$H NMR (300 MHz, DMSO-d$_6$) δ 2.36-2.48 (1H, m), 3.04-3.19 (2H, m), 3.19-3.31 (3H, m), 3.46 (1H, dd, J=14.0, 3.0 Hz), 3.80 (1H, ddd, J=13.4, 8.9, 4.2 Hz), 4.05 (1H, dt, J=13.6, 4.2 Hz), 4.44 (1H, d, J=10.6 Hz), 4.97 (1H, brs), 7.38 (1H, dd, J=8.3, 1.9 Hz), 7.61-7.71 (2H, m), 9.33 (2H, brs).

Example 5

(6RS,7RS)-7-(3,4-dichlorophenyl)-6-[(methylsulfonyl)methyl]-1,4-oxazepane monohydrochloride A) tert-butyl (6RS,7SR)-7-(3,4-dichlorophenyl)-6-{[(methylsulfonyl)oxy]methyl}-1,4-oxazepane-4-carboxylate To a solution of tert-butyl (6RS,7SR)-7-(3,4-dichlorophenyl)-6-(hydroxymethyl)-1,4-oxazepane-4-carboxylate (735 mg) in THF (10 ml) were added triethylamine (0.41 mL) and methanesulfonyl chloride (0.21 mL) under ice-cooling, and the mixture was stirred for 1 hr. Triethylamine (0.14 ml) and methanesulfonyl chloride (0.076 ml) were added, and the mixture was stirred for 1 hr. The reaction mixture was concentrated under reduced pressure, and the residue was diluted with ethyl acetate. The diluted solution was washed with 1 N hydrochloric acid, distilled water and brine, and dried over anhydrous magnesium sulfate, and the solvent was evaporated under reduced pressure to give the title compound (863 mg).
$^1$H NMR (300 MHz, CDCl$_3$) δ 1.50 (9H, s), 2.40 (1H, brs), 2.81-3.08 (3H, m), 3.35-3.90 (5H, m), 3.94-4.17 (3H, m), 4.20 (1H, d, J=9.4 Hz), 7.16 (1H, dd, J=8.3, 1.9 Hz), 7.38-7.50 (2H, m).

B) tert-butyl (6RS,7RS)-7-(3,4-dichlorophenyl)-6-[(methylsulfanyl)methyl]-1,4-oxazepane-4-carboxylate To a solution of tert-butyl (6RS,7SR)-7-(3,4-dichlorophenyl)-6-{[(methylsulfonyl)oxy]methyl}-1,4-oxazepane-4-carboxylate (200 mg) in DMF (3 ml) was added sodium thiomethoxide (46.3 mg), and the mixture was stirred at room temperature for 16 hr. The reaction mixture was concentrated under reduced pressure, and the residue was diluted with ethyl acetate. The diluted solution was washed with distilled water and brine, and dried over anhydrous magnesium sulfate. The solvent was evaporated under reduced pressure. The residue was purified by silica gel chromatography (hexane/ethyl acetate) to give the title compound (110 mg).
$^1$H NMR (300 MHz, CDCl$_3$) δ 1.51 (9H, s), 1.81-2.02 (3H, m), 2.06-2.47 (3H, m), 3.36-3.99 (5H, m), 4.00-4.23 (2H, m), 7.17 (1H, d, J=7.6 Hz), 7.42 (2H, d, J=8.0 Hz).

C) tert-butyl (6RS,7RS)-7-(3,4-dichlorophenyl)-6-[(methylsulfonyl)methyl]-1,4-oxazepane-4-carboxylate To a solution of tert-butyl (6RS,7RS)-7-(3,4-dichlorophenyl)-6-[(methylsulfanyl)methyl]-1,4-oxazepane-4-carboxylate (110 mg) in toluene (1.5 mL) was added methachloroperbenzoic acid (170 mg), and the mixture was stirred at room temperature for 20 hr. The reaction mixture was diluted with ethyl acetate, and the mixture was washed with saturated aqueous sodium hydrogen carbonate and brine, and dried over anhydrous magnesium sulfate. The solvent was evaporated under reduced pressure. The residue was purified by silica gel chromatography (hexane/ethyl acetate) to give the title compound (111 mg).
$^1$H NMR (300 MHz, CDCl$_3$) δ 1.52 (9H, d, J=9.4 Hz), 2.50-2.96 (5H, m), 3.17-3.76 (4H, m), 3.76-4.35 (4H, m), 7.21 (1H, dd, J=8.3, 1.9 Hz), 7.40-7.53 (2H, m).

D) (6RS,7RS)-7-(3,4-dichlorophenyl)-6-[(methylsulfonyl)methyl]-1,4-oxazepane monohydrochloride To a solution of tert-butyl (6RS,7RS)-7-(3,4-dichlorophenyl)-6-[(methylsulfonyl)methyl]-1,4-oxazepane-4-carboxylate (111 mg) in ethyl acetate (1 ml) was added 4 N hydrogen chloride-ethyl acetate solution (3 mL), and the mixture was stirred at room temperature for 2 hr. The crystals obtained by concentration under reduced pressure were recrystallized from ethanol-water to give the title compound (70.3 mg).

$^1$H NMR (300 MHz, DMSO-$d_6$) δ 2.77 (1H, d, J=13.2 Hz), 2.94 (3H, s), 3.05-3.31 (4H, m), 3.44 (1H, dd, J=14.0, 9.4 Hz), 3.69 (1H, dd, J=14.2, 2.8 Hz), 3.84 (1H, ddd, J=13.7, 9.2, 4.3 Hz), 4.06 (1H, dt, J=13.6, 4.3 Hz), 4.48 (1H, d, J=9.8 Hz), 7.43 (1H, dd, J=8.3, 1.9 Hz), 7.69 (1H, d, J=8.3 Hz), 7.72 (1H, d, J=1.9 Hz), 9.45 (2H, brs).

Example 6

N-{[(6RS,7SR)-7-(3,4-dichlorophenyl)-1,4-oxazepan-6-yl]methyl}acetamide monohydrochloride

A) tert-butyl (6RS,7SR)-6-(azidomethyl)-7-(3,4-dichlorophenyl)-1,4-oxazepane-4-carboxylate To a solution of tert-butyl (6RS,7SR)-7-(3,4-dichlorophenyl)-6-{[(methylsulfonyl)oxy]methyl}-1,4-oxazepane-4-carboxylate (660 mg) in DMF (7 mL) was added sodium azide (142 mg), and the mixture was stirred at 70° C. for 20 hr. The reaction mixture was concentrated under reduced pressure, and the residue was diluted with ethyl acetate. The diluted solution was washed with distilled water and brine, and dried over anhydrous magnesium sulfate. The solvent was evaporated under reduced pressure. The residue was purified by silica gel chromatography (hexane/ethyl acetate) to give the title compound (570 mg).

$^1$H NMR (300 MHz, CDCl$_3$) δ 1.51 (9H, brs), 2.14 (1H, brs), 3.20 (2H, d, J=7.5 Hz), 3.39-3.88 (5H, m), 4.02-4.22 (2H, m), 7.14 (1H, dd, J=8.3, 1.9 Hz), 7.37-7.49 (2H, m).

B) tert-butyl (6RS,7RS)-6-(aminomethyl)-7-(3,4-dichlorophenyl)-1,4-oxazepane-4-carboxylate To a solution of tert-butyl (6RS,7SR)-6-(azidomethyl)-7-(3,4-dichlorophenyl)-1,4-oxazepane-4-carboxylate (570 mg) in THF (5 mL) were added triphenylphosphine (447 mg) and water (1 mL), and the mixture was stirred at room temperature for 20 hr. The reaction mixture was concentrated under reduced pressure, and the residue was diluted with ethyl acetate. The diluted solution was washed with distilled water and brine, and dried over anhydrous magnesium sulfate. The solvent was evaporated under reduced pressure. The residue was purified by silica gel chromatography (ethyl acetate/methanol) to give the title compound (477 mg).

$^1$H NMR (300 MHz, CDCl$_3$) δ 1.53 (9H, s), 1.85-2.04 (1H, m), 2.43-2.67 (2H, m), 3.23-3.38 (1H, m), 3.53 (1H, dd, J=14.7, 4.5 Hz), 3.61 (1H, d, J=10.6 Hz), 3.76-4.14 (4H, m), 7.16 (1H, d, J=7.9 Hz), 7.36-7.47 (2H, m), 2H not detected.

C) tert-butyl (6RS,7RS)-6-[(acetylamino)methyl]-7-(3,4-dichlorophenyl)-1,4-oxazepane-4-carboxylate To a solution of tert-butyl (6RS,7RS)-6-(aminomethyl)-7-(3,4-dichlorophenyl)-1,4-oxazepane-4-carboxylate (144 mg) in THF (1.5 ml) were added triethylamine (0.08 mL) and acetyl chloride (45 mg), and the mixture was stirred at room temperature for 18 hr. The reaction mixture was concentrated under reduced pressure, and the residue was diluted with ethyl acetate. The diluted solution was washed with distilled water and brine, and dried over anhydrous magnesium sulfate. The solvent was evaporated under reduced pressure. The residue was purified by silica gel chromatography (hexane/ethyl acetate) to give the title compound (177 mg).

$^1$H NMR (300 MHz, CDCl$_3$) δ 1.51 (9H, s), 1.85-2.02 (3H, m), 2.26 (1H, brs), 3.03 (1H, dt, J=14.0, 7.4 Hz), 3.09-3.32 (2H, m), 3.36 (1H, dd, J=14.9, 5.5 Hz), 3.54 (1H, td, J=12.1, 2.3 Hz), 3.92-4.20 (4H, m), 7.13-7.26 (2H, m), 7.41 (1H, d, J=8.3 Hz), 7.53 (1H, d, J=1.5 Hz).

D) N-{[(6RS,7SR)-7-(3,4-dichlorophenyl)-1,4-oxazepan-6-yl]methyl}acetamide monohydrochloride To a solution of tert-butyl (6RS,7RS)-6-[(acetylamino)methyl]-7-(3,4-dichlorophenyl)-1,4-oxazepane-4-carboxylate (176 mg) in ethyl acetate (0.5 mL) was added 4 N hydrogen chloride-ethyl acetate solution (3 mL), and the mixture was stirred at room temperature for 2 hr. The crystals obtained by concentration under reduced pressure were recrystallized from ethanol-water to give the title compound (102 mg).

$^1$H NMR (300 MHz, DMSO-$d_6$) δ 1.77 (3H, s), 2.53-2.60 (1H, m), 2.86 (2H, t, J=5.9 Hz), 3.07-3.31 (4H, m), 3.71-3.88 (1H, m), 3.98 (1H, dt, J=13.9, 4.4 Hz), 4.37 (1H, d, J=10.2 Hz), 7.44 (1H, dd, J=8.3, 1.9 Hz), 7.67 (1H, d, J=8.3 Hz), 7.76 (1H, d, J=1.9 Hz), 8.06 (1H, t, J=5.9 Hz), 9.24 (2H, brs).

Example 7

1-{[(6RS,7SR)-7-(3,4-dichlorophenyl)-1,4-oxazepan-6-yl]methyl}urea monohydrochloride Using tert-butyl (6RS,7RS)-6-(aminomethyl)-7-(3,4-dichlorophenyl)-1,4-oxazepane-4-carboxylate, and by a method similar to that of Example 3, steps D) and E), the title compound (45.8 mg) was obtained.

$^1$H NMR (300 MHz, DMSO-$d_6$) δ 2.75 (1H, d), 2.93 (3H, s), 3.02-3.14 (1H, m), 3.18-3.35 (3H, m), 3.44 (1H, dd, J=13.5, 9.9 Hz), 3.69 (1H, dd, J=13.8, 2.3 Hz), 3.84 (1H, ddd, J=13.7, 9.0, 4.4 Hz), 4.05 (1H, dt, J=13.8, 4.4 Hz), 4.46 (1H, d, J=10.0 Hz), 7.40-7.51 (2H, m), 7.63-7.72 (1H, m), 8.90-9.74 (2H, m).

Example 8

N-{[(6RS,7SR)-7-(3,4-dichlorophenyl)-1,4-oxazepan-6-yl]methyl}methanesulfonamide monohydrochloride

A) tert-butyl (6RS,7SR)-7-(3,4-dichlorophenyl)-6-{[(methylsulfonyl)amino]methyl}-1,4-oxazepane-4-carboxylate To a solution of tert-butyl (6RS,7RS)-6-(aminomethyl)-7-(3,4-dichlorophenyl)-1,4-oxazepane-4-carboxylate (144 mg) in THF (1.5 mL) were added triethylamine (0.08 mL) and methanesulfonyl chloride (66 mg), and the mixture was stirred at room temperature for 18 hr. The reaction mixture was concentrated under reduced pressure, and the residue was diluted with ethyl acetate. The diluted solution was washed with distilled water and brine, and dried over anhydrous magnesium sulfate. The solvent was evaporated under reduced pressure. The residue was purified by silica gel chromatography (hexane/ethyl acetate) to give the title compound (186 mg).

$^1$H NMR (300 MHz, CDCl$_3$) δ 1.51 (9H, s), 2.21-2.34 (1H, m), 2.79-2.94 (4H, m), 2.98-3.18 (2H, m), 3.43 (1H, dd, J=15.1, 6.4 Hz), 3.58 (1H, td, J=12.3, 2.6 Hz), 3.99-4.17 (3H, m), 4.32 (1H, d, J=9.8 Hz), 6.55 (1H, dd, J=8.5, 4.3 Hz), 7.20-7.30 (1H, m), 7.37-7.46 (1H, m), 7.53 (1H, d, J=1.5 Hz).

B) N-{[(6RS,7SR)-7-(3,4-dichlorophenyl)-1,4-oxazepan-6-yl]methyl}methanesulfonamide monohydrochloride To a solution of tert-butyl (6RS,7SR)-7-(3,4-dichlorophenyl)-6-{[methylsulfonyl)amino]methyl}-1,4-oxazepane-4-carboxylate (186 mg) in ethyl acetate (0.5 mL) was added 4 N hydrogen chloride-ethyl acetate solution (3 mL), and the mixture was stirred at room temperature for 2 hr. The crystals obtained by concentration under reduced pressure were recrystallized from ethanol-water to give the title compound (119 mg).

$^1$H NMR (300 MHz, DMSO-$d_6$) δ 2.53-2.66 (1H, m), 2.75 (2H, t, J=6.1 Hz), 2.82 (3H, s), 3.08-3.20 (1H, m), 3.22-3.31 (2H, m), 3.39-3.51 (1H, m), 3.72-3.88 (1H, m), 3.97-4.10 (1H, m), 4.39 (1H, d, J=10.2 Hz), 7.28 (1H, t, J=6.4 Hz), 7.43 (1H, dd, J=8.3, 1.9 Hz), 7.68 (1H, d, J=8.0 Hz), 7.73 (1H, d, J=1.9 Hz), 9.36 (2H, brs).

Example 9

N-{[(6RS,7SR)-7-(3,4-dichlorophenyl)-1,4-oxazepan-6-yl]methyl}sulfamide monohydrochloride A) tert-butyl (6RS,7SR)-7-(3,4-dichlorophenyl)-6-[(sulfamoylamino)methyl]-1,4-oxazepane-4-carboxylate To a solution of tert-butyl (6RS,7RS)-6-(aminomethyl)-7-(3,4-dichlorophenyl)-1,4-oxazepane-4-carboxylate (144 mg) in acetonitrile (2 mL) was added N-(tert-butoxycarbonyl)-N-[4-(dimethylazaniumylidene)-1,4-dihydropyridin-1-ylsulfonyl]azanide (190 mg) prepared by the method described in Organic Letters, 2001, 3 (14), 2241-2243, and the mixture was stirred at room temperature for 20 hr. The reaction mixture was concentrated under reduced pressure, and the residue was diluted with ethyl acetate. The diluted solution was washed with 1 N hydrochloric acid and brine, and dried over anhydrous magnesium sulfate. The solvent was evaporated under reduced pressure. The residue was purified by silica gel chromatography (hexane/ethyl acetate) to give the title compound (205 mg).

$^1$H NMR (300 MHz, CDCl$_3$) δ 1.49 (9H, s), 1.51 (9H, s), 2.10-2.37 (1H, m), 2.79-2.97 (1H, m), 2.97-3.22 (2H, m), 3.43 (1H, dd, J=15.1, 6.4 Hz), 3.52-3.67 (1H, m), 4.08 (3H, td, J=11.1, 3.0 Hz), 4.28 (1H, d, J=9.8 Hz), 7.16 (1H, brs), 7.21-7.27 (1H, m), 7.41 (1H, d, J=7.9 Hz), 7.52 (1H, s), 1H not detected.

B) N-{[(6RS,7SR)-7-(3,4-dichlorophenyl)-1,4-oxazepan-6-yl]methyl}sulfamide monohydrochloride To a solution of tert-butyl (6RS,7SR)-7-(3,4-dichlorophenyl)-6-[(sulfamoylamino)methyl]-1,4-oxazepane-4-carboxylate (202 mg) in ethanol (1 mL) was added 4 N hydrogen chloride-ethyl acetate solution (3 mL), and the mixture was stirred at room temperature for 18 hr. The crystals obtained by concentration under reduced pressure were recrystallized from ethanol-water to give the title compound (103 mg).

$^1$H NMR (300 MHz, DMSO-$d_6$) δ 2.65 (2H, t), 3.08-3.32 (4H, m), 3.40-3.54 (1H, m), 3.80 (1H, ddd, J=13.5, 8.9, 4.1 Hz), 4.02 (1H, dt, J=13.8, 4.3 Hz), 4.40 (1H, d, J=10.0 Hz), 6.56 (2H, s), 6.79 (1H, t, J=6.4 Hz), 7.41 (1H, dd, J=8.4, 2.0 Hz), 7.68 (1H, d, J=8.3 Hz), 7.71 (1H, d, J=1.9 Hz), 8.59-9.90 (2H, m).

Example 10

[(6RS,7SR)-7-(3-chloro-4-fluorophenyl)-1,4-oxazepan-6-yl]methanol monohydrochloride A) methyl 2-[(3-chloro-4-fluorophenyl)(hydroxy)methyl]prop-2-enoate To a solution of 3-chloro-4-fluorobenzaldehyde (10.0 g) and methyl acrylate (8.5 mL) in acetonitrile (63 mL) was added 1,4-diazabicyclo[2.2.2]octane (1.41 g), and the mixture was stirred at room temperature for 5 days. The reaction mixture was concentrated under reduced pressure, and the residue was purified by silica gel chromatography (hexane/ethyl acetate) to give the title compound (11.5 g).

$^1$H NMR (300 MHz, CDCl$_3$) δ 3.11 (1H, d, J=6.0 Hz), 3.75 (3H, s), 5.51 (1H, d, J=5.7 Hz), 5.85 (1H, t, J=0.9 Hz), 6.37 (1H, s), 7.06-7.17 (1H, m), 7.20-7.28 (1H, m), 7.44 (1H, dd, J=7.2, 2.3 Hz).

B) methyl (2RS,3RS)-2-[(benzylamino)methyl]-3-(3-chloro-4-fluorophenyl)-3-hydroxypropanoate To a solution of methyl 2-[(3-chloro-4-fluorophenyl)(hydroxy)methyl]prop-2-enoate (11.5 g) and triethylamine (6.85 mL) in methanol (100 mL) was added benzylamine (5.38 mL), and the mixture was stirred at room temperature for 16 hr. The reaction mixture was concentrated under reduced pressure, and the residue was purified by silica gel chromatography (hexane/ethyl acetate) to give the title compound (12.0 g).

$^1$H NMR (300 MHz, CDCl$_3$) δ 2.65-2.80 (2H, m), 3.16 (1H, dd, J=11.7, 5.7 Hz), 3.67 (3H, s), 3.73 (2H, dd, J=17.8, 12.8 Hz), 5.25 (1H, d, J=5.3 Hz), 7.04 (1H, t, J=8.7 Hz), 7.13 (1H, ddd, J=8.3, 4.2, 2.3 Hz), 7.26-7.45 (6H, m), 2H not detected.

C) (1RS,2SR)-2-[(benzylamino)methyl]-1-(3-chloro-4-fluorophenyl) propane-1,3-diol To a suspension of calcium chloride (5.66 g) in THF (80 ml) and ethanol (50 mL) was added sodium borohydride (2.57 g), and the mixture was stirred at room temperature for 30 min. To the reaction mixture was added a solution of methyl (2RS,3RS)-2-[(benzylamino)methyl]-3-(3-chloro-4-fluorophenyl)-3-hydroxypropanoate (12.0 g) in THF (20 mL) and ethanol (20 ml) under ice-cooling, and the mixture was stirred at room temperature for 4 hr. To the reaction mixture was added aqueous 1 N hydrochloric acid (15 mL) solution, the mixture was stirred for 1 hr, and neutralized with 1 N aqueous sodium hydroxide solution (15 ml), and the mixture was filtered through celite. The obtained oil was diluted with ethyl acetate, and the mixture was washed with distilled water and brine, dried over anhydrous magnesium sulfate and concentrated under reduced pressure to give the title compound as a crude product.

MS (ESI+): [M+H]$^+$ 324.1.

D) (1RS,2SR)-3-(benzylamino)-2-({[tert-butyl(dimethyl)silyl]oxy}methyl)-1-(3-chloro-4-fluorophenyl) propan-1-ol To a solution of (1RS,2SR)-2-[(benzylamino)methyl]-1-(3-chloro-4-fluorophenyl)propane-1,3-diol (the above-mentioned crude product) in THF (170 ml) were added tert-butylchlorodimethylsilane (5.38 g), triethylamine (7.1 ml) and 4-(dimethylamino)pyridine (415 mg) under ice-cooling, and the mixture was stirred at room temperature for 18 hr. The reaction mixture was concentrated under reduced pressure, and the residue was diluted with ethyl acetate. The diluted solution was washed with distilled water, saturated aqueous sodium hydrogen carbonate and brine, dried over anhydrous magnesium sulfate and concentrated under reduced pressure to give the title compound (14.1 g).
MS (ESI+): [M+H]$^+$ 438.4.

E) (6RS,7SR)-4-benzyl-6-({[tert-butyl(dimethyl)silyl]oxy}methyl)-7-(3-chloro-4-fluorophenyl)-1,4-oxazepan-3-one To a solution of (1RS,2SR)-3-(benzylamino)-2-({[tert-butyl(dimethyl)silyl]oxy}methyl)-1-(3-chloro-4-fluorophenyl)propan-1-ol (14.1 g) and triethylamine (4.95 mL) in THF (100 mL) was added chloroacetyl chloride (2.59 ml) under ice-cooling, and the mixture was stirred at 0° C. for 18 hr. The reaction mixture was concentrated under reduced pressure, and the residue was diluted with ethyl acetate. The diluted solution was washed with distilled water and brine, dried over anhydrous magnesium sulfate and concentrated under reduced pressure. The obtained mixture was diluted with THF (300 ml), 1 N aqueous sodium hydroxide solution (63 mL) was added dropwise under ice-cooling, and the mixture was stirred at room temperature for 2 hr. The reaction mixture was concentrated under reduced pressure, and the residue was diluted with ethyl acetate. The diluted solution was washed with distilled water, saturated aqueous sodium hydrogen carbonate and brine, dried over anhydrous magnesium sulfate and concentrated under reduced pressure. The residue was purified by silica gel chromatography (hexane/ethyl acetate) to give the title compound (6.72 g).
MS (ESI+): [M+H]$^+$ 478.1.

F) (6RS,7SR)-4-benzyl-6-({[tert-butyl(dimethyl)silyl]oxy}methyl)-7-(3-chloro-4-fluorophenyl)-1,4-oxazepane To a solution of aluminum(III) chloride (1.12 g) in diethyl ether (85 mL)-THF (40 mL) was added, under a nitrogen stream, lithium aluminum hydride (960 mg) under ice-cooling, and the mixture was stirred at room temperature for 30 min. The reaction mixture was cooled to 0° C., a solution of (6RS,7SR)-4-benzyl-6-({[tert-butyl(dimethyl)silyl]oxy}methyl)-7-(3-chloro-4-fluorophenyl)-1,4-oxazepan-3-one (6.72 g) in THF (60 mL) was added dropwise, and the mixture was stirred at 0° C. for 2 hr. To the reaction mixture was added 1 N aqueous sodium hydroxide solution (14 ml) at −78° C., the mixture was stirred at room temperature for 2 hr, and filtered through celite, and the filtrate was concentrated under reduced pressure. The residue was purified by silica gel chromatography (hexane/ethyl acetate) to give the title compound (4.16 g).
$^1$H NMR (300 MHz, CDCl$_3$) δ −0.06 (6H, d, J=2.6 Hz), 0.83 (9H, s), 2.08-2.24 (1H, m), 2.58-2.76 (2H, m), 2.89 (2H, d, J=3.8 Hz), 3.39-3.47 (1H, m), 3.50-3.64 (2H, m), 3.66 (2H, s), 3.94-4.04 (1H, m), 4.40 (1H, d, J=8.3 Hz), 7.03-7.13 (1H, m), 7.20-7.28 (2H, m), 7.28-7.39 (4H, m), 7.44 (1H, dd, J=7.2, 1.9 Hz).

G) tert-butyl (6RS,7SR)-7-(3-chloro-4-fluorophenyl)-6-(hydroxymethyl)-1,4-oxazepane-4-carboxylate To a solution of (6RS,7SR)-4-benzyl-6-({[tert-butyl(dimethyl)silyl]oxy}methyl)-7-(3-chloro-4-fluorophenyl)-1,4-oxazepane (4.15 g) in acetonitrile (40 mL) was added 1-chloroethyl chloroformate (1.16 ml), and the mixture was stirred at room temperature for 1 hr. The reaction mixture was concentrated under reduced pressure, and methanol (40 ml) and 1 N hydrochloric acid (0.50 mL) were added. The reaction mixture was stirred under reflux for 1 hr, and triethylamine (1.50 ml) and di-tert-butyl dicarbonate (2.16 mL) were added at room temperature. The reaction mixture was stirred at room temperature for 2 hr, and concentrated under reduced pressure, and the residue was diluted with ethyl acetate. The diluted solution was washed with distilled water and brine, dried over anhydrous magnesium sulfate and concentrated under reduced pressure. The residue was purified by silica gel chromatography (hexane/ethyl acetate) to give the title compound (2.90 g).
$^1$H NMR (300 MHz, CDCl$_3$) δ 1.51 (9H, s), 2.05-2.19 (1H, m), 3.04-3.30 (2H, m), 3.43 (1H, dd, J=14.7, 6.8 Hz), 3.49-3.67 (2H, m), 4.01-4.16 (3H, m), 4.19 (1H, dd, J=10.0, 4.7 Hz), 4.33 (1H, d, J=9.8 Hz), 7.09 (1H, t, J=8.7 Hz), 7.16-7.25 (1H, m), 7.43 (1H, dd, J=7.2, 1.9 Hz).

H) [(6RS,7SR)-7-(3-chloro-4-fluorophenyl)-1,4-oxazepan-6-yl]methanol monohydrochloride To a solution of tert-butyl (6RS,7SR)-7-(3-chloro-4-fluorophenyl)-6-(hydroxymethyl)-1,4-oxazepane-4-carboxylate (81 mg) in ethanol (1 mL) was added 14.7 N hydrogen chloride-ethanol solution (2.0 mL), and the mixture was stirred at room temperature for 1 hr. The crystals obtained by concentration under reduced pressure were recrystallized from ethyl acetate-ethanol to give the title compound (48 mg).
$^1$H NMR (300 MHz, DMSO-d$_6$) δ 2.34-2.47 (1H, m), 3.03-3.32 (5H, m), 3.46 (1H, dd, J=13.8, 2.8 Hz), 3.70-3.87 (1H, m), 4.04 (1H, dt, J=13.8, 4.5 Hz), 4.43 (1H, d, J=10.4 Hz), 4.96 (1H, brs), 7.35-7.50 (2H, m), 7.63 (1H, dd, J=7.3, 1.9 Hz), 9.22 (2H, brs).

Example 11

1-{[(6RS,7SR)-7-(3-chloro-4-fluorophenyl)-1,4-oxazepan-6-yl]methyl}urea monohydrochloride Using tert-butyl (6RS,7SR)-7-(3-chloro-4-fluorophenyl)-6-(hydroxymethyl)-1,4-oxazepane-4-carboxylate, and by a method similar to that of Example 3, the title compound (69.0 mg) was obtained.
$^1$H NMR (300 MHz, DMSO-d$_6$) δ 2.81 (2H, brs), 3.04-3.29 (3H, m), 3.29-3.42 (1H, m), 3.70-3.84 (1H, m), 3.90-4.04 (1H, m), 4.34 (1H, d, J=10.0 Hz), 6.32 (1H, brs), 7.38-7.51 (2H, m), 7.68-7.75 (1H, m), 9.04 (1H, brs), 9.41 (1H, brs), 3H not detected.

Example 12

(6RS,7SR)-7-(3-chloro-4-fluorophenyl)-6-[(methylsulfonyl)methyl]-1,4-oxazepane monohydrochloride Using tert-butyl (6RS,7SR)-7-(3-chloro-4-fluorophenyl)-6-(hydroxymethyl)-1,4-oxazepane-4-carboxylate, and by a method similar to that of Example 5, the title compound (45.8 mg) was obtained.
$^1$H NMR (300 MHz, DMSO-d$_6$) δ 2.75 (1H, d), 2.93 (3H, s), 3.02-3.14 (1H, m), 3.18-3.35 (3H, m), 3.44 (1H, dd, J=13.5, 9.9 Hz), 3.69 (1H, dd, J=13.8, 2.3 Hz), 3.84 (1H, ddd, J=13.7, 9.0, 4.4 Hz), 4.05 (1H, dt, J=13.8, 4.4 Hz), 4.46 (1H, d, J=10.0 Hz), 7.40-7.51 (2H, m), 7.63-7.72 (1H, m), 8.90-9.74 (2H, m).

Example 13

[(6RS,7SR)-7-(4-chloro-3-fluorophenyl)-1,4-oxazepan-6-yl]methanol monohydrochloride

A) methyl 2-[(4-chloro-3-fluorophenyl)(hydroxy)methyl]prop-2-enoate

To a solution of 4-chloro-3-fluorobenzaldehyde (50.0 g) and methyl acrylate (42.6 mL) in acetonitrile (158 mL) was added 1,4-diazabicyclo[2.2.2]octane (10.6 g), and the mixture was stirred at room temperature for 3 days. The reaction mixture was concentrated under reduced pressure, and the residue was purified by silica gel chromatography (hexane/ethyl acetate) to give the title compound (69.1 g).
$^1$H NMR (300 MHz, CDCl$_3$) δ 3.19 (1H, d, J=6.1 Hz), 3.75 (3H, s), 5.51 (1H, d, J=6.1 Hz), 5.84 (1H, s), 6.36 (1H, s), 7.11 (1H, d, J=8.3 Hz), 7.20 (1H, dd, J=9.8, 1.9 Hz), 7.32-7.42 (1H, m).

B) methyl (2RS,3RS)-2-[(benzylamino)methyl]-3-(4-chloro-3-fluorophenyl)-3-hydroxypropanoate To a solution of methyl 2-[(4-chloro-3-fluorophenyl)(hydroxy)methyl]prop-2-enoate (69.1 g) and triethylamine (47.3 mL) in methanol (706 mL) was added benzylamine (37.1 ml), and the mixture was stirred at room temperature overnight. The reaction mixture was concentrated under reduced pressure, and the residue was purified by silica gel chromatography (hexane/ethyl acetate) to give the title compound (58.2 g).
MS (ESI+): [M+H]$^+$ 352.1.

C) (1RS,2SR)-2-[(benzylamino)methyl]-1-(4-chloro-3-fluorophenyl)propane-1,3-diol To a suspension of calcium chloride (27.6 g) in THF (234 mL) and ethanol (176 mL) was added, under a nitrogen stream, sodium borohydride (12.5 g), and the mixture was stirred at room temperature for 1 hr. To the reaction mixture was added a solution of methyl (2RS,3RS)-2-[(benzylamino)methyl]-3-(4-chloro-3-fluorophenyl)-3-hydroxypropanoate (58.2 g) in THF (200 mL) and ethanol (150 mL) under ice-cooling, and the mixture was stirred at room temperature for 5 hr. To the reaction mixture was added 6 N aqueous hydrochloric acid solution (28 ml), the mixture was neutralized with 8 N aqueous sodium hydroxide solution, and the mixture was filtered through celite. The obtained oil was diluted with ethyl acetate, and the diluted solution was washed with distilled water and brine, dried over anhydrous sodium sulfate, and concentrated under reduced pressure to give the title compound (44.5 g).
MS (ESI+): [M+H]$^+$ 324.1.

D) (1RS,2SR)-3-(benzylamino)-2-({[tert-butyl(dimethyl)silyl]oxy}methyl)-1-(4-chloro-3-fluorophenyl)propan-1-ol To a solution of (1RS,2SR)-2-[(benzylamino)methyl]-1-(4-chloro-3-fluorophenyl)propane-1,3-diol (44.5 g) and triethylamine (21.1 ml) in THF (416 mL) was added a solution of tert-butylchlorodimethylsilane (22.8 g) in THF (42 mL) under ice-cooling, and the mixture was stirred at room temperature overnight. The reaction mixture was concentrated under reduced pressure, and the residue was diluted with ethyl acetate. The diluted solution was washed with distilled water and brine, and dried over anhydrous sodium sulfate. The solvent was evaporated under reduced pressure. The residue was purified by silica gel chromatography (NH, hexane/ethyl acetate) to give the title compound (29.3 g).
MS (ESI+): [M+H]$^+$ 438.4.

E) N-benzyl-N-[(2RS,3SR)-2-({[tert-butyl(dimethyl)silyl]oxy}methyl)-3-(4-chloro-3-fluorophenyl)-3-hydroxypropyl]-2-chloroacetamide To a solution of (1RS,2SR)-3-(benzylamino)-2-({[tert-butyl(dimethyl)silyl]oxy}methyl)-1-(4-chloro-3-fluorophenyl)propan-1-ol (29.3 g) and triethylamine (11.2 ml) in THF (335 ml) was added chloroacetyl chloride (5.37 ml) under ice-cooling, and the mixture was stirred at 0° C. for 2 hr. The reaction mixture was concentrated under reduced pressure, and the residue was diluted with ethyl acetate. The diluted solution was washed with distilled water and brine, dried over anhydrous sodium sulfate, and concentrated under reduced pressure to give the title compound (35.0 g).
MS (ESI+): [M+H]$^+$ 514.1.

F) (6RS,7SR)-4-benzyl-6-({[tert-butyl(dimethyl)silyl]oxy}methyl)-7-(4-chloro-3-fluorophenyl)-1,4-oxazepan-3-one To a solution of N-benzyl-N-[(2RS,3SR)-2-({[tert-butyl(dimethyl)silyl]oxy}methyl)-3-(4-chloro-3-fluorophenyl)-3-hydroxypropyl]-2-chloroacetamide (34.5 g) in THF (1340 mL) was added 1 N aqueous sodium hydroxide solution (80.0 mL) under ice-cooling, and the mixture was stirred at room temperature overnight. The reaction mixture was concentrated under reduced pressure, and the residue was diluted with ethyl acetate. The diluted solution was washed with distilled water and brine, dried over anhydrous sodium sulfate, and concentrated under reduced pressure to give the title compound (31.5 g).
MS (ESI+): [M+H]$^+$ 478.1.

G) (6RS,7SR)-4-benzyl-6-({[tert-butyl(dimethyl)silyl]oxy}methyl)-7-(4-chloro-3-fluorophenyl)-1,4-oxazepane To a solution of aluminum(III) chloride (5.28 g) in THF (396 mL) was added, under a nitrogen stream, lithium aluminum hydride (4.51 g) under ice-cooling, and the mixture was stirred at 0° C. for 1 hr. To the reaction mixture was added dropwise a solution of (6RS,7SR)-4-benzyl-6-({[tert-butyl(dimethyl)silyl]oxy}methyl)-7-(4-chloro-3-fluorophenyl)-1,4-oxazepan-3-one (31.5 g) in THF (264 ml), and the mixture was stirred at 0° C. for 2 hr. To the reaction mixture was added aqueous potassium sodium (+)-tartrate tetrahydrate (93.0 g) solution at 0° C., and the mixture was stirred at room temperature overnight, and filtered through celite. The obtained oil was diluted with ethyl acetate, and the mixture was washed with distilled water and brine, dried over anhydrous sodium sulfate, and concentrated under reduced pressure to give the title compound (26.4 g).
$^1$H NMR (300 MHz, CDCl$_3$) δ −0.02-0.02 (6H, m), 0.89 (9H, s), 2.14-2.28 (1H, m), 2.64-2.82 (2H, m), 2.94 (2H, d, J=4.2 Hz), 3.46-3.74 (5H, m), 4.00-4.10 (1H, m), 4.48 (1H, d, J=7.9 Hz), 7.12-7.46 (8H, m).

H) tert-butyl (6RS,7SR)-7-(4-chloro-3-fluorophenyl)-6-(hydroxymethyl)-1,4-oxazepane-4-carboxylate To a solution of (6RS,7SR)-4-benzyl-6-({[tert-butyl(dimethyl)silyl]oxy}methyl)-7-(4-chloro-3-fluorophenyl)-1,4- oxazepane (26.4 g) in acetonitrile (300 mL) was added 1-chloroethyl chloroformate (7.35 ml), and the mixture was stirred at room temperature for 30 min. The reaction mixture was concentrated under reduced pressure, and methanol (300 mL) was added. The mixture was heated to 80° C., and 1 N hydrochloric acid (3.00 mL) was added. The reaction mixture was stirred at 80° C. for 2 hr, and ice-cooled, and triethylamine (9.50 mL) and di-tert-butyl dicarbonate (13.7 ml) were added. The reaction mixture was stirred at room temperature overnight, and concentrated under reduced pressure, and the residue was diluted with ethyl acetate. The diluted solution was washed with distilled water and brine, dried over anhydrous sodium sulfate, and concentrated under reduced pressure. The residue was purified by silica gel chromatography (hexane/ethyl acetate) to give the title compound (15.9 g).

$^1$H NMR (300 MHz, CDCl$_3$) δ 1.51 (9H, s), 2.06-2.18 (1H, m), 3.04-3.34 (2H, m), 3.35-3.71 (3H, m), 4.01-4.29 (4H, m), 4.34 (1H, d, J=9.5 Hz), 7.08 (1H, d, J=8.0 Hz), 7.18 (1H, dd, J=9.8, 1.9 Hz), 7.30-7.43 (1H, m).

I) [(6RS,7SR)-7-(4-chloro-3-fluorophenyl)-1,4-oxazepan-6-yl]methanol monohydrochloride To tert-butyl (6RS,7SR)-7-(4-chloro-3-fluorophenyl)-6-(hydroxymethyl)-1,4-oxazepane-4-carboxylate (229 mg) was added 2 N hydrogen chloride-ethanol solution (1.02 ml), and the mixture was stirred at room temperature for 1 hr. Further, 14.7 N hydrogen chloride-ethanol solution (2 mL) was added, and the mixture was stirred for 10 min. The oil obtained by concentration under reduced pressure was crystallized from diisopropyl ether-ethanol to give the title compound (146 mg).

$^1$H NMR (300 MHz, CDCl$_3$) δ 3.07-3.36 (6H, m), 3.41-3.53 (1H, m), 3.74-3.87 (1H, m), 3.97-4.12 (1H, m), 4.45 (1H, d, J=10.2 Hz), 4.98 (1H, brs), 7.27 (1H, dd, J=8.3, 1.9 Hz), 7.47 (1H, dd, J=10.6, 1.9 Hz), 7.57-7.68 (1H, m), 9.28-9.75 (2H, m).

Example 14

[(5RS,6SR)-6-(3,4-dichlorophenyl)-1,4-oxazepan-5-yl]methanol monohydrochloride

A) ethyl N-(tert-butoxycarbonyl)-N-[2-(2-ethoxy-2-oxoethoxy)ethyl]glycinate To a solution of ethyl N-(tert-butoxycarbonyl)-N-(2-hydroxyethyl)glycinate (1.2 g) in THF (17 mL) was added ethyl bromoacetate (0.8 ml) under ice-cooling, and the mixture was stirred for 5 min. To this solution was added sodium hydride (288 mg), and the mixture was stirred under ice-cooling for 5 min, and at room temperature for 60 min. The reaction mixture was ice-cooled again, ice water was added, and the mixture was extracted with ethyl acetate. The extract was washed successively with water and brine, and dried over anhydrous sodium sulfate. The solvent was evaporated under reduced pressure, and the residue was purified by silica gel column chromatography (ethyl acetate/hexane) to give the title compound (788 mg).

$^1$H NMR (300 MHz, CDCl$_3$) δ 1.23-1.31 (6H, m), 1.42-1.47 (9H, m), 3.47-3.56 (2H, m), 3.65-3.71 (2H, m), 4.03-4.08 (4H, m), 4.13-4.22 (4H, m).

B) 4-tert-butyl 5-ethyl 6-hydroxy-2,3-dihydro-1,4-oxazepane-4,5(7H)-dicarboxylate To a solution of ethyl N-(tert-butoxycarbonyl)-N-[2-(2-ethoxy-2-oxoethoxy)ethyl]glycinate (200 mg) in toluene (5 mL) was added 1.0 M potassium tert-butoxide/tetrahydrofuran solution (2.2 mL), and the mixture was stirred at 90° C. for 2 hr. The reaction mixture was cooled to room temperature, 1 N hydrochloric acid (2.0 mL) was added, and the mixture was extracted with ethyl acetate. The organic layer was washed with water and brine, and dried over anhydrous magnesium sulfate. The solvent was evaporated under reduced pressure. The residue was purified by silica gel column chromatography (ethyl acetate/hexane) to give the title compound (33 mg).

$^1$H NMR (300 MHz, DMSO-d$_6$) δ 1.19-1.28 (3H, m), 1.35-1.42 (9H, m), 3.40-3.65 (2H, m), 3.76-4.30 (6H, m), 11.2 (1H, s).

C) 4-tert-butyl 5-ethyl 6-(3,4-dichlorophenyl)-2,3-dihydro-1,4-oxazepane-4,5(7H)-dicarboxylate To a mixture of 60% sodium hydride (233 mg) and anhydrous diethyl ether (12 mL) was added a solution of 4-tert-butyl 5-ethyl 6-hydroxy-2,3-dihydro-1,4-oxazepane-4,5(7H)-dicarboxylate (837 mg) in diethyl ether (8 ml) under ice-cooling and the mixture was stirred for 90 min. A solution of trifluoromethanesulfonic anhydride (0.59 mL) in diethyl ether (8 ml) was added dropwise. After stirring at room temperature for 40 min, aqueous saturated ammonium chloride was added for partitioning. The aqueous layer was extracted twice with ethyl acetate, the extract was dried over anhydrous sodium sulfate, and the solvent was evaporated under reduced pressure. The residue was used without further purification for the next reaction.

To a mixture of the above-mentioned resultant product and tetrakis(triphenylphosphine)palladium(0) (168 mg) in toluene (20 mL)-ethanol (4 ml) was added 2.5 M aqueous sodium hydrogen carbonate solution (1.8 ml), and the reaction system was purged with argon. To the reaction mixture was added 3,4-dichlorophenylboronic acid (667 mg), and the mixture was heated at 80° C. for 2 hr. The reaction mixture was cooled to room temperature, and diluted with ethyl acetate. The diluted solution was washed with water and brine, and dried over anhydrous sodium sulfate. The solvent was evaporated under reduced pressure. The residue was purified by silica gel column chromatography (ethyl acetate/hexane) to give the title compound (0.99 g).

$^1$H NMR (300 MHz, CDCl$_3$) δ 0.93-0.98 (3H, m), 1.42 (9H, s), 3.83-3.86 (4H, m), 3.93-4.00 (2H, m), 4.41 (2H, s), 7.02 (1H, dd, J=8.4, 2.1 Hz), 7.28 (1H, d, J=2.1 Hz), 7.40 (1H, d, J=8.4 Hz).

D) 4-tert-butyl 5-ethyl (5RS,6SR)-6-(3,4-dichlorophenyl)-1,4-oxazepane-4,5-dicarboxylate To a solution (4.5 mL) of 4-tert-butyl 5-ethyl 6-(3,4-dichlorophenyl)-2,3-dihydro-1,4-oxazepane-4,5(7H)-dicarboxylate (450 mg) in THF were added sodium borohydride (86 mg) and water (3 drops), and the mixture was stirred at room temperature for 3 days. To the reaction solution were added water and 0.1 N hydrochloric acid, and the mixture was extracted with ethyl acetate. The ethyl acetate layer was washed with water and brine, and dried over anhydrous sodium sulfate. The solvent was evaporated under reduced pressure. The residue was purified by silica gel column chromatography (ethyl acetate/hexane) to give the title compound (135 mg).

$^1$H NMR (300 MHz, CDCl$_3$) δ 1.11 (1.68H, t, J=7.2 Hz), 1.15 (1.32H, t, J=7.2 Hz), 1.47 (3.96H, s), 1.50 (5.04H, s), 3.40-3.48 (2H, m), 3.60-3.88 (5H, m), 4.03-4.11 (2H, m), 4.59 (0.44H, d, J=9.0 Hz), 4.87 (0.56H, d, J=9.0 Hz), 7.09-7.15 (1H, m), 7.35-7.40 (2H, m).

E) tert-butyl (5RS,6SR)-6-(3,4-dichlorophenyl)-5-(hydroxymethyl)-1,4-oxazepane-4-carboxylate To a solution of sodium borohydride (49 mg) in THF (1.25 mL)-EtOH (0.9 mL) was added calcium chloride (72 mg), and the mixture was stirred at room temperature for 20 min. To this reaction mixture was added a solution of 4-tert-butyl 5-ethyl (5RS,6SR)-6-(3,4-dichlorophenyl)-1,4-oxazepane-4,5-dicarboxylate (135 mg) in THF (1.25 ml), and the mixture was stirred at room temperature for 16 hr. The reaction mixture was poured into 10% aqueous citric acid solution, and the mixture was extracted with ethyl acetate. The extract was washed with water and brine, and dried over anhydrous sodium sulfate. The solvent was evaporated under reduced pressure. The residue was purified by silica gel column chromatography (ethyl acetate/hexane) to give the title compound (118 mg).
$^1$H NMR (300 MHz, CDCl$_3$) δ 1.51 (9H, s), 3.00-3.28 (2H, m), 3.44-3.90 (8H, m), 4.00-4.26 (1H, m), 7.14-7.18 (1H, m), 7.37 (1H, d, J=8.1 Hz), 7.42 (1H, brs).

F) [(5RS,6SR)-6-(3,4-dichlorophenyl)-1,4-oxazepan-5-yl]methanol monohydrochloride Using tert-butyl (5RS,6SR)-6-(3,4-dichlorophenyl)-5-(hydroxymethyl)-1,4-oxazepane-4-carboxylate (88 mg), and by a method similar to that of Example 1, step I), the title compound (67 mg) was obtained.
MS (ESI+): [M+H]$^+$ 276.2.

Example 15

(5RS,6SR)-6-(3,4-dichlorophenyl)-5-[(methylsulfonyl)methyl]-1,4-oxazepane monohydrochloride A) tert-butyl (5RS,6SR)-6-(3,4-dichlorophenyl)-5-[(methylsulfanyl)methyl]-1,4-oxazepane-4-carboxylate Using tert-butyl (5RS,6SR)-6-(3,4-dichlorophenyl)-5-(hydroxymethyl)-1,4-oxazepane-4-carboxylate (114 mg), and by a method similar to that of Example 5, steps A) and B), the title compound (106 mg) was obtained.
$^1$H NMR (300 MHz, CDCl$_3$) δ 1.52 (4.5H, s), 1.54 (4.5H, s), 1.98 (3H, d, J=3.3 Hz), 2.60 (2H, brs), 3.00-3.40 (2H, m), 3.52-3.84 (5H, m), 4.45 (1H, brs), 7.02-7.12 (1H, m), 7.30-7.42 (2H, m).

B) tert-butyl (5RS,6SR)-6-(3,4-dichlorophenyl)-5-[(methylsulfonyl)methyl]-1,4-oxazepane-4-carboxylate Using tert-butyl (5RS,6SR)-6-(3,4-dichlorophenyl)-5-[(methylsulfanyl)methyl]-1,4-oxazepane-4-carboxylate (100 mg), and by a method similar to that of Example 5, step C), the title compound (102 mg) was obtained.
$^1$H NMR (300 MHz, CDCl$_3$) δ 1.37 (9H, s), 1.72 (1H, brs), 2.46 (3H, s), 3.20 (3H, s), 4.23 (4H, s), 5.08-5.34 (1H, m), 5.40-5.61 (1H, m), 6.62-6.86 (3H, m).

C) (5RS,6SR)-6-(3,4-dichlorophenyl)-5-[(methylsulfonyl)methyl]-1,4-oxazepane monohydrochloride Using tert-butyl (5RS,6SR)-6-(3,4-dichlorophenyl)-5-[(methylsulfonyl)methyl]-1,4-oxazepane-4-carboxylate (100 mg), and by a method similar to that of Example 1, step I), the title compound (72 mg) was obtained.
MS (ESI+): [M+H]$^+$ 338.0.

Example 16

(6RS)-6-(3,4-dichlorophenyl)-1,4-oxazepan-6-ol monohydrochloride

A) tert-butyl (6RS)-6-(3,4-dichlorophenyl)-6-hydroxy-1,4-oxazepane-4-carboxylate To a solution of tert-butyl 6-oxo-1,4-oxazepane-4-carboxylate (418 mg) prepared by the method described in WO2004/074291 in THF (12 mL) was added 0.5 M 3,4-dichlorophenylmagnesium bromide-THF (4.7 mL) under ice-cooling. The reaction mixture was stirred at room temperature for 1.5 hr, and poured into water, and the mixture was extracted with ethyl acetate. The extract was washed successively with dil. hydrochloric acid, saturated aqueous sodium hydrogen carbonate, water and brine, and dried over anhydrous magnesium sulfate. The solvent was evaporated under reduced pressure, and the residue was purified by silica gel column chromatography (ethyl acetate/hexane) to give the title compound (455 mg).
$^1$H NMR (300 MHz, CDCl$_3$) δ 1.52 (9H, s), 3.10-3.27 (2H, m), 3.54-3.72 (2H, m), 3.88-4.15 (4H, m), 5.09 (1H, s), 7.40 (1H, d, J=8.7 Hz), 7.49-7.52 (1H, m), 7.77 (1H, s).

B) (6RS)-6-(3,4-dichlorophenyl)-1,4-oxazepan-6-ol monohydrochloride

Using tert-butyl (6RS)-6-(3,4-dichlorophenyl)-6-hydroxy-1,4-oxazepane-4-carboxylate (108 mg), and by a method similar to that of Example 1, step I), the title compound (84 mg) was obtained.
MS (ESI+): [M+H]$^+$ 262.0.

Example 17

(6RS)-6-(3,4-dichlorophenyl)-6-methoxy-1,4-oxazepane monohydrochloride

A) tert-butyl (6RS)-6-(3,4-dichlorophenyl)-6-methoxy-1,4-oxazepane-4-carboxylate To a solution of tert-butyl (6RS)-6-(3,4-dichlorophenyl)-6-hydroxy-1,4-oxazepane-4-carboxylate (130 mg) in DMF (3.0 mL) were added 60% sodium hydride (44 mg) and methyl iodide (0.068 ml) at room temperature, and the mixture was stirred for 30 min. To the reaction mixture was added ice water, and the mixture was extracted with ethyl acetate. The extract was washed with water and brine, and dried over anhydrous magnesium sulfate. The solvent was evaporated under reduced pressure. The residue was purified by silica gel column chromatography (ethyl acetate/hexane) to give the title compound (186 mg).
$^1$H NMR (300 MHz, CDCl$_3$) δ 1.28-1.34 (9H, m), 3.13 (3H, s), 3.59-3.95 (8H, m), 7.32-7.35 (1H, m), 7.43 (1H, d, J=8.4 Hz), 7.56-7.60 (1H, m).

B) (6RS)-6-(3,4-dichlorophenyl)-6-methoxy-1,4-oxazepane monohydrochloride

Using tert-butyl (6RS)-6-(3,4-dichlorophenyl)-6-methoxy-1,4-oxazepane-4-carboxylate (114 mg), and by a method similar to that of Example 1, step I), the title compound (84 mg) was obtained.
MS (ESI+): [M+H]$^+$ 276.1.

Example 18

(6RS)-6-(3,4-dichlorophenyl)-6-ethoxy-1,4-oxazepane monohydrochloride

A) tert-butyl (6RS)-6-(3,4-dichlorophenyl)-6-ethoxy-1,4-oxazepane-4-carboxylate

Using tert-butyl (6RS)-6-(3,4-dichlorophenyl)-6-hydroxy-1,4-oxazepane-4-carboxylate (158 mg) and ethyl iodide (0.052 mL), and by a method similar to that of Example 17, step A), the title compound (160 mg) was obtained.
$^1$H NMR (300 MHz, CDCl$_3$) δ 1.17 (3H, t, J=6.9 Hz), 1.36 (9H, brs), 3.12 (1H, brs), 3.46 (2H, brs), 3.60-3.66 (3H, m), 3.78-3.93 (4H, m), 7.35 (1H, dd, J=8.4, 2.1 Hz), 7.42 (1H, d, J=8.4 Hz), 7.57 (1H, brs).

B) (6RS)-6-(3,4-dichlorophenyl)-6-ethoxy-1,4-oxazepane monohydrochloride

Using tert-butyl (6RS)-6-(3,4-dichlorophenyl)-6-ethoxy-1,4-oxazepane-4-carboxylate (140 mg), and by a method similar to that of Example 1, step I), the title compound (104 mg) was obtained.
MS (ESI+): [M+H]$^+$ 290.0.

Example 19

(7RS)-7-(3,4-dichlorophenyl)-7-(methoxymethyl)-1,4-oxazepane monohydrochloride

A) 1-(3,4-dichlorophenyl)-2-methoxyethanone

A solution (about 100 mL) of 3,4-dichlorophenylmagnesium bromide in diethyl ether was prepared from a mixture of magnesium (flakes) (2.07 g) in diethyl ether (100 mL) and 1-bromo-3,4-dichlorobenzene (17.5 g). A solution of methoxyacetonitrile (5.0 g) in diethyl ether (10 mL) was added dropwise to a solution of 3,4-dichlorophenylmagnesium bromide in diethyl ether under ice-cooling, and the resulting mixture was stirred under ice-cooling for 20 min. The reaction mixture was quenched with water, the mixture was acidified with 1 N hydrochloric acid, and the mixture was stirred under ice-cooling for 15 min. The reaction mixture was extracted with ethyl acetate, the organic layer was washed with water and brine, and dried over anhydrous magnesium sulfate, and the solvent was evaporated to give a pale-yellow oil. The oil was purified by silica gel column chromatography (eluent; hexane:ethyl acetate (19:1-1:1)) to give the title compound (10.5 g).
$^1$H NMR (300 MHz, CDCl$_3$) δ 3.49 (3H, s), 4.63 (2H, s), 7.55 (1H, d, J=8.4 Hz), 7.77 (1H, dd, J=8.4, 1.8 Hz), 8.03 (1H, d, J=1.8 Hz).

B) (3RS)-3-(3,4-dichlorophenyl)-3-hydroxy-4-methoxybutanenitrile

To a solution of 1.6 M n-butyllithium/hexane solution (20 ml) in THF (50 mL) was added dropwise a solution of acetonitrile (1.23 g) in THF (5 mL) at −78° C., and the mixture was stirred for 15 min, and at −40° C. for 15 min. A solution of 1-(3,4-dichlorophenyl)-2-methoxyethanone (5.00 g) in THF (30 mL) was added dropwise at −78° C., and the mixture was gradually warmed with stirring to room temperature, and stirred for 20 min. The reaction mixture was quenched with water, and the mixture was extracted with ethyl acetate. The organic layer was washed with brine, and dried over anhydrous magnesium sulfate, and the solvent was evaporated. The residue was purified by silica gel column chromatography (eluent; hexane:ethyl acetate (0%-100%)) to give the title compound (5.63 g).
$^1$H NMR (300 MHz, CDCl$_3$) δ 2.82 (1H, d, J=16.5 Hz), 2.92 (1H, d, J=16.5 Hz), 3.24 (1H, s), 3.45 (3H, s), 3.54 (1H, d, J=9.3 Hz), 3.68 (1H, d, J=9.3 Hz), 7.32 (1H, dd, J=8.7, 2.1 Hz), 7.46 (1H, d, J=8.7 Hz), 7.62 (1H, d, J=2.1 Hz).

C) (2RS)-4-amino-2-(3,4-dichlorophenyl)-1-methoxybutan-2-ol

To a solution of (3RS)-3-(3,4-dichlorophenyl)-3-hydroxy-4-methoxybutanenitrile (5.56 g) in THF (100 mL) was added lithium aluminum hydride (812 mg) by small portions at room temperature. The mixture was stirred at room temperature for 10 min, and the reaction mixture was quenched with water. The precipitate was filtered off, and washed with THF. The filtrate was concentrated, 0.1 N aqueous potassium hydroxide solution was added, and the mixture was extracted with ethyl acetate. The organic layer was washed with brine, and dried over anhydrous sodium sulfate, and the solvent was evaporated. The residue was purified by silica gel column chromatography (NH, eluent; hexane:ethyl acetate (0%-100%)) to give the title compound (3.02 g).
$^1$H NMR (300 MHz, CDCl$_3$) δ 1.87 (1H, ddd, J=14.6, 5.3, 3.3 Hz), 2.00-2.20 (3H, m), 2.63 (1H, ddd, J=12.6, 10.5, 3.3 Hz), 3.00 (1H, ddd, J=12.6, 4.0, 5.3 Hz), 3.20-3.50 (3H, m), 3.35 (3H, s), 7.32 (1H, dd, J=8.4, 2.1 Hz), 7.39 (1H, d, J=8.4 Hz), 7.66 (1H, d, J=2.1 Hz).

D) 2-chloro-N-[(3RS)-3-(3,4-dichlorophenyl)-3-hydroxy-4-methoxybutyl]acetamide

To a solution of (2RS)-4-amino-2-(3,4-dichlorophenyl)-1-methoxybutan-2-ol (3.00 g) and triethylamine (1.60 mL) in THF (50 mL) was added dropwise chloroacetyl chloride (0.91 ml) under ice-cooling, and the mixture was stirred for 20 min. The reaction mixture was quenched with water, and the mixture was extracted with ethyl acetate. The organic layer was washed with brine, and dried over anhydrous magnesium sulfate, and the solvent was evaporated. The residue was purified by silica gel column chromatography (eluent; hexane:ethyl acetate (0%-100%)) to give the title compound (2.13 g).
$^1$H NMR (300 MHz, CDCl$_3$) δ 1.60-2.00 (1H, br), 1.95-2.20 (2H, m), 3.05-3.20 (1H, m), 3.20-3.55 (1H, m), 3.37 (3H, s), 3.50 (2H, s), 3.93 (2H, s), 7.05-7.20 (1H, m), 7.24 (1H, dd, J=8.4, 2.1 Hz), 7.43 (1H, d, J=8.4 Hz), 7.55 (1H, d, J=2.1 Hz).

E) (7RS)-7-(3,4-dichlorophenyl)-7-(methoxymethyl)-1,4-oxazepan-3-one

To a solution of 2-chloro-N-[(3RS)-3-(3,4-dichlorophenyl)-3-hydroxy-4-methoxybutyl]acetamide (2.10 g) in THF (150 ml) was added sodium tert-butoxide (592 mg), and the mixture was heated under reflux for 10 min. The reaction mixture was quenched with water, and the mixture was extracted with ethyl acetate. The organic layer was washed with brine, and dried over anhydrous magnesium sulfate, and the solvent was evaporated. The residue was purified by silica gel column chromatography (eluent; hexane:ethyl acetate (1:1)-ethyl acetate:methanol (4:1)) to give the title compound (2.13 g).

$^1$H NMR (300 MHz, CDCl$_3$) δ 2.34 (1H, dd, J=15.3, 9.9 Hz), 2.72 (1H, dd, J=15.3, 7.8 Hz), 3.10-3.25 (1H, m), 3.25 (3H, s), 3.35 (1H, d, J=9.9 Hz), 3.53 (1H, d, J=9.9 Hz), 3.55-3.70 (1H, m), 4.03 (1H, d, J=17.1 Hz), 4.30 (1H, d, J=17.1 Hz), 6.20-6.35 (1H, m), 7.22 (1H, dd, J=8.6, 2.1 Hz), 7.40-7.50 (2H, m).

F) (7RS)-7-(3,4-dichlorophenyl)-7-(methoxymethyl)-1,4-oxazepane monohydrochloride To a solution of (7RS)-7-(3,4-dichlorophenyl)-7-(methoxymethyl)-1,4-oxazepan-3-one (535 mg) in THF (10 ml) was added 1 M borane-THF solution (5 ml), and the mixture was stirred at 70° C. for 30 min. The reaction mixture was quenched with water, 2N hydrochloric acid (5 mL) was added, and the mixture was stirred at 70° C. for 10 min. The solvent was evaporated under reduced pressure, the residue was alkalified with potassium hydroxide, and the mixture was extracted three times with ethyl acetate. The organic layer was washed with brine, and dried over anhydrous sodium sulfate, and the solvent was evaporated. The residue was purified by silica gel column chromatography (NH, eluent; hexane:ethyl acetate (1:1)-(0:10)) to give the title compound as a free amine form (397 mg).

The free amine form (390 mg) of the title compound was dissolved in ethanol, 2 N hydrogen chloride-ethanol (1 ml) was added, and the solvent was evaporated. The residue was crystallized from ethanol-ethyl acetate to give the title compound (372 mg).

$^1$H NMR (300 MHz, DMSO-d$_6$) δ 2.30-2.45 (1H, m), 2.75 (1H, dd, J=16.4, 7.8 Hz), 3.00-3.55 (8H, m), 3.19 (3H, s), 3.65 (1H, dd, J=14.3, 7.8 Hz), 3.95-4.10 (1H, m), 7.38 (1H, dd, J=8.5, 2.1 Hz), 7.61 (1H, d, J=8.5 Hz), 7.64 (1H, d, J=2.1 Hz).

Example 20

[(7RS)-7-(3,4-dichlorophenyl)-1,4-oxazepan-7-yl] methanol monohydrochloride

A) 1-(3,4-dichlorophenyl)-2-(4-methoxyphenoxy) ethanone

To a solution of magnesium (2.23 g) and iodine (5 mg) in diethyl ether (20 mL) was added dropwise a solution of 1-bromo-3,4-dichlorobenzene (20.7 g) in diethyl ether (20 ml), and the mixture was stirred at 35° C. for 1 hr. The reaction mixture was cooled to −10° C., and diethyl ether (100 mL) was added. A solution of (4-methoxyphenoxy)acetonitrile (10 g) in diethyl ether (20 ml) was added dropwise at −10° C., and the mixture was stirred for 1 hr while warming to room temperature. To the reaction mixture was added 1 N aqueous HCl solution (200 ml), and the mixture was stirred at room temperature for 1 hr, and extracted with ethyl acetate. The obtained extract was washed with water and brine, and dried over anhydrous magnesium sulfate. The solvent was evaporated under reduced pressure. The obtained residue was purified by silica gel column chromatography (NH, ethyl acetate/hexane) to give the title compound (15.6 g).

$^1$H NMR (300 MHz, CDCl$_3$) δ 3.72-3.86 (3H, s), 5.12 (2H, s), 6.76-6.98 (4H, m), 7.57 (1H, d, J=8.3 Hz), 7.84 (1H, dd, J=8.5, 2.1 Hz), 8.09 (1H, d, J=1.9 Hz).

B) (3RS)-3-(3,4-dichlorophenyl)-3-hydroxy-4-(4-methoxyphenoxy)butanenitrile

To a mixed solution of acetonitrile (3.54 mL) and THF (30 mL) was added dropwise a solution of n-butyllithium in hexane (1.6 M, 42.1 ml), and the mixture was stirred at −78° C. for 30 min. To the reaction mixture was added dropwise a solution of 1-(3,4-dichlorophenyl)-2-(4-methoxyphenoxy) ethanone (14 g) in THF (45 mL), and the mixture was stirred at −78° C. for 10 min, and then stirred for 1 hr while warming to room temperature. The reaction mixture was diluted with water, and the mixture was extracted with ethyl acetate. The obtained extract was washed with brine, and dried over anhydrous magnesium sulfate. The solvent was evaporated under reduced pressure. The obtained residue was purified by silica gel column chromatography (ethyl acetate/hexane) to give the title compound (11.73 g).

$^1$H NMR (300 MHz, CDCl$_3$) δ 2.86-3.14 (2H, m), 3.29 (1H, s), 3.77 (3H, s), 4.06-4.24 (2H, m), 6.84 (4H, s), 7.33-7.42 (1H, m), 7.50 (1H, d, J=8.7 Hz), 7.70 (1H, d, J=2.3 Hz).

C) (2RS)-4-amino-2-(3,4-dichlorophenyl)-1-(4-methoxyphenoxy)butan-2-ol

To a solution of lithium aluminum hydride (2.53 g) in diethyl ether (50 mL) was added aluminum chloride (2.96 g), and the mixture was stirred at 0° C. for 30 min. To the reaction mixture was added dropwise a solution of (3RS)-3-(3,4-dichlorophenyl)-3-hydroxy-4-(4-methoxyphenoxy)butanenitrile (11.7 g) in THF (50 mL), and the mixture was stirred at 0° C. for 15 min, and then stirred while warming to room temperature for 2 hr. To the reaction mixture was added ice, and the precipitate was filtered off through celite. The filtrate was diluted with water, and the mixture was extracted with ethyl acetate. The obtained extract was washed with brine, and dried over anhydrous magnesium sulfate. The solvent was evaporated under reduced pressure to give the title compound (10.8 g).

$^1$H NMR (300 MHz, CDCl$_3$) δ 1.94-2.10 (1H, m), 2.25 (1H, ddd, J=14.4, 10.2, 3.8 Hz), 2.63-2.83 (1H, m), 2.99-3.14 (1H, m), 3.17-3.47 (3H, m), 3.68-3.78 (3H, m), 3.85 (1H, d, J=9.1 Hz), 3.94-4.05 (1H, m), 6.67-6.89 (4H, m), 7.41 (2H, s), 7.75 (1H, s).

D) N-benzyl-2-chloro-N-[(3RS)-3-(3,4-dichlorophenyl)-3-hydroxy-4-(4-methoxyphenoxy)butyl]acetamide To a solution of (2RS)-4-amino-2-(3,4-dichlorophenyl)-1-(4-methoxyphenoxy)butan-2-ol (6.7 g) in methanol (20 mL) were added magnesium sulfate (3.35 g), triethylamine (1.3 mL) and benzaldehyde (2.1 mL), and the mixture was stirred at room temperature for 1.5 hr. To the reaction mixture was added sodium borohydride (3.55 g), and the mixture was stirred at 0° C. for 10 min, and then stirred while warming to room temperature for 1.5 hr. The reaction mixture was filtered through celite, and the filtrate was concentrated. The concentrated residue was diluted with water, and the mixture was extracted with ethyl acetate. The obtained extract was washed with brine, and dried over anhydrous magnesium sulfate. The solvent was evaporated under reduced pressure to give 4-(benzylamino)-2-(3,4-dichlorophenyl)-1-(4-methoxyphenoxy)butan-2-ol (8.47 g). To a solution of 4-(benzylamino)-2-(3,4-dichlorophenyl)-1-(4-methoxyphenoxy)butan-2-ol (8.47 g) in THF (45 mL) were added triethylamine (2.85 mL) and chloroacetyl chloride (1.64 ml), and the mixture was stirred at 0° C. for 10 min, and then stirred while warming to room temperature for 2 hr. The reaction mixture was diluted with water, and the mixture was extracted with ethyl acetate. The obtained extract was washed with brine, and dried over anhydrous magnesium sulfate. The solvent was evaporated under reduced pressure. The obtained residue was purified by silica gel column chromatography (ethyl acetate/hexane) to give the title compound (7.41 g).

$^1$H NMR (300 MHz, CDCl$_3$) δ 2.13-2.43 (2H, m), 2.99 (1H, ddd, J=15.4, 11.0, 4.9 Hz), 3.26-3.60 (2H, m), 3.68-4.22 (7H, m), 4.40-4.66 (2H, m), 6.67-6.97 (4H, m), 7.07-7.72 (8H, m).

E) (7RS)-4-benzyl-7-(3,4-dichlorophenyl)-7-[(4-methoxyphenoxy)methyl]-1,4-oxazepan-3-one To a solution of N-benzyl-2-chloro-N-[(3RS)-3-(3,4-dichlorophenyl)-3-hydroxy-4-(4-methoxyphenoxy)butyl]acetamide (7.41 g) in THF (741 mL) was added sodium tert-butoxide (1.37 g), and the mixture was stirred at 0° C. for 2 hr, and then stirred while warming to room temperature for 14 hr. To the reaction mixture was added water, and the mixture was concentrated. The concentrated residue was diluted with water, and the mixture was extracted with ethyl acetate. The obtained extract was washed with brine, and dried over anhydrous magnesium sulfate. The solvent was evaporated under reduced pressure. The obtained residue was purified by silica gel column chromatography (ethyl acetate/hexane) to give the title compound (6.02 g).

$^1$H NMR (300 MHz, CDCl$_3$) δ 2.36 (1H, dd, J=15.3, 10.0 Hz), 2.80 (1H, dd, J=15.6, 8.1 Hz), 3.22 (1H, dd, J=13.8, 7.7 Hz), 3.56-3.88 (5H, m), 4.00 (1H, d, J=9.4 Hz), 4.20 (1H, d, J=17.0 Hz), 4.41-4.62 (2H, m), 4.63-4.76 (1H, m), 6.60-6.85 (4H, m), 7.15-7.40 (6H, m), 7.45 (1H, d, J=8.7 Hz), 7.53 (1H, d, J=1.9 Hz).

F) (7RS)-4-benzyl-7-(3,4-dichlorophenyl)-7-[(4-methoxyphenoxy)methyl]-1,4-oxazepane To a solution of lithium aluminum hydride (934 mg) in diethyl ether (30 mL) was added aluminum chloride (1.09 g), and the mixture was stirred at 0° C. for 10 min. To the reaction mixture was added dropwise a solution of (7RS)-4-benzyl-7-(3,4-dichlorophenyl)-7-[(4-methoxyphenoxy)methyl]-1,4-oxazepan-3-one (6.02 g) in THF (30 mL), and the mixture was stirred at 0° C. for 15 min, and stirred while warming to room temperature for 2 hr. To the reaction mixture was added ice, and the precipitate was filtered off through celite. The filtrate was diluted with water, and the mixture was extracted with ethyl acetate. The obtained extract was washed with brine, and dried over anhydrous magnesium sulfate. The solvent was evaporated under reduced pressure to give the title compound (5.46 g).

$^1$H NMR (300 MHz, CDCl$_3$) δ 2.18-2.45 (1H, m), 2.52-2.88 (5H, m), 3.46-3.63 (2H, m), 3.63-3.84 (5H, m), 3.85-4.00 (2H, m), 6.57-6.83 (4H, m), 7.16-7.44 (7H, m), 7.60 (1H, d, J=2.3 Hz).

G) tert-butyl (7RS)-7-(3,4-dichlorophenyl)-7-[(4-methoxyphenoxy)methyl]-1,4-oxazepane-4-carboxylate To a solution of (7RS)-4-benzyl-7-(3,4-dichlorophenyl)-7-[(4-methoxyphenoxy)methyl]-1,4-oxazepane (5.46 g) in acetonitrile (30 ml) were added triethylamine (2.2 mL) and 1-chloroethyl chloroformate (1.76 mL), and the mixture was stirred at 90° C. for 1.5 hr. 1-Chloroethyl chloroformate (1.0 mL) was added, and the mixture was stirred at 90° C. for 1 hr. The solvent was evaporated under reduced pressure. To the residue was added methanol (50 mL), and the mixture was stirred at 80° C. for 1 hr. The solvent was evaporated under reduced pressure. To a solution of the residue in THF (50 mL) were added triethylamine (1.75 mL) and di-tert-butyl dicarbonate (2.92 mL), and the mixture was stirred at room temperature for 1.5 hr. The reaction mixture was diluted with water, and the mixture was extracted with ethyl acetate. The obtained extract was washed with brine, and dried over anhydrous magnesium sulfate. The solvent was evaporated under reduced pressure. The obtained residue was purified by silica gel column chromatography (ethyl acetate/hexane) to give the title compound (4.75 g).

$^1$H NMR (300 MHz, CDCl$_3$) δ 1.44 (9H, s), 2.12-2.36 (1H, m), 2.71 (1H, dd, J=15.3, 7.3 Hz), 3.25-3.63 (3H, m), 3.67-4.00 (8H, m), 6.64-6.89 (4H, m), 7.18-7.33 (1H, m), 7.43 (1H, d, J=8.3 Hz), 7.57 (1H, d, J=2.3 Hz).

H) tert-butyl (7RS)-7-(3,4-dichlorophenyl)-7-(hydroxymethyl)-1,4-oxazepane-4-carboxylate To a solution of tert-butyl (7RS)-7-(3,4-dichlorophenyl)-7-[(4-methoxyphenoxy)methyl]-1,4-oxazepane-4-carboxylate (4.75 g) in acetonitrile (70 mL) and water (14 mL) was added ceric ammonium nitrate (16.18 g) at 0° C., and the mixture was stirred at 0° C. for 30 min. The reaction mixture was diluted with water, and the mixture was extracted with ethyl acetate. The obtained extract was washed with brine, and dried over anhydrous magnesium sulfate. The solvent was evaporated under reduced pressure. The obtained residue was purified by silica gel column chromatography (ethyl acetate/hexane) to give the title compound (3.36 g).

$^1$H NMR (300 MHz, CDCl$_3$) δ 1.42 (9H, s), 1.87-2.08 (1H, m), 2.17 (1H, d, J=9.1 Hz), 2.45 (1H, dd, J=14.9, 7.4 Hz), 3.20-3.97 (8H, m), 7.19 (1H, dd, J=8.5, 2.1 Hz), 7.39-7.52 (2H, m).

I) [(7RS)-7-(3,4-dichlorophenyl)-1,4-oxazepan-7-yl]methanol monohydrochloride Using tert-butyl (7RS)-7-(3,4-dichlorophenyl)-7-(hydroxymethyl)-1,4-oxazepane-4-carboxylate (200 mg), and by a method similar to that of Example 1, step I), the title compound (172 mg) was obtained.

$^1$H NMR (300 MHz, DMSO-d$_6$) δ 2.36 (1H, dd, J=16.3, 9.8 Hz), 2.76 (1H, dd, J=16.3, 8.0 Hz), 3.13 (3H, brs), 3.24-3.52 (3H, m), 3.62 (1H, dd, J=13.8, 7.8 Hz), 3.93-4.08 (1H, m), 4.97-5.21 (1H, m), 7.35 (1H, dd, J=8.3, 1.9 Hz), 7.57 (1H, d, J=1.9 Hz), 7.63 (1H, d, J=8.7 Hz), 9.18 (2H, brs).

Example 21

N-{[(7RS)-7-(3,4-dichlorophenyl)-1,4-oxazepan-7-yl]methyl}methanesulfonamide monohydrochloride

A) tert-butyl (7RS)-7-(3,4-dichlorophenyl)-7-[(1,3-dioxo-1,3-dihydro-2H-isoindol-2-yl)methyl]-1,4-oxazepane-4-carboxylate To a solution of tert-butyl (7RS)-7-(3,4-dichlorophenyl)-7-(hydroxymethyl)-1,4-oxazepane-4-carboxylate (2 g), phthalimide (0.86 g) and triphenylphosphine (4.17 g) in THF (40 ml) was added dropwise a solution (2.2 M, 7.2 ml) of diethyl azodicarboxylate in toluene at 0° C., and the mixture was stirred at 0° C. for 30 min, and then for 6 hr while warming to room temperature. To the reaction mixture were added phthalimide (0.43 g) and a solution (2.2 M, 3.6 mL) of diethyl azodicarboxylate in toluene, and the mixture was stirred at room temperature for 14 hr. The reaction mixture was diluted with water, and the mixture was extracted with ethyl acetate. The obtained extract was washed with brine, and dried over anhydrous magnesium sulfate. The solvent was evaporated under reduced pressure. The obtained residue was purified by silica gel column chromatography (ethyl acetate/hexane) and silica gel column chromatography (NH, ethyl acetate/hexane) to give the title compound (1.49 g).

$^1$H NMR (300 MHz, CDCl$_3$) δ 1.42 (9H, s), 2.26 (1H, brs), 2.45-2.62 (1H, m), 3.31-3.77 (5H, m), 3.83-3.97 (3H, m), 7.22 (1H, dd, J=8.5, 2.1 Hz), 7.34-7.42 (1H, m), 7.50 (1H, d, J=1.9 Hz), 7.66-7.74 (2H, m), 7.74-7.83 (2H, m).

B) tert-butyl (7RS)-7-(aminomethyl)-7-(3,4-dichlorophenyl)-1,4-oxazepane-4-carboxylate To a solution of tert-butyl (7RS)-7-(3,4-dichlorophenyl)-7-[(1,3-dioxo-1,3-dihydro-2H-isoindol-2-yl)methyl]-1,4-oxazepane-4-carboxylate (1.39 g) in ethanol (14 ml) was added hydrazine (2.8 ml), and the mixture was stirred at room temperature for 14 hr. The precipitate was removed by filtration, and the solvent of the filtrate was evaporated under reduced pressure. Water was added to the residue, and the mixture was extracted with ethyl acetate. The obtained extract was washed with water and brine, and dried over anhydrous magnesium sulfate. The solvent was evaporated under reduced pressure to give the title compound (0.9 g).

$^1$H NMR (300 MHz, CDCl$_3$) δ 1.20-1.32 (2H, m), 1.43 (9H, s), 2.07-2.20 (1H, m), 2.25-2.40 (1H, m), 2.64 (1H, d, J=13.2 Hz), 2.91 (1H, d, J=13.6 Hz), 3.28-3.44 (2H, m), 3.47-3.91 (4H, m), 7.16 (1H, dd, J=8.5, 2.1 Hz), 7.41-7.47 (2H, m).

C) tert-butyl (7RS)-7-(3,4-dichlorophenyl)-7-{[(methylsulfonyl)amino]methyl}-1,4-oxazepane-4-carboxylate Using tert-butyl (7RS)-7-(aminomethyl)-7-(3,4-dichlorophenyl)-1,4-oxazepane-4-carboxylate (160 mg), and in the same manner as in Example 8, step A), the title compound (167 mg) was obtained.

$^1$H NMR (300 MHz, CDCl$_3$) δ 1.37-1.49 (9H, m), 2.13-2.31 (1H, m), 2.43 (1H, brs), 2.75 (3H, s), 3.13-3.25 (1H, m), 3.29-3.92 (7H, m), 4.44 (1H, t, J=6.4 Hz), 7.18 (1H, dd, J=8.5, 2.1 Hz), 7.43-7.50 (2H, m).

D) N-{[(7RS)-7-(3,4-dichlorophenyl)-1,4-oxazepan-7-yl]methyl}methanesulfonamide monohydrochloride Using tert-butyl (7RS)-7-(3,4-dichlorophenyl)-7-{[(methylsulfonyl)amino]methyl}-1,4-oxazepane-4-carboxylate (167 mg), and in the same manner as in Example 8, step B), the title compound (99 mg) was obtained.

$^1$H NMR (300 MHz, DMSO-d$_6$) δ 2.30-2.48 (1H, m), 2.67-2.88 (4H, m), 2.99-3.48 (6H, m), 3.58-3.76 (1H, m), 3.88-4.09 (1H, m), 7.05 (1H, t, J=6.6 Hz), 7.33-7.46 (1H, m), 7.57-7.73 (2H, m), 9.22 (2H, brs).

Example 22

N-{[(7RS)-7-(3,4-dichlorophenyl)-1,4-oxazepan-7-yl]methyl}sulfamide monohydrochloride A) tert-butyl (7RS)-7-({[(tert-butoxycarbonyl)sulfamoyl]amino}methyl)-7-(3,4-dichlorophenyl)-1,4-oxazepane-4-carboxylate Using tert-butyl (7RS)-7-(aminomethyl)-7-(3,4-dichlorophenyl)-1,4-oxazepane-4-carboxylate (160 mg), and in the same manner as in Example 9, step A), the title compound (101 mg) was obtained.

$^1$H NMR (300 MHz, CDCl$_3$) δ 1.45 (18H, d, J=14.4 Hz), 2.19 (1H, d, J=13.6 Hz), 2.48 (1H, brs), 3.16 (2H, brs), 3.32-3.99 (6H, m), 5.25 (1H, brs), 7.12-7.21 (1H, m), 7.39-7.54 (2H, m), 1H not detected.

B) N-{[(7RS)-7-(3,4-dichlorophenyl)-1,4-oxazepan-7-yl]methyl}sulfamide monohydrochloride Using tert-butyl (7RS)-7-({[(tert-butoxycarbonyl)sulfamoyl]amino}methyl)-7-(3,4-dichlorophenyl)-1,4-oxazepane-4-carboxylate (101 mg), and in the same manner as in Example 9, step B), the title compound (64 mg) was obtained.

$^1$H NMR (300 MHz, DMSO-d$_6$) δ 2.39 (1H, dd, J=16.2, 9.8 Hz), 2.70-2.85 (1H, m), 2.86-3.00 (1H, m), 3.06-3.19 (4H, m), 3.24-3.30 (1H, m), 3.54-3.66 (1H, m), 3.97 (1H, d, J=15.1 Hz), 6.43-6.63 (3H, m), 7.35 (1H, dd, J=8.5, 2.1 Hz), 7.58 (1H, d, J=2.3 Hz), 7.65 (1H, d, J=8.7 Hz), 9.18 (2H, brs).

Example 23

[(2RS)-2-(3,4-dichlorophenyl)-1,4-oxazepan-2-yl]methanol monohydrochloride

A) 1,2-dichloro-4-{1-[(4-methoxyphenoxy)methyl]ethenyl}benzene

To a solution of methyltriphenylphosphonium bromide (60.3 g) in THF (800 mL) was added potassium tert-butoxide (20.7 g), and the mixture was stirred at room temperature for 1 hr. To the reaction mixture was added dropwise a solution of 1-(3,4-dichlorophenyl)-2-(4-methoxyphenoxy)ethanone (48 g) in THF (400 ml), and the mixture was stirred at room temperature for 3 hr. The reaction mixture was diluted with water, and the mixture was extracted with ethyl acetate. The obtained extract was washed with brine, and dried over anhydrous magnesium sulfate. The solvent was evaporated under reduced pressure. The obtained residue was purified by silica gel column chromatography (ethyl acetate/hexane) to give the title compound (15.1 g).

$^1$H NMR (300 MHz, CDCl$_3$) δ 3.73-3.88 (3H, m), 4.79 (2H, s), 5.49 (1H, s), 5.60 (1H, s), 6.81-6.93 (4H, m), 7.27-7.38 (2H, m), 7.57 (1H, d, J=1.9 Hz).

B) (2RS)-2-(3,4-dichlorophenyl)-2-[(4-methoxyphenoxy)methyl]oxirane

To a solution of 1,2-dichloro-4-{1-[(4-methoxyphenoxy)methyl]ethenyl}benzene (15.1 g) in toluene (161 ml) was added methachloroperbenzoic acid (21.6 g), and the mixture was stirred at 60° C. for 14 hr. The reaction mixture was cooled to 0° C., and diluted with saturated aqueous sodium hydrogen carbonate, and the mixture was extracted with ethyl acetate. The obtained extract was washed with brine, and dried over anhydrous magnesium sulfate. The solvent was evaporated under reduced pressure. The obtained residue was purified by silica gel column chromatography (ethyl acetate/hexane) to give the title compound (5.08 g).

$^1$H NMR (300 MHz, CDCl$_3$) δ 2.85 (1H, d, J=5.3 Hz), 3.22 (1H, d, J=5.3 Hz), 3.77 (3H, s), 4.20-4.26 (1H, m), 4.32-4.39 (1H, m), 6.79-6.88 (4H, m), 7.29-7.35 (1H, m), 7.40-7.45 (1H, m), 7.57 (1H, d, J=2.3 Hz).

C) tert-butyl [(2RS)-2-(3,4-dichlorophenyl)-2-hydroxy-3-(4-methoxyphenoxy)propyl](3-hydroxypropyl)carbamate To a solution of (2RS)-2-(3,4-dichlorophenyl)-2-[(4-methoxyphenoxy)methyl]oxirane (5.0 g) in acetonitrile (15 mL)

were added potassium carbonate (4.2 g) and 3-amino-1-propanol (1.41 mL), and the mixture was stirred at 100° C. for 5 hr. The reaction mixture was cooled to room temperature, di-tert-butyl dicarbonate (5.28 mL) was added, and the mixture was stirred at room temperature for 2 hr. The reaction mixture was diluted with water, and the mixture was extracted with ethyl acetate. The obtained extract was washed with brine, and dried over anhydrous magnesium sulfate. The solvent was evaporated under reduced pressure. The obtained residue was purified by silica gel column chromatography (ethyl acetate/hexane) to give the title compound (5.55 g).

$^1$H NMR (300 MHz, CDCl$_3$) δ 1.39-1.86 (12H, m), 3.09-3.90 (10H, m), 3.92-4.08 (1H, m), 5.70 (1H, brs), 6.82 (4H, s), 7.27-7.58 (2H, m), 7.61-7.87 (1H, m).

D) tert-butyl (2RS)-2-(3,4-dichlorophenyl)-2-[(4-methoxyphenoxy)methyl]-1,4-oxazepane-4-carboxylate To a solution of tert-butyl [(2RS)-2-(3,4-dichlorophenyl)-2-hydroxy-3-(4-methoxyphenoxy)propyl] (3-hydroxypropyl)carbamate (5.55 g) in toluene (120 mL) was added cyanomethylenetributylphosphorane (4.7 mL), and the mixture was stirred at 100° C. for 10 hr. The reaction mixture was diluted with water, and the mixture was extracted with ethyl acetate. The obtained extract was washed with brine, and dried over anhydrous magnesium sulfate. The solvent was evaporated under reduced pressure. The obtained residue was purified by silica gel column chromatography (ethyl acetate/hexane) to give the title compound (3.18 g).

$^1$H NMR (300 MHz, CDCl$_3$) δ 1.29-1.55 (9H, m), 1.68-1.84 (1H, m), 1.93-2.09 (1H, m), 2.91-3.10 (1H, m), 3.41-4.08 (9H, m), 4.29-4.65 (1H, m), 6.65-6.81 (4H, m), 7.28-7.36 (1H, m), 7.38-7.48 (1H, m), 7.52-7.70 (1H, m).

E) tert-butyl (2RS)-2-(3,4-dichlorophenyl)-2-(hydroxymethyl)-1,4-oxazepane-4-carboxylate To a solution of tert-butyl (2RS)-2-(3,4-dichlorophenyl)-2-[(4-methoxyphenoxy)methyl]-1,4-oxazepane-4-carboxylate (3.18 g) in acetonitrile (80 ml) and water (20 mL) was added ceric ammonium nitrate (10.8 g) at 0° C., and the mixture was stirred at 0° C. for 1 hr. The reaction mixture was diluted with water, and the mixture was extracted with ethyl acetate. The obtained extract was washed with brine, and dried over anhydrous magnesium sulfate. The solvent was evaporated under reduced pressure. The obtained residue was purified by silica gel column chromatography (NH, ethyl acetate/hexane) to give the title compound (1.9 g).

$^1$H NMR (300 MHz, CDCl$_3$) δ 1.46-1.78 (10H, m), 1.93-2.12 (1H, m), 2.65-2.89 (1H, m), 3.05 (1H, d, J=15.4 Hz), 3.23-3.40 (1H, m), 3.51-3.77 (2H, m), 3.89-4.36 (3H, m), 4.66 (1H, d, J=15.1 Hz), 7.20-7.36 (1H, m), 7.42 (1H, d, J=8.3 Hz), 7.55 (1H, d, J=1.9 Hz).

F) [(2RS)-2-(3,4-dichlorophenyl)-1,4-oxazepan-2-yl]methanol monohydrochloride Using tert-butyl (2RS)-2-(3,4-dichlorophenyl)-2-(hydroxymethyl)-1,4-oxazepane-4-carboxylate (240 mg), and by a method similar to that in Example 1, step I), the title compound (165 mg) was obtained.

$^1$H NMR (300 MHz, DMSO-d$_6$) δ 1.05 (1H, t, J=7.0 Hz), 1.78 (1H, dd, J=14.4, 2.6 Hz), 1.91-2.09 (1H, m), 2.91 (1H, d, J=11.7 Hz), 3.29 (1H, d, J=11.0 Hz), 3.37-3.69 (4H, m), 3.97 (1H, d, J=13.2 Hz), 4.15 (1H, dd, J=14.4, 6.0 Hz), 7.36 (1H, dd, J=8.5, 2.1 Hz), 7.58 (1H, d, J=1.9 Hz), 7.68 (1H, d, J=8.7 Hz), 8.34 (1H, brs), 9.87 (1H, d).

Example 24

N-{[(2RS)-2-(3,4-dichlorophenyl)-1,4-oxazepan-2-yl]methyl}methanesulfonamide monohydrochloride

A) tert-butyl (2RS)-2-(3,4-dichlorophenyl)-2-[(1,3-dioxo-1,3-dihydro-2H-isoindol-2-yl)methyl]-1,4-oxazepane-4-carboxylate Using tert-butyl (2RS)-2-(3,4-dichlorophenyl)-2-(hydroxymethyl)-1,4-oxazepane-4-carboxylate (1.0 g), and in the same manner as in Example 21, step A), the title compound (1.01 g) was obtained.

$^1$H NMR (300 MHz, CDCl$_3$) δ 1.44 (9H, d, J=11.3 Hz), 1.70-1.93 (2H, m), 3.02-3.43 (1H, m), 3.57-4.24 (7H, m), 7.28-7.43 (2H, m), 7.54 (1H, brs), 7.62-7.83 (4H, m).

B) tert-butyl (2RS)-2-(aminomethyl)-2-(3,4-dichlorophenyl)-1,4-oxazepane-4-carboxylate Using tert-butyl (2RS)-2-(3,4-dichlorophenyl)-2-[(1,3-dioxo-1,3-dihydro-2H-isoindol-2-yl)methyl]-1,4-oxazepane-4-carboxylate (1.0 g), and in the same manner as in Example 21, step B), the title compound (0.54 g) was obtained.

$^1$H NMR (300 MHz, CDCl$_3$) δ 1.46 (9H, d, J=5.3 Hz), 1.75 (1H, brs), 1.90-2.03 (1H, m), 2.71-3.17 (3H, m), 3.23-3.47 (1H, m), 3.53-3.72 (1H, m), 3.87-4.06 (2H, m), 4.16-4.51 (1H, m), 7.13-7.26 (1H, m), 7.39-7.59 (2H, m), 2H not detected.

C) tert-butyl (2RS)-2-(3,4-dichlorophenyl)-2-{[(methylsulfonyl)amino]methyl}-1,4-oxazepane-4-carboxylate Using tert-butyl (2RS)-2-(aminomethyl)-2-(3,4-dichlorophenyl)-1,4-oxazepane-4-carboxylate (135 mg), and in the same manner as in Example 8, step A), the title compound (117 mg) was obtained.

$^1$H NMR (300 MHz, CDCl$_3$) δ 1.48 (9H, s), 1.72 (1H, brs), 2.01 (1H, brs), 2.68 (3H, s), 2.73-2.88 (1H, m), 3.10-3.66 (4H, m), 3.89-4.20 (2H, m), 4.54 (1H, d, J=15.4 Hz), 5.74 (1H, brs), 7.14-7.23 (1H, m), 7.41-7.56 (2H, m).

D) N-{[(2RS)-2-(3,4-dichlorophenyl)-1,4-oxazepan-2-yl]methyl}methanesulfonamide monohydrochloride Using tert-butyl (2RS)-2-(3,4-dichlorophenyl)-2-{[(methylsulfonyl)amino]methyl}-1,4-oxazepane-4-carboxylate (117 mg), and in the same manner as in Example 8, step B), the title compound (73 mg) was obtained.

$^1$H NMR (300 MHz, DMSO-d$_6$) δ 1.67-1.84 (4H, m), 1.92-2.09 (1H, m), 2.97 (1H, brs), 3.08-3.29 (2H, m), 3.47-3.61 (2H, m), 3.72 (1H, dd, J=13.6, 7.2 Hz), 3.87-4.02 (2H, m), 7.34 (1H, dd, J=8.5, 2.1 Hz), 7.58 (1H, d, J=1.9 Hz), 7.66 (1H, d, J=8.3 Hz), 7.90 (1H, t, J=6.2 Hz), 9.01 (1H, brs), 9.48 (1H, brs).

Example 25

[(6RS,7SR)-6-(3,4-dichlorophenyl)-1,4-oxazepan-7-yl]methanol monohydrochloride

A) (4SR)-4-[(1RS)-1-(3,4-dichlorophenyl)-2-nitroethyl]-2,2-dimethyl-1,3-dioxolane To a solution of (E)-2,2-dimethyl-4-(2-nitrovinyl)-1,3-dioxolane (22.29 g) synthesized according to the method described in Tetrahedron Letters, 36 (25), 4447-4450 (1995) in THF (200 ml) was added 1 M THF solution (193 mL) of bromo(3,4-dichlorophenyl)magnesium in an inert atmosphere at −78° C. The reaction mixture was stirred at room temperature for 2 hr, and added to aqueous ammonium chloride, and the mixture was extracted with ethyl acetate. The extract was washed with brine, and dried over anhydrous magnesium sulfate. The solvent was evaporated under reduced pressure. The residue was purified by silica gel column chromatography (ethyl acetate/hexane) to give the title compound (12.16 g).

$^1$H NMR (300 MHz, CDCl$_3$) δ 1.30 (3H, s), 1.32 (3H, s), 3.38-3.46 (1H, m), 3.66 (1H, ddd, J=8.7, 6.4, 3.8 Hz), 3.99 (1H, dd, J=8.3, 6.4 Hz), 4.37 (1H, td, J=6.9, 3.6 Hz), 4.70-4.85 (2H, m), 7.13 (1H, dd, J=8.3, 2.3 Hz), 7.37-7.47 (2H, m).

B) (2RS)-2-(3,4-dichlorophenyl)-2-[(4SR)-2,2-dimethyl-1,3-dioxolan-4-yl]ethanamine A solution of (4SR)-4-[(1RS)-1-(3,4-dichlorophenyl)-2-nitroethyl]-2,2-dimethyl-1,3-dioxolane (12.16 g) and Raney-nickel (10 g) in ethanol (100 ml) was stirred under a hydrogen atmosphere at room temperature for 5 hr. The reaction mixture was filtered through celite, and the solvent of the filtrate was evaporated under reduced pressure. The residue was purified by silica gel column chromatography (methanol/ethyl acetate) to give the title compound (3.40 g).

MS (ESI+): [M+H]$^+$ 290.3.

C) (2RS)—N-benzyl-2-(3,4-dichlorophenyl)-2-[(4SR)-2,2-dimethyl-1,3-dioxolan-4-yl]ethanamine A solution of (2RS)-2-(3,4-dichlorophenyl)-2-[(4SR)-2,2-dimethyl-1,3-dioxolan-4-yl]ethanamine (3.40 g) and benzaldehyde (1.22 ml) in toluene (30 mL) was subjected to azeotropic distillation with dehydration, and the reaction mixture was concentrated. To the residue was added methanol (20 mL), and sodium borohydride (222 mg) was added at 0° C. The reaction mixture was stirred at room temperature for 30 min, and 1 N hydrochloric acid was added. The reaction mixture was basified with aqueous sodium hydrogen carbonate solution, and the mixture was extracted with ethyl acetate. The extract was washed with brine, and dried over anhydrous magnesium sulfate. The solvent was evaporated under reduced pressure. The residue was purified by silica gel column chromatography (ethyl acetate/hexane) to give the title compound (3.72 g).

$^1$H NMR (300 MHz, CDCl$_3$) δ 1.27 (3H, s), 1.30 (3H, s), 1.45 (1H, brs), 2.84-2.93 (3H, m), 3.52 (1H, t, J=7.9 Hz), 3.67-3.81 (2H, m), 4.00 (1H, dd, J=8.1, 6.2 Hz), 4.26-4.35 (1H, m), 7.08 (1H, dd, J=8.1, 2.1 Hz), 7.19-7.41 (7H, m).

D) N-benzyl-2-chloro-N-{(2RS)-2-(3,4-dichlorophenyl)-2-[(4SR)-2,2-dimethyl-1,3-dioxolan-4-yl]ethyl}acetamide To a solution of (2RS)—N-benzyl-2-(3,4-dichlorophenyl)-2-[(4SR)-2,2-dimethyl-1,3-dioxolan-4-yl]ethanamine (3.72 g) and triethylamine (1.63 ml) in THF (30 ml) was added chloroacetyl chloride (0.783 ml) at 0° C., and the reaction mixture was stirred at room temperature for 2 hr. The reaction mixture was added to water, and the mixture was extracted with ethyl acetate. The extract was washed with brine, and dried over anhydrous magnesium sulfate. The solvent was evaporated under reduced pressure. The residue was purified by silica gel column chromatography (ethyl acetate/hexane) to give the title compound (3.99 g).

$^1$H NMR (300 MHz, CDCl$_3$) δ 1.29 (3H, s), 1.33 (3H, s), 3.23-3.58 (3H, m), 3.70-4.01 (3H, m), 4.10-4.87 (4H, m), 7.01-7.22 (3H, m), 7.27-7.46 (5H, m).

E) N-benzyl-N-[(2R,3S)-4-{[tert-butyl(dimethyl)silyl]oxy}-2-(3,4-dichlorophenyl)-3-hydroxybutyl]-2-chloroacetamide A solution of N-benzyl-2-chloro-N-{(2RS)-2-(3,4-dichlorophenyl)-2-[(4SR)-2,2-dimethyl-1,3-dioxolan-4-yl]ethyl}acetamide (3.99 g) and 2N hydrochloric acid (10 ml) in THF (10 ml) was stirred at 50° C. for 4 hr. The reaction mixture was basified with 1 N aqueous sodium hydroxide solution, and the mixture was extracted with ethyl acetate. The extract was washed with brine, and dried over anhydrous magnesium sulfate. The solvent was evaporated under reduced pressure. The residue was dissolved in DMF (20 ml), triethylamine (1.45 ml), tert-butyl(dimethyl)silyl chloride (1.45 g) and 4-dimethylaminopyridine (10 mg) were added, and the mixture was stirred at room temperature for 5 hr. The reaction mixture was added to water, and the mixture was extracted with ethyl acetate. The extract was washed with brine, and dried over anhydrous magnesium sulfate. The solvent was evaporated under reduced pressure. The residue was purified by silica gel column chromatography (ethyl acetate/hexane) to give the title compound (4.13 g).

$^1$H NMR (300 MHz, CDCl$_3$) δ −0.02 (3H, s), −0.01 (3H, s), 0.87 (9H, s), 3.05-3.26 (3H, m), 3.41 (1H, dd, J=10.2, 6.8 Hz), 3.60 (1H, d, J=3.4 Hz), 3.80-3.89 (1H, m), 4.03-4.27 (3H, m), 4.38 (1H, d, J=17.3 Hz), 4.70 (1H, d, J=17.0 Hz), 7.06-7.25 (3H, m), 7.27-7.45 (5H, m).

F) (6RS,7SR)-4-benzyl-7-({[tert-butyl(dimethyl)silyl]oxy}methyl)-6-(3,4-dichlorophenyl)-1,4-oxazepan-3-one To a solution of N-benzyl-N-[(2R,3S)-4-{[tert-butyl(dimethyl)silyl]oxy}-2-(3,4-dichlorophenyl)-3-hydroxybutyl]-2-chloroacetamide (4.13 g) in THF (100 mL) was added sodium tert-butoxide (897 mg) at 0° C., and the mixture was stirred at room temperature for 1 hr. The reaction mixture was added to water, and the mixture was extracted with ethyl acetate. The extract was washed with brine, and dried over anhydrous magnesium sulfate. The solvent was evaporated under reduced pressure. The residue was purified by silica gel column chromatography (ethyl acetate/hexane) to give the title compound (3.52 g).

MS (ESI+): [M+H]$^+$ 494.2.

G) [(6RS,7SR)-4-benzyl-6-(3,4-dichlorophenyl)-1,4-oxazepan-7-yl]methanol

To a solution of (6RS,7SR)-4-benzyl-7-({[tert-butyl(dimethyl)silyl]oxy}methyl)-6-(3,4-dichlorophenyl)-1,4-oxazepan-3-one (3.11 g) in THF (20 mL) was added 1 M THF solution (13.8 mL) of borane-THF complex at 0° C., and the mixture was stirred at 60° C. for 2 hr. To the reaction mixture was added methanol, and the solvent was evaporated under reduced pressure. To the residue was added 6 N hydrochloric acid (8 mL), and the reaction mixture was stirred at 60° C. overnight. The reaction mixture was basified with 8 N aqueous sodium hydroxide solution, and the mixture was extracted with ethyl acetate. The extract was washed with brine, and dried over anhydrous magnesium sulfate. The solvent was evaporated under reduced pressure. The residue was purified by silica gel column chromatography (ethyl acetate/hexane) to give the title compound (2.22 g).

¹H NMR (300 MHz, CDCl₃) δ 1.86 (1H, brs), 2.63-2.80 (2H, m), 2.82-2.91 (1H, m), 2.95-3.14 (2H, m), 3.18 (2H, d, J=8.7 Hz), 3.64-3.76 (3H, m), 4.04-4.10 (1H, m), 4.20 (1H, dt, J=8.7, 4.3 Hz), 7.13 (1H, dd, J=8.3, 2.3 Hz), 7.27-7.38 (6H, m), 7.44 (1H, d, J=1.9 Hz).

H) (6RS,7SR)-4-benzyl-7-({[tert-butyl(dimethyl)silyl]oxy}methyl)-6-(3,4-dichlorophenyl)-1,4-oxazepane A solution of [(6RS,7SR)-4-benzyl-6-(3,4-dichlorophenyl)-1,4-oxazepan-7-yl]methanol (1.63 g), triethylamine (0.741 mL), tert-butyldimethylsilyl chloride (738 mg) and 4-dimethylaminopyridine (catalytic amount) in DMF (10 ml) was stirred at room temperature for 2 hr. The reaction mixture was added to water, and the mixture was extracted with ethyl acetate. The extract was washed with brine, and dried over anhydrous magnesium sulfate. The solvent was evaporated under reduced pressure. The residue was purified by silica gel column chromatography (ethyl acetate/hexane) to give the title compound (1.93 g).

¹H NMR (300 MHz, CDCl₃) δ −0.08 (3H, s), −0.04 (3H, s), 0.86 (9H, s), 2.59-2.88 (3H, m), 2.99-3.16 (3H, m), 3.34 (1H, dd, J=10.2, 6.8 Hz), 3.60-3.71 (3H, m), 3.98 (1H, dt, J=12.1, 3.6 Hz), 4.08-4.17 (1H, m), 7.18-7.38 (7H, m), 7.48 (1H, d, J±1.9 Hz).

I) [(6RS,7SR)-6-(3,4-dichlorophenyl)-1,4-oxazepan-7-yl]methanol monohydrochloride To a solution of (6RS,7SR)-4-benzyl-7-({[tert-butyl(dimethyl)silyl]oxy}methyl)-6-(3,4-dichlorophenyl)-1,4-oxazepane (250 mg) in acetonitrile (1.5 mL) was added 1-chloroethyl chloroformate (0.0786 mL), and the mixture was stirred at room temperature for 1.5 hr. The solvent was evaporated under reduced pressure. To the residue was added methanol (1.5 ml), and the reaction mixture was stirred at 60° C. for 3 hr. The solvent was evaporated under reduced pressure. The residue was solidified with diisopropyl ether, and the obtained crude crystals were recrystallized from ethanol/ether/water to give the title compound (76.8 mg).

MS (ESI+): [M+H]⁺ 276.2.

Example 26

(6RS,7SR)-6-(3,4-dichlorophenyl)-7-[(methylsulfonyl)methyl]-1,4-oxazepane monohydrochloride A) tert-butyl (6RS,7SR)-6-(3,4-dichlorophenyl)-7-(hydroxymethyl)-1,4-oxazepane-4-carboxylate A solution of [(6RS,7SR)-6-(3,4-dichlorophenyl)-1,4-oxazepan-7-yl]methanol monohydrochloride (1.04 g), di-tert-butyl dicarbonate (799 mg) and triethylamine (1.02 mL) in THF (10 ml) was stirred at room temperature for 3 hr. The solvent was evaporated under reduced pressure. The residue was added to water, and the mixture was extracted with ethyl acetate. The extract was washed with brine, and dried over anhydrous magnesium sulfate. The solvent was evaporated under reduced pressure. The residue was purified by silica gel column chromatography (ethyl acetate/hexane) to give the title compound (1.02 g).

¹H NMR (300 MHz, CDCl₃) δ 1.46 (9H, d, J=11.3 Hz), 1.73-1.85 (1H, m), 2.94-3.45 (5H, m), 3.57-3.85 (2H, m), 3.94-4.27 (3H, m), 7.06-7.20 (1H, m), 7.29-7.48 (2H, m).

B) (6RS,7SR)-6-(3,4-dichlorophenyl)-7-[(methylsulfonyl)methyl]-1,4-oxazepane monohydrochloride Using tert-butyl (6RS,7SR)-6-(3,4-dichlorophenyl)-7-(hydroxymethyl)-1,4-oxazepane-4-carboxylate (101.8 mg), and by a method similar to that in Example 5, the title compound (30.4 mg) was obtained.

MS (ESI+): [M+H]⁺ 338.2.

Example 27

N-{[(6RS,7SR)-6-(3,4-dichlorophenyl)-1,4-oxazepan-7-yl]methyl}acetamide monohydrochloride Using tert-butyl (6RS,7SR)-6-(3,4-dichlorophenyl)-7-(hydroxymethyl)-1,4-oxazepane-4-carboxylate (920 mg) and by a method similar to that in Example 21, steps A) and B) and Example 6, steps C) and D), the title compound (55.7 mg) was obtained.

MS (ESI+): [M+H]⁺ 317.3.

Example 28

1-{[(6RS,7SR)-6-(3,4-dichlorophenyl)-1,4-oxazepan-7-yl]methyl}urea monohydrochloride Using tert-butyl (6RS,7SR)-6-(3,4-dichlorophenyl)-7-(hydroxymethyl)-1,4-oxazepane-4-carboxylate (920 mg), and by a method similar to that in Example 21, steps A) and B) and Example 3, steps D) and E), the title compound (74.3 mg) was obtained.

MS (ESI+): [M+H]⁺ 318.2.

Example 29

N-{[(6RS,7SR)-6-(3,4-dichlorophenyl)-1,4-oxazepan-7-yl]methyl}methanesulfonamide monohydrochloride Using tert-butyl (6RS,7SR)-6-(3,4-dichlorophenyl)-7-(hydroxymethyl)-1,4-oxazepane-4-carboxylate (920 mg), and by a method similar to that in Example 21, the title compound (39.0 mg) was obtained.

MS (ESI+): [M+H]⁺ 353.2.

Example 30

N-{[(6RS,7SR)-6-(3,4-dichlorophenyl)-1,4-oxazepan-7-yl]methyl}sulfamide monohydrochloride Using tert-butyl (6RS,7SR)-6-(3,4-dichlorophenyl)-7-(hydroxymethyl)-1,4-oxazepane-4-carboxylate (920 mg), and by a method similar to that in Example 21, steps A) and B) and Example 9, the title compound (66.6 mg) was obtained.

MS (ESI+): [M+H]⁺ 354.2.

Example 31

1-{[(6S,7R)-7-(3,4-dichlorophenyl)-1,4-oxazepan-6-yl]methyl}-3-(5-oxo-4,5-dihydro-1,2,4-oxadiazol-3-yl)pyridin-2(1H)-one monohydrochloride A) tert-butyl (6S,7R)-7-(3,4-dichlorophenyl)-6-(hydroxymethyl)-1,4-oxazepane-4-carboxylate tert-Butyl (6RS,7SR)-7-(3,4-dichlorophenyl)-6-(hydroxymethyl)-1,4-oxazepane-4-carboxylate (67.28 g) was separated by HPLC (CHIRALPAK AD, 50 mmID×500 mL, manufactured by DAICEL CHEMICAL INDUSTRIES, LTD., mobile phase: hexane/ethanol=900/100) to give tert-butyl (6R,7S)-7-(3,4-dichlorophenyl)-6-(hydroxymethyl)-1,4-oxazepane-4-carboxylate (29.9 g, >99.6% ee., recovery rate 98%) having a longer retention time and the title compound (31.3 g, >99.9% ee., recovery rate 100%) having a shorter retention time.

$^1$H NMR (300 MHz, CDCl$_3$) δ 1.51 (9H, s), 2.06-2.17 (1H, m), 3.05-3.28 (2H, m), 3.43 (1H, dd, J=14.9, 6.6 Hz), 3.49-3.65 (2H, m), 4.02-4.12 (3H, m), 4.21 (1H, dd, J=9.8, 4.5 Hz), 4.33 (1H, d, J=9.8 Hz), 7.19 (1H, dd, J=8.3, 1.9 Hz), 7.40 (1H, d, J=8.3 Hz), 7.48 (1H, d, J=1.9 Hz).

B) tert-butyl (6S,7R)-7-(3,4-dichlorophenyl)-6-{[(methylsulfonyl)oxy]methyl}-1,4-oxazepane-4-carboxylate Methanesulfonyl chloride (1.366 mL, 17.65 mmol) was added dropwise to a solution of tert-butyl (6S,7R)-7-(3,4-dichlorophenyl)-6-(hydroxymethyl)-1,4-oxazepane-4-carboxylate (5.11 g, 13.58 mmol) and triethylamine (2.84 mL, 20.37 mmol) in THF (50 mL) under ice-cooling, and the mixture was stirred under ice-cooling for 2 hr. The reaction mixture was diluted with aqueous sodium hydrogen carbonate solution, and the mixture was extracted with ethyl acetate. The extract was washed with water and brine, and dried over anhydrous sodium sulfate, and the solvent was evaporated to give the title compound (5.95 g).

$^1$H NMR (300 MHz, CDCl$_3$) δ 1.50 (9H, s), 2.33-2.46 (1H, m), 2.89 (1H, brs), 3.02 (2H, brs), 3.41-3.55 (1H, m), 3.57-3.90 (4H, m), 3.97-4.16 (3H, m), 4.20 (1H, d, J=9.4 Hz), 7.16 (1H, dd, J=8.3, 1.9 Hz), 7.41-7.47 (2H, m).

C) tert-butyl (6R,7R)-6-[(3-cyano-2-oxopyridin-1(2H)-yl)methyl]-7-(3,4-dichlorophenyl)-1,4-oxazepane-4-carboxylate 60% Sodium hydride (0.086 g) was added to a mixed solution of 3-cyano-2-hydroxypyridine (0.206 g) in 1,2-dimethoxyethane (4 ml)-DMF (2 ml) under ice-cooling, and the mixture was stirred for 5 min. To the reaction solution was added lithium bromide (0.248 g), and the mixture was stirred at room temperature for 0.5 hr. To the reaction solution was added a solution of tert-butyl (6S,7R)-7-(3,4-dichlorophenyl)-6-{[(methylsulfonyl)oxy]methyl}-1,4-oxazepane-4-carboxylate (0.65 g) in 1,2-dimethoxyethane (4 mL), and the mixture was stirred at 60° C. overnight. To the reaction mixture was added water, and the mixture was extracted with ethyl acetate. The extract was washed with brine, and dried over anhydrous sodium sulfate. The solvent was evaporated under reduced pressure. The residue was purified by silica gel column chromatography to give the title compound (0.59 g, 86%).

$^1$H NMR (300 MHz, CDCl$_3$) δ 1.52 (9H, s), 2.91 (1H, brs), 3.06-3.28 (2H, m), 3.56-3.76 (2H, m), 3.79-4.12 (5H, m), 6.25 (1H, t, J=6.2 Hz), 7.32 (1H, d, J=7.9 Hz), 7.37-7.53 (2H, m), 7.76 (1H, d, J=6.0 Hz), 8.27 (1H, d, J=4.9 Hz).

D) tert-butyl (6R,7R)-7-(3,4-dichlorophenyl)-6-{[2-oxo-3-(5-oxo-4,5-dihydro-1,2,4-oxadiazol-3-yl)pyridin-1(2H)-yl]methyl}-1,4-oxazepane-4-carboxylate Sodium hydrogen carbonate (829 mg, 9.87 mmol) and hydroxylamine hydrochloride (686 mg, 9.87 mmol) were added to a solution of tert-butyl (6R,7R)-6-[(3-cyano-2-oxopyridin-1(2H)-yl)methyl]-7-(3,4-dichlorophenyl)-1,4-oxazepane-4-carboxylate (590 mg, 1.23 mmol) in DMSO (4 mL), and the mixture was stirred at 80° C. for 5 hr. The reaction mixture was diluted with water, and the mixture was extracted with ethyl acetate. The extract was washed with brine, and dried over anhydrous sodium sulfate. The solvent was evaporated under reduced pressure. The residue was diluted with THF (10 mL), diazabicycloundecene (0.184 mL, 1.23 mmol) and carbonyl-1,1'-bisimidazole (299 mg, 1.85 mmol) were added, and the mixture was stirred at 70° C. for 2 hr. The reaction mixture was concentrated under reduced pressure, and the residue was acidified with 1 N hydrochloric acid, and the mixture was extracted with ethyl acetate. The extract was washed with brine, and dried over anhydrous sodium sulfate. The solvent was evaporated under reduced pressure. The residue was purified by silica gel column chromatography, and recrystallized from ethanol-hexane to give the title compound (480 mg, 0.893 mmol, 72.6%).

$^1$H NMR (300 MHz, CDCl$_3$) δ 1.53 (9H, s), 2.89 (1H, brs), 3.05-3.30 (2H, m), 3.62 (1H, t, J=11.7 Hz), 3.77 (1H, t, J=11.5 Hz), 3.95-4.16 (4H, m), 4.34 (1H, d, J=12.1 Hz), 6.47 (1H, t, J=6.6 Hz), 7.19-7.28 (1H, m), 7.29-7.35 (1H, m), 7.53 (1H, brs), 8.26 (1H, d, J=6.4 Hz), 8.57 (1H, d, J=5.3 Hz), 10.39 (1H, brs).

E) 1-{[(6S,7R)-7-(3,4-dichlorophenyl)-1,4-oxazepan-6-yl]methyl}-3-(5-oxo-4,5-dihydro-1,2,4-oxadiazol-3-yl)pyridin-2(1H)-one monohydrochloride A 14 N hydrogen chloride-ethanol solution (2 mL, 28.00 mmol) was added to a solution of tert-butyl (6R,7R)-7-(3,4-dichlorophenyl)-6-{[2-oxo-3-(5-oxo-4,5-dihydro-1,2,4-oxadiazol-3-yl)pyridin-1(2H)-yl]methyl}-1,4-oxazepane-4-carboxylate (795 mg, 1.48 mmol) in ethanol (8 mL). The reaction mixture was stirred at room temperature for 3 hr, and at 80° C. for 15 min. The reaction mixture was concentrated under reduced pressure, and the residue was collected by filtration, and washed with ethanol-hexane to give the title compound (655 mg, 1.383 mmol, 93%).

$^1$H NMR (300 MHz, DMSO-d$_6$) δ 3.10-3.39 (5H, m), 3.76-3.90 (2H, m), 3.98-4.09 (2H, m), 4.55 (1H, d, J=9.8 Hz), 6.39 (1H, t, J=7.0 Hz), 7.42 (1H, dd, J=8.3, 1.9 Hz), 7.59 (1H, d, J=8.3 Hz), 7.66 (1H, d, J=1.9 Hz), 7.85 (1H, dd, J=6.8, 1.9 Hz), 7.90 (1H, dd, J=7.2, 2.3 Hz), 9.45 (1H, brs), 12.00 (1H, brs), 1H not detected.

MS (ESI+): [M+H]$^+$ 437.0.

Example 32

N-{[(6S,7R)-7-(3,4-dichlorophenyl)-1,4-oxazepan-6-yl]methyl}acetamide 0.5 fumarate A) tert-butyl (6S,7R)-6-(azidomethyl)-7-(3,4-dichlorophenyl)-1,4-oxazepane-4-carboxylate To a solution of tert-butyl (6S,7R)-7-(3,4-dichlorophenyl)-6-{[(methylsulfonyl)oxy]methyl}-1,4-oxazepane-4-carboxylate (1.43 g) in DMF (15 mL) was added sodium azide (322 mg), and the mixture was stirred at 70° C. overnight. The solvent was evaporated under reduced pressure, distilled water was added to the reaction mixture, and the mixture was extracted twice with ethyl acetate. The combined organic layers were washed with brine, and dried over anhydrous magnesium sulfate. The solvent was evaporated under reduced pressure to give the title compound (1.23 g).

MS (ESI+): [M+H-Boc]$^+$ 301.0, 302.9.

B) tert-butyl (6R,7R)-6-(aminomethyl)-7-(3,4-dichlorophenyl)-1,4-oxazepane-4-carboxylate To a solution of tert-butyl (6S,7R)-6-(azidomethyl)-7-(3,4-dichlorophenyl)-1,4-oxazepane-4-carboxylate (1.23 g) in THF (12.5 mL) and distilled water (2.5 mL) was added triphenylphosphine (967 mg), and the mixture was stirred at room temperature overnight. To the reaction mixture was added distilled water, and the mixture was extracted twice with ethyl acetate. The combined organic layers were washed with brine, and dried over anhydrous magnesium sulfate. The solvent was evaporated under reduced pressure. The residue was purified by silica gel chromatography (ethyl acetate/methanol) to give the title compound (1.12 g).
MS (ESI+): [M+H]$^+$ 375.4, 377.3.

C) tert-butyl (6R,7R)-6-[(acetylamino)methyl]-7-(3,4-dichlorophenyl)-1,4-oxazepane-4-carboxylate To a solution of tert-butyl (6R,7R)-6-(aminomethyl)-7-(3,4-dichlorophenyl)-1,4-oxazepane-4-carboxylate (150 mg) in THF (2 ml) were added triethylamine (0.084 mL) and acetyl chloride (47 mg), and the mixture was stirred at under ice-cooling for 2 hr. The solvent was evaporated under reduced pressure, distilled water was added to the reaction mixture, and the mixture was extracted twice with ethyl acetate. The combined organic layers were washed with brine, and dried over anhydrous magnesium sulfate. The solvent was evaporated under reduced pressure. The residue was purified by silica gel chromatography (hexane/ethyl acetate) to give the title compound (162 mg).
MS (ESI+): [M+H-Boc]$^+$ 317.0.

D) N-{[(6S,7R)-7-(3,4-dichlorophenyl)-1,4-oxazepan-6-yl]methyl}acetamide 0.5 fumarate To a solution of tert-butyl (6R,7R)-6-[(acetylamino)methyl]-7-(3,4-dichlorophenyl)-1,4-oxazepane-4-carboxylate (160 mg) in ethanol (0.5 mL) was added 4.0 M hydrogen chloride-ethyl acetate solution (3 mL), and the mixture was stirred at room temperature for 1.5 hr. The solvent was evaporated under reduced pressure. To the residue was added 1 N aqueous sodium hydroxide solution, and the mixture was extracted twice with ethyl acetate. The combined organic layers were washed with brine, and dried over anhydrous magnesium sulfate. The solvent was evaporated under reduced pressure. The residue was dissolved in ethanol, and a solution of fumaric acid (39.3 mg) in ethanol was added. The solvent was evaporated under reduced pressure. The obtained crystals were recrystallized from ethanol-ethyl acetate to give the title compound (73.5 mg) as colorless crystals.
$^1$H NMR (300 MHz, DMSO-d$_6$) δ 1.73 (3H, s), 2.17 (1H, td, J=8.9, 4.4 Hz), 2.78-3.05 (6H, m), 3.58 (1H, ddd, J=12.7, 8.7, 4.2 Hz), 3.91 (1H, dt, J=12.6, 3.2 Hz), 4.27 (1H, d, J=9.5 Hz), 6.49 (1H, s), 7.29-7.46 (1H, m), 7.54-7.72 (2H, m), 7.88 (1H, t, J=5.3 Hz), 2H not detected.
MS (ESI+): [M+H]$^+$ 317.3, 319.3.

Example 33

N-{[(6S,7R)-7-(3,4-dichlorophenyl)-1,4-oxazepan-6-yl]methyl}-2-methoxyacetamide monohydrochloride A) tert-butyl (6R,7R)-7-(3,4-dichlorophenyl)-6-{[(methoxyacetyl)amino]methyl}-1,4-oxazepane-4-carboxylate To a solution of tert-butyl (6R,7R)-6-(aminomethyl)-7-(3,4-dichlorophenyl)-1,4-oxazepane-4-carboxylate (165 mg) in THF (2.5 mL) were added triethylamine (89 mg) and methoxyacetyl chloride (71.6 mg), and the mixture was stirred at room temperature for 1 hr. The solvent was evaporated under reduced pressure, distilled water was added to the residue, and the mixture was extracted twice with ethyl acetate. The combined organic layers were washed with brine, and dried over anhydrous magnesium sulfate. The solvent was evaporated under reduced pressure. The residue was purified by silica gel chromatography (hexane/ethyl acetate) to give the title compound (161 mg).
MS (ESI+): [M+1]$^+$ 447.1, 449.0.

B) N-{[(6S,7R)-7-(3,4-dichlorophenyl)-1,4-oxazepan-6-yl]methyl}-2-methoxyacetamide monohydrochloride To a solution of tert-butyl (6R,7R)-7-(3,4-dichlorophenyl)-6-{[(methoxyacetyl)amino]methyl}-1,4-oxazepane-4-carboxylate (161 mg) in ethanol (1 ml) was added 14.0 M hydrogen chloride-ethanol solution (2 mL), and the mixture was stirred at room temperature for 1 hr. The solvent was evaporated under reduced pressure. The obtained crystals were recrystallized from ethanol to give the title compound (125 mg) as colorless crystals.
$^1$H NMR (300 MHz, DMSO-d$_6$) δ 2.54-2.69 (1H, m), 2.79-2.90 (1H, m), 3.01 (1H, dq, J=8.5, 7.0 Hz), 3.07-3.32 (7H, m), 3.71-3.86 (3H, m), 3.91-4.03 (1H, m), 4.39 (1H, d, J=10.2 Hz), 7.45 (1H, dd, J=8.3, 2.1 Hz), 7.67 (1H, d, J=8.3 Hz), 7.76 (1H, d, J=1.9 Hz), 8.07 (1H, t, J=6.1 Hz), 9.02 (1H, brs), 9.42 (1H, brs).
MS (ESI+): [M+H]$^+$ 347.0, 349.0.

Example 34

N-{[(6S,7R)-7-(3,4-dichlorophenyl)-1,4-oxazepan-6-yl]methyl}methanesulfonamide monohydrochloride A) tert-butyl (6S,7R)-7-(3,4-dichlorophenyl)-6-{[(methylsulfonyl)amino]methyl}-1,4-oxazepane-4-carboxylate To a solution of tert-butyl (6R,7R)-6-(aminomethyl)-7-(3,4-dichlorophenyl)-1,4-oxazepane-4-carboxylate (150 mg) in THF (2 mL) were added triethylamine (60.7 mg) and methanesulfonyl chloride (68.7 mg) under ice-cooling, and the mixture was stirred for 1 hr. The solvent was evaporated under reduced pressure, distilled water was added to the residue, and the mixture was extracted twice with ethyl acetate. The combined organic layers were washed with brine, and dried over anhydrous magnesium sulfate. The solvent was evaporated under reduced pressure. The residue was purified by silica gel chromatography (hexane/ethyl acetate) to give the title compound (161 mg).
MS (ESI+): [M+H-Boc]$^+$ 353.0, 355.0.

B) N-{[(6S,7R)-7-(3,4-dichlorophenyl)-1,4-oxazepan-6-yl]methyl}methanesulfonamide monohydrochloride To a solution of tert-butyl (6S,7R)-7-(3,4-dichlorophenyl)-6-{[(methylsulfonyl)amino]methyl}-1,4-oxazepane-4-carboxylate (162 mg) in ethanol (0.5 mL) was added 4.0 M hydrogen chloride-ethyl acetate solution (3 mL), and the mixture was stirred at room temperature for 2 hr. The solvent was evaporated under reduced pressure. The obtained crystals were recrystallized from ethanol-water to give the title compound (109 mg) as colorless crystals.

¹H NMR (300 MHz, DMSO-d₆) δ 2.52-2.61 (1H, m), 2.69-2.79 (2H, m), 2.83 (3H, s), 3.15 (1H, dt, J=13.1, 4.0 Hz), 3.20-3.32 (2H, m), 3.44 (1H, dd, J=13.8, 2.3 Hz), 3.79 (1H, ddd, J=13.6, 8.9, 4.2 Hz), 4.02 (1H, dt, J=13.8, 4.4 Hz), 4.38 (1H, d, J=10.2 Hz), 7.26 (1H, t, J=6.4 Hz), 7.42 (1H, dd, J=8.3, 2.1 Hz), 7.69 (1H, d, J=8.1 Hz), 7.72 (1H, d, J=1.9 Hz), 9.19 (2H, brs).

MS (ESI+): [M+H]⁺ 352.9, 355.0.

Example 35

N-{[(6S,7R)-7-(3,4-dichlorophenyl)-1,4-oxazepan-6-yl]methyl}sulfamide monohydrochloride A) tert-butyl (6S,7R)-6-({[(tert-butoxycarbonyl)sulfamoyl]amino}methyl)-7-(3,4-dichlorophenyl)-1,4-oxazepane-4-carboxylate To a solution of tert-butyl (6R,7R)-6-(aminomethyl)-7-(3,4-dichlorophenyl)-1,4-oxazepane-4-carboxylate (100 mg) in acetonitrile (2 mL) was added N-(tert-butoxycarbonyl)-N-[4-(dimethylazaniumylidene)-1,4-dihydropyridin-1-ylsulfonyl]azanide (181 mg) prepared by the method described in Organic Letters, 2001, 3 (14), 2241-2243, and the mixture was stirred at room temperature for 12 hr. The reaction mixture was concentrated under reduced pressure, distilled water was added to the residue, and the mixture was extracted twice with ethyl acetate. The combined organic layers were washed with brine, and dried over anhydrous magnesium sulfate. The solvent was evaporated under reduced pressure. The residue was purified by silica gel chromatography (hexane/ethyl acetate) to give the title compound (172 mg).

¹H NMR (300 MHz, CDCl₃) δ 1.50 (18H, d, J=5.3 Hz), 2.16-2.36 (1H, m), 2.79-2.94 (1H, m), 2.97-3.19 (2H, m), 3.43 (1H, dd, J=15.1, 6.4 Hz), 3.58 (1H, td, J=12.3, 2.3 Hz), 4.01-4.15 (3H, m), 4.28 (1H, d, J=9.4 Hz), 6.88 (1H, brs), 7.15 (1H, dd, J=8.1, 4.3 Hz), 7.20-7.29 (1H, m), 7.41 (1H, d, J=8.3 Hz), 7.52 (1H, d, J=1.5 Hz).

B) N-{[(6S,7R)-7-(3,4-dichlorophenyl)-1,4-oxazepan-6-yl]methyl}sulfamide monohydrochloride To a solution of tert-butyl (6S,7R)-6-({[(tert-butoxycarbonyl)sulfamoyl]amino}methyl)-7-(3,4-dichlorophenyl)-1,4-oxazepane-4-carboxylate (172 mg) in ethanol (0.5 mL) was added 4.0 M hydrogen chloride-ethyl acetate solution (3 mL), and the mixture was stirred at room temperature for 2 hr. The solvent was evaporated under reduced pressure. The obtained crystals were recrystallized from ethanol-water to give the title compound (89 mg) as colorless crystals.

¹H NMR (300 MHz, DMSO-d₆) δ 2.52-2.61 (1H, m), 2.61-2.70 (2H, m), 3.10-3.31 (3H, m), 3.39-3.54 (1H, m), 3.80 (1H, ddd, J=12.5, 8.3, 3.8 Hz), 4.02 (1H, dt, J=14.0, 3.8 Hz), 4.40 (1H, d, J=10.2 Hz), 6.56 (2H, s), 6.78 (1H, t, J=6.4 Hz), 7.41 (1H, dd, J=8.3, 1.9 Hz), 7.67 (1H, d, J=8.3 Hz), 7.71 (1H, d, J=1.9 Hz), 9.19 (2H, brs).

MS (ESI+): [M+H]⁺ 354.1, 356.0.

Example 36

N-[(6R,7S)-7-(3,4-dichlorophenyl)-1,4-oxazepan-6-yl]acetamide monofumarate

A) tert-butyl (6R,7R)-7-(3,4-dichlorophenyl)-6-formyl-1,4-oxazepane-4-carboxylate To a solution of tert-butyl (6S,7R)-7-(3,4-dichlorophenyl)-6-(hydroxymethyl)-1,4-oxazepane-4-carboxylate (10 g) in acetonitrile (133 ml) was added Dess-Martin periodinane (13.53 g) under ice-cooling, and the mixture was stirred under ice-cooling for 3 hr. To the reaction mixture were added saturated aqueous sodium hydrogen carbonate and aqueous saturated sodium thiosulfate solution at room temperature, and the mixture was stirred at room temperature for 1 hr. The reaction mixture was extracted with ethyl acetate. The extract was washed with distilled water and brine, and dried over anhydrous magnesium sulfate. The solvent was evaporated under reduced pressure, and the residue was purified by silica gel chromatography (hexane/ethyl acetate) to give the title compound (8.3 g).

¹H NMR (300 MHz, CDCl₃) δ 1.43-1.56 (9H, m), 2.87-3.37 (2H, m), 3.48-3.77 (2H, m), 3.80-4.20 (2H, m), 4.34 (1H, d, J=15.1 Hz), 4.69-5.13 (1H, m), 7.18 (1H, d, J=8.3 Hz), 7.33-7.40 (1H, m), 7.40-7.56 (1H, m), 9.46-9.85 (1H, m).

MS (ESI+): [M+H-Boc]⁺ 274.0.

B) (6R,7R)-4-(tert-butoxycarbonyl)-7-(3,4-dichlorophenyl)-1,4-oxazepane-6-carboxylic acid To a mixed solution of tert-butyl (6R,7R)-7-(3,4-dichlorophenyl)-6-formyl-1,4-oxazepane-4-carboxylate (7.3 g) in 2-methyl-2-butene (45 mL), tert-butanol (100 ml) and THF (100 ml) was added dropwise a solution of sodium chlorite (10.58 g) and potassium dihydrogenphosphate (16.38 g) in water (160 ml) under ice-cooling, and the mixture was stirred under ice-cooling for 2 hr. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (7.0 g).

¹H NMR (300 MHz, CDCl₃) δ 1.34-1.56 (9H, m), 2.73-3.08 (1H, m), 3.14-3.91 (3H, m), 3.94-4.25 (3H, m), 4.73 (1H, d, J=10.2 Hz), 7.16 (1H, dd, J=8.3, 1.9 Hz), 7.37 (1H, d, J=8.3 Hz), 7.45 (1H, d, J=1.9 Hz), 1H not detected.

C) tert-butyl (6R,7S)-7-(3,4-dichlorophenyl)-6-({[2-(trimethylsilyl)ethoxy]carbonyl}amino)-1,4-oxazepane-4-carboxylate To a solution of (6R,7R)-4-(tert-butoxycarbonyl)-7-(3,4-dichlorophenyl)-1,4-oxazepane-6-carboxylic acid (1.0 g) in toluene (10 mL) were added diphenylphosphoryl azide (0.828 mL) and triethylamine (0.536 mL) at room temperature, and the mixture was stirred at 90° C. for 30 min. To the reaction mixture was added 2-(trimethylsilyl)ethanol (0.727 mL) at 90° C., and the mixture was stirred at 90° C. for 2 hr. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (0.67 g).

¹H NMR (300 MHz, CDCl₃) δ 0.00 (9H, s), 1.53 (9H, s), 1.61-1.65 (2H, m), 3.04-3.24 (1H, m), 3.41-3.77 (2H, m), 3.86-4.20 (7H, m), 5.05-6.02 (1H, m), 7.14-7.25 (1H, m), 7.37 (2H, s).

D) tert-butyl (6R,7S)-6-amino-7-(3,4-dichlorophenyl)-1,4-oxazepane-4-carboxylate To a solution of tert-butyl (6R,7S)-7-(3,4-dichlorophenyl)-6-({[2-(trimethylsilyl)ethoxy]carbonyl}amino)-1,4-oxazepane-4-carboxylate (0.67 g) in THF (5 mL) was added tetra-n-butylammonium fluoride (5.2 mL) at room temperature, and the mixture was stirred at 50° C. for 5 hr. The reaction mixture was diluted with ethyl acetate. The diluted solution was washed with distilled water and brine, and dried over anhydrous magnesium sulfate. The solvent was evaporated under reduced pressure to give the title compound (0.4 mg).

$^1$H NMR (300 MHz, CDCl$_3$) δ 1.51 (11H, s), 3.08 (1H, brs), 3.32-3.84 (5H, m), 3.94 (1H, d, J=9.1 Hz), 4.05-4.13 (1H, m), 7.22 (1H, dd, J=8.3, 1.9 Hz), 7.39-7.46 (1H, m), 7.50 (1H, d, J=1.9 Hz).

MS (ESI+): [M+H]$^+$ 361.1.

E) tert-butyl (6R,7S)-6-(acetylamino)-7-(3,4-dichlorophenyl)-1,4-oxazepane-4-carboxylate To a solution of tert-butyl (6R,7S)-6-amino-7-(3,4-dichlorophenyl)-1,4-oxazepane-4-carboxylate (1.3 g) in THF (13 ml) were added triethylamine (0.752 ml) and acetyl chloride (0.385 mL) at 0° C., and the mixture was gradually warmed from 0° C. to room temperature, and stirred overnight. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (0.965 g).

$^1$H NMR (300 MHz, CDCl$_3$) δ 1.54 (9H, s), 1.87 (3H, s), 3.02-3.23 (1H, m), 3.45-3.73 (2H, m), 3.83-4.17 (4H, m), 4.45 (1H, brs), 6.83 (1H, brs), 7.20 (1H, dd, J=8.3, 1.9 Hz), 7.32-7.58 (2H, m).

MS (ESI+): [M+H-t-Bu]$^+$ 346.9.

F) N-[(6R,7S)-7-(3,4-dichlorophenyl)-1,4-oxazepan-6-yl]acetamide monofumarate To tert-butyl (6R,7S)-6-(acetylamino)-7-(3,4-dichlorophenyl)-1,4-oxazepane-4-carboxylate (200 mg) was added 4.0 M hydrogen chloride-ethyl acetate solution (4 mL), and the mixture was stirred at room temperature for 1 hr. The residue obtained by concentration under reduced pressure was desalted by a solid phase extraction resin (column: PL StrastoSphere solid phase extraction resin (PL-HCO$_3$ MP StratoSpheres™), 500 mg, StrastoSphere, mobile phase: methanol). To a solution of the residue obtained by concentration under reduced pressure in ethanol was added a solution of fumaric acid (33.7 mg) in ethanol. The mixture was concentrated under reduced pressure to give the title compound (130 mg).

$^1$H NMR (300 MHz, DMSO-d$_6$) δ 1.74 (3H, s), 2.87-3.14 (4H, m), 3.59-3.80 (1H, m), 3.97-4.17 (2H, m), 4.47 (1H, d, J=8.7 Hz), 6.56 (2H, s), 7.23-7.39 (1H, m), 7.47-7.67 (2H, m), 8.31 (1H, d, J=8.7 Hz).

MS (ESI+): [M+H]$^+$ 303.2.

Example 37

N-[(6R,7S)-7-(3,4-dichlorophenyl)-1,4-oxazepan-6-yl]sulfamide monohydrochloride

A) tert-butyl (6R,7S)-6-{[(tert-butoxycarbonyl)sulfamoyl]amino}-7-(3,4-dichlorophenyl)-1,4-oxazepane-4-carboxylate To a solution of tert-butyl (6R,7S)-6-amino-7-(3,4-dichlorophenyl)-1,4-oxazepane-4-carboxylate (300 mg) in acetonitrile (5 mL) was added N-(tert-butoxycarbonyl)-N-[4-(dimethylazaniumylidene)-1,4-dihydropyridin-1-ylsulfonyl]azanide (375 mg) prepared by the method described in Organic Letters, 3 (14), 2241-2243 (2001), and the mixture was stirred at room temperature overnight. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (200 mg).

$^1$H NMR (300 MHz, CDCl$_3$) δ 1.36-1.65 (18H, m), 2.92-3.28 (1H, m), 3.41-4.29 (7H, m), 6.79 (1H, brs), 7.19 (1H, dd, J=8.1, 2.1 Hz), 7.36-7.43 (1H, m), 7.47 (1H, d, J=1.9 Hz), 1H not detected.

MS (ESI+): [M−H]$^+$ 538.1.

B) N-[(6R,7S)-7-(3,4-dichlorophenyl)-1,4-oxazepan-6-yl]sulfamide monohydrochloride To tert-butyl (6R,7S)-6-{[(tert-butoxycarbonyl)sulfamoyl]amino}-7-(3,4-dichlorophenyl)-1,4-oxazepane-4-carboxylate (200 mg) was added 4.0 M hydrogen chloride-ethyl acetate solution (4 mL), and the mixture was stirred at room temperature for 2 hr. The residue obtained by concentration under reduced pressure was washed with ethyl acetate-hexane to give the title compound (105 mg).

$^1$H NMR (300 MHz, DMSO-d$_6$) δ 3.24 (2H, dd, J=6.2, 4.0 Hz), 3.41 (1H, dd, J=14.4, 7.6 Hz), 3.51-3.62 (1H, m), 3.79-3.97 (2H, m), 4.02-4.20 (1H, m), 4.48 (1H, d, J=8.7 Hz), 6.71 (2H, s), 7.20 (1H, d, J=9.1 Hz), 7.40 (1H, dd, J=8.3, 2.3 Hz), 7.61 (1H, d, J=8.3 Hz), 7.67 (1H, d, J=1.9 Hz), 9.41-9.83 (2H, m).

MS (ESI+): [M+H]$^+$ 340.0.

Example 38

N-{[(6S,7R)-7-(4-chloro-3-fluorophenyl)-1,4-oxazepan-6-yl]methyl}-2-methoxyacetamide monohydrochloride

A) tert-butyl (6S,7R)-7-(4-chloro-3-fluorophenyl)-6-(hydroxymethyl)-1,4-oxazepane-4-carboxylate A racemate (14.7 g) of tert-butyl (6RS,7SR)-7-(3-chloro-4-fluorophenyl)-6-(hydroxymethyl)-1,4-oxazepane-4-carboxylate was separated by HPLC (CHIRALPAK AD, 50 mmID×500 mL, manufactured by DAICEL CHEMICAL INDUSTRIES, LTD., mobile phase: hexane/ethanol=900/100) to give the title compound (7.1 g) having a shorter retention time.

$^1$H NMR (300 MHz, CDCl$_3$) δ 1.51 (9H, s), 2.03-2.20 (1H, m), 3.02-3.74 (5H, m), 4.02-4.16 (3H, m), 4.21 (1H, dd, J=9.8, 4.5 Hz), 4.34 (1H, d, J=9.8 Hz), 7.08 (1H, d, J=8.3 Hz), 7.18 (1H, dd, J=10.0, 1.7 Hz), 7.29-7.41 (1H, m).

B) tert-butyl (6S,7R)-7-(4-chloro-3-fluorophenyl)-6-{[(methylsulfonyl)oxy]methyl}-1,4-oxazepane-4-carboxylate To a solution of tert-butyl (6S,7R)-7-(4-chloro-3-fluorophenyl)-6-(hydroxymethyl)-1,4-oxazepane-4-carboxylate (4.50 g) in THF (41.7 mL) were added triethylamine (3.49 mL) and methanesulfonyl chloride (1.94 mL) under ice-cooling, and the mixture was stirred for 3 hr. To the reaction mixture was added distilled water, and the mixture was extracted with ethyl acetate. The extract was washed with distilled water and brine, and dried over anhydrous sodium sulfate, and the solvent was evaporated under reduced pressure to give the title compound (6.01 g).

$^1$H NMR (300 MHz, CDCl$_3$) δ 1.50 (9H, s), 2.33-2.46 (1H, m), 2.85-3.08 (3H, m), 3.42-3.57 (1H, m), 3.57-3.92 (5H, m), 3.96-4.18 (2H, m), 4.22 (1H, d, J=9.4 Hz), 7.05 (1H, d, J=8.3 Hz), 7.15 (1H, dd, J=9.4, 1.9 Hz), 7.34-7.43 (1H, m).

C) tert-butyl (6S,7R)-6-(azidomethyl)-7-(4-chloro-3-fluorophenyl)-1,4-oxazepane-4-carboxylate To a solution of tert-butyl (6S,7R)-7-(4-chloro-3-fluorophenyl)-6-{[(methylsulfonyl)oxy]methyl}-1,4-oxazepane-4-carboxylate (4.00 g) in DMF (46 mL) was added sodium azide (891 mg), and the mixture was stirred at 70° C. overnight. To the reaction mixture was added distilled water, and the mixture was extracted with ethyl acetate. The extract was washed with distilled water and brine, and dried over anhydrous sodium sulfate. The solvent was evaporated under reduced pressure. The residue was purified by silica gel filtration to give the title compound (6.76 g).

MS (ESI+): [M+H-Boc]$^+$ 285.1.

D) tert-butyl (6R,7R)-6-(aminomethyl)-7-(4-chloro-3-fluorophenyl)-1,4-oxazepane-4-carboxylate To a solution of tert-butyl (6S,7R)-6-(azidomethyl)-7-(4-chloro-3-fluorophenyl)-1,4-oxazepane-4-carboxylate (3.51 g) in THF (38 mL) and distilled water (7.7 mL) was added triphenylphosphine (2.87 g), and the mixture was stirred at room temperature overnight. To the reaction mixture was added distilled water, and the mixture was extracted with ethyl acetate. The diluted solution was washed with distilled water and brine, and dried over anhydrous sodium sulfate. The solvent was evaporated under reduced pressure. The residue was purified by silica gel chromatography (ethyl acetate/methanol) to give the title compound (2.42 g).

MS (ESI+): [M+H]$^+$ 359.1.

E) tert-butyl (6R,7R)-7-(4-chloro-3-fluorophenyl)-6-{[(methoxyacetyl)amino]methyl}-1,4-oxazepane-4-carboxylate To a solution of tert-butyl (6R,7R)-6-(aminomethyl)-7-(4-chloro-3-fluorophenyl)-1,4-oxazepane-4-carboxylate (1.30 g) in THF (18 mL) were added triethylamine (0.757 ml) and methoxyacetyl chloride (472 mg), and the mixture was stirred at room temperature for 4 hr. To the reaction mixture was added distilled water, and the mixture was extracted with ethyl acetate. The diluted solution was washed with distilled water and brine, and dried over anhydrous sodium sulfate. The solvent was evaporated under reduced pressure. The residue was purified by silica gel chromatography (hexane/ethyl acetate) to give the title compound (1.11 g).

MS (ESI+): [M+H]$^+$ 431.2.

F) N-{[(6S,7R)-7-(4-chloro-3-fluorophenyl)-1,4-oxazepan-6-yl]methyl}-2-methoxyacetamide monohydrochloride To a solution of tert-butyl (6R,7R)-7-(4-chloro-3-fluorophenyl)-6-{[(methoxyacetyl)amino]methyl}-1,4-oxazepane-4-carboxylate (1.11 g) in ethanol (13 mL) was added 14.0 M hydrogen chloride-ethanol solution (12.0 ml), and the mixture was stirred at room temperature for 1 hr. The crystals obtained by concentration under reduced pressure were recrystallized from ethanol-hexane to give the title compound (715 mg).

$^1$H NMR (300 MHz, DMSO-d$_6$) δ 2.55-2.69 (1H, m), 2.80-2.90 (1H, m), 2.95-3.31 (8H, m), 3.72-3.85 (3H, m), 3.92-4.01 (1H, m), 4.39 (1H, d, J=10.2 Hz), 7.33 (1H, dd, J=8.3, 1.5 Hz), 7.55 (1H, dd, J=10.6, 1.5 Hz), 7.58-7.66 (1H, m), 8.00-8.14 (1H, m), 8.92-9.58 (2H, m).

MS (ESI+): [M+H]$^+$ 331.1.

Example 39

N-{[(6S,7R)-7-(4-chloro-3-fluorophenyl)-1,4-oxazepan-6-yl]methyl}-2-[($^2$H$_3$)methyloxy]acetamide monohydrochloride

A) tert-butyl (6R,7R)-7-(4-chloro-3-fluorophenyl)-6-[({[($^2$H$_3$)methyloxy]acetyl}amino)methyl]-1,4-oxazepane-4-carboxylate To a solution of tert-butyl (6R,7R)-6-(aminomethyl)-7-(4-chloro-3-fluorophenyl)-1,4-oxazepane-4-carboxylate (300 mg), 2-($^2$H$_3$)methoxyacetic acid (93 mg), 1H-benzotriazol-1-ol (136 mg) and triethylamine (0.291 mL) in THF (4.2 mL) was added N-[3-(dimethylamino)propyl]-N'-ethylcarbodiimide hydrochloride (192 mg), and the mixture was stirred overnight. To the reaction mixture was added distilled water, and the mixture was extracted with ethyl acetate. The extract was washed with distilled water and brine, and dried over anhydrous sodium sulfate, and the solvent was evaporated under reduced pressure. The residue was purified by silica gel chromatography (hexane/ethyl acetate) to give the title compound (275 mg).

MS (ESI+): [M+H-Boc]$^+$ 334.3.

B) N-{[(6S,7R)-7-(4-chloro-3-fluorophenyl)-1,4-oxazepan-6-yl]methyl}-2-[($^2$H$_3$)methyloxy]acetamide monohydrochloride To tert-butyl (6R,7R)-7-(4-chloro-3-fluorophenyl)-6-[({[($^2$H$_3$)methyloxy]acetyl}amino)methyl]-1,4-oxazepane-4-carboxylate (275 mg) was added 4.0 M hydrogen chloride-ethyl acetate solution (4.75 mL), and the mixture was stirred at room temperature for 1 hr. The crystals obtained by concentration under reduced pressure were pulverized with ethanol-diisopropyl ether to give the title compound (206 mg).

$^1$H NMR (300 MHz, DMSO-d$_6$) δ 2.54-2.71 (1H, m), 2.78-2.91 (1H, m), 2.93-3.38 (7H, m), 3.77-3.86 (1H, m), 3.90-4.05 (1H, m), 4.40 (1H, d, J=10.2 Hz), 7.33 (1H, dd, J=8.3, 1.5 Hz), 7.48-7.66 (2H, m), 8.00-8.14 (1H, m), 8.94-9.75 (2H, m).

Example 40

N-{[(6S,7R)-7-(4-chloro-3-fluorophenyl)-1,4-oxazepan-6-yl]methyl}-2-ethoxyacetamide monohydrochloride

A) tert-butyl (6R,7R)-7-(4-chloro-3-fluorophenyl)-6-{[(ethoxyacetyl)amino]methyl}-1,4-oxazepane-4-carboxylate To a solution of tert-butyl (6R,7R)-6-(aminomethyl)-7-(4-chloro-3-fluorophenyl)-1,4-oxazepane-4-carboxylate (150 mg), ethoxyacetic acid (35 mg), 1H-benzotriazol-1-ol (67.8 mg) and triethylamine (0.146 ml) in THF (2.1 mL) was added N-[3-(dimethylamino)propyl]-N'-ethylcarbodiimide hydrochloride (96 mg), and the mixture was stirred overnight. To the reaction mixture was added distilled water, and the mixture was extracted with ethyl acetate. The extract was washed with distilled water and brine, and dried over anhydrous sodium sulfate, and the solvent was evaporated under reduced pressure. The residue was purified by silica gel chromatography (hexane/ethyl acetate) to give the title compound (125 mg).

MS (ESI+): [M+H]$^+$ 445.1.

B) N-{[(6S,7R)-7-(4-chloro-3-fluorophenyl)-1,4-oxazepan-6-yl]methyl}-2-ethoxyacetamide monohydrochloride To tert-butyl (6R,7R)-7-(4-chloro-3-fluorophenyl)-6-{[(ethoxyacetyl)amino]methyl}-1,4-oxazepane-4-carboxylate (125 mg) was added 4.0 M hydrogen chloride-ethyl acetate solution (2.11 ml), and the mixture was stirred at room temperature for 1 hr. The residue obtained by concentration under reduced pressure was recrystallized from ethanol-diisopropyl ether to give the title compound (92.0 mg).

$^1$H NMR (300 MHz, DMSO-d$_6$) δ 1.14 (3H, t, J=7.0 Hz), 2.57-2.72 (1H, m), 2.78-2.90 (1H, m), 2.97-3.29 (5H, m), 3.44 (2H, q, J=6.9 Hz), 3.73-3.86 (3H, m), 3.91-4.03 (1H, m), 4.40 (1H, d, J=10.2 Hz), 7.33 (1H, dd, J=8.1, 1.7 Hz), 7.55 (1H, dd, J=10.6, 1.9 Hz), 7.58-7.67 (1H, m), 7.97 (1H, t), 8.99-9.70 (2H, m).

Example 41

N-{[(6S,7R)-7-(4-chloro-3-fluorophenyl)-1,4-oxazepan-6-yl]methyl}-2-(1-methylethoxy)acetamide monohydrochloride A) tert-butyl (6R,7R)-7-(4-chloro-3-fluorophenyl)-6-({[(1-methylethoxy)acetyl]amino}methyl)-1,4-oxazepane-4-carboxylate To a solution of tert-butyl (6R,7R)-6-(aminomethyl)-7-(4-chloro-3-fluorophenyl)-1,4-oxazepane-4-carboxylate (300 mg), (1-methylethoxy)acetic acid (119 mg), 1H-benzotriazol-1-ol (136 mg) and triethylamine (0.291 ml) in THF (4.2 mL) was added N-[3-(dimethylamino)propyl]-N'-ethylcarbodiimide hydrochloride (192 mg), and the mixture was stirred at room temperature overnight. To the reaction mixture was added distilled water, and the mixture was extracted with ethyl acetate. The extract was washed with distilled water and brine, and dried over anhydrous sodium sulfate, and the solvent was evaporated under reduced pressure. The residue was purified by silica gel chromatography (hexane/ethyl acetate) to give the title compound (384 mg).

MS (ESI+): [M+H-Boc]$^+$ 359.3.

B) N-{[(6S,7R)-7-(4-chloro-3-fluorophenyl)-1,4-oxazepan-6-yl]methyl}-2-(1-methylethoxy)acetamide monohydrochloride To tert-butyl (6R,7R)-7-(4-chloro-3-fluorophenyl)-6-({[(1-methylethoxy)acetyl]amino}methyl)-1,4-oxazepane-4-carboxylate (384 mg) was added 4.0 M hydrogen chloride-ethyl acetate solution (6.28 ml), and the mixture was stirred at room temperature for 1 hr. The residue obtained by concentration under reduced pressure was crystallized from ethanol-hexane solvent to give the title compound (153.4 mg).

$^1$H NMR (300 MHz, DMSO-d$_6$) δ 1.11 (6H, d, J=6.0 Hz), 2.56-2.71 (1H, m), 2.78-2.91 (1H, m), 2.99-3.33 (7H, m), 3.48-3.62 (1H, m), 3.76-3.87 (1H, m), 3.90-4.05 (1H, m), 4.40 (1H, d, J=9.8 Hz), 7.32 (1H, d, J=8.3 Hz), 7.48-7.69 (2H, m), 7.83 (1H, t, J=6.0 Hz), 8.92-9.62 (2H, m).

MS (ESI+): [M+H]$^+$ 359.2.

Example 42

1-{[(6S,7R)-7-(4-chloro-3-fluorophenyl)-1,4-oxazepan-6-yl]methyl}pyridin-2(1H)-one monohydrochloride A) tert-butyl (6R,7R)-7-(4-chloro-3-fluorophenyl)-6-[(2-oxopyridin-1(2H)-yl)methyl]-1,4-oxazepane-4-carboxylate 60% Sodium hydride (45.3 mg, 1.13 mmol) was added to a mixed solution of 2-hydroxypyridine (86 mg, 0.91 mmol) in 1,2-dimethoxyethane (2 ml) and DMF (1 mL) at room temperature. After stirring at room temperature for 5 min, lithium bromide (131 mg, 1.51 mmol) was added at room temperature. After stirring for 10 min, to the reaction mixture was added a solution of tert-butyl (6S,7R)-7-(4-chloro-3-fluorophenyl)-6-{[(methylsulfonyl)oxy]methyl}-1,4-oxazepane-4-carboxylate (331 mg, 0.76 mmol) in 1,2-dimethoxyethane (2 mL). The reaction mixture was stirred at 80° C. overnight. To the reaction mixture was added water, and the mixture was extracted with ethyl acetate. The extract was washed with brine, and dried over anhydrous sodium sulfate. The solvent was evaporated under reduced pressure. The residue was purified by silica gel column chromatography to give the title compound (267 mg, 0.611 mmol, 81%).

$^1$H NMR (300 MHz, CDCl$_3$) δ 1.33-1.58 (9H, m), 2.55-2.96 (1H, m), 3.11-3.35 (1H, m), 3.45-3.80 (3H, m), 3.82-4.01 (2H, m), 4.02-4.26 (2H, m), 6.12 (1H, brs), 6.44 (1H, d, J=9.1 Hz), 6.88-7.31 (4H, m), 7.37 (1H, t, J=7.6 Hz), 7.78 (1H, brs).

MS (ESI+): [M+H]$^+$ 437.2.

B) 1-{[(6S,7R)-7-(4-chloro-3-fluorophenyl)-1,4-oxazepan-6-yl]methyl}pyridin-2(1H)-one monohydrochloride 14 N Hydrogen chloride-ethanol solution (1 mL, 14.00 mmol) was added to a solution (3 mL) of tert-butyl (6R,7R)-7-(4-chloro-3-fluorophenyl)-6-[(2-oxopyridin-1(2H)-yl)methyl]-1,4-oxazepane-4-carboxylate (267 mg, 0.61 mmol) in ethanol, and the mixture was stirred at room temperature for 3 hr. The residue was concentrated, diethyl ether was added, and the mixture was stirred for a while. The insoluble material was collected by filtration to give the title compound (227 mg, 0.608 mmol, 100%).

$^1$H NMR (300 MHz, DMSO-d$_6$) δ 3.04-3.32 (5H, m), 3.64 (1H, dd, J=13.2, 5.3 Hz), 3.77-3.88 (1H, m), 3.91-4.06 (2H, m), 4.54 (1H, d, J=9.4 Hz), 6.17 (1H, td, J=6.7, 1.3 Hz), 6.27-6.33 (1H, m), 7.29-7.40 (2H, m), 7.46 (1H, dd, J=6.6, 1.7 Hz), 7.50-7.61 (2H, m), 9.24 (1H, brs), 9.80 (1H, brs).

MS (ESI+): [M+H]$^+$ 337.1.

Example 43

1-{[(6S,7R)-7-(4-chloro-3-fluorophenyl)-1,4-oxazepan-6-yl]methyl}-3-(5-oxo-4,5-dihydro-1,2,4-oxadiazol-3-yl)pyridin-2(1H)-one monohydrochloride A) tert-butyl (6R,7R)-7-(4-chloro-3-fluorophenyl)-6-[(3-cyano-2-oxopyridin-1(2H)-yl)methyl]-1,4-oxazepane-4-carboxylate 60% Sodium hydride (0.274 g, 6.85 mmol) was added to a mixed solution of 3-cyano-2-hydroxypyridine (0.658 g, 5.48 mmol) in 1,2-dimethoxyethane (10 mL)-DMF (5 ml) under ice-cooling, and the mixture was stirred for 20 min. To the reaction solution was added lithium bromide (0.793 g, 9.13 mmol), and the mixture was stirred at room temperature for 1.5 hr. To the reaction solution was added a solution of tert-butyl (6S,7R)-7-(4-chloro-3-fluorophenyl)-6-{[(methylsulfonyl)oxy]methyl}-1,4-oxazepane-4-carboxylate (2 g, 4.57 mmol) in 1,2-dimethoxyethane (10 ml), and the mixture was stirred at 60° C. overnight. The reaction mixture was concentrated under reduced pressure, water was added to the residue, and the mixture was extracted with ethyl acetate. The extract was washed with brine, and dried over anhydrous sodium sulfate. The solvent was evaporated under reduced pressure. The residue was purified by silica gel column chromatography to give the title compound (1.757 g, 3.80 mmol, 83%).

$^1$H NMR (300 MHz, CDCl$_3$) δ 1.52 (9H, s), 2.90 (1H, brs), 3.06-3.28 (2H, m), 3.55-3.75 (2H, m), 3.81-4.12 (5H, m), 6.26 (1H, t, J=6.2 Hz), 7.18 (2H, d, J=7.9 Hz), 7.41 (1H, t, J=7.9 Hz), 7.76 (1H, d, J=6.4 Hz), 8.31 (1H, d, J=5.3 Hz).

B) tert-butyl (6R,7R)-7-(4-chloro-3-fluorophenyl)-6-{[2-oxo-3-(5-oxo-4,5-dihydro-1,2,4-oxadiazol-3-yl)pyridin-1(2H)-yl]methyl}-1,4-oxazepane-4-carboxylate Sodium hydrogen carbonate (2.53 g, 30.14 mmol) and hydroxylamine monohydrochloride (2.094 g, 30.14 mmol) were added to a solution of tert-butyl (6R,7R)-7-(4-chloro-3-fluorophenyl)-6-[(3-cyano-2-oxopyridin-1(2H)-yl)methyl]-1,4-oxazepane-4-carboxylate (1.74 g, 3.77 mmol) in DMSO (4 mL), and the mixture was stirred at 80° C. overnight. To the reaction mixture was added water, and the mixture was extracted with ethyl acetate. The extract was washed with brine, and dried over anhydrous sodium sulfate. The solvent was evaporated under reduced pressure. The residue was dissolved in THF (15 mL), diazabicycloundecene (0.564 mL, 3.77 mmol) and 1,1'-carbonyldiimidazole (0.917 g, 5.66 mmol) were added, and the mixture was heated under reflux for 2 hr. The reaction mixture was concentrated under reduced pressure, 1 N hydrochloric acid was added to the residue, and the mixture was extracted with ethyl acetate. The extract was washed with brine, and dried over anhydrous sodium sulfate. The solvent was evaporated under reduced pressure. The residue was purified by silica gel column chromatography to give the title compound (1.826 g, 3.51 mmol, 93%).

$^1$H NMR (300 MHz, CDCl$_3$) δ 1.54 (9H, s), 2.79-2.96 (1H, m), 3.13 (1H, t, J=11.5 Hz), 3.26 (1H, dd, J=14.7, 4.5 Hz), 3.61 (1H, t, J=11.3 Hz), 3.76 (1H, t, J=11.9 Hz), 4.01 (1H, d, J=10.2 Hz), 4.05-4.18 (3H, m), 4.49 (1H, d, J=12.5 Hz), 6.49 (1H, t, J=7.0 Hz), 7.07 (1H, dd, J=8.3, 1.5 Hz), 7.15 (1H, t, J=7.7 Hz), 7.35 (1H, d, J=9.8 Hz), 8.28 (1H, dd, J=7.4, 1.7 Hz), 8.69 (1H, d, J=6.0 Hz), 10.46 (1H, brs).

C) 1-{[(6S,7R)-7-(4-chloro-3-fluorophenyl)-1,4-oxazepan-6-yl]methyl}-3-(5-oxo-4,5-dihydro-1,2,4-oxadiazol-3-yl)pyridin-2(1H)-one monohydrochloride 14 N Hydrogen chloride-ethanol solution (0.5 ml, 7.00 mmol) was added to a solution of tert-butyl (6R,7R)-7-(4-chloro-3-fluorophenyl)-6-{[2-oxo-3-(5-oxo-4,5-dihydro-1,2,4-oxadiazol-3-yl)pyridin-1(2H)-yl]methyl}-1,4-oxazepane-4-carboxylate (180 mg, 0.35 mmol) in ethanol (2 mL), and the mixture was stirred at room temperature for 3 hr. The reaction mixture was diluted with ethanol (4 ml), and the mixture was heated under reflux for 10 min. The precipitated crystals were collected by filtration to give the title compound (149 mg, 0.325 mmol, 94%).

$^1$H NMR (300 MHz, DMSO-d$_6$) δ 3.08-3.35 (5H, m), 3.76-3.89 (2H, m), 3.98-4.10 (2H, m), 4.55 (1H, d, J=9.8 Hz), 6.41 (1H, t, J=7.0 Hz), 7.30 (1H, dd, J=8.1, 1.7 Hz), 7.49 (1H, dd, J=10.6, 1.9 Hz), 7.56 (1H, t, J=8.1 Hz), 7.85 (1H, dd, J=6.6, 2.1 Hz), 7.91 (1H, dd, J=7.2, 2.3 Hz), 9.19 (1H, brs), 9.71 (1H, brs), 12.22 (1H, brs).

MS (ESI+): [M+H]$^+$ 421.0.

Example 44

1-{[(6S,7R)-7-(4-chloro-3-fluorophenyl)-1,4-oxazepan-6-yl]methyl}-2-oxo-1,2-dihydropyridine-3-carboxylic acid monohydrochloride A) tert-butyl (6R,7R)-7-(4-chloro-3-fluorophenyl)-6-{[3-(methoxycarbonyl)-2-oxopyridin-1(2H)-yl]methyl}-1,4-oxazepane-4-carboxylate Methyl 2-hydroxypyridine-3-carboxylate (1.48 g) and potassium carbonate (2.23 g) were added to a solution of tert-butyl (6S,7R)-7-(4-chloro-3-fluorophenyl)-6-{[(methylsulfonyl)oxy]methyl}-1,4-oxazepane-4-carboxylate (3.53 g) in 1,2-dimethoxyethane (70 ml). The reaction mixture was stirred at 80° C. overnight. The reaction mixture was concentrated under reduced pressure, water was added to the residue, and the mixture was extracted with ethyl acetate. The extract was washed with brine, and dried over anhydrous sodium sulfate. The solvent was evaporated under reduced pressure. The residue was purified by silica gel column chromatography to give the title compound (2.88 g).

$^1$H NMR (300 MHz, CDCl$_3$) δ 1.51 (9H, brs), 2.99 (1H, brs), 3.17 (2H, d, J=13.6 Hz), 3.43-3.79 (3H, m), 3.87 (3H, s), 3.89-4.12 (4H, m), 6.23 (1H, brs), 7.06-7.24 (2H, m), 7.29-7.44 (1H, m), 7.97-8.16 (1H, m), 8.20 (1H, brs).

MS (ESI+): [M+H]$^+$ 495.1.

B) 1-{[(6S,7R)-7-(4-chloro-3-fluorophenyl)-1,4-oxazepan-6-yl]methyl}-2-oxo-1,2-dihydropyridine-3-carboxylic acid monohydrochloride 2 N Aqueous sodium hydroxide solution (8.73 mL) was added to a solution of tert-butyl (6R,7R)-7-(4-chloro-3-fluorophenyl)-6-{[3-(methoxycarbonyl)-2-oxopyridin-1(2H)-yl]methyl}-1,4-oxazepane-4-carboxylate (2.88 g) in ethanol (25 mL), and the mixture was stirred at 40° C. for 2 hr. The reaction mixture was concentrated under reduced pressure, diethyl ether was added to the residue, and the mixture was extracted with water. The aqueous layer was neutralized with 1 N hydrochloric acid, and the mixture was extracted with ethyl acetate. The extract was washed with brine, and dried over anhydrous sodium sulfate. The solvent was evaporated under reduced pressure. To a solution of the residue in ethyl acetate (5 mL) was added 4 N hydrogen chloride-ethyl acetate solution (22 mL), and the mixture was stirred at room temperature for 2 hr. The reaction mixture was concentrated under reduced pressure, acetonitrile was added to the residue, and the precipitate was collected by filtration. The obtained solid was dissolved in 10% aqueous acetonitrile (17 mL), and an insoluble material was filtered off. To the mother liquor was added acetonitrile (50 ml), and the mixture was stirred overnight. The obtained crystals were collected by filtration to give the title compound (2.01 g).

$^1$H NMR (300 MHz, DMSO-d$_6$) δ 3.10-3.31 (5H, m), 3.77-3.87 (1H, m), 3.92 (1H, dd, J=13.6, 5.7 Hz), 4.03 (1H, dt,

J=13.8, 4.4 Hz), 4.15 (1H, dd, J=13.6, 7.6 Hz), 4.58 (1H, d, J=9.4 Hz), 6.66 (1H, t, J=7.0 Hz), 7.26 (1H, dd, J=8.1, 1.7 Hz), 7.46 (1H, dd, J=10.4, 1.7 Hz), 7.51-7.58 (1H, m), 8.06 (1H, dd, J=6.8, 1.9 Hz), 8.27 (1H, dd, J=7.2, 1.9 Hz), 9.12 (1H, brs), 9.70 (1H, brs), 14.24 (1H, brs).

MS (ESI+): [M+H]$^+$ 381.1.

Example 45

(1S)-1-[(6R,7R)-6-(3,4-dichlorophenyl)-1,4-oxazepan-7-yl]ethane-1,2-diol monohydrochloride A) (2RS,3RS)-4-{[tert-butyl(dimethyl)silyl]oxy}-2-(3,4-dichlorophenyl)-3-hydroxybutanenitrile To a solution of 3,4-dichlorobenzyl cyanide (28.3 g) in THF (300 mL) was added dropwise 1.6 M n-butyllithium/hexane solution (100 ml) under argon purging at −78° C., and the mixture was stirred for 10 min. Then, 2-(tert-butyldimethylsilyloxy)acetaldehyde (29.2 g) was added dropwise at −78° C., and the mixture was stirred for 10 min. The mixture was quenched with water at −78° C., and the mixture was extracted with ethyl acetate. The organic layer was washed with brine, and dried over anhydrous magnesium sulfate, and the solvent was evaporated. The residue was purified by silica gel column chromatography (eluent; hexane:ethyl acetate (10%-50%)) to give a yellow oil (53.5 g), which was crystallized from ice-cooled hexane to give the title compound (23.3 g) as colorless crystals.

$^1$H NMR (300 MHz, CDCl$_3$) δ 0.10 (6H, d, J=3.0 Hz), 0.92 (9H, s), 2.54 (1H, d, J=6.4 Hz), 3.50-3.63 (1H, m), 3.64-3.74 (1H, m), 3.85-3.96 (1H, m), 4.05 (1H, d, J=5.3 Hz), 7.15-7.31 (1H, m), 7.48 (2H, m).

The mother liquor in the above-mentioned crystallization was concentrated to give an about 6:1 mixture of (2RS,3SR)-4-{[tert-butyl(dimethyl)silyl]oxy}-2-(3,4-dichlorophenyl)-3-hydroxybutanenitrile and (2RS,3RS)-4-{[tert-butyl(dimethyl)silyl]oxy}-2-(3,4-dichlorophenyl)-3-hydroxybutanenitrile as a yellow oil (27.5 g).

B) (2RS)-(3,4-dichlorophenyl)[(4RS)-2,2-dimethyl-1,3-dioxolan-4-yl]ethanenitrile To a solution of (2RS,3RS)-4-{[tert-butyl(dimethyl)silyl]oxy}-2-(3,4-dichlorophenyl)-3-hydroxybutanenitrile (152 g) in toluene (1000 ml) were added 2,2-dimethoxypropane (131.8 g) and p-toluenesulfonic acid (8.02 g), and the mixture was stirred under nitrogen purging at 80° C. for 2 hr. Under ice-cooling, the mixture was neutralized with saturated aqueous sodium hydrogen carbonate, and the mixture was extracted with ethyl acetate. The organic layer was washed with brine, and dried over anhydrous magnesium sulfate, and the solvent was evaporated. The residue was crystallized from diisopropyl ether to give the title compound (99 g) as colorless crystals.

$^1$H NMR (300 MHz, CDCl$_3$) δ 1.35 (3H, s), 1.48 (3H, s), 3.79-3.90 (2H, m), 4.06 (1H, dd, J=9.1, 6.1 Hz), 4.37 (1H, q, J=5.7 Hz), 7.24 (1H, dd, J=8.3, 2.3 Hz), 7.47-7.51 (2H, m).

C) (2RS)-2-(3,4-dichlorophenyl)-2-[(4RS)-2,2-dimethyl-1,3-dioxolan-4-yl]ethanamine To a solution of (2RS)-(3,4-dichlorophenyl)[(4RS)-2,2-dimethyl-1,3-dioxolan-4-yl]ethanenitrile (10.0 g) in toluene (100 ml) was added dropwise 1.5 M diisobutylaluminum hydride/toluene solution (51.3 under nitrogen purging at −78° C., and the mixture was stirred for 3 hr. The reaction was quenched with water at −78° C., aqueous potassium carbonate solution was added, and the mixture was extracted with ethyl acetate. The organic layer was washed with brine, and dried over anhydrous sodium sulfate, and the solvent was evaporated to give the title compound (10.2 g) as a colorless oil. This was used for the next step without purification.

$^1$H NMR (300 MHz, CDCl$_3$) δ 1.2-1.7 (2H, br), 1.36 (3H, s), 1.44 (3H, s), 2.70 (1H, td, J=8.7, 4.9 Hz), 2.97 (1H, dd, J=12.8, 8.3 Hz), 3.26 (1H, dd, J=12.8, 4.9 Hz), 3.46-3.52 (1H, m), 3.76 (1H, dd, J=8.3, 6.0 Hz), 4.19-4.28 (1H, m), 7.06 (1H, dd, J=8.1, 2.1 Hz), 7.32 (1H, d, J=2.3 Hz), 7.41 (1H, d, J=8.3 Hz).

D) (2RS)—N-benzyl-2-(3,4-dichlorophenyl)-2-[(4RS)-2,2-dimethyl-1,3-dioxolan-4-yl]ethanamine To a solution of (2RS)-2-(3,4-dichlorophenyl)-2-[(4RS)-2,2-dimethyl-1,3-dioxolan-4-yl]ethanamine (10.1 g) in toluene (200 mL) was added benzaldehyde (4.43 g) at room temperature. The mixture was heated under reflux for 1 hr while dehydrating by a Dean-Stark trap, cooled to room temperature, and concentrated under reduced pressure. To the residue was added methanol (60 ml), sodium tetrahydroborate (658 mg) was added under ice-cooling, and the mixture was stirred for 1 hr. The reaction was quenched with water, methanol was evaporated under reduced pressure, and the mixture was extracted with ethyl acetate. The organic layer was washed with brine, and dried over anhydrous sodium sulfate, and the solvent was evaporated. The residue was purified by silica gel column chromatography (eluent; hexane:ethyl acetate (5%-100%)) to give the title compound (7.96 g) as a yellow oil.

$^1$H NMR (300 MHz, CDCl$_3$) δ 1.31-1.37 (3H, m), 1.38-1.44 (3H, m), 1.59 (2H, brs), 2.82-2.96 (1H, m), 3.08-3.22 (1H, m), 3.49 (1H, dd, J=8.7, 6.8 Hz), 3.67-3.85 (2H, m), 4.07-4.25 (1H, m), 4.70 (1H, s), 7.03 (1H, dd, J=8.3, 1.9 Hz), 7.17-7.41 (7H, m).

MS (ESI+): [M+H]$^+$ 380.2.

E) (2RS,3RS)-4-(benzylamino)-3-(3,4-dichlorophenyl)butane-1,2-diol

To a solution of (2RS)—N-benzyl-2-(3,4-dichlorophenyl)-2-[(4RS)-2,2-dimethyl-1,3-dioxolan-4-yl]ethanamine (7.95 g) in THF (32 mL) was added 1.0 N hydrochloric acid (31.4 ml) at room temperature, and the mixture was stirred under nitrogen purging at 50° C. for 3 hr. Saturated aqueous sodium hydrogen carbonate solution was added, and the mixture was extracted twice with ethyl acetate. The organic layer was washed with brine, and dried over anhydrous sodium sulfate, and the solvent was evaporated to give the title compound (7.50 g) as a pale-brown oil. This was used without purification for the next step.

$^1$H NMR (300 MHz, CDCl$_3$) δ 1.60-2.63 (2H, m), 2.89 (1H, ddd, J=11.2, 8.4, 3.0 Hz), 3.01 (1H, dd), 3.11 (1H, d, J=11.3 Hz), 3.23 (1H, dd, J=11.7, 3.8 Hz), 3.47 (1H, dd, J=11.5, 3.2 Hz), 3.76-3.91 (2H, m), 3.97 (1H, dt, J=8.3, 3.4 Hz), 4.70 (1H, s), 7.03 (1H, dd, J=8.3, 1.9 Hz), 7.18-7.47 (7H, m).

MS (ESI+): [M+H]$^+$ 340.2.

F) (2RS,3RS)-4-(benzylamino)-1-{[tert-butyl(dimethyl)silyl]oxy}-3-(3,4-dichlorophenyl)butan-2-ol A solution of tert-butyldimethylchlorosilane (3.65 g) in THF (10 mL) was added dropwise to a solution of (2RS,3RS)-4-(benzylamino)-3-(3,4-dichlorophenyl)butane-1,2-diol (7.50 g) and triethylamine (9.22 mL) in THF (35 ml) at 0°

C. Under nitrogen purging, the mixture was stirred at room temperature for 3 hr, water was added at 0° C., and the mixture was extracted with ethyl acetate. The organic layer was washed with brine, and dried over anhydrous sodium sulfate, and the solvent was evaporated. The residue was purified by silica gel column chromatography (eluent; hexane:ethyl acetate (0%-100%)) to give the title compound (6.42 g) as a pale-yellow oil.

$^1$H NMR (300 MHz, CDCl$_3$) δ −0.09-0.05 (6H, m), 0.80-0.93 (9H, m), 1.55-2.67 (1H, m), 2.91-3.05 (2H, m), 3.07-3.19 (1H, m), 3.28 (1H, dd, J=10.6, 4.5 Hz), 3.39-3.51 (1H, m), 3.79 (2H, s), 3.87 (1H, dt, J=7.7, 4.1 Hz), 4.71 (1H, s), 7.06 (1H, dd, J=8.1, 2.1 Hz), 7.19-7.45 (7H, m).

MS (ESI+): [M+H]$^+$ 454.2.

G) N-benzyl-N-[(2RS,3RS)-4-{[tert-butyl(dimethyl)silyl]oxy}-2-(3,4-dichlorophenyl)-3-hydroxybutyl]-2-chloroacetamide To a solution of (2RS,3RS)-4-(benzylamino)-1-{[tert-butyl(dimethyl)silyl]oxy}-3-(3,4-dichlorophenyl)butan-2-ol (6.40 g) and triethylamine (2.16 mL) in THF (50 mL) was added dropwise chloroacetyl chloride (1.23 mL) at 0° C. The mixture was stirred at 0° C. for 20 min, water was added, and the mixture was extracted with ethyl acetate. The organic layer was washed with brine, and dried over anhydrous sodium sulfate, and the solvent was evaporated. The residue was purified by silica gel column chromatography (eluent; hexane:ethyl acetate (0%-30%)) to give the title compound (6.83 g) as a pale-yellow oil.

$^1$H NMR (300 MHz, CDCl$_3$) δ 0.00 (6H, s), 0.87 (9H, s), 1.55-1.80 (1H, br), 3.00-5.00 (10H, m), 6.95-7.50 (8H, m).

H) (6RS,7RS)-4-benzyl-7-({[tert-butyl(dimethyl)silyl]oxy}methyl)-6-(3,4-dichlorophenyl)-1,4-oxazepan-3-one To a solution of N-benzyl-N-[(2RS,3RS)-4-{[tert-butyl(dimethyl)silyl]oxy}-2-(3,4-dichlorophenyl)-3-hydroxybutyl]-2-chloroacetamide (44.7 g) in THF (450 ml) was added sodium methoxide (5.46 g) at 0° C. The mixture was stirred at room temperature for 2 hr, water was added, and methanol was evaporated under reduced pressure. Water was added to the residue, and the mixture was extracted with ethyl acetate. The organic layer was washed with brine, and dried over anhydrous sodium sulfate, and the solvent was evaporated. The residue was purified by silica gel column chromatography (eluent; hexane:ethyl acetate (10%-50%)) to give the title compound (40.6 g) as a pale-yellow oil.

$^1$H NMR (300 MHz, CDCl$_3$) δ 0.86-0.91 (6H, m), 2.05-2.11 (9H, m), 2.98 (1H, ddd, J=10.0, 7.4, 3.0 Hz), 3.39-3.48 (1H, m), 3.50-3.78 (3H, m), 4.10 (1H, d, J=14.8 Hz), 4.47 (1H, d, J=15.9 Hz), 4.68-4.79 (1H, m), 5.05 (1H, d, J=14.8 Hz), 6.89 (1H, dd, J=8.3, 1.9 Hz), 7.13 (1H, d, J=1.9 Hz), 7.21-7.27 (2H, m), 7.28-7.45 (5H, m).

MS (ESI+): [M+H]$^+$ 494.1.

I) (6RS,7RS)-4-benzyl-7-({[tert-butyl(dimethyl)silyl]oxy}methyl)-6-(3,4-dichlorophenyl)-1,4-oxazepane To a solution of (6RS,7RS)-4-benzyl-7-({[tert-butyl(dimethyl)silyl]oxy}methyl)-6-(3,4-dichlorophenyl)-1,4-oxazepan-3-one (40.5 g) in THF (150 mL) was added dropwise 1.2 M borane.THF complex/THF solution (150 mL) at room temperature, and the mixture was stirred under nitrogen purging at 60° C. for 2 hr. After cooling to room temperature, water was added carefully, and the mixture was stirred at room temperature for 1 hr, and extracted with ethyl acetate. The organic layer was washed with brine, and dried over anhydrous sodium sulfate, and the solvent was evaporated. The residue was purified by silica gel column chromatography (eluent; hexane:ethyl acetate (0%-50%)) to give the title compound (30.7 g) as a pale-yellow oil.

$^1$H NMR (300 MHz, CDCl$_3$) δ 0.00-0.03 (6H, m), 0.84-0.90 (9H, m), 1.58-1.65 (2H, m), 2.52-2.65 (1H, m), 2.69-2.79 (1H, m), 2.82-3.07 (2H, m), 3.41-3.57 (2H, m), 3.59 (1H, d, J=2.7 Hz), 3.61-3.72 (1H, m), 3.73-3.84 (1H, m), 4.06-4.20 (1H, m), 7.17 (1H, dd, J=8.3, 1.9 Hz), 7.20-7.36 (6H, m), 7.59 (1H, d, J=2.3 Hz).

MS (ESI+): [M+H]$^+$ 480.2.

J) tert-butyl (6R,7R)-6-(3,4-dichlorophenyl)-7-(hydroxymethyl)-1,4-oxazepane-4-carboxylate To a solution of (6RS,7RS)-4-benzyl-7-({[tert-butyl(dimethyl)silyl]oxy}methyl)-6-(3,4-dichlorophenyl)-1,4-oxazepane (10.0 g) in acetonitrile (50 mL) was added 1-chloroethyl chloroformate (4.46 g), and the mixture was stirred under nitrogen purging at 80° C. for 2 hr. After cooling to room temperature, water was added, the mixture was stirred at 80° C. for 10 min, and the solvent was evaporated. To the residue were added water (50 ml), THF (50 ml) and triethylamine (3.16 g), then di-tert-butyl dicarbonate (6.81 g) was added dropwise, and the mixture was stirred at room temperature overnight. After evaporation of the solvent, the mixture was extracted with ethyl acetate. The organic layer was washed with brine, and dried over anhydrous magnesium sulfate, and the solvent was evaporated. The residue was purified by silica gel column chromatography (eluent: hexane:ethyl acetate (10%-100%)) to give tert-butyl (6RS,7RS)-6-(3,4-dichlorophenyl)-7-(hydroxymethyl)-1,4-oxazepane-4-carboxylate (7.14 g) as a colorless solid.

$^1$H NMR (300 MHz, CDCl$_3$) δ 1.29-1.55 (9H, m), 1.61-1.79 (1H, m), 2.07-2.27 (1H, m), 2.82-2.99 (1H, m), 3.22-3.99 (7H, m), 4.11-4.33 (1H, m), 7.03 (1H, d, J=8.3 Hz), 7.29 (1H, d, J=1.9 Hz), 7.38 (1H, d, J=7.9 Hz).

MS (ESI+): [M+H-Boc]$^+$ 276.0.

tert-Butyl (6RS,7RS)-6-(3,4-dichlorophenyl)-7-(hydroxymethyl)-1,4-oxazepane-4-carboxylate (25.6 g) was separated by HPLC (column: CHIRALPAK AD LF001, 50 mmID×500 mL, manufactured by DAICEL CHEMICAL INDUSTRIES, LTD., mobile phase: hexane/2-propanol=900/100) to give the title compound (11.4 g) having a longer retention time (enantiomer excess 99.9% ee).

In addition, tert-butyl (6S,7S)-6-(3,4-dichlorophenyl)-7-(hydroxymethyl)-1,4-oxazepane-4-carboxylate was obtained as a compound (12.3 g) having a shorter retention time (enantiomer excess >99.9% ee).

K) tert-butyl (6R,7R)-6-(3,4-dichlorophenyl)-7-formyl-1,4-oxazepane-4-carboxylate To a solution of oxalyl chloride (1.52 g) in THF (20 mL) was added dimethyl sulfoxide (1.87 g) at −78° C., and the mixture was stirred for 20 min. A solution of tert-butyl (6R,7R)-6-(3,4-dichlorophenyl)-7-(hydroxymethyl)-1,4-oxazepane-4-carboxylate (3.0 g) in THF (10 mL) and triethylamine (7.78 mL) were added at −78° C., and the mixture was warmed to room temperature and stirred for 1 hr. Water was added, and the mixture was extracted with ethyl acetate. The organic layer was washed with brine, and dried over anhydrous magnesium sulfate, and the solvent was evaporated.

The residue was purified by silica gel column chromatography (eluent; hexane:ethyl acetate (0%-50%)) to give the title compound (2.89 g) as a colorless solid.

$^1$H NMR (300 MHz, CDCl$_3$) δ 1.29-1.54 (9H, m), 3.30 (1H, dt, J=9.4, 5.5 Hz), 3.67 (4H, brs), 3.89 (1H, brs), 4.04-4.23 (2H, m), 7.10 (1H, dd, J=8.3, 2.3 Hz), 7.33-7.37 (1H, m), 7.40 (1H, d, J=8.3 Hz), 9.60 (1H, brs).

L) tert-butyl (6R,7S)-6-(3,4-dichlorophenyl)-7-ethenyl-1,4-oxazepane-4-carboxylate A suspension of methyltriphenylphosphonium bromide (3.59 g) in THF (30 mL) was cooled under nitrogen purging to −78° C., and 1.6 M n-butyllithium/hexane solution (5.79 ml) was added. The mixture was warmed to 0° C., and stirred for 20 min, and a solution of tert-butyl (6R,7R)-6-(3,4-dichlorophenyl)-7-formyl-1,4-oxazepane-4-carboxylate (2.89 g) in THF (50 ml) was added. After stirring at 0° C. for 20 min, and at room temperature for 2 hr, water was added, and the mixture was extracted with ethyl acetate. The organic layer was washed with brine, and dried over anhydrous magnesium sulfate, and the solvent was evaporated. The residue was purified by silica gel column chromatography (eluent; hexane:ethyl acetate (0%-30%)) to give the title compound (1.10 g) as a colorless oil.

$^1$H NMR (300 MHz, CDCl$_3$) δ 1.30-1.50 (9H, m), 2.88 (1H, brs), 3.25-3.60 (3H, m), 3.65-4.40 (4H, m), 4.95-5.15 (2H, m), 5.51-5.72 (1H, m), 6.96-7.04 (1H, m), 7.24-7.29 (1H, m), 7.37 (1H, d, J=7.9 Hz).

MS (ESI+): [M+H-t-Bu]$^+$ 316.0.

M) tert-butyl (6R,7R)-6-(3,4-dichlorophenyl)-7-[(1S)-1,2-dihydroxyethyl]-1,4-oxazepane-4-carboxylate To a mixed solution of tert-butyl (6R,7S)-6-(3,4-dichlorophenyl)-7-ethenyl-1,4-oxazepane-4-carboxylate (1.08 g) and 4-methylmorpholine N-oxide (680 mg) in acetonitrile (6 mL)/acetone (6 mL)/water (6 ml) was added osmium(VIII) oxide immobilized catalyst I (Wako Pure Chemical Industries, Ltd. cat. 153-02581) (700 mg), and the mixture was stirred under nitrogen purging at room temperature overnight. The catalyst was filtered off through celite, and the filtrate was concentrated. Water was added, and the mixture was extracted with ethyl acetate. The organic layer was washed with brine, and dried over anhydrous magnesium sulfate, and the solvent was evaporated (product about 1.07 g). 900 mg therefrom was purified by HPLC (column: Sunrise C18-SAC 20×150 mm, mobile phase: water/acetonitrile (containing 5 mM ammonium acetate)) to give the title compound (diastereomer having a shorter retention time) (610 mg) as a colorless oil.

$^1$H NMR (300 MHz, CDCl$_3$) δ 1.30-1.54 (9H, m), 2.22 (1H, brs), 2.65 (1H, brs), 2.91-3.06 (1H, m), 3.19-3.83 (7H, m), 3.89 (1H, brs), 3.95 (1H, dd, J=10.6, 3.0 Hz), 4.26 (1H, brs), 6.99-7.08 (1H, m), 7.29 (1H, d, J=2.3 Hz), 7.40 (1H, d, J=8.3 Hz).

MS (ESI+): [M+H-Boc]$^+$ 306.0.

In addition, tert-butyl (6R,7R)-6-(3,4-dichlorophenyl)-7-[(1R)-1,2-dihydroxyethyl]-1,4-oxazepane-4-carboxylate (170 mg) having a longer retention time was obtained as a colorless oil.

$^1$H NMR (300 MHz, CDCl$_3$) δ 1.31-1.56 (9H, m), 2.09-2.66 (2H, m), 3.17-4.01 (10H, m), 4.21 (1H, brs), 7.08 (1H, dd, J=8.3, 1.5 Hz), 7.33 (1H, d, J=1.5 Hz), 7.39 (1H, d, J=8.3 Hz).

MS (ESI+): [M+H-Boc]$^+$ 306.0.

N) (1S)-1-[(6R,7R)-6-(3,4-dichlorophenyl)-1,4-oxazepan-7-yl]ethane-1,2-diol monohydrochloride To a solution of tert-butyl (6R,7R)-6-(3,4-dichlorophenyl)-7-[(1S)-1,2-dihydroxyethyl]-1,4-oxazepane-4-carboxylate (450 mg) in ethanol (8 mL) was added 12 mol/kg hydrogen chloride-ethanol solution (8 mL), and the mixture was stirred at room temperature for 15 min. The solvent was evaporated under reduced pressure, and the residue was crystallized from water-ethanol-diethyl ether to give the title compound (340 mg) as colorless crystals.

$^1$H NMR (300 MHz, DMSO-d$_6$) δ 2.86-3.74 (8H, m), 3.74-4.25 (3H, m), 4.49 (1H, brs), 4.74 (1H, brs), 7.34 (1H, dd, J=8.3, 1.9 Hz), 7.62 (1H, d, J=8.3 Hz), 7.66 (1H, d, J=1.9 Hz), 9.17 (1H, brs), 9.77 (1H, brs).

MS (ESI+): [M+H]$^+$ 306.2.

Example 46

(1R)-1-[(6R,7R)-6-(3,4-dichlorophenyl)-1,4-oxazepan-7-yl]ethane-1,2-diol monohydrochloride To a solution of tert-butyl (6R,7R)-6-(3,4-dichlorophenyl)-7-[(1R)-1,2-dihydroxyethyl]-1,4-oxazepane-4-carboxylate (170 mg) obtained in Example 45, step M) in ethanol (5 ml) was added 12 mol/kg hydrogen chloride-ethanol solution (5 mL), and the mixture was stirred at room temperature for 15 min. The solvent was evaporated under reduced pressure, and the residue was crystallized from water-ethanol-diethyl ether to give the title compound (115 mg) as colorless crystals.

$^1$H NMR (300 MHz, DMSO-d$_6$) δ 2.83-4.67 (12H, m), 4.90 (1H, brs), 7.34 (1H, d, J=7.6 Hz), 7.64 (2H, brs), 9.09 (1H, brs), 9.74 (1H, brs).

MS (ESI+): [M+H]$^+$ 306.2.

Example 47

[(7S)-7-(3,4-dichlorophenyl)-1,4-oxazepan-7-yl]methanol monohydrochloride

A) tert-butyl (7S)-7-(3,4-dichlorophenyl)-7-(hydroxymethyl)-1,4-oxazepane-4-carboxylate A racemate (50.4 g) of tert-butyl (7RS)-7-(3,4-dichlorophenyl)-7-(hydroxymethyl)-1,4-oxazepane-4-carboxylate was separated by SFC (column: CHIRALPAK AD-H, 30 mmID×250 mmL, manufactured by DAICEL CHEMICAL INDUSTRIES, LTD., mobile phase: carbon dioxide/2-propanol=65/35) to give the title compound (20 g) having a longer retention time.

$^1$H NMR (400 MHz, MeOD) δ 1.39 (9H, s), 2.17-2.11 (1H, m), 2.48-2.43 (1H, m), 3.54-3.43 (5H, m), 3.73-3.62 (2H, m), 3.87-3.84 (1H, d, J=12 Hz), 7.30-7.27 (1H, d, J=12 Hz), 7.48-7.46 (1H, d, J=8 Hz), 7.53 (1H, s), 1H not detected.

MS (ESI+): [M+H]$^+$ 376.0.

B) [(7S)-7-(3,4-dichlorophenyl)-1,4-oxazepan-7-yl]methanol monohydrochloride To a solution of tert-butyl (7S)-7-(3,4-dichlorophenyl)-7-(hydroxymethyl)-1,4-oxazepane-4-carboxylate (206.2 mg) in ethanol (2 mL) was added 4 N hydrogen chloride/ethyl acetate solution (2 ml), and the mixture was stirred overnight.

The solvent was evaporated under reduced pressure, and the obtained crystals were recrystallized from ethanol and ethyl acetate to give the title compound (134.5 mg).

$^1$H NMR (300 MHz, DMSO-d$_6$) δ 2.34 (1H, dd, J=16.2, 9.8 Hz), 2.76 (1H, dd, J=16.6, 7.6 Hz), 3.01-3.21 (3H, m), 3.24-3.37 (2H, m), 3.40-3.50 (1H, m), 3.55-3.67 (1H, m), 3.95-4.07 (1H, m), 5.08 (1H, t, J=5.9 Hz), 7.35 (1H, dd, J=8.7, 2.3 Hz), 7.57 (1H, d, J=1.9 Hz), 7.61-7.67 (1H, m), 8.83-9.24 (2H, m).

MS (ESI+): [M+H]$^+$ 277.1.

Example 48

[(6R*,7R*)-7-(3,4-dichlorophenyl)-1,4-oxazepan-6-yl]methanol monohydrochloride (retention time short)

tert-Butyl (6RS,7RS)-7-(3,4-dichlorophenyl)-6-(hydroxymethyl)-1,4-oxazepane-4-carboxylate (15.8 g) was separated by HPLC(CHIRALPAK AD, 50 mmID×500 mL, manufactured by DAICEL CHEMICAL INDUSTRIES, LTD., mobile phase: hexane/2-propanol=800/200) to give tert-butyl (6R*,7R*)-7-(3,4-dichlorophenyl)-6-(hydroxymethyl)-1,4-oxazepane-4-carboxylate (7.9 g, >99.9% ee., recovery rate 100%) having a shorter retention time. Using this compound, and in the same manner as in Example 1, step I, the title compound was obtained.

MS (ESI+): [M+H]$^+$ 276.1.

Example 49

[(6R*,7R*)-7-(3,4-dichlorophenyl)-1,4-oxazepan-6-yl]methanol monohydrochloride (retention time long)

tert-Butyl (6RS,7RS)-7-(3,4-dichlorophenyl)-6-(hydroxymethyl)-1,4-oxazepane-4-carboxylate was separated by a method similar to that in Example 48, and the title compound was obtained using tert-butyl (6R*,7R*)-7-(3,4-dichlorophenyl)-6-(hydroxymethyl)-1,4-oxazepane-4-carboxylate having a longer retention time and in the same manner as in Example 1, step I.

MS (ESI+): [M+H]$^+$ 276.1.

Example 50

(6RS,7SR)-7-(3,4-dichlorophenyl)-6-[(methylsulfonyl)methyl]-1,4-oxazepane monohydrochloride Using tert-butyl (6RS,7RS)-7-(3,4-dichlorophenyl)-6-(hydroxymethyl)-1,4-oxazepane-4-carboxylate, and in the same manner as in Example 5, the title compound was obtained.

MS (ESI+): [M+H]$^+$ 338.0.

Example 51

N-{[(6RS,7RS)-7-(3,4-dichlorophenyl)-1,4-oxazepan-6-yl]methyl}acetamide monohydrochloride Using tert-butyl (6RS,7SR)-6-(aminomethyl)-7-(3,4-dichlorophenyl)-1,4-oxazepane-4-carboxylate, and in the same manner as in Example 6, steps C and D, the title compound was obtained.

MS (ESI+): [M+H]$^+$ 317.0.

Example 52

1-{[(6RS,7RS)-7-(3,4-dichlorophenyl)-1,4-oxazepan-6-yl]methyl}-3-ethylurea monohydrochloride Using tert-butyl (6RS,7SR)-6-(aminomethyl)-7-(3,4-dichlorophenyl)-1,4-oxazepane-4-carboxylate and ethyl isocyanate, and in the same manner as in Example 3, steps D and E, the title compound was obtained.

MS (ESI+): [M+H]$^+$ 346.1.

Example 53

N-{[(6RS,7RS)-7-(3,4-dichlorophenyl)-1,4-oxazepan-6-yl]methyl}methanesulfonamide monohydrochloride Using tert-butyl (6RS,7SR)-6-(aminomethyl)-7-(3,4-dichlorophenyl)-1,4-oxazepane-4-carboxylate, and in the same manner as in Example B, the title compound was obtained.

MS (ESI+): [M+H]$^+$ 353.0.

Example 54

N-{[(6RS,7RS)-7-(3,4-dichlorophenyl)-1,4-oxazepan-6-yl]methyl}sulfamide monohydrochloride Using tert-butyl (6RS,7SR)-6-(aminomethyl)-7-(3,4-dichlorophenyl)-1,4-oxazepane-4-carboxylate, and in the same manner as in Example 9, the title compound was obtained.

MS (ESI+): [M+H]$^+$ 354.1.

Example 55

{[(6R*,7R*)-7-(3,4-dichlorophenyl)-1,4-oxazepan-6-yl]methoxy}acetic acid monohydrochloride A) tert-butyl (6R*,7R*)-7-(3,4-dichlorophenyl)-6-{[2-(morpholin-4-yl)-2-oxoethoxy]methyl}-1,4-oxazepane-4-carboxylate To a solution of tert-butyl (6R*,7R*)-7-(3,4-dichlorophenyl)-6-(hydroxymethyl)-1,4-oxazepane-4-carboxylate (retention time long) (500 mg) obtained in Example 49 in THF (4.5 mL) was added 4-(chloroacetyl)morpholine (0.346 mL), and the mixture was stirred at room temperature for 3 hr. To the reaction mixture was added distilled water, and the mixture was extracted with ethyl acetate. The diluted solution was washed with distilled water and brine, and dried over anhydrous sodium sulfate. The solvent was evaporated under reduced pressure. The residue was purified by silica gel chromatography (hexane/ethyl acetate) to give the title compound (649 mg).

$^1$H NMR (300 MHz, CDCl$_3$) δ 1.46-1.56 (9H, m), 2.54-2.67 (1H, m), 3.12-4.08 (18H, m), 4.56-4.64 (1H, m), 7.05-7.15 (1H, m), 7.36-7.48 (2H, m).

B) {[(6R*,7R*)-4-(tert-butoxycarbonyl)-7-(3,4-dichlorophenyl)-1,4-oxazepan-6-yl]methoxy}acetic acid To a solution of tert-butyl (6R*,7R*)-7-(3,4-dichlorophenyl)-6-{[2-(morpholin-4-yl)-2-oxoethoxy]methyl}-1,4-oxazepane-4-carboxylate (649 mg) in THF (2.5 mL) and methanol (2.5 mL) was added a solution of lithium hydroxide monohydrate (108 mg) in distilled water (1.5 mL), and the mixture was stirred at 70° C. for 2 hr. Furthermore, a solution of lithium hydroxide monohydrate (108 mg) in distilled water (1.5 mL) was added, the mixture was stirred at 70° C. overnight, and neutralized with aqueous ammonium chloride solution, and the mixture was extracted with ethyl acetate. The extract was washed with distilled water and brine, and dried over anhydrous sodium sulfate, and the solvent was evaporated under reduced pressure to give the title compound (381 mg).

MS (ESI+): [M−H]$^+$ 432.2.

C) {[(6R*,7R*)-7-(3,4-dichlorophenyl)-1,4-oxazepan-6-yl]methoxy}acetic acid monohydrochloride Using {[(6R*,7R*)-4-(tert-butoxycarbonyl)-7-(3,4-dichlorophenyl)-1,4-oxazepan-6-yl]methoxy}acetic acid (127 mg), and in the same manner as in Example 38, step F, the title compound (159 g) was obtained.

MS (ESI+): [M+H]$^+$ 334.6.

Example 56

1-({[(6R*,7R*)-7-(3,4-dichlorophenyl)-1,4-oxazepan-6-yl]methoxy}acetyl)azetidin-3-ol monohydrochloride tert-Butyl (6R*,7R*)-7-(3,4-dichlorophenyl)-6-(hydroxymethyl)-1,4-oxazepane-4-carboxylate (retention time long) obtained in Example 49 was led to a carboxylic acid derivative by an operation similar to that in Example 55, steps A and B. Using the carboxylic acid derivative and azetidin-3-ol, and by amidation according to Example 41, step A and an operation similar to that in Example 1, step 1, the title compound was obtained.

MS (ESI+): [M+H]$^+$ 389.3.

Example 57

(6R*,7R*)-7-(3,4-dichlorophenyl)-6-{[2-(1,1-dioxidothiomorpholin-4-yl)-2-oxoethoxy]methyl}-1,4-oxazepane monohydrochloride tert-Butyl (6R*,7R*)-7-(3,4-dichlorophenyl)-6-(hydroxymethyl)-1,4-oxazepane-4-carboxylate (retention time long) obtained in Example 49 was led to a carboxylic acid derivative by an operation similar to that in Example 55, steps A and B. Using the carboxylic acid derivative and thiomorpholine 1,1-dioxide, and by amidation according to Example 41, step A and an operation similar to that in Example 1, step 1, the title compound was obtained.

MS (ESI+): [M+H]$^+$ 451.3.

Example 58

2-{[(6R*,7R*)-7-(3,4-dichlorophenyl)-1,4-oxazepan-6-yl]methoxy}benzoic acid monohydrochloride A) tert-butyl (6R*,7R*)-7-(3,4-dichlorophenyl)-6-{[2-(methoxycarbonyl)phenoxy]methyl}-1,4-oxazepane-4-carboxylate To a solution of tert-butyl (6R*,7R*)-7-(3,4-dichlorophenyl)-6-(hydroxymethyl)-1,4-oxazepane-4-carboxylate (retention time long) (500 mg) obtained in Example 49, methyl salicylate (0.257 mL) and triphenylphosphine (1.05 g) in THF (5 mL) was added dropwise diethyl azodicarboxylate (1.8 mL, 2.2 M toluene solution) under ice-cooling, and the mixture was gradually warmed from 0° C. to room temperature and stirred overnight. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (160 mg).

$^1$H NMR (300 MHz, CDCl$_3$) δ 1.40-1.52 (9H, m), 3.15-3.52 (2H, m), 3.54-3.75 (3H, m), 3.77-4.02 (6H, m), 4.18-4.32 (1H, m), 4.73 (1H, d, J=3.0 Hz), 6.70 (1H, d, J=8.3 Hz), 6.93 (1H, t, J=7.4 Hz), 7.15 (1H, d, J=7.9 Hz), 7.31-7.43 (2H, m), 7.46 (1H, brs), 7.75 (1H, d, J=6.4 Hz).

MS (ESI+): [M+H−Boc]$^+$ 410.2.

B) 2-{[(6R*,7R*)-4-(tert-butoxycarbonyl)-7-(3,4-dichlorophenyl)-1,4-oxazepan-6-yl]methoxy}benzoic acid To a solution of tert-butyl (6R*,7R*)-7-(3,4-dichlorophenyl)-6-{[2-(methoxycarbonyl)phenoxy]methyl}-1,4-oxazepane-4-carboxylate (160 mg) in methanol (2 mL) was added 8 N aqueous sodium hydroxide solution (1 mL) at room temperature, and the mixture was stirred at room temperature overnight. The reaction mixture was neutralized with 10% aqueous citric acid solution, and the mixture was extracted with ethyl acetate. The extract was dried over anhydrous magnesium sulfate. The solvent was evaporated under reduced pressure to give the title compound (110 mg).

MS (ESI−): [M−H]$^+$ 494.0.

C) 2-{[(6R*,7R*)-7-(3,4-dichlorophenyl)-1,4-oxazepan-6-yl]methoxy}benzoic acid monohydrochloride To 2-{[(6R*,7R*)-4-(tert-butoxycarbonyl)-7-(3,4-dichlorophenyl)-1,4-oxazepan-6-yl]methoxy}benzoic acid (50 mg) was added 4.0 M hydrogen chloride-ethyl acetate solution (4 mL), and the mixture was stirred at room temperature for 1 hr. The residue obtained by concentration under reduced pressure was washed with ethyl acetate-hexane to give the title compound (20 mg).

$^1$H NMR (300 MHz, DMSO-d$_6$) δ 3.01 (1H, brs), 3.43 (2H, brs), 3.56-4.16 (6H, m), 5.19 (1H, d, J=3.8 Hz), 6.91 (1H, d, J=8.3 Hz), 7.00 (1H, t, J=7.2 Hz), 7.34-7.49 (2H, m), 7.55-7.61 (1H, m), 7.66 (1H, d, J=1.9 Hz), 7.72 (1H, dd, J=7.6, 1.9 Hz), 9.06 (1H, brs), 9.70 (1H, brs).

MS (ESI+): [M+H]$^+$ 396.1.

Example 59

3-{[(6R*,7R*)-7-(3,4-dichlorophenyl)-1,4-oxazepan-6-yl]methoxy}benzoic acid monohydrochloride In the same manner as in Example 58, the title compound was obtained.

MS (ESI+): [M+H]$^+$ 396.2.

Example 60

4-{[(6R*,7R*)-7-(3,4-dichlorophenyl)-1,4-oxazepan-6-yl]methoxy}benzoic acid monohydrochloride In the same manner as in Example 58, the title compound was obtained.

MS (ESI+): [M+H]$^+$ 395.9.

Example 61

1-[(2-{[(6R*,7R*)-7-(3,4-dichlorophenyl)-1,4-oxazepan-6-yl]methoxy}phenyl)carbonyl]azetidin-3-ol monohydrochloride Using 2-{[(6R*,7R*)-4-(tert-butoxycarbonyl)-7-(3,4-dichlorophenyl)-1,4-oxazepan-6-yl]methoxy}benzoic acid (60 mg) obtained in Example 58, step B), and in the same manner as in Example 39, the title compound (20 mg) was obtained.
MS (ESI+): [M+H]$^+$ 451.0.

Example 62

N-[(6RS,7RS)-7-(3,4-dichlorophenyl)-1,4-oxazepan-6-yl]acetamide monohydrochloride

A) methyl (2RS,3SR)-3-(3,4-dichlorophenyl)oxirane-2-carboxylate

To a solution of 3,4-dichlorobenzaldehyde (51.0 g) and methyl chloroacetate (51 mL) in methanol (500 mL) was added 28% sodium methoxide/methanol (68 mL) solution under ice-cooling, and the mixture was stirred at room temperature overnight. The resultant product was collected by filtration, and washed with distilled water to give the title compound (90.9 g).
$^1$H NMR (300 MHz, CDCl$_3$) δ 3.46 (1H, d, J=1.5 Hz), 3.84 (3H, s), 4.07 (1H, d, J=1.9 Hz), 7.14 (1H, dd, J=8.3, 1.9 Hz), 7.38 (1H, d, J=1.9 Hz), 7.45 (1H, d, J=8.3 Hz).

B) (2RS,3SR)-3-(3,4-dichlorophenyl)oxirane-2-carboxylic acid

To a solution of methyl (2RS,3SR)-3-(3,4-dichlorophenyl)oxirane-2-carboxylate (90.9 g) in methanol (500 ml) was added 4 N sodium hydroxide solution (138 mL), and the mixture was stirred at room temperature for 2 hr. The reaction solution was filtered and washed with methanol. To the mother liquor was added 3 N hydrochloric acid (400 ml), and the mixture was stirred at room temperature for 1 hr. The resultant product was collected by filtration, and washed with distilled water to give the title compound (57.3 g).
$^1$H NMR (300 MHz, CDCl$_3$) δ 3.72 (1H, d, J=1.9 Hz), 4.20 (1H, d, J=1.9 Hz), 7.37 (1H, dd, J=8.3, 1.9 Hz), 7.58-7.84 (2H, m), 13.39 (1H, brs).

C) (2RS,3SR)—N-benzyl-3-(3,4-dichlorophenyl)-N-(2-hydroxyethyl)oxirane-2-carboxamide To a mixed solution of (2RS,3SR)-3-(3,4-dichlorophenyl)oxirane-2-carboxylic acid (50.0 g) and 2-(benzylamino)ethanol (38.9 g) in THF (700 mL)-methanol (100 mL) was added 4-(4,6-dimethoxy-1,3,5-triazin-2-yl)-4-methylmorpholinium chloride (71.2 g), and the mixture was stirred at room temperature overnight. The reaction solution was concentrated, the residue was diluted with ethyl acetate, and the mixture was washed with saturated aqueous sodium hydrogen carbonate, water and brine, and dried over anhydrous sodium sulfate. The solvent was evaporated under reduced pressure. The residue was purified by silica gel chromatography (hexane/ethyl acetate) to give the title compound (42.2 g).
$^1$H NMR (300 MHz, CDCl$_3$) δ 1.93-2.82 (1H, m), 3.42-4.26 (6H, m), 4.45-4.92 (2H, m), 6.76-7.60 (8H, m).

D) (6RS,7RS)-4-benzyl-7-(3,4-dichlorophenyl)-6-hydroxy-1,4-oxazepan-5-one

To a solution of (2RS,3SR)—N-benzyl-3-(3,4-dichlorophenyl)-N-(2-hydroxyethyl)oxirane-2-carboxamide (42.2 g) in acetonitrile (350 ml) was added scandium(III)trifluoromethanesulfonate (5.67 g), and the mixture was stirred at room temperature for 20 min. The reaction mixture was concentrated under reduced pressure, and the residue was purified by silica gel chromatography (hexane/ethyl acetate) to give the title compound (31.0 g).
$^1$H NMR (300 MHz, CDCl$_3$) δ 3.08-3.56 (2H, m), 3.66-4.10 (2H, m), 4.09-4.51 (3H, m), 4.55-4.96 (2H, m), 7.21 (1H, dd, J=8.3, 1.9 Hz), 7.27-7.56 (7H, m).

E) (6RS,7SR)-4-benzyl-7-(3,4-dichlorophenyl)-1,4-oxazepan-6-ol

To a solution of lithium aluminum hydride (11.2 g) in THF (120 ml) was added, in an argon stream, aluminum(III) chloride (10.5 g) at room temperature, and the mixture was stirred at room temperature for 40 min. The reaction mixture was cooled to 0° C., a solution of (6RS,7RS)-4-benzyl-7-(3,4-dichlorophenyl)-6-hydroxy-1,4-oxazepan-5-one (28.9 g) in THF (100 mL) was added dropwise, and the mixture was stirred for 3 hr. To the reaction mixture was added 10% aqueous Rochelle salt solution (90 mL) at 0° C., and the mixture was stirred at room temperature for 30 min, and filtered through celite. The filtrate was washed with brine, the organic layer was concentrated under reduced pressure, and the residue was purified by silica gel chromatography (hexane/ethyl acetate) to give the title compound (27.7 g).
$^1$H NMR (300 MHz, CDCl$_3$) δ 2.53-3.13 (4H, m), 3.57-4.08 (5H, m), 4.48 (1H, brs), 4.73 (1H, d, J=1.9 Hz), 7.02-7.60 (8H, m).

F) (6RS,7SR)-4-benzyl-6-{[tert-butyl(dimethyl)silyl]oxy}-7-(3,4-dichlorophenyl)-1,4-oxazepane To a solution of (6RS,7SR)-4-benzyl-7-(3,4-dichlorophenyl)-1,4-oxazepan-6-ol (27.7 g) in DMF (154 mL) were added tert-butylchlorodimethylsilane (17.8 g) and imidazole (10.7 g), and the mixture was stirred at room temperature overnight. The reaction mixture was diluted with water-ethyl acetate for partitioning, and the organic layer was washed with distilled water and brine, and dried over anhydrous sodium sulfate. The solvent was evaporated under reduced pressure. The residue was purified by silica gel chromatography (hexane/ethyl acetate) to give the title compound (37.0 g).
$^1$H NMR (300 MHz, CDCl$_3$) δ −0.55 (3H, s), −0.34 (3H, s), 0.46-0.80 (9H, m), 2.64-3.12 (4H, m), 3.54-3.86 (4H, m), 3.88-4.08 (1H, m), 4.35 (1H, d, J=8.3 Hz), 6.98-7.24 (3H, m), 7.27-7.50 (5H, m).

G) tert-butyl (6RS,7SR)-7-(3,4-dichlorophenyl)-6-hydroxy-1,4-oxazepane-4-carboxylate To a solution of (6RS,7SR)-4-benzyl-6-{[tert-butyl(dimethyl)silyl]oxy}-7-(3,4-dichlorophenyl)-1,4-oxazepane (37.0 g) in acetonitrile (200 mL) was added 1-chloroethyl chloroformate (13.0 mL), and the mixture was stirred at 80° C. for 1 hr. The reaction mixture was concentrated under reduced pressure, and the residue was diluted with methanol (200 mL). The reaction mixture was stirred at 80° C. for 1 hr, and ice-cooled, and THF (200 mL), triethylamine (16.6 mL) and di-tert-butyl dicarbonate (27.6 mL) were added. The reaction mixture was stirred at room temperature for 1 hr, and diluted with water-ethyl acetate for partitioning, and the organic layer was washed with distilled water and brine, dried over anhydrous magnesium sulfate and concentrated under reduced pressure. The residue was dissolved in THF (200 mL), 1 M tetrabutylammonium fluoride (159 mL) was added, and the mixture was stirred at room temperature overnight. The reaction solution was concentrated under reduced pressure, and the residue was purified by silica gel chromatography (hexane/ethyl acetate) to give the title compound (23.2 g).

$^1$H NMR (300 MHz, CDCl$_3$) δ 1.52 (9H, s), 3.08-3.26 (1H, m), 3.45 (1H, dd, J=14.9, 4.3 Hz), 3.55-3.75 (1H, m), 3.77-4.26 (6H, m), 7.27-7.47 (2H, m), 7.56 (1H, s).

H) tert-butyl (6SR,7SR)-6-azido-7-(3,4-dichlorophenyl)-1,4-oxazepane-4-carboxylate Methanesulfonyl chloride (316 mg) was added to a solution of tert-butyl (6RS,7RS)-7-(3,4-dichlorophenyl)-6-hydroxy-1,4-oxazepane-4-carboxylate (500 mg) and triethylamine (0.58 mL) in THF (5 mL), and the mixture was stirred at room temperature for 1 hr. Water was added to the reaction mixture, and the mixture was extracted with ethyl acetate. The extract was washed with brine, and dried over anhydrous magnesium sulfate. The solvent was evaporated under reduced pressure. To a solution of the residue in DMF (5 ml) was added sodium azide (270 mg), and the mixture was stirred at 80° C. overnight. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (272 mg).

$^1$H NMR (300 MHz, CDCl$_3$) δ 1.51 (9H, d, J=8.7 Hz), 3.16-4.38 (8H, m), 4.60 (1H, d, J=4.5 Hz), 7.18 (1H, d, J=9.4 Hz), 7.35-7.65 (1H, m).

I) tert-butyl (6SR,7SR)-6-amino-7-(3,4-dichlorophenyl)-1,4-oxazepane-4-carboxylate To a solution of cobalt bromide (15 mg) in ethanol (5 mL) was added 2,2'-bipyridyl (33 mg), sodium tetrahydroborate (53 mg) was added, and the mixture was stirred at 0-5° C. for 5 min. To the reaction mixture was added a solution of tert-butyl (6SR,7SR)-6-azido-7-(3,4-dichlorophenyl)-1,4-oxazepane-4-carboxylate (270 mg) in ethanol (5 mL), and the mixture was stirred at 0-5° C. for 30 min. Acetic acid was added to the reaction mixture, and the mixture was stirred at room temperature for 5 min. The solvent was evaporated under reduced pressure. The residue was neutralized with saturated aqueous sodium hydrogen carbonate, and the mixture was extracted with ethyl acetate. The extract was washed with brine, and dried over anhydrous sodium sulfate. The solvent was evaporated under reduced pressure. The residue was purified by silica gel column chromatography to give the title compound (191 mg).

$^1$H NMR (300 MHz, CDCl$_3$) δ 1.50 (9H, d, J=5.3 Hz), 1.62 (2H, s), 2.90-4.23 (7H, m), 4.50 (1H, brs), 7.11 (1H, t, J=8.9 Hz), 7.35-7.63 (2H, m).

MS (ESI+): [M+H]$^+$ 361.1.

J) tert-butyl (6S,7S)-6-(acetylamino)-7-(3,4-dichlorophenyl)-1,4-oxazepane-4-carboxylate Acetyl chloride (23 mg) was added to a solution of tert-butyl (6SR,7SR)-6-amino-7-(3,4-dichlorophenyl)-1,4-oxazepane-4-carboxylate (90 mg) and triethylamine (33 mg) in THF (5 ml), and the mixture was stirred at room temperature for 1 hr. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (93 mg).

$^1$H NMR (300 MHz, CDCl$_3$) δ 1.48 (9H, s), 1.83 (3H, s), 3.31-4.84 (8H, m), 5.73 (1H, d, J=9.8 Hz), 7.10 (1H, d, J=8.7 Hz), 7.38 (1H, d, J=8.7 Hz), 7.46 (1H, brs).

MS (ESI+): [M+H]$^+$ 401.0.

K) N-[(6RS,7RS)-7-(3,4-dichlorophenyl)-1,4-oxazepan-6-yl]acetamide monohydrochloride Using tert-butyl (6S,7S)-6-(acetylamino)-7-(3,4-dichlorophenyl)-1,4-oxazepane-4-carboxylate (93 mg), and in the same manner as in Example 39, step B, the title compound (75 mg) was obtained.

$^1$H NMR (300 MHz, DMSO-d$_6$) δ 1.72 (3H, s), 3.12-3.31 (1H, m), 3.44-3.62 (1H, m), 3.81-4.02 (1H, m), 4.08-4.23 (1H, m), 4.32 (2H, brs), 4.45-4.69 (1H, m), 5.02 (1H, d, J=1.5 Hz), 7.30 (1H, dd, J=8.7, 1.9 Hz), 7.49-7.68 (2H, m), 7.94 (1H, d, J=9.1 Hz), 9.34 (1H, brs), 9.77 (1H, brs).

MS (ESI+): [M+H]$^+$ 303.1.

Example 63

N-[(6RS,7RS)-7-(3,4-dichlorophenyl)-1,4-oxazepan-6-yl]methanesulfonamide monohydrochloride A) tert-butyl (6SR,7SR)-7-(3,4-dichlorophenyl)-6-[(methylsulfonyl)amino]-1,4-oxazepane-4-carboxylate Methanesulfonyl chloride (34 mg) was added to a solution of tert-butyl (6SR,7SR)-6-amino-7-(3,4-dichlorophenyl)-1,4-oxazepane-4-carboxylate (90 mg) and triethylamine (33 mg) in THF (5 mL), and the mixture was stirred at room temperature for 1 hr. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (90 mg).

$^1$H NMR (300 MHz, CDCl$_3$) δ 1.52 (9H, brs), 2.19 (2H, s), 2.53 (1H, brs), 3.21-4.29 (7H, m), 4.54-4.89 (2H, m), 7.16 (1H, dd, J=8.3, 1.9 Hz), 7.45 (1H, d, J=8.3 Hz), 7.50 (1H, d, J=1.5 Hz).

MS (ESI+): [M+H]$^+$ 437.0.

B) N-[(6RS,7RS)-7-(3,4-dichlorophenyl)-1,4-oxazepan-6-yl]methanesulfonamide monohydrochloride Using tert-butyl (6SR,7SR)-7-(3,4-dichlorophenyl)-6-[(methylsulfonyl)amino]-1,4-oxazepane-4-carboxylate (90 mg), and in the same manner as in Example 39, step B, the title compound (57 mg) was obtained.

$^1$H NMR (300 MHz, DMSO-d$_6$) δ 2.53 (3H, s), 3.35-3.67 (4H, m), 3.92 (1H, ddd, J=13.3, 6.9, 4.0 Hz), 4.10 (2H, qd), 5.07 (1H, d, J=1.5 Hz), 7.31 (1H, d, J=9.1 Hz), 7.38 (1H, dd, J=8.3, 1.9 Hz), 7.63 (1H, d, J=8.3 Hz), 7.66 (1H, d, J=1.9 Hz), 9.63 (2H, brs).

MS (ESI+): [M+H]$^+$ 339.1.

Example 64

1-[(6RS,7SR)-7-(3,4-dichlorophenyl)-1,4-oxazepan-6-yl]-3-(5-oxo-4,5-dihydro-1,2,4-oxadiazol-3-yl)pyridin-2(1H)-one monohydrochloride A) tert-butyl (6RS,7SR)-6-(3-cyano-2-oxopyridin-1(2H)-yl)-7-(3,4-dichlorophenyl)-1,4-oxazepane-4-carboxylate Methanesulfonyl chloride (949 mg) was added to a solution of tert-butyl (6RS,7SR)-7-(3,4-dichlorophenyl)-6-hydroxy-1,4-oxazepane-4-carboxylate (1.50 g) and triethylamine (1.73 mL) in THF (30 ml), and the mixture was stirred at room temperature for 1 hr. Water was added to the reaction mixture, and the mixture was extracted with ethyl acetate. The extract was washed with brine, and dried over anhydrous magnesium sulfate. The solvent was evaporated under reduced pressure. To a solution of the residue (608 mg) in DMF (12 mL) were added 2-oxo-1,2-dihydropyridine-3-carbonitrile (199 mg) and potassium carbonate (286 mg), and the mixture was stirred at 80° C. overnight. To the reaction mixture was added distilled water, and the mixture was extracted with ethyl acetate. The extract was washed with 0.1 N hydrochloric acid and brine, and dried over anhydrous sodium sulfate, and the solvent was evaporated under reduced pressure. The residue was purified by silica gel chromatography (hexane/ethyl acetate) to give the title compound (108 mg).

$^1$H NMR (300 MHz, CDCl$_3$) δ 1.43 (9H, s), 3.44-3.99 (4H, m), 4.00-4.22 (1H, m), 4.27-4.60 (1H, m), 4.98 (1H, d, J=4.1 Hz), 5.82-6.16 (2H, m), 6.23 (1H, t, J=7.0 Hz), 6.99 (1H, d, J=8.3 Hz), 7.29-7.66 (2H, m), 7.72-8.11 (1H, m).

B) tert-butyl (6RS,7SR)-7-(3,4-dichlorophenyl)-6-[2-oxo-3-(5-oxo-4,5-dihydro-1,2,4-oxadiazol-3-yl)pyridin-1(2H)-yl]-1,4-oxazepane-4-carboxylate Sodium hydrogen carbonate (145 mg) and hydroxylamine monohydrochloride (120 mg) were added to a solution of tert-butyl (6RS,7SR)-6-(3-cyano-2-oxopyridin-1(2H)-yl)-7-(3,4-dichlorophenyl)-1,4-oxazepane-4-carboxylate (100 mg) in DMSO (4 mL), and the mixture was stirred at 80° C. overnight. Water was added to the reaction mixture, and the mixture was extracted with ethyl acetate. The extract was washed with brine, and dried over anhydrous magnesium sulfate. The solvent was evaporated under reduced pressure. The residue was dissolved in THF (10 mL), diazabicycloundecene (0.032 mL) and CDI (52 mg) were added, and the mixture was heated under reflux for 1 hr. To the reaction mixture was added 1 N aqueous hydrochloric acid solution, and the mixture was extracted with ethyl acetate. The extract was washed with water and brine, and dried over anhydrous magnesium sulfate. The solvent was evaporated under reduced pressure. The residue was purified by silica gel column chromatography (hexane/ethyl acetate) to give the title compound (56 mg).

$^1$H NMR (300 MHz, CDCl$_3$) δ 1.41 (9H, brs), 3.38-4.26 (4H, m), 4.27-4.60 (1H, m), 4.89-5.15 (1H, m), 5.87-6.32 (2H, m), 6.93-7.14 (1H, m), 7.27-7.63 (3H, m), 7.79-8.22 (2H, m), 10.28 (1H, brs).

C) 1-[(6RS,7SR)-7-(3,4-dichlorophenyl)-1,4-oxazepan-6-yl]-3-(5-oxo-4,5-dihydro-1,2,4-oxadiazol-3-yl)pyridin-2(1H)-one monohydrochloride Using tert-butyl (6RS,7SR)-7-(3,4-dichlorophenyl)-6-[2-oxo-3-(5-oxo-4,5-dihydro-1,2,4-oxadiazol-3-yl)pyridin-1(2H)-yl]-1,4-oxazepane-4-carboxylate, and in the same manner as in Example 2, step B, the title compound (26 mg) was obtained.

MS (ESI+): [M+H]$^+$ 423.1.

Example 65

[(6RS,7RS)-7-(3,4-dichlorophenyl)-1,4-oxazepan-6-yl]acetonitrile monohydrochloride A) tert-butyl (6RS,7RS)-6-(cyanomethyl)-7-(3,4-dichlorophenyl)-1,4-oxazepane-4-carboxylate To a solution of tert-butyl (6RS,7SR)-7-(3,4-dichlorophenyl)-6-{[(methylsulfonyl)oxy]methyl}-1,4-oxazepane-4-carboxylate (1.26 g) in DMF (10 mL) was added sodium cyanide (204 mg), and the mixture was stirred at 80° C. for 18 hr. The reaction mixture was concentrated under reduced pressure, and the residue was diluted with ethyl acetate. The diluted solution was washed with distilled water and brine, and dried over anhydrous magnesium sulfate. The solvent was evaporated under reduced pressure. The residue was purified by silica gel chromatography (hexane/ethyl acetate) to give the title compound (990 mg).

MS (ESI+): [M+H-Boc]$^+$ 285.1.

B) [(6RS,7RS)-7-(3,4-dichlorophenyl)-1,4-oxazepan-6-yl]acetonitrile monohydrochloride To a solution of tert-butyl (6RS,7RS)-6-(cyanomethyl)-7-(3,4-dichlorophenyl)-1,4-oxazepane-4-carboxylate (88 mg) in ethyl acetate (0.5 mL) was added 2 N hydrogen chloride-ethanol solution (3 ml), and the mixture was stirred at room temperature for 18 hr. The reaction mixture was crystallized from ethyl acetate and diisopropyl ether to give the title compound (63 mg).

MS (ESI+): [M+H]$^+$ 285.1.

Example 66

[(6R,7R)-7-(3,4-dichlorophenyl)-1,4-oxazepan-6-yl]acetic acid monohydrochloride

A) tert-butyl (6R,7R)-6-(cyanomethyl)-7-(3,4-dichlorophenyl)-1,4-oxazepane-4-carboxylate Potassium cyanide (1.720 g) was added to a solution of tert-butyl (6S,7R)-7-(3,4-dichlorophenyl)-6-{[(methylsulfonyl)oxy]methyl}-1,4-oxazepane-4-carboxylate (3 g) in DMF (30 ml), and the mixture was stirred at 80° C. overnight. To the reaction mixture was added aqueous sodium hydrogen carbonate solution, and the mixture was extracted with ethyl acetate. The extract was washed with brine, and dried over anhydrous sodium sulfate. The solvent was evaporated under reduced pressure. The residue was purified by silica gel column chromatography to give the title compound (2.00 g).

$^1$H NMR (300 MHz, CDCl$_3$) δ 1.47-1.56 (9H, m), 2.06-2.37 (3H, m), 3.33-4.24 (7H, m), 7.11-7.22 (1H, m), 7.40-7.49 (2H, m).

B) tert-butyl (6R,7R)-6-(2-amino-2-oxoethyl)-7-(3,4-dichlorophenyl)-1,4-oxazepane-4-carboxylate To a solution of tert-butyl (6R,7R)-6-(cyanomethyl)-7-(3,4-dichlorophenyl)-1,4-oxazepane-4-carboxylate (1 g) in DMSO (10 mL) were added potassium carbonate (0.502 g) and 30% aqueous hydrogen peroxide (1.22 mL) at room temperature. The reaction mixture was stirred at room temperature for 1.5 hr. Diluted aqueous sodium thiosulfate solution was added, and the mixture was extracted with ethyl acetate. The extract was washed with brine, and dried over anhydrous sodium sulfate. The solvent was evaporated under reduced pressure. The residue was purified by silica gel column chromatography to give the title compound (746 mg).

$^1$H NMR (300 MHz, CDCl$_3$) δ 1.50 (9H, s), 1.90 (1H, d, J=12.5 Hz), 2.29 (1H, t, J=12.1 Hz), 2.38-2.54 (1H, m), 3.19-3.32 (1H, m), 3.42 (1H, dd, J=14.6, 4.7 Hz), 3.60 (1H, td, J=12.3, 3.0 Hz), 3.88-4.15 (4H, m), 5.41 (1H, brs), 7.16 (1H, dd, J=8.3, 2.3 Hz), 7.30 (1H, brs), 7.39-7.45 (2H, m).

C) [(6R,7R)-4-(tert-butoxycarbonyl)-7-(3,4-dichlorophenyl)-1,4-oxazepan-6-yl]acetic acid 8 N Aqueous sodium hydroxide solution (0.620 mL) was added to a solution of tert-butyl (6R,7R)-6-(2-amino-2-oxoethyl)-7-(3,4-dichlorophenyl)-1,4-oxazepane-4-carboxylate (500 mg) in n-butanol (5 mL), and the mixture was stirred at 120° C. for 4.5 hr. The reaction mixture was neutralized with 1 N hydrochloric acid, and the mixture was extracted with ethyl acetate. The extract was washed with brine, and dried over anhydrous sodium sulfate. The solvent was evaporated under reduced pressure. The residue was purified by silica gel column chromatography to give the title compound (434 mg).

$^1$H NMR (300 MHz, DMSO-d$_6$) δ 1.21-1.39 (1H, m), 1.43 (9H, s), 1.85 (1H, d, J=13.6 Hz), 2.11-2.36 (2H, m), 3.34-3.74 (4H, m), 3.89-4.03 (1H, m), 4.14-4.29 (1H, m), 7.32 (1H, d, J=6.8 Hz), 7.51-7.65 (2H, m), 12.14 (1H, brs).

D) [(6R,7R)-7-(3,4-dichlorophenyl)-1,4-oxazepan-6-yl]acetic acid monohydrochloride Using [(6R,7R)-4-(tert-butoxycarbonyl)-7-(3,4-dichlorophenyl)-1,4-oxazepan-6-yl]acetic acid (150 mg), and in the same manner as in Example 39, step B, the title compound (75 mg) was obtained.

MS (ESI+): [M+H]$^+$ 304.0.

Example 67

3-[(6R,7R)-7-(3,4-dichlorophenyl)-1,4-oxazepan-6-yl]propanoic acid monohydrochloride

A) tert-butyl (6R,7R)-7-(3,4-dichlorophenyl)-6-[(1E)-3-ethoxy-3-oxoprop-1-en-1-yl]-1,4-oxazepane-4-carboxylate To a solution of lithium chloride (136 mg) and diazabicycloundecene (0.403 mL) in acetonitrile (26.7 mL) was added ethyl(diethoxyphosphoryl)acetate (0.642 mL), and the mixture was stirred at 20 min. tert-Butyl (6R,7R)-7-(3,4-dichlorophenyl)-6-formyl-1,4-oxazepane-4-carboxylate (1.00 g) was added and the mixture was stirred overnight. The reaction mixture was concentrated under reduced pressure, distilled water was added, and the mixture was extracted with ethyl acetate. The extract was washed with distilled water and brine, and dried over anhydrous sodium sulfate, and the solvent was evaporated under reduced pressure. The residue was purified by silica gel chromatography (hexane/ethyl acetate) to give the title compound (902 mg).

$^1$H NMR (300 MHz, CDCl$_3$) δ 1.26 (3H, t, J=7.2 Hz), 1.51 (9H, s), 2.68-4.31 (10H, m), 5.47-5.68 (1H, m), 6.59-6.96 (1H, m), 7.03 (1H, d, J=8.3 Hz), 7.32-7.42 (2H, m).

B) tert-butyl (6R,7R)-7-(3,4-dichlorophenyl)-6-(3-ethoxy-3-oxopropyl)-1,4-oxazepane-4-carboxylate To a solution (1.1 mL) of tert-butyl (6R,7R)-7-(3,4-dichlorophenyl)-6-[(1E)-3-ethoxy-3-oxoprop-1-en-1-yl]-1,4-oxazepane-4-carboxylate (100 mg) in methanol was added, under a nitrogen atmosphere, 3% platinum/activated carbon (23 mg), and the mixture was stirred under a hydrogen atmosphere for 1 hr. The reaction mixture was filtered through celite, and concentrated under reduced pressure to give the title compound (113 mg).

$^1$H NMR (300 MHz, CDCl$_3$) δ 1.18 (3H, t, J=7.2 Hz), 1.32-1.46 (2H, m), 1.50 (9H, s), 1.86-2.60 (3H, m), 3.35-3.90 (5H, m), 3.93-4.15 (4H, m), 7.15 (1H, dd, J=8.1, 2.1 Hz), 7.41 (1H, d, J=5.3 Hz), 7.43 (1H, s).

C) 3-[(6R,7R)-7-(3,4-dichlorophenyl)-1,4-oxazepan-6-yl]propanoic acid monohydrochloride Using tert-butyl (6R,7R)-7-(3,4-dichlorophenyl)-6-(3-ethoxy-3-oxopropyl)-1,4-oxazepane-4-carboxylate (103 mg), and in the same manner as in Example 44, step B, the title compound (45.8 g) was obtained.

MS (ESI+): [M+H]$^+$ 318.2.

Example 68

2-[(6RS,7RS)-7-(3,4-dichlorophenyl)-1,4-oxazepan-6-yl]acetamide monohydrochloride

A) tert-butyl (6RS,7RS)-6-(2-amino-2-oxoethyl)-7-(3,4-dichlorophenyl)-1,4-oxazepane-4-carboxylate To a solution of tert-butyl (6RS,7RS)-6-(cyanomethyl)-7-(3,4-dichlorophenyl)-1,4-oxazepane-4-carboxylate (900 mg) in methanol (7 mL)-water (2 mL) were added saturated aqueous sodium hydrogen carbonate (1 mL) and 35% aqueous hydrogen peroxide (3 mL), and the mixture was stirred for 3 days. To the reaction mixture was added saturated aqueous sodium thiosulfate solution, and the mixture was extracted twice with ethyl acetate. The combined organic layers were washed with brine, and dried over anhydrous magnesium sulfate. The solvent was evaporated under reduced pressure. The residue was purified by silica gel chromatography (hexane/ethyl acetate) to give the title compound (492 mg).

MS (ESI+): [M+H-Boc]$^+$ 302.9.

B) 2-[(6RS,7RS)-7-(3,4-dichlorophenyl)-1,4-oxazepan-6-yl]acetamide monohydrochloride To a solution of tert-butyl (6RS,7RS)-6-(2-amino-2-oxoethyl)-7-(3,4-dichlorophenyl)-1,4-oxazepane-4-carboxylate (100 mg) in ethyl acetate (0.5 ml) was added 2 N hydrogen chloride-ethanol solution (1 mL), and the mixture was stirred at room temperature for 3 hr. To the reaction mixture was added saturated aqueous sodium hydrogen carbonate, and the mixture was extracted twice with ethyl acetate. The combined organic layers were washed with brine, and dried over anhydrous magnesium sulfate. The solvent was evaporated under reduced pressure. To the residue was added 1 N hydrochloric acid. The solvent was evaporated under reduced pressure to give the title compound (14 mg).

MS (ESI+): [M+H-Boc]$^+$ 302.9.

Example 69

N-{[(6R,7R)-7-(3,4-dichlorophenyl)-1,4-oxazepan-6-yl]acetyl}-2-methylalanine monohydrochloride In the same manner as in Example 39, step A, and Example 44, step B, the title compound was obtained.
MS (ESI+): [M+H]$^+$ 389.0.

Example 70

3-({[(6R,7R)-7-(3,4-dichlorophenyl)-1,4-oxazepan-6-yl]acetyl}amino)benzoic acid monohydrochloride In the same manner as in Example 39, step A and Example 44, step B, the title compound was obtained.
MS (ESI+): [M+H]$^+$ 423.1.

Example 71

[(6RS,7SR)-7-(3,4-dichlorophenyl)-1,4-oxazepan-6-yl]methyl acetate monohydrochloride Using tert-butyl (6RS,7SR)-7-(3,4-dichlorophenyl)-6-(hydroxymethyl)-1,4-oxazepane-4-carboxylate obtained in Example 4, step G, and by O-acetylation under similar conditions as in the acetylation in Example 6, step C, and in the same manner as in Example 6, step D, the title compound was obtained.
MS (ESI+): [M+H]$^+$ 318.2

Example 72

[(6S,7R)-7-(3,4-dichlorophenyl)-1,4-oxazepan-6-yl]methanol monohydrochloride

Using tert-butyl (6S,7R)-7-(3,4-dichlorophenyl)-6-(hydroxymethyl)-1,4-oxazepane-4-carboxylate, and in the same manner as in Example 1, step I, the title compound was obtained.
MS (ESI+): [M+H]$^+$ 276.1.

Example 73

[(6R,7S)-7-(3,4-dichlorophenyl)-1,4-oxazepan-6-yl]methanol monohydrochloride

Using tert-butyl (6R,7S)-7-(3,4-dichlorophenyl)-6-(hydroxymethyl)-1,4-oxazepane-4-carboxylate, and in the same manner as in Example 1, step I, the title compound was obtained.
MS (ESI+): [M+H]$^+$ 275.9.

Example 74

7-(3,4-dichlorophenyl)-6-(hydroxymethyl)-1,4-oxazepan-6-ol monohydrochloride

A) tert-butyl (7RS)-7-(3,4-dichlorophenyl)-6-oxo-1,4-oxazepane-4-carboxylate

Dess-Martin reagent (1.4 g) was added to a solution of tert-butyl (6RS,7SR)-7-(3,4-dichlorophenyl)-6-hydroxy-1,4-oxazepane-4-carboxylate (800 mg) in acetonitrile (10 ml), and the mixture was stirred at 0° C. for 1 hr. To the reaction mixture were added saturated aqueous sodium hydrogen carbonate and aqueous sodium sulfite solution, and the mixture was extracted with ethyl acetate. The extract was washed with brine, and dried over anhydrous sodium sulfate. The solvent was evaporated under reduced pressure. The residue was purified by silica gel column chromatography to give the title compound (624 mg).
$^1$H NMR (300 MHz, CDCl$_3$) δ 1.50 (9H, s), 2.95-3.49 (1H, m), 3.60-4.77 (5H, m), 4.85 (1H, brs), 7.10 (1H, dd, J=8.3, 1.5 Hz), 7.33-7.50 (2H, m).

B) tert-butyl (3RS,4SR)-4-(3,4-dichlorophenyl)-1,5-dioxa-8-azaspiro[2.6]nonane-8-carboxylate A solution (3 M, 0.56 mL) of methyllithium in diethyl ether was added to a solution of tert-butyl (7RS)-7-(3,4-dichlorophenyl)-6-oxo-1,4-oxazepane-4-carboxylate (300 mg) and diiodomethane (335 mg) in THF (3 mL), and the mixture was stirred at 0° C. for 30 min, and at room temperature for 1 hr. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography and HPLC to give the title compound (59 mg).
$^1$H NMR (300 MHz, CDCl$_3$) δ 1.50 (9H, s), 2.08-2.37 (1H, m), 2.69 (1H, brs), 3.08-3.37 (1H, m), 3.41-3.91 (2H, m), 3.91-4.32 (3H, m), 4.61 (1H, s), 7.11 (1H, dd, J=8.3, 1.9 Hz), 7.32-7.47 (2H, m).
MS (ESI+): [M+H-Boc]$^+$ 274.0.

C) 7-(3,4-dichlorophenyl)-6-(hydroxymethyl)-1,4-oxazepan-6-ol monohydrochloride

Bismuth(III)trifluoromethanesulfonate (228 mg) was added to a mixed solution of tert-butyl (3RS,4SR)-4-(3,4-dichlorophenyl)-1,5-dioxa-8-azaspiro[2.6]nonane-8-carboxylate (59 mg) in THF/water (v/v=4/1, 5 mL), and the mixture was stirred at 80° C. overnight. To the reaction mixture was added saturated aqueous sodium hydrogen carbonate, and the mixture was extracted with ethyl acetate. The extract was washed with brine, and dried over anhydrous sodium sulfate. The solvent was evaporated under reduced pressure. To the residue was added a solution (4 M, 4 mL) of hydrogen chloride in ethyl acetate. The solvent was evaporated under reduced pressure. To a solution of the residue in THF (4 mL) were added triethylamine (0.033 mL) and di-tert-butyl dicarbonate (52 mg), and the mixture was stirred at room temperature for 1 hr. Water was added to the reaction mixture, and the mixture was extracted with ethyl acetate. The extract was washed with brine, and dried over anhydrous sodium sulfate. The solvent was evaporated under reduced pressure. To the residue was added a solution (4 M, 3 mL) of hydrogen chloride in ethyl acetate, and the mixture was stirred at room temperature for 30 min. The solvent was evaporated under reduced pressure, 8 M aqueous sodium hydroxide solution (3 mL) was added, and the mixture was stirred at 90° C. overnight. Water was added to the reaction mixture, and the mixture was extracted with ethyl acetate. The extract was washed with brine, and dried over anhydrous sodium sulfate. The solvent was evaporated under reduced pressure. To the residue was added a solution (4 M, 3 mL) of hydrogen chloride in ethyl acetate. The solvent was evaporated under reduced pressure to give the title compound (7 mg).
MS (ESI+): [M+H]$^+$ 292.1.

Example 75

2-[(6R,7R)-7-(3,4-dichlorophenyl)-1,4-oxazepan-6-yl]propan-2-ol monohydrochloride

A) 4-tert-butyl 6-methyl (6R,7R)-7-(3,4-dichlorophenyl)-1,4-oxazepane-4,6-dicarboxylate To a mixed solution of (6R,7R)-4-(tert-butoxycarbonyl)-7-(3,4-dichlorophenyl)-1,4-oxazepane-6-carboxylic acid (0.82 g) in toluene (10 ml) and methanol (2 mL) was added trimethylsilyldiazomethane (1.576 mL, 2 mol/l hexane solution) at 0° C. and the mixture was stirred for 30 min. Acetic acid was added until the solution became colorless. The solvent was evaporated under reduced pressure, and the residue was extracted with ethyl acetate and water. The organic layer was washed with brine, and dried over anhydrous sodium sulfate. The solvent was evaporated under reduced pressure to give the title compound (0.51 g).

$^1$H NMR (300 MHz, CDCl$_3$) δ 1.48 (9H, s), 2.84-2.99 (1H, m), 3.32-3.56 (1H, m), 3.60 (3H, s), 3.63-4.04 (4H, m), 4.09-4.19 (1H, m), 4.70-4.83 (1H, m), 7.13 (1H, dd, J=8.3, 2.3 Hz), 7.37 (1H, d, J=8.3 Hz), 7.43 (1H, d, J=1.9 Hz).

MS (ESI+): [M+H-Boc]$^+$ 304.1.

B) tert-butyl (6R,7R)-7-(3,4-dichlorophenyl)-6-(1-hydroxy-1-methylethyl)-1,4-oxazepane-4-carboxylate To a solution of 4-tert-butyl 6-methyl (6R,7R)-7-(3,4-dichlorophenyl)-1,4-oxazepane-4,6-dicarboxylate (0.51 g) in THF (10 mL) was added methyllithium (925 μL, 3 mol/L diethyl ether solution) at −78° C., and the mixture was stirred for 3 hr. A saturated ammonium chloride solution was added at −78° C. to discontinue the reaction, and the mixture was warmed to room temperature, and partitioned with ethyl acetate. The organic layer was washed with brine, and dried over anhydrous magnesium sulfate. The solvent was evaporated under reduced pressure. The residue was purified by silica gel column chromatography (hexane/ethyl acetate) to give the title compound (0.12 g).

$^1$H NMR (300 MHz, CDCl$_3$) δ 0.91-1.31 (6H, m), 1.50 (9H, s), 2.32-2.43 (1H, m), 3.04-4.35 (7H, m), 4.61-4.74 (1H, m), 7.21 (1H, dd, J=8.3, 2.3 Hz), 7.42 (1H, d, J=8.3 Hz), 7.47 (1H, d, J=1.9 Hz).

C) 2-[(6R,7R)-7-(3,4-dichlorophenyl)-1,4-oxazepan-6-yl]propan-2-01 monohydrochloride To a solution of tert-butyl (6R,7R)-7-(3,4-dichlorophenyl)-6-(1-hydroxy-1-methylethyl)-1,4-oxazepane-4-carboxylate (0.12 g) in ethyl acetate (1 mL) was added 4 N hydrogen chloride/ethyl acetate solution (1 ml) at room temperature, and the mixture was stirred overnight. The solvent was evaporated under reduced pressure to give the title compound (0.10 g).

$^1$H NMR (300 MHz, DMSO-d$_6$) δ 1.01 (6H, d, J=5.7 Hz), 2.71-2.81 (1H, m), 3.09 (2H, t, J=4.5 Hz), 3.24-3.31 (1H, m), 3.48-3.68 (2H, m), 3.80-3.93 (1H, m), 4.82 (1H, d, J=8.3 Hz), 7.50-7.56 (1H, m), 7.63-7.69 (1H, m), 7.82-7.85 (1H, m), 3H not detected.

Example 76

2-{[(6S,7R)-7-(3,4-dichlorophenyl)-1,4-oxazepan-6-yl]methoxy}benzonitrile monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 44, step A and Example 39, step B, the title compound was obtained.

MS (ESI+): [M+H]$^+$ 377.0.

Example 77

2-{[(6S,7R)-7-(3,4-dichlorophenyl)-1,4-oxazepan-6-yl]methoxy}benzoic acid monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 44, step A, Example 58, step B and Example 39, step B, the title compound was obtained.

MS (ESI+): [M+H]$^+$ 395.9.

Example 78

2-{[(6S,7R)-7-(3,4-dichlorophenyl)-1,4-oxazepan-6-yl]methoxy}-6-fluorobenzoic acid monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 44, step A, Example 58, step B and Example 39, step B, the title compound was obtained.

MS (ESI+): [M+H]$^+$ 414.1.

Example 79

Methyl 2-{[(6S,7R)-7-(3,4-dichlorophenyl)-1,4-oxazepan-6-yl]methoxy}benzoate monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 44, step A and Example 39, step B, the title compound was obtained.

MS (ESI+): [M+H]$^+$ 410.0.

Example 80

2-{[(6S,7R)-7-(3,4-dichlorophenyl)-1,4-oxazepan-6-yl]methoxy}-N-(methylsulfonyl)benzamide monohydrochloride

A) tert-butyl (6S,7R)-7-(3,4-dichlorophenyl)-6-{[2-(methoxycarbonyl)phenoxy]methyl}-1,4-oxazepane-4-carboxylate Using tert-butyl (6S,7R)-7-(3,4-dichlorophenyl)-6-{[(methylsulfonyl)oxy]methyl}-1,4-oxazepane-4-carboxylate (300 mg), and in the same manner as in Example 44, step A, the title compound (260 mg) was obtained.

MS (ESI+): [M+H-Boc]$^+$ 410.2.

B) 2-{[(6S,7R)-4-(tert-butoxycarbonyl)-7-(3,4-dichlorophenyl)-1,4-oxazepan-6-yl]methoxy}benzoic acid Using tert-butyl (6S,7R)-7-(3,4-dichlorophenyl)-6-{[2-(methoxycarbonyl)phenoxy]methyl}-1,4-oxazepane-4-carboxylate (260 mg), and in the same manner as in Example 58, step B, the title compound (260 mg) was obtained.
MS (ESI+): [M+H-Boc]$^+$ 396.1.

C) tert-butyl (6S,7R)-7-(3,4-dichlorophenyl)-6-({2-[(methylsulfonyl)carbamoyl]phenoxy}methyl)-1,4-oxazepane-4-carboxylate To a solution of 2-{[(6S,7R)-4-(tert-butoxycarbonyl)-7-(3,4-dichlorophenyl)-1,4-oxazepan-6-yl]methoxy}benzoic acid (100 mg) in DMF (1 ml) were added methanesulfonamide (38.3 mg), N-[3-(dimethylamino)propyl]-N'-ethylcarbodiimide hydrochloride (62.5 mg) and N,N-dimethyl-4-aminopyridine (49.2 mg) at room temperature, and the mixture was stirred at room temperature for 2 hr. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (40 mg).
MS (ESI+): [M+H-Boc]$^+$ 472.9.

D) 2-{[(6S,7R)-7-(3,4-dichlorophenyl)-1,4-oxazepan-6-yl]methoxy}-N-(methylsulfonyl)benzamide monohydrochloride Using tert-butyl (6S,7R)-7-(3,4-dichlorophenyl)-6-({2-[(methylsulfonyl)carbamoyl]phenoxy}methyl)-1,4-oxazepane-4-carboxylate (40 mg), and in the same manner as in Example 58, step C, the title compound (17 mg) was obtained.
MS (ESI+): [M+H]$^+$ 473.2.

Example 81

3-{[(6S,7R)-7-(3,4-dichlorophenyl)-1,4-oxazepan-6-yl]methoxy}-N-(methylsulfonyl)benzamide monohydrochloride In the same manner as in Example 80, the title compound was obtained.
MS (ESI+): [M+H]$^+$ 473.0.

Example 82

(6S,7R)-7-(3,4-dichlorophenyl)-6-{[2-(methylsulfonyl)phenoxy]methyl}-1,4-oxazepane monohydrochloride In the same manner as in Example 44, step A and Example 38, step F, the title compound was obtained.
MS (ESI+): [M+H]$^+$ 430.3.

Example 83

3-(2-{[(6S,7R)-7-(3,4-dichlorophenyl)-1,4-oxazepan-6-yl]methoxy}phenyl)-1,2,4-oxadiazol-5(4H)-one monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 44, step A, Example 31, step D and Example 39, step B, the title compound was obtained.
MS (ESI+): [M+H]$^+$ 436.0.

Example 84

3-(3-{[(6S,7R)-7-(3,4-dichlorophenyl)-1,4-oxazepan-6-yl]methoxy}phenyl)-1,2,4-oxadiazol-5(4H)-one monohydrochloride In the same manner as in Example 44, step A and Example 43, steps B and C, the title compound was obtained.
MS (ESI+): [M+H]$^+$ 436.0.

Example 85

3-(3-{[(6S,7R)-7-(3,4-dichlorophenyl)-1,4-oxazepan-6-yl]methoxy}phenyl)-1,2,4-oxadiazole-5(4H)-thione monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 44, step A, Example 31, step D and Example 39, step B, the title compound was obtained.
MS (ESI+): [M+H]$^+$ 452.0.

Example 86

3-(2-{[(6S,7R)-7-(3,4-dichlorophenyl)-1,4-oxazepan-6-yl]methoxy}pyridin-3-yl)-1,2,4-oxadiazol-5(4H)-one monohydrochloride In the same manner as in Example 44, step A and Example 43, steps B and C, the title compound was obtained.
MS (ESI+): [M+H]$^+$ 436.9.

Example 87

3-(6-{[(6S,7R)-7-(3,4-dichlorophenyl)-1,4-oxazepan-6-yl]methoxy}pyridin-3-yl)-1,2,4-oxadiazol-5(4H)-one monohydrochloride In the same manner as in Example 44, step A and Example 43, steps B and C, the title compound was obtained.
MS (ESI+): [M+H]$^+$ 437.0.

Example 88

3-[3-({[(6S,7R)-7-(3,4-dichlorophenyl)-1,4-oxazepan-6-yl]methoxy}methyl)phenyl]-1,2,4-oxadiazol-5(4H)-one monohydrochloride A) tert-butyl (6S,7R)-6-{[(3-cyanobenzyl)oxy]methyl}-7-(3,4-dichlorophenyl)-1,4-oxazepane-4-carboxylate To a solution of tert-butyl (6S,7R)-7-(3,4-dichlorophenyl)-6-(hydroxymethyl)-1,4-oxazepane-4-carboxylate (144.5 mg) in DMF (3 mL) was added 60% sodium hydride (36.9 mg) at 0° C., and the mixture was stirred for 30 min. 3-(Bromomethyl)benzonitrile (90 mg) was added, and the mixture was warmed to room temperature and stirred overnight. The reaction mixture was poured into water, and the mixture was extracted twice with ethyl acetate. The organic layers were combined, and the mixture was washed with brine, and dried over anhydrous magnesium sulfate. The solvent was evaporated under reduced pressure. The residue was purified by silica gel column chromatography (ethyl acetate/hexane) to give the title compound (162 mg).

$^1$H NMR (300 MHz, CDCl$_3$) δ 1.49 (9H, s), 2.13-2.27 (1H, m), 3.14-3.38 (2H, m), 3.45-3.96 (5H, m), 4.02-4.17 (1H, m), 4.21-4.42 (3H, m), 7.12 (1H, dd, J=8.3, 1.9 Hz), 7.35-7.69 (6H, m).

B) 3-[3-({[(6S,7R)-7-(3,4-dichlorophenyl)-1,4-oxazepan-6-yl]methoxy}methyl)phenyl]-1,2,4-oxadiazol-5(4H)-one monohydrochloride tert-Butyl (6S,7R)-6-{[(3-cyanobenzyl)oxy]methyl}-7-(3,4-dichlorophenyl)-1,4-oxazepane-4-carboxylate was reacted under conditions similar to those in Example 31, steps D and E to give the title compound.

$^1$H NMR (300 MHz, DMSO-d$_6$) δ 2.58-2.74 (1H, m), 3.10-3.55 (6H, m), 3.76-3.90 (1H, m), 3.97-4.12 (1H, m), 4.32-4.41 (1H, m), 4.44-4.55 (2H, m), 7.31 (1H, dd, J=8.3, 1.5 Hz), 7.45-7.64 (4H, m), 7.70-7.78 (2H, m), 3H not detected.

MS (ESI+): [M+H]$^+$ 450.1.

Example 89

3-(2-{[(6S,7R)-7-(3,4-dichlorophenyl)-1,4-oxazepan-6-yl]methoxy}pyridin-4-yl)-1,2,4-oxadiazol-5(4H)-one monohydrochloride In the same manner as in Example 44, step A and Example 43, steps B and C, the title compound was obtained.
MS (ESI+): [M+H]$^+$ 436.9.

Example 90

(6R,7R)-7-(3,4-dichlorophenyl)-6-[(methylsulfanyl) methyl]-1,4-oxazepane monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 5, step B, and Example 39, step B, the title compound was obtained.
MS (ESI+): [M+H]$^+$ 306.1.

Example 91

(6R,7R)-7-(3,4-dichlorophenyl)-6-[(methylsulfinyl) methyl]-1,4-oxazepane monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 5, steps B and C and Example 39, step B, the title compound was obtained.
MS (ESI+): [M+H]$^+$ 322.0.

Example 92

(6R,7R)-7-(3,4-dichlorophenyl)-6-[(methylsulfonyl) methyl]-1,4-oxazepane monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 5, steps B, C and D, the title compound was obtained.
MS (ESI+): [M+H]$^+$ 338.3.

Example 93

(6S,7S)-7-(3,4-dichlorophenyl)-6-[(methylsulfonyl) methyl]-1,4-oxazepane monohydrochloride Using tert-butyl (6R,7S)-7-(3,4-dichlorophenyl)-6-(hydroxymethyl)-1,4-oxazepane-4-carboxylate, and in the same manner as in Example 5, the title compound was obtained.
MS (ESI+): [M+H]$^+$ 338.2.

Example 94

2-({[(6R,7R)-7-(3,4-dichlorophenyl)-1,4-oxazepan-6-yl]methyl}sulfanyl)benzoic acid monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 44, step A, Example 58, step B and Example 39, step B, the title compound was obtained.
MS (ESI+): [M+H]$^+$ 412.0.

Example 95

2-({[(6R,7R)-7-(3,4-dichlorophenyl)-1,4-oxazepan-6-yl]methyl}sulfonyl)benzoic acid monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 44, step A, Example 5, step C, Example 58, step B and Example 39, step B, the title compound was obtained.
MS (ESI+): [M+H]$^+$ 443.9.

Example 96

3-[3-({[(6R,7R)-7-(3,4-dichlorophenyl)-1,4-oxazepan-6-yl]methyl}sulfonyl)phenyl]-1,2,4-oxadiazol-5(4H)-one monohydrochloride Using tert-butyl (6S,7R)-7-(3,4-dichlorophenyl)-6-{[(methylsulfonyl)oxy]methyl}-1,4-oxazepane-4-carboxylate and, 3-sulfanylbenzonitrile, and in the same manner as in Example 44, step A, Example 5, step C and Example 31, steps D and E, the title compound was obtained.
MS (ESI+): [M+H]$^+$ 484.1.

Example 97

1-{[(6S,7R)-7-(3,4-dichlorophenyl)-1,4-oxazepan-6-yl]methyl}azetidine-3-carboxylic acid monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 44, step A, Example 58, step B and Example 39, step B, the title compound was obtained.
MS (ESI+): [M+H]$^+$ 359.1.

Example 98

N-{[(6R,7S)-7-(3,4-dichlorophenyl)-1,4-oxazepan-6-yl]methyl}acetamide monofumarate Using tert-butyl (6R,7S)-7-(3,4-dichlorophenyl)-6-{[(methylsulfonyl)oxy]methyl}-1,4-oxazepane-4-carboxylate, and in the same manner as in Example 6, steps A, B and C and Example 32, step D, the title compound was obtained.
MS (ESI+): [M+H]$^+$ 317.0.

Example 99

N-{[(6S,7R)-7-(3,4-dichlorophenyl)-1,4-oxazepan-6-yl]methyl}-N-methylacetamide monohydrochloride

A) tert-butyl (6R,7R)-6-{[acetyl(methyl)amino]methyl}-7-(3,4-dichlorophenyl)-1,4-oxazepane-4-carboxylate To a solution of tert-butyl (6R,7R)-6-[(acetylamino)methyl]-7-(3,4-dichlorophenyl)-1,4-oxazepane-4-carboxylate (180 mg) in THF (4 mL) was added sodium hydride (32 mg, 60%) under ice-cooling, and the mixture was stirred under ice-cooling for 30 min. To the reaction mixture was added methyl iodide (0.107 mL) under ice-cooling, and the mixture was stirred at room temperature overnight. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (100 mg).
MS (ESI+): [M+H]$^+$ 431.3.

B) N-{[(6S,7R)-7-(3,4-dichlorophenyl)-1,4-oxazepan-6-yl]methyl}-N-methylacetamide monohydrochloride To tert-butyl (6R,7R)-6-{[acetyl(methyl)amino]methyl}-7-(3,4-dichlorophenyl)-1,4-oxazepane-4-carboxylate (100 mg) was added 4.0 M hydrogen chloride-ethyl acetate solution (4 mL), and the mixture was stirred at room temperature for 1 hr. The residue obtained by concentration under reduced pressure was separated by HPLC (C18, mobile phase: water/acetonitrile (containing 10 mM NH$_4$HCO$_3$)), and the obtained fraction was concentrated under reduced pressure to give the title compound (60 mg).
MS (ESI+): [M+H]$^+$ 331.3.

Example 100

N-{[(6RS,7SR)-7-(3,4-dichlorophenyl)-6-hydroxy-1,4-oxazepan-6-yl]methyl}acetamide monohydrochloride

A) tert-butyl (6RS,7SR)-6-(azidomethyl)-7-(3,4-dichlorophenyl)-6-hydroxy-1,4-oxazepane-4-carboxylate To a solution of tert-butyl (3RS,4SR)-4-(3,4-dichlorophenyl)-1,5-dioxa-8-azaspiro[2.6]nonane-8-carboxylate (460 mg) in DMF (5 ml) was added sodium azide (240 mg), and the mixture was stirred at 80° C. overnight. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (232 mg).
$^1$H NMR (300 MHz, CDCl$_3$) δ 1.52 (9H, s), 2.96-3.10 (1H, m), 3.09-3.27 (1H, m), 3.29-4.22 (7H, m), 4.27 (1H, s), 7.19 (1H, brs), 7.42 (1H, d, J=7.9 Hz), 7.45-7.59 (1H, m).

B) tert-butyl (6SR,7SR)-6-(aminomethyl)-7-(3,4-dichlorophenyl)-6-hydroxy-1,4-oxazepane-4-carboxylate Using tert-butyl (6RS,7SR)-6-(azidomethyl)-7-(3,4-dichlorophenyl)-6-hydroxy-1,4-oxazepane-4-carboxylate (230 mg), and in the same manner as in Example 62, step I, the title compound was obtained.
MS (ESI+): [M+H]$^+$ 391.2.

C) N-{[(6RS,7SR)-7-(3,4-dichlorophenyl)-6-hydroxy-1,4-oxazepan-6-yl]methyl}acetamide monohydrochloride Using tert-butyl (6SR,7SR)-6-(aminomethyl)-7-(3,4-dichlorophenyl)-6-hydroxy-1,4-oxazepane-4-carboxylate (½ weight), and in the same manner as in Example 62, step J, tert-butyl (6SR,7SR)-6-[(acetylamino)methyl]-7-(3,4-dichlorophenyl)-6-hydroxy-1,4-oxazepane-4-carboxylate (45 mg) was obtained.

Using the obtained tert-butyl (6SR,7SR)-6-[(acetylamino)methyl]-7-(3,4-dichlorophenyl)-6-hydroxy-1,4-oxazepane-4-carboxylate (45 mg), and in the same manner as in Example 39, step B, the title compound (20 mg) was obtained.
$^1$H NMR (300 MHz, DMSO-d$_6$) δ 1.87 (3H, s), 2.76-2.97 (2H, m), 2.96-3.26 (4H, m), 3.70-4.00 (1H, m), 4.08-4.30 (1H, m), 4.58 (1H, s), 5.64 (1H, s), 7.43 (1H, dd, J=8.3, 1.9 Hz), 7.61 (1H, d, J=8.3 Hz), 7.69 (1H, d, J=1.9 Hz), 8.08 (1H, t, J=5.9 Hz), 8.33 (1H, brs), 9.69 (1H, brs).
MS (ESI+): [M+H]$^+$ 333.1.

Example 101

N-{[(6RS,7SR)-7-(3,4-dichlorophenyl)-6-methoxy-1,4-oxazepan-6-yl]methyl}acetamide monohydrochloride

A) tert-butyl (6RS,7SR)-6-(azidomethyl)-7-(3,4-dichlorophenyl)-6-methoxy-1,4-oxazepane-4-carboxylate Under ice-cooling, sodium hydride (60% oil, 8 mg) was added to a solution of tert-butyl (6RS,7SR)-6-(azidomethyl)-7-(3,4-dichlorophenyl)-6-hydroxy-1,4-oxazepane-4-carboxylate (120 mg) in DMF (5 mL). The mixture was stirred at room temperature for 20 min, methyl iodide (122 mg) was added, and the mixture was stirred at the same temperature for 30 min. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (115 mg).
$^1$H NMR (300 MHz, CDCl$_3$) δ 1.50 (9H, s), 2.07-2.82 (1H, m), 2.92-4.78 (11H, m), 7.02-7.23 (1H, m), 7.32-7.60 (2H, m).

B) tert-butyl (6SR,7SR)-6-(aminomethyl)-7-(3,4-dichlorophenyl)-6-methoxy-1,4-oxazepane-4-carboxylate Using tert-butyl (6RS,7SR)-6-(azidomethyl)-7-(3,4-dichlorophenyl)-6-methoxy-1,4-oxazepane-4-carboxylate (115 mg), and in the same manner as in Example 62, step I, the title compound was obtained.

MS (ESI+): [M+H]$^+$ 405.2.

C) tert-butyl (6SR,7SR)-6-[(acetylamino)methyl]-7-(3,4-dichlorophenyl)-6-methoxy-1,4-oxazepane-4-carboxylate Using tert-butyl (6SR,7SR)-6-(aminomethyl)-7-(3,4-dichlorophenyl)-6-methoxy-1,4-oxazepane-4-carboxylate, and in the same manner as in Example 62, step J, the title compound (56 mg) was obtained.

MS (ESI+): [M+H]$^+$ 447.3.

D) N-{[(6RS,7SR)-7-(3,4-dichlorophenyl)-6-methoxy-1,4-oxazepan-6-yl]methyl}acetamide monohydrochloride Using tert-butyl (6SR,7SR)-6-[(acetylamino)methyl]-7-(3,4-dichlorophenyl)-6-methoxy-1,4-oxazepane-4-carboxylate (56 mg), and in the same manner as in Example 39, step B, the title compound (37 mg) was obtained.

MS (ESI+): [M+H]$^+$ 347.1.

Example 102

N-{[(6S,7R)-7-(3,4-dichlorophenyl)-1,4-oxazepan-6-yl]methyl}propanamide monohydrochloride Using tert-butyl (6R,7R)-6-(aminomethyl)-7-(3,4-dichlorophenyl)-1,4-oxazepane-4-carboxylate, and in the same manner as in Example 32, step C and Example 39, step B, the title compound was obtained.

MS (ESI+): [M+H]$^+$ 331.3.

Example 103

N-{[(6S,7R)-7-(3,4-dichlorophenyl)-1,4-oxazepan-6-yl]methyl}butanamide monohydrochloride Using tert-butyl (6R,7R)-6-(aminomethyl)-7-(3,4-dichlorophenyl)-1,4-oxazepane-4-carboxylate, and in the same manner as in Example 32, step C and Example 39, step B, the title compound was obtained.

MS (ESI+): [M+H]$^+$ 345.4.

Example 104

2-cyano-N-{[(6S,7R)-7-(3,4-dichlorophenyl)-1,4-oxazepan-6-yl]methyl}acetamide monohydrochloride Using tert-butyl (6R,7R)-6-(aminomethyl)-7-(3,4-dichlorophenyl)-1,4-oxazepane-4-carboxylate, and in the same manner as in Example 39, the title compound was obtained.

MS (ESI+): [M+H]$^+$ 342.1.

Example 105

2-({[(6S,7R)-7-(3,4-dichlorophenyl)-1,4-oxazepan-6-yl]methyl}amino)-2-oxoethyl acetate monofumarate A) tert-butyl (6R,7R)-6-({[(acetyloxy)acetyl]amino}methyl)-7-(3,4-dichlorophenyl)-1,4-oxazepane-4-carboxylate Using tert-butyl (6R,7R)-6-(aminomethyl)-7-(3,4-dichlorophenyl)-1,4-oxazepane-4-carboxylate, and in the same manner as in Example 6, step C, the title compound was obtained.

MS (ESI+): [M+H-Boc]$^+$ 375.1.

B) 2-({[(6S,7R)-7-(3,4-dichlorophenyl)-1,4-oxazepan-6-yl]methyl}amino)-2-oxoethyl acetate monofumarate Using tert-butyl (6R,7R)-6-({[(acetyloxy)acetyl]amino}methyl)-7-(3,4-dichlorophenyl)-1,4-oxazepane-4-carboxylate, and in the same manner as in Example 32, step D, the title compound was obtained.

MS (ESI+): [M+H]$^+$ 375.1.

Example 106

N-{[(6S,7R)-7-(3,4-dichlorophenyl)-1,4-oxazepan-6-yl]methyl}-2-hydroxyacetamide 0.5 fumarate A) tert-butyl (6R,7R)-7-(3,4-dichlorophenyl)-6-{[(hydroxyacetyl)amino]methyl}-1,4-oxazepane-4-carboxylate To a solution of tert-butyl (6R,7R)-6-(aminomethyl)-7-(3,4-dichlorophenyl)-1,4-oxazepane-4-carboxylate (171 mg) in dimethoxyethane (3 mL) was added 1 N aqueous sodium hydroxide solution (0.72 ml), and the mixture was stirred overnight. The solvent was evaporated under reduced pressure. Water was added to the residue, and the mixture was extracted twice with ethyl acetate. The combined organic layers were washed with brine, and dried over anhydrous magnesium sulfate. The solvent was evaporated under reduced pressure. The residue was purified by silica gel chromatography (ethyl acetate/hexane) to give the title compound (157 mg).

MS (ESI+): [M+H-t-Bu]$^+$ 376.9.

B) N-{[(6S,7R)-7-(3,4-dichlorophenyl)-1,4-oxazepan-6-yl]methyl}-2-hydroxyacetamide 0.5 fumarate Using tert-butyl (6R,7R)-7-(3,4-dichlorophenyl)-6-{[(hydroxyacetyl)amino]methyl}-1,4-oxazepane-4-carboxylate, and in the same manner as in Example 32, step D, the title compound was obtained.

MS (ESI+): [M+H]$^+$ 333.1.

Example 107

N-{[(6RS,7SR)-7-(3,4-dichlorophenyl)-6-hydroxy-1,4-oxazepan-6-yl]methyl}-2-methoxyacetamide monohydrochloride Using tert-butyl (6RS,7SR)-6-(azidomethyl)-7-(3,4-dichlorophenyl)-6-hydroxy-1,4-oxazepane-4-carboxylate (½ weight) obtained in Example 100, step A, and in the same manner as in Example 38, step E, tert-butyl (6SR,7SR)-7-(3,4-dichlorophenyl)-6-hydroxy-6-{[(methoxyacetyl)amino]methyl}-1,4-oxazepane-4-carboxylate (55 mg) was obtained.

MS (ESI+): [M−H]+ 461.0.

Using obtained tert-butyl (6SR,7SR)-7-(3,4-dichlorophenyl)-6-hydroxy-6-{[(methoxyacetyl)amino]methyl}-1,4-oxazepane-4-carboxylate (55 mg), and in the same manner as in Example 39, step B, the title compound (35 mg) was obtained.

MS (ESI+): [M+H]+ 363.1.

Example 108

N-{[(6S,7R)-7-(3,4-dichlorophenyl)-1,4-oxazepan-6-yl]methyl}-2-phenoxyacetamide monohydrochloride Using tert-butyl (6R,7R)-6-(aminomethyl)-7-(3,4-dichlorophenyl)-1,4-oxazepane-4-carboxylate and 2-phenoxyacetic acid, and in the same manner as in Example 39, the title compound was obtained.

$^1$H NMR (300 MHz, DMSO-$d_6$) δ 2.81-2.95 (1H, m), 3.00-3.25 (2H, m), 3.70-3.85 (1H, m), 3.91-4.08 (2H, m), 4.38 (1H, d, J=10.2 Hz), 4.44 (3H, s), 6.88-7.02 (4H, m), 7.25-7.37 (3H, m), 7.40-7.50 (1H, m), 7.66 (1H, d, J=8.3 Hz), 7.76 (1H, d, J=1.9 Hz), 8.26-8.38 (1H, m), 8.78-9.42 (2H, m).

MS (ESI+): [M+H]+ 409.1.

Example 109

2-[2-({[(6S,7R)-7-(3,4-dichlorophenyl)-1,4-oxazepan-6-yl]methyl}amino)-2-oxoethoxy]benzoic acid monohydrochloride Using tert-butyl (6R,7R)-6-(aminomethyl)-7-(3,4-dichlorophenyl)-1,4-oxazepane-4-carboxylate and 2-(2-methoxycarbonyl)phenoxy)acetic acid, and in the same manner as in Example 39, step A and Example 44, step B, the title compound was obtained.

$^1$H NMR (300 MHz, DMSO-$d_6$) δ 2.87-4.09 (10H, m), 4.37-4.62 (3H, m), 7.00-7.14 (2H, m), 7.37-7.59 (2H, m), 7.60-7.67 (1H, m), 7.68-7.84 (2H, m), 8.39-8.90 (2H, m), 1H not detected.

MS (ESI+): [M+H]+ 453.1.

Example 110

N-{[(6S,7R)-7-(3,4-dichlorophenyl)-1,4-oxazepan-6-yl]methyl}-2-[2-(5-oxo-4,5-dihydro-1,2,4-oxadiazol-3-yl)phenoxy]acetamide monohydrochloride Using tert-butyl (6R,7R)-6-(aminomethyl)-7-(3,4-dichlorophenyl)-1,4-oxazepane-4-carboxylate and 2-cyanophenoxyacetic acid, and in the same manner as in Example 39, step A and Example 31, steps D and E, the title compound was obtained.

$^1$H NMR (300 MHz, DMSO-$d_6$) δ 2.55-2.76 (1H, m), 2.92-3.43 (6H, m), 3.81 (1H, td, J=9.1, 4.5 Hz), 3.94-4.05 (1H, m), 4.41 (1H, d, J=10.2 Hz), 4.65 (2H, s), 7.09-7.21 (2H, m), 7.44 (1H, dd, J=8.3, 1.9 Hz), 7.56-7.67 (2H, m), 7.71-7.77 (2H, m), 8.51 (1H, brs), 8.83-9.58 (2H, m), 12.41-12.86 (1H, m).

MS (ESI+): [M+H]+ 493.0.

Example 111

N-{[(6S,7R)-7-(3,4-dichlorophenyl)-1,4-oxazepan-6-yl]methyl}-N-(2-hydroxyethyl)-2-pyrrolidin-1-ylacetamide dihydrochloride A) tert-butyl (6R,7R)-7-(3,4-dichlorophenyl)-6-{[(2-hydroxyethyl)amino]methyl}-1,4-oxazepane-4-carboxylate To a solution of tert-butyl (6S,7R)-7-(3,4-dichlorophenyl)-6-{[(methylsulfonyl)oxy]methyl}-1,4-oxazepane-4-carboxylate (1.9 g) in ethanol (41.8 mL) was added ethanolamine (7.57 mL), and the mixture was stirred at 80° C. overnight. The reaction mixture was concentrated under reduced pressure, distilled water was added, and the mixture was extracted with ethyl acetate. The extract was washed with distilled water and brine, and dried over anhydrous magnesium sulfate, and the solvent was evaporated under reduced pressure to give the title compound (1.65 g).

$^1$H NMR (300 MHz, CDCl$_3$) δ 1.49 (9H, s), 2.11-2.24 (1H, m), 2.29-2.42 (1H, m), 2.45-2.64 (2H, m), 2.71-2.84 (1H, m), 3.18-3.78 (6H, m), 3.79-4.04 (2H, m), 4.04-4.20 (2H, m), 7.16 (1H, d, J=8.0 Hz), 7.38-7.50 (2H, m), 1H not detected.

B) tert-butyl (6R,7R)-6-{[(2-{[tert-butyl(dimethyl)silyl]oxy}ethyl)amino]methyl}-7-(3,4-dichlorophenyl)-1,4-oxazepane-4-carboxylate To a solution (13.2 mL) of tert-butyl (6R,7R)-7-(3,4-dichlorophenyl)-6-{[(2-hydroxyethyl)amino]methyl}-1,4-oxazepane-4-carboxylate (1.65 g) and triethylamine (0.605 mL) in THF was added, under ice-cooling, tert-butylchlorodimethylsilane (654 mg), and the mixture was stirred at room temperature overnight. Then, tert-butylchlorodimethylsilane (654 mg) and triethylamine (0.605 mL) were added, and the mixture was stirred at 50° C. for 1 hr. Distilled water was added, and the mixture was extracted with ethyl acetate. The extract was washed with distilled water and brine, and dried over anhydrous magnesium sulfate, and the solvent was evaporated under reduced pressure. The residue was purified by silica gel chromatography (hexane/ethyl acetate) to give the title compound (1.96 g).

$^1$H NMR (300 MHz, CDCl$_3$) δ −0.08 (6H, s), 0.77 (9H, s), 1.40 (9H, d, J=4.5 Hz), 1.96-2.11 (1H, m), 2.19-2.55 (4H, m), 3.24-3.40 (1H, m), 3.44-3.78 (6H, m), 3.92-4.12 (2H, m), 7.06 (1H, d, J=7.9 Hz), 7.26-7.36 (2H, m), 1H not detected.

C) tert-butyl (6R,7R)-6-{[(2-{[tert-butyl(dimethyl)silyl]oxy}ethyl)(pyrrolidin-1-ylacetyl)amino]methyl}-7-(3,4-dichlorophenyl)-1,4-oxazepane-carboxylate Using tert-butyl (6R,7R)-6-{[(2-{[tert-butyl(dimethyl)silyl]oxy}ethyl)amino]methyl}-7-(3,4-dichlorophenyl)-1,4-oxazepane-4-carboxylate (180 mg), and in the same manner as in Example 39, step A, the title compound (118 mg) was obtained.

$^1$H NMR (300 MHz, CDCl$_3$) δ −0.10--0.04 (6H, m), 0.81 (9H, s), 1.49 (9H, s), 1.70-1.84 (4H, m), 2.25-2.65 (5H, m), 2.83-3.81 (13H, m), 3.98-4.21 (2H, m), 7.08-7.46 (3H, m).

D) tert-butyl (6R,7R)-7-(3,4-dichlorophenyl)-6-{[(2-hydroxyethyl)(pyrrolidin-1-ylacetyl)amino]methyl}-1,4-oxazepane-4-carboxylate To a solution of tert-butyl (6R,7R)-6-{[(2-{[tert-butyl(dimethyl)silyl]oxy}ethyl)(pyrrolidin-1-ylacetyl)amino]methyl}-7-(3,4-dichlorophenyl)-1,4-oxazepane-4-carboxylate (118 g) in THF (0.6 ml) was added, under ice-cooling, a solution (1.0 M, 0.219 ml) of tetrabutylammonium fluoride in THF, and the mixture was stirred at room temperature overnight. To the reaction mixture was added distilled water, and the mixture was extracted with ethyl acetate. The extract was washed with distilled water and brine, and dried over anhydrous magnesium sulfate, and the solvent was evaporated under reduced pressure. The residue was purified by silica gel chromatography (NH, hexane/ethyl acetate/methanol) to give the title compound (81.3 mg).

MS (ESI+): [M+H]$^+$ 530.1.

E) N-{[(6S,7R)-7-(3,4-dichlorophenyl)-1,4-oxazepan-6-yl]methyl}-N-(2-hydroxyethyl)-2-pyrrolidin-1-ylacetamide dihydrochloride Using tert-butyl (6R,7R)-7-(3,4-dichlorophenyl)-6-{[(2-hydroxyethyl)(pyrrolidin-1-ylacetyl)amino]methyl}-1,4-oxazepane-4-carboxylate (81.3 mg), and in the same manner as in Example 38, step F, the title compound (56.9 mg) was obtained.

MS (ESI+): [M+H]$^+$ 430.4.

Example 112

N-{[(6S,7R)-7-(3,4-dichlorophenyl)-1,4-oxazepan-6-yl]methyl}-2-(methylsulfanyl)acetamide monofumarate A) tert-butyl (6R,7R)-7-(3,4-dichlorophenyl)-6-({[(methylsulfanyl)acetyl]amino}methyl)-1,4-oxazepane-4-carboxylate Using tert-butyl (6R,7R)-6-(aminomethyl)-7-(3,4-dichlorophenyl)-1,4-oxazepane-4-carboxylate, and in the same manner as in Example 6, step C and Example 5, step B, the title compound was obtained.

MS (ESI+): [M+H]$^+$ 463.1.

B) N-{[(6S,7R)-7-(3,4-dichlorophenyl)-1,4-oxazepan-6-yl]methyl}-2-(methylsulfanyl)acetamide monofumarate Using tert-butyl (6R,7R)-7-(3,4-dichlorophenyl)-6-({[(methylsulfanyl)acetyl]amino}methyl)-1,4-oxazepane-4-carboxylate, and in the same manner as in Example 32, step D, the title compound was obtained.

MS (ESI+): [M+H]$^+$ 362.9.

Example 113

N-{[(6R,7S)-7-(3,4-dichlorophenyl)-1,4-oxazepan-6-yl]methyl}-2-(methylsulfanyl)acetamide monohydrochloride Using tert-butyl (6S,7S)-6-(aminomethyl)-7-(3,4-dichlorophenyl)-1,4-oxazepane-4-carboxylate, and in the same manner as in Example 112, the title compound was obtained.

MS (ESI+): [M+H]$^+$ 362.9.

Example 114

N-{[(6S,7R)-7-(3,4-dichlorophenyl)-1,4-oxazepan-6-yl]methyl}-2-(methylsulfonyl)acetamide monohydrochloride A) tert-butyl (6R,7R)-7-(3,4-dichlorophenyl)-6-({[(methylsulfonyl)acetyl]amino}methyl)-1,4-oxazepane-4-carboxylate Using tert-butyl (6R,7R)-7-(3,4-dichlorophenyl)-6-({[(methylsulfanyl)acetyl]amino}methyl)-1,4-oxazepane-4-carboxylate, and in the same manner as in Example 5, step C, the title compound was obtained.

MS (ESI+): [M+H-Boc]$^+$ 395.0.

B) N-{[(6S,7R)-7-(3,4-dichlorophenyl)-1,4-oxazepan-6-yl]methyl}-2-(methylsulfonyl)acetamide monohydrochloride Using tert-butyl (6R,7R)-7-(3,4-dichlorophenyl)-6-({[(methylsulfonyl)acetyl]amino}methyl)-1,4-oxazepane-4-carboxylate, and in the same manner as in Example 5, step D, the title compound was obtained.

MS (ESI+): [M+H]$^+$ 395.0.

Example 115

N-{[(6R,7S)-7-(3,4-dichlorophenyl)-1,4-oxazepan-6-yl]methyl}-2-(methylsulfonyl)acetamide monohydrochloride Using tert-butyl (6S,7S)-7-(3,4-dichlorophenyl)-6-({[(methylsulfanyl)acetyl]amino}methyl)-1,4-oxazepane-4-carboxylate, and in the same manner as in Example 114, the title compound was obtained.

MS (ESI+): [M+H]$^+$ 395.0.

Example 116

N-{[(6S,7R)-7-(3,4-dichlorophenyl)-1,4-oxazepan-6-yl]methyl}-2-phenylacetamide monohydrochloride Using tert-butyl (6R,7R)-6-(aminomethyl)-7-(3,4-dichlorophenyl)-1,4-oxazepane-4-carboxylate, and in the same manner as in Example 32, step C and Example 39, step B, the title compound was obtained.

MS (ESI+): [M+H]$^+$ 393.1.

Example 117

N-{[(6S,7R)-7-(3,4-dichlorophenyl)-1,4-oxazepan-6-yl]methyl}-2-[3-(5-oxo-4,5-dihydro-1,2,4-oxadiazol-3-yl)phenyl]acetamide monofumarate Using tert-butyl (6R,7R)-6-(aminomethyl)-7-(3,4-dichlorophenyl)-1,4-oxazepane-4-carboxylate, and in the same manner as in Example 39, step A, Example 31, step D and 39, step B, the title compound was obtained.

MS (ESI+): [M+H]$^+$ 477.1.

Example 118

N-{[(6S,7R)-7-(3,4-dichlorophenyl)-1,4-oxazepan-6-yl]methyl}-4-(5-oxo-4,5-dihydro-1,2,4-oxadiazol-3-yl)benzamide monohydrochloride Using tert-butyl (6R,7R)-6-(aminomethyl)-7-(3,4-dichlorophenyl)-1,4-oxazepane-4-carboxylate and 4-cyanobenzoic acid, and by a method similar to that in Example 39, step A and Example 31, steps D and E, the title compound was obtained.

$^1$H NMR (300 MHz, DMSO-d$_6$) δ 2.65-2.81 (1H, m), 2.98-3.49 (6H, m), 3.76-3.89 (1H, m), 3.93-4.05 (1H, m), 4.47 (1H, d, J=10.2 Hz), 7.49 (1H, dd, J=8.3, 2.3 Hz), 7.67 (1H, d, J=8.3 Hz), 7.79 (1H, d, J=1.9 Hz), 7.84-8.00 (5H, m), 8.71-9.55 (3H, m).

MS (ESI+): [M+H]$^+$ 463.0.

Example 119

N-{[(6S,7R)-7-(3,4-dichlorophenyl)-1,4-oxazepan-6-yl]methyl}-2-(1H-1,2,4-triazol-1-yl)acetamide monohydrochloride Using tert-butyl (6R,7R)-6-(aminomethyl)-7-((3,4-dichlorophenyl)-1,4-oxazepane-4-carboxylate and 2-(1H-1,2,4-triazol-1-yl)acetic acid, and by a method similar to that in Example 39, steps A and B, the title compound was obtained.

$^1$H NMR (300 MHz, DMSO-d$_6$) δ 2.54-2.67 (1H, m), 2.93 (2H, t, J=5.9 Hz), 3.05-3.44 (4H, m), 3.75-3.89 (1H, m), 4.02 (1H, dt, J=13.6, 4.3 Hz), 4.17-5.10 (3H, m), 7.45 (1H, dd, J=8.3, 1.9 Hz), 7.62-7.70 (1H, m), 7.75 (1H, d, J=1.9 Hz), 7.99-8.10 (1H, m), 8.55-8.71 (2H, m), 9.12-9.34 (1H, m), 9.61-9.86 (1H, m).

MS (ESI+): [M+H]$^+$ 384.1.

Example 120

N-{[(6S,7R)-7-(3,4-dichlorophenyl)-1,4-oxazepan-6-yl]methyl}-2-(1H-tetrazol-1-yl)acetamide monohydrochloride Using tert-butyl (6R,7R)-6-(aminomethyl)-7-(3,4-dichlorophenyl)-1,4-oxazepane-4-carboxylate and 2-(1H-tetrazol-1-yl)acetic acid, and by a method similar to that in Example 39, steps A and B, the title compound was obtained.

$^1$H NMR (300 MHz, DMSO-d$_6$) δ 2.55-2.70 (1H, m), 2.90-3.00 (2H, m), 3.07-3.31 (3H, m), 3.07-3.39 (5H, m), 3.96-4.09 (1H, m), 4.43 (1H, d, J=10.5 Hz), 5.26 (2H, s), 7.45 (1H, dd, J=8.3, 1.9 Hz), 7.67 (1H, d, J=8.3 Hz), 7.75 (1H, d, J=1.9 Hz), 8.74-8.86 (1H, m), 9.10-9.29 (1H, m), 9.37 (1H, s), 9.57-9.76 (1H, m).

MS (ESI+): [M+H]$^+$ 385.0.

Example 121

1-[2-({[(6S,7R)-7-(3,4-dichlorophenyl)-1,4-oxazepan-6-yl]methyl}amino)-2-oxoethyl]-3-methyl-1H-pyrazole-5-carboxylic acid monohydrochloride A) ethyl 1-(2-tert-butoxy-2-oxoethyl)-3-methyl-1H-pyrazole-5-carboxylate In the same manner as in Example 44, step A, the title compound was obtained.

$^1$H NMR (300 MHz, CDCl$_3$) δ 1.35 (3H, t, J=7.2 Hz), 1.46 (9H, s), 2.29 (3H, s), 4.30 (2H, q, J=7.2 Hz), 5.12 (2H, s), 6.67 (1H, s).

MS (ESI+): [M+H]$^+$ 269.2.

B) [5-(ethoxycarbonyl)-3-methyl-1H-pyrazol-1-yl]acetic acid

6 N Hydrochloric acid (4 mL, 24.00 mmol) was added to a solution of ethyl 1-(2-tert-butoxy-2-oxoethyl)-3-methyl-1H-pyrazole-5-carboxylate (324 mg, 1.21 mmol) in THF (4 mL). The reaction mixture was stirred at room temperature overnight. The reaction mixture was extracted with ethyl acetate. The extract was washed with brine, and dried over anhydrous sodium sulfate. The solvent was evaporated under reduced pressure. The residue was purified by silica gel column chromatography to give the title compound (206 mg).

$^1$H NMR (300 MHz, CDCl$_3$) δ 1.35 (3H, t, J=7.2 Hz), 2.29 (3H, s), 4.32 (2H, q, J=7.2 Hz), 5.33 (2H, s), 6.68 (1H, s), 8.27 (1H, brs).

MS (ESI+): [M+H]$^+$ 211.3.

C) 1-[2-({[(6S,7R)-7-(3,4-dichlorophenyl)-1,4-oxazepan-6-yl]methyl}amino)-2-oxoethyl]-3-methyl-1H-pyrazole-5-carboxylic acid monohydrochloride Using [5-(ethoxycarbonyl)-3-methyl-1H-pyrazol-1-yl]acetic acid, and in the same manner as in Example 39, step A and Example 44, step B, the title compound was obtained.

$^1$H NMR (300 MHz, DMSO-d$_6$) δ 2.21 (3H, s), 2.53-2.67 (1H, m), 2.94 (2H, t, J=5.3 Hz), 3.05-3.21 (1H, m), 3.21-3.44 (3H, m), 3.75-3.90 (1H, m), 3.94-4.08 (1H, m), 4.42 (1H, d, J=10.2 Hz), 4.82 (2H, s), 6.47 (1H, s), 7.45 (1H, dd, J=8.3, 1.9 Hz), 7.66 (1H, d, J=8.3 Hz), 7.75 (1H, d, J=1.9 Hz), 8.59 (1H, t, J=5.7 Hz), 9.25 (1H, brs), 9.72 (1H, brs), 1H not detected.

MS (ESI+): [M+H]$^+$ 440.9.

Example 122

N-{[(6S,7R)-7-(3,4-dichlorophenyl)-1,4-oxazepan-6-yl]methyl}-2-(2-oxopyrrolidin-1-yl)acetamide monohydrochloride Using tert-butyl (6R,7R)-6-(aminomethyl)-7-(3,4-dichlorophenyl)-1,4-oxazepane-4-carboxylate and (2-oxopyrrolidin-1-yl)acetic acid, and by a method similar to that in Example 39, the title compound was obtained.

$^1$H NMR (300 MHz, DMSO-d$_6$) δ 1.85-2.02 (2H, m), 2.17-2.29 (2H, m), 2.79-3.02 (2H, m), 3.06-3.36 (7H, m), 3.66-3.88 (3H, m), 3.93-4.06 (1H, m), 4.38 (1H, d, J=10.2 Hz), 7.44 (1H, dd, J=8.3, 1.9 Hz), 7.64-7.70 (1H, m), 7.74 (1H, d, J=1.9 Hz), 8.09-8.21 (1H, m), 8.96-9.16 (1H, m), 9.37-9.54 (1H, m).

MS (ESI+): [M+H]$^+$ 400.0.

Example 123

N-{[(6S,7R)-7-(3,4-dichlorophenyl)-1,4-oxazepan-6-yl]methyl}-2-(5-oxo-4,5-dihydro-1,2,4-oxadiazol-3-yl)acetamide monohydrochloride Using tert-butyl (6R,7R)-6-(aminomethyl)-7-(3,4-dichlorophenyl)-1,4-oxazepane-4-carboxylate, and in the same manner as in Example 39, step A, Example 31, step D and Example 39, step B, the title compound was obtained.

MS (ESI+): [M+H]$^+$ 401.0.

Example 124

N-{[(6S,7R)-7-(3,4-dichlorophenyl)-1,4-oxazepan-6-yl]methyl}-2-(2,4-dioxoimidazolidin-1-yl)acetamide monohydrochloride In the same manner as in Example 41, the title compound was obtained.
MS (ESI+): [M+H]$^+$ 415.0.

Example 125

1-[2-({[(6S,7R)-7-(3,4-dichlorophenyl)-1,4-oxazepan-6-yl]methyl}amino)-2-oxoethyl]-5-methyl-1H-pyrazole-3-carboxylic acid monohydrochloride In the same manner as in Example 121, the title compound was obtained.
MS (ESI+): [M+H]$^+$ 441.4:

Example 126

N-{[(6S,7R)-7-(3,4-dichlorophenyl)-1,4-oxazepan-6-yl]methyl}benzamide monohydrochloride Using tert-butyl (6R,7R)-6-(aminomethyl)-7-(3,4-dichlorophenyl)-1,4-oxazepane-4-carboxylate, and in the same manner as in Example 32, step C and Example 39, step B, the title compound was obtained.
MS (ESI+): [M+H]$^+$ 379.0.

Example 127

3,5-di-tert-butyl-N-{[(6S,7R)-7-(3,4-dichlorophenyl)-1,4-oxazepan-6-yl]methyl}benzamide monohydrochloride In the same manner as in Example 39, the title compound was obtained.
MS (ESI+): [M+H]$^+$ 491.0.

Example 128

N-{[(6S,7R)-7-(3,4-dichlorophenyl)-1,4-oxazepan-6-yl]methyl}biphenyl-2-carboxamide monohydrochloride In the same manner as in Example 39, the title compound was obtained.
MS (ESI+): [M+H]$^+$ 455.0.

Example 129

N-{[(6S,7R)-7-(3,4-dichlorophenyl)-1,4-oxazepan-6-yl]methyl}biphenyl-3-carboxamide monohydrochloride In the same manner as in Example 39, the title compound was obtained.
MS (ESI+): [M+H]$^+$ 455.0.

Example 130

N-{[(6S,7R)-7-(3,4-dichlorophenyl)-1,4-oxazepan-6-yl]methyl}-2-hydroxybiphenyl-3-carboxamide monohydrochloride In the same manner as in Example 39, the title compound was obtained.
MS (ESI+): [M+H]$^+$ 471.2.

Example 131

2-({[(6S,7R)-7-(3,4-dichlorophenyl)-1,4-oxazepan-6-yl]methyl}carbamoyl)benzoic acid monohydrochloride Using tert-butyl (6R,7R)-6-(aminomethyl)-7-(3,4-dichlorophenyl)-1,4-oxazepane-4-carboxylate, and in the same manner as in Example 39, step A, Example 58, step B and Example 39, step B, the title compound was obtained.
MS (ESI+): [M+H]$^+$ 423.1.

Example 132

N-{[(6R*,7S*)-7-(4-chloro-3-methylphenyl)-1,4-oxazepan-6-yl]methyl}methanesulfonamide monohydrochloride Using tert-butyl (6R*,7S*)-7-(4-chloro-3-methylphenyl)-6-(hydroxymethyl)-1,4-oxazepane-4-carboxylate, and in the same manner as in Example 38, steps B to D and Example 34, step A, the title compound was obtained.
MS (ESI+): [M+H]$^+$ 333.2.

Example 133

2-({[(6S,7R)-7-(3,4-dichlorophenyl)-1,4-oxazepan-6-yl]methyl}carbamoyl)-4,5-difluorobenzoic acid monohydrochloride A) 2-({[(6R,7R)-4-(tert-butoxycarbonyl)-7-(3,4-dichlorophenyl)-1,4-oxazepan-6-yl]methyl}carbamoyl)-4,5-difluorobenzoic acid To a solution of tert-butyl (6R,7R)-6-(aminomethyl)-7-(3,4-dichlorophenyl)-1,4-oxazepane-4-carboxylate (100 mg) in DMF (2 mL) was added 5,6-difluoro-2-benzofuran-1,3-dione (73.6 mg) at room temperature, and the mixture was stirred at 80° C. overnight. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (102 mg).
MS (ESI+): [M+H-t-Bu]$^+$ 502.9.

B) 2-({[(6S,7R)-7-(3,4-dichlorophenyl)-1,4-oxazepan-6-yl]methyl}carbamoyl)-4,5-difluorobenzoic acid monohydrochloride To 2-({[(6R,7R)-4-(tert-butoxycarbonyl)-7-(3,4-dichlorophenyl)-1,4-oxazepan-6-yl]methyl}carbamoyl)-4,5-difluorobenzoic acid (102 mg) was added 4.0 M hydrogen chloride-ethyl acetate solution (4 mL), and the mixture was stirred at room temperature for 1 hr. The residue obtained by concentration under reduced pressure was separated by HPLC (C18, mobile phase: water/acetonitrile (containing 5 mM AcONH$_4$)), and the obtained fraction was concentrated under reduced pressure to give the title compound (17 mg).
MS (ESI+): [M+H]$^+$ 459.1.

Example 134

N-{[(6S,7R)-7-(3,4-dichlorophenyl)-1,4-oxazepan-6-yl]methyl}-2-[(5-oxo-4,5-dihydro-1,2,4-oxadiazol-3-yl)methyl]benzamide monohydrochloride Using tert-butyl (6R,7R)-6-(aminomethyl)-7-(3,4-dichlorophenyl)-1,4-oxazepane-4-carboxylate, and in the same manner as in Example 39, step A, Example 31, step D and Example 39, step B, the title compound was obtained.
MS (ESI+): [M+H]$^+$ 477.1.

Example 135

3-({[(6S,7R)-7-(3,4-dichlorophenyl)-1,4-oxazepan-6-yl]methyl}carbamoyl)benzoic acid monohydrochloride Using tert-butyl (6R,7R)-6-(aminomethyl)-7-(3,4-dichlorophenyl)-1,4-oxazepane-4-carboxylate, and in the same manner as in Example 39, step A, Example 58, step B and Example 39, step B, the title compound was obtained.
MS (ESI+): [M+H]$^+$ 423.1.

Example 136

4-({[(6S,7R)-7-(3,4-dichlorophenyl)-1,4-oxazepan-6-yl]methyl}carbamoyl)benzoic acid monohydrochloride Using tert-butyl (6R,7R)-6-(aminomethyl)-7-(3,4-dichlorophenyl)-1,4-oxazepane-4-carboxylate, and in the same manner as in Example 39, step A, Example 58, step B and Example 39, step B, the title compound was obtained.
MS (ESI+): [M+H]$^+$ 423.1.

Example 137

3-cyano-N-{[(6S,7R)-7-(3,4-dichlorophenyl)-1,4-oxazepan-6-yl]methyl}benzamide monohydrochloride Using tert-butyl (6R,7R)-6-(aminomethyl)-7-(3,4-dichlorophenyl)-1,4-oxazepane-4-carboxylate, and in the same manner as in Example 39, the title compound was obtained.
MS (ESI+): [M+H]$^+$ 404.0.

Example 138

3-cyano-N-{[(6S,7R)-7-(3,4-dichlorophenyl)-1,4-oxazepan-6-yl]methyl}-N-methylbenzamide monohydrochloride Using tert-butyl (6R,7R)-6-(aminomethyl)-7-(3,4-dichlorophenyl)-1,4-oxazepane-4-carboxylate, and in the same manner as in Example 39, step A, Example 99, step A and Example 39, step B, the title compound was obtained.
MS (ESI+): [M+H]$^+$ 418.3.

Example 139

N-{[(6S,7R)-7-(3,4-dichlorophenyl)-1,4-oxazepan-6-yl]methyl}-2-(5-oxo-4,5-dihydro-1,2,4-oxadiazol-3-yl)benzamide monohydrochloride Using tert-butyl (6R,7R)-6-(aminomethyl)-7-(3,4-dichlorophenyl)-1,4-oxazepane-4-carboxylate, and in the same manner as in Example 39, step A, Example 31, step D and Example 39, step B, the title compound was obtained.
MS (ESI+): [M+H]$^+$ 463.3.

Example 140

3-(2{[(6S,7R)-7-(3,4-dichlorophenyl)-1,4-oxazepan-6-yl]methoxy}-6-fluorophenyl)-1,2,4-oxadiazol-5(4H)-one monohydrochloride In the same manner as in Example 44, step A and Example 43, steps B and C, the title compound was obtained.
MS (ESI+): [M+H]$^+$ 454.0.

Example 141

3-(2-chloro-6-{[(6S,7R)-7-(3,4-dichlorophenyl)-1,4-oxazepan-6-yl]methoxy}phenyl)-1,2,4-oxadiazol-5(4H)-one monohydrochloride In the same manner as in Example 44, step A and Example 43, steps B and C, the title compound was obtained.
MS (ESI+): [M+H]$^+$ 469.9.

Example 142

N-{[(6S,7R)-7-(3,4-dichlorophenyl)-1,4-oxazepan-6-yl]methyl}-3-(5-oxo-4,5-dihydro-1,2,4-oxadiazol-3-yl)benzamide monohydrochloride Using tert-butyl (6R,7R)-6-(aminomethyl)-7-(3,4-dichlorophenyl)-1,4-oxazepane-4-carboxylate, and in the same manner as in Example 39, step A, Example 31, step D and Example 39, step B, the title compound was obtained.
MS (ESI+): [M+H]$^+$ 463.0.

Example 143

N-{[(6S,7R)-7-(3,4-dichlorophenyl)-1,4-oxazepan-6-yl]methyl}-N-methyl-3-(5-oxo-4,5-dihydro-1,2,4-oxadiazol-3-yl)benzamide monohydrochloride Using tert-butyl (6R,7R)-6-(aminomethyl)-7-(3,4-dichlorophenyl)-1,4-oxazepane-4-carboxylate, and in the same manner as in Example 39, step A, Example 99, step A, Example 31, step D and Example 39, step B, the title compound was obtained.
MS (ESI+): [M+H]$^+$ 477.4.

Example 144

N-{[(6S,7R)-7-(3,4-dichlorophenyl)-1,4-oxazepan-6-yl]methyl}-3-(1H-tetrazol-5-yl)benzamide monohydrochloride A) tert-butyl (6R,7R)-6-({[(3-cyanophenyl)carbonyl]amino}methyl)-7-(3,4-dichlorophenyl)-1,4-oxazepane-4-carboxylate Using tert-butyl (6R,7R)-6-(aminomethyl)-7-(3,4-dichlorophenyl)-1,4-oxazepane-4-carboxylate (300 mg), and in the same manner as in Example 39, step A, the title compound (324 mg) was obtained.
MS (ESI+): [M+H-t-Bu]$^+$ 448.0.

B) tert-butyl (6R,7R)-7-(3,4-dichlorophenyl)-6-[({[3-(1H-tetrazol-5-yl)phenyl]carbonyl}amino)methyl]-1,4-oxazepane-4-carboxylate To a solution of tert-butyl (6R,7R)-6-({[(3-cyanophenyl)carbonyl]amino}methyl)-7-(3,4-dichlorophenyl)-1,4-oxazepane-4-carboxylate (100 mg) in DMF (4 mL) were added sodium azide (38.7 mg) and ammonium chloride (37.1 mg) at room temperature, and the mixture was stirred at 100° C. overnight. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (32 mg).
[M+H-Boc]$^+$ 447.2.

C) N-{[(6S,7R)-7-(3,4-dichlorophenyl)-1,4-oxazepan-6-yl]methyl}-3-(1H-tetrazol-5-yl)benzamide monohydrochloride Using tert-butyl (6R,7R)-7-(3,4-dichlorophenyl)-6-[({[3-(1H-tetrazol-5-yl)phenyl]carbonyl}amino)methyl]-1,4-oxazepane-4-carboxylate (32 mg), and in the same manner as in Example 58, step C, the title compound (17 mg) was obtained.
MS (ESI+): [M+H]$^+$ 447.2.

Example 145

N-{[(6S,7R)-7-(3,4-dichlorophenyl)-1,4-oxazepan-6-yl]methyl}pyridine-2-carboxamide dihydrochloride Using tert-butyl (6R,7R)-6-(aminomethyl)-7-(3,4-dichlorophenyl)-1,4-oxazepane-4-carboxylate, and in the same manner as in Example 32, step C and Example 39, step B, the title compound was obtained.
MS (ESI+): [M+H]$^+$ 380.0.

Example 146

N-{[(6S,7R)-7-(3,4-dichlorophenyl)-1,4-oxazepan-6-yl]methyl}-4-(5-oxo-4,5-dihydro-1,2,4-oxadiazol-3-yl)pyridine-2-carboxamide monohydrochloride In the same manner as in Example 41, step A and Example 31, steps D and E, the title compound was obtained.
MS (ESI+): [M+H]$^+$ 464.1.

Example 147

N-{[(6S,7R)-7-(3,4-dichlorophenyl)-1,4-oxazepan-6-yl]methyl}-6-(5-oxo-4,5-dihydro-1,2,4-oxadiazol-3-yl)pyridine-2-carboxamide monohydrochloride In the same manner as in Example 146, the title compound was obtained.
MS (ESI+): [M+H]$^+$ 464.0.

Example 148

N-{[(6S,7R)-7-(3,4-dichlorophenyl)-1,4-oxazepan-6-yl]methyl}-4-methyl-1,3-thiazole-5-carboxamide monohydrochloride Using tert-butyl (6R,7R)-6-(aminomethyl)-7-(3,4-dichlorophenyl)-1,4-oxazepane-4-carboxylate, and in the same manner as in Example 39, the title compound was obtained.
MS (ESI+): [M+H]$^+$ 400.0.

Example 149

N-{[(6S,7R)-7-(3,4-dichlorophenyl)-1,4-oxazepan-6-yl]methyl}-2-oxobutanamide monohydrochloride Using tert-butyl (6R,7R)-6-(aminomethyl)-7-(3,4-dichlorophenyl)-1,4-oxazepane-4-carboxylate, and in the same manner as in Example 39, the title compound was obtained.
MS (ESI+): [M+H]$^+$ 359.0.

Example 150

Methyl {[(6S,7R)-7-(3,4-dichlorophenyl)-1,4-oxazepan-6-yl]methyl}carbamate monohydrochloride In the same manner as in Example 38, steps E and F, the title compound was obtained.
MS (ESI+): [M+H]$^+$ 333.4.

Example 151

1-methylethyl {[(6S,7R)-7-(3,4-dichlorophenyl)-1,4-oxazepan-6-yl]methyl}carbamate monohydrochloride In the same manner as in Example 150, the title compound was obtained.
MS (ESI+): [M+H]$^+$ 361.1.

Example 152

1-{[(6S,7R)-7-(3,4-dichlorophenyl)-1,4-oxazepan-6-yl]methyl}urea monofumarate

Using tert-butyl (6R,7R)-6-(aminomethyl)-7-(3,4-dichlorophenyl)-1,4-oxazepane-4-carboxylate, and in the same manner as in Example 3, the title compound was obtained.
MS (ESI+): [M+H]$^+$ 318.1.

Example 153

1-{[(6R,7S)-7-(3,4-dichlorophenyl)-1,4-oxazepan-6-yl]methyl}urea monofumarate

Using tert-butyl (6S,7S)-6-(aminomethyl)-7-(3,4-dichlorophenyl)-1,4-oxazepane-4-carboxylate, and in the same manner as in Example 3, the title compound was obtained.
MS (ESI+): [M+H]$^+$ 318.1.

Example 154

1-{[(6RS,7SR)-7-(3,4-dichlorophenyl)-1,4-oxazepan-6-yl]methyl}-3-ethylurea monohydrochloride Using tert-butyl (6RS,7RS)-6-(aminomethyl)-7-(3,4-dichlorophenyl)-1,4-oxazepane-4-carboxylate and ethyl isocyanate, and in the same manner as in Example 3, the title compound was obtained.
MS (ESI+): [M+H]$^+$ 346.1.

Example 155

1-{[(6S,7R)-7-(3,4-dichlorophenyl)-1,4-oxazepan-6-yl]methyl}-3-ethylurea monofumarate Using tert-butyl (6R,7R)-6-(aminomethyl)-7-(3,4-dichlorophenyl)-1,4-oxazepane-4-carboxylate, and in the same manner as in Example 154, the title compound was obtained.
MS (ESI+): [M+H]$^+$ 346.3.

Example 156

1-{[(6R,7S)-7-(3,4-dichlorophenyl)-1,4-oxazepan-6-yl]methyl}-3-ethylurea monohydrochloride Using tert-butyl (6S,7S)-6-(aminomethyl)-7-(3,4-dichlorophenyl)-1,4-oxazepane-4-carboxylate, and in the same manner as in Example 154, the title compound was obtained.
MS (ESI+): [M+H]$^+$ 346.1.

Example 157

1-tert-butyl-3-{[(6S,7R)-7-(3,4-dichlorophenyl)-1,4-oxazepan-6-yl]methyl}urea monohydrochloride Using tert-butyl (6R,7R)-6-(aminomethyl)-7-(4-chloro-3-fluorophenyl)-1,4-oxazepane-4-carboxylate and tert-butyl isocyanate, and by a method similar to that in Example 158, steps A and C, the title compound was obtained.
$^1$H NMR (300 MHz, DMSO-d$_6$) δ 1.19 (9H, s), 2.69-2.92 (2H, m), 3.06-3.52 (5H, m), 3.72-3.87 (1H, m), 3.94-4.08 (1H, m), 4.36 (1H, d, J=9.8 Hz), 5.67-5.86 (1H, m), 6.02-6.16 (1H, m), 7.43 (1H, dd, J=8.3, 1.5 Hz), 7.66 (1H, d, J=8.3 Hz), 7.72 (1H, d, J=1.5 Hz), 9.05-9.26 (1H, m), 9.48-9.67 (1H, m).
MS (ESI+): [M+H]$^+$ 374.2.

Example 158

N-{[(6S,7R)-7-(3,4-dichlorophenyl)-1,4-oxazepan-6-yl]methyl}pyrrolidine-1-carboxamide monohydrochloride A) tert-butyl (6R,7R)-7-(3,4-dichlorophenyl)-6-{[(4-nitrophenoxy)carbonylamino]methyl}-1,4-oxazepane-4-carboxylate To a solution of tert-butyl (6R,7R)-6-(aminomethyl)-7-(3,4-dichlorophenyl)-1,4-oxazepane-4-carboxylate (250.2 mg) and triethylamine (186 μL) in THF (5 mL) was added 4-nitrophenyl chloroformate (161 mg) at 0° C., and the mixture was stirred overnight. The reaction mixture was poured into water, and the mixture was extracted twice with ethyl acetate. The organic layers were combined, and the mixture was washed with brine, and dried over anhydrous magnesium sulfate. The solvent was evaporated under reduced pressure. The residue was purified by silica gel column chromatography (ethyl acetate/hexane) to give the title compound (295 mg).
$^1$H NMR (300 MHz, CDCl$_3$) δ 1.53 (9H, s), 2.26-2.41 (1H, m), 3.00-3.66 (5H, m), 4.02-4.22 (4H, m), 6.97-7.07 (1H, m), 7.21 (1H, dd, J=8.3, 1.9 Hz), 7.30 (2H, d, J=9.0 Hz), 7.41 (1H, d, J=8.3 Hz), 7.48-7.53 (1H, m), 8.19-8.27 (2H, m).

B) tert-butyl (6R,7R)-7-(3,4-dichlorophenyl)-6-[(pyrrolidine-1-carboxamide)methyl]-1,4-oxazepane-4-carboxylate A solution of tert-butyl (6R,7R)-7-(3,4-dichlorophenyl)-6-{[(4-nitrophenoxy)carbonylamino]methyl}-1,4-oxazepane-4-carboxylate (187.8 mg), pyrrolidine (35 μL) and potassium carbonate (96 mg) in DMF (3 mL) was stirred at 80° C. overnight. The reaction mixture was poured into water, and the mixture was extracted twice with ethyl acetate. The organic layers were combined, and the mixture was washed with brine, and dried over anhydrous magnesium sulfate. The solvent was evaporated under reduced pressure. The residue was purified by silica gel column chromatography (ethyl acetate/hexane) to give the title compound (151 mg).
$^1$H NMR (300 MHz, CDCl$_3$) δ 1.49 (9H, s), 1.80-1.93 (3H, m), 2.30 (1H, d, J=6.8 Hz), 2.78-2.92 (1H, m), 3.09-3.25 (2H, m), 3.26-3.40 (4H, m), 3.47-3.63 (2H, m), 3.90-4.19 (4H, m), 5.79 (1H, d, J=1.9 Hz), 7.21-7.30 (1H, m), 7.37-7.44 (1H, m), 7.51 (1H, s), 8.02 (1H, s).

C) N-{[(6S,7R)-7-(3,4-dichlorophenyl)-1,4-oxazepan-6-yl]methyl}pyrrolidine-1-carboxamide monohydrochloride Using tert-butyl (6R,7R)-7-(3,4-dichlorophenyl)-6-[(pyrrolidine-1-carboxamide)methyl]-1,4-oxazepane-4-carboxylate, and by a method similar to that in Example 39, step B, the title compound was obtained.
$^1$H NMR (300 MHz, DMSO-d$_6$) δ 1.66-1.83 (4H, m), 2.58-2.71 (1H, m), 2.77-3.02 (3H, m), 3.04-3.28 (6H, m), 3.29-3.42 (1H, m), 3.77 (1H, ddd, J=13.8, 7.8, 3.6 Hz), 3.88-4.01 (1H, m), 4.39 (1H, d, J=10.2 Hz), 6.19-6.31 (1H, m), 7.45 (1H, dd, J=8.7, 2.1 Hz), 7.66 (1H, d, J=8.3 Hz), 7.74 (1H, d, J=1.9 Hz), 8.92-9.12 (1H, m), 9.35-9.52 (1H, m).
MS (ESI+): [M+H]$^+$ 372.1.

Example 159

N-{[(6S,7R)-7-(3,4-dichlorophenyl)-1,4-oxazepan-6-yl]methyl}morpholine-4-carboxamide monohydrochloride Using tert-butyl (6R,7R)-7-(3,4-dichlorophenyl)-6-{[(4-nitrophenoxy)carbonylamino]methyl}-1,4-oxazepane-4-carboxylate and morpholine, and by a method similar to that in Example 158, steps B and C, the title compound was obtained.
$^1$H NMR (300 MHz, DMSO-d$_6$) δ 2.57-2.71 (1H, m), 2.79-3.01 (2H, m), 3.11-3.26 (6H, m), 3.34 (2H, s), 3.45-3.54 (4H, m), 3.72-3.84 (1H, m), 3.90-4.01 (1H, m), 4.39 (1H, d, J=9.8 Hz), 6.68-6.78 (1H, m), 7.45 (1H, dd, J=8.5, 2.1 Hz), 7.66 (1H, d, J=8.3 Hz), 7.75 (1H, d, J=1.9 Hz), 8.95-9.19 (1H, m), 9.41-9.66 (1H, m).
MS (ESI+): [M+H]$^+$ 388.0.

217

Example 160

1-{[(6S,7R)-7-(3,4-dichlorophenyl)-1,4-oxazepan-6-yl]methyl}-1-(2-hydroxyethyl)-3-methylurea monohydrochloride Using tert-butyl (6R,7R)-6-{[(2-{[tert-butyl(dimethyl)silyl]oxy}ethyl)amino]methyl}-7-(3,4-dichlorophenyl)-1,4-oxazepane-4-carboxylate, and in the same manner as in Example 38, step E and Example 111, steps D and E, the title compound was obtained.
MS (ESI+): [M+H]$^+$ 376.1.

Example 161

N-{[(6R,7S)-7-(3,4-dichlorophenyl)-1,4-oxazepan-6-yl]methyl}methanesulfonamide monohydrochloride Using tert-butyl (6S,7S)-6-(aminomethyl)-7-(3,4-dichlorophenyl)-1,4-oxazepane-4-carboxylate, and in the same manner as in Example 8, the title compound was obtained.
MS (ESI+): [M+H]$^+$ 353.0.

Example 162

N-{[(6RS,7SR)-7-(3,4-dichlorophenyl)-6-hydroxy-1,4-oxazepan-6-yl]methyl}methanesulfonamide monohydrochloride A) tert-butyl (6RS,7SR)-7-(3,4-dichlorophenyl)-6-hydroxy-6-{[(methylsulfonyl)amino]methyl}-1,4-oxazepane-4-carboxylate Triphenylphosphine (330 mg) was added to a solution of tert-butyl (6RS,7SR)-6-(azidomethyl)-7-(3,4-dichlorophenyl)-6-hydroxy-1,4-oxazepane-4-carboxylate (120 mg) in acetonitrile (5 mL), and the mixture was stirred at 80° C. overnight. To the reaction mixture was added saturated aqueous sodium hydrogen carbonate, and the mixture was extracted with ethyl acetate. The extract was washed with brine, and dried over anhydrous sodium sulfate. The solvent was evaporated under reduced pressure. To a solution of the residue in THF (5 mL) were successively added dropwise triethylamine (0.11 mL) and methanesulfonyl chloride (86 mg), and the mixture was stirred at 0° C. for 1 hr. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography and HPLC to give the title compound (133 mg).
$^1$H NMR (300 MHz, CDCl$_3$) δ 1.51 (9H, s), 2.16 (1H, s), 2.79-2.93 (1H, m), 2.95 (3H, s), 2.99-3.13 (1H, m), 3.15-3.41 (2H, m), 3.46-3.79 (1H, m), 3.90-4.25 (3H, m), 4.41 (1H, s), 6.31 (1H, brs), 7.24 (1H, brs), 7.43 (1H, d, J=8.3 Hz), 7.54 (1H, s).
MS (ESI+): [M+H]$^+$ 467.0.

B) N-{[(6RS,7SR)-7-(3,4-dichlorophenyl)-6-hydroxy-1,4-oxazepan-6-yl]methyl}methanesulfonamide monohydrochloride Using tert-butyl (6RS,7SR)-7-(3,4-dichlorophenyl)-6-hydroxy-6-{[(methylsulfonyl)amino]methyl}-1,4-oxazepane-4-carboxylate (133 mg), and in the same manner as in Example 39, step B, the title compound (99 mg) was obtained.
MS (ESI+): [M+H]$^+$ 369.1.

218

Example 163

N-{[(6S,7R)-7-(3,4-dichlorophenyl)-1,4-oxazepan-6-yl]methyl}-2-methoxyethanesulfonamide monohydrochloride A) tert-butyl (6S,7R)-7-(3,4-dichlorophenyl)-6-{[(ethenylsulfonyl)amino]methyl}-1,4-oxazepane-4-carboxylate To a solution of tert-butyl (6R,7R)-6-(aminomethyl)-7-(3,4-dichlorophenyl)-1,4-oxazepane-4-carboxylate (633 mg) in THF (10 mL) were added triethylamine (0.705 mL) and 2-chloroethanesulfonyl chloride (0.213 mL) at 0° C., and the mixture was gradually warmed from 0° C. to room temperature, and stirred overnight. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (0.965 g).
MS (ESI+): [M+H-Boc]$^+$ 365.2.

B) tert-butyl (6S,7R)-7-(3,4-dichlorophenyl)-6-({[(2-methoxyethyl)sulfonyl]amino}methyl)-1,4-oxazepane-4-carboxylate To a solution of tert-butyl (6S,7R)-7-(3,4-dichlorophenyl)-6-{[(ethenylsulfonyl)amino]methyl}-1,4-oxazepane-4-carboxylate (200 mg) in methanol (1 mL) was added 28% sodium methoxide-methanol (4 mL) solution at room temperature, and the mixture was stirred at 60° C. for 4 hr. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (132 mg).
MS (ESI+): [M+H-Boc]$^+$ 397.0.

C) N-{[(6S,7R)-7-(3,4-dichlorophenyl)-1,4-oxazepan-6-yl]methyl}-2-methoxyethanesulfonamide monohydrochloride Using tert-butyl (6S,7R)-7-(3,4-dichlorophenyl)-6-({[(2-methoxyethyl)sulfonyl]amino}methyl)-1,4-oxazepane-4-carboxylate (132 mg), and in the same manner as in Example 58, step C, the title compound (81 mg) was obtained.
MS (ESI+): [M+H]$^+$ 397.0.

Example 164

N-{[(6S,7R)-7-(3,4-dichlorophenyl)-1,4-oxazepan-6-yl]methyl}-2-(morpholin-4-yl)ethanesulfonamide dihydrochloride Using tert-butyl (6R,7R)-6-(aminomethyl)-7-(3,4-dichlorophenyl)-1,4-oxazepane-4-carboxylate, and in the same manner as in Example 163, the title compound was obtained.
MS (ESI+): [M+H]$^+$ 452.3.

Example 165

N-{[(6S,7R)-7-(3,4-dichlorophenyl)-1,4-oxazepan-6-yl]methyl}-1,1,1-trifluoromethanesulfonamide monohydrochloride Using tert-butyl (6R,7R)-6-(aminomethyl)-7-(3,4-dichlorophenyl)-1,4-oxazepane-4-carboxylate, and in the same manner as in Example 32, step C and Example 39, step B, the title compound was obtained.
MS (ESI+): [M+H]$^+$ 406.9.

Example 166

3-({[(6S,7R)-7-(3,4-dichlorophenyl)-1,4-oxazepan-6-yl]methyl}sulfamoyl)benzoic acid monohydrochloride In the same manner as in Example 38, step E and Example 44, step B, the title compound was obtained.
MS (ESI+): [M+H]$^+$ 458.9.

Example 167

3-[2-({[(6R,7R)-7-(3,4-dichlorophenyl)-1,4-oxazepan-6-yl]methyl}sulfonyl)phenyl]-1,2,4-oxadiazol-5(2H)-one monohydrochloride A) tert-butyl (6R,7R)-6-{[(2-bromophenyl)sulfanyl]methyl}-7-(3,4-dichlorophenyl)-1,4-oxazepane-4-carboxylate Using tert-butyl (6S,7R)-7-(3,4-dichlorophenyl)-6-{[(methylsulfonyl)oxy]methyl}-1,4-oxazepane-4-carboxylate (400 mg), and in the same manner as in Example 44, step A, the title compound (424 mg) was obtained.
$^1$H NMR (300 MHz, CDCl$_3$) δ 1.50 (9H, s), 2.08-2.29 (1H, m), 2.62-2.87 (2H, m), 3.26-3.80 (3H, m), 3.86-4.26 (4H, m), 6.50-6.89 (1H, m), 6.94-7.16 (3H, m), 7.34-7.52 (3H, m).

B) tert-butyl (6R,7R)-6-{[(2-cyanophenyl)sulfanyl]methyl}-7-(3,4-dichlorophenyl)-1,4-oxazepane-4-carboxylate To a solution (7.8 mL) of tert-butyl (6R,7R)-6-{[(2-bromophenyl)sulfanyl]methyl}-7-(3,4-dichlorophenyl)-1,4-oxazepane-4-carboxylate (424 mg) in DMF was added copper cyanide (139 mg), and the mixture was stirred under an argon atmosphere at 150° C. overnight. The reaction mixture was filtered through celite, distilled water was added, and the mixture was extracted with ethyl acetate. The extract was washed with distilled water and brine, and dried over anhydrous sodium sulfate, and the solvent was evaporated under reduced pressure. The residue was purified by silica gel chromatography (hexane/ethyl acetate) to give the title compound (146 mg).
$^1$H NMR (300 MHz, CDCl$_3$) δ 1.51 (9H, s), 2.06-2.27 (1H, m), 2.68-2.98 (2H, m), 3.23-3.82 (3H, m), 3.86-4.26 (4H, m), 6.67-7.15 (2H, m), 7.17-7.47 (4H, m), 7.51-7.59 (1H, m).

C) tert-butyl (6R,7R)-6-{[(2-cyanophenyl)sulfonyl]methyl}-7-(3,4-dichlorophenyl)-1,4-oxazepane-4-carboxylate Using tert-butyl (6R,7R)-6-{[(2-cyanophenyl)sulfanyl]methyl}-7-(3,4-dichlorophenyl)-1,4-oxazepane-4-carboxylate (146 mg), and in the same manner as in Example 5, step C, the title compound (133 mg) was obtained.
$^1$H NMR (300 MHz, CDCl$_3$) δ 1.45-1.67 (9H, m), 2.08-2.37 (1H, m), 3.04-3.28 (2H, m), 3.46-3.67 (2H, m), 3.80-4.49 (5H, m), 6.88-7.11 (2H, m), 7.27-7.35 (1H, m), 7.53-7.66 (1H, m), 7.67-7.78 (2H, m), 7.89-8.08 (1H, m).

D) 3-[2-({[(6R,7R)-7-(3,4-dichlorophenyl)-1,4-oxazepan-6-yl]methyl}sulfonyl)phenyl]-1,2,4-oxadiazol-5(2H)-one monohydrochloride Using tert-butyl (6R,7R)-6-{[(2-cyanophenyl)sulfonyl]methyl}-7-(3,4-dichlorophenyl)-1,4-oxazepane-4-carboxylate (133 mg), and in the same manner as in Example 31, steps D and E, the title compound (85.7 mg) was obtained.
MS (ESI+): [M+H]$^+$ 484.1.

Example 168

N-{[(6S,7R)-7-(3,4-dichlorophenyl)-1,4-oxazepan-6-yl]methyl}-3-(5-oxo-4,5-dihydro-1,2,4-oxadiazol-3-yl)benzenesulfonamide monohydrochloride In the same manner as in Example 38, step E and Example 31, steps D and E, the title compound was obtained.
MS (ESI+): [M+H]$^+$ 499.3.

Example 169

N-{[(6S,7R)-7-(3,4-dichlorophenyl)-1,4-oxazepan-6-yl]methyl}pyridine-3-sulfonamide monohydrochloride Using tert-butyl (6R,7R)-6-(aminomethyl)-7-(3,4-dichlorophenyl)-1,4-oxazepane-4-carboxylate, and in the same manner as in Example 32, step C and Example 39, step B, the title compound was obtained.
MS (ESI+): [M+H]$^+$ 416.0.

Example 170

6-({[(6S,7R)-7-(3,4-dichlorophenyl)-1,4-oxazepan-6-yl]methyl}sulfamoyl)pyridine-2-carboxylic acid monohydrochloride In the same manner as in Example 166, the title compound was obtained.
MS (ESI+): [M+H]$^+$ 460.0.

Example 171

5-({[(6S,7R)-7-(3,4-dichlorophenyl)-1,4-oxazepan-6-yl]methyl}sulfamoyl)pyridine-3-carboxylic acid monohydrochloride In the same manner as in Example 166, the title compound was obtained.
MS (ESI+): [M+H]$^+$ 460.3.

Example 172

5-({[(6S,7R)-7-(3,4-dichlorophenyl)-1,4-oxazepan-6-yl]methyl}sulfamoyl)pyridine-2-carboxylic acid monohydrochloride In the same manner as in Example 166, the title compound was obtained.
MS (ESI+): [M+H]$^+$ 460.0.

Example 173

N-{[(6S,7R)-7-(3,4-dichlorophenyl)-1,4-oxazepan-6-yl]methyl}-5-(5-oxo-4,5-dihydro-1,2,4-oxadiazol-3-yl)pyridine-3-sulfonamide monohydrochloride In the same manner as in Example 168, the title compound was obtained.
MS (ESI+): [M+H]$^+$ 500.2.

Example 174

N-{[(6R,7S)-7-(3,4-dichlorophenyl)-1,4-oxazepan-6-yl]methyl}sulfamide monohydrochloride Using tert-butyl (6S,7S)-6-(aminomethyl)-7-(3,4-dichlorophenyl)-1,4-oxazepane-4-carboxylate, and in the same manner as in Example 9, the title compound was obtained.
MS (ESI+): [M+H]$^+$ 354.2.

Example 175

N-{[(6S,7R)-7-(3,4-dichlorophenyl)-1,4-oxazepan-6-yl]methyl}-N'-methoxysulfamide monohydrochloride Using tert-butyl (6R,7R)-6-(aminomethyl)-7-(3,4-dichlorophenyl)-1,4-oxazepane-4-carboxylate and o-methylhydroxylamine, and in the same manner as in Example 9, the title compound was obtained.
MS (ESI+): [M+H]$^+$ 383.9.

Example 176

2-({[(6S,7R)-7-(3,4-dichlorophenyl)-1,4-oxazepan-6-yl]methyl}amino)pyridine-3-carboxylic acid monohydrochloride A) tert-butyl (6R,7R)-7-(3,4-dichlorophenyl)-6-({[3-(methoxycarbonyl)pyridin-2-yl]amino}methyl)-1,4-oxazepane-4-carboxylate To a solution of tert-butyl (6R,7R)-6-(aminomethyl)-7-(3,4-dichlorophenyl)-1,4-oxazepane-4-carboxylate (200 mg) in DMF (4 mL) were added potassium carbonate (110 mg) and methyl 2-chloronicotinate (137 mg) at room temperature, and the mixture was stirred at 100° C. for 48 hr. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (120 mg).
MS (ESI+): [M+H]$^+$ 510.4.

B) 2-({[(6R,7R)-4-(tert-butoxycarbonyl)-7-(3,4-dichlorophenyl)-1,4-oxazepan-6-yl]methyl}amino)pyridine-3-carboxylic acid Using tert-butyl (6R,7R)-7-(3,4-dichlorophenyl)-6-({[3-(methoxycarbonyl)pyridin-2-yl]amino}methyl)-1,4-oxazepane-4-carboxylate (120 mg), and in the same manner as in Example 58, step B, the title compound (60 mg) was obtained.
MS (ESI+): [M+H]$^+$ 496.3.

C) 2-({[(6S,7R)-7-(3,4-dichlorophenyl)-1,4-oxazepan-6-yl]methyl}amino)pyridine-3-carboxylic acid monohydrochloride Using 2-({[(6R,7R)-4-(tert-butoxycarbonyl)-7-(3,4-dichlorophenyl)-1,4-oxazepan-6-yl]methyl}amino)pyridine-3-carboxylic acid (60 mg), and in the same manner as in Example 58, step C, the title compound (40 mg) was obtained.
MS (ESI+): [M+H]$^+$ 396.1.

Example 177

N-{2-[(6R,7R)-7-(3,4-dichlorophenyl)-1,4-oxazepan-6-yl]ethyl}acetamide monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 66, step A, Example 1, step G, Example 32, step C and Example 39, step B, the title compound was obtained.
MS (ESI+): [M+H]$^+$ 331.1.

Example 178

(6S,7R)-7-(3,4-dichlorophenyl)-6-[(4-methyl-1H-pyrazol-1-yl)methyl]-1,4-oxazepane monohydrochloride In the same manner as in Example 44, step A and Example 43, step C, the title compound was obtained.
MS (ESI+): [M+H]$^+$ 340.0.

Example 179

1-{[(6S,7R)-7-(3,4-dichlorophenyl)-1,4-oxazepan-6-yl]methyl}-1H-pyrazole-3-carboxylic acid monohydrochloride In the same manner as in Example 44, the title compound was obtained.
MS (ESI+): [M+H]$^+$ 370.3.

Example 180

1-{[(6S,7R)-7-(3,4-dichlorophenyl)-1,4-oxazepan-6-yl]methyl}-1H-pyrazole-4-carboxylic acid monohydrochloride In the same manner as in Example 44, the title compound was obtained.
MS (ESI+): [M+H]$^+$ 370.0.

Example 181

1-{[(6S,7R)-7-(3,4-dichlorophenyl)-1,4-oxazepan-6-yl]methyl}-1H-pyrazole-5-carboxylic acid monohydrochloride In the same manner as in Example 44, the title compound was obtained.
MS (ESI+): [M+H]$^+$ 370.3.

Example 182

1-{[(6S,7R)-7-(3,4-dichlorophenyl)-1,4-oxazepan-6-yl]methyl}-3-(trifluoromethyl)-1H-pyrazole-4-carboxylic acid monohydrochloride In the same manner as in Example 44, the title compound was obtained.
MS (ESI+): [M+H]$^+$ 437.9.

Example 183

[1-{[(6S,7R)-7-(3,4-dichlorophenyl)-1,4-oxazepan-6-yl]methyl}-3-(trifluoromethyl)-1H-pyrazol-4-yl]methanol In the same manner as in Example 44, step A and Example 1, steps G and I, the title compound was obtained.
MS (ESI+): [M+H]$^+$ 424.0.

Example 184

1-{[(6S,7R)-7-(3,4-dichlorophenyl)-1,4-oxazepan-6-yl]methyl}-3-methyl-1H-pyrazole-5-carboxylic acid monohydrochloride In the same manner as in Example 44, the title compound was obtained.
MS (ESI+): [M+H]$^+$ 384.2.

Example 185

5-cyclopropyl-1-{[(6S,7R)-7-(3,4-dichlorophenyl)-1,4-oxazepan-6-yl]methyl}-1H-pyrazole-3-carboxylic acid monohydrochloride Using tert-butyl (6S,7R)-7-(3,4-dichlorophenyl)-6-{[(methylsulfonyl)oxy]methyl}-1,4-oxazepane-4-carboxylate and, ethyl 3-cyclopropyl-1H-pyrazole-5-carboxylate, and in the same manner as in Example 44, the title compound was obtained.
MS (ESI+): [M+H]$^+$ 410.3.

Example 186

1-{[(6S,7R)-7-(3,4-dichlorophenyl)-1,4-oxazepan-6-yl]methyl}-5-(2-methoxyethoxy)-1H-pyrazole-3-carboxylic acid monohydrochloride In the same manner as in Example 185, the title compound was obtained.
MS (ESI+): [M+H]$^+$ 444.2.

Example 187

1-{[(6S,7R)-7-(3,4-dichlorophenyl)-1,4-oxazepan-6-yl]methyl}-5-methyl-1H-pyrazole-3-carboxylic acid monohydrochloride In the same manner as in Example 44, the title compound was obtained.
MS (ESI+): [M+H]$^+$ 384.2.

Example 188

3-tert-butyl-1-{[(6S,7R)-7-(3,4-dichlorophenyl)-1,4-oxazepan-6-yl]methyl}-1H-pyrazole-5-carboxylic acid monohydrochloride In the same manner as in Example 185, the title compound was obtained.
MS (ESI+): [M+H]$^+$ 426.2.

Example 189

3-cyclopropyl-1-{[(6S,7R)-7-(3,4-dichlorophenyl)-1,4-oxazepan-6-yl]methyl}-1H-pyrazole-5-carboxylic acid monohydrochloride In the same manner as in Example 185, the title compound was obtained.
MS (ESI+): [M+H]$^+$ 410.3.

Example 190

1-{[(6S,7R)-7-(3,4-dichlorophenyl)-1,4-oxazepan-6-yl]methyl}-3-(2-methoxyethoxy)-1H-pyrazole-5-carboxylic acid monohydrochloride In the same manner as in Example 185, the title compound was obtained.
MS (ESI+): [M+H]$^+$ 444.2.

Example 191

3-{[(6R,7R)-7-(3,4-dichlorophenyl)-1,4-oxazepan-6-yl]methyl}-1-methyl-1H-pyrazole-4-carboxylic acid monohydrochloride A) tert-butyl (6R,7R)-7-(3,4-dichlorophenyl)-6-(4-ethoxy-2,4-dioxobutyl)-1,4-oxazepane-4-carboxylate CDI (0.991 g, 6.11 mmol) was added to a solution of [(6R,7R)-4-(tert-butoxycarbonyl)-7-(3,4-dichlorophenyl)-1,4-oxazepan-6-yl]acetic acid (1.9 g, 4.70 mmol) in THF (20 ml), and the mixture was stirred at room temperature for 1 hr. To the reaction mixture were added potassium 3-ethoxy-3-oxopropanoate (0.880 g, 5.17 mmol) and magnesium chloride (0.492 g, 5.17 mmol). The reaction mixture was stirred at 60° C. for 5 hr. To the reaction mixture was added 1 N hydrochloric acid, and the mixture was extracted with ethyl acetate. The extract was washed with brine, and dried over anhydrous sodium sulfate. The solvent was evaporated under reduced pressure. The residue was purified by silica gel column chromatography to give the title compound (1.959 g).
$^1$H NMR (300 MHz, CDCl$_3$) δ 1.17-1.25 (3H, m), 1.49 (9H, s), 2.23-2.34 (1H, m), 2.48-2.80 (2H, m), 3.25-3.87 (7H, m), 4.01-4.18 (4H, m), 7.13 (1H, dd, J=8.3, 1.9 Hz), 7.37-7.45 (2H, m).

B) tert-butyl (6R,7R)-7-(3,4-dichlorophenyl)-6-{[4-(ethoxycarbonyl)-1-methyl-1H-pyrazol-3-yl]methyl}-1,4-oxazepane-4-carboxylate N,N-Dimethylformamide dimethyl acetal (0.210 mL, 1.58 mmol) was added to a solution of tert-butyl (6R,7R)-7-(3,4-dichlorophenyl)-6-(4-ethoxy-2,4-dioxobutyl)-1,4-oxazepane-4-carboxylate (500 mg, 1.05 mmol) in toluene (5 mL), and the mixture was stirred at 80° C. for 2 hr, and concentrated under reduced pressure. The residue was dissolved in ethanol (5 mL), and methylhydrazine (0.062 mL, 1.16 mmol) was added. The reaction mixture was stirred at 80° C. for 1.5 hr, and concentrated under reduced pressure. The residue was purified by silica gel column chromatography to give the title compound (175 mg).

MS (ESI+): [M+H-Boc]$^+$ 412.3.

C) 3-{[(6R,7R)-7-(3,4-dichlorophenyl)-1,4-oxazepan-6-yl]methyl}-1-methyl-1H-pyrazole-4-carboxylic acid monohydrochloride Using tert-butyl (6R,7R)-7-(3,4-dichlorophenyl)-6-{[4-(ethoxycarbonyl)-1-methyl-1H-pyrazol-3-yl]methyl}-1,4-oxazepane-4-carboxylate, and in the same manner as in Example 44, step B, the title compound was obtained.

MS (ESI+): [M+H]$^+$ 384.2.

Example 192

(6R,7R)-7-(3,4-dichlorophenyl)-6-[(5-methyl-1,2,4-oxadiazol-3-yl)methyl]-1,4-oxazepane monohydrochloride A) tert-butyl (6R,7R)-6-[2-amino-2-(hydroxyimino)ethyl]-7-(3,4-dichlorophenyl)-1,4-oxazepane-4-carboxylate Sodium hydrogen carbonate (872 mg, 10.38 mmol) was added to a suspension of hydroxylamine monohydrochloride (721 mg, 10.38 mmol) in DMSO (3 mL), and the mixture was stirred at 80° C. for 15 min. The precipitate was filtered off, and a solution of tert-butyl (6R,7R)-6-(cyanomethyl)-7-(3,4-dichlorophenyl)-1,4-oxazepane-4-carboxylate (500 mg, 1.30 mmol) in DMSO (4 mL) was added to the filtrate. The reaction mixture was stirred at 80° C. overnight. To the reaction mixture was added water, and the mixture was extracted with ethyl acetate. The extract was washed with brine, and dried over anhydrous sodium sulfate. The solvent was evaporated under reduced pressure to give the title compound (588 mg). This compound was used for the next reaction without purification.

MS (ESI+): [M+H]$^+$ 418.2.

B) tert-butyl (6R,7R)-7-(3,4-dichlorophenyl)-6-[(5-methyl-1,2,4-oxadiazol-3-yl)methyl]-1,4-oxazepane-4-carboxylate To a solution of tert-butyl (6R,7R)-6-[2-amino-2-(hydroxyimino)ethyl]-7-(3,4-dichlorophenyl)-1,4-oxazepane-4-carboxylate (388 mg, 0.93 mmol) in toluene (4 mL) were added potassium tert-butoxide (208 mg, 1.86 mmol) and ethyl acetate (1 mL, 0.93 mmol). The reaction mixture was stirred at 100° C. overnight. To the reaction mixture was added water, and the mixture was extracted with ethyl acetate. The extract was washed with brine, and dried over anhydrous sodium sulfate. The solvent was evaporated under reduced pressure. The residue was purified by silica gel column chromatography to give the title compound (183.4 mg).

$^1$H NMR (300 MHz, CDCl$_3$) δ 1.38-1.55 (9H, m), 2.48 (3H, s), 2.49-2.79 (3H, m), 3.43-3.57 (1H, m), 3.59-3.83 (4H, m), 4.00-4.27 (2H, m), 7.15 (1H, dd, J=8.3, 1.9 Hz), 7.35-7.44 (2H, m).

C) (6R,7R)-7-(3,4-dichlorophenyl)-6-[(5-methyl-1,2,4-oxadiazol-3-yl)methyl]-1,4-oxazepane monohydrochloride Using tert-butyl (6R,7R)-7-(3,4-dichlorophenyl)-6-[(5-methyl-1,2,4-oxadiazol-3-yl)methyl]-1,4-oxazepane-4-carboxylate, and in the same manner as in Example 39, step B, the title compound was obtained.

MS (ESI+): [M+H]$^+$ 342.1.

Example 193

3-{[(6R,7R)-7-(3,4-dichlorophenyl)-1,4-oxazepan-6-yl]methyl}-1,2,4-oxadiazol-5(4H)-one monohydrochloride In the same manner as in Example 31, steps D and E, the title compound was obtained.

MS (ESI+): [M+H]$^+$ 344.0.

Example 194

2-{[(6R,7R)-7-(3,4-dichlorophenyl)-1,4-oxazepan-6-yl]methyl}-1,3-thiazole-4-carboxylic acid monohydrochloride A) tert-butyl (6R,7R)-6-(2-amino-2-thioxoethyl)-7-(3,4-dichlorophenyl)-1,4-oxazepane-4-carboxylate To a solution of tert-butyl (6R,7R)-6-(2-amino-2-oxoethyl)-7-(3,4-dichlorophenyl)-1,4-oxazepane-4-carboxylate (528 mg, 1.31 mmol) in THF (6 mL) was added Lawesson's reagent (794 mg, 1.96 mmol), and the mixture was stirred at 70° C. for 2.5 hr. To the reaction mixture was added aqueous sodium hydrogen carbonate solution, and the mixture was extracted with ethyl acetate. The extract was washed with brine, and dried over anhydrous sodium sulfate. The solvent was evaporated under reduced pressure. The residue was purified by silica gel column chromatography to give the title compound (289 mg).

$^1$H NMR (300 MHz, CDCl$_3$) δ 1.50 (9H, s), 2.45 (1H, d, J=11.3 Hz), 2.59-2.81 (2H, m), 3.15 (1H, ddd, J=14.0, 12.3, 4.0 Hz), 3.31 (1H, dd, J=14.9, 4.7 Hz), 3.59 (1H, td, J=12.3, 3.0 Hz), 3.93 (1H, d, J=9.4 Hz), 3.99-4.09 (2H, m), 4.11-4.19 (1H, m), 7.23-7.30 (1H, m), 7.42-7.47 (1H, m), 7.49 (1H, d, J=2.3 Hz), 7.55 (1H, brs), 9.48 (1H, brs).

B) tert-butyl (6R,7R)-7-(3,4-dichlorophenyl)-6-{[4-(ethoxycarbonyl)-1,3-thiazol-2-yl]methyl}-1,4-oxazepane-4-carboxylate Ethyl bromopyruvate (0.070 mL, 0.50 mmol) was added to a solution of tert-butyl (6R,7R)-6-(2-amino-2-thioxoethyl)-7-(3,4-dichlorophenyl)-1,4-oxazepane-4-carboxylate (140 mg, 0.33 mmol) in EtOH (5 mL). The reaction mixture was stirred at 80° C. for 2 hr, triethylamine (0.140 mL, 1.00 mmol) and di-tert-butyl dicarbonate (0.115 mL, 0.50 mmol) were added at room temperature, and the mixture was stirred at room temperature for 5 hr. To the reaction mixture was added aqueous sodium hydrogen carbonate solution, and the mixture was extracted with ethyl acetate. The extract was washed with brine, and dried over anhydrous sodium sulfate. The solvent was evaporated under reduced pressure. The residue was purified by silica gel column chromatography to give the title compound (173 mg).

$^1$H NMR (300 MHz, CDCl$_3$) δ 1.35-1.56 (12H, m), 2.63 (1H, brs), 2.80-3.15 (2H, m), 3.38-3.82 (5H, m), 4.02-4.29

(2H, m), 4.40 (2H, q, J=7.2 Hz), 7.13 (1H, dd, J=8.3, 1.9 Hz), 7.32-7.41 (2H, m), 7.99 (1H, s).
MS (ESI+): [M+H]+ 515.0.

C) 2-{[(6R,7R)-7-(3,4-dichlorophenyl)-1,4-oxazepan-6-yl]methyl}-1,3-thiazole-4-carboxylic acid monohydrochloride Using tert-butyl (6R,7R)-7-(3,4-dichlorophenyl)-6-{[4-(ethoxycarbonyl)-1,3-thiazol-2-yl]methyl}-1,4-oxazepane-4-carboxylate, and in the same manner as in Example 44, step B, the title compound was obtained.
MS (ESI+): [M+H]+ 386.9.

Example 195

2-{[(6R,7R)-7-(3,4-dichlorophenyl)-1,4-oxazepan-6-yl]methyl}-1,3-thiazole-5-carboxylic acid monohydrochloride In the same manner as in Example 194, the title compound was obtained.
MS (ESI+): [M+H]+ 386.9.

Example 196

4-{[(6R,7R)-7-(3,4-dichlorophenyl)-1,4-oxazepan-6-yl]methyl}-2-methyl-1,3-thiazole-5-carboxylic acid monohydrochloride A) tert-butyl (6R,7R)-7-(3,4-dichlorophenyl)-6-{[5-(ethoxycarbonyl)-2-methyl-1,3-thiazol-4-yl]methyl}-1,4-oxazepane-4-carboxylate Sulfuryl chloride (0.094 mL, 1.16 mmol) was added to a solution of tert-butyl (6R,7R)-7-(3,4-dichlorophenyl)-6-(4-ethoxy-2,4-dioxobutyl)-1,4-oxazepane-4-carboxylate (500 mg, 1.05 mmol) in toluene (5 mL). The reaction mixture was stirred at room temperature for 45 min, and concentrated under reduced pressure. To the residue were added ethanol (5 ml) and thioacetamide (87 mg, 1.16 mmol), and the mixture was stirred at 80° C. for 1.5 hr. To the reaction mixture were added triethylamine (0.294 mL, 2.11 mmol) and di-tert-butyl dicarbonate (0.291 ml, 1.26 mmol) at room temperature, and the mixture was stirred at room temperature for 30 min, and concentrated under reduced pressure. To the residue was added aqueous sodium hydrogen carbonate solution, and the mixture was extracted with ethyl acetate. The extract was washed with brine, and dried over anhydrous sodium sulfate. The solvent was evaporated under reduced pressure. The residue was purified by silica gel column chromatography to give the title compound (358 mg).
$^1$H NMR (300 MHz, CDCl$_3$) δ 1.34 (3H, t, J=7.2 Hz), 1.38-1.52 (9H, m), 2.58 (3H, s), 2.69-2.90 (1H, m), 2.96-3.15 (2H, m), 3.51-3.80 (5H, m), 3.99-4.32 (4H, m), 7.02-7.09 (1H, m), 7.23-7.32 (2H, m).
MS (ESI+): [M+H]+ 529.0.

B) 4-{[(6R,7R)-7-(3,4-dichlorophenyl)-1,4-oxazepan-6-yl]methyl}-2-methyl-1,3-thiazole-5-carboxylic acid monohydrochloride Using tert-butyl (6R,7R)-7-(3,4-dichlorophenyl)-6-{[5-(ethoxycarbonyl)-2-methyl-1,3-thiazol-4-yl]methyl}-1,4-oxazepane-4-carboxylate, and in the same manner as in Example 44, step B, the title compound was obtained.
MS (ESI+): [M+H]+ 401.2.

Example 197

2-{[(6R,7R)-7-(3,4-dichlorophenyl)-1,4-oxazepan-6-yl]methyl}-4-methyl-1,3-thiazole-5-carboxylic acid monohydrochloride In the same manner as in Example 194, the title compound was obtained.
MS (ESI+): [M+H]+ 401.0.

Example 198

(2-{[(6R,7R)-7-(3,4-dichlorophenyl)-1,4-oxazepan-6-yl]methyl}-1,3-thiazol-4-yl)acetic acid monohydrochloride In the same manner as in Example 194, the title compound was obtained.
MS (ESI+): [M+H]+ 401.0.

Example 199

3-(2-{[(6R,7R)-7-(3,4-dichlorophenyl)-1,4-oxazepan-6-yl]methyl}-1,3-thiazol-4-yl)-1,2,4-oxadiazol-5(4H)-one monohydrochloride A) tert-butyl (6R,7R)-6-[(4-carbamoyl-1,3-thiazol-2-yl)methyl]-7-(3,4-dichlorophenyl)-1,4-oxazepane-4-carboxylate Using 2-{[(6R,7R)-4-(tert-butoxycarbonyl)-7-(3,4-dichlorophenyl)-1,4-oxazepan-6-yl]methyl}-1,3-thiazole-4-carboxylic acid, and in the same manner as in Example 39, step A, the title compound was obtained.
$^1$H NMR (300 MHz, CDCl$_3$) δ 1.33-1.56 (9H, m), 2.55-2.81 (2H, m), 2.86-3.09 (1H, m), 3.45-3.85 (4H, m), 4.04-4.20 (3H, m), 5.71 (1H, d, J=19.3 Hz), 7.14 (1H, dd, J=8.1, 2.1 Hz), 7.38-7.46 (2H, m), 7.55 (1H, brs), 7.97 (1H, brs).
MS (ESI+): [M+H]+ 485.9.

B) tert-butyl (6R,7R)-6-[(4-cyano-1,3-thiazol-2-yl)methyl]-7-(3,4-dichlorophenyl)-1,4-oxazepane-4-carboxylate Trifluoroacetic anhydride (0.080 mL, 0.57 mmol) was added to a solution of tert-butyl (6R,7R)-6-[(4-carbamoyl-1,3-thiazol-2-yl)methyl]-7-(3,4-dichlorophenyl)-1,4-oxazepane-4-carboxylate (126 mg, 0.26 mmol) and pyridine (0.084 mL, 1.04 mmol) in THF (4 mL) under ice-cooling. The reaction mixture was stirred at room temperature overnight, triethylamine (0.144 mL, 1.04 mmol) and trifluoroacetic anhydride (0.080 mL, 0.57 mmol) were added, and the mixture was stirred at room temperature for 15 min. To the reaction mixture was added aqueous sodium hydrogen carbonate solution, and the mixture was extracted with ethyl acetate. The extract was washed with brine, and dried over anhydrous sodium sulfate. The solvent was evaporated under reduced pressure. The residue was purified by silica gel column chromatography to give the title compound (100 mg).
$^1$H NMR (300 MHz, CDCl$_3$) δ 1.36-1.54 (9H, m), 2.56-2.85 (2H, m), 2.96-3.16 (1H, m), 3.35-3.51 (1H, m), 3.51-3.84 (4H, m), 4.04-4.27 (2H, m), 7.17 (1H, d, J=7.6 Hz), 7.37-7.45 (2H, m), 7.84 (1H, s).
MS (ESI+): [M+H]+ 468.1.

C) 3-(2-{[(6R,7R)-7-(3,4-dichlorophenyl)-1,4-oxazepan-6-yl]methyl}-1,3-thiazol-4-yl)-1,2,4-oxadiazol-5(4H)-one monohydrochloride Using tert-butyl (6R,7R)-6-[(4-cyano-1,3-thiazol-2-yl)methyl]-7-(3,4-dichlorophenyl)-1,4-oxazepane-4-carboxylate, and in the same manner as in Example 31, steps D and E, the title compound was obtained.
MS (ESI+): [M+H]$^+$ 427.0.

Example 200

(6R,7R)-7-(3,4-dichlorophenyl)-6-[(5-methyl-4H-1,2,4-triazol-3-yl)methyl]-1,4-oxazepane monohydrochloride A) tert-butyl (6R,7R)-7-(3,4-dichlorophenyl)-6-[(5-methyl-4H-1,2,4-triazol-3-yl)methyl]-1,4-oxazepane-4-carboxylate Methyl iodide (0.214 mL, 3.43 mmol) was added to a suspension of tert-butyl (6R,7R)-6-(2-amino-2-thioxoethyl)-7-(3,4-dichlorophenyl)-1,4-oxazepane-4-carboxylate (288 mg, 0.69 mmol) and potassium carbonate (142 mg, 1.03 mmol) in acetone (5 mL) at room temperature. The reaction mixture was stirred at room temperature for 4 hr, and concentrated under reduced pressure. To the residue was added aqueous sodium hydrogen carbonate solution, and the mixture was extracted with ethyl acetate. The extract was washed with brine, and dried over anhydrous sodium sulfate. The solvent was evaporated under reduced pressure. The residue was dissolved in toluene (5 ml), acetohydrazide (61.1 mg, 0.82 mmol) was added, and the mixture was stirred at 120° C. overnight while using a Dean-Stark trap. To the reaction mixture was added aqueous sodium hydrogen carbonate solution, and the mixture was extracted with ethyl acetate. The extract was washed with brine, and dried over anhydrous sodium sulfate. The solvent was evaporated under reduced pressure. The residue was purified by silica gel column chromatography to give the title compound (241 mg, 0.545 mmol, 79%).
$^1$H NMR (300 MHz, CDCl$_3$) δ 1.52 (9H, s), 2.33 (4H, s), 2.55-2.74 (2H, m), 3.22-3.42 (2H, m), 3.64 (1H, td, J=12.3, 3.0 Hz), 3.75-3.83 (1H, m), 3.94 (1H, d, J=14.0 Hz), 4.01 (1H, d, J=9.4 Hz), 4.12-4.19 (1H, m), 7.16 (1H, dd, J=8.3, 1.9 Hz), 7.39-7.45 (2H, m), 1H not detected.
MS (ESI+): [M+H]$^+$ 441.4.

B) (6R,7R)-7-(3,4-dichlorophenyl)-6-[(5-methyl-4H-1,2,4-triazol-3-yl)methyl]-1,4-oxazepane monohydrochloride Using tert-butyl (6R,7R)-7-(3,4-dichlorophenyl)-6-[(5-methyl-4H-1,2,4-triazol-3-yl)methyl]-1,4-oxazepane-4-carboxylate, and in the same manner as in Example 31, step E, the title compound was obtained.
MS (ESI+): [M+H]$^+$ 341.3.

Example 201

1-{[(6S,7R)-7-(3,4-dichlorophenyl)-1,4-oxazepan-6-yl]methyl}-5-methyl-1H-1,2,3-triazole-4-carboxylic acid monohydrochloride A) tert-butyl (6S,7R)-7-(3,4-dichlorophenyl)-6-{[4-(methoxycarbonyl)-5-methyl-1H-1,2,3-triazol-1-yl]methyl}-1,4-oxazepane-4-carboxylate To a solution of tert-butyl (6S,7R)-6-(azidomethyl)-7-(3,4-dichlorophenyl)-1,4-oxazepane-4-carboxylate (200 mg) in DMSO (2 mL) were added potassium carbonate (276 mg) and methyl acetoacetate (0.08 mL) at room temperature, and the mixture was stirred at 80° C. overnight. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (149 mg).
MS (ESI+): [M+H]$^+$ 499.0.

B) 1-{[(6S,7R)-4-(tert-butoxycarbonyl)-7-(3,4-dichlorophenyl)-1,4-oxazepan-6-yl]methyl}-5-methyl-1H-1,2,3-triazole-4-carboxylic acid Using tert-butyl (6S,7R)-7-(3,4-dichlorophenyl)-6-{[4-(methoxycarbonyl)-5-methyl-1H-1,2,3-triazol-1-yl]methyl}-1,4-oxazepane-4-carboxylate (149 mg), and in the same manner as in Example 58, step B, the title compound (149 mg) was obtained.
MS (ESI+): [M+H-t-Bu]$^+$ 429.1.

C) 1-{[(6S,7R)-7-(3,4-dichlorophenyl)-1,4-oxazepan-6-yl]methyl}-5-methyl-1H-1,2,3-triazole-4-carboxylic acid monohydrochloride Using 1-{[(6S,7R)-4-(tert-butoxycarbonyl)-7-(3,4-dichlorophenyl)-1,4-oxazepan-6-yl]methyl}-5-methyl-1H-1,2,3-triazole-4-carboxylic acid (149 mg), and in the same manner as in Example 58, step C, the title compound (85 mg) was obtained.
MS (ESI+): [M+H]$^+$ 385.3.

Example 202

1-{[(6S,7R)-7-(3,4-dichlorophenyl)-1,4-oxazepan-6-yl]methyl}-1H-indazole-3-carboxylic acid monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 44, step A, Example 58, step B and Example 39, step B, the title compound was obtained.
MS (ESI+): [M+H]$^+$ 420.1.

Example 203

1-{[(6S,7R)-7-(3,4-dichlorophenyl)-1,4-oxazepan-6-yl]methyl}imidazolidine-2,4-dione monohydrochloride A) tert-butyl (6R,7R)-7-(3,4-dichlorophenyl)-6-{[(2-ethoxy-2-oxoethyl)amino]methyl}-1,4-oxazepane-4-carboxylate Using tert-butyl (6R,7R)-6-(aminomethyl)-7-(3,4-dichlorophenyl)-1,4-oxazepane-4-carboxylate, and in the same manner as in Example 44, step A, the title compound was obtained.
MS (ESI+): [M+H]$^+$ 461.2.

B) tert-butyl (6R,7R)-7-(3,4-dichlorophenyl)-6-[(2,4-dioxoimidazolidin-1-yl)methyl]-1,4-oxazepane-4-carboxylate To a solution (1.9 mL) of tert-butyl (6R,7R)-7-(3,4-dichlorophenyl)-6-{[(2-ethoxy-2-oxoethyl)amino]methyl}-1,4- oxazepane-4-carboxylate (180 mg) in THF were added isocyanatotrimethylsilane (0.078 mL) and triethylamine (0.082 mL), and the mixture was stirred at room temperature for 2 hr. Then, isocyanatotrimethylsilane (0.156 ml) and triethylamine (0.164 mL) were added, and the mixture was stirred at 50° C. for 2 hr, and concentrated under reduced pressure. The residue was purified by silica gel chromatography (hexane/ethyl acetate). The obtained residue was diluted with methanol (1.4 mL), triethylamine (0.080 ml) was added, and the mixture was stirred at 50° C. for 2 hr. The reaction mixture was concentrated under reduced pressure, and the residue was purified by silica gel chromatography (hexane/ethyl acetate) to give the title compound (115 mg).

$^1$H NMR (300 MHz, CDCl$_3$) δ 1.49 (9H, s), 2.24-2.50 (1H, m), 2.99-4.12 (11H, m), 7.16 (1H, d, J=8.3 Hz), 7.38-7.47 (2H, m), 7.59-7.90 (1H, m).

C) 1-{[(6S,7R)-7-(3,4-dichlorophenyl)-1,4-oxazepan-6-yl]methyl}imidazolidine-2,4-dione monohydrochloride Using tert-butyl (6R,7R)-7-(3,4-dichlorophenyl)-6-[(2,4-dioxoimidazolidin-1-yl)methyl]-1,4-oxazepane-4-carboxylate, and in the same manner as in Example 38, step F, the title compound was obtained.
MS (ESI+): [M+H]$^+$ 358.0.

Example 204

1-{[(6S,7R)-7-(3,4-dichlorophenyl)-1,4-oxazepan-6-yl]methyl}-2-oxo-1,2-dihydropyridine-3-carbonitrile monohydrochloride In the same manner as in Example 44, step A and Example 31, step E, the title compound was obtained.
MS (ESI+): [M+H]$^+$ 378.1.

Example 205

1-{[(6S,7R)-7-(3,4-dichlorophenyl)-1,4-oxazepan-6-yl]methyl}-2-oxo-1,2-dihydropyridine-3-carboxylic acid monohydrochloride In the same manner as in Example 44, the title compound was obtained.
MS (ESI+): [M+H]$^+$ 397.1.

Example 206

1-{[(6S,7R)-7-(3,4-dichlorophenyl)-1,4-oxazepan-6-yl]methyl}-5-(5-oxo-4,5-dihydro-1,2,4-oxadiazol-3-yl)pyridin-2(1H)-one monohydrochloride In the same manner as in Example 44, step A and Example 31, steps D and E, the title compound was obtained.
MS (ESI+): [M+H]$^+$ 437.0.

Example 207

1-{[(6S,7R)-7-(3,4-dichlorophenyl)-1,4-oxazepan-6-yl]methyl}-4-(5-oxo-4,5-dihydro-1,2,4-oxadiazol-3-yl)pyridin-2(1H)-one monohydrochloride In the same manner as in Example 44, step A and Example 31, steps D and E, the title compound was obtained.
MS (ESI+): [M+H]$^+$ 436.9.

Example 208

1-{[(6S,7R)-7-(3,4-dichlorophenyl)-1,4-oxazepan-6-yl]methyl}-3-(1H-tetrazol-5-yl)pyridin-2(1H)-one monohydrochloride A) tert-butyl (6R,7R)-7-(3,4-dichlorophenyl)-6-{[2-oxo-3-(1H-tetrazol-5-yl)pyridin-1(2H)-yl]methyl}-1,4-oxazepane-4-carboxylate Tributyltin azide (0.340 mL, 1.24 mmol) was added to a solution of tert-butyl (6R,7R)-6-[(3-cyano-2-oxopyridin-1(2H)-yl)methyl]-7-(3,4-dichlorophenyl)-1,4-oxazepane-4-carboxylate (198 mg, 0.41 mmol) in toluene (5 mL). The reaction mixture was stirred at 100° C. overnight. The reaction mixture was concentrated under reduced pressure. The residue was purified by silica gel column chromatography to give the title compound (148 mg, 0.284 mmol, 68.6%).

$^1$H NMR (300 MHz, CDCl$_3$) δ 1.55 (9H, s), 2.98 (1H, brs), 3.08-3.35 (2H, m), 3.65 (1H, t, J=11.1 Hz), 3.89-4.15 (5H, m), 4.29-4.42 (1H, m), 6.59 (1H, t, J=6.6 Hz), 7.06 (1H, d, J=7.9 Hz), 7.16 (1H, dd, J=7.9, 1.9 Hz), 7.57 (1H, brs), 8.57 (1H, d, J=5.3 Hz), 8.66 (1H, d, J=6.8 Hz), 14.40 (1H, brs).
MS (ESI+): [M+H]$^+$ 521.3.

B) 1-{[(6S,7R)-7-(3,4-dichlorophenyl)-1,4-oxazepan-6-yl]methyl}-3-(1H-tetrazol-5-yl)pyridin-2(1H)-one monohydrochloride Using tert-butyl (6R,7R)-7-(3,4-dichlorophenyl)-6-{[2-oxo-3-(1H-tetrazol-5-yl)pyridin-1(2H)-yl]methyl}-1,4-oxazepane-4-carboxylate, and in the same manner as in Example 31, step E, the title compound was obtained.
MS (ESI+): [M+H]$^+$ 421.0.

Example 209

2-{[(6S,7R)-7-(3,4-dichlorophenyl)-1,4-oxazepan-6-yl]methyl}-4-(5-oxo-4,5-dihydro-1,2,4-oxadiazol-3-yl)pyridazin-3(2H)-one monohydrochloride Using tert-butyl (6S,7R)-7-(3,4-dichlorophenyl)-6-{[(methylsulfonyl)oxy]methyl}-1,4-oxazepane-4-carboxylate and 3-hydroxypyridazine-4-carbonitrile, and in the same manner as in Example 44, step A and Example 31, steps D and E, the title compound was obtained.
MS (ESI+): [M+H]$^+$ 438.1.

Example 210

2-{[(6S,7R)-7-(3,4-dichlorophenyl)-1,4-oxazepan-6-yl]methyl}-5,6-dimethyl-3-oxo-2,3-dihydropyridazine-4-carbonitrile monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 44, step A and Example 39, step B, the title compound was obtained.
MS (ESI+): [M+H]$^+$ 407.3.

Example 211

2-{[(6S,7R)-7-(3,4-dichlorophenyl)-1,4-oxazepan-6-yl]methyl}-5,6-dimethyl-4-(5-oxo-4,5-dihydro-1,2,4-oxadiazol-3-yl)pyridazin-3(2H)-one monohydrochloride Using tert-butyl (6S,7R)-7-(3,4-dichlorophenyl)-6-{[(methylsulfonyl)oxy]methyl}-1,4-oxazepane-4-carboxylate, and in the same manner as in Example 44, step A, Example 31, step D and Example 39, step B, the title compound was obtained.
MS (ESI−): [M−H]+ 464.2.

Example 212

3-[(6R,7R)-7-(3,4-dichlorophenyl)-1,4-oxazepan-6-yl]propan-1-ol monohydrochloride Using tert-butyl (6R,7R)-7-(3,4-dichlorophenyl)-6-(3-ethoxy-3-oxopropyl)-1,4-oxazepane-4-carboxylate, and in the same manner as in Example 4, step B and Example 38, step F, the title compound was obtained.
MS (ESI+): [M+H]+ 304.3

Example 213

1-{3-[(6R,7R)-7-(3,4-dichlorophenyl)-1,4-oxazepan-6-yl]propyl}-3-methyl-1H-pyrazole-5-carboxylic acid monohydrochloride Using tert-butyl (6R,7R)-7-(3,4-dichlorophenyl)-6-(3-ethoxy-3-oxopropyl)-1,4-oxazepane-4-carboxylate, and in the same manner as in Example 4, step B, Example 3, step A and Example 44, the title compound was obtained.
MS (ESI+): [M+H]+ 412.3.

Example 214

1-{3-[(6R,7R)-7-(3,4-dichlorophenyl)-1,4-oxazepan-6-yl]propyl}-5-methyl-1H-pyrazole-3-carboxylic acid monohydrochloride In the same manner as in Example 213, the title compound was obtained.
MS (ESI+): [M+H]+ 412.3.

Example 215

1-[(6S,7R)-7-(3,4-dichlorophenyl)-1,4-oxazepan-6-yl]-2,2,2-trifluoroethanol monohydrochloride (diastereomer ratio about 3:1 mixture)

A) tert-butyl (6S,7R)-7-(3,4-dichlorophenyl)-6-(2,2,2-trifluoro-1-hydroxyethyl)-1,4-oxazepane-4-carboxylate (diastereomer mixture)

To a solution (2.6 mL) of tert-butyl (6R,7R)-7-(3,4-dichlorophenyl)-6-formyl-1,4-oxazepane-4-carboxylate (100 mg) in THF were added a solution (1.0 M, 0.534 mL) of trimethyl (trifluoromethyl)silane (190 mg) and tetrabutylammonium fluoride in THF under ice-cooling, and the mixture was stirred at room temperature overnight. To the reaction mixture was added 1 M hydrochloric acid (0.5 ml), and the mixture was further stirred for 3 hr. Distilled water was added, and the mixture was extracted with ethyl acetate. The extract was washed with distilled water and brine, and dried over anhydrous magnesium sulfate, and the solvent was evaporated under reduced pressure. The residue was purified by silica gel chromatography (hexane/ethyl acetate) to give the title compound (91.7 mg).
$^1$H NMR (300 MHz, CDCl$_3$) δ 1.50 (9H, s), 2.60-2.72 (1H, m), 3.01-4.41 (8H, m), 4.68 (1H, d, J=8.7 Hz), 7.17 (1H, dd, J=8.3, 1.9 Hz), 7.41 (1H, d, J=8.3 Hz), 7.45 (1H, d, J=1.9 Hz).

B) 1-[(6S,7R)-7-(3,4-dichlorophenyl)-1,4-oxazepan-6-yl]-2,2,2-trifluoroethanol monohydrochloride (diastereomer ratio about 3:1 mixture)

Using tert-butyl (6S,7R)-7-(3,4-dichlorophenyl)-6-(2,2,2-trifluoro-1-hydroxyethyl)-1,4-oxazepane-4-carboxylate, and in the same manner as in Example 38, step F, the title compound was obtained.
MS (ESI+): [M+H]+ 344.0.

Example 216

1-[(6R,7R)-7-(3,4-dichlorophenyl)-1,4-oxazepan-6-yl]ethanone monohydrochloride

Using (6R,7R)-4-(tert-butoxycarbonyl)-7-(3,4-dichlorophenyl)-1,4-oxazepane-6-carboxylic acid, and in the same manner as in Example 75, the title compound was obtained.
$^1$H NMR (300 MHz, DMSO-d$_6$) δ 2.45-2.54 (3H, m), 2.98 (2H, t, J=5.3 Hz), 3.62 (2H, q, J=5.0 Hz), 3.89 (2H, s), 5.23 (1H, t, J=4.9 Hz), 7.61 (1H, dd, J=8.3, 1.9 Hz), 7.73-7.80 (1H, m), 7.90 (1H, d, J=1.9 Hz), 8.07 (1H, s), 8.58-8.82 (2H, m).
MS (ESI+): [M+H]+ 288.2.

Example 217

(6S,7R)-7-(3,4-dichlorophenyl)-1,4-oxazepane-6-carbonitrile monohydrochloride

A) tert-butyl (6R,7R)-6-carbamoyl-7-(3,4-dichlorophenyl)-1,4-oxazepane-4-carboxylate To a solution of (6R,7R)-4-(tert-butoxycarbonyl)-7-(3,4-dichlorophenyl)-1,4-oxazepane-6-carboxylic acid (450 mg) and 1H-benzotriazol-1-ol ammonium salt (211 mg) in DMF (5.8 mL) was added N-[3-(dimethylamino)propyl]-N'-ethylcarbodiimide hydrochloride (265 mg), and the mixture was stirred overnight. To the reaction mixture was added distilled water, and the mixture was extracted with ethyl acetate. The extract was washed with distilled water and brine, and dried over anhydrous sodium sulfate, and the solvent was evaporated under reduced pressure. The residue was purified by silica gel chromatography (hexane/ethyl acetate) to give the title compound (437 mg).
$^1$H NMR (300 MHz, CDCl$_3$) δ 1.50 (9H, s), 2.49-2.86 (1H, m), 3.46-4.05 (6H, m), 4.75 (1H, d, J=9.1 Hz), 5.05-6.38 (2H, m), 7.17 (1H, dd, J=8.3, 1.9 Hz), 7.38 (1H, d, J=8.0 Hz), 7.46 (1H, d, J=1.9 Hz).

B) tert-butyl (6S,7R)-6-cyano-7-(3,4-dichlorophenyl)-1,4-oxazepane-4-carboxylate To a solution of tert-butyl (6R,7R)-6-carbamoyl-7-(3,4-dichlorophenyl)-1,4-oxazepane-4-carboxylate (437 mg) and triethylamine (0.344 ml) in THF (5.6 mL) was added trifluoroacetic anhydride (0.171 mL), and the mixture was stirred at 0° C. for 2 hr. Then, the mixture was stirred at room temperature for 1 hr, distilled water was added to the reaction mixture, and the mixture was extracted with ethyl acetate. The extract was washed with distilled water and brine, and dried over anhydrous sodium sulfate, and the solvent was evaporated under reduced pressure. The residue was purified by silica gel chromatography (hexane/ethyl acetate) to give the title compound (205 mg).
$^1$H NMR (300 MHz, CDCl$_3$) δ 1.56 (9H, s), 2.90-3.10 (1H, m), 3.18-3.34 (1H, m), 3.52-3.87 (3H, m), 4.03-4.31 (2H, m), 4.50 (1H, d, J=9.8 Hz), 7.20-7.26 (1H, m), 7.46 (1H, d, J=8.3 Hz), 7.53 (1H, s).

C) (6S,7R)-7-(3,4-dichlorophenyl)-1,4-oxazepane-6-carbonitrile monohydrochloride Using tert-butyl (6S,7R)-6-cyano-7-(3,4-dichlorophenyl)-1,4-oxazepane-4-carboxylate, and in the same manner as in Example 38, step F, the title compound was obtained.
MS (ESI+): [M+H]$^+$ 271.0.

Example 218

(6R,7R)-7-(3,4-dichlorophenyl)-1,4-oxazepane-6-carboxylic acid monohydrochloride Using (6R,7R)-4-(tert-butoxycarbonyl)-7-(3,4-dichlorophenyl)-1,4-oxazepane-6-carboxylic acid, and in the same manner as in Example 39, step B, the title compound was obtained.
MS (ESI+): [M+H]$^+$ 290.0.

Example 219

(6R,7R)-7-(3,4-dichlorophenyl)-1,4-oxazepane-6-carboxamide monohydrochloride

Using tert-butyl (6R,7R)-6-carbamoyl-7-(3,4-dichlorophenyl)-1,4-oxazepane-4-carboxylate, and in the same manner as in Example 38, step F, the title compound was obtained.
MS (ESI+): [M+H]$^+$ 289.0.

Example 220

(6R,7R)-7-(3,4-dichlorophenyl)-N-methyl-1,4-oxazepane-6-carboxamide monohydrochloride Using (6R,7R)-4-(tert-butoxycarbonyl)-7-(3,4-dichlorophenyl)-1,4-oxazepane-6-carboxylic acid, and in the same manner as in Example 41, the title compound was obtained.
MS (ESI+): [M+H]$^+$ 303.0.

Example 221

(6R,7R)-7-(3,4-dichlorophenyl)-N,N-dimethyl-1,4-oxazepane-6-carboxamide monohydrochloride Using (6R,7R)-4-(tert-butoxycarbonyl)-7-(3,4-dichlorophenyl)-1,4-oxazepane-6-carboxylic acid, and in the same manner as in Example 39, the title compound was obtained.
MS (ESI+): [M+H]$^+$ 317.3.

Example 222

(6R,7R)-7-(3,4-dichlorophenyl)-N-(2-hydroxy-2-methylpropyl)-1,4-oxazepane-6-carboxamide monohydrochloride Using (6R,7R)-4-(tert-butoxycarbonyl)-7-(3,4-dichlorophenyl)-1,4-oxazepane-6-carboxylic acid, and in the same manner as in Example 41, the title compound was obtained.
MS (ESI+): [M+H]$^+$ 361.0.

Example 223

(6R,7R)-7-(3,4-dichlorophenyl)-N-[2-(methylsulfonyl)ethyl]-1,4-oxazepane-6-carboxamide monohydrochloride Using (6R,7R)-4-(tert-butoxycarbonyl)-7-(3,4-dichlorophenyl)-1,4-oxazepane-6-carboxylic acid, and in the same manner as in Example 41, the title compound was obtained.
MS (ESI+): [M+H]$^+$ 395.0.

Example 224

3-({[(6R,7R)-7-(3,4-dichlorophenyl)-1,4-oxazepan-6-yl]carbonyl}amino)benzoic acid monohydrochloride Using (6R,7R)-4-(tert-butoxycarbonyl)-7-(3,4-dichlorophenyl)-1,4-oxazepane-6-carboxylic acid, and in the same manner as in Example 41, step A and Example 44, step B, the title compound was obtained.
MS (ESI+): [M+H]$^+$ 409.0.

Example 225

(6R,7R)-7-(3,4-dichlorophenyl)-N-(methylsulfonyl)-1,4-oxazepane-6-carboxamide monohydrochloride Using (6R,7R)-4-(tert-butoxycarbonyl)-7-(3,4-dichlorophenyl)-1,4-oxazepane-6-carboxylic acid, and in the same manner as in Example 226, step A and Example 39, step B, the title compound was obtained.
MS (ESI+): [M+H]$^+$ 367.0.

Example 226

(6R,7R)-7-(3,4-dichlorophenyl)-N-methyl-N-(methylsulfonyl)-1,4-oxazepane-6-carboxamide monohydrochloride A) tert-butyl (6R,7R)-7-(3,4-dichlorophenyl)-6-[(methylsulfonyl)carbamoyl]-1,4-oxazepane-4-carboxylate To a solution of (6R,7R)-4-(tert-butoxycarbonyl)-7-(3,4-dichlorophenyl)-1,4-oxazepane-6-carboxylic acid (590 mg) in acetonitrile (15.1 mL) were added N,N-dimethyl-4-aminopyridine (203 mg), methanesulfonamide (158 mg) and 2-methyl-6-nitrobenzoic anhydride (625 mg) at room temperature, and the mixture was stirred at room temperature for 2 hr. To the reaction mixture was added aqueous ammonium chloride solution, and the mixture was extracted with ethyl acetate. The extract was washed with distilled water and brine, and dried over anhydrous magnesium sulfate. The solvent was evaporated under reduced pressure, and the residue was purified by silica gel chromatography (hexane/ethyl acetate) to give the title compound (323 mg).
MS (ESI+): [M+H-t-Bu]$^+$ 411.2.

B) tert-butyl (6R,7R)-7-(3,4-dichlorophenyl)-6-[methyl(methylsulfonyl)carbamoyl]-1,4-oxazepane-4-carboxylate To a solution of tert-butyl (6R,7R)-7-(3,4-dichlorophenyl)-6-[(methylsulfonyl)carbamoyl]-1,4-oxazepane-4-carboxylate (246 mg) in DMF (3 mL) were added potassium carbonate (109 mg) and methyl iodide (0.049 mL) at room temperature, and the mixture was stirred at room temperature overnight. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (174 mg).
MS (ESI−): [M−H]$^+$ 479.0.

C) (6R,7R)-7-(3,4-dichlorophenyl)-N-methyl-N-(methylsulfonyl)-1,4-oxazepane-6-carboxamide monohydrochloride Using tert-butyl (6R,7R)-7-(3,4-dichlorophenyl)-6-[methyl(methylsulfonyl)carbamoyl]-1,4-oxazepane-4-carboxylate (174 mg), and in the same manner as in Example 58, step C, the title compound (133 mg) was obtained.
MS (ESI+): [M+H]$^+$ 381.1.

Example 227

(6R,7R)-7-(3,4-dichlorophenyl)-N-{[4-(difluoromethoxy)phenyl]sulfonyl}-1,4-oxazepane-6-carboxamide monohydrochloride Using (6R,7R)-4-(tert-butoxycarbonyl)-7-(3,4-dichlorophenyl)-1,4-oxazepane-6-carboxylic acid, and in the same manner as in Example 226, step A and Example 38, step F, the title compound was obtained.
MS (ESI+): [M+H]$^+$ 495.2.

Example 228

(6R,7R)-7-(3,4-dichlorophenyl)-N-{[4-(trifluoromethyl)phenyl]sulfonyl}-1,4-oxazepane-6-carboxamide monohydrochloride Using (6R,7R)-4-(tert-butoxycarbonyl)-7-(3,4-dichlorophenyl)-1,4-oxazepane-6-carboxylic acid, and in the same manner as in Example 226, step A and Example 38, step F, the title compound was obtained.
MS (ESI+): [M+H]$^+$ 496.9.

Example 229

2-[(6R,7R)-7-(3,4-dichlorophenyl)-1,4-oxazepan-6-yl]-1,3-thiazole-4-carboxylic acid monohydrochloride Using tert-butyl (6R,7R)-6-carbamoyl-7-(3,4-dichlorophenyl)-1,4-oxazepane-4-carboxylate, and in the same manner as in Example 194, the title compound was obtained.
MS (ESI+): [M+H]$^+$ 373.0.

Example 230

(6RS,7SR)-7-(3,4-dichlorophenyl)-1,4-oxazepan-6-ol monohydrochloride

Using tert-butyl (6RS,7SR)-7-(3,4-dichlorophenyl)-6-hydroxy-1,4-oxazepane-4-carboxylate (150 mg), and in the same manner as in Example 39, step B, the title compound (93 mg) was obtained.
MS (ESI+): [M+H]$^+$ 262.1.

Example 231

6-{[(6RS,7SR)-7-(3,4-dichlorophenyl)-1,4-oxazepan-6-yl]oxy}pyridine-2-carboxylic acid monohydrochloride A) tert-butyl (6RS,7SR)-7-(3,4-dichlorophenyl)-6-{[6-(methoxycarbonyl)pyridin-2-yl]oxy}-1,4-oxazepane-4-carboxylate Under ice-cooling, sodium hydride (60% in oil, 53 mg) was added to a solution of tert-butyl (6RS,7SR)-7-(3,4-dichlorophenyl)-6-hydroxy-1,4-oxazepane-4-carboxylate (400 mg) in DMF (5 mL). After stirring at room temperature for 20 min, methyl 6-chloropicolinate (280 mg) and sodium iodide (330 mg) were added, and the mixture was stirred at the same temperature for 1 hr. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (207 mg).
$^1$H NMR (300 MHz, CDCl$_3$) δ 1.16-1.54 (9H, m), 2.92-4.98 (11H, m), 7.28-7.89 (6H, m).
MS (ESI+): [M+H]$^+$ 497.3.

B) 6-{[(6RS,7SR)-4-(tert-butoxycarbonyl)-7-(3,4-dichlorophenyl)-1,4-oxazepan-6-yl]oxy}pyridine-2-carboxylic acid 2M Aqueous sodium hydroxide solution (1.7 mL) was added to a solution of tert-butyl (6RS,7SR)-7-(3,4-dichlorophenyl)-6-{[6-(methoxycarbonyl)pyridin-2-yl]oxy}-1,4-oxazepane-4-carboxylate (210 mg) in ethanol (5 ml), and the mixture was stirred at room temperature overnight and at 70° C. for 2 hr. Water was added to the reaction mixture, and the mixture was washed with diethyl ether. The obtained aqueous layer was neutralized with 1 M hydrochloric acid, and the mixture was extracted with ethyl acetate. The obtained extract was washed with brine, and dried over anhydrous sodium sulfate. The solvent was evaporated under reduced pressure to give the title compound (69 mg).
$^1$H NMR (300 MHz, CDCl$_3$) δ 1.54 (9H, s), 3.07-3.44 (2H, m), 3.73-3.94 (1H, m), 3.97-4.09 (1H, m), 4.25 (1H, ddd, J=13.1, 5.6, 1.7 Hz), 4.46 (1H, d, J=9.0 Hz), 4.62-4.89 (2H, m), 6.82 (1H, d, J=8.3 Hz), 7.22 (1H, dd, J=8.3, 2.3 Hz), 7.36 (1H, d, J=8.3 Hz), 7.51 (1H, d, J=1.9 Hz), 7.66-7.78 (1H, m), 7.83 (1H, d, J=7.2 Hz), 1H not detected.
MS (ESI+): [M+H]$^+$ 481.0.

C) 6-{[(6RS,7SR)-7-(3,4-dichlorophenyl)-1,4-oxazepan-6-yl]oxy}pyridine-2-carboxylic acid monohydrochloride Using 6-{[(6RS,7SR)-4-(tert-butoxycarbonyl)-7-(3,4-dichlorophenyl)-1,4-oxazepan-6-yl]oxy}pyridine-2-carboxylic acid (69 mg), and in the same manner as in Example 39, step B, the title compound (50 mg) was obtained.
MS (ESI+): [M+H]$^+$ 383.1.

Example 232

6-{[(6RS,7SR)-7-(3,4-dichlorophenyl)-1,4-oxazepan-6-yl]oxy}pyridine-2-carbonitrile monohydrochloride A) tert-butyl (6RS,7SR)-6-[(6-cyanopyridin-2-yl)oxy]-7-(3,4-dichlorophenyl)-1,4-oxazepane-4-carboxylate Using tert-butyl (6RS,7SR)-7-(3,4-dichlorophenyl)-6-hydroxy-1,4-oxazepane-4-carboxylate (400 mg), and in the same manner as in Example 231, step A, the title compound (237 mg) was obtained.
$^1$H NMR (300 MHz, CDCl$_3$) δ 1.54 (9H, s), 2.86-5.38 (8H, m), 6.78-7.85 (6H, m).
MS (ESI+): [M+H-Boc]$^+$ 364.1.

B) 6-{[(6RS,7SR)-7-(3,4-dichlorophenyl)-1,4-oxazepan-6-yl]oxy}pyridine-2-carbonitrile monohydrochloride Using tert-butyl (6RS,7SR)-6-[(6-cyanopyridin-2-yl)oxy]-7-(3,4-dichlorophenyl)-1,4-oxazepane-4-carboxylate (60 mg), and in the same manner as in Example 39, step B, the title compound (32 mg) was obtained.
MS (ESI+): [M+H]$^+$ 364.1.

Example 233

2-{[(6RS,7SR)-7-(3,4-dichlorophenyl)-1,4-oxazepan-6-yl]oxy}pyridine-3-carbonitrile monohydrochloride A) tert-butyl (6RS,7SR)-6-[(3-cyanopyridin-2-yl)oxy]-7-(3,4-dichlorophenyl)-1,4-oxazepane-4-carboxylate Using tert-butyl (6RS,7SR)-7-(3,4-dichlorophenyl)-6-hydroxy-1,4-oxazepane-4-carboxylate (400 mg), and by a method similar to that of Example 231, step A, the title compound (430 mg) was obtained.
$^1$H NMR (300 MHz, CDCl$_3$) δ 1.26-1.50 (9H, m), 2.98-3.47 (1H, m), 3.58 (1H, dd, J=15.6, 4.0 Hz), 3.74-4.09 (1H, m), 4.09-4.53 (3H, m), 4.53-4.85 (1H, m), 4.93-5.62 (1H, m), 6.84-7.11 (1H, m), 7.28-7.65 (3H, m), 7.75-8.10 (1H, m), 8.17-8.76 (1H, m).
MS (ESI+): [M+H-t-Bu]$^+$ 407.2.

B) 2-{[(6RS,7SR)-7-(3,4-dichlorophenyl)-1,4-oxazepan-6-yl]oxy}pyridine-3-carbonitrile monohydrochloride Using tert-butyl (6RS,7SR)-6-[(3-cyanopyridin-2-yl)oxy]-7-(3,4-dichlorophenyl)-1,4-oxazepane-4-carboxylate (60 mg), and in the same manner as in Example 39, step B, the title compound (77 mg) was obtained.
MS (ESI+): [M+H]$^+$ 364.1.

Example 234

2-{[(6RS,7SR)-7-(3,4-dichlorophenyl)-1,4-oxazepan-6-yl]oxy}pyridine-3-carboxamide monohydrochloride A) tert-butyl (6RS,7SR)-6-[(3-carbamoylpyridin-2-yl)oxy]-7-(3,4-dichlorophenyl)-1,4-oxazepane-4-carboxylate 33% Aqueous hydrogen peroxide (1 mL) was added to a solution of tert-butyl (6RS,7SR)-6-[(3-cyanopyridin-2-yl)oxy]-7-(3,4-dichlorophenyl)-1,4-oxazepane-4-carboxylate (100 mg) and potassium carbonate (45 mg) in DMSO (3 mL), and the mixture was stirred at room temperature for 2 hr. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography and HPLC to give the title compound (57 mg).
MS (ESI+): [M+H]$^+$ 482.2.

B) 2-{[(6RS,7SR)-7-(3,4-dichlorophenyl)-1,4-oxazepan-6-yl]oxy}pyridine-3-carboxamide monohydrochloride Using tert-butyl (6RS,7SR)-6-[(3-carbamoylpyridin-2-yl)oxy]-7-(3,4-dichlorophenyl)-1,4-oxazepane-4-carboxylate (57 mg), and in the same manner as in Example 39, step B, the title compound (39 mg) was obtained.
MS (ESI+): [M+H]$^+$ 382.2.

Example 235

3-(6-{[(6RS,7SR)-7-(3,4-dichlorophenyl)-1,4-oxazepan-6-yl]oxy}pyridin-2-yl)-1,2,4-oxadiazol-5(4H)-one monohydrochloride A) tert-butyl (6RS,7SR)-7-(3,4-dichlorophenyl)-6-{[6-(5-oxo-4,5-dihydro-1,2,4-oxadiazol-3-yl)pyridin-2-yl]oxy}-1,4-oxazepane-4-carboxylate Using tert-butyl (6RS,7SR)-6-[(6-cyanopyridin-2-yl)oxy]-7-(3,4-dichlorophenyl)-1,4-oxazepane-4-carboxylate (170 mg), and in the same manner as in Example 31, step D, the title compound (165 mg) was obtained.
$^1$H NMR (300 MHz, CDCl$_3$) δ 1.60 (9H, s), 3.11 (1H, dd, J=14.0, 10.2 Hz), 3.18-3.33 (1H, m), 3.84 (1H, td, J=12.5, 4.2 Hz), 4.02-4.20 (1H, m), 4.20-4.37 (1H, m), 4.44 (1H, d, J=9.4 Hz), 4.72 (1H, td, J=9.8, 3.4 Hz), 4.87 (1H, dd, J=14.4, 3.0 Hz), 6.72 (1H, d, J=7.9 Hz), 7.23 (1H, dd, J=8.3, 1.9 Hz), 7.37 (1H, d, J=8.3 Hz), 7.51 (1H, d, J=2.3 Hz), 7.59-7.72 (2H, m), 11.68 (1H, brs).
MS (ESI+): [M−H]$^+$ 521.1.

B) 3-(6-{[(6RS,7SR)-7-(3,4-dichlorophenyl)-1,4-oxazepan-6-yl]oxy}pyridin-2-yl)-1,2,4-oxadiazol-5(4H)-one monohydrochloride Using tert-butyl (6RS,7SR)-7-(3,4-dichlorophenyl)-6-{[6-(5-oxo-4,5-dihydro-1,2,4-oxadiazol-3-yl)pyridin-2-yl]oxy}-1,4-oxazepane-4-carboxylate (165 mg), and in the same manner as in Example 39, step B, the title compound (111 mg) was obtained.
MS (ESI+): [M+H]$^+$ 423.1.

Example 236

3-(2-{[(6RS,7SR)-7-(3,4-dichlorophenyl)-1,4-oxazepan-6-yl]oxy}pyridin-3-yl)-1,2,4-oxadiazol-5(4H)-one monohydrochloride A) tert-butyl (6RS,7SR)-7-(3,4-dichlorophenyl)-6-{[3-(5-oxo-4,5-dihydro-1,2,4-oxadiazol-3-yl)pyridin-2-yl]oxy}-1,4-oxazepane-4-carboxylate Using tert-butyl (6RS,7SR)-6-[(3-cyanopyridin-2-yl)oxy]-7-(3,4-dichlorophenyl)-1,4-oxazepane-4-carboxylate (330 mg), and in the same manner as in Example 31, step D, the title compound (290 mg) was obtained.
$^1$H NMR (300 MHz, DMSO-$d_6$) δ 0.96-1.49 (9H, m), 3.53-3.95 (4H, m), 3.98-4.36 (2H, m), 4.68-5.00 (1H, m), 5.05-5.62 (1H, m), 7.03-7.23 (1H, m), 7.25-7.42 (1H, m), 7.43-7.54 (1H, m), 7.54-7.69 (1H, m), 7.95-8.17 (1H, m), 8.26 (1H, m, J=3.8 Hz), 12.36 (1H, brs).
MS (ESI+): [M−H]$^+$ 521.1.

B) 3-(2-{[(6RS,7SR)-7-(3,4-dichlorophenyl)-1,4-oxazepan-6-yl]oxy}pyridin-3-yl)-1,2,4-oxadiazol-5(4H)-one monohydrochloride Using tert-butyl (6RS,7SR)-7-(3,4-dichlorophenyl)-6-{[3-(5-oxo-4,5-dihydro-1,2,4-oxadiazol-3-yl)pyridin-2-yl]oxy}-1,4-oxazepane-4-carboxylate (290 mg), and in the same manner as in Example 39, step B, the title compound (241 mg) was obtained.
MS (ESI+): [M+H]$^+$ 423.1.

Example 237

(6R,7S)-7-(3,4-dichlorophenyl)-1,4-oxazepan-6-amine dihydrochloride

Using tert-butyl (6R,7S)-6-amino-7-(3,4-dichlorophenyl)-1,4-oxazepane-4-carboxylate, and in the same manner as in Example 39, step B, the title compound was obtained.
MS (ESI+): [M+H]$^+$ 261.2.

Example 238

(6R,7S)-7-(3,4-dichlorophenyl)-N,N-dimethyl-1,4-oxazepan-6-amine dihydrochloride A) tert-butyl (6R,7S)-7-(3,4-dichlorophenyl)-6-(dimethylamino)-1,4-oxazepane-4-carboxylate To a solution of tert-butyl (6R,7S)-6-amino-7-(3,4-dichlorophenyl)-1,4-oxazepane-4-carboxylate (200 mg) in ethyl acetate (2 ml) were added formaldehyde (46 mg) and sodium triacetoxy borohydride (352 mg) at room temperature, and the mixture was stirred at room temperature for 5 hr. To the reaction mixture was added saturated aqueous sodium hydrogen carbonate, and the mixture was extracted with ethyl acetate. The extract was washed with distilled water and brine, and dried over anhydrous magnesium sulfate. The solvent was evaporated under reduced pressure, and the residue was purified by silica gel chromatography (hexane/ethyl acetate) to give the title compound (124 mg).
MS (ESI+): [M+H]$^+$ 389.3.

B) (6R,7S)-7-(3,4-dichlorophenyl)-N,N-dimethyl-1,4-oxazepan-6-amine dihydrochloride Using tert-butyl (6R,7S)-7-(3,4-dichlorophenyl)-6-(dimethylamino)-1,4-oxazepane-4-carboxylate (123 mg), and in the same manner as in Example 58, step C, the title compound (100 mg) was obtained.
MS (ESI+): [M+H]$^+$ 289.0.

Example 239

(6R,7S)—N-benzyl-7-(3,4-dichlorophenyl)-1,4-oxazepan-6-amine monohydrochloride

A) tert-butyl (6R,7S)-6-(benzylamino)-7-(3,4-dichlorophenyl)-1,4-oxazepane-4-carboxylate To a solution of tert-butyl (6R,7S)-6-amino-7-(3,4-dichlorophenyl)-1,4-oxazepane-4-carboxylate (100 mg) in THF (2 mL) was added benzyl bromide (0.036 mL) at 50° C., and the mixture was stirred at 50° C. overnight. The reaction mixture was diluted with ethyl acetate. The diluted solution was washed with brine, and dried over anhydrous magnesium sulfate. The solvent was evaporated under reduced pressure, and the residue was purified by silica gel chromatography (hexane/ethyl acetate) to give the title compound (80 mg).
MS (ESI+): [M+H]$^+$ 451.1.

B) (6R,7S)—N-benzyl-7-(3,4-dichlorophenyl)-1,4-oxazepan-6-amine monohydrochloride To tert-butyl (6R,7S)-6-(benzylamino)-7-(3,4-dichlorophenyl)-1,4-oxazepane-4-carboxylate (80 mg) was added 4.0 M hydrogen chloride-ethyl acetate solution (4 mL), and the mixture was stirred at room temperature for 1 hr. The residue obtained by concentration under reduced pressure was washed with diethyl ether to give the title compound (20 mg).
MS (ESI+): [M+H]$^+$ 351.1.

Example 240

N-[(6S,7R)-7-(3,4-dichlorophenyl)-1,4-oxazepan-6-yl]acetamide monohydrochloride

Using tert-butyl (6R,7S)-7-(3,4-dichlorophenyl)-6-(hydroxymethyl)-1,4-oxazepane-4-carboxylate, and in the same manner as in Example 36, steps A, B, C and D, Example 32, step C and Example 39, step B, the title compound was obtained.
MS (ESI+): [M+H]$^+$ 303.2.

Example 241

N-[(6R,7S)-7-(3,4-dichlorophenyl)-1,4-oxazepan-6-yl]propanamide monohydrochloride Using tert-butyl (6R,7S)-6-amino-7-(3,4-dichlorophenyl)-1,4-oxazepane-4-carboxylate, and in the same manner as in Example 32, step C and Example 39, step B, the title compound was obtained.
MS (ESI+): [M+H]$^+$ 317.0.

Example 242

N-[(6R,7S)-7-(3,4-dichlorophenyl)-1,4-oxazepan-6-yl]cyclopropanecarboxamide monohydrochloride Using tert-butyl (6R,7S)-6-amino-7-(3,4-dichlorophenyl)-1,4-oxazepane-4-carboxylate, and in the same manner as in Example 32, step C and Example 39, step B, the title compound was obtained.
MS (ESI+): [M+H]$^+$ 329.1.

Example 243

N-[(6R,7S)-7-(3,4-dichlorophenyl)-1,4-oxazepan-6-yl]-2,2-difluoroacetamide

Using tert-butyl (6R,7S)-6-amino-7-(3,4-dichlorophenyl)-1,4-oxazepane-4-carboxylate, and in the same manner as in Example 39, the title compound was obtained.
MS (ESI+): [M+H]$^+$ 339.2.

Example 244

N-[(6R,7S)-7-(3,4-dichlorophenyl)-1,4-oxazepan-6-yl]-2-hydroxyacetamide monohydrochloride Using tert-butyl (6R,7S)-6-amino-7-(3,4-dichlorophenyl)-1,4-oxazepane-4-carboxylate, and in the same manner as in Example 39, the title compound was obtained.
MS (ESI+): [M+H]$^+$ 319.1.

Example 245

N-[(6R,7S)-7-(3,4-dichlorophenyl)-1,4-oxazepan-6-yl]-2-methoxyacetamide monohydrochloride Using tert-butyl (6R,7S)-6-amino-7-(3,4-dichlorophenyl)-1,4-oxazepane-4-carboxylate, and in the same manner as in Example 32, step C and Example 39, step B, the title compound was obtained.
MS (ESI+): [M+H]$^+$ 333.1.

Example 246

3-[2-({[(6S,7R)-7-(3,4-dichlorophenyl)-1,4-oxazepan-6-yl]methyl}amino)-2-oxoethoxy]benzoic acid monohydrochloride Using tert-butyl (6R,7R)-6-(aminomethyl)-7-(3,4-dichlorophenyl)-1,4-oxazepane-4-carboxylate and 2-[(3-methoxycarbonyl)phenoxy]acetic acid, and by a method similar to that of Example 39, step A and Example 67, step C, the title compound was obtained.
$^1$H NMR (300 MHz, DMSO-d$_6$) δ 2.82-3.50 (8H, m), 3.67-4.05 (3H, m), 4.38 (1H, d, J=9.8 Hz), 4.51 (2H, s), 7.20 (1H, dd, J=7.9, 2.3 Hz), 7.38-7.51 (3H, m), 7.52-7.59 (1H, m), 7.66 (1H, d, J=8.3 Hz), 7.76 (1H, s), 8.32-8.44 (1H, m).
MS (ESI+): [M+H]$^+$ 453.1.

Example 247

N-[(6R,7S)-7-(3,4-dichlorophenyl)-1,4-oxazepan-6-yl]-2-phenylacetamide monohydrochloride Using tert-butyl (6R,7S)-6-amino-7-(3,4-dichlorophenyl)-1,4-oxazepane-4-carboxylate, and in the same manner as in Example 32, step C and Example 39, step B, the title compound was obtained.
MS (ESI+): [M+H]$^+$ 379.1.

Example 248

N-[(6R,7S)-7-(3,4-dichlorophenyl)-1,4-oxazepan-6-yl]-2-[3-(5-oxo-4,5-dihydro-1,2,4-oxadiazol-3-yl)phenyl]acetamide monohydrochloride In the same manner as in Example 39, step A and Example 31, steps D and E, the title compound was obtained.
MS (ESI+): [M+H]$^+$ 463.1.

Example 249

N-[(6R,7S)-7-(3,4-dichlorophenyl)-1,4-oxazepan-6-yl]-2-[4-(5-oxo-4,5-dihydro-1,2,4-oxadiazol-3-yl)phenyl]acetamide monohydrochloride In the same manner as in Example 39, step A and Example 31, steps D and E, the title compound was obtained.
MS (ESI+): [M+H]$^+$ 463.1.

Example 250

N-[(6R,7S)-7-(3,4-dichlorophenyl)-1,4-oxazepan-6-yl]-2-(1H-1,2,4-triazol-1-yl)acetamide trihydrochloride Using tert-butyl (6R,7S)-6-amino-7-(3,4-dichlorophenyl)-1,4-oxazepane-4-carboxylate, and in the same manner as in Example 39, the title compound was obtained.
MS (ESI+): [M+H]$^+$ 370.0.

Example 251

N-[(6R,7S)-7-(3,4-dichlorophenyl)-1,4-oxazepan-6-yl]-2-(5-oxo-4,5-dihydro-1,2,4-oxadiazol-3-yl)acetamide monohydrochloride Using tert-butyl (6R,7S)-6-amino-7-(3,4-dichlorophenyl)-1,4-oxazepane-4-carboxylate, and in the same manner as in Example 39, step A, Example 31, step D and Example 39, step B, the title compound was obtained.
MS (ESI+): [M+H]$^+$ 386.9.

Example 252

N-[(6R,7S)-7-(3,4-dichlorophenyl)-1,4-oxazepan-6-yl]benzamide monohydrochloride

Using tert-butyl (6R,7S)-6-amino-7-(3,4-dichlorophenyl)-1,4-oxazepane-4-carboxylate, and in the same manner as in Example 32, step C and Example 39, step B, the title compound was obtained.
MS (ESI+): [M+H]$^+$ 365.0.

Example 253

N-[(6R,7S)-7-(3,4-dichlorophenyl)-1,4-oxazepan-6-yl]-N-methylbenzamide monohydrochloride A) tert-butyl (6R,7S)-7-(3,4-dichlorophenyl)-6-(methylamino)-1,4-oxazepane-4-carboxylate To a solution of tert-butyl (6R,7S)-6-amino-7-(3,4-dichlorophenyl)-1,4-oxazepane-4-carboxylate (150 mg) in THF (4 mL) was added methyl iodide (0.026 ml) at room temperature, and the mixture was stirred at room temperature overnight. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (30 mg).
MS (ESI+): [M+H]$^+$ 375.1.

B) tert-butyl (6R,7S)-7-(3,4-dichlorophenyl)-6-[methyl(phenylcarbonyl)amino]-1,4-oxazepane-4-carboxylate To a solution of tert-butyl (6R,7S)-7-(3,4-dichlorophenyl)-6-(methylamino)-1,4-oxazepane-4-carboxylate (30 mg) in THF (2 mL) were added triethylamine (0.017 ml), benzoyl chloride (0.014 ml) and N,N-dimethyl-4-aminopyridine (0.5 mg) at room temperature, and the mixture was stirred at room temperature overnight. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (24 mg).
MS (ESI+): [M+H-Boc]$^+$ 379.3.

C) N-[(6R,7S)-7-(3,4-dichlorophenyl)-1,4-oxazepan-6-yl]-N-methylbenzamide monohydrochloride Using tert-butyl (6R,7S)-7-(3,4-dichlorophenyl)-6-[methyl(phenylcarbonyl)amino]-1,4-oxazepane-4-carboxylate (24 mg), and in the same manner as in Example 239, step B, the title compound (7 mg) was obtained.
MS (ESI+): [M+H]$^+$ 379.3.

Example 254

2-{[(6R,7S)-7-(3,4-dichlorophenyl)-1,4-oxazepan-6-yl]carbamoyl}benzoic acid monohydrochloride Using tert-butyl (6R,7S)-6-amino-7-(3,4-dichlorophenyl)-1,4-oxazepane-4-carboxylate, and in the same manner as in Example 39, step A, Example 58, step B and Example 39, step B, the title compound was obtained.
MS (ESI+): [M+H]$^+$ 409.1.

Example 255

3-{[(6R,7S)-7-(3,4-dichlorophenyl)-1,4-oxazepan-6-yl]carbamoyl}benzoic acid monohydrochloride Using tert-butyl (6R,7S)-6-amino-7-(3,4-dichlorophenyl)-1,4-oxazepane-4-carboxylate, and in the same manner as in Example 39, step A, Example 58, step B and Example 39, step B, the title compound was obtained.
MS (ESI+): [M+H]$^+$ 409.0.

Example 256

4-{[(6R,7S)-7-(3,4-dichlorophenyl)-1,4-oxazepan-6-yl]carbamoyl}benzoic acid monohydrochloride Using tert-butyl (6R,7S)-6-amino-7-(3,4-dichlorophenyl)-1,4-oxazepane-4-carboxylate, and in the same manner as in Example 39, step A, Example 58, step B and Example 39, step B, the title compound was obtained.
MS (ESI+): [M+H]$^+$ 409.1.

Example 257

Ethyl 2-{[(6R,7S)-7-(3,4-dichlorophenyl)-1,4-oxazepan-6-yl]carbamoyl}benzoate monohydrochloride Using tert-butyl (6R,7S)-6-amino-7-(3,4-dichlorophenyl)-1,4-oxazepane-4-carboxylate, and in the same manner as in Example 39, the title compound was obtained.
MS (ESI+): [M+H]$^+$ 437.3.

Example 258

2-cyano-N-[(6R,7S)-7-(3,4-dichlorophenyl)-1,4-oxazepan-6-yl]benzamide monohydrochloride Using tert-butyl (6R,7S)-6-amino-7-(3,4-dichlorophenyl)-1,4-oxazepane-4-carboxylate, and in the same manner as in Example 39, the title compound was obtained.
MS (ESI+): [M+H]$^+$ 390.1.

Example 259

N-[(6R,7S)-7-(3,4-dichlorophenyl)-1,4-oxazepan-6-yl]-2-[(methylsulfonyl)amino]benzamide monohydrochloride Using tert-butyl (6R,7S)-6-amino-7-(3,4-dichlorophenyl)-1,4-oxazepane-4-carboxylate, and in the same manner as in Example 39, the title compound was obtained.
MS (ESI+): [M+H]$^+$ 458.0.

Example 260

N-[(6R,7S)-7-(3,4-dichlorophenyl)-1,4-oxazepan-6-yl]-2-(5-oxo-4,5-dihydro-1,2,4-oxadiazol-3-yl)benzamide monohydrochloride Using tert-butyl (6R,7S)-6-amino-7-(3,4-dichlorophenyl)-1,4-oxazepane-4-carboxylate, and in the same manner as in Example 39, step A, Example 31, step D and Example 39, step B, the title compound was obtained.
MS (ESI+): [M+H]$^+$ 449.0.

Example 261

N-[(6R,7S)-7-(3,4-dichlorophenyl)-1,4-oxazepan-6-yl]-1,3-oxazole-5-carboxamide monohydrochloride Using tert-butyl (6R,7S)-6-amino-7-(3,4-dichlorophenyl)-1,4-oxazepane-4-carboxylate, and in the same manner as in Example 39, the title compound was obtained.
MS (ESI+): [M+H]$^+$ 356.0.

Example 262

1-[(6R,7S)-7-(3,4-dichlorophenyl)-1,4-oxazepan-6-yl]urea monohydrochloride

Using tert-butyl (6R,7S)-6-amino-7-(3,4-dichlorophenyl)-1,4-oxazepane-4-carboxylate, and in the same manner as in Example 3, steps D and E, the title compound was obtained.
MS (ESI+): [M+H]$^+$ 304.0.

Example 263

1-[(6R,7S)-7-(3,4-dichlorophenyl)-1,4-oxazepan-6-yl]-3-methylurea monohydrochloride Using tert-butyl (6R,7S)-6-amino-7-(3,4-dichlorophenyl)-1,4-oxazepane-4-carboxylate, and in the same manner as in Example 3, step D and Example 39, step B, the title compound was obtained.
MS (ESI+): [M+H]+ 318.1.

Example 264

N-[(6R,7S)-7-(3,4-dichlorophenyl)-1,4-oxazepan-6-yl]morpholine-4-carboxamide monohydrochloride Using tert-butyl (6R,7S)-6-amino-7-(3,4-dichlorophenyl)-1,4-oxazepane-4-carboxylate, and in the same manner as in Example 158, steps A and B and Example 39, step B, the title compound was obtained.
MS (ESI+): [M+H]+ 374.0.

Example 265

N-[(6R,7S)-7-(3,4-dichlorophenyl)-1,4-oxazepan-6-yl]methanesulfonamide monohydrochloride Using tert-butyl (6R,7S)-6-amino-7-(3,4-dichlorophenyl)-1,4-oxazepane-4-carboxylate, and in the same manner as in Example 32, step C and Example 39, step B, the title compound was obtained.
MS (ESI+): [M+H]+ 339.1.

Example 266

N-[(6S,7R)-7-(3,4-dichlorophenyl)-1,4-oxazepan-6-yl]methanesulfonamide monohydrochloride Using tert-butyl (6R,7S)-7-(3,4-dichlorophenyl)-6-(hydroxymethyl)-1,4-oxazepane-4-carboxylate, and in the same manner as in Example 36, steps A, B, C and D, Example 32, step C and Example 39, step B, the title compound was obtained.
MS (ESI+): [M+H]+ 339.2.

Example 267

N-[(6R,7S)-7-(3,4-dichlorophenyl)-1,4-oxazepan-6-yl]ethanesulfonamide monohydrochloride Using tert-butyl (6R,7S)-6-amino-7-(3,4-dichlorophenyl)-1,4-oxazepane-4-carboxylate, and in the same manner as in Example 32, step C and Example 39, step B, the title compound was obtained.
MS (ESI+): [M+H]+ 353.0.

Example 268

N-[(6R,7S)-7-(3,4-dichlorophenyl)-1,4-oxazepan-6-yl]cyclopropanesulfonamide monohydrochloride Using tert-butyl (6R,7S)-6-amino-7-(3,4-dichlorophenyl)-1,4-oxazepane-4-carboxylate, and in the same manner as in Example 32, step C and Example 39, step B, the title compound was obtained.
MS (ESI+): [M+H]+ 365.0.

Example 269

N-[(6R,7S)-7-(3,4-dichlorophenyl)-1,4-oxazepan-6-yl]benzenesulfonamide monohydrochloride Using tert-butyl (6R,7S)-6-amino-7-(3,4-dichlorophenyl)-1,4-oxazepane-4-carboxylate, and in the same manner as in Example 32, step C and Example 39, step B, the title compound was obtained.
MS (ESI+): [M+H]+ 401.0.

Example 270

N-[(6R,7S)-7-(3,4-dichlorophenyl)-1,4-oxazepan-6-yl]pyridine-3-sulfonamide trihydrochloride Using tert-butyl (6R,7S)-6-amino-7-(3,4-dichlorophenyl)-1,4-oxazepane-4-carboxylate, and in the same manner as in Example 32, step C and Example 39, step B, the title compound was obtained.
MS (ESI+): [M+H]+ 402.1.

Example 271

N-[(6S,7R)-7-(3,4-dichlorophenyl)-1,4-oxazepan-6-yl]sulfamide monohydrochloride

Using tert-butyl (6R,7S)-7-(3,4-dichlorophenyl)-6-(hydroxymethyl)-1,4-oxazepane-4-carboxylate, and in the same manner as in Example 36, steps A, B, C and D, Example 37, step A and Example 39, step B, the title compound was obtained.
MS (ESI+): [M+H]+ 340.1.

Example 272

N-[(6R,7S)-7-(3,4-dichlorophenyl)-1,4-oxazepan-6-yl]-N-methylsulfamide monohydrochloride Using tert-butyl (6R,7S)-7-(3,4-dichlorophenyl)-6-({[2-(trimethylsilyl)ethoxy]carbonyl}amino)-1,4-oxazepane-4-carboxylate, and in the same manner as in Example 99, step A, Example 36, step D, Example 37, step A and Example 39, step B, the title compound was obtained.
MS (ESI+): [M+H]+ 354.2.

Example 273

N-[(6R,7S)-7-(3,4-dichlorophenyl)-1,4-oxazepan-6-yl]-N'-methylsulfamide monohydrochloride A) 2-hydroxyphenyl methylsulfamate To a solution of 1,3,2-benzodioxathiol 2,2-dioxide (300 mg) in THF (6 mL) was added methylamine (0.871 mL, 2 M THF solution) at room temperature, and the mixture was stirred at room temperature for 3 hr. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (86 mg).
MS (ESI−): [M−H]+ 202.1.

B) tert-butyl (6R,7S)-7-(3,4-dichlorophenyl)-6-[(methylsulfamoyl)amino]-1,4-oxazepane-4-carboxylate To a solution of tert-butyl (6R,7S)-6-amino-7-(3,4-dichlorophenyl)-1,4-oxazepane-4-carboxylate (100 mg) in acetonitrile (3 mL) were added 2-hydroxyphenyl methylsulfamate (86 mg), triethylamine (56 mg) and N,N-dimethyl-4-aminopyridine (3.3 mg) at room temperature, and the mixture was stirred at 80° C. overnight. The reaction mixture was diluted with ethyl acetate. The diluted solution was washed with distilled water and brine, and dried over anhydrous magnesium sulfate. The solvent was evaporated under reduced pressure, and the residue was purified by silica gel chromatography (hexane/ethyl acetate) to give the title compound (81 mg).
MS (ESI−): [M−H]$^+$ 452.2.

C) N-[(6R,7S)-7-(3,4-dichlorophenyl)-1,4-oxazepan-6-yl]-N'-methylsulfamide monohydrochloride Using tert-butyl (6R,7S)-7-(3,4-dichlorophenyl)-6-[(methylsulfamoyl)amino]-1,4-oxazepane-4-carboxylate (81 mg), and in the same manner as in Example 239, step B, the title compound (61 mg) was obtained.
MS (ESI+): [M+H]$^+$ 354.1.

Example 274

N-[(6R,7S)-7-(3,4-dichlorophenyl)-1,4-oxazepan-6-yl]-N'-ethylsulfamide monohydrochloride Using 1,3,2-benzodioxathiol 2,2-dioxide, and in the same manner as in Example 273, the title compound was obtained.
MS (ESI+): [M+H]$^+$ 368.0.

Example 275

N-cyclopropyl-N'-[(6R,7S)-7-(3,4-dichlorophenyl)-1,4-oxazepan-6-yl]sulfamide monohydrochloride Using 1,3,2-benzodioxathiol 2,2-dioxide, and in the same manner as in Example 273, the title compound was obtained.
MS (ESI+): [M+H]$^+$ 380.0.

Example 276

1-[(6R,7S)-7-(3,4-dichlorophenyl)-1,4-oxazepan-6-yl]imidazolidine-2,4-dione monohydrochloride Using tert-butyl (6R,7S)-6-amino-7-(3,4-dichlorophenyl)-1,4-oxazepane-4-carboxylate, and in the same manner as in Example 203, the title compound was obtained.
MS (ESI+): [M+H]$^+$ 344.3.

Example 277

3-[(6R,7S)-7-(3,4-dichlorophenyl)-1,4-oxazepan-6-yl]imidazolidine-2,4-dione monohydrochloride To a solution of tert-butyl (6R,7S)-6-amino-7-(3,4-dichlorophenyl)-1,4-oxazepane-4-carboxylate (100 mg) in THF (3 mL) were added triethylamine (0.058 ml) and ethyl isocyanatoacetate (0.047 mL) at room temperature, and the mixture was stirred at room temperature overnight. The reaction mixture was diluted with ethyl acetate. The diluted solution was washed with distilled water and brine, and dried over anhydrous magnesium sulfate. The solvent was evaporated under reduced pressure, 2.0 M hydrogen chloride-ethanol solution (8 mL) was added to the obtained residue at room temperature, and the mixture was stirred at 80° C. for 3 weeks. The residue obtained by concentration under reduced pressure was washed with diethyl ether to give the title compound (89 mg).
MS (ESI+): [M+H]$^+$ 344.3.

Example 278

[(6RS,7RS)-7-(3-chloro-4-fluorophenyl)-1,4-oxazepan-6-yl]methanol monohydrochloride Using 3-chloro-4-fluorobenzaldehyde, and in the same manner as in Example 1, the title compound was obtained.
MS (ESI+): [M+H]$^+$ 260.3.

Example 279

N-{[(6RS,7RS)-7-(3-chloro-4-fluorophenyl)-1,4-oxazepan-6-yl]methyl}acetamide monohydrochloride Using tert-butyl (6RS,7RS)-7-(3-chloro-4-fluorophenyl)-6-(hydroxymethyl)-1,4-oxazepane-4-carboxylate, and in the same manner as in Example 3, steps A, B and C and Example 6, steps C and D, the title compound was obtained.
MS (ESI+): [M+H]$^+$ 301.3.

Example 280

1-{[(6RS,7RS)-7-(3-chloro-4-fluorophenyl)-1,4-oxazepan-6-yl]methyl}urea monohydrochloride Using tert-butyl (6RS,7RS)-7-(3-chloro-4-fluorophenyl)-6-(hydroxymethyl)-1,4-oxazepane-4-carboxylate, and in the same manner as in Example 3, the title compound was obtained.
MS (ESI+): [M+H]$^+$ 302.3.

Example 281

(6RS,7SR)-7-(3-chloro-4-fluorophenyl)-6-[(methylsulfonyl)methyl]-1,4-oxazepane monohydrochloride Using tert-butyl (6RS,7RS)-7-(3-chloro-4-fluorophenyl)-6-(hydroxymethyl)-1,4-oxazepane-4-carboxylate, and in the same manner as in Example 5, the title compound was obtained.
MS (ESI+): [M+H]$^+$ 322.3.

Example 282

N-{[(6RS,7RS)-7-(3-chloro-4-fluorophenyl)-1,4-oxazepan-6-yl]methyl}methanesulfonamide monohydrochloride Using tert-butyl (6RS,7RS)-7-(3-chloro-4-fluorophenyl)-6-(hydroxymethyl)-1,4-oxazepane-4-carboxylate, and in the same manner as in Example 3, steps A, B and C and Example 8, the title compound was obtained.
MS (ESI+): [M+H]$^+$ 337.3.

Example 283

N-{[(6RS,7RS)-7-(3-chloro-4-fluorophenyl)-1,4-oxazepan-6-yl]methyl}sulfamide monohydrochloride Using tert-butyl (6RS,7RS)-7-(3-chloro-4-fluorophenyl)-6-(hydroxymethyl)-1,4-oxazepane-4-carboxylate, and in the same manner as in Example 3, steps A, B and C and Example 9, the title compound was obtained.
MS (ESI+): [M+H]$^+$ 338.3.

Example 284

[(6S,7R)-7-(3-chloro-4-fluorophenyl)-1,4-oxazepan-6-yl]methanol monofumarate tert-Butyl (6RS,7RS)-7-(3-chloro-4-fluorophenyl)-6-(hydroxymethyl)-1,4-oxazepane-4-carboxylate (1.96 g) was separated by HPLC (CHIRALPAK AD, 50 mmID×500 mL, manufactured by DAICEL CHEMICAL INDUSTRIES, LTD., mobile phase: hexane/ethanol=950/50) to give tert-butyl (6S,7R)-7-(3-chloro-4-fluorophenyl)-6-(hydroxymethyl)-1,4-oxazepane-4-carboxylate (974 mg, >99.9% ee., recovery rate 99%) having a shorter retention time. The title compound was obtained from this compound in the same manner as in Example 32, step D.
MS (ESI+): [M+H]$^+$ 260.3.

Example 285

[(6R,7S)-7-(3-chloro-4-fluorophenyl)-1,4-oxazepan-6-yl]methanol 0.5 fumarate tert-Butyl (6RS,7RS)-7-(3-chloro-4-fluorophenyl)-6-(hydroxymethyl)-1,4-oxazepane-4-carboxylate (1.96 g) was separated by HPLC (CHIRALPAK AD, 50 mmID×500 mL, manufactured by DAICEL CHEMICAL INDUSTRIES, LTD., mobile phase: hexane/ethanol=950/50) to give tert-butyl (6R,7S)-7-(3-chloro-4-fluorophenyl)-6-(hydroxymethyl)-1,4-oxazepane-4-carboxylate (862 mg, >99.9% ee., recovery rate 99%) having a longer retention time. The title compound was obtained from this compound in the same manner as in Example 32, step D.
MS (ESI+): [M+H]$^+$ 260.3.

Example 286

N-{[(6RS,7SR)-7-(3-chloro-4-fluorophenyl)-1,4-oxazepan-6-yl]methyl}acetamide monohydrochloride Using tert-butyl (6RS,7SR)-7-(3-chloro-4-fluorophenyl)-6-(hydroxymethyl)-1,4-oxazepane-4-carboxylate, and in the same manner as in Example 3, steps A, B and C and Example 6, steps C and D, the title compound was obtained.
MS (ESI+): [M+H]$^+$ 301.4.

Example 287

N-{[(6S,7R)-7-(3-chloro-4-fluorophenyl)-1,4-oxazepan-6-yl]methyl}acetamide 0.5 fumarate Using tert-butyl (6S,7R)-7-(3-chloro-4-fluorophenyl)-6-(hydroxymethyl)-1,4-oxazepane-4-carboxylate, and in the same manner as in Example 286, the title compound was obtained.
MS (ESI+): [M+H]$^+$ 301.1.

Example 288

N-{[(6R,7S)-7-(3-chloro-4-fluorophenyl)-1,4-oxazepan-6-yl]methyl}acetamide 0.5 fumarate Using tert-butyl (6R,7S)-7-(3-chloro-4-fluorophenyl)-6-(hydroxymethyl)-1,4-oxazepane-4-carboxylate, and in the same manner as in Example 286, the title compound was obtained.
MS (ESI+): [M+H]$^+$ 301.0.

Example 289

1-{[(6S,7R)-7-(3-chloro-4-fluorophenyl)-1,4-oxazepan-6-yl]methyl}urea monofumarate Using tert-butyl (6S,7R)-7-(3-chloro-4-fluorophenyl)-6-(hydroxymethyl)-1,4-oxazepane-4-carboxylate, and in the same manner as in Example 3, the title compound was obtained.
MS (ESI+): [M+H]$^+$ 302.0.

Example 290

1-{[(6R,7S)-7-(3-chloro-4-fluorophenyl)-1,4-oxazepan-6-yl]methyl}urea monofumarate Using tert-butyl (6R,7S)-7-(3-chloro-4-fluorophenyl)-6-(hydroxymethyl)-1,4-oxazepane-4-carboxylate, and in the same manner as in Example 3, the title compound was obtained.
MS (ESI+): [M+H]$^+$ 302.0.

Example 291

(6R,7R)-7-(3-chloro-4-fluorophenyl)-6-[(methylsulfonyl)methyl]-1,4-oxazepane monohydrochloride Using tert-butyl (6S,7R)-7-(3-chloro-4-fluorophenyl)-6-(hydroxymethyl)-1,4-oxazepane-4-carboxylate, and in the same manner as in Example 5, the title compound was obtained.
MS (ESI+): [M+H]$^+$ 322.0.

Example 292

(6S,7S)-7-(3-chloro-4-fluorophenyl)-6-[(methylsulfonyl)methyl]-1,4-oxazepane monohydrochloride Using tert-butyl (6R,7S)-7-(3-chloro-4-fluorophenyl)-6-(hydroxymethyl)-1,4-oxazepane-4-carboxylate, and in the same manner as in Example 5, the title compound was obtained.
MS (ESI+): [M+H]$^+$ 322.0.

Example 293

N-{[(6RS,7SR)-7-(3-chloro-4-fluorophenyl)-1,4-oxazepan-6-yl]methyl}methanesulfonamide monohydrochloride Using tert-butyl (6RS,7SR)-7-(3-chloro-4-fluorophenyl)-6-(hydroxymethyl)-1,4-oxazepane-4-carboxylate, and in the same manner as in Example 3, steps A, B and C and Example 8, the title compound was obtained.
MS (ESI+): [M+H]$^+$ 337.3.

Example 294

N-{[(6S,7R)-7-(3-chloro-4-fluorophenyl)-1,4-oxazepan-6-yl]methyl}methanesulfonamide monohydrochloride Using tert-butyl (6S,7R)-7-(3-chloro-4-fluorophenyl)-6-(hydroxymethyl)-1,4-oxazepane-4-carboxylate, and in the same manner as in Example 3, steps A, B and C and Example 8, the title compound was obtained.
MS (ESI+): [M+H]$^+$ 337.0.

Example 295

N-{[(6R,7S)-7-(3-chloro-4-fluorophenyl)-1,4-oxazepan-6-yl]methyl}methanesulfonamide monohydrochloride Using tert-butyl (6R,7S)-7-(3-chloro-4-fluorophenyl)-6-(hydroxymethyl)-1,4-oxazepane-4-carboxylate, and in the same manner as in Example 3, steps A, B and C and Example 8, the title compound was obtained.
MS (ESI+): [M+H]$^+$ 337.1.

Example 296

N-{[(6RS,7SR)-7-(3-chloro-4-fluorophenyl)-1,4-oxazepan-6-yl]methyl}sulfamide monohydrochloride Using tert-butyl (6RS,7SR)-7-(3-chloro-4-fluorophenyl)-6-(hydroxymethyl)-1,4-oxazepane-4-carboxylate, and in the same manner as in Example 3, steps A, B and C and Example 9, the title compound was obtained.
MS (ESI+): [M+H]$^+$ 338.3.

Example 297

N-{[(6S,7R)-7-(3-chloro-4-fluorophenyl)-1,4-oxazepan-6-yl]methyl}sulfamide monohydrochloride Using tert-butyl (6S,7R)-7-(3-chloro-4-fluorophenyl)-6-(hydroxymethyl)-1,4-oxazepane-4-carboxylate, and in the same manner as in Example 3, steps A, B and C and Example 9, the title compound was obtained.
MS (ESI+): [M+H]$^+$ 338.0.

Example 298

N-{[(6R,7S)-7-(3-chloro-4-fluorophenyl)-1,4-oxazepan-6-yl]methyl}sulfamide monohydrochloride Using tert-butyl (6R,7S)-7-(3-chloro-4-fluorophenyl)-6-(hydroxymethyl)-1,4-oxazepane-4-carboxylate, and in the same manner as in Example 3, steps A, B and C and Example 9, the title compound was obtained.
MS (ESI+): [M+H]$^+$ 338.0.

Example 299

N-{[(6S,7R)-7-(3-chloro-4-fluorophenyl)-1,4-oxazepan-6-yl]methyl}-N'-methylsulfamide monohydrochloride Using tert-butyl (6S,7R)-7-(3-chloro-4-fluorophenyl)-6-(hydroxymethyl)-1,4-oxazepane-4-carboxylate, and in the same manner as in Example 3, steps A, B and C and Example 273, steps B and C, the title compound was obtained.
MS (ESI+): [M+H]$^+$ 352.0.

Example 300

N-{[(6R,7S)-7-(3-chloro-4-fluorophenyl)-1,4-oxazepan-6-yl]methyl}-N'-methylsulfamide monohydrochloride Using tert-butyl (6R,7S)-7-(3-chloro-4-fluorophenyl)-6-(hydroxymethyl)-1,4-oxazepane-4-carboxylate, and in the same manner as in Example 3, steps A, B and C and Example 273, steps B and C, the title compound was obtained.
MS (ESI+): [M+H]$^+$ 352.0.

Example 301

[(6S,7R)-7-(4-chloro-3-fluorophenyl)-1,4-oxazepan-6-yl]methanol monohydrochloride Using tert-butyl (6S,7R)-7-(4-chloro-3-fluorophenyl)-6-(hydroxymethyl)-1,4-oxazepane-4-carboxylate, and in the same manner as in Example 38, step F, the title compound was obtained.
MS (ESI+): [M+H]$^+$ 260.3.

Example 302

[(6R,7S)-7-(4-chloro-3-fluorophenyl)-1,4-oxazepan-6-yl]methanol monohydrochloride Using tert-butyl (6R,7S)-7-(4-chloro-3-fluorophenyl)-6-(hydroxymethyl)-1,4-oxazepane-4-carboxylate, and in the same manner as in Example 301, the title compound was obtained.
MS (ESI+): [M+H]$^+$ 260.3.

Example 303

1-[(6S,7R)-7-(4-chloro-3-fluorophenyl)-1,4-oxazepan-6-yl]ethane-1,2-diol monohydrochloride (retention time short)

A) tert-butyl (6R,7R)-7-(4-chloro-3-fluorophenyl)-6-formyl-1,4-oxazepane-4-carboxylate In the same manner as in Example 36, step A, the title compound was obtained.
MS (ESI+): [M+H]$^+$ 357.2.

B) 1-[(6S,7R)-7-(4-chloro-3-fluorophenyl)-1,4-oxazepan-6-yl]ethane-1,2-diol monohydrochloride (retention time short)

Using tert-butyl (6R,7R)-7-(4-chloro-3-fluorophenyl)-6-formyl-1,4-oxazepane-4-carboxylate, and in the same manner as in Example 45, steps L and M and Example 38, step F, the title compound was obtained. The diol intermediate obtained in a step corresponding to Example, step M, was a mixture of stereoisomers at 1-position. The mixture was separated and purified by silica gel column chromatography (eluent: hexane/ethyl acetate), and a compound with a shorter retention time was used for the next reaction, i.e., the above-mentioned Example 38, step F.
MS (ESI+): [M+H]$^+$ 290.3.

Example 304

1-[(6S,7R)-7-(4-chloro-3-fluorophenyl)-1,4-oxazepan-6-yl]ethane-1,2-diol monohydrochloride (retention time long)

In the same manner as in Example 303, step B, except that a compound with a longer retention time, which was obtained by separation and purification by silica gel column chromatography after the step corresponding to Step M, was used for the next reaction, the title compound was obtained.
MS (ESI+): [M+H]$^+$ 290.3.

Example 305

(6S,7R)-7-(4-chloro-3-fluorophenyl)-6-[(pyridin-2-yloxy)methyl]-1,4-oxazepane monohydrochloride In the same manner as in Example 44, step A and Example 31, step E, the title compound was obtained.
MS (ESI+): [M+H]$^+$ 337.1.

Example 306

2-{[(6S,7R)-7-(4-chloro-3-fluorophenyl)-1,4-oxazepan-6-yl]methoxy}pyridine-3-carboxylic acid monohydrochloride In the same manner as in Example 44, the title compound was obtained.
MS (ESI+): [M+H]$^+$ 381.1.

Example 307

1-[(6R,7R)-7-(4-chloro-3-fluorophenyl)-1,4-oxazepan-6-yl]methanamine dihydrochloride In the same manner as in Example 38, step F, the title compound was obtained.
MS (ESI+): [M+H]$^+$ 259.0.

Example 308

N-{[(6S,7R)-7-(4-chloro-3-fluorophenyl)-1,4-oxazepan-6-yl]methyl}acetamide monohydrochloride In the same manner as in Example 38, step F, the title compound was obtained.
MS (ESI+): [M+H]$^+$ 301.3.

Example 309

N-{[(6S,7R)-7-(4-chloro-3-fluorophenyl)-1,4-oxazepan-6-yl]methyl}butanamide monohydrochloride In the same manner as in Example 308, the title compound was obtained.
MS (ESI+): [M+H]$^+$ 329.2.

Example 310

N-{[(6S,7R)-7-(4-chloro-3-fluorophenyl)-1,4-oxazepan-6-yl]methyl}cyclopropanecarboxamide monohydrochloride In the same manner as in Example 308, the title compound was obtained.
MS (ESI+): [M+H]$^+$ 327.2.

Example 311

N-{[(6S,7R)-7-(4-chloro-3-fluorophenyl)-1,4-oxazepan-6-yl]methyl}-2,2-difluoroacetamide monohydrochloride In the same manner as in Example 41, step A and Example 38, step F, the title compound was obtained.
MS (ESI+): [M+H]$^+$ 337.3.

Example 312

N-{[(6S,7R)-7-(4-chloro-3-fluorophenyl)-1,4-oxazepan-6-yl]methyl}-2,2-difluoropropanamide In the same manner as in Example 311, the title compound was obtained.
MS (ESI+): [M+H]$^+$ 351.2

Example 313

N-{[(6S,7R)-7-(4-chloro-3-fluorophenyl)-1,4-oxazepan-6-yl]methyl}-2,2-difluorobutanamide monohydrochloride In the same manner as in Example 311, the title compound was obtained.
MS (ESI+): [M+H]$^+$ 365.2.

Example 314

N-{[(6S,7R)-7-(4-chloro-3-fluorophenyl)-1,4-oxazepan-6-yl]methyl}-3,3,3-trifluoropropanamide monohydrochloride In the same manner as in Example 311, the title compound was obtained.
MS (ESI+): [M+H]$^+$ 369.2.

Example 315

N-{[(6S,7R)-7-(4-chloro-3-fluorophenyl)-1,4-oxazepan-6-yl]methyl}-2-hydroxyacetamide monohydrochloride In the same manner as in Examples 105 and 106, the title compound was obtained.
MS (ESI+): [M+H]$^+$ 318.2.

Example 316

N-{[(6S,7R)-7-(4-chloro-3-fluorophenyl)-1,4-oxazepan-6-yl]methyl}-2-methoxy-N-methylacetamide monohydrochloride In the same manner as in Example 99, step A and Example 38, step F, the title compound was obtained.
MS (ESI+): [M+H]$^+$ 345.2.

Example 317

N-{[(6S,7R)-7-(4-chloro-3-fluorophenyl)-1,4-oxazepan-6-yl]methyl}-2-methoxypropanamide monohydrochloride In the same manner as in Example 311, the title compound was obtained.
MS (ESI+): [M+H]$^+$ 345.2.

Example 318

N-{[(6S,7R)-7-(4-chloro-3-fluorophenyl)-1,4-oxazepan-6-yl]methyl}-3-methoxypropanamide monohydrochloride In the same manner as in Example 311, the title compound was obtained.
MS (ESI+): [M+H]$^+$ 345.4.

Example 319

N-{[(6S,7R)-7-(4-chloro-3-fluorophenyl)-1,4-oxazepan-6-yl]methyl}-2-(cyclopropyloxy)acetamide monohydrochloride In the same manner as in Example 311, the title compound was obtained.
MS (ESI+): [M+H]$^+$ 357.2.

Example 320

N-{[(6S,7R)-7-(4-chloro-3-fluorophenyl)-1,4-oxazepan-6-yl]methyl}-2-(cyclopropylmethoxy)acetamide monohydrochloride In the same manner as in Example 311, the title compound was obtained.
MS (ESI+): [M+H]$^+$ 371.0.

Example 321

N-{[(6S,7R)-7-(4-chloro-3-fluorophenyl)-1,4-oxazepan-6-yl]methyl}-2-(difluoromethoxy)acetamide monohydrochloride In the same manner as in Example 311, the title compound was obtained.
MS (ESI+): [M+H]$^+$ 367.1.

Example 322

N-{[(6S,7R)-7-(4-chloro-3-fluorophenyl)-1,4-oxazepan-6-yl]methyl}-2-(2,2,2-trifluoroethoxy)acetamide monohydrochloride In the same manner as in Example 311, the title compound was obtained.
MS (ESI+): [M+H]$^+$ 399.2.

Example 323

N-{[(6S,7R)-7-(4-chloro-3-fluorophenyl)-1,4-oxazepan-6-yl]methyl}-2-(2-methoxyethoxy)acetamide monohydrochloride In the same manner as in Example 311, the title compound was obtained.
MS (ESI+): [M+H]$^+$ 375.1.

Example 324

N-{[(6S,7R)-7-(4-chloro-3-fluorophenyl)-1,4-oxazepan-6-yl]methyl}-2-hydroxy-2-methylpropanamide monohydrochloride In the same manner as in Example 311, the title compound was obtained.
MS (ESI+): [M+H]$^+$ 345.1.

Example 325

N-{[(6S,7R)-7-(4-chloro-3-fluorophenyl)-1,4-oxazepan-6-yl]methyl}-2-methoxy-2-methylpropanamide monohydrochloride In the same manner as in Example 311, the title compound was obtained.
MS (ESI+): [M+H]$^+$ 359.2.

Example 326

N-{[(6S,7R)-7-(4-chloro-3-fluorophenyl)-1,4-oxazepan-6-yl]methyl}-2-(pyridin-2-yloxy)acetamide monohydrochloride A) tert-butyl(pyridin-2-yloxy)acetate A solution of pyridin-2-ol (1 g), tert-butyl bromoacetate (2.33 mL) and cesium carbonate (6.85 g) in DMF (20 mL) was stirred at 60° C. overnight. The reaction mixture was poured into water, and the mixture was partitioned twice with ethyl acetate. The organic layers were combined, and the mixture was washed with brine, and dried over anhydrous magnesium sulfate. The solvent was evaporated under reduced pressure. The residue was purified by silica gel column chromatography (ethyl acetate/hexane) to give the title compound (0.18 g).
$^1$H NMR (300 MHz, CDCl$_3$) δ 1.46 (9H, s), 4.79 (2H, s), 6.82-6.93 (2H, m), 7.55-7.64 (1H, m), 8.07-8.13 (1H, m).

B) (pyridin-2-yloxy)acetic acid monohydrochloride

To a solution of tert-butyl(pyridin-2-yloxy)acetate (0.18 g) in THF (1.5 mL) was added 6 mol/L hydrochloric acid (1.5 mL) at 0° C., and the mixture was warmed to room temperature, and stirred for 2 hr. The solvent was evaporated under reduced pressure, and the resultant solid was recrystallized from ethyl acetate and diisopropyl ether to give the title compound (0.11 g).
$^1$H NMR (300 MHz, DMSO-d$_6$) δ 4.82 (2H, s), 6.85-6.94 (1H, m), 7.01 (1H, ddd, J=7.2, 5.1, 0.9 Hz), 7.68-7.82 (1H, m), 8.08-8.18 (1H, m), 9.17-10.75 (2H, m).

C) N-{[(6S,7R)-7-(4-chloro-3-fluorophenyl)-1,4-oxazepan-6-yl]methyl}-2-(pyridin-2-yloxy)acetamide monohydrochloride Using tert-butyl (6R,7R)-6-(aminomethyl)-7-(4-chloro-3-fluorophenyl)-1,4-oxazepane-4-carboxylate and (pyridin-2-yloxy)acetic acid monohydrochloride, and by a method similar to that of Example 39, the title compound was obtained.
$^1$H NMR (300 MHz, DMSO-d$_6$) δ 2.54-3.38 (8H, m), 3.71-3.84 (1H, m), 4.38 (1H, d, J=10.2 Hz), 4.66 (2H, s), 6.87-6.94 (1H, m), 6.98-7.05 (1H, m), 7.28-7.35 (1H, m), 7.49-7.65 (2H, m), 7.71-7.79 (1H, m), 8.13-8.20 (1H, m), 8.26 (1H, t, J=6.0 Hz), 9.16 (1H, dd, J=5.5, 2.1 Hz), 9.53-9.70 (1H, m).
MS (ESI+): [M+H]$^+$ 394.3.

Example 327

N-{[(6S,7R)-7-(4-chloro-3-fluorophenyl)-1,4-oxazepan-6-yl]methyl}-2-[(3-chloropyridin-2-yl)oxy]acetamide monohydrochloride In the same manner as in Example 121, the title compound was obtained.
MS (ESI+): [M+H]$^+$ 428.0.

Example 328

N-{[(6S,7R)-7-(4-chloro-3-fluorophenyl)-1,4-ox-azepan-6-yl]methyl}-2-(pyrimidin-2-yloxy)acetamide monohydrochloride Using tert-butyl (6R,7R)-6-(aminomethyl)-7-(4-chloro-3-fluorophenyl)-1,4-oxazepane-4-carboxylate and (pyrimidin-2-yloxy)acetic acid, and by a method similar to that of Example 39, the title compound was obtained.
$^1$H NMR (300 MHz, DMSO-$d_6$) δ 2.55-2.70 (1H, m), 2.82-3.40 (6H, m), 3.74-3.88 (1H, m), 3.94-4.08 (3H, m), 4.42 (1H, d, J=10.2 Hz), 6.66-6.77 (1H, m), 7.29-7.39 (1H, m), 7.49-7.68 (2H, m), 8.48-8.71 (3H, m), 9.13-9.38 (1H, m), 9.61-9.84 (1H, m).
MS (ESI+): [M+H]$^+$ 395.2.

Example 329

N-{[(6S,7R)-7-(4-chloro-3-fluorophenyl)-1,4-ox-azepan-6-yl]methyl}tetrahydrofuran-2-carboxamide monohydrochloride In the same manner as in Example 311, the title compound was obtained.
MS (ESI+): [M+H]$^+$ 357.4.

Example 330

N-{[(6S,7R)-7-(4-chloro-3-fluorophenyl)-1,4-ox-azepan-6-yl]methyl}tetrahydrofuran-3-carboxamide monohydrochloride In the same manner as in Example 311, the title compound was obtained.
MS (ESI+): [M+H]$^+$ 357.1.

Example 331

N-{[(6S,7R)-7-(4-chloro-3-fluorophenyl)-1,4-ox-azepan-6-yl]methyl}tetrahydro-2H-pyran-4-carboxamide monohydrochloride Using tert-butyl (6R,7R)-6-(aminomethyl)-7-(4-chloro-3-fluorophenyl)-1,4-oxazepane-4-carboxylate, and in the same manner as in Example 39, the title compound was obtained.
MS (ESI+): [M+H]$^+$ 371.3.

Example 332

N-{[(6S,7R)-7-(4-chloro-3-fluorophenyl)-1,4-ox-azepan-6-yl]methyl}-1,4-dioxane-2-carboxamide monohydrochloride In the same manner as in Example 311, the title compound was obtained.
MS (ESI+): [M+H]$^+$ 373.0.

Example 333

N-{[(6S,7R)-7-(4-chloro-3-fluorophenyl)-1,4-ox-azepan-6-yl]methyl}-2-(methylamino)acetamide dihydrochloride Using N-(tert-butoxycarbonyl)-N-methylglycine, and in the same manner as in Example 311, the title compound was obtained.
MS (ESI+): [M+H]$^+$ 330.1.

Example 334

N-{[(6S,7R)-7-(4-chloro-3-fluorophenyl)-1,4-ox-azepan-6-yl]methyl}-2-(dimethylamino)acetamide dihydrochloride In the same manner as in Example 311, the title compound was obtained.
MS (ESI+): [M+H]$^+$ 344.1.

Example 335

N-{[(6S,7R)-7-(4-chloro-3-fluorophenyl)-1,4-ox-azepan-6-yl]methyl}-2-(pyrrolidin-1-yl)acetamide dihydrochloride In the same manner as in Example 311, the title compound was obtained.
MS (ESI+): [M+H]$^+$ 370.1.

Example 336

N-{[(6S,7R)-7-(4-chloro-3-fluorophenyl)-1,4-ox-azepan-6-yl]methyl}-2-(4,4-difluoropiperidin-1-yl)acetamide dihydrochloride A) tert-butyl (6R,7R)-6-{[(chloroacetyl)amino]methyl}-7-(4-chloro-3-fluorophenyl)-1,4-oxazepane-4-carboxylate In the same manner as in Example 38, step E, the title compound was obtained.
$^1$H NMR (300 MHz, CDCl$_3$) δ 1.51 (9H, s), 2.23-3.80 (7H, m), 3.87-4.20 (5H, m), 6.48-8.06 (4H, m).

B) tert-butyl (6R,7R)-7-(4-chloro-3-fluorophenyl)-6-({[(4,4-difluoropiperidin-1-yl)acetyl]amino}methyl)-1,4-oxazepane-4-carboxylate To a solution of tert-butyl (6R,7R)-6-{[(chloroacetyl)amino]methyl}-7-(4-chloro-3-fluorophenyl)-1,4-oxazepane-4-carboxylate (130 mg), 4,4-difluoropiperidine monohydrochloride (94 mg) and potassium iodide (9.91 mg) in THF (3.0 mL) was added potassium carbonate (248 mg), and the mixture was stirred at 60° C. overnight. To the reaction mixture was added distilled water, and the mixture was extracted with ethyl acetate. The extract was washed with distilled water and brine, and dried over anhydrous sodium sulfate, and the solvent was evaporated under reduced pressure. The residue was purified by silica gel chromatography (hexane/ethyl acetate) to give the title compound (133 mg).
$^1$H NMR (300 MHz, CDCl$_3$) δ 1.48 (9H, s), 1.91-2.36 (6H, m), 2.50-3.11 (6H, m), 3.18-3.47 (2H, m), 3.47-3.73 (2H, m), 3.80-4.24 (4H, m), 6.84-8.41 (4H, m).

C) N-{[(6S,7R)-7-(4-chloro-3-fluorophenyl)-1,4-oxazepan-6-yl]methyl}-2-(4,4-difluoropiperidin-1-yl)acetamide dihydrochloride Using tert-butyl (6R,7R)-7-(4-chloro-3-fluorophenyl)-6-({[(4,4-difluoropiperidin-1-yl)acetyl]amino}methyl)-1,4-oxazepane-4-carboxylate, and in the same manner as in Example 38, step F, the title compound was obtained.
MS (ESI+): [M+H]$^+$ 420.2.

Example 337

N-{[(6S,7R)-7-(4-chloro-3-fluorophenyl)-1,4-oxazepan-6-yl]methyl}-2-(morpholin-4-yl)acetamide dihydrochloride In the same manner as in Example 311, the title compound was obtained.
MS (ESI+): [M+H]+ 386.3.

Example 338

N-{[(6S,7R)-7-(4-chloro-3-fluorophenyl)-1,4-oxazepan-6-yl]methyl}-2-(8-oxa-3-azabicyclo[3.2.1]oct-3-yl)acetamide dihydrochloride Using tert-butyl (6R,7R)-6-{[(chloroacetyl)amino]methyl}-7-(4-chloro-3-fluorophenyl)-1,4-oxazepane-4-carboxylate and 8-oxa-3-azabicyclo[3.2.1]octane monohydrochloride, and in the same manner as in Example 336, steps B and C, the title compound was obtained.
MS (ESI+): [M+H]+ 412.1.

Example 339

N-[2-({[(6S,7R)-7-(4-chloro-3-fluorophenyl)-1,4-oxazepan-6-yl]methyl}amino)-2-oxoethyl]-N-methylacetamide monohydrochloride In the same manner as in Example 311, the title compound was obtained.
MS (ESI+): [M+H]+ 372.1.

Example 340

N-[2-({[(6S,7R)-7-(4-chloro-3-fluorophenyl)-1,4-oxazepan-6-yl]methyl}amino)-2-oxoethyl]benzamide monohydrochloride Using tert-butyl (6R,7R)-6-(aminomethyl)-7-(4-chloro-3-fluorophenyl)-1,4-oxazepane-4-carboxylate and N-(phenylcarbonyl)glycine, and by a method similar to that of Example 39, the title compound was obtained.
$^1$H NMR (300 MHz, DMSO-$d_6$) δ 2.79-3.90 (10H, m), 3.95-4.06 (1H, m), 4.40 (1H, d, J=10.2 Hz), 7.33 (1H, dd, J=8.3, 1.5 Hz), 7.43-7.67 (5H, m), 7.86-7.93 (2H, m), 8.17 (1H, t, J=5.7 Hz), 8.82 (1H, t, J=5.7 Hz), 9.01-9.20 (1H, m), 9.38-9.53 (1H, m).
MS (ESI+): [M+H]+ 420.2.

Example 341

N-[2-({[(6S,7R)-7-(4-chloro-3-fluorophenyl)-1,4-oxazepan-6-yl]methyl}amino)-2-oxoethyl]pyridine-2-carboxamide monohydrochloride Using tert-butyl (6R,7R)-6-(aminomethyl)-7-(4-chloro-3-fluorophenyl)-1,4-oxazepane-4-carboxylate and N-(pyridin-2-ylcarbonyl)glycine, and by a method similar to that of Example 39, the title compound was obtained.
$^1$H NMR (300 MHz, DMSO-$d_6$) δ 2.41-2.65 (2H, m), 2.82-3.42 (5H, m), 3.75-3.87 (1H, m), 3.90 (2H, d, J=5.7 Hz), 3.95-4.07 (1H, m), 4.40 (1H, d, J=10.2 Hz), 7.29-7.39 (1H, m), 7.51-7.69 (3H, m), 7.96-8.10 (2H, m), 8.18-8.29 (1H, m), 8.64-8.72 (1H, m), 8.87-8.96 (1H, m), 9.04-9.25 (1H, m), 9.41-9.67 (1H, m).
MS (ESI+): [M+H]+ 421.2.

Example 342

N-[2-({[(6S,7R)-7-(4-chloro-3-fluorophenyl)-1,4-oxazepan-6-yl]methyl}amino)-2-oxoethyl]-N-methylpyridine-2-carboxamide monohydrochloride Using tert-butyl (6R,7R)-6-(aminomethyl)-7-(4-chloro-3-fluorophenyl)-1,4-oxazepane-4-carboxylate and N-methyl-N-(pyridin-2-ylcarbonyl)glycine, and by a method similar to that of Example 39, the title compound was obtained.
$^1$H NMR (300 MHz, DMSO-$d_6$) δ 2.47-2.87 (2H, m), 2.89-3.06 (5H, m), 3.07-3.47 (4H, m), 3.72-3.90 (1H, m), 3.96-4.09 (2H, m), 4.30-4.48 (1H, m), 7.24-7.76 (5H, m), 7.90-8.01 (1H, m), 8.11-8.33 (1H, m), 8.55-8.65 (1H, m), 9.12-9.34 (1H, m), 9.48-9.71 (1H, m).
MS (ESI+): [M+H]+ 435.2.

Example 343

N-{[(6S,7R)-7-(4-chloro-3-fluorophenyl)-1,4-oxazepan-6-yl]methyl}-2-[(phenylsulfonyl)amino]acetamide monohydrochloride Using tert-butyl (6R,7R)-6-(aminomethyl)-7-(4-chloro-3-fluorophenyl)-1,4-oxazepane-4-carboxylate and N-(phenylsulfonyl)glycine, and by a method similar to that of Example 39, the title compound was obtained.
$^1$H NMR (300 MHz, DMSO-$d_6$) δ 2.76-2.98 (1H, m), 3.05-3.41 (8H, m), 3.72-3.86 (1H, m), 3.94-4.04 (1H, m), 4.36 (1H, d, J=10.2 Hz), 7.31 (1H, dd, J=8.3, 1.9 Hz), 7.48-7.69 (5H, m), 7.76-7.85 (2H, m), 8.06 (1H, t, J=6.0 Hz), 8.17 (1H, t, J=5.9 Hz), 8.95-9.23 (1H, m), 9.37-9.60 (1H, m).
MS (ESI+): [M+H]+ 456.1.

Example 344

N-{[(6S,7R)-7-(4-chloro-3-fluorophenyl)-1,4-oxazepan-6-yl]methyl}-2-(pyridin-2-yl)acetamide monohydrochloride Using tert-butyl (6R,7R)-6-(aminomethyl)-7-(4-chloro-3-fluorophenyl)-1,4-oxazepane-4-carboxylate and (pyridin-2-yl)acetic acid, and by a method similar to that of Example 39, the title compound was obtained.
$^1$H NMR (300 MHz, DMSO-$d_6$) δ 2.55-4.13 (11H, m), 4.45 (1H, d, J=10.6 Hz), 7.28-7.38 (1H, m), 7.49-7.66 (2H, m), 7.75-7.87 (2H, m), 8.35 (1H, t, J=7.6 Hz), 8.65-8.82 (2H, m), 9.18-9.36 (1H, m), 9.61-9.80 (1H, m).
MS (ESI+): [M+H]+ 378.4.

Example 345

N-{[(6S,7R)-7-(4-chloro-3-fluorophenyl)-1,4-oxazepan-6-yl]methyl}-3-(pyridin-2-yl)propanamide monohydrochloride Using tert-butyl (6R,7R)-6-(aminomethyl)-7-(4-chloro-3-fluorophenyl)-1,4-oxazepane-4-carboxylate and 3-(pyridin-2-yl)propanoic acid, and by a method similar to that of Example 39, the title compound was obtained.
$^1$H NMR (300 MHz, DMSO-$d_6$) δ 2.62-2.74 (2H, m), 2.77-2.96 (2H, m), 3.03-3.37 (7H, m), 3.73-3.86 (1H, m), 3.94-4.07 (1H, m), 4.39 (1H, d, J=10.2 Hz), 7.25-7.36 (1H, m), 7.53 (1H, dd, J=10.6, 1.9 Hz), 7.61 (1H, t, J=7.9 Hz), 7.80-7.94 (2H, m), 8.30-8.39 (1H, m), 8.42-8.52 (1H, m), 8.72-8.81 (1H, m), 9.24-9.44 (1H, m), 9.67-9.89 (1H, m).
MS (ESI+): [M+H]$^+$ 392.2.

Example 346

N-{[(6S,7R)-7-(4-chloro-3-fluorophenyl)-1,4-oxazepan-6-yl]methyl}-2-(2-oxopyridin-1(2H)-yl)acetamide monohydrochloride Using tert-butyl (6R,7R)-6-(aminomethyl)-7-(4-chloro-3-fluorophenyl)-1,4-oxazepane-4-carboxylate and (2-oxopyridin-1(2H)-yl)acetic acid, and by a method similar to that of Example 39, the title compound was obtained.
$^1$H NMR (300 MHz, DMSO-d$_6$) δ 2.81-3.44 (6H, m), 3.76-3.89 (1H, m), 3.94-4.32 (2H, m), 4.41 (1H, d, J=10.2 Hz), 4.50 (2H, s), 6.22 (1H, td, J=6.6, 1.5 Hz), 6.33-6.40 (1H, m), 7.33 (1H, dd, J=8.3, 1.5 Hz), 7.44 (1H, ddd, J=9.0, 6.7, 2.1 Hz), 7.49-7.67 (3H, m), 8.38-8.50 (1H, m), 9.08-9.27 (1H, m), 9.42-9.60 (1H, m).
MS (ESI+): [M+H]$^+$ 394.1.

Example 347

N-{[(6S,7R)-7-(4-chloro-3-fluorophenyl)-1,4-oxazepan-6-yl]methyl}-2-(3-chloro-2-oxopyridin-1(2H)-yl)acetamide monohydrochloride In the same manner as in Example 121, the title compound was obtained.
MS (ESI+): [M+H]$^+$ 428.0.

Example 348

N-{[(6S,7R)-7-(4-chloro-3-fluorophenyl)-1,4-oxazepan-6-yl]methyl}-2-[(3-fluoropyridin-2-yl)oxy]acetamide Using tert-butyl (6R,7R)-6-(aminomethyl)-7-(4-chloro-3-fluorophenyl)-1,4-oxazepane-4-carboxylate and [(3-fluoropyridin-2-yl)oxy]acetic acid, and by a method similar to that of Example 39, followed by neutralization, the title compound was obtained.
$^1$H NMR (300 MHz, CDCl$_3$) δ 2.01-2.11 (1H, m), 2.78-2.94 (2H, m), 3.07-3.31 (4H, m), 3.58-3.71 (1H, m), 3.96-4.06 (1H, m), 4.23 (1H, d, J=9.1 Hz), 4.82-4.91 (1H, m), 5.00-5.09 (1H, m), 6.90-6.98 (1H, m), 6.98-7.05 (1H, m), 7.15 (1H, dd, J=9.8, 1.9 Hz), 7.28-7.43 (2H, m), 7.96 (1H, dd, J=4.9, 1.5 Hz), 8.58-8.69 (1H, m), 1H not detected.
MS (ESI+): [M+H]$^+$ 412.2.

Example 349

N-{[(6S,7R)-7-(4-chloro-3-fluorophenyl)-1,4-oxazepan-6-yl]methyl}-2-[(3-cyanopyridin-2-yl)oxy]acetamide Using sodium [(3-cyanopyridin-2-yl)oxy]acetate synthesized in the same manner as in Example 58, steps A and B, an operation similar to that of Example 311 and then neutralization were performed to give the title compound.
MS (ESI+): [M+H]$^+$ 419.0.

Example 350

N-{[(6S,7R)-7-(4-chloro-3-fluorophenyl)-1,4-oxazepan-6-yl]methyl}-2-methyl-2-(pyridin-2-yloxy)propanamide An operation similar to that of Example 121 and then neutralization were performed to give the title compound.
MS (ESI+): [M+H]$^+$ 422.2.

Example 351

N-{[(6S,7R)-7-(4-chloro-3-fluorophenyl)-1,4-oxazepan-6-yl]methyl}-2-(3-methylisoxazol-5-yl)acetamide monohydrochloride In the same manner as in Example 311, the title compound was obtained.
MS (ESI+): [M+H]$^+$ 382.0.

Example 352

N-{[(6S,7R)-7-(4-chloro-3-fluorophenyl)-1,4-oxazepan-6-yl]methyl}-2-(1H1,2,4-triazol-1-yl)acetamide trihydrochloride In the same manner as in Example 311, the title compound was obtained.
MS (ESI+): [M+H]$^+$ 368.0.

Example 353

N-{[(6S,7R)-7-(4-chloro-3-fluorophenyl)-1,4-oxazepan-6-yl]methyl}-3-(5-oxo-4,5-dihydro-1,2,4-oxadiazol-3-yl)benzamide monohydrochloride Using tert-butyl (6R,7R)-6-(aminomethyl)-7-(4-chloro-3-fluorophenyl)-1,4-oxazepane-4-carboxylate, and in the same manner as in Example 139, the title compound was obtained.
MS (ESI+): [M+H]$^+$ 447.1.

Example 354

N-{[(6S,7R)-7-(4-chloro-3-fluorophenyl)-1,4-oxazepan-6-yl]methyl}-2-methoxy-3-(5-oxo-4,5-dihydro-1,2,4-oxadiazol-3-yl)benzamide monohydrochloride In the same manner as in Example 353, the title compound was obtained.
MS (ESI+): [M+H]$^+$ 476.9.

Example 355

N-{[(6S,7R)-7-(4-chloro-3-fluorophenyl)-1,4-oxazepan-6-yl]methyl}-4-ethoxy-3-(5-oxo-4,5-dihydro-1,2,4-oxadiazol-3-yl)benzamide monohydrochloride In the same manner as in Example 353, the title compound was obtained.
MS (ESI+): [M+H]$^+$ 491.0.

Example 356

N-{[(6S,7R)-7-(4-chloro-3-fluorophenyl)-1,4-oxazepan-6-yl]methyl}-2-fluoro-3-(5-oxo-4,5-dihydro-1,2,4-oxadiazol-3-yl)benzamide monohydrochloride In the same manner as in Example 353, the title compound was obtained.
MS (ESI+): [M+H]$^+$ 465.1.

Example 357

N-{[(6S,7R)-7-(4-chloro-3-fluorophenyl)-1,4-oxazepan-6-yl]methyl}-2-fluoro-5-(5-oxo-4,5-dihydro-1,2,4-oxadiazol-3-yl)benzamide monohydrochloride In the same manner as in Example 353, the title compound was obtained.
MS (ESI+): [M+H]$^+$ 465.1.

Example 358

N-{[(6S,7R)-7-(4-chloro-3-fluorophenyl)-1,4-oxazepan-6-yl]methyl}-4-fluoro-3-(5-oxo-4,5-dihydro-1,2,4-oxadiazol-3-yl)benzamide monohydrochloride In the same manner as in Example 353, the title compound was obtained.
MS (ESI+): [M+H]$^+$ 465.1.

Example 359

N-{[(6S,7R)-7-(4-chloro-3-fluorophenyl)-1,4-oxazepan-6-yl]methyl}-3-fluoro-5-(5-oxo-4,5-dihydro-1,2,4-oxadiazol-3-yl)benzamide monohydrochloride In the same manner as in Example 353, the title compound was obtained.
MS (ESI+): [M+H]$^+$ 464.9.

Example 360

N-{[(6S,7R)-7-(4-chloro-3-fluorophenyl)-1,4-oxazepan-6-yl]methyl}-2-methyl-5-(5-oxo-4,5-dihydro-1,2,4-oxadiazol-3-yl)benzamide monohydrochloride In the same manner as in Example 353, the title compound was obtained.
MS (ESI+): [M+H]$^+$ 461.2.

Example 361

N-{[(6S,7R)-7-(4-chloro-3-fluorophenyl)-1,4-oxazepan-6-yl]methyl}-2-(5-methyl-1,2,4-oxadiazol-3-yl)benzamide monohydrochloride Using tert-butyl (6R,7R)-6-(aminomethyl)-7-(4-chloro-3-fluorophenyl)-1,4-oxazepane-4-carboxylate and 2-(5-methyl-1,2,4-oxadiazol-3-yl)benzoic acid, and by a method similar to that of Example 39, the title compound was obtained.
$^1$H NMR (300 MHz, DMSO-d$_6$) δ 2.40 (3H, s), 2.62-2.80 (1H, m), 2.99-3.90 (7H, m), 3.97-4.11 (1H, m), 4.50 (1H, d, J=10.2 Hz), 7.36 (1H, d, J=8.3 Hz), 7.50-7.78 (5H, m), 7.96 (1H, d, J=7.6 Hz), 8.66-8.77 (1H, m), 9.04-9.76 (2H, m).
MS (ESI+): [M+H]$^+$ 445.2.

Example 362

N-{[(6S,7R)-7-(4-chloro-3-fluorophenyl)-1,4-oxazepan-6-yl]methyl}-2-(methylsulfonyl)benzamide monohydrochloride Using tert-butyl (6R,7R)-6-(aminomethyl)-7-(4-chloro-3-fluorophenyl)-1,4-oxazepane-4-carboxylate and 2-(methylsulfonyl)benzoic acid, and by a method similar to that of Example 39, the title compound was obtained.
$^1$H NMR (300 MHz, DMSO-d$_6$) δ 2.58-2.77 (1H, m), 2.95-3.30 (5H, m), 3.38 (3H, s), 3.47-3.59 (1H, m), 3.77-3.92 (1H, m), 3.97-4.10 (1H, m), 4.49 (1H, d, J=10.2 Hz), 7.39 (1H, d, J=8.3 Hz), 7.49-7.84 (5H, m), 7.98 (1H, d, J=7.6 Hz), 8.74-8.84 (1H, m), 8.90-9.20 (1H, m), 9.31-9.64 (1H, m).
MS (ESI+): [M+H]$^+$ 441.2.

Example 363

N-{[(6S,7R)-7-(4-chloro-3-fluorophenyl)-1,4-oxazepan-6-yl]methyl}-2-(2-oxopyrrolidin-1-yl)benzamide monohydrochloride A) ethyl 2-[(4-chlorobutanoyl)amino]benzoate To a solution of ethyl 2-aminobenzoate (5 g) in pyridine (50 mL) was added 4-chlorobutanoyl chloride (3.6 mL) at 0° C., and the mixture was warmed to room temperature and stirred overnight. The reaction mixture was poured into water, and the mixture was partitioned twice with ethyl acetate. The organic layers were combined, and the mixture was washed with brine, and dried over anhydrous magnesium sulfate. The solvent was evaporated under reduced pressure. The residue was purified by silica gel column chromatography (ethyl acetate/hexane) to give the title compound (8.03 g).
$^1$H NMR (300 MHz, CDCl$_3$) δ 1.42 (3H, t, J=7.2 Hz), 2.16-2.29 (2H, m), 2.65 (2H, t, J=7.2 Hz), 3.66 (2H, t, J=6.5 Hz), 4.39 (2H, q, J=7.2 Hz), 7.09 (1H, ddd, J=8.1, 7.2, 1.3 Hz), 7.48-7.59 (1H, m), 7.99-8.10 (1H, m), 8.70 (1H, dd, J=8.5, 0.9 Hz), 11.18 (1H, brs).

B) ethyl 2-(2-oxopyrrolidin-1-yl)benzoate

To a solution of ethyl 2-[(4-chlorobutanoyl)amino]benzoate (8.03 g) in THF (120 ml) was added 60% sodium hydride (2.14 g) at 0° C., and the mixture was warmed to room temperature and stirred overnight. The reaction mixture was poured into water, and the mixture was partitioned twice with ethyl acetate. The organic layers were combined, and the mixture was washed with brine, and dried over anhydrous magnesium sulfate. The solvent was evaporated under reduced pressure. The residue was purified by silica gel column chromatography (ethyl acetate/hexane) to give the title compound (4.3 g).
$^1$H NMR (300 MHz, CDCl$_3$) δ 1.37 (3H, t, J=7.2 Hz), 2.16-2.29 (2H, m), 2.50-2.59 (2H, m), 3.81-3.89 (2H, m), 4.33 (2H, q, J=6.9 Hz), 7.24 (1H, dd, J=8.0, 1.1 Hz), 7.35 (1H, td, J=7.6, 1.1 Hz), 7.50-7.58 (1H, m), 7.93 (1H, dd, J=7.6, 1.5 Hz).

C) 2-(2-oxopyrrolidin-1-yl)benzoic acid

To a solution of ethyl 2-(2-oxopyrrolidin-1-yl)benzoate (4.3 g) in methanol (30 mL) was added 8 N aqueous sodium hydroxide solution (6.9 mL) at room temperature, and the mixture was heated to 50° C., and stirred overnight. The reaction mixture was allowed to cool to room temperature, and neutralized with 6 N aqueous hydrochloric acid solution (3 mL), and the solvent was evaporated under reduced pressure. The resultant crystals were recrystallized from ethanol to give the title compound (2.58 g).

$^1$H NMR (300 MHz, DMSO-$d_6$) δ 2.02-2.16 (2H, m), 2.28-2.38 (2H, m), 3.77 (2H, t, J=6.8 Hz), 7.31-7.42 (2H, m), 7.60 (1H, td, J=7.7, 1.7 Hz), 7.78 (1H, dd, J=7.6, 1.5 Hz), 12.79 (1H, brs).

D) N-{[(6S,7R)-7-(4-chloro-3-fluorophenyl)-1,4-oxazepan-6-yl]methyl}-2-(2-oxopyrrolidin-1-yl)benzamide monohydrochloride Using tert-butyl (6R,7R)-6-(aminomethyl)-7-(4-chloro-3-fluorophenyl)-1,4-oxazepane-4-carboxylate and 2-(2-oxopyrrolidin-1-yl)benzoic acid, and by a method similar to that of Example 39, the title compound was obtained.

$^1$H NMR (300 MHz, DMSO-$d_6$) δ 2.01-2.15 (2H, m), 2.32-2.42 (2H, m), 2.56-2.72 (1H, m), 2.95-3.61 (7H, m), 3.72-3.93 (3H, m), 3.97-4.08 (1H, m), 4.43-4.51 (1H, m), 7.28-7.69 (6H, m), 8.42 (1H, t, J=5.9 Hz), 9.11 (1H, brs), 9.59 (1H, brs).

MS (ESI+): [M+H]$^+$ 446.2.

Example 364

N-{[(6S,7R)-7-(4-chloro-3-fluorophenyl)-1,4-oxazepan-6-yl]methyl}-2-[(methylsulfonyl)amino]benzamide monohydrochloride Using tert-butyl (6R,7R)-6-(aminomethyl)-7-(4-chloro-3-fluorophenyl)-1,4-oxazepane-4-carboxylate and 2-[(methylsulfonyl)amino]benzoic acid, and by a method similar to that of Example 39, the title compound was obtained.

$^1$H NMR (300 MHz, DMSO-$d_6$) δ 2.67-2.82 (1H, m), 2.98-3.28 (8H, m), 3.35-3.47 (1H, m), 3.75-3.90 (1H, m), 3.96-4.10 (1H, m), 4.48 (1H, d, J=10.2 Hz), 7.10-7.21 (1H, m), 7.36 (1H, d, J=1.5 Hz), 7.50-7.67 (4H, m), 7.73 (1H, d, J=7.9 Hz), 8.94-9.05 (1H, m), 3H not detected.

MS (ESI+): [M+H]$^+$ 456.2.

Example 365

N-{[(6S,7R)-7-(4-chloro-3-fluorophenyl)-1,4-oxazepan-6-yl]methyl}pyridine-2-carboxamide monohydrochloride Using tert-butyl (6R,7R)-6-(aminomethyl)-7-(4-chloro-3-fluorophenyl)-1,4-oxazepane-4-carboxylate and pyridine-2-carboxylic acid, and by a method similar to that of Example 39, the title compound was obtained.

$^1$H NMR (300 MHz, DMSO-$d_6$) δ 2.75-2.93 (1H, m), 2.97-3.47 (6H, m), 3.73-3.89 (1H, m), 3.93-4.07 (1H, m), 4.48 (1H, d, J=10.2 Hz), 7.37 (1H, dd, J=8.3, 1.5 Hz), 7.53-7.69 (3H, m), 7.95-8.06 (2H, m), 8.64 (1H, d, J=4.9 Hz), 9.11 (1H, t, J=6.2 Hz), 9.30 (1H, brs), 9.84 (1H, brs).

MS (ESI+): [M+H]$^+$ 364.3.

Example 366

N-{[(6S,7R)-7-(4-chloro-3-fluorophenyl)-1,4-oxazepan-6-yl]methyl}pyridine 3-carboxamide monohydrochloride Using tert-butyl (6R,7R)-6-(aminomethyl)-7-(4-chloro-3-fluorophenyl)-1,4-oxazepane-4-carboxylate and pyridine-3-carboxylic acid, and by a method similar to that of Example 39, the title compound was obtained.

$^1$H NMR (300 MHz, DMSO-$d_6$) δ 2.69-2.89 (1H, m), 3.04-3.51 (6H, m), 3.74-3.90 (1H, m), 3.93-4.07 (1H, m), 4.50 (1H, d, J=10.2 Hz), 7.33-7.42 (1H, m), 7.50-7.79 (3H, m), 8.31-8.48 (1H, m), 8.76-8.86 (1H, m), 8.99-9.28 (3H, m), 9.49-9.70 (1H, m).

MS (ESI+): [M+H]$^+$ 364.3.

Example 367

N-{[(6S,7R)-7-(4-chloro-3-fluorophenyl)-1,4-oxazepan-6-yl]methyl}-2-oxo-1,2-dihydropyridine-3-carboxamide monohydrochloride Using tert-butyl (6R,7R)-6-(aminomethyl)-7-(4-chloro-3-fluorophenyl)-1,4-oxazepane-4-carboxylate and 2-methoxypyridine-3-carboxylic acid, and by a method similar to that of Example 39, the title compound was obtained.

$^1$H NMR (300 MHz, DMSO-$d_6$) δ 2.66-2.83 (1H, m), 3.05-4.33 (9H, m), 4.43 (1H, d, J=10.2 Hz), 6.46 (1H, t, J=6.6 Hz), 7.32 (1H, dd, J=8.3, 1.5 Hz), 7.49-7.63 (1H, m), 7.67-7.76 (1H, m), 8.27 (1H, dd, J=7.2, 2.3 Hz), 8.97-9.26 (1H, m), 9.34-9.70 (1H, m), 9.79 (1H, t, J=6.1 Hz), 12.48-12.62 (1H, m).

MS (ESI+): [M+H]$^+$ 380.2.

Example 368

N-{[(6S,7R)-7-(4-chloro-3-fluorophenyl)-1,4-oxazepan-6-yl]methyl}-3-[(methylsulfonyl)amino]pyridine-2-carboxamide monohydrochloride A) tert-butyl (6R,7R)-6-({[(3-aminopyridin-2-yl)carbonyl]amino}methyl)-7-(4-chloro-3-fluorophenyl)-1,4-oxazepane-4-carboxylate Using tert-butyl (6R,7R)-6-(aminomethyl)-7-(4-chloro-3-fluorophenyl)-1,4-oxazepane-4-carboxylate and 3-aminopyridine-2-carboxylic acid, and by a method similar to that of Example 39, step A, the title compound was obtained.

$^1$H NMR (300 MHz, CDCl$_3$) δ 1.51 (9H, s), 2.28-2.48 (1H, m), 3.12-3.95 (7H, m), 4.04-4.17 (2H, m), 5.86 (1H, brs), 6.88-6.99 (1H, m), 7.06-7.17 (2H, m), 7.18-7.26 (2H, m), 7.28-7.38 (1H, m), 7.71-7.89 (1H, m), 8.05-8.57 (1H, m).

B) tert-butyl (6R,7R)-7-(4-chloro-3-fluorophenyl)-6-{[({3-[(methylsulfonyl)amino]pyridin-2-yl}carbonyl)amino]methyl}-1,4-oxazepane-4-carboxylate To a solution of tert-butyl (6R,7R)-6-({[(3-aminopyridin-2-yl)carbonyl]amino}methyl)-7-(4-chloro-3-fluorophenyl)-1,4-oxazepane-4-carboxylate (110 mg) in DMF (3 ml) was added 60% sodium hydride at 0° C., and the mixture was stirred for 30 min. Methanesulfonyl chloride (53 μL) was added, and the mixture was warmed to room temperature, and stirred overnight. The reaction mixture was poured into water, and the mixture was partitioned twice with ethyl acetate. The organic layers were combined, and the mixture was washed with brine, and dried over anhydrous magnesium sulfate. The solvent was evaporated under reduced pressure. The residue was purified by silica gel column chromatography (ethyl acetate/hexane) to give the title compound (44.4 mg).

¹H NMR (300 MHz, CDCl₃) δ 1.52 (9H, s), 2.31-2.48 (1H, m), 3.04 (3H, s), 3.12-4.20 (9H, m), 7.07-7.24 (2H, m), 7.30-7.46 (2H, m), 8.09 (1H, dd, J=8.7, 1.1 Hz), 8.13-8.93 (2H, m), 11.59-11.76 (1H, m).

C) N-{[(6S,7R)-7-(4-chloro-3-fluorophenyl)-1,4-oxazepan-6-yl]methyl}-3-[(methylsulfonyl)amino]pyridine-2-carboxamide monohydrochloride Using tert-butyl (6R,7R)-7-(4-chloro-3-fluorophenyl)-6-{[({3-[(methylsulfonyl)amino]pyridin-2-yl}carbonyl)amino]methyl}-1,4-oxazepane-4-carboxylate, and by a method similar to that of Example 39, step B, the title compound was obtained.
¹H NMR (300 MHz, DMSO-d₆) δ 2.75-2.89 (1H, m), 2.96-3.33 (8H, m), 3.54-3.63 (1H, m), 3.74-3.91 (1H, m), 3.94-4.07 (1H, m), 4.47 (1H, d, J=10.2 Hz), 7.29-7.39 (1H, m), 7.49-7.67 (3H, m), 8.00 (1H, dd, J=8.7, 1.1 Hz), 8.33 (1H, dd, J=4.3, 1.3 Hz), 8.90-9.09 (1H, m), 9.25-9.47 (2H, m), 11.68 (1H, s).
MS (ESI+): [M+H]⁺ 457.3.

Example 369

N-{[(6S,7R)-7-(4-chloro-3-fluorophenyl)-1,4-oxazepan-6-yl]methyl}-2-oxo-2-(pyrrolidin-1-yl)acetamide monohydrochloride A) tert-butyl (6R,7R)-6-({[bromo(difluoro)acetyl]amino}methyl)-7-(4-chloro-3-fluorophenyl)-1,4-oxazepane-4-carboxylate In the same manner as in Example 38, step E, the title compound was obtained.
¹H NMR (300 MHz, CDCl₃) δ 1.52 (9H, s), 2.29-2.42 (1H, m), 3.06-3.63 (5H, m), 3.98-4.20 (4H, m), 7.07 (1H, d, J=7.9 Hz), 7.20 (1H, dd, J=9.8, 1.9 Hz), 7.33-7.43 (1H, m), 8.50 (1H, brs).

B) N-{[(6S,7R)-7-(4-chloro-3-fluorophenyl)-1,4-oxazepan-6-yl]methyl}-2-oxo-2-(pyrrolidin-1-yl)acetamide monohydrochloride To a solution of tert-butyl (6R,7R)-6-({[bromo(difluoro)acetyl]amino}methyl)-7-(4-chloro-3-fluorophenyl)-1,4-oxazepane-4-carboxylate (176 mg), pyrrolidine (0.085 mL) and potassium iodide (11.3 mg) in THF (3.4 ml) was added potassium carbonate (282 mg), and the mixture was stirred at 60° C. overnight. To the reaction mixture was added distilled water, and the mixture was extracted with ethyl acetate. The extract was washed with distilled water and brine, and dried over anhydrous sodium sulfate, and the solvent was evaporated under reduced pressure. The residue was purified by silica gel chromatography (hexane/ethyl acetate). The obtained residue was subjected to an operation similar to that of Example 38, step E to give the title compound (11.7 mg).
MS (ESI+): [M+H]⁺ 384.4.

Example 370

N-{[(6S,7R)-7-(4-chloro-3-fluorophenyl)-1,4-oxazepan-6-yl]methyl}methanesulfonamide monohydrochloride Using tert-butyl (6R,7R)-6-(aminomethyl)-7-(4-chloro-3-fluorophenyl)-1,4-oxazepane-4-carboxylate, and in the same manner as in Example 8, the title compound was obtained.
MS (ESI+): [M+H]⁺ 337.3.

Example 371

N-{[(6S,7R)-7-(4-chloro-3-fluorophenyl)-1,4-oxazepan-6-yl]methyl}-1,1-difluoromethanesulfonamide monohydrochloride In the same manner as in Example 370, the title compound was obtained.
MS (ESI+): [M+H]⁺ 373.0.

Example 372

1-{[(6S,7R)-7-(4-chloro-3-fluorophenyl)-1,4-oxazepan-6-yl]methyl}tetrahydropyrimidin-2(1H)-one monohydrochloride A) tert-butyl (6R,7R)-7-(4-chloro-3-fluorophenyl)-6-({[(3-chloropropyl)carbamoyl]amino}methyl)-1,4-oxazepane-4-carboxylate Using 3-chloropropyl isocyanate, and in the same manner as in Example 38, step E, the title compound was obtained.
MS (ESI+): [M+H]⁺ 478.1.

B) tert-butyl (6R,7R)-7-(4-chloro-3-fluorophenyl)-6-[(2-oxotetrahydropyrimidin-1(2H)-yl)methyl]-1,4-oxazepane-4-carboxylate To a solution of tert-butyl (6R,7R)-7-(4-chloro-3-fluorophenyl)-6-({[(3-chloropropyl)carbamoyl]amino}methyl)-1,4-oxazepane-4-carboxylate (531 mg) in DMF (22 mL) was added sodium hydride (48.8 mg, 60% in oil) under ice-cooling, and the mixture was stirred at 0° C. for 2 hr. To the reaction mixture was added distilled water, and the mixture was extracted with ethyl acetate. The extract was washed with distilled water and brine, and dried over anhydrous sodium sulfate, and the solvent was evaporated under reduced pressure. The residue was purified by silica gel chromatography (hexane/ethyl acetate) to give the title compound (563 mg).
¹H NMR (300 MHz, CDCl₃) δ 1.41-1.91 (11H, m), 2.24-2.49 (1H, m), 2.66-3.90 (11H, m), 3.99-4.17 (1H, m), 4.23 (1H, d, J=9.1 Hz), 4.55 (1H, brs), 7.07 (1H, d, J=8.3 Hz), 7.16 (1H, dd, J=9.8, 1.9 Hz), 7.31-7.41 (1H, m).

C) 1-{[(6S,7R)-7-(4-chloro-3-fluorophenyl)-1,4-oxazepan-6-yl]methyl}tetrahydropyrimidin-2(1H)-one monohydrochloride Using tert-butyl (6R,7R)-7-(4-chloro-3-fluorophenyl)-6-[(2-oxotetrahydropyrimidin-1(2H)-yl)methyl]-1,4-oxazepane-4-carboxylate, and in the same manner as in Example 38, step F, the title compound was obtained.
MS (ESI+): [M+H]⁺ 342.2.

Example 373

1-{[(6S,7R)-7-(4-chloro-3-fluorophenyl)-1,4-oxazepan-6-yl]methyl}-3-methyl-1H-pyrazole-5-carboxylic acid monohydrochloride Using tert-butyl (6S,7R)-7-(4-chloro-3-fluorophenyl)-6-{[(methylsulfonyl)oxy]methyl}-1,4-oxazepane-4-carboxylate, and in the same manner as in Example 185, the title compound was obtained.
MS (ESI+): [M+H]⁺ 368.3.

Example 374

1-{[(6S,7R)-7-(4-chloro-3-fluorophenyl)-1,4-oxazepan-6-yl]methyl}-5-methyl-1H-pyrazole-3-carboxylic acid monohydrochloride In the same manner as in Example 373, the title compound was obtained.
MS (ESI+): [M+H]⁺ 368.3.

Example 375

1-{[(6S,7R)-7-(4-chloro-3-fluorophenyl)-1,4-oxazepan-6-yl]methyl}pyrrolidin-2-one monohydrochloride Using tert-butyl (6R,7R)-6-(aminomethyl)-7-(4-chloro-3-fluorophenyl)-1,4-oxazepane-4-carboxylate and 4-chlorobutanoyl chloride, and by a method similar to that of Example 363, steps A and B and Example 39, step B, the title compound was obtained.
$^1$H NMR (300 MHz, DMSO-$d_6$) δ 1.62-1.89 (2H, m), 1.98-2.30 (2H, m), 2.62 (1H, dd, J=14.0, 4.9 Hz), 2.80-3.04 (2H, m), 3.06-3.40 (4H, m), 3.71-4.12 (4H, m), 4.42 (1H, d, J=9.8 Hz), 7.29 (1H, dd, J=8.1, 1.7 Hz), 7.50 (1H, dd, J=10.4, 1.7 Hz), 7.63 (1H, t, J=7.9 Hz), 9.19-9.48 (2H, m).
MS (ESI+): [M+H]⁺ 327.2.

Example 376

1-{[(6S,7R)-7-(4-chloro-3-fluorophenyl)-1,4-oxazepan-6-yl]methyl}piperidin-2-one monohydrochloride Using tert-butyl (6R,7R)-6-(aminomethyl)-7-(4-chloro-3-fluorophenyl)-1,4-oxazepane-4-carboxylate and 5-chloropentanoyl chloride, and by a method similar to that of Example 363, steps A and B and Example 39, step B, the title compound was obtained.
$^1$H NMR (300 MHz, DMSO-$d_6$) δ 1.42-1.68 (4H, m), 2.01-2.20 (2H, m), 2.65 (1H, dd, J=13.8, 5.1 Hz), 2.78-3.33 (7H, m), 3.61 (1H, dd, J=13.6, 9.4 Hz), 3.73-3.88 (1H, m), 3.98-4.11 (1H, m), 4.42 (1H, d, J=10.2 Hz), 7.24-7.33 (1H, m), 7.51 (1H, dd, J=10.6, 1.9 Hz), 7.63 (1H, t, J=8.1 Hz), 9.18-9.63 (2H, m).
MS (ESI+): [M+H]⁺ 341.1.

Example 377

1-{[(6S,7R)-7-(4-chloro-3-fluorophenyl)-1,4-oxazepan-6-yl]methyl}-4-(5-oxo-4,5-dihydro-1,2,4-oxadiazol-3-yl)pyridin-2(1H)-one monohydrochloride In the same manner as in Example 43, the title compound was obtained.
MS (ESI+): [M+H]⁺ 421.3.

Example 378

1-{[(6S,7R)-7-(4-chloro-3-fluorophenyl)-1,4-oxazepan-6-yl]methyl}-3-(5-methyl-4H-1,2,4-triazol-3-yl)pyridin-2(1H)-one monohydrochloride A) tert-butyl (6R,7R)-6-[(3-carbamothioyl-2-oxopyridin-1(2H)-yl)methyl]-7-(4-chloro-3-fluorophenyl)-1,4-oxazepane-4-carboxylate Diethyl dithiophosphate (0.189 mL, 1.13 mmol) was added to a solution (5 mL, 20.00 mmol) of tert-butyl (6R,7R)-7-(4-chloro-3-fluorophenyl)-6-[(3-cyano-2-oxopyridin-1(2H)-yl)methyl]-1,4-oxazepane-4-carboxylate (348 mg, 0.75 mmol) in 4 N hydrogen chloride-ethyl acetate. The reaction mixture was stirred at room temperature overnight. The reaction mixture was concentrated under reduced pressure. The residue was diluted with saturated aqueous sodium hydrogen carbonate solution (10 mL) and ethyl acetate (10 ml), and di-tert-butyl dicarbonate (0.210 mL, 0.90 mmol) was added. The reaction mixture was stirred at room temperature for 4 hr. To the reaction mixture was added water, and the mixture was extracted with ethyl acetate. The extract was washed with brine, and dried over anhydrous sodium sulfate. The solvent was evaporated under reduced pressure. The residue was purified by silica gel column chromatography to give the title compound (225 mg, 0.454 mmol, 60.2%).
$^1$H NMR (300 MHz, CDCl$_3$) δ 1.52 (9H, brs), 2.82 (1H, brs), 3.05-3.23 (2H, m), 3.57-3.82 (2H, m), 3.87-4.13 (5H, m), 6.44 (1H, t, J=6.6 Hz), 7.07-7.28 (2H, m), 7.35-7.44 (1H, m), 7.90 (1H, brs), 8.35 (1H, brs), 9.12 (1H, d, J=7.2 Hz), 11.39 (1H, brs).
MS (ESI+): [M+H]⁺ 496.1.

B) 1-{[(6S,7R)-7-(4-chloro-3-fluorophenyl)-1,4-oxazepan-6-yl]methyl}-3-(5-methyl-4H-1,2,4-triazol-3-yl)pyridin-2(1H)-one monohydrochloride Using tert-butyl (6R,7R)-6-[(3-carbamothioyl-2-oxopyridin-1(2H)-yl)methyl]-7-(4-chloro-3-fluorophenyl)-1,4-oxazepane-4-carboxylate, and in the same manner as in Example 200, the title compound was obtained.
MS (ESI+): [M+H]⁺ 418.1.

Example 379

1-{[(6S,7R)-7-(4-chloro-3-fluorophenyl)-1,4-oxazepan-6-yl]methyl}-3-(5-oxo-4,5-dihydro-1H-1,2,4-triazol-3-yl)pyridin-2(1H)-one monohydrochloride Using tert-butyl (6R,7R)-6-[(3-carbamothioyl-2-oxopyridin-1(2H)-yl)methyl]-7-(4-chloro-3-fluorophenyl)-1,4-oxazepane-4-carboxylate and methyl carbazate, and in the same manner as in Example 200, the title compound was obtained.
MS (ESI+): [M+H]⁺ 420.1.

Example 380

1-{[(6S,7R)-7-(4-chloro-3-fluorophenyl)-1,4-oxazepan-6-yl]methyl}-3-(1H-tetrazol-5-yl)pyridin-2(1H)-one In the same manner as in Example 208, the title compound was obtained.
MS (ESI+): [M+H]⁺ 405.1.

Example 381

2-{[(6S,7R)-7-(4-chloro-3-fluorophenyl)-1,4-oxazepan-6-yl]methyl}pyridazin-3(2H)-one monohydrochloride In the same manner as in Example 44, step A and Example 31, step E, the title compound was obtained.
MS (ESI+): [M+H]⁺ 338.2.

Example 382

2-{[(6S,7R)-7-(4-chloro-3-fluorophenyl)-1,4-oxazepan-6-yl]methyl}-4-(5-oxo-4,5-dihydro-1,2,4-oxadiazol-3-yl)pyridazin-3(2H)-one monohydrochloride In the same manner as in Example 209, the title compound was obtained.
MS (ESI+): [M+H]$^+$ 422.3.

Example 383

3-{[(6S,7R)-7-(4-chloro-3-fluorophenyl)-1,4-oxazepan-6-yl]methyl}quinazoline-2,4(1H,3H)-dione monohydrochloride A) tert-butyl (6R,7R)-6-({[(2-aminophenyl)carbonyl]amino}methyl)-7-(4-chloro-3-fluorophenyl)-1,4-oxazepane-4-carboxylate Using tert-butyl (6R,7R)-6-(aminomethyl)-7-(4-chloro-3-fluorophenyl)-1,4-oxazepane-4-carboxylate and 2-aminobenzoic acid, and by a method similar to that of Example 39, step A, the title compound was obtained.
$^1$H NMR (300 MHz, CDCl$_3$) δ 1.48 (9H, s), 2.30-2.45 (1H, m), 3.03-3.23 (2H, m), 3.31-3.44 (1H, m), 3.49-3.65 (2H, m), 3.96-4.18 (4H, m), 5.51-5.64 (1H, m), 6.59-6.70 (1H, m), 7.10-7.29 (3H, m), 7.32-7.41 (1H, m), 7.46-7.55 (1H, m), 7.78-7.92 (1H, m), 2H not detected.

B) tert-butyl (6R,7R)-7-(4-chloro-3-fluorophenyl)-6-[(2,4-dioxo-1,4-dihydroquinazolin-3(2H)-yl)methyl]-1,4-oxazepane-4-carboxylate To a solution of tert-butyl (6R,7R)-6-({[(2-aminophenyl)carbonyl]amino}methyl)-7-(4-chloro-3-fluorophenyl)-1,4-oxazepane-4-carboxylate (191.1 mg) and triethylamine (167 μL) in THF (5 mL) was added bis(trichloromethyl) carbonate (142 mg) at 0° C., and the mixture was stirred at 50° C. for 3 hr. The reaction mixture was allowed to cool to room temperature, and poured into water, and the mixture was partitioned twice with ethyl acetate. The organic layers were combined, and the mixture was washed with brine, and dried over anhydrous magnesium sulfate. The solvent was evaporated under reduced pressure. The residue was purified by silica gel column chromatography (ethyl acetate/hexane) to give the title compound (193.8 mg).
$^1$H NMR (300 MHz, CDCl$_3$) δ 1.40-1.52 (9H, m), 2.92-3.09 (1H, m), 3.41-3.55 (1H, m), 3.62-4.12 (6H, m), 4.23-4.39 (2H, m), 6.87 (1H, d, J=8.3 Hz), 6.95-7.13 (3H, m), 7.15-7.25 (1H, m), 7.50-7.62 (1H, m), 7.97 (1H, d, J=7.9 Hz), 8.21-8.41 (1H, m).

C) 3-{[(6S,7R)-7-(4-chloro-3-fluorophenyl)-1,4-oxazepan-6-yl]methyl}quinazoline-2,4(1H,3H)-dione monohydrochloride Using tert-butyl (6R,7R)-7-(4-chloro-3-fluorophenyl)-6-[(2,4-dioxo-1,4-dihydroquinazolin-3(2H)-yl)methyl]-1,4-oxazepane-4-carboxylate, and by a method similar to that of Example 39, step B, the title compound was obtained.
$^1$H NMR (300 MHz, DMSO-d$_6$) δ 2.90-3.04 (1H, m), 3.06-3.30 (4H, m), 3.43-3.55 (1H, m), 3.77-3.89 (1H, m), 3.94-4.07 (2H, m), 4.52 (1H, d, J=10.2 Hz), 7.13-7.23 (2H, m), 7.32 (1H, dd, J=8.5, 1.3 Hz), 7.50-7.59 (2H, m), 7.61-7.69 (1H, m), 7.84-7.90 (1H, m), 8.50-9.26 (2H, m), 11.44 (1H, s).
MS (ESI+): [M+H]$^+$ 404.3.

Example 384

3-{[(6S,7R)-7-(4-chloro-3-fluorophenyl)-1,4-oxazepan-6-yl]methyl}-1-methylquinazoline-2,4(1H,3H)-dione monohydrochloride Using tert-butyl (6R,7R)-7-(4-chloro-3-fluorophenyl)-6-[(2,4-dioxo-1,4-dihydroquinazolin-3(2H)-yl)methyl]-1,4-oxazepane-4-carboxylate, and by a method similar to that of Example 99, step A and Example 39, step B, the title compound was obtained.

$^1$H NMR (300 MHz, DMSO-d$_6$) δ 2.93-3.35 (5H, m), 3.45 (3H, s), 3.59 (1H, dd, J=13.6, 5.3 Hz), 3.78-3.91 (1H, m), 3.95-4.12 (2H, m), 4.52 (1H, d, J=10.2 Hz), 7.25-7.34 (2H, m), 7.38-7.58 (3H, m), 7.78 (1H, ddd, J=8.5, 7.2, 1.7 Hz), 7.99 (1H, dd, J=7.9, 1.5 Hz), 8.67-9.30 (2H, m).

MS (ESI+): [M+H]$^+$ 418.3.

Example 385

3-{[(6S,7R)-7-(4-chloro-3-fluorophenyl)-1,4-oxazepan-6-yl]methyl}pyrido[3,2-d]pyrimidine-2,4(1H,3H)-dione monohydrochloride Using tert-butyl (6R,7R)-6-(aminomethyl)-7-(4-chloro-3-fluorophenyl)-1,4-oxazepane-4-carboxylate and 3-aminopyridine-2-carboxylic acid, and by a method similar to that of Example 383, the title compound was obtained.
$^1$H NMR (300 MHz, DMSO-d$_6$) δ 2.91-3.40 (5H, m), 3.49 (1H, dd, J=13.2, 4.9 Hz), 3.78-3.91 (1H, m), 3.95-4.09 (2H, m), 4.53 (1H, d, J=10.2 Hz), 7.33 (1H, dd, J=8.3, 1.5 Hz), 7.49-7.70 (4H, m), 8.42-8.51 (1H, m), 8.76-8.98 (1H, m), 9.35-9.54 (1H, m), 11.58 (1H, s).
MS (ESI+): [M+H]$^+$ 405.2.

Example 386

3-{[(6S,7R)-7-(4-chloro-3-fluorophenyl)-1,4-oxazepan-6-yl]methyl}pteridine-2,4(1H,3H)-dione monohydrochloride Using tert-butyl (6R,7R)-6-(aminomethyl)-7-(4-chloro-3-fluorophenyl)-1,4-oxazepane-4-carboxylate and 3-aminopyrazine-2-carboxylic acid, and by a method similar to that of Example 383, the title compound was obtained.
$^1$H NMR (300 MHz, DMSO-d$_6$) δ 2.85-3.29 (4H, m), 3.34-3.48 (2H, m), 3.79-3.92 (1H, m), 3.97-4.09 (2H, m), 4.53 (1H, d, J=9.8 Hz), 7.34 (1H, dd, J=8.1, 1.7 Hz), 7.52-7.62 (2H, m), 8.56 (1H, d, J=2.3 Hz), 8.68 (1H, d, J=2.3 Hz), 8.70-8.89 (1H, m), 9.11-9.41 (1H, m), 12.17-12.33 (1H, m).
MS (ESI+): [M+H]$^+$ 406.3.

Example 387

3-{[(6S,7R)-7-(4-chloro-3-fluorophenyl)-1,4-oxazepan-6-yl]methyl}-1-methylpteridine-2,4(1H,3H)-dione monohydrochloride Using tert-butyl (6R,7R)-7-(4-chloro-3-fluorophenyl)-6-[(2,4-dioxo-1,4-dihydropteridin-3(2H)-yl)methyl]-1,4-oxazepane-4-carboxylate synthesized by a method similar to that in Example 383, steps A and B, and by N-methylation by a method similar to that in Example 99, step A, tert-butyl (6R,7R)-7-(4-chloro-3-fluorophenyl)-6-[(1-methyl-2,4-dioxo-1,4-dihydropteridin-3(2H)-yl)methyl]-1,4-oxazepane-4-carboxylate was obtained. Using this compound, and in the same manner as in Example 386, the title compound was obtained.

$^1$H NMR (300 MHz, DMSO-$d_6$) δ 2.89-3.06 (1H, m), 3.09-3.44 (5H, m), 3.46-3.57 (4H, m), 3.80-3.93 (1H, m), 3.97-4.16 (2H, m), 4.53 (1H, d, J=10.2 Hz), 7.31 (1H, dd, J=8.3, 1.5 Hz), 7.48-7.62 (2H, m), 8.62 (1H, d, J=2.3 Hz), 8.69-8.92 (1H, m), 9.08-9.39 (1H, m).
MS (ESI+): [M+H]$^+$ 420.4.

Example 388

2-{[(6R,7R)-7-(4-chloro-3-fluorophenyl)-1,4-oxazepan-6-yl]methyl}-1H-benzimidazole monohydrochloride A) tert-butyl (6R,7R)-6-{2-[(2-aminophenyl)amino]-2-oxoethyl}-7-(4-chloro-3-fluorophenyl)-1,4-oxazepane-4-carboxylate Using [(6R,7R)-4-(tert-butoxycarbonyl)-7-(4-chloro-3-fluorophenyl)-1,4-oxazepan-6-yl]acetic acid synthesized in a method similar to that of Example 66, and in the same manner as in Example 39, step A, the title compound was obtained.
MS (ESI+): [M+H]$^+$ 478.3.

B) tert-butyl (6R,7R)-6-(1H-benzimidazol-2-ylmethyl)-7-(4-chloro-3-fluorophenyl)-1,4-oxazepane-4-carboxylate A solution of tert-butyl (6R,7R)-6-{2-[(2-aminophenyl)amino]-2-oxoethyl}-7-(4-chloro-3-fluorophenyl)-1,4-oxazepane-4-carboxylate (155 mg) in acetic acid (1.1 mL) was stirred at 100° C. for 2 hr. The reaction mixture was neutralized with saturated aqueous sodium hydrogen carbonate solution, and the mixture was extracted with ethyl acetate. The extract was washed with distilled water and brine, and dried over anhydrous sodium sulfate, and the solvent was evaporated under reduced pressure. The residue was purified by silica gel chromatography (hexane/ethyl acetate) to give the title compound (128 mg).
$^1$H NMR (300 MHz, CDCl$_3$) δ 1.59 (9H, s), 2.36-2.52 (1H, m), 2.77-2.90 (2H, m), 3.16-3.40 (2H, m), 3.59-3.76 (1H, m), 3.94-4.21 (4H, m), 7.10 (1H, d, J=8.3 Hz), 7.15-7.24 (3H, m), 7.33-7.43 (1H, m), 7.44-7.72 (2H, m), 11.66 (1H, brs).

C) 2-{[(6R,7R)-7-(4-chloro-3-fluorophenyl)-1,4-oxazepan-6-yl]methyl}-1H-benzimidazole monohydrochloride Using tert-butyl (6R,7R)-6-(1H-benzimidazol-2-ylmethyl)-7-(4-chloro-3-fluorophenyl)-1,4-oxazepane-4-carboxylate, and in the same manner as in Example 38, step F, the title compound was obtained.
MS (ESI+): [M+H]$^+$ 360.1.

Example 389

N-{[(6S,7R)-7-(4-chloro-3-fluorophenyl)-1,4-oxazepan-6-yl]methyl}pyridin-2-amine dihydrochloride A) tert-butyl (6R,7R)-7-(4-chloro-3-fluorophenyl)-6-[(pyridin-2-ylamino)methyl]-1,4-oxazepane-4-carboxylate To a solution of tert-butyl (6R,7R)-7-(4-chloro-3-fluorophenyl)-6-formyl-1,4-oxazepane-4-carboxylate (150 mg) and pyridin-2-amine (79 mg) in THF (1.3 mL) and methanol (0.1 ml) was added borane-2-picoline complex (90 mg), and the mixture was stirred at room temperature for 3 hr. The reaction mixture was concentrated under reduced pressure, the residue was stirred in 1 M aqueous hydrochloric acid solution, and neutralized with saturated aqueous sodium hydrogen carbonate solution, and the mixture was extracted with ethyl acetate. The extract was washed with distilled water and brine, and dried over anhydrous sodium sulfate, and the solvent was evaporated under reduced pressure. The residue was purified by silica gel chromatography (hexane/ethyl acetate) to give the title compound (112 mg).
MS (ESI+): [M+H]$^+$ 436.1.

B) N-{[(6S,7R)-7-(4-chloro-3-fluorophenyl)-1,4-oxazepan-6-yl]methyl}pyridin-2-amine dihydrochloride Using tert-butyl (6R,7R)-7-(4-chloro-3-fluorophenyl)-6-[(pyridin-2-ylamino)methyl]-1,4-oxazepane-4-carboxylate, and in the same manner as in Example 38, step F, the title compound was obtained.
MS (ESI+): [M+H]$^+$ 336.1.

Example 390

N-{[(6S,7R)-7-(4-chloro-3-fluorophenyl)-1,4-oxazepan-6-yl]methyl}pyrimidin-2-amine monohydrochloride A) tert-butyl (6R,7R)-7-(4-chloro-3-fluorophenyl)-6-[(pyrimidin-2-ylamino)methyl]-1,4-oxazepane-4-carboxylate A solution of tert-butyl (6R,7R)-6-(aminomethyl)-7-(4-chloro-3-fluorophenyl)-1,4-oxazepane-4-carboxylate (120.7 mg), 2-chloropyrimidine (40.5 mg) and potassium carbonate (46.5 mg) in ethanol (3 mL) was stirred at room temperature overnight, and the solvent was evaporated under reduced pressure. The residue was partitioned between ethyl acetate and water, and the organic layer was washed with brine, and dried over anhydrous magnesium sulfate. The solvent was evaporated under reduced pressure. The residue was purified by silica gel column chromatography (ethyl acetate/hexane) to give the title compound (97.8 mg).
$^1$H NMR (300 MHz, CDCl$_3$) δ 1.40-1.55 (9H, m), 2.31-2.50 (1H, m), 3.06-4.21 (9H, m), 5.15-6.56 (2H, m), 7.08-7.43 (3H, m), 8.11-8.27 (2H, m).

B) N-{[(6S,7R)-7-(4-chloro-3-fluorophenyl)-1,4-oxazepan-6-yl]methyl}pyrimidin-2-amine monohydrochloride Using tert-butyl (6R,7R)-7-(4-chloro-3-fluorophenyl)-6-[(pyrimidin-2-ylamino)methyl]-1,4-oxazepane-4-carboxylate, and by a method similar to that of Example 39, step B, the title compound was obtained.

$^1$H NMR (300 MHz, DMSO-d$_6$) δ 2.78-2.94 (1H, m), 3.04-3.36 (5H, m), 3.37-3.49 (1H, m), 3.75-3.88 (1H, m), 3.93-4.05 (1H, m), 4.50 (1H, d, J=10.2 Hz), 6.75 (1H, t, J=5.1 Hz), 7.37 (1H, dd, J=8.3, 1.9 Hz), 7.55-7.67 (2H, m), 7.96-8.15 (1H, m), 8.38 (2H, d, J=5.3 Hz), 9.19-9.39 (1H, m), 9.74-9.88 (1H, m).

MS (ESI+): [M+H]$^+$ 337.1.

Example 391

N-{[(6S,7R)-7-(4-chloro-3-fluorophenyl)-1,4-oxazepan-6-yl]methyl}-1,3-benzoxazol-2-amine dihydrochloride A) tert-butyl (6R,7R)-6-[(1,3-benzoxazol-2-ylamino)methyl]-7-(4-chloro-3-fluorophenyl)-1,4-oxazepane-4-carboxylate To a solution of tert-butyl (6R,7R)-6-(aminomethyl)-7-(4-chloro-3-fluorophenyl)-1,4-oxazepane-4-carboxylate (150 mg) and 2-chlorobenzoxazole (0.0573 ml) in DMF (1.4 mL) was added ethyldiisopropylamine (0.183 ml), and the mixture was stirred at 60° C. for 4 hr. To the reaction mixture was added distilled water, and the mixture was extracted with ethyl acetate. The extract was washed with distilled water and brine, and dried over anhydrous sodium sulfate, and the solvent was evaporated under reduced pressure. The residue was purified by silica gel chromatography (hexane/ethyl acetate) to give the title compound (175 mg).

$^1$H NMR (300 MHz, CDCl$_3$) δ 1.54 (9H, s), 2.38-2.53 (1H, m), 3.09-3.71 (5H, m), 3.97-4.26 (4H, m), 6.79-7.43 (8H, m).

B) N-{[(6S,7R)-7-(4-chloro-3-fluorophenyl)-1,4-oxazepan-6-yl]methyl}-1,3-benzoxazol-2-amine dihydrochloride Using tert-butyl (6R,7R)-6-[(1,3-benzoxazol-2-ylamino)methyl]-7-(4-chloro-3-fluorophenyl)-1,4-oxazepane-4-carboxylate, and in the same manner as in Example 38, step F, the title compound was obtained.

MS (ESI+): [M+H]$^+$ 376.3.

Example 392

3-[2-({[(6S,7R)-7-(4-chloro-3-fluorophenyl)-1,4-oxazepan-6-yl]methyl}amino)-1,3-benzoxazol-4-yl]-1,2,4-oxadiazol-5(4H)-one monohydrochloride A) 2-sulfanyl-1,3-benzoxazole-4-carbonitrile A solution of 2-amino-3-hydroxybenzonitrile (298 mg) and potassium ethylxanthate (427 mg) in pyridine (7.4 ml) was heated under reflux for 3 hr. To the reaction mixture was added distilled water, the mixture was acidified with 1 M hydrochloric acid, and the mixture was extracted with ethyl acetate. The extract was washed with distilled water and brine, and dried over anhydrous magnesium sulfate, and the solvent was evaporated under reduced pressure. The residue was purified by silica gel chromatography (hexane/ethyl acetate) to give the title compound (178 mg).

$^1$H NMR (300 MHz, CDCl$_3$) δ 7.28-7.56 (3H, m), 8.87 (1H, d, J=4.2 Hz).

B) 2-chloro-1,3-benzoxazole-4-carbonitrile

A mixture of 2-sulfanyl-1,3-benzoxazole-4-carbonitrile (178 mg), thionyl chloride (427 mg) and DMF (0.0468 mL) was stirred at 80° C. for 5 min. The reaction mixture was concentrated under reduced pressure, ethyl acetate and THF were added, and the mixture was neutralized with saturated aqueous sodium hydrogen carbonate solution. The mixture was extracted with ethyl acetate, and the extract was washed with distilled water and brine, and dried over anhydrous magnesium sulfate, and the solvent was evaporated under reduced pressure. The residue was washed with diisopropyl ether to give the title compound (178 mg).

$^1$H NMR (300 MHz, CDCl$_3$) δ 7.42-7.54 (1H, m), 7.70 (1H, d, J=8.0 Hz), 7.77 (1H, d, J=8.3 Hz).

C) tert-butyl (6R,7R)-7-(4-chloro-3-fluorophenyl)-6-{[(4-cyano-1,3-benzoxazol-2-yl)amino]methyl}-1,4-oxazepane-4-carboxylate Using tert-butyl (6R,7R)-6-(aminomethyl)-7-(4-chloro-3-fluorophenyl)-1,4-oxazepane-4-carboxylate and 2-chloro-1,3-benzoxazole-4-carbonitrile, and in the same manner as in Example 391, step A, the title compound was obtained.

$^1$H NMR (300 MHz, CDCl$_3$) δ 1.54 (9H, s), 2.43-2.55 (1H, m), 3.08-3.23 (1H, m), 3.32-3.48 (2H, m), 3.48-3.67 (2H, m), 4.02-4.22 (5H, m), 6.98-7.07 (1H, m), 7.28-7.46 (4H, m), 7.45-7.55 (1H, m).

D) tert-butyl (6R,7R)-7-(4-chloro-3-fluorophenyl)-6-({[4-(5-oxo-4,5-dihydro-1,2,4-oxadiazol-3-yl)-1,3-benzoxazol-2-yl]amino}methyl)-1,4-oxazepane-4-carboxylate Using tert-butyl (6R,7R)-7-(4-chloro-3-fluorophenyl)-6-{[(4-cyano-1,3-benzoxazol-2-yl)amino]methyl}-1,4-oxazepane-4-carboxylate, and in the same manner as in Example 31, steps D and E, the title compound was obtained.

$^1$H NMR (300 MHz, CDCl$_3$) δ 1.50-1.65 (9H, m), 2.39-2.53 (1H, m), 3.12-3.65 (5H, m), 4.05-4.23 (4H, m), 6.99-7.19 (3H, m), 7.33 (1H, d, J=7.6 Hz), 7.41-7.48 (1H, m), 7.63-7.72 (1H, m), 7.77 (1H, d, J=7.9 Hz), 9.99 (1H, brs).

E) 3-[2-({[(6S,7R)-7-(4-chloro-3-fluorophenyl)-1,4-oxazepan-6-yl]methyl}amino)-1,3-benzoxazol-4-yl]-1,2,4-oxadiazol-5(4H)-one monohydrochloride Using tert-butyl (6R,7R)-7-(4-chloro-3-fluorophenyl)-6-({[4-(5-oxo-4,5-dihydro-1,2,4-oxadiazol-3-yl)-1,3-benzoxazol-2-yl]amino}methyl)-1,4-oxazepane-4-carboxylate, and in the same manner as in Example 38, step F, the title compound was obtained.

MS (ESI+): [M+H]$^+$ 460.3.

Example 393

3-{[(6S,7R)-7-(4-chloro-3-fluorophenyl)-1,4-oxazepan-6-yl]methyl}-2-methylquinazolin-4(3H)-one monohydrochloride Using tert-butyl (6R,7R)-6-(aminomethyl)-7-(4-chloro-3-fluorophenyl)-1,4-oxazepane-4-carboxylate and 2-(acetylamino)benzoic acid, and by a method similar to that of Example 39, the title compound was obtained.

$^1$H NMR (300 MHz, DMSO-d$_6$) δ 2.45-2.55 (3H, m), 3.05-3.47 (5H, m), 3.65 (1H, dd, J=14.5, 5.5 Hz), 3.81-3.94 (1H, m), 4.05-4.16 (1H, m), 4.31 (1H, dd, J=14.4, 9.1 Hz), 4.61 (1H, d, J=9.8 Hz), 7.28-7.36 (1H, m), 7.46-7.59 (3H, m), 7.62-7.71 (1H, m), 7.80-7.90 (1H, m), 8.04 (1H, d, J=7.9 Hz), 9.17-9.36 (1H, m), 9.46-9.64 (1H, m), 2H not detected.

MS (ESI+): [M+H]$^+$ 402.1.

Example 394

N-{2-[(6R,7R)-7-(4-chloro-3-fluorophenyl)-1,4-oxazepan-6-yl]ethyl}-2-methoxyacetamide monohydrochloride Using tert-butyl (6S,7R)-7-(4-chloro-3-fluorophenyl)-6-{[(methylsulfonyl)oxy]methyl}-1,4-oxazepane-4-carboxylate, and in the same manner as in Example 66, step A, Example 1, step G, Example 32, step C and Example 39, step B, the title compound was obtained.

MS (ESI+): [M+H]$^+$ 345.2.

Example 395

(6R,7R)-7-(4-chloro-3-fluorophenyl)-N-(2-methoxyethyl)-1,4-oxazepane-6-carboxamide monohydrochloride A) (6R,7R)-4-(tert-butoxycarbonyl)-7-(4-chloro-3-fluorophenyl)-1,4-oxazepane-6-carboxylic acid Using tert-butyl (6R,7R)-7-(4-chloro-3-fluorophenyl)-6-formyl-1,4-oxazepane-4-carboxylate, and in the same manner as in Example 36, step B, the title compound was obtained.

MS (ESI+): [M−H]$^+$ 372.2.

B) (6R,7R)-7-(4-chloro-3-fluorophenyl)-N-(2-methoxyethyl)-1,4-oxazepane-6-carboxamide monohydrochloride Using (6R,7R)-4-(tert-butoxycarbonyl)-7-(4-chloro-3-fluorophenyl)-1,4-oxazepane-6-carboxylic acid, and in the same manner as in Example 311, the title compound was obtained.

MS (ESI+): [M+H]$^+$ 331.0.

Example 396

(6R,7R)-7-(4-chloro-3-fluorophenyl)-N-methoxy-N-methyl-1,4-oxazepane-6-carboxamide monohydrochloride Using tert-butyl (6S,7R)-7-(4-chloro-3-fluorophenyl)-6-(hydroxymethyl)-1,4-oxazepane-4-carboxylate, and in the same manner as in Example 36, steps A and B and Example 39, the title compound was obtained.

MS (ESI+): [M+H]$^+$ 317.3.

Example 397

N-[(6R,7S)-7-(4-chloro-3-fluorophenyl)-1,4-oxazepan-6-yl]acetamide

Using tert-butyl (6S,7R)-7-(4-chloro-3-fluorophenyl)-6-(hydroxymethyl)-1,4-oxazepane-4-carboxylate, and in the same manner as in Example 36, steps A, B, C and D, Example 32, step C and Example 39, step B, the title compound was obtained.

MS (ESI+): [M+H]$^+$ 287.2.

Example 398

N-[(6R,7S)-7-(4-chloro-3-fluorophenyl)-1,4-oxazepan-6-yl]methanesulfonamide monohydrochloride Using tert-butyl (6S,7R)-7-(4-chloro-3-fluorophenyl)-6-(hydroxymethyl)-1,4-oxazepane-4-carboxylate, and in the same manner as in Example 36, steps A, B, C and D, Example 32, step C and Example 39, step B, the title compound was obtained.

MS (ESI+): [M+H]$^+$ 323.3.

Example 399

N-[(6R,7S)-7-(4-chloro-3-fluorophenyl)-1,4-oxazepan-6-yl]ethanesulfonamide monohydrochloride Using tert-butyl (6S,7R)-7-(4-chloro-3-fluorophenyl)-6-(hydroxymethyl)-1,4-oxazepane-4-carboxylate, and in the same manner as in Example 36, steps A, B, C and D, Example 32, step C and Example 39, step B, the title compound was obtained.

MS (ESI+): [M+H]$^+$ 337.0

Example 400

N-[(6R,7S)-7-(4-chloro-3-fluorophenyl)-1,4-oxazepan-6-yl]-N'-methylsulfamide monohydrochloride Using tert-butyl (6S,7R)-7-(4-chloro-3-fluorophenyl)-6-(hydroxymethyl)-1,4-oxazepane-4-carboxylate, and in the same manner as in Example 36, steps A, B, C and D and Example 273, the title compound was obtained.

MS (ESI+): [M+H]$^+$ 337.9

Example 401

[(6R*,7S*)-7-(4-chloro-3-methylphenyl)-1,4-oxazepan-6-yl]methanol monohydrochloride (retention time short)

A) tert-butyl (6R*,7S*)-7-(4-chloro-3-methylphenyl)-6-(hydroxymethyl)-1,4-oxazepane-4-carboxylate (retention time short)

The racemate (6.0 g) obtained using 4-chloro-3-methylbenzaldehyde, and in the same manner as in Example 13, steps A to H, was separated by HPLC (LC-8A, 50 mmID×300 mL, manufactured by Shimazu, mobile phase: distilled water/acetonitrile) and SFC (column: CHIRALPAK AD-H, 30 mmID×250 mL, manufactured by DAICEL CHEMICAL INDUSTRIES, LTD., mobile phase: carbon dioxide/methanol=850/150) to give the title compound having a shorter retention time.

$^1$H NMR (300 MHz, CDCl$_3$) δ 1.51 (9H, s), 2.17-2.21 (1H, m), 2.37 (3H, s), 3.09-3.27 (2H, m), 3.42-3.48 (1H, m), 3.53-3.61 (2H, m), 4.05-4.20 (4H, m), 4.29-4.32 (1H, d, J=9.6 Hz), 7.11-7.14 (1H, m), 7.27 (1H, s), 7.29-7.31 (1H, d, J=8 Hz).

B) [(6R*,7S*)-7-(4-chloro-3-methylphenyl)-1,4-oxazepan-6-yl]methanol monohydrochloride (retention time short)

Using tert-butyl (6R*,7S*)-7-(4-chloro-3-methylphenyl)-6-(hydroxymethyl)-1,4-oxazepane-4-carboxylate (retention time short), and in the same manner as in Example 13, step I, the title compound was obtained.
MS (ESI+): [M+H]$^+$ 256.0.

Example 402

[(6R*,7S*)-7-(4-chloro-3-methylphenyl)-1,4-oxazepan-6-yl]methanol monohydrochloride (retention time long)

A) tert-butyl (6R*,7S*)-7-(4-chloro-3-methylphenyl)-6-(hydroxymethyl)-1,4-oxazepane-4-carboxylate (retention time long)

Using 4-chloro-3-methylbenzaldehyde, and in the same manner as in Example 401, step A, the title compound having a longer retention time was obtained.
$^1$H NMR (300 MHz, CDCl$_3$) δ 1.52 (9H, s), 2.17-2.19 (1H, m), 2.37 (3H, s), 3.09-3.27 (2H, m), 3.43-3.48 (1H, m), 3.53-3.61 (2H, m), 4.05-4.20 (4H, m), 4.29-4.32 (1H, d, J=9.6 Hz), 7.11-7.14 (1H, m), 7.27 (1H, s), 7.29-7.31 (1H, d, J=8 Hz).

B) [(6R*,7S*)-7-(4-chloro-3-methylphenyl)-1,4-oxazepan-6-yl]methanol monohydrochloride (retention time long)

Using tert-butyl (6R*,7S*)-7-(4-chloro-3-methylphenyl)-6-(hydroxymethyl)-1,4-oxazepane-4-carboxylate (retention time long), and in the same manner as in Example 13, step I, the title compound was obtained.
MS (ESI+): [M+H]$^+$ 256.0.

Example 403

N-{[(6R*,7S*)-7-(4-chloro-3-methylphenyl)-1,4-oxazepan-6-yl]methyl}-2-methoxyacetamide monohydrochloride Using tert-butyl (6R*,7S*)-7-(4-chloro-3-methylphenyl)-6-(hydroxymethyl)-1,4-oxazepane-4-carboxylate (retention time short) obtained in Example 401, and in the same manner as in Example 38, steps B to F, the title compound was obtained.
MS (ESI+): [M+H]$^+$ 327.4.

Example 404

1-{[(6R*,7S*)-7-(4-chloro-3-methylphenyl)-1,4-oxazepan-6-yl]methyl}-3-(5-oxo-4,5-dihydro-1,2,4-oxadiazol-3-yl)pyridin-2(1H)-one monohydrochloride Using tert-butyl (6R*,7S*)-7-(4-chloro-3-methylphenyl)-6-(hydroxymethyl)-1,4-oxazepane-4-carboxylate (retention time short) (500 mg) obtained in Example 401, and in the same manner as in Example 31, steps B to E, the title compound (166 mg) was obtained.
MS (ESI+): [M+H]$^+$ 417.2.

Example 405

[(6R*,7S*)-7-(3-chloro-4-methylphenyl)-1,4-oxazepan-6-yl]methanol monohydrochloride (retention time short)

A) tert-butyl (6R*,7S*)-7-(3-chloro-4-methylphenyl)-6-(hydroxymethyl)-1,4-oxazepane-4-carboxylate (retention time short)

The racemate obtained using 3-chloro-4-methylbenzaldehyde, and in the same manner as in Example 13, steps A to H was separated by HPLC (LC-8A, 50 mmID×300 mL, manufactured by Shimazu, mobile phase: distilled water/acetonitrile) and SFC (column: CHIRALPAK AD-H, 30 mmID×250 mL, manufactured by DAICEL CHEMICAL INDUSTRIES, LTD., mobile phase: carbon dioxide/methanol=800/200) to give the title compound having a shorter retention time.
$^1$H NMR (300 MHz, CDCl$_3$) δ 1.51 (9H, s), 2.17 (1H, s), 2.35 (3H, s), 3.08-3.16 (1H, m), 3.21-3.28 (1H, m), 3.41-3.46 (1H, m), 3.52-3.61 (2H, m), 4.04-4.10 (2H, m), 4.14-4.17 (1H, m), 4.28-4.30 (1H, d, J=9.6 Hz), 7.12-7.14 (1H, t), 7.17-7.19 (1H, d, J=8.0 Hz), 7.36 (1H, s), 1H not detected.

B) [(6R*,7S*)-7-(3-chloro-4-methylphenyl)-1,4-oxazepan-6-yl]methanol monohydrochloride (retention time short)

Using tert-butyl (6R*,7S*)-7-(3-chloro-4-methylphenyl)-6-(hydroxymethyl)-1,4-oxazepane-4-carboxylate (retention time short), and in the same manner as in Example 13, step I, the title compound was obtained.
MS (ESI+): [M+H]$^+$ 256.3.

Example 406

[(6R*,7S*)-7-(3-chloro-4-methylphenyl)-1,4-oxazepan-6-yl]methanol monohydrochloride (retention time long)

A) tert-butyl (6R*,7S*)-7-(3-chloro-4-methylphenyl)-6-(hydroxymethyl)-1,4-oxazepane-4-carboxylate (retention time long)

Using 3-chloro-4-methylbenzaldehyde, and in the same manner as in Example 405, step A, the title compound having a longer retention time was obtained.
$^1$H NMR (300 MHz, CDCl$_3$) δ 1.43 (9H, s), 2.10 (1H, s), 2.28 (3H, s), 3.01-3.09 (1H, m), 3.14-3.21 (1H, m), 3.34-3.39 (1H, m), 3.45-3.54 (2H, m), 3.97-4.08 (2H, m), 4.10-4.11 (1H, m), 4.21-4.23 (1H, d, J=9.6 Hz), 7.05-7.09 (1H, d, J=15.6 Hz), 7.10-7.12 (1H, d, J=8.0 Hz), 7.29 (1H, s), 1H not detected.

B) [(6R*,7S*)-7-(3-chloro-4-methylphenyl)-1,4-oxazepan-6-yl]methanol monohydrochloride (retention time long)

Using tert-butyl (6R*,7S*)-7-(3-chloro-4-methylphenyl)-6-(hydroxymethyl)-1,4-oxazepane-4-carboxylate (retention time long), and in the same manner as in Example 13, step I, the title compound was obtained.
MS (ESI+): [M+H]$^+$ 256.0.

Example 407

N-{[(6R*,7S*)-7-(3-chloro-4-methylphenyl)-1,4-oxazepan-6-yl]methyl}-2-methoxyacetamide monohydrochloride Using tert-butyl (6R*,7S*)-7-(3-chloro-4-methylphenyl)-6-(hydroxymethyl)-1,4-oxazepane-4-carboxylate (retention time short) obtained in Example 405, and in the same manner as in Example 38, steps B to F, the title compound was obtained.
MS (ESI+): [M+H]$^+$ 327.4.

Example 408

1-{[(6R*,7S*)-7-(3-chloro-4-methylphenyl)-1,4-oxazepan-6-yl]methyl}-3-(5-oxo-4,5-dihydro-1,2,4-oxadiazol-3-yl)pyridin-2(1H)-one monohydrochloride Using tert-butyl (6R*,7S*)-7-(3-chloro-4-methylphenyl)-6-(hydroxymethyl)-1,4-oxazepane-4-carboxylate (retention time short) (500 mg) obtained in Example 405, and in the same manner as in Example 31, steps B to E, the title compound (20 mg) was obtained.
MS (ESI+): [M+H]$^+$ 417.2.

Example 409

N-{[(6R*,7S*)-7-(3-chloro-4-methylphenyl)-1,4-oxazepan-6-yl]methyl}methanesulfonamide monohydrochloride Using tert-butyl (6R*,7S*)-7-(3-chloro-4-methylphenyl)-6-(hydroxymethyl)-1,4-oxazepane-4-carboxylate (retention time short) obtained in Example 405, and in the same manner as in Example 5, step A, Example 6, steps A and B and Example 8, the title compound was obtained.
MS (ESI+): [M+H]$^+$ 333.2.

Example 410

[(6RS,7SR)-7-(1-benzothiophen-2-yl)-1,4-oxazepan-6-yl]methanol monohydrochloride A) tert-butyl (6RS,7SR)-7-(1-benzothiophen-2-yl)-6-(hydroxymethyl)-1,4-oxazepane-4-carboxylate Using 1-benzothiophene-2-carbaldehyde, and in the same manner as in Example 13, steps A to H, the title compound was obtained.
$^1$H NMR (300 MHz, CDCl$_3$) δ 1.51 (9H, s), 2.35-2.49 (1H, m), 3.09-3.77 (5H, m), 3.99-4.26 (3H, m), 4.75 (1H, d, J=9.4 Hz), 7.23 (1H, s), 7.28-7.38 (2H, m), 7.68-7.75 (1H, m), 7.77-7.85 (1H, m), 1H not detected.

B) [(6RS,7SR)-7-(1-benzothiophen-2-yl)-1,4-oxazepan-6-yl]methanol monohydrochloride Using tert-butyl (6RS,7SR)-7-(1-benzothiophen-2-yl)-6-(hydroxymethyl)-1,4-oxazepane-4-carboxylate, and in the same manner as in Example 13, step I, the title compound was obtained.
MS (ESI+): [M−H]$^+$ 264.2.

Example 411

Ethyl (5RS,6RS)-6-(3,4-dichlorophenyl)-1,4-oxazepane-5-carboxylate monohydrochloride A) 4-tert-butyl 5-ethyl (5RS,6RS)-6-(3,4-dichlorophenyl)-1,4-oxazepane-4,5-dicarboxylate To a solution (2.0 mL) of 4-tert-butyl 5-ethyl 6-(3,4-dichlorophenyl)-2,3-dihydro-1,4-oxazepane-4,5(7H)-dicarboxylate (200 mg) obtained in Example 14, step C in THF is were added sodium borohydride (36 mg) and water (2 drops), and the mixture was stirred at room temperature for 3 days. To the reaction solution were added water and 0.1 N hydrochloric acid, and the mixture was extracted with ethyl acetate. The ethyl acetate layer was washed with water and brine, and dried over anhydrous sodium sulfate. The solvent was evaporated under reduced pressure. The residue was purified by silica gel column chromatography (ethyl acetate/hexane) to give the title compound (124 mg) as a high-polar compound of the obtained diastereomer.
$^1$H NMR (300 MHz, CDCl$_3$) δ 1.11 (1.68H, t, J=7.2 Hz), 1.15 (1.32H, t, J=7.2 Hz), 1.47 (3.96H, s), 1.50 (5.04H, s), 3.40-3.48 (2H, m), 3.60-3.88 (5H, m), 4.03-4.11 (2H, m), 4.59 (0.44H, d, J=9.0 Hz), 4.87 (0.56H, d, J=9.0 Hz), 7.09-7.15 (1H, m), 7.35-7.40 (2H, m).

B) ethyl (5RS,6RS)-6-(3,4-dichlorophenyl)-1,4-oxazepane-5-carboxylate monohydrochloride Using 4-tert-butyl 5-ethyl (5RS,6RS)-6-(3,4-dichlorophenyl)-1,4-oxazepane-4,5-dicarboxylate, and in the same manner as in Example 1, step I, the title compound (55 mg) was obtained.
MS (ESI+): [M+H]$^+$ 318.1.

Example 412

Ethyl (5RS,6SR)-6-(3,4-dichlorophenyl)-1,4-oxazepane-5-carboxylate monohydrochloride Using 4-tert-butyl 5-ethyl (5RS,6SR)-6-(3,4-dichlorophenyl)-1,4-oxazepane-4,5-dicarboxylate obtained in Example 14, step D, and in the same manner as in Example 10, step H, the title compound (54 mg) was obtained.
MS (ESI+): [M+H]$^+$ 318.2.

Example 413

(7RS)-7-(3,4-dichlorophenyl)-7-[(4-methoxyphenoxy)methyl]-1,4-oxazepane monohydrochloride Using tert-butyl (7RS)-7-(3,4-dichlorophenyl)-7-[(4-methoxyphenoxy)methyl]-1,4-oxazepane-4-carboxylate, and in the same manner as in Example 39, step B, the title compound was obtained.
MS (ESI+): [M+H]$^+$ 382.1

Example 414

[(7R)-7-(3,4-dichlorophenyl)-1,4-oxazepan-7-yl]methanol monohydrochloride

By a method similar to that of Example 47, the title compound was obtained.

¹H NMR (300 MHz, DMSO-d₆) δ 2.36 (1H, dd, J=16.4, 9.6 Hz), 2.76 (1H, dd, J=16.4, 7.7 Hz), 3.00-3.20 (3H, m), 3.24-3.37 (2H, m), 3.40-3.49 (1H, m), 3.56-3.69 (1H, m), 3.94-4.07 (1H, m), 5.09 (1H, t, J=5.9 Hz), 7.35 (1H, dd, J=8.5, 2.1 Hz), 7.57 (1H, d, J=2.3 Hz), 7.60-7.67 (1H, m), 9.00-9.27 (2H, m).

MS (ESI+): [M+H]⁺ 276.1.

Example 415

2-{[(7R)-7-(3,4-dichlorophenyl)-1,4-oxazepan-7-yl]methoxy}ethanol monohydrochloride Using tert-butyl (7R)-7-(3,4-dichlorophenyl)-7-(hydroxymethyl)-1,4-oxazepane-4-carboxylate and (2-bromoethoxy)(tert-butyl)dimethylsilane, and by a method similar to that of Example 363, step B and Example 39, step B, the title compound was obtained.

¹H NMR (300 MHz, DMSO-d₆) δ 2.23-2.40 (1H, m), 2.68-2.82 (1H, m), 3.00-3.22 (3H, m), 3.23-3.50 (7H, m), 3.61 (1H, dd, J=14.0, 8.3 Hz), 3.93-4.08 (1H, m), 4.84-5.30 (1H, m), 7.35 (1H, dd, J=8.5, 2.1 Hz), 7.57 (1H, d, J=1.9 Hz), 7.63 (1H, d, J=8.3 Hz), 8.66-9.18 (2H, m).

MS (ESI+): [M+H]⁺ 320.1.

Example 416

2-{[(7S)-7-(3,4-dichlorophenyl)-1,4-oxazepan-7-yl]methoxy}ethanol monohydrochloride Using tert-butyl (7S)-7-(3,4-dichlorophenyl)-7-(hydroxymethyl)-1,4-oxazepane-4-carboxylate and (2-bromoethoxy)(tert-butyl)dimethylsilane, and by a method similar to that of Example 363, step B and Example 39, step B, the title compound was obtained.

¹H NMR (300 MHz, DMSO-d₆) δ 2.23-2.37 (1H, m), 2.75 (1H, dd, J=16.1, 7.8 Hz), 3.02-3.21 (4H, m), 3.24-3.37 (5H, m), 3.41-3.50 (1H, m), 3.53-3.66 (1H, m), 3.95-4.06 (1H, m), 5.07 (1H, t, J=5.9 Hz), 7.36 (1H, dd, J=8.5, 2.1 Hz), 7.58 (1H, d, J=1.9 Hz), 7.64 (1H, d, J=8.3 Hz), 8.72-8.95 (2H, m).

MS (ESI+): [M+H]⁺ 320.1.

Example 417

3-{[(7S)-7-(3,4-dichlorophenyl)-1,4-oxazepan-7-yl]methoxy}propane-1,2-diol monohydrochloride A) tert-butyl (7S)-7-(3,4-dichlorophenyl)-7-[(prop-2-en-1-yloxy)methyl]-1,4-oxazepane-4-carboxylate To a solution of tert-butyl (7S)-7-(3,4-dichlorophenyl)-7-(hydroxymethyl)-1,4-oxazepane-4-carboxylate (1.01 g) in DMF (7 mL) was added sodium hydride (129 mg) at 0° C. After stirring for 10 min, allyl bromide (0.272 mL) was added, and the mixture was stirred at room temperature for 10 min. Under ice-cooling, the reaction was quenched with water, and the mixture was extracted with ethyl acetate. The organic layer was washed with brine, and dried over anhydrous magnesium sulfate, and the solvent was evaporated. The residue was purified by silica gel column chromatography (eluent; hexane:ethyl acetate (0%-50%)) to give the title compound (917 mg) as a colorless oil.

¹H NMR (300 MHz, CDCl₃) δ 1.36-1.51 (9H, m), 2.02-2.23 (1H, m), 2.57 (1H, dd, J=15.4, 6.8 Hz), 3.24-3.64 (5H, m), 3.66-3.98 (5H, m), 5.07-5.22 (2H, m), 5.67-5.85 (1H, m), 7.22 (1H, dd, J=8.5, 2.1 Hz), 7.42 (1H, d, J=9.0 Hz), 7.50 (1H, d, J=2.3 Hz).

B) tert-butyl (7S)-7-(3,4-dichlorophenyl)-7-[(2,3-dihydroxypropoxy)methyl]-1,4-oxazepane-4-carboxylate To a mixed solution of tert-butyl (7S)-7-(3,4-dichlorophenyl)-7-[(prop-2-en-1-yloxy)methyl]-1,4-oxazepane-4-carboxylate (760 mg) and 4-methylmorpholine N-oxide (428 mg) in acetonitrile (3 mL)/acetone (3 mL)/water (3 mL) was added osmium(VIII) oxide immobilized catalyst I (Wako Pure Chemical Industries, Ltd. cat. 153-02581) (150 mg), and the mixture was stirred at room temperature overnight under nitrogen purging. The catalyst was filtered off through celite, and the filtrate was concentrated. Water was added, and the mixture was extracted with ethyl acetate. The organic layer was washed with brine, and dried over anhydrous magnesium sulfate, and the solvent was evaporated. The residue was purified by silica gel column chromatography (eluent; hexane:ethyl acetate (0%-1000)) to give the title compound (single diastereomer) (444 mg) as a colorless oil.

¹H NMR (300 MHz, CDCl₃) δ 1.34-1.51 (9H, m), 1.67-1.89 (1H, m), 2.01-2.35 (3H, m), 2.50 (1H, dd, J=15.7, 8.1 Hz), 2.73 (1H, brs), 3.20-3.97 (11H, m), 7.20 (1H, dd, J=8.5, 1.7 Hz), 7.43 (1H, d), 7.47 (1H, d, J=1.9 Hz).

C) 3-{[(7S)-7-(3,4-dichlorophenyl)-1,4-oxazepan-7-yl]methoxy}propane-1,2-diol monohydrochloride Using tert-butyl (7S)-7-(3,4-dichlorophenyl)-7-[(2,3-dihydroxypropoxy)methyl]-1,4-oxazepane-4-carboxylate (440 mg), and by a method similar to that of Example 45, step N, the title compound (270 mg) was obtained as a colorless amorphous powder.

¹H NMR (300 MHz, DMSO-d₆) δ 2.40 (1H, dd, J=16.2, 9.4 Hz), 2.82 (1H, dd, J=16.2, 7.9 Hz), 3.12 (2H, brs), 3.22-3.56 (9H, m), 3.65 (1H, dd, J=14.0, 6.8 Hz), 4.06 (1H, d, J=15.5 Hz), 4.34 (2H, brs), 7.40 (1H, dd, J=8.5, 2.1 Hz), 7.59-7.68 (2H, m), 9.20 (2H, brs).

MS (ESI+): [M+H]⁺ 350.1.

Example 418

2-{[(7R)-7-(3,4-dichlorophenyl)-1,4-oxazepan-7-yl]methoxy}acetamide monohydrochloride Using tert-butyl (7R)-7-(3,4-dichlorophenyl)-7-(hydroxymethyl)-1,4-oxazepane-4-carboxylate and 2-bromoacetamide, and by a method similar to that of Example 363, step B and Example 39, step B, the title compound was obtained.

¹H NMR (300 MHz, DMSO-d₆) δ 2.30-2.43 (1H, m), 2.88 (1H, dd, J=16.1, 7.4 Hz), 3.04-3.33 (4H, m), 3.43-3.90 (5H, m), 3.97-4.12 (1H, m), 6.99 (1H, brs), 7.28 (1H, brs), 7.43 (1H, dd, J=8.5, 2.1 Hz), 7.61-7.71 (2H, m), 8.68-9.11 (2H, m).

MS (ESI+): [M+H]⁺ 333.1.

Example 419

(7RS)-7-(3,4-dichlorophenyl)-7-[(methylsulfonyl)methyl]-1,4-oxazepane monohydrochloride Using tert-butyl (7RS)-7-(3,4-dichlorophenyl)-7-(hydroxymethyl)-1,4-oxazepane-4-carboxylate, and in the same manner as in Example 5, steps A, B, C and Example 39, step B, the title compound was obtained.

MS (ESI+): [M+H]⁺ 338.2

Example 420

2-{[(7RS)-7-(3,4-dichlorophenyl)-1,4-oxazepan-7-yl]methyl}-1H-isoindole-1,3(2H)-dione monohydrochloride Using tert-butyl (7RS)-7-(3,4-dichlorophenyl)-7-[(1,3-dioxo-1,3-dihydro-2H-isoindol-2-yl)methyl]-1,4-oxazepane-4-carboxylate, and in the same manner as in Example 39, step B, the title compound was obtained.
MS (ESI+): [M+H]$^+$ 405.1.

Example 421

1-[(7RS)-7-(3,4-dichlorophenyl)-1,4-oxazepan-7-yl]methanamine monohydrochloride

Using tert-butyl (7RS)-7-(aminomethyl)-7-(3,4-dichlorophenyl)-1,4-oxazepane-4-carboxylate, and in the same manner as in Example 39, step B, the title compound was obtained.
MS (ESI+): [M+H]$^+$ 275.2.

Example 422

N-{[(7RS)-7-(3,4-dichlorophenyl)-1,4-oxazepan-7-yl]methyl}acetamide monohydrochloride Using tert-butyl (7RS)-7-(aminomethyl)-7-(3,4-dichlorophenyl)-1,4-oxazepane-4-carboxylate, and in the same manner as in Example 32, step C and Example 39, step B, the title compound was obtained.
MS (ESI+): [M+H]$^+$ 317.2.

Example 423

N-{[(7S)-7-(3,4-dichlorophenyl)-1,4-oxazepan-7-yl]methyl}acetamide monofumarate

The racemate of tert-butyl (7RS)-7-(3,4-dichlorophenyl)-7-(hydroxymethyl)-1,4-oxazepane-4-carboxylate was separated by SFC (column: CHIRALPAK AD-H, 30 mmID×250 mL, manufactured by DAICEL CHEMICAL INDUSTRIES, LTD., mobile phase: carbon dioxide/2-propanol=65/35). Using a compound having a shorter retention time, and in the same manner as in Example 21, steps A and B and Example 32, steps C and D, the title compound was obtained.
MS (ESI+): [M+H]$^+$ 317.0.

Example 424

N-{[(7R)-7-(3,4-dichlorophenyl)-1,4-oxazepan-7-yl]methyl}acetamide monofumarate

The racemate of tert-butyl (7RS)-7-(3,4-dichlorophenyl)-7-(hydroxymethyl)-1,4-oxazepane-4-carboxylate was separated by SFC (column: CHIRALPAK AD-H, 30 mmID×250 mmL, manufactured by DAICEL CHEMICAL INDUSTRIES, LTD., mobile phase: carbon dioxide/2-propanol=65/35). Using a compound having a longer retention time, and in the same manner as in Example 21, steps A and B and Example 32, steps C and D, the title compound was obtained.
MS (ESI+): [M+H]$^+$ 317.0.

Example 425

N-{[(7S)-7-(3,4-dichlorophenyl)-1,4-oxazepan-7-yl]methyl}-3-(5-oxo-4,5-dihydro-1,2,4-oxadiazol-3-yl)benzamide monohydrochloride Using tert-butyl (7S)-7-(aminomethyl)-7-(3,4-dichlorophenyl)-1,4-oxazepane-4-carboxylate and 3-cyanobenzoic acid, and by a method similar to that of Example 39, step A, Example 31, step D and Example 39, step B, the title compound was obtained.
$^1$H NMR (300 MHz, DMSO-d$_6$) δ 2.34-2.48 (1H, m), 2.66-2.85 (1H, m), 3.03-3.24 (2H, m), 3.40-3.52 (2H, m), 3.56-3.75 (2H, m), 3.94-4.09 (2H, m), 7.40 (1H, dd, J=8.5, 2.1 Hz), 7.55-7.72 (3H, m), 7.85-7.97 (2H, m), 8.20 (1H, s), 8.55 (1H, t, J=6.0 Hz), 8.78-9.14 (2H, m), 13.04-13.20 (1H, m).
MS (ESI+): [M+H]$^+$ 463.0.

Example 426

1-{[(7RS)-7-(3,4-dichlorophenyl)-1,4-oxazepan-7-yl]methyl}urea monohydrochloride Using tert-butyl (7RS)-7-(aminomethyl)-7-(3,4-dichlorophenyl)-1,4-oxazepane-4-carboxylate, and in the same manner as in Example 3, steps D and E, the title compound was obtained.
MS (ESI+): [M+H]$^+$ 318.2.

Example 427

1-{[(7R)-7-(3,4-dichlorophenyl)-1,4-oxazepan-7-yl]methyl}urea monohydrochloride

The racemate of tert-butyl (7RS)-7-(3,4-dichlorophenyl)-7-(hydroxymethyl)-1,4-oxazepane-4-carboxylate was separated by SFC (column: CHIRALPAK AD-H, 30 mmID×250 mL, manufactured by DAICEL CHEMICAL INDUSTRIES, LTD., mobile phase: carbon dioxide/2-propanol=65/35). Using a compound having a shorter retention time, and in the same manner as in Example 21, steps A and B and Example 3, steps D and E, the title compound was obtained.
MS (ESI+): [M+H]$^+$ 318.1.

Example 428

1-{[(7S)-7-(3,4-dichlorophenyl)-1,4-oxazepan-7-yl]methyl}urea monohydrochloride

The racemate of tert-butyl (7RS)-7-(3,4-dichlorophenyl)-7-(hydroxymethyl)-1,4-oxazepane-4-carboxylate was separated by SFC (column: CHIRALPAK AD-H, 30 mmID×250 mL, manufactured by DAICEL CHEMICAL INDUSTRIES, LTD., mobile phase: carbon dioxide/2-propanol=65/35). Using a compound having a longer retention time, and in the same manner as in Example 21, steps A and B, and Example 3, steps D and E, the title compound was obtained.
MS (ESI+): [M+H]$^+$ 318.1.

Example 429

1-{[(7RS)-7-(3,4-dichlorophenyl)-1,4-oxazepan-7-yl]methyl}-3-ethylurea monohydrochloride Using tert-butyl (7RS)-7-(aminomethyl)-7-(3,4-dichlorophenyl)-1,4-oxazepane-4-carboxylate, and in the same manner as in Example 3, steps D and E, the title compound was obtained.
MS (ESI+): [M+H]+ 346.3.

Example 430

N-{[(7S)-7-(3,4-dichlorophenyl)-1,4-oxazepan-7-yl]methyl}thiomorpholine-4-carboxamide 1,1-dioxide monohydrochloride

A) 4-nitrophenyl 1,1-dioxidothiomorpholine-4-carboxylate

Using thiomorpholine 1,1-dioxide, and by a method similar to that of Example 158, step A, the title compound was obtained.
$^1$H NMR (300 MHz, CDCl$_3$) δ 3.11-3.22 (4H, m), 4.07-4.26 (4H, m), 7.28-7.35 (2H, m), 8.25-8.33 (2H, m).

B) tert-butyl (7S)-7-(3,4-dichlorophenyl)-7-({[(1,1-dioxidothiomorpholin-4-yl)carbonyl]amino}methyl)-1,4-oxazepane-4-carboxylate Using tert-butyl (7S)-7-(aminomethyl)-7-(4-chloro-3-fluorophenyl)-1,4-oxazepane-4-carboxylate and 4-nitrophenyl 1,1-dioxidothiomorpholine-4-carboxylate, and by a method similar to that of Example 158, step B, the title compound was obtained.
$^1$H NMR (300 MHz, CDCl$_3$) δ 1.42 (9H, s), 2.06-2.19 (1H, m), 2.23-2.38 (1H, m), 2.88 (2H, s), 2.96 (2H, s), 3.12-3.21 (1H, m), 3.25-3.66 (6H, m), 3.75-3.87 (1H, m), 4.17-4.25 (1H, m), 4.41-4.54 (1H, m), 7.13 (1H, dd, J=8.3, 2.3 Hz), 7.28-7.35 (1H, m), 7.39-7.46 (2H, m), 8.01 (1H, s), 8.24-8.34 (1H, m).

C) N-{[(7S)-7-(3,4-dichlorophenyl)-1,4-oxazepan-7-yl]methyl}thiomorpholine-4-carboxamide 1,1-dioxide monohydrochloride Using tert-butyl (7S)-7-(3,4-dichlorophenyl)-7-({[(1,1-dioxidothiomorpholin-4-yl)carbonyl]amino}methyl)-1,4-oxazepane-4-carboxylate, and by a method similar to that of Example 39, step B, the title compound was obtained.
$^1$H NMR (300 MHz, DMSO-d$_6$) δ 2.31 (1H, dd, J=16.1, 8.5 Hz), 2.94-3.42 (9H, m), 3.45-3.61 (3H, m), 3.75-4.09 (3H, m), 5.81 (1H, t, J=5.9 Hz), 7.24-7.35 (1H, m), 7.47-7.68 (3H, m), 8.27-8.35 (1H, m), 8.83-9.23 (2H, m).
MS (ESI+): [M+H]+ 436.2.

Example 431

N-{[(7R)-7-(3,4-dichlorophenyl)-1,4-oxazepan-7-yl]methyl}methanesulfonamide monohydrochloride The racemate of tert-butyl (7RS)-7-(3,4-dichlorophenyl)-7-(hydroxymethyl)-1,4-oxazepane-4-carboxylate was separated by SFC (column: CHIRALPAK AD-H, 30 mmID×250 mL, manufactured by DAICEL CHEMICAL INDUSTRIES, LTD., mobile phase: carbon dioxide/2-propanol=65/35). Using a compound having a shorter retention time, and in the same manner as in Example 21, the title compound was obtained.
MS (ESI+): [M+H]+ 353.0.

Example 432

N-{[(7S)-7-(3,4-dichlorophenyl)-1,4-oxazepan-7-yl]methyl}methanesulfonamide monohydrochloride The racemate of tert-butyl (7RS)-7-(3,4-dichlorophenyl)-7-(hydroxymethyl)-1,4-oxazepane-4-carboxylate was separated by SFC (column: CHIRALPAK AD-H, 30 mmID×250 mL, manufactured by DAICEL CHEMICAL INDUSTRIES, LTD., mobile phase: carbon dioxide/2-propanol=65/35). Using a compound having a longer retention time, and in the same manner as in Example 21, the title compound was obtained.
MS (ESI+): [M+H]+ 353.0.

Example 433

N-{[(7R)-7-(3,4-dichlorophenyl)-1,4-oxazepan-7-yl]methyl}sulfamide

The racemate of tert-butyl (7RS)-7-(3,4-dichlorophenyl)-7-(hydroxymethyl)-1,4-oxazepane-4-carboxylate was separated by SFC (column: CHIRALPAK AD-H, 30 mmID×250 mL, manufactured by DAICEL CHEMICAL INDUSTRIES, LTD., mobile phase: carbon dioxide/2-propanol=65/35). Using a compound having a shorter retention time, and in the same manner as in Example 21, steps A and B, Example 22, step A, and Example 36, step F, the title compound was obtained.
MS (ESI+): [M+H]+ 353.9.

Example 434

N-{[(7)-7-(3,4-dichlorophenyl)-1,4-oxazepan-7-yl]methyl}sulfamide

The racemate of tert-butyl (7RS)-7-(3,4-dichlorophenyl)-7-(hydroxymethyl)-1,4-oxazepane-4-carboxylate was separated by SFC (column: CHIRALPAK AD-H, 30 mmID×250 mL, manufactured by DAICEL CHEMICAL INDUSTRIES, LTD., mobile phase: carbon dioxide/2-propanol=65/35). Using a compound having a longer retention time, and in the same manner as in Example 21, steps A and B, Example 22, step A and Example 36, step F, the title compound was obtained.
MS (ESI+): [M+H]+ 354.1.

Example 435

N-{[(7R)-7-(3,4-dichlorophenyl)-1,4-oxazepan-7-yl]methyl}-N'-methylsulfamide monohydrochloride From tert-butyl (7R)-7-(aminomethyl)-7-(3,4-dichlorophenyl)-1,4-oxazepane-4-carboxylate and in the same manner as in Example 175, the title compound was obtained.
MS (ESI+): [M+H]+ 368.0.

Example 436

N-{[(7S)-7-(3,4-dichlorophenyl)-1,4-oxazepan-7-yl]methyl}-N'-methylsulfamide

From tert-butyl (7S)-7-(aminomethyl)-7-(3,4-dichlorophenyl)-1,4-oxazepane-4-carboxylate and in the same manner as in Example 175, the title compound was obtained.
MS (ESI+): [M+H]+ 368.0.

Example 437

N-{[(7S)-7-(3,4-dichlorophenyl)-1,4-oxazepan-7-yl]methyl}-N-methylsulfamide

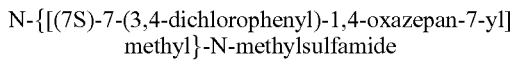

From tert-butyl (7S)-7-(hydroxymethyl)-7-(3,4-dichlorophenyl)-1,4-oxazepane-4-carboxylate and in the same manner as in Example 22, the title compound was obtained.
MS (ESI+): [M+H]$^+$ 368.0.

Example 438

3-{[(7R)-7-(3,4-dichlorophenyl)-1,4-oxazepan-7-yl]methyl}imidazolidine-2,4-dione monohydrochloride

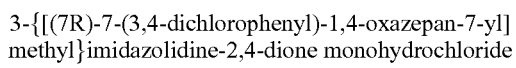

From tert-butyl (7R)-7-(aminomethyl)-7-(3,4-dichlorophenyl)-1,4-oxazepane-4-carboxylate and in the same manner as in Example 277, the title compound was obtained.
MS (ESI+): [M+H]$^+$ 358.3.

Example 439

3-{[(7S)-7-(3,4-dichlorophenyl)-1,4-oxazepan-7-yl]methyl}imidazolidine-2,4-dione monohydrochloride

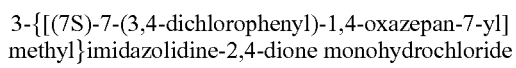

From tert-butyl (7S)-7-(aminomethyl)-7-(3,4-dichlorophenyl)-1,4-oxazepane-4-carboxylate and in the same manner as in Example 277, the title compound was obtained.
MS (ESI+): [M+H]$^+$ 358.1.

Example 440

[(6R*,7R*)-7-(4-chloro-3-fluorophenyl)-1,4-oxazepan-6-yl]methanol monohydrochloride (retention time short)

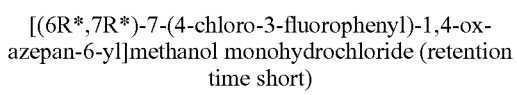

tert-Butyl (6RS,7RS)-7-(4-chloro-3-fluorophenyl)-6-(hydroxymethyl)-1,4-oxazepane-4-carboxylate (5.28 g) synthesized in a method similar to that of Example 1, steps A to H was separated by HPLC (CHIRALPAK AD, 50 mmID×500 mL, manufactured by DAICEL CHEMICAL INDUSTRIES, LTD., mobile phase: hexane/ethanol=800/200). Using tert-Butyl (6R*,7R*)-7-(4-chloro-3-fluorophenyl)-6-(hydroxymethyl)-1,4-oxazepane-4-carboxylate (2.46 g, >99.9% ee., recovery rate 93%) having a shorter retention time, and in the same manner as in Example 1, step I, the title compound was obtained.
MS (ESI+): [M+H]$^+$ 260.2.

Example 441

[(6R*,7R*)-7-(4-chloro-3-fluorophenyl)-1,4-oxazepan-6-yl]methanol monohydrochloride (retention time long)

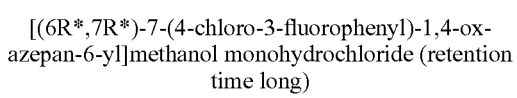

Using tert-butyl (6S*,7S*)-7-(4-chloro-3-fluorophenyl)-6-(hydroxymethyl)-1,4-oxazepane-4-carboxylate having a longer retention time obtained in Example 440, and in the same manner as in Example 1, step I, the title compound was obtained.
MS (ESI+): [M+H]$^+$ 260.2.

Example 442

(2RS)-2-(3,4-dichlorophenyl)-2-[(4-methoxyphenoxy)methyl]-1,4-oxazepane monohydrochloride

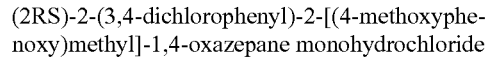

Using tert-butyl (2RS)-2-(3,4-dichlorophenyl)-2-[(4-methoxyphenoxy)methyl]-1,4-oxazepane-4-carboxylate, and in the same manner as in Example 39, step B, the title compound was obtained.
MS (ESI+): [M+H]$^+$ 382.3.

Example 443

2-{[(2RS)-2-(3,4-dichlorophenyl)-1,4-oxazepan-2-yl]methyl}-1H-isoindole-1,3(2H)-dione monohydrochloride

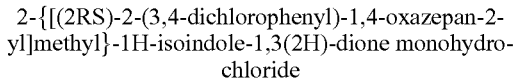

Using tert-butyl (2RS)-2-(3,4-dichlorophenyl)-2-[(1,3-dioxo-1,3-dihydro-2H-isoindol-2-yl)methyl]-1,4-oxazepane-4-carboxylate, and in the same manner as in Example 39, step B, the title compound was obtained.
MS (ESI+): [M+H]$^+$ 405.1.

Example 444

N-{[(2RS)-2-(3,4-dichlorophenyl)-1,4-oxazepan-2-yl]methyl}acetamide monohydrochloride

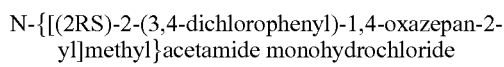

Using tert-butyl (2RS)-2-(aminomethyl)-2-(3,4-dichlorophenyl)-1,4-oxazepane-4-carboxylate, and in the same manner as in Example 32, step C and Example 39, step B, the title compound was obtained.
MS (ESI+): [M+H]$^+$ 316.9.

Example 445

1-{[(2RS)-2-(3,4-dichlorophenyl)-1,4-oxazepan-2-yl]methyl}urea monohydrochloride

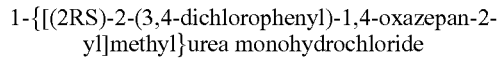

Using tert-butyl (2RS)-2-(aminomethyl)-2-(3,4-dichlorophenyl)-1,4-oxazepane-4-carboxylate, and in the same manner as in Example 3, steps D and E, the title compound was obtained.
MS (ESI+): [M+H]$^+$ 318.1.

Example 446

N-{[(2RS)-2-(3,4-dichlorophenyl)-1,4-oxazepan-2-yl]methyl}sulfamide monohydrochloride

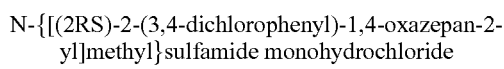

Using tert-butyl (2RS)-2-(aminomethyl)-2-(3,4-dichlorophenyl)-1,4-oxazepane-4-carboxylate, and in the same manner as in Example 22, steps A, B, the title compound was obtained.
MS (ESI+): [M+H]$^+$ 353.9.

Example 447

[(6R,7S)-6-(3,4-dichlorophenyl)-1,4-oxazepan-7-yl]methanol monohydrochloride

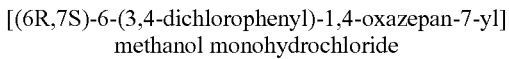

A) (2RS,3SR)-2-(3,4-dichlorophenyl)-3,4-dihydroxybutanenitrile (2RS,3SR)-2-(3,4-Dichlorophenyl)-3,4-dihydroxybutanenitrile (54 g) was obtained as a byproduct in Example 45, step A.

B) (2RS)-(3,4-dichlorophenyl)[(4SR)-2,2-dimethyl-1,3-dioxolan-4-yl]ethanenitrile From (2RS,3SR)-2-(3,4-dichlorophenyl)-3,4-dihydroxybutanenitrile (54 g) and in the same manner as in Example 45, step B, the title compound (29.3 g) was obtained.
$^1$H NMR (300 MHz, CDCl$_3$) δ 1.35 (3H, s), 1.50 (3H, s), 3.96-4.05 (2H, m), 4.06-4.17 (1H, m), 4.24-4.41 (1H, m), 7.22 (1H, dd, J=8.3, 2.3 Hz), 7.48 (1H, s), 7.49 (1H, d, J=6.8 Hz).

C) (2RS)-2-(3,4-dichlorophenyl)-2-[(4SR)-2,2-dimethyl-1,3-dioxolan-4-yl]ethanamine From (2RS)-(3,4-dichlorophenyl)[(4SR)-2,2-dimethyl-1,3-dioxolan-4-yl]ethanenitrile (53 g) and in the same manner as in Example 45, step C, the title compound was obtained.
MS (ESI+): [M+H]$^+$ 290.1.

D) (2RS)—N-benzyl-2-(3,4-dichlorophenyl)-2-[(4SR)-2,2-dimethyl-1,3-dioxolan-4-yl]ethanamine From (2RS)-2-(3,4-dichlorophenyl)-2-[(4SR)-2,2-dimethyl-1,3-dioxolan-4-yl]ethanamine and in the same manner as in Example 45, step D, the title compound (42 g) was obtained.
$^1$H NMR (300 MHz, CDCl$_3$) δ 1.27 (3H, s), 1.30 (3H, s), 2.77-2.99 (3H, m), 3.52 (1H, t, J=7.8 Hz), 3.62-3.83 (2H, m), 4.00 (1H, dd, J=8.1, 6.2 Hz), 4.23-4.41 (1H, m), 7.08 (1H, dd, J=8.1, 2.1 Hz), 7.16-7.51 (8H, m).
MS (ESI+): [M+H]$^+$ 380.2.

E) tert-butyl (6R,7S)-6-(3,4-dichlorophenyl)-7-(hydroxymethyl)-1,4-oxazepane-4-carboxylate From (2RS)—N-benzyl-2-(3,4-dichlorophenyl)-2-[(4SR)-2,2-dimethyl-1,3-dioxolan-4-yl]ethanamine (42 g), and according to Example 25, steps D-I and Example 26, step A, tert-butyl (6RS,7SR)-6-(3,4-dichlorophenyl)-7-(hydroxymethyl)-1,4-oxazepane-4-carboxylate (18.94 g) was obtained.
tert-Butyl (6RS,7SR)-6-(3,4-dichlorophenyl)-7-(hydroxymethyl)-1,4-oxazepane-4-carboxylate (8.9 g) was separated by HPLC (column: CHIRALPAK AD, 50 mmID× 500 mL, manufactured by DAICEL CHEMICAL INDUSTRIES, LTD., mobile phase: hexane/ethanol=90/10) to give the title compound (4.4 g, >99.9% ee) as a compound having a shorter retention time.
In addition, tert-butyl (6S,7R)-6-(3,4-dichlorophenyl)-7-(hydroxymethyl)-1,4-oxazepane-4-carboxylate was obtained as a compound having a longer retention time (4.3 g, >99.9% ee).
$^1$H NMR (300 MHz, CDCl$_3$) δ 1.41-1.50 (9H, m), 1.65-1.88 (1H, m), 2.83-3.51 (5H, m), 3.50-3.90 (2H, m), 3.89-4.42 (3H, m), 7.16 (1H, t, J=7.2 Hz), 7.36 (1H, dd, J=8.1, 4.7 Hz), 7.43 (1H, d).
MS (ESI+): [M+H-Boc]$^+$ 275.9.

F) [(6R,7S)-6-(3,4-dichlorophenyl)-1,4-oxazepan-7-yl]methanol monohydrochloride

From tert-butyl (6R,7S)-6-(3,4-dichlorophenyl)-7-(hydroxymethyl)-1,4-oxazepane-4-carboxylate (50 mg) and in the same manner as in Example 26, step B, the title compound (34 mg) was obtained.
MS (ESI+): [M+H]$^+$ 276.2.

Example 448

[(6S,7R)-6-(3,4-dichlorophenyl)-1,4-oxazepan-7-yl]methanol monohydrochloride

From tert-butyl (6S,7R)-6-(3,4-dichlorophenyl)-7-(hydroxymethyl)-1,4-oxazepane-4-carboxylate (50 mg) obtained in Example 447, step E, and in the same manner as in Example 26, step B, the title compound (33 mg) was obtained.
MS (ESI+): [M+H]$^+$ 276.2.

Example 449

(6RS,7SR)-6-(3,4-dichlorophenyl)-7-(methoxymethyl)-1,4-oxazepane monohydrochloride A) tert-butyl (6RS,7SR)-6-(3,4-dichlorophenyl)-7-(methoxymethyl)-1,4-oxazepane-4-carboxylate To a solution of tert-butyl (6RS,7SR)-6-(3,4-dichlorophenyl)-7-(hydroxymethyl)-1,4-oxazepane-4-carboxylate (150 mg) in THF (3 mL) was added sodium hydride (24 mg), and the mixture was stirred at room temperature for 15 min. To this solution was added methyl iodide (85 mg), and the mixture was stirred for 2 hr. Furthermore, sodium hydride (24 mg) was added, and the mixture was stirred at room temperature for 4 hr. To the reaction solution was added ice water, and the mixture was extracted with ethyl acetate. The extract was washed with water and brine, and dried over anhydrous sodium sulfate, and the solvent was evaporated under reduced pressure. The residue was purified by silica gel chromatography (hexane/ethyl acetate) to give the title compound (151 mg).
$^1$H NMR (300 MHz, CDCl$_3$) δ 1.46 (9H, d, J=11.7 Hz), 2.89-3.19 (4H, m), 3.21 (3H, d, J=4.5 Hz), 3.24-3.48 (1H, m), 3.55-3.75 (1H, m), 3.79-3.90 (1H, m), 3.93-4.25 (3H, m), 7.13-7.24 (1H, m), 7.36 (1H, dd, J=8.3, 4.5 Hz), 7.46 (1H, dd, J=17.7, 1.5 Hz).

B) (6RS,7SR)-6-(3,4-dichlorophenyl)-7-(methoxymethyl)-1,4-oxazepane monohydrochloride To a solution of tert-butyl (6RS,7SR)-6-(3,4-dichlorophenyl)-7-(methoxymethyl)-1,4-oxazepane-4-carboxylate (147 mg) in ethanol (1.5 ml) was added 14.0 N hydrogen chloride-ethanol solution (1.2 ml), and the mixture was stirred at room temperature for 1 hr. The residue obtained by concentration under reduced pressure was crystallized from ethanol-diisopropyl ether to give the title compound (118 mg).
MS (ESI+): [M+H]$^+$ 290.0.

Example 450

{[(6RS,7SR)-6-(3,4-dichlorophenyl)-1,4-oxazepan-7-yl]methoxy}acetic acid monohydrochloride A) tert-butyl (6SR,7RS)-6-(3,4-dichlorophenyl)-7-[(2-ethoxy-2-oxoethoxy)methyl]-1,4-oxazepane-4-carboxylate Under a nitrogen atmosphere at 80° C., to a solution of tert-butyl (6SR,7RS)-6-(3,4-dichlorophenyl)-7-(hydroxymethyl)-1,4-oxazepane-4-carboxylate (600 mg) and rhodium acetate dimer (7 mg) in toluene (5 ml) was added dropwise a solution of ethyl diazoacetate (860 mg) in toluene (5 mL) over 10 min. The reaction mixture was stirred at the same temperature for 10 min. The solvent was evaporated under reduced pressure. The residue was purified by silica gel column chromatography to give the title compound (615 mg).

$^1$H NMR (300 MHz, CDCl$_3$) δ 1.19-1.34 (3H, m), 1.45 (9H, d, J=13.6 Hz), 2.79-4.48 (14H, m), 7.10-7.24 (1H, m), 7.35 (1H, dd, J=8.1, 4.4 Hz), 7.45 (1H, d, J=16.7 Hz).

MS (ESI+): [M+H-Boc]$^+$ 362.0.

B) {[(6SR,7RS)-4-(tert-butoxycarbonyl)-6-(3,4-dichlorophenyl)-1,4-oxazepan-7-yl]methoxy}acetic acid 2 M Aqueous sodium hydroxide solution (0.32 mL) was added dropwise to a solution of tert-butyl (6SR,7RS)-6-(3,4-dichlorophenyl)-7-[(2-ethoxy-2-oxoethoxy)methyl]-1,4-oxazepane-4-carboxylate (150 mg) in ethanol (5 mL), and the mixture was stirred at room temperature for 30 min. Water was added to the reaction mixture, and the mixture was washed with diethyl ether. The obtained aqueous layer was neutralized with 1 M hydrochloric acid, and the mixture was extracted with ethyl acetate. The extract was washed with brine, and dried over anhydrous sodium sulfate. The solvent was evaporated under reduced pressure to give the title compound.

C) {[(6RS,7SR)-6-(3,4-dichlorophenyl)-1,4-oxazepan-7-yl]methoxy}acetic acid monohydrochloride From {[(6SR,7RS)-4-(tert-butoxycarbonyl)-6-(3,4-dichlorophenyl)-1,4-oxazepan-7-yl]methoxy}acetic acid and in the same manner as in Example 26, step B, the title compound (11 mg) was obtained.

MS (ESI+): [M+H]$^+$ 334.3

Example 451

Methyl 2-{[(6RS,7SR)-6-(3,4-dichlorophenyl)-1,4-oxazepan-7-yl]methoxy}benzoate monohydrochloride Using tert-butyl (6RS,7SR)-6-(3,4-dichlorophenyl)-7-(hydroxymethyl)-1,4-oxazepane-4-carboxylate, and in the same manner as in Example 31, step B, Example 44, step A and Example 2, step B, the title compound (18 mg) was obtained.

MS (ESI+): [M+H]$^+$ 410.0.

Example 452

Methyl 3-{[(6RS,7SR)-6-(3,4-dichlorophenyl)-1,4-oxazepan-7-yl]methoxy}benzoate monohydrochloride Using tert-butyl (6RS,7SR)-6-(3,4-dichlorophenyl)-7-(hydroxymethyl)-1,4-oxazepane-4-carboxylate, and in the same manner as in Example 31, step B, Example 44, step A and Example 2, step B, the title compound (27 mg) was obtained.

MS (ESI+): [M+H]$^+$ 410.2.

Example 453

N-{[(6R,7S)-6-(3,4-dichlorophenyl)-1,4-oxazepan-7-yl]methyl}acetamide monohydrochloride Using tert-butyl (6R,7S)-6-(3,4-dichlorophenyl)-7-(hydroxymethyl)-1,4-oxazepane-4-carboxylate obtained in Example 447, step E, an operation similar to that in Example 5, step A and Example 6 was performed to give the title compound (110 mg).

MS (ESI+): [M+H]$^+$ 317.0.

Example 454

N-{[(6R,7S)-6-(3,4-dichlorophenyl)-1,4-oxazepan-7-yl]methyl}-2-methoxyacetamide monohydrochloride A) tert-butyl (6R,7S)-7-(azidomethyl)-6-(3,4-dichlorophenyl)-1,4-oxazepane-4-carboxylate To a solution of tert-butyl (6R,7S)-6-(3,4-dichlorophenyl)-7-(hydroxymethyl)-1,4-oxazepane-4-carboxylate (950 mg) in THF (5 mL) were successively added dropwise triethylamine (1.1 mL) and methanesulfonyl chloride (0.39 mL), and the mixture was stirred at room temperature for 3 hr. Water was added to the reaction mixture, and the mixture was extracted with ethyl acetate. The extract was washed with brine, and dried over anhydrous sodium sulfate. The solvent was evaporated under reduced pressure.

To a solution of the residue in DMF (4 mL) were added sodium iodide (1.1 g) and sodium azide (490 mg), and the mixture was stirred at 120° C. overnight. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (394 mg).

$^1$H NMR (300 MHz, CDCl$_3$) δ 1.47 (9H, d, J=10.2 Hz), 2.70 (1H, d, J=12.8 Hz), 2.92-3.47 (4H, m), 3.52-3.93 (2H, m), 3.94-4.38 (3H, m), 7.18 (1H, t, J=6.6 Hz), 7.31-7.52 (2H, m).

B) tert-butyl (6R,7S)-7-(aminomethyl)-6-(3,4-dichlorophenyl)-1,4-oxazepane-4-carboxylate Using tert-butyl (6R,7S)-7-(azidomethyl)-6-(3,4-dichlorophenyl)-1,4-oxazepane-4-carboxylate (390 mg), and in the same manner as in Example 62, step I, the title compound was obtained.

C) tert-butyl (6R,7S)-6-(3,4-dichlorophenyl)-7-{[(methoxyacetyl)amino]methyl}-1,4-oxazepane-4-carboxylate Using tert-butyl (6R,7S)-7-(aminomethyl)-6-(3,4-dichlorophenyl)-1,4-oxazepane-4-carboxylate, and in the same manner as in Example 38, step E, the title compound (280 mg) was obtained.

$^1$H NMR (300 MHz, CDCl$_3$) δ 1.38-1.52 (9H, m), 2.46-2.86 (1H, m), 2.95-3.31 (3H, m), 3.40 (3H, s), 3.46-4.32 (8H, m), 6.51-6.81 (1H, m), 7.07-7.20 (1H, m), 7.38 (1H, d, J=8.3 Hz), 7.42-7.55 (1H, m).

MS (ESI+): [M+H-Boc]$^+$ 346.9.

D) N-{[(6R,7S)-6-(3,4-dichlorophenyl)-1,4-oxazepan-7-yl]methyl}-2-methoxyacetamide monohydrochloride From tert-butyl (6R,7S)-6-(3,4-dichlorophenyl)-7-{[(methoxyacetyl)amino]methyl}-1,4-oxazepane-4-carboxylate (100 mg) and in the same manner as in Example 26, step B, the title compound (24 mg) was obtained.

MS (ESI+): [M+H]$^+$ 347.3.

Example 455

N-{[(6R,7S)-6-(3,4-dichlorophenyl)-1,4-oxazepan-7-yl]methyl}-2-methoxy-N-methylacetamide monohydrochloride A) tert-butyl (6R,7S)-6-(3,4-dichlorophenyl)-7-{[(methoxyacetyl)(methyl)amino]methyl}-1,4-oxazepane-4-carboxylate Sodium hydride (60% in oil, 16 mg) was added to a solution of tert-butyl (6R,7S)-6-(3,4-dichlorophenyl)-7-{[(methoxyacetyl)amino]methyl}-1,4-oxazepane-4-carboxylate (180 mg) in DMF (5 ml), and the mixture was stirred at room temperature for 20 min. Methyl iodide (57 mg) was added dropwise to the reaction mixture, and the mixture was stirred at room temperature overnight. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (170 mg).
MS (ESI+): [M+H]+ 461.3.

B) N-{[(6R,7S)-6-(3,4-dichlorophenyl)-1,4-oxazepan-7-yl]methyl}-2-methoxy-N-methylacetamide monohydrochloride From tert-butyl (6R,7S)-6-(3,4-dichlorophenyl)-7-{[(methoxyacetyl)(methyl)amino]methyl}-1,4-oxazepane-4-carboxylate (170 mg) and in the same manner as in Example 26, step B, the title compound (19 mg) was obtained.
MS (ESI+): [M+H]+ 361.3.

Example 456

N-{[(6RS,7SR)-6-(3,4-dichlorophenyl)-1,4-oxazepan-7-yl]methyl}-2-hydroxy-2-methylpropanamide monohydrochloride A) tert-butyl (6SR,7RS)-7-({[2-(acetyloxy)-2-methylpropanoyl]amino}methyl)-6-(3,4-dichlorophenyl)-1,4-oxazepane-4-carboxylate Using tert-butyl (6SR,7RS)-7-(aminomethyl)-6-(3,4-dichlorophenyl)-1,4-oxazepane-4-carboxylate, and in the same manner as in Example 454, step C, the title compound (365 mg) was obtained.
$^1$H NMR (300 MHz, CDCl$_3$) δ 1.34-1.50 (9H, m), 1.57-1.61 (6H, m), 2.07 (3H, s), 2.35-2.70 (1H, m), 2.95-4.31 (9H, m), 6.19 (1H, brs), 7.09-7.21 (1H, m), 7.31-7.40 (1H, m), 7.46 (1H, d, J=15.9 Hz).

B) tert-butyl (6SR,7RS)-6-(3,4-dichlorophenyl)-7-{[(2-hydroxy-2-methylpropanoyl)amino]methyl}-1,4-oxazepane-4-carboxylate 2 M Aqueous sodium hydroxide solution (0.3 mL) was added dropwise to a solution of tert-butyl (6SR,7RS)-7-({[2-(acetyloxy)-2-methylpropanoyl]amino}methyl)-6-(3,4-dichlorophenyl)-1,4-oxazepane-4-carboxylate (150 mg) in ethanol (5 mL), and the mixture was stirred at room temperature for 1 hr. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (130 mg).
$^1$H NMR (300 MHz, CDCl$_3$) δ 1.34-1.51 (15H, m), 1.99-2.26 (1H, m), 2.45-2.80 (1H, m), 2.90-4.30 (9H, m), 6.71-6.96 (1H, m), 7.18 (1H, m, J=8.3 Hz), 7.33-7.43 (1H, m), 7.47 (1H, d, J=14.7 Hz).

C) N-{[(6RS,7SR)-6-(3,4-dichlorophenyl)-1,4-oxazepan-7-yl]methyl}-2-hydroxy-2-methylpropanamide monohydrochloride From tert-butyl (6SR,7RS)-6-(3,4-dichlorophenyl)-7-{[(2-hydroxy-2-methylpropanoyl)amino]methyl}-1,4-oxazepane-4-carboxylate (130 mg) and in the same manner as in Example 26, step B, the title compound (70 mg) was obtained.
MS (ESI+): [M+H]+ 361.1.

Example 457

N-{[(6RS,7SR)-6-(3,4-dichlorophenyl)-1,4-oxazepan-7-yl]methyl}-2-(1H-1,2,4-triazol-1-yl)acetamide monohydrochloride Using tert-butyl (6RS,7SR)-7-(aminomethyl)-6-(3,4-dichlorophenyl)-1,4-oxazepane-4-carboxylate and 2-(1H-1,2,4-triazol-1-yl)acetic acid, and by a method similar to that of Example 39, step A and Example 449, step B, the title compound was obtained.
MS (ESI+): [M+H]+ 384.2.

Example 458

N-{[(6RS,7SR)-6-(3,4-dichlorophenyl)-1,4-oxazepan-7-yl]methyl}benzamide monohydrochloride Using tert-butyl (6RS,7SR)-7-(aminomethyl)-6-(3,4-dichlorophenyl)-1,4-oxazepane-4-carboxylate, and in the same manner as in Example 32, step C and Example 449, step B, the title compound was obtained.
MS (ESI+): [M+H]+ 379.3.

Example 459

N-{[(6RS,7SR)-6-(3,4-dichlorophenyl)-1,4-oxazepan-7-yl]methyl}-N-methylbenzamide monohydrochloride Using tert-butyl (6RS,7SR)-7-(aminomethyl)-6-(3,4-dichlorophenyl)-1,4-oxazepane-4-carboxylate, and in the same manner as in Example 32, step C and Example 449, steps A and B, the title compound (92 mg) was obtained.
MS (ESI+): [M+H]+ 393.1.

Example 460

N-{[(6R,7S)-6-(3,4-dichlorophenyl)-1,4-oxazepan-7-yl]methyl}pyridine-2-carboxamide monohydrochloride Using tert-butyl (6R,7S)-7-(aminomethyl)-6-(3,4-dichlorophenyl)-1,4-oxazepane-4-carboxylate, and by a method similar to that of Example 39, step A and Example 449, step B, the title compound was obtained.
MS (ESI+): [M+H]+ 380.0.

Example 461

N-{[(6R,7S)-6-(3,4-dichlorophenyl)-1,4-oxazepan-7-yl]methyl}-N-methylpyridine-2-carboxamide monohydrochloride Using tert-butyl (6R,7S)-7-(aminomethyl)-6-(3,4-dichlorophenyl)-1,4-oxazepane-4-carboxylate, and in the same manner as in Example 32, step C and Example 449, steps A and B, the title compound (59 mg) was obtained.
MS (ESI+): [M+H]$^+$ 394.1.

Example 462

1-{[(6RS,7SR)-6-(3,4-dichlorophenyl)-1,4-oxazepan-7-yl]methyl}-3-ethylurea monohydrochloride Using tert-butyl (6RS,7SR)-7-(aminomethyl)-6-(3,4-dichlorophenyl)-1,4-oxazepane-4-carboxylate, and in the same manner as in Example 3, step D and Example 449, step B, the title compound (98 mg) was obtained.
MS (ESI+): [M+H]$^+$ 346.0.

Example 463

3-{[(6RS,7SR)-6-(3,4-dichlorophenyl)-1,4-oxazepan-7-yl]methyl}-1,1-dimethylurea monohydrochloride Using tert-butyl (6RS,7SR)-7-(aminomethyl)-6-(3,4-dichlorophenyl)-1,4-oxazepane-4-carboxylate, and in the same manner as in Example 32, step C and Example 449, step B, the title compound (83 mg) was obtained.
MS (ESI+): [M+H]$^+$ 346.1.

Example 464

1-{[(6RS,7SR)-6-(3,4-dichlorophenyl)-1,4-oxazepan-7-yl]methyl}-3-(2-hydroxyethyl)urea monohydrochloride Using tert-butyl (6RS,7SR)-7-(aminomethyl)-6-(3,4-dichlorophenyl)-1,4-oxazepane-4-carboxylate, and in the same manner as in Example 3, step D, Example 14, step E and Example 449, step B, the title compound (79 mg) was obtained.
MS (ESI+): [M+H]$^+$ 362.3.

Example 465

3-{[(6R,7S)-6-(3,4-dichlorophenyl)-1,4-oxazepan-7-yl]methyl}-1-(2-hydroxyethyl)-1-methylurea monohydrochloride A) tert-butyl (6R,7S)-6-(3,4-dichlorophenyl)-7-({[(4-nitrophenoxy)carbonyl]amino}methyl)-1,4-oxazepane-4-carboxylate To a solution of tert-butyl (6R,7S)-7-(aminomethyl)-6-(3,4-dichlorophenyl)-1,4-oxazepane-4-carboxylate (200 mg) and triethylamine (0.149 mL) in THF (4.0 mL) was added 4-nitrophenyl chloroformate (129 mg) under ice-cooling, and the mixture was stirred at room temperature for 5 hr. To the reaction solution was added water, and the mixture was extracted with ethyl acetate. The organic layer was washed with water and brine, and dried over anhydrous magnesium sulfate. The solvent was evaporated under reduced pressure. The residue was purified by silica gel chromatography (hexane/ethyl acetate) to give the title compound (99 mg).
$^1$H NMR (300 MHz, CDCl$_3$) δ 1.44-1.48 (9H, m), 2.53-2.94 (1H, m), 2.94-3.54 (4H, m), 3.54-3.92 (2H, m), 3.93-4.33 (3H, m), 5.17-5.45 (1H, m), 7.19 (1H, d, J=8.3 Hz), 7.23-7.31 (2H, m), 7.34-7.56 (2H, m), 8.24 (2H, d, J=9.0 Hz).

B) tert-butyl (6R,7S)-6-(3,4-dichlorophenyl)-7-({[(2-methoxy-2-oxoethyl)(methyl)carbamoyl]amino}methyl)-1,4-oxazepane-4-carboxylate To a solution of tert-butyl (6R,7S)-6-(3,4-dichlorophenyl)-7-({[(4-nitrophenoxy)carbonyl]amino}methyl)-1,4-oxazepane-4-carboxylate (94 mg) in THF (2.0 mL) were added sarcosine methyl ester hydrochloride (36 mg) and potassium carbonate (72 mg), and the mixture was stirred at room temperature overnight. To the reaction solution was added water, and the mixture was extracted with ethyl acetate. The organic layer was washed with water and brine, and dried over anhydrous magnesium sulfate. The solvent was evaporated under reduced pressure. The residue was purified by silica gel chromatography (hexane/ethyl acetate) to give the title compound (79 mg).
$^1$H NMR (300 MHz, CDCl$_3$) δ 1.41-1.46 (9H, m), 2.47-2.72 (1H, m), 2.81-3.01 (3H, m), 2.99-3.69 (5H, m), 3.72 (3H, s), 3.75-4.24 (6H, m), 4.65-4.86 (1H, m), 7.07-7.22 (1H, m), 7.30-7.54 (2H, m).

C) 3-{[(6R,7S)-6-(3,4-dichlorophenyl)-1,4-oxazepan-7-yl]methyl}-1-(2-hydroxyethyl)-1-methylurea monohydrochloride Using tert-butyl (6R,7S)-6-(3,4-dichlorophenyl)-7-({[(2-methoxy-2-oxoethyl)(methyl)carbamoyl]amino}methyl)-1,4-oxazepane-4-carboxylate, and in the same manner as in Example 14, step E and Example 449, step B, the title compound (35 mg) was obtained.
MS (ESI+): [M+H]$^+$ 376.1.

Example 466

1-{[(6RS,7SR)-6-(3,4-dichlorophenyl)-1,4-oxazepan-7-yl]methyl}-3-(2-methoxyethyl)urea monohydrochloride Using tert-butyl (6RS,7SR)-6-(3,4-dichlorophenyl)-7-({[(4-nitrophenoxy)carbonyl]amino}methyl)-1,4-oxazepane-4-carboxylate, and in the same manner as in Example 465, steps B and C, the title compound (81 mg) was obtained.
MS (ESI+): [M+H]$^+$ 376.3.

Example 467

N-{[(6R,7S)-6-(3,4-dichlorophenyl)-1,4-oxazepan-7-yl]methyl}methanesulfonamide monohydrochloride Using tert-butyl (6R,7S)-6-(3,4-dichlorophenyl)-7-(hydroxymethyl)-1,4-oxazepane-4-carboxylate obtained in Example 447, step E, operations similar to those in Example 5, step A, Example 6, steps A and B and Example 8 were successively performed to give the title compound (139 mg).
MS (ESI+): [M+H]$^+$ 353.0.

Example 468

N-{[(6R,7S)-6-(3,4-dichlorophenyl)-1,4-oxazepan-7-yl]methyl}propane-2-sulfonamide monohydrochloride Using tert-butyl (6R,7S)-7-(aminomethyl)-6-(3,4-dichlorophenyl)-1,4-oxazepane-4-carboxylate, and in the same manner as in Example B, the title compound (29 mg) was obtained.

MS (ESI+): [M+H]$^+$ 381.2.

Example 469

N-{[(6R,7S)-6-(3,4-dichlorophenyl)-1,4-oxazepan-7-yl]methyl}-2-methoxyethanesulfonamide monohydrochloride A) tert-butyl (6R,7S)-6-(3,4-dichlorophenyl)-7-{[(ethenylsulfonyl)amino]methyl}-1,4-oxazepane-4-carboxylate 2-Chloroethanesulfonyl chloride (390 mg) was added dropwise to a solution of tert-butyl (6R,7S)-7-(aminomethyl)-6-(3,4-dichlorophenyl)-1,4-oxazepane-4-carboxylate (600 mg) and triethylamine (0.67 mL) in THF (5 mL), and the mixture was stirred at room temperature overnight. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (235 mg).

$^1$H NMR (300 MHz, CDCl$_3$) δ 1.45 (9H, d, J=17.0 Hz), 2.43-3.46 (5H, m), 3.47-4.28 (5H, m), 4.51 (1H, dd, J=9.5, 2.7 Hz), 5.88 (1H, d, J=9.5 Hz), 6.17 (1H, m, J=16.3 Hz), 6.33-6.56 (1H, m), 7.14 (1H, t, J=6.6 Hz), 7.31-7.52 (2H, m).

MS (ESI+): [M−H]$^+$ 463.0.

B) tert-butyl (6R,7S)-6-(3,4-dichlorophenyl)-7-({[(2-methoxyethyl)sulfonyl]amino}methyl)-1,4-oxazepane-4-carboxylate A 28% solution (5 ml) of sodium methoxide in methanol was added dropwise to a solution of tert-butyl (6R,7S)-6-(3,4-dichlorophenyl)-7-{[(ethenylsulfonyl)amino]methyl}-1,4-oxazepane-4-carboxylate (235 mg) in methanol (1 mL), and the mixture was stirred at 60° C. overnight. To the reaction mixture was added saturated aqueous ammonium chloride solution, and the mixture was extracted with ethyl acetate. The extract was washed with brine, and dried over anhydrous sodium sulfate. The solvent was evaporated under reduced pressure. The residue was purified by silica gel column chromatography to give the title compound (215 mg).

MS (ESI+): [M−H]$^+$ 495.1.

C) N-{[(6R,7S)-6-(3,4-dichlorophenyl)-1,4-oxazepan-7-yl]methyl}-2-methoxyethanesulfonamide monohydrochloride From tert-butyl (6R,7S)-6-(3,4-dichlorophenyl)-7-({[(2-methoxyethyl)sulfonyl]amino}methyl)-1,4-oxazepane-4-carboxylate (215 mg) and in the same manner as in Example 26, step B, the title compound (160 mg) was obtained.

MS (ESI+): [M+H]$^+$ 397.1.

Example 470

N-{[(6R,7S)-6-(3,4-dichlorophenyl)-1,4-oxazepan-7-yl]methyl}-1,1-difluoromethanesulfonamide monohydrochloride Using tert-butyl (6R,7S)-7-(aminomethyl)-6-(3,4-dichlorophenyl)-1,4-oxazepane-4-carboxylate, and in the same manner as in Example 8, the title compound (102 mg) was obtained.

MS (ESI+): [M+H]$^+$ 389.0.

Example 471

N-{[(6R,7S)-6-(3,4-dichlorophenyl)-1,4-oxazepan-7-yl]methyl}-2,2,2-trifluoroethanesulfonamide monohydrochloride Using tert-butyl (6R,7S)-7-(aminomethyl)-6-(3,4-dichlorophenyl)-1,4-oxazepane-4-carboxylate, and in the same manner as in Example 8, the title compound (103 mg) was obtained.

MS (ESI+): [M+H]$^+$ 421.3.

Example 472

N-{[(6RS,7SR)-6-(3,4-dichlorophenyl)-1,4-oxazepan-7-yl]methyl}-N-methylmethanesulfonamide monohydrochloride A) tert-butyl (6SR,7RS)-6-(3,4-dichlorophenyl)-7-[(methylamino)methyl]-1,4-oxazepane-4-carboxylate To a solution of tert-butyl (6SR,7RS)-6-(3,4-dichlorophenyl)-7-(hydroxymethyl)-1,4-oxazepane-4-carboxylate (1.0 g) in THF (10 mL) were successively added dropwise triethylamine (1.1 mL) and methanesulfonyl chloride (0.41 mL), and the mixture was stirred at room temperature overnight. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give tert-butyl (6SR,7RS)-6-(3,4-dichlorophenyl)-7-{[(methylsulfonyl)oxy]methyl}-1,4-oxazepane-4-carboxylate (1.2 g).

MS (ESI+): [M−H]$^+$ 258.1.

To a solution of tert-butyl (6SR,7RS)-6-(3,4-dichlorophenyl)-7-{[(methylsulfonyl)oxy]methyl}-1,4-oxazepane-4-carboxylate (1.2 g) in acetone (10 mL) was added sodium iodide (4.0 g), and the mixture was heated under reflux for 3 hr. Water was added to the reaction mixture, and the mixture was extracted with ethyl acetate. The extract was washed with brine, and dried over anhydrous sodium sulfate. The solvent was evaporated under reduced pressure. To a solution of the residue in ethanol (10 mL) was added dropwise a 33% solution (10 mL) of methylamine in methanol, and the mixture was stirred at 50° C. overnight. The solvent was evaporated under reduced pressure, and the residue was purified by silica gel column chromatography to give the title compound (160 mg).

MS (ESI+): [M+H]$^+$ 390.0.

B) tert-butyl (6SR,7RS)-6-(3,4-dichlorophenyl)-7-{[methyl(methylsulfonyl)amino]methyl}-1,4-oxazepane-4-carboxylate To a solution of tert-butyl (6SR,7RS)-6-(3,4-dichlorophenyl)-7-[(methylamino)methyl]-1,4-oxazepane-4-carboxylate (150 mg) in THF (5 mL) were successively added dropwise triethylamine (0.070 mL) and methanesulfonyl chloride (0.036 mL), and the mixture was stirred at room temperature overnight. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (133 mg).
$^1$H NMR (300 MHz, CDCl$_3$) δ 1.45 (9H, d, J=13.6 Hz), 2.50-2.71 (1H, m), 2.73 (3H, s), 2.86 (3H, d, J=4.1 Hz), 2.90-3.49 (4H, m), 3.54-3.80 (1H, m), 3.83-4.31 (4H, m), 7.15-7.25 (1H, m), 7.38 (1H, dd, J=8.1, 3.6 Hz), 7.45 (1H, d, J=12.1 Hz).
MS (ESI+): [M+H-Boc]$^+$ 367.0.

C) N-{[(6RS,7SR)-6-(3,4-dichlorophenyl)-1,4-oxazepan-7-yl]methyl}-N-methylmethanesulfonamide monohydrochloride From tert-butyl (6SR,7RS)-6-(3,4-dichlorophenyl)-7-{[methyl(methylsulfonyl)amino]methyl}-1,4-oxazepane-4-carboxylate (130 mg), and in the same manner as in Example 26, step B, the title compound (83 mg) was obtained.
MS (ESI+): [M+H]$^+$ 367.3.

Example 473

N-{[(6RS,7SR)-6-(3,4-dichlorophenyl)-1,4-oxazepan-7-yl]methyl}-N-(4-methoxybenzyl)methanesulfonamide monohydrochloride A) tert-butyl (6SR,7RS)-6-(3,4-dichlorophenyl)-7-{[(4-methoxybenzyl)amino]methyl}-1,4-oxazepane-4-carboxylate To a solution of tert-butyl (6SR,7RS)-6-(3,4-dichlorophenyl)-7-(iodomethyl)-1,4-oxazepane-4-carboxylate (1.4 g) in DMF (5 mL) were added potassium carbonate (1.2 g) and 4-methoxybenzylamine (0.79 g), and the mixture was stirred at 80° C. for 3 hr. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (650 mg).
$^1$H NMR (300 MHz, CDCl$_3$) δ 1.44 (9H, d, J=13.6 Hz), 2.15-2.51 (2H, m), 2.86-4.24 (14H, m), 6.82 (2H, d, J=8.7 Hz), 7.04-7.21 (3H, m), 7.34 (1H, dd, J=8.0, 4.2 Hz), 7.42 (1H, d, J=16.3 Hz).
MS (ESI+): [M+H]$^+$ 495.3.

B) tert-butyl (6SR,7RS)-6-(3,4-dichlorophenyl)-7-{[(4-methoxybenzyl)(methylsulfonyl)amino]methyl}-1,4-oxazepane-4-carboxylate Using tert-butyl (6SR,7RS)-6-(3,4-dichlorophenyl)-7-{[(4-methoxybenzyl)amino]methyl}-1,4-oxazepane-4-carboxylate (650 mg), and in the same manner as in Example 472, step B, the title compound (570 mg) was obtained.
$^1$H NMR (300 MHz, CDCl$_3$) δ 1.45 (9H, d, J=17.3 Hz), 2.56-3.71 (9H, m), 3.80 (3H, s), 3.85-4.60 (6H, m), 6.85 (2H, d, J=8.7 Hz), 7.06-7.22 (3H, m), 7.34 (1H, dd, J=8.5, 4.3 Hz), 7.39 (1H, m).

C) N-{[(6RS,7SR)-6-(3,4-dichlorophenyl)-1,4-oxazepan-7-yl]methyl}-N-(4-methoxybenzyl)methanesulfonamide monohydrochloride From tert-butyl (6SR,7RS)-6-(3,4-dichlorophenyl)-7-{[(4-methoxybenzyl)(methylsulfonyl)amino]methyl}-1,4-oxazepane-4-carboxylate (250 mg) and in the same manner as in Example 26, step B, the title compound (170 mg) was obtained.
MS (ESI+): [M+H]$^+$ 473.2.

Example 474

N-{[(6RS,7SR)-6-(3,4-dichlorophenyl)-1,4-oxazepan-7-yl]methyl}benzenesulfonamide monohydrochloride A) tert-butyl (6SR,7RS)-6-(3,4-dichlorophenyl)-7-{[(phenylsulfonyl)amino]methyl}-1,4-oxazepane-4-carboxylate Benzenesulfonyl chloride (130 mg) was added dropwise to a solution of tert-butyl (6SR,7RS)-7-(aminomethyl)-6-(3,4-dichlorophenyl)-1,4-oxazepane-4-carboxylate (280 mg) and triethylamine (0.14 mL) in THF (5 mL), and the mixture was stirred at room temperature for 1 hr. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (195 mg).
$^1$H NMR (300 MHz, CDCl$_3$) δ 1.34-1.52 (9H, m), 2.32-4.78 (10H, m), 6.98-7.16 (1H, m), 7.28-7.41 (3H, m), 7.40-7.64 (3H, m), 7.74 (2H, d, J=7.9 Hz).
MS (ESI+): [M–H]$^+$ 513.1.

B) N-{[(6RS,7SR)-6-(3,4-dichlorophenyl)-1,4-oxazepan-7-yl]methyl}benzenesulfonamide monohydrochloride Using tert-butyl (6SR,7RS)-6-(3,4-dichlorophenyl)-7-{[(phenylsulfonyl)amino]methyl}-1,4-oxazepane-4-carboxylate (195 mg), and in the same manner as in Example 26, step B, the title compound (100 mg) was obtained.
MS (ESI+): [M+H]$^+$ 415.1.

Example 475

N-{[(6R,7S)-6-(3,4-dichlorophenyl)-1,4-oxazepan-7-yl]methyl}furan-2-sulfonamide monohydrochloride Using tert-butyl (6R,7S)-7-(aminomethyl)-6-(3,4-dichlorophenyl)-1,4-oxazepane-4-carboxylate, and in the same manner as in Example 8, the title compound (94 mg) was obtained.
MS (ESI+): [M+H]$^+$ 405.2.

Example 476

1-[(6R,7S)-6-(3,4-dichlorophenyl)-1,4-oxazepan-7-yl]-N-(1-methylethyl)methanesulfonamide monohydrochloride

A) tert-butyl (6R,7S)-7-[(acetylsulfanyl)methyl]-6-(3,4-dichlorophenyl)-1,4-oxazepane-4-carboxylate To a solution of tert-butyl (6R,7S)-6-(3,4-dichlorophenyl)-7-(hydroxymethyl)-1,4-oxazepane-4-carboxylate (2.15 g) in THF (45 ml) were added triethylamine (2.39 mL) and methanesulfonyl chloride (0.98 mL) under ice-cooling, and the mixture was stirred at room temperature for 2 hr. To the reaction solution was added water, and the mixture was extracted with ethyl acetate. The organic layer was washed with water and brine, and dried over anhydrous magnesium sulfate. The solvent was evaporated under reduced pressure. The residue (244 mg) was dissolved in acetonitrile (5 mL), cesium carbonate (184 mg) and thioacetic acid (0.04 mL) were added, and the mixture was stirred at room temperature overnight. To the reaction solution was added water, and the mixture was extracted with ethyl acetate. The organic layer was washed with water and brine, and dried over anhydrous magnesium sulfate. The solvent was evaporated under reduced pressure. The residue was purified by silica gel chromatography (hexane/ethyl acetate) to give the title compound (45 mg).
$^1$H NMR (300 MHz, CDCl$_3$) δ 1.45 (9H, s), 2.30 (3H, s), 2.41-2.77 (2H, m), 2.91-3.83 (5H, m), 3.86-4.27 (3H, m), 7.10-7.25 (1H, m), 7.30-7.54 (2H, m).

B) tert-butyl (6R,7S)-7-[(chlorosulfonyl)methyl]-6-(3,4-dichlorophenyl)-1,4-oxazepane-4-carboxylate To a solution of tert-butyl (6R,7S)-7-[(acetylsulfanyl)methyl]-6-(3,4-dichlorophenyl)-1,4-oxazepane-4-carboxylate (115 mg) in acetonitrile (1.1 mL) were added 1 N hydrochloric acid (0.13 mL) and N-chlorosuccinimide (141 mg), and the mixture was stirred at room temperature for 30 min. To the reaction solution was added brine, and the mixture was extracted with ethyl acetate. The organic layer was washed with water and brine, and dried over anhydrous magnesium sulfate. The solvent was evaporated under reduced pressure. The residue was purified by silica gel chromatography (hexane/ethyl acetate) to give the title compound (96 mg).
$^1$H NMR (300 MHz, CDCl$_3$) δ 1.24-1.35 (1H, m), 1.48-1.50 (9H, m), 2.87-3.88 (5H, m), 4.00-4.58 (4H, m), 7.14-7.25 (1H, m), 7.29-7.67 (2H, m).

C) tert-butyl (6R,7S)-6-(3,4-dichlorophenyl)-7-{[(1-methylethyl)sulfamoyl]methyl}-1,4-oxazepane-4-carboxylate To a solution of tert-butyl (6R,7S)-7-[(chlorosulfonyl)methyl]-6-(3,4-dichlorophenyl)-1,4-oxazepane-4-carboxylate (95 mg) in ethyl acetate (2.0 mL) were added triethylamine (0.06 mL) and isopropylamine (0.03 mL) under ice-cooling, and the mixture was stirred at room temperature overnight. To the reaction solution was added water, and the mixture was extracted with ethyl acetate. The organic layer was washed with water and brine, and dried over anhydrous magnesium sulfate. The solvent was evaporated under reduced pressure. The residue was purified by silica gel chromatography (hexane/ethyl acetate) to give the title compound (33 mg).
$^1$H NMR (300 MHz, CDCl$_3$) δ 1.16 (3H, d, J=6.4 Hz), 1.20 (3H, d, J=6.4 Hz), 1.43-1.49 (9H, m), 2.53-3.12 (2H, m), 3.11-3.64 (3H, m), 3.63-4.39 (7H, m), 7.16 (1H, td, J=8.4, 2.1 Hz), 7.34-7.54 (2H, m).

D) 1-[(6R,7S)-6-(3,4-dichlorophenyl)-1,4-oxazepan-7-yl]-N-(1-methylethyl)methanesulfonamide monohydrochloride Using tert-butyl (6R,7S)-6-(3,4-dichlorophenyl)-7-{[(1-methylethyl)sulfamoyl]methyl}-1,4-oxazepane-4-carboxylate, and in the same manner as in Example 1, step I, the title compound (23 mg) was obtained.
MS (ESI+): [M+H]$^+$ 381.2.

Example 477

N-(1-{[(6RS,7SR)-6-(3,4-dichlorophenyl)-1,4-oxazepan-7-yl]methyl}piperidin-4-yl)acetamide dihydrochloride

A) tert-butyl (6SR,7RS)-7-{[4-(acetylamino)piperidin-1-yl]methyl}-6-(3,4-dichlorophenyl)-1,4-oxazepane-4-carboxylate To a solution of tert-butyl (6SR,7RS)-6-(3,4-dichlorophenyl)-7-(iodomethyl)-1,4-oxazepane-4-carboxylate (300 mg) in DMF (5 mL) were added potassium carbonate (260 mg) and 4-acetamidopiperidine (130 mg), and the mixture was stirred at 80° C. overnight. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (190 mg).
MS (ESI+): [M+H]$^+$ 500.3.

B) N-(1-{[(6RS,7SR)-6-(3,4-dichlorophenyl)-1,4-oxazepan-7-yl]methyl}piperidin-4-yl)acetamide dihydrochloride Using tert-butyl (6SR,7RS)-7-{[4-(acetylamino)piperidin-1-yl]methyl}-6-(3,4-dichlorophenyl)-1,4-oxazepane-4-carboxylate (190 mg), and in the same manner as in Example 26, step B, the title compound (117 mg) was obtained.
MS (ESI+): [M+H]$^+$ 400.2.

Example 478

Ethyl 1-{[(6R,7S)-6-(3,4-dichlorophenyl)-1,4-oxazepan-7-yl]methyl}piperidine-4-carboxylate dihydrochloride

A) tert-butyl (6R,7S)-6-(3,4-dichlorophenyl)-7-{[4-(methoxycarbonyl)piperidin-1-yl]methyl}-1,4-oxazepane-4-carboxylate To a solution of tert-butyl (6R,7S)-6-(3,4-dichlorophenyl)-7-(iodomethyl)-1,4-oxazepane-4-carboxylate (200 mg) in DMF (5 mL) were added potassium carbonate (170 mg), sodium iodide (190 mg) and methyl piperidine-4-carboxylate (88 mg), and the mixture was stirred at 100° C. overnight. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (110 mg).
MS (ESI+): [M+H]$^+$ 501.3.

B) 1-{[(6R,7S)-4-(tert-butoxycarbonyl)-6-(3,4-dichlorophenyl)-1,4-oxazepan-7-yl]methyl}piperidine-4-carboxylic acid 2 M Aqueous sodium hydroxide solution (0.2 mL) was added dropwise to a solution of tert-butyl (6R,7S)-6-(3,4-dichlorophenyl)-7-{[4-(methoxycarbonyl)piperidin-1-yl]methyl}-1,4-oxazepane-4-carboxylate (110 mg) in ethanol (5 mL), and the mixture was stirred at room temperature for 1 hr. Water was added to the reaction mixture, and the mixture was washed with diethyl ether. The obtained aqueous layer was neutralized with 1 M hydrochloric acid, and the mixture was extracted with ethyl acetate. The extract was washed with brine, and dried over anhydrous sodium sulfate. The solvent was evaporated under reduced pressure to give the title compound (70 mg).
MS (ESI+): [M+H]$^+$ 487.3.

C) ethyl 1-{[(6R,7S)-6-(3,4-dichlorophenyl)-1,4-oxazepan-7-yl]methyl}piperidine-4-carboxylate dihydrochloride Using 1-{[(6R,7S)-4-(tert-butoxycarbonyl)-6-(3,4-dichlorophenyl)-1,4-oxazepan-7-yl]methyl}piperidine-4-carboxylic acid (70 mg), and in the same manner as in Example 1, step I, the title compound (32 mg) was obtained.
MS (ESI+): [M+H]$^+$ 415.2.

Example 479

1-{[(6R,7S)-6-(3,4-dichlorophenyl)-1,4-oxazepan-7-yl]methyl}piperidine-4-carboxylic acid dihydrochloride Using 1-{[(6R,7S)-4-(tert-butoxycarbonyl)-6-(3,4-dichlorophenyl)-1,4-oxazepan-7-yl]methyl}piperidine-4-carboxylic acid (180 mg), and in the same manner as in Example 26, step B, the title compound (117 mg) was obtained.
MS (ESI+): [M+H]$^+$ 387.2.

Example 480

(6RS,7SR)-6-(3,4-dichlorophenyl)-7-[(4-methyl-1H-pyrazol-1-yl)methyl]-1,4-oxazepane monohydrochloride

A) tert-butyl (6RS,7SR)-6-(3,4-dichlorophenyl)-7-[(4-methyl-1H-pyrazol-1-yl)methyl]-1,4-oxazepane-4-carboxylate 1) To a solution of tert-butyl (6RS,7SR)-6-(3,4-dichlorophenyl)-7-(hydroxymethyl)-1,4-oxazepane-4-carboxylate (1.2 g) in THF (24 mL) were added triethylamine (1.33 ml) and methanesulfonyl chloride (0.49 ml) under ice-cooling, and the mixture was stirred at room temperature for 2 hr. To the reaction solution was added water, and the mixture was extracted with ethyl acetate. The organic layer was washed with water and brine, and dried over anhydrous magnesium sulfate. The solvent was evaporated under reduced pressure.
2) To a solution of 4-methylpyrazole (0.10 mL) in DMF (4.0 mL) was added sodium hydride (62 mg) under ice-cooling, and the mixture was stirred at room temperature for 30 min. To this reaction solution was added a solution of the residue (468 mg) obtained in the above-mentioned 1) in DMF (2 ml) under ice-cooling, and the mixture was stirred at 70° C. for 3 hr. The reaction solution was allowed to cool to room temperature, water was added, and the mixture was extracted with ethyl acetate. The organic layer was washed with water and brine, and dried over anhydrous magnesium sulfate. The solvent was evaporated under reduced pressure. The residue was purified by silica gel chromatography (hexane/ethyl acetate) to give the title compound (158 mg).
$^1$H NMR (300 MHz, CDCl$_3$) δ 1.42-1.45 (9H, m), 2.04 (3H, s), 2.89-4.07 (8H, m), 4.08-4.26 (2H, m), 6.99 (1H, d, J=7.6 Hz), 7.16-7.25 (1H, m), 7.27 (1H, s), 7.35-7.55 (2H, m).

B) (6RS,7SR)-6-(3,4-dichlorophenyl)-7-[(4-methyl-1H-pyrazol-1-yl)methyl]-1,4-oxazepane monohydrochloride Using tert-butyl (6RS,7SR)-6-(3,4-dichlorophenyl)-7-[(4-methyl-1H-pyrazol-1-yl)methyl]-1,4-oxazepane-4-carboxylate, and in the same manner as in Example 10, step H, the title compound (125 mg) was obtained.
MS (ESI+): [M+H]$^+$ 340.1.

Example 481

2-{[(6R,7S)-6-(3,4-dichlorophenyl)-1,4-oxazepan-7-yl]methyl}pyridazin-3(2H)-one monohydrochloride

A) tert-butyl (6R,7S)-6-(3,4-dichlorophenyl)-7-[(6-oxopyridazin-1(6H)-yl)methyl]-1,4-oxazepane-4-carboxylate To a solution of tert-butyl (6R,7S)-6-(3,4-dichlorophenyl)-7-(iodomethyl)-1,4-oxazepane-4-carboxylate (335 mg) in DMF (7.0 mL) were added 3(2H)-pyridazinone (79 mg) and potassium carbonate (143 mg), and the mixture was heated at 60° C. for 4 hr. The reaction solution was allowed to cool to room temperature, water was added, and the mixture was extracted with ethyl acetate. The organic layer was washed with brine, and dried over anhydrous magnesium sulfate. The solvent was evaporated under reduced pressure. The residue was purified by silica gel chromatography (hexane/ethyl acetate) to give the title compound (2.49 g).
$^1$H NMR (300 MHz, CDCl$_3$) δ 1.46 (9H, s), 3.03-3.59 (4H, m), 3.62-4.37 (6H, m), 6.90 (1H, dd, J=9.4, 1.9 Hz), 7.04-7.23 (1H, m), 7.28-7.47 (2H, m), 7.46-7.63 (1H, m), 7.61-7.85 (1H, m).

B) 2-{[(6R,7S)-6-(3,4-dichlorophenyl)-1,4-oxazepan-7-yl]methyl}pyridazin-3(2H)-one monohydrochloride Using tert-butyl (6R,7S)-6-(3,4-dichlorophenyl)-7-[(6-oxopyridazin-1(6H)-yl)methyl]-1,4-oxazepane-4-carboxylate, and in the same manner as in Example 2, step B, the title compound (43 mg) was obtained.
MS (ESI+): [M+H]$^+$ 354.2.

Example 482

3-{[(6RS,7SR)-6-(3,4-dichlorophenyl)-1,4-oxazepan-7-yl]methyl}quinazoline-2,4(1H,3H)-dione monohydrochloride

A) tert-butyl (6SR,7RS)-6-(3,4-dichlorophenyl)-7-[({[2-(methoxycarbonyl)phenyl]carbamoyl}amino)methyl]-1,4-oxazepane-4-carboxylate Triphosgene (95 mg) was added to a solution of methyl 2-aminobenzoate (120 mg) and triethylamine (0.17 mL) in toluene (5 mL), and the mixture was stirred at 0° C. for 30 min. To the reaction mixture were added tert-butyl (6SR,7RS)-7-(aminomethyl)-6-(3,4-dichlorophenyl)-1,4-oxazepane-4-carboxylate (300 mg) and triethylamine (0.17 mL), and the mixture was stirred at room temperature for 1 hr. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (190 mg).

$^1$H NMR (300 MHz, CDCl$_3$) δ 1.35-1.49 (9H, m), 2.53-2.88 (1H, m), 3.00-4.31 (11H, m), 4.88 (1H, m, J=17.7 Hz), 6.96 (1H, t, J=7.2 Hz), 7.12-7.24 (2H, m), 7.38 (1H, m, J=8.3, 2.6 Hz), 7.43-7.57 (2H, m), 7.97 (1H, dd, J=8.1, 1.7 Hz), 8.46 (1H, t, J=8.7 Hz), 10.30 (1H, brs).

MS (ESI+): [M+H]$^+$ 552.3.

B) tert-butyl (6SR,7RS)-6-(3,4-dichlorophenyl)-7-[(2,4-dioxo-1,4-dihydroquinazolin-3(2H)-yl)methyl]-1,4-oxazepane-4-carboxylate A 28% solution (0.2 ml) of sodium methoxide in methanol was added dropwise to a solution of tert-butyl (6SR,7RS)-6-(3,4-dichlorophenyl)-7-[({[2-(methoxycarbonyl)phenyl]carbamoyl}amino)methyl]-1,4-oxazepane-4-carboxylate (190 mg) in methanol (5 mL), and the mixture was stirred at 80° C. for 1 hr. Saturated aqueous ammonium chloride solution was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (135 mg).

$^1$H NMR (300 MHz, CDCl$_3$) δ 1.41-1.50 (9H, m), 2.96-3.69 (5H, m), 3.74-4.31 (5H, m), 7.00 (1H, d, J=8.3 Hz), 7.17-7.24 (1H, m), 7.30-7.77 (4H, m), 8.11 (1H, d, J=7.6 Hz), 8.32-8.81 (1H, m).

MS (ESI+): [M−H]$^+$ 518.2.

C) 3-{[(6RS,7SR)-6-(3,4-dichlorophenyl)-1,4-oxazepan-7-yl]methyl}quinazoline-2,4(1H,3H)-dione monohydrochloride Using tert-butyl (6SR,7RS)-6-(3,4-dichlorophenyl)-7-[(2,4-dioxo-1,4-dihydroquinazolin-3(2H)-yl)methyl]-1,4-oxazepane-4-carboxylate (135 mg), and in the same manner as in Example 26, step B, the title compound (99 mg) was obtained.

MS (ESI+): [M+H]$^+$ 420.1.

Example 483

[(6RS,7RS)-6-(3,4-dichlorophenyl)-1,4-oxazepan-7-yl]acetonitrile monohydrochloride A) tert-butyl (6RS,7RS)-7-(cyanomethyl)-6-(3,4-dichlorophenyl)-1,4-oxazepane-4-carboxylate To a solution of tert-butyl (6RS,7SR)-6-(3,4-dichlorophenyl)-7-(hydroxymethyl)-1,4-oxazepane-4-carboxylate (2.0 g) in THF (40 mL) were added triethylamine (2.22 mL) and methanesulfonyl chloride (0.82 mL) under ice-cooling, and the mixture was stirred at room temperature for 2 hr. To the reaction solution was added water, and the mixture was extracted with ethyl acetate. The organic layer was washed with water and brine, and dried over anhydrous magnesium sulfate. The solvent was evaporated under reduced pressure.

To a solution of the obtained residue (1.6 g) in DMF (9.0 ml) was added sodium cyanide (345 mg), and the mixture was stirred at 80° C. for 2 days. The reaction solution was allowed to cool to room temperature, water was added, and the mixture was extracted with ethyl acetate. The organic layer was washed with water and brine, and dried over anhydrous magnesium sulfate. The solvent was evaporated under reduced pressure. The residue was purified by silica gel chromatography (hexane/ethyl acetate) to give the title compound (331 mg).

$^1$H NMR (300 MHz, CDCl$_3$) δ 1.47 (9H, d, J=10.5 Hz), 2.00-2.42 (2H, m), 2.89-3.51 (3H, m), 3.55-3.84 (1H, m), 3.88-4.34 (4H, m), 7.19 (1H, t, J=8.9 Hz), 7.33-7.55 (2H, m).

B) [(6RS,7RS)-6-(3,4-dichlorophenyl)-1,4-oxazepan-7-yl]acetonitrile monohydrochloride Using tert-butyl (6RS,7RS)-7-(cyanomethyl)-6-(3,4-dichlorophenyl)-1,4-oxazepane-4-carboxylate, and in the same manner as in Example 449, step B, the title compound (62 mg) was obtained.

MS (ESI+): [M+H]$^+$ 285.2.

Example 484

N-{2-[(6RS,7RS)-6-(3,4-dichlorophenyl)-1,4-oxazepan-7-yl]ethyl}acetamide monohydrochloride A) tert-butyl (6RS,7RS)-7-(2-aminoethyl)-6-(3,4-dichlorophenyl)-1,4-oxazepane-4-carboxylate To a solution of aluminum chloride (190 mg) in THF (4.0 mL) was added lithium aluminum hydride (203 mg) under ice-cooling, and the mixture was stirred for 40 min. To this reaction solution was added dropwise a solution of tert-butyl (6RS,7RS)-7-(cyanomethyl)-6-(3,4-dichlorophenyl)-1,4-oxazepane-4-carboxylate (550 mg) obtained in Example 483, step A in THF (4.0 ml), and the mixture was stirred at 0° C. for 1 hr under an argon atmosphere. To the reaction solution was added aqueous sodium sulfate solution, and the mixture was stirred for 1 hr, and filtered through celite. The solvent of the filtrate was evaporated under reduced pressure to give the title compound (404 mg).

$^1$H NMR (400 MHz, CDCl$_3$) δ 1.02-1.37 (4H, m), 1.43-1.47 (9H, m), 2.55-2.86 (2H, m), 2.90-3.36 (3H, m), 3.43-3.81 (2H, m), 3.90-4.26 (3H, m), 7.09-7.23 (1H, m), 7.36 (1H, dd, J=7.9, 4.1 Hz), 7.44 (1H, d, J=17.0 Hz).

B) tert-butyl (6RS,7RS)-7-[2-(acetylamino)ethyl]-6-(3,4-dichlorophenyl)-1,4-oxazepane-4-carboxylate To a solution of tert-butyl (6RS,7RS)-7-(2-aminoethyl)-6-(3,4-dichlorophenyl)-1,4-oxazepane-4-carboxylate (125 mg) in THF (2.5 mL) were added triethylamine (0.134 mL) and acetyl chloride (0.046 ml), and the mixture was stirred at room temperature for 1 hr. To the reaction solution was added water, and the mixture was extracted with ethyl acetate. The organic layer was washed with water and brine, and dried over anhydrous magnesium sulfate. The solvent was evaporated under reduced pressure. The residue was purified by silica gel chromatography (hexane/ethyl acetate) to give the title compound (121 mg).

$^1$H NMR (300 MHz, CDCl$_3$) δ 1.43-1.48 (9H, m), 1.92 (3H, s), 2.94-3.74 (8H, m), 3.93-4.22 (4H, m), 5.45-5.66 (1H, m), 7.10-7.21 (1H, m), 7.36 (1H, dd, J=7.9, 2.3 Hz), 7.43 (1H, d, J=14.3 Hz).

C) N-{2-[(6RS,7RS)-6-(3,4-dichlorophenyl)-1,4-oxazepan-7-yl]ethyl}acetamide monohydrochloride Using tert-butyl (6RS,7RS)-7-[2-(acetylamino)ethyl]-6-(3,4-dichlorophenyl)-1,4-oxazepane-4-carboxylate, and in the same manner as in Example 449, step B, the title compound (79 mg) was obtained.
MS (ESI+): [M+H]$^+$ 331.1.

Example 485

N-{2-[(6RS,7RS)-6-(3,4-dichlorophenyl)-1,4-oxazepan-7-yl]ethyl}-2-methoxyacetamide monohydrochloride A) tert-butyl (6RS,7RS)-6-(3,4-dichlorophenyl)-7-{2-[(methoxyacetyl)amino]ethyl}-1,4-oxazepane-4-carboxylate To a solution of tert-butyl (6RS,7RS)-7-(2-aminoethyl)-6-(3,4-dichlorophenyl)-1,4-oxazepane-4-carboxylate (140 mg) obtained in Example 484, step A in THF (3.0 ml) were added triethylamine (0.150 ml) and methoxyacetyl chloride (0.066 ml) under ice-cooling, and the mixture was stirred at room temperature for 2 hr. Water was added to the reaction solution, and the mixture was extracted with ethyl acetate. The organic layer was washed with water and brine, and dried over anhydrous magnesium sulfate. The solvent was evaporated under reduced pressure. The residue was purified by silica gel chromatography (hexane/ethyl acetate) to give the title compound (157 mg).
$^1$H NMR (300 MHz, CDCl$_3$) δ 1.29-1.39 (1H, m), 1.43-1.48 (9H, m), 2.93-3.35 (4H, m), 3.39 (3H, s), 3.42-3.73 (3H, m), 3.84 (2H, s), 3.92-4.04 (1H, m), 4.04-4.26 (3H, m), 6.63 (1H, d, J=15.1 Hz), 7.05-7.24 (1H, m), 7.28-7.55 (2H, m).

B) N-{2-[(6RS,7RS)-6-(3,4-dichlorophenyl)-1,4-oxazepan-7-yl]ethyl}-2-methoxyacetamide monohydrochloride Using tert-butyl (6RS,7RS)-6-(3,4-dichlorophenyl)-7-{2-[(methoxyacetyl)amino]ethyl}-1,4-oxazepane-4-carboxylate, and in the same manner as in Example 449, step B, the title compound (79 mg) was obtained.
MS (ESI+): [M+H]$^+$ 361.1.

Example 486

N-{2-[(6RS,7RS)-6-(3,4-dichlorophenyl)-1,4-oxazepan-7-yl]ethyl}methanesulfonamide monohydrochloride A) tert-butyl (6RS,7RS)-6-(3,4-dichlorophenyl)-7-{2-[(methylsulfonyl)amino]ethyl}-1,4-oxazepane-4-carboxylate To a solution of tert-butyl (6RS,7RS)-7-(2-aminoethyl)-6-(3,4-dichlorophenyl)-1,4-oxazepane-4-carboxylate (135 mg) obtained in Example 484, step A in THF (3.0 mL) were added triethylamine (0.145 mL) and methanesulfonyl chloride (0.054 mL) under ice-cooling, and the mixture was stirred at room temperature for 2 hr. To the reaction solution was added water, and the mixture was extracted with ethyl acetate. The organic layer was washed with water and brine, and dried over anhydrous magnesium sulfate. The solvent was evaporated under reduced pressure. The residue was purified by silica gel chromatography (hexane/ethyl acetate) to give the title compound (157 mg).
$^1$H NMR (300 MHz, CDCl$_3$) δ 1.27-1.39 (1H, m), 1.42-1.48 (9H, m), 2.90 (3H, s), 2.99-3.38 (5H, m), 3.51-3.87 (2H, m), 3.89-4.05 (1H, m), 4.06-4.35 (3H, m), 4.47 (1H, brs), 7.16 (1H, t, J=6.6 Hz), 7.28-7.59 (2H, m).

B) N-{2-[(6RS,7RS)-6-(3,4-dichlorophenyl)-1,4-oxazepan-7-yl]ethyl}methanesulfonamide monohydrochloride Using tert-butyl (6RS,7RS)-6-(3,4-dichlorophenyl)-7-{2-[(methylsulfonyl)amino]ethyl}-1,4-oxazepane-4-carboxylate, and in the same manner as in Example 449, step B, the title compound (110 mg) was obtained.
MS (ESI+): [M+H]$^+$ 367.1.

Example 487

[(6S,7S)-6-(3,4-dichlorophenyl)-1,4-oxazepan-7-yl]methanol monohydrochloride

Using tert-butyl (6S,7S)-6-(3,4-dichlorophenyl)-7-(hydroxymethyl)-1,4-oxazepane-4-carboxylate, and in the same manner as in Example 26, step B, the title compound was obtained.
MS (ESI+): [M+H]$^+$ 276.1.

Example 488

[(6R,7R)-6-(3,4-dichlorophenyl)-1,4-oxazepan-7-yl]methanol monohydrochloride

Using tert-butyl (6R,7R)-6-(3,4-dichlorophenyl)-7-(hydroxymethyl)-1,4-oxazepane-4-carboxylate, and in the same manner as in Example 26, step B, the title compound was obtained.
MS (ESI+): [M+H]$^+$ 276.1.

Example 489

(1R)-1-[(6S,7S)-6-(3,4-dichlorophenyl)-1,4-oxazepan-7-yl]ethane-1,2-diol monohydrochloride In the same manner as in Example 45, the title compound was obtained.
MS (ESI+): [M+H]$^+$ 306.0.

Example 490

(1S)-1-[(6S,7S)-6-(3,4-dichlorophenyl)-1,4-oxazepan-7-yl]ethane-1,2-diol monohydrochloride In the same manner as in Example 46, the title compound was obtained.
MS (ESI+): [M+H]$^+$ 306.1.

Example 491

2-[(6R,7R)-6-(3,4-dichlorophenyl)-1,4-oxazepan-7-yl]propane-1,2,3-triol monohydrochloride A) (6R,7R)-4-(tert-butoxycarbonyl)-6-(3,4-dichlorophenyl)-1,4-oxazepane-7-carboxylic acid To a mixed solution of tert-butyl (6R,7R)-6-(3,4-dichlorophenyl)-7-(hydroxymethyl)-1,4-oxazepane-4-carboxylate (3.0 g) and sodium periodate (3.41 g) in acetonitrile (16 mL)/ethyl acetate (16 mL)/water (24 mL) was added ruthenium (III) chloride (17 mg), and the mixture was stirred at room temperature for 10 min. The solid was filtered off through celite, and the filtrate was concentrated. The residue was crystallized from ethyl acetate to give the title compound (311 mg) as a colorless amorphous powder.

$^1$H NMR (300 MHz, CDCl$_3$) δ 1.26-1.56 (9H, m), 3.25-3.40 (1H, m), 3.40-4.02 (5H, m), 4.06-4.24 (1H, m), 4.32 (1H, brs), 4.61-6.80 (1H, m), 7.07 (1H, dd, J=8.3, 1.9 Hz), 7.33 (1H, d, J=1.9 Hz), 7.38 (1H, d, J=7.9 Hz).

B) 4-tert-butyl 7-methyl (6R,7R)-6-(3,4-dichlorophenyl)-1,4-oxazepane-4,7-dicarboxylate To a solution of (6R,7R)-4-(tert-butoxycarbonyl)-6-(3,4-dichlorophenyl)-1,4-oxazepane-7-carboxylic acid (3.11 g) in DMF (10 mL) were added potassium carbonate (1.32 g) and methyl iodide (0.748 mL). The mixture was stirred at room temperature for 2 hr under nitrogen purging, water was added, and the mixture was extracted with ethyl acetate. The organic layer was washed with brine, and dried over anhydrous magnesium sulfate, and the solvent was evaporated. The residue was purified by silica gel column chromatography (eluent; hexane:ethyl acetate (0%-50%)) to give the title compound (2.86 g) as a colorless oil.

$^1$H NMR (300 MHz, CDCl$_3$) δ 1.32-1.54 (9H, m), 3.36 (1H, ddd, J=9.6, 7.9, 4.2 Hz), 3.41-4.04 (8H, m), 4.07-4.41 (2H, m), 7.07 (1H, d, J=8.3 Hz), 7.32 (1H, d, J=1.9 Hz), 7.37 (1H, d, J=8.3 Hz).

C) tert-butyl (6R,7R)-6-(3,4-dichlorophenyl)-7-(3-hydroxypent-1,4-dien-3-yl)-1,4-oxazepane-4-carboxylate To a solution of 4-tert-butyl 7-methyl (6R,7R)-6-(3,4-dichlorophenyl)-1,4-oxazepane-4,7-dicarboxylate (2.86 g) in THF (30 mL) was added 1.0 M vinylmagnesium bromide/THF solution (15.6 ml) under ice-cooling. The mixture was stirred at 0° C. for 20 min under nitrogen purging, water was added, and the mixture was extracted with ethyl acetate. The organic layer was washed with brine, and dried over anhydrous magnesium sulfate, and the solvent was evaporated. The residue was purified by silica gel column chromatography (eluent; hexane:ethyl acetate (0%-50%)) to give the title compound (2.31 g) as a colorless oil.

$^1$H NMR (300 MHz, CDCl$_3$) δ 1.02-1.49 (9H, m), 2.31 (1H, s), 3.11 (1H, brs), 3.26-3.33 (1H, m), 3.33-3.43 (1H, m), 3.66-3.91 (3H, m), 4.11-4.35 (2H, m), 5.02-5.18 (2H, m), 5.23-5.38 (2H, m), 5.68 (1H, dd, J=16.8, 10.8 Hz), 5.77-5.97 (1H, m), 7.03 (1H, d, J=7.2 Hz), 7.29 (1H, d, J=1.9 Hz), 7.35 (1H, d, J=8.3 Hz).

D) tert-butyl (6R,7R)-6-(3,4-dichlorophenyl)-7-(1,2,3-trihydroxypropan-2-yl)-1,4-oxazepane-4-carboxylate Into a solution of tert-butyl (6R,7R)-6-(3,4-dichlorophenyl)-7-(3-hydroxypent-1,4-dien-3-yl)-1,4-oxazepane-4-carboxylate (2.31 g) in methanol (50 ml) was introduced an ozone gas (from ozone developing apparatus) at −78° C. with stirring. When the solution turned pale-blue, introduction was stopped, and a nitrogen gas was introduced instead until the pale-blue color disappeared. Sodium tetrahydroborate (612 mg) was added at −78° C., and the mixture was warmed with stirring to room temperature, and stirred for 10 min. Water was added to quench the reaction, methanol was evaporated under reduced pressure, and the residue was extracted three times with ethyl acetate. The organic layer was washed with brine, and dried over anhydrous sodium sulfate, and the solvent was evaporated. The residue was purified by silica gel column chromatography (eluent; hexane:ethyl acetate (10%-100%)) to give the title compound (800 mg) as a colorless oil.

$^1$H NMR (300 MHz, CDCl$_3$) δ 0.96-1.57 (9H, m), 1.63 (1H, s), 1.94-2.11 (2H, m), 2.37 (1H, brs), 2.94 (1H, s), 3.20 (1H, d, J=9.4 Hz), 3.32-3.66 (5H, m), 3.67-3.88 (2H, m), 3.94 (1H, d, J=8.7 Hz), 4.00-4.40 (2H, m), 7.11 (1H, dd, J=8.3, 1.9 Hz), 7.34-7.44 (1H, m).

E) 2-[(6R,7R)-6-(3,4-dichlorophenyl)-1,4-oxazepan-7-yl]propane-1,2,3-triol monohydrochloride Using tert-butyl (6R,7R)-6-(3,4-dichlorophenyl)-7-(1,2,3-trihydroxypropan-2-yl)-1,4-oxazepane-4-carboxylate (800 mg), and by a method similar to that of Example 45, step N, the title compound (581 mg) was obtained as colorless crystals.

$^1$H NMR (300 MHz, DMSO-d$_6$) δ 2.67 (1H, d, J=10.6 Hz), 2.90-3.57 (6H, m), 3.59-4.21 (7H, m), 4.29 (1H, ddd, J=13.5, 6.5, 3.4 Hz), 7.35 (1H, dd, J=8.3, 1.9 Hz), 7.58 (1H, d, J=8.3 Hz), 7.64 (1H, d, J=1.9 Hz), 9.02-9.49 (2H, m).

MS (ESI+): [M+H]$^+$ 336.0.

Example 492

2-[(6S,7S)-6-(3,4-dichlorophenyl)-1,4-oxazepan-7-yl]propane-1,2,3-triol monohydrochloride Using tert-butyl (6S,7S)-6-(3,4-dichlorophenyl)-7-(hydroxymethyl)-1,4-oxazepane-4-carboxylate, and by a method similar to that of Example 491, the title compound was obtained.

$^1$H NMR (300 MHz, DMSO-d$_6$) δ 2.67 (1H, d, J=10.6 Hz), 2.89-3.75 (8H, m), 3.79-4.77 (6H, m), 7.35 (1H, dd, J=8.3, 1.9 Hz), 7.55-7.61 (1H, m), 7.64 (1H, d, J=1.9 Hz), 9.11-9.53 (2H, m).

MS (ESI+): [M+H]$^+$ 335.9.

Example 493

(1RS)-1-[(6SR,7SR)-6-(3,4-dichlorophenyl)-1,4-oxazepan-7-yl]-2-(methylsulfonyl)ethanol monohydrochloride A) tert-butyl (6RS,7SR)-6-(3,4-dichlorophenyl)-7-ethenyl-1,4-oxazepane-4-carboxylate Using tert-butyl (6RS,7RS)-6-(3,4-dichlorophenyl)-7-(hydroxymethyl)-1,4-oxazepane-4-carboxylate, and by a method similar to that of Example 45, steps K and L, the title compound was obtained.

$^1$H NMR (300 MHz, CDCl$_3$) δ 1.32-1.56 (9H, m), 2.88 (1H, brs), 3.20-4.30 (7H, m), 4.87-5.23 (2H, m), 5.50-5.70 (1H, m), 6.91-7.07 (1H, m), 7.25-7.28 (1H, m), 7.37 (1H, d, J=7.9 Hz).

B) a mixture of tert-butyl (6RS,7RS)-6-(3,4-dichlorophenyl)-7-[(2RS)-oxiran-2-yl]-1,4-oxazepane-4-carboxylate and tert-butyl (6SR,7RS)-6-(3,4-dichlorophenyl)-7-[(2RS)-oxiran-2-yl]-1,4-oxazepane-4-carboxylate To a solution of tert-butyl (6RS,7SR)-6-(3,4-dichlorophenyl)-7-ethenyl-1,4-oxazepane-4-carboxylate (510 mg) in ethyl acetate (10 mL) was added mCPBA (439 mg) at room temperature. After stirring for 5 hr, additional mCPBA (300 mg) was added, and the mixture was stirred at room temperature overnight. Water was added, and the mixture was extracted with ethyl acetate. The organic layer was washed with aqueous potassium carbonate and brine, and dried over anhydrous magnesium sulfate, and the solvent was evaporated. The residue was purified by silica gel column chromatography (eluent; hexane:ethyl acetate (0%-50%)) to give the title compound (mixture) (420 mg) as a colorless oil.

$^1$H NMR (300 MHz, CDCl$_3$) δ 1.29-1.61 (9H, m), 2.19-2.47 (1H, m), 2.47-2.94 (2H, m), 2.94-3.24 (1H, m), 3.24-4.01 (6H, m), 4.01-4.32 (1H, m), 7.08 (1H, dd, J=8.3, 1.9 Hz), 7.30-7.47 (2H, m).

C) tert-butyl (6SR,7SR)-6-(3,4-dichlorophenyl)-7-[(1RS)-1-hydroxy-2-(methylsulfanyl)ethyl]-1,4-oxazepane-4-carboxylate To a solution of a mixture (420 mg) of tert-butyl (6RS,7RS)-6-(3,4-dichlorophenyl)-7-[(2RS)-oxiran-2-yl]-1,4-oxazepane-4-carboxylate and tert-butyl (6SR,7SR)-6-(3,4-dichlorophenyl)-7-[(2RS)-oxiran-2-yl]-1,4-oxazepane-4-carboxylate in DMF (2 mL) was added sodium thiomethoxide (114 mg), and the mixture was stirred at room temperature for 10 min. Water was added, and the mixture was extracted with ethyl acetate. The organic layer was washed with aqueous potassium carbonate and brine, and dried over anhydrous magnesium sulfate, and the solvent was evaporated. The residue was purified by silica gel column chromatography (eluent; hexane:ethyl acetate (0%-50%)) to give the title compound (130 mg) in a less polar fraction as colorless crystals.

$^1$H NMR (300 MHz, CDCl$_3$) δ 1.29-1.55 (9H, m), 1.61 (1H, d, J=4.5 Hz), 1.93 (3H, s), 2.32 (1H, brs), 2.52-2.69 (2H, m), 3.13-4.03 (7H, m), 4.06-4.31 (1H, m), 7.10 (1H, d, J=8.0 Hz), 7.36 (1H, d, J=1.9 Hz), 7.39 (1H, d, J=8.3 Hz).

In addition, tert-butyl (6RS,7RS)-6-(3,4-dichlorophenyl)-7-[(1RS)-1-hydroxy-2-(methylsulfanyl)ethyl]-1,4-oxazepane-4-carboxylate (160 mg) was obtained by the abovementioned silica gel column chromatography as a high-polar component.

$^1$H NMR (300 MHz, CDCl$_3$) δ 1.19-1.61 (9H, m), 1.67 (1H, brs), 1.80-2.03 (3H, m), 2.36-2.73 (3H, m), 3.07 (1H, brs), 3.23-3.97 (6H, m), 4.13-4.33 (1H, m), 7.06 (1H, dd, J=8.3, 2.3 Hz), 7.32 (1H, d, J=2.3 Hz), 7.39 (1H, d, J=8.3 Hz).

D) tert-butyl (6SR,7SR)-6-(3,4-dichlorophenyl)-7-[(1RS)-1-hydroxy-2-(methylsulfonyl)ethyl]-1,4-oxazepane-4-carboxylate To a solution of tert-butyl (6SR,7SR)-6-(3,4-dichlorophenyl)-7-[(1RS)-1-hydroxy-2-(methylsulfanyl)ethyl]-1,4-oxazepane-4-carboxylate (130 mg) in ethyl acetate (5 mL) was added mCPBA (184 mg) at room temperature, and the mixture was stirred for 2 hr. Water was added, and the mixture was extracted with ethyl acetate. The organic layer was washed with aqueous potassium carbonate and brine, and dried over anhydrous magnesium sulfate, and the solvent was evaporated. The residue was purified by silica gel column chromatography (eluent; hexane:ethyl acetate (0%-50%)) to give the title compound (120 mg) as a colorless oil.

$^1$H NMR (300 MHz, CDCl$_3$) δ 1.29-1.55 (9H, m), 1.63 (1H, t, J=11.0 Hz), 2.76 (1H, brs), 2.87-3.08 (4H, m), 3.22-4.04 (8H, m), 4.15-4.36 (1H, m), 7.07 (1H, d, J=7.9 Hz), 7.32 (1H, s), 7.41 (1H, d, J=8.3 Hz).

E) (1RS)-1-[(6SR,7SR)-6-(3,4-dichlorophenyl)-1,4-oxazepan-7-yl]-2-(methylsulfonyl)ethanol monohydrochloride Using tert-butyl (6SR,7SR)-6-(3,4-dichlorophenyl)-7-[(1RS)-1-hydroxy-2-(methylsulfonyl)ethyl]-1,4-oxazepane-4-carboxylate (120 mg), and by a method similar to that of Example 45, step N, the title compound (77 mg) was obtained as colorless crystals.

$^1$H NMR (300 MHz, DMSO-d$_6$) δ 2.95 (3H, s), 2.99-3.49 (5H, m), 3.52-3.85 (4H, m), 3.87-3.99 (1H, m), 4.29 (1H, ddd, J=13.8, 7.3, 3.4 Hz), 5.71 (1H, d, J=6.4 Hz), 7.38 (1H, dd, J=8.3, 1.9 Hz), 7.62-7.74 (2H, m), 9.12 (1H, brs), 9.77 (1H, brs).

MS (ESI+): [M+H]$^+$ 367.9.

Example 494

(1RS)-1-[(6RS,7RS)-6-(3,4-dichlorophenyl)-1,4-oxazepan-7-yl]-2-(methylsulfonyl)ethanol monohydrochloride Using tert-butyl (6RS,7RS)-6-(3,4-dichlorophenyl)-7-[(1RS)-1-hydroxy-2-(methylsulfanyl)ethyl]-1,4-oxazepane-4-carboxylate (160 mg) obtained in Example 493, step C, and by a method similar to that of Example 493, steps D and E, the title compound (68 mg) was obtained as colorless crystals.

$^1$H NMR (300 MHz, DMSO-d$_6$) δ 2.92 (3H, s), 3.07-3.39 (5H, m), 3.50-3.73 (2H, m), 3.87 (1H, dd, J=10.4, 2.1 Hz), 3.96-4.24 (2H, m), 4.35 (1H, brs), 5.48 (1H, d, J=6.4 Hz), 7.38 (1H, dd, J=8.5, 2.1 Hz), 7.66 (1H, d, J=8.3 Hz), 7.76 (1H, d, J=2.3 Hz), 9.05 (1H, brs), 9.60 (1H, brs).

MS (ESI+): [M+H]$^+$ 367.9.

Example 495

2-{[(6RS,7RS)-6-(3,4-dichlorophenyl)-1,4-oxazepan-7-yl]methoxy}ethanol monohydrochloride A) tert-butyl (6SR,7SR)-6-(3,4-dichlorophenyl)-7-[(2-ethoxy-2-oxoethoxy)methyl]-1,4-oxazepane-4-carboxylate Using tert-butyl (6SR,7SR)-6-(3,4-dichlorophenyl)-7-(hydroxymethyl)-1,4-oxazepane-4-carboxylate (600 mg), and in the same manner as in Example 450, step A, the title compound (570 mg) was obtained.

MS (ESI+): [M+H-Boc]$^+$ 362.0.

B) tert-butyl (6SR,7SR)-6-(3,4-dichlorophenyl)-7-[(2-hydroxyethoxy)methyl]-1,4-oxazepane-4-carboxylate Lithium aluminum hydride (90 mg) was added to a solution of aluminum chloride (90 mg) in THF (5 mL), and the mixture was stirred at room temperature for 40 min. A solution of tert-butyl (6SR,7SR)-6-(3,4-dichlorophenyl)-7-[(2-ethoxy-2-oxoethoxy)methyl]-1,4-oxazepane-4-carboxylate (300 mg) in THF (5 ml) was added dropwise to the reaction mixture, and the mixture was stirred at 0° C. for 1 hr. Sodium sulfate 10 hydrate was added to the reaction mixture, the mixture was stirred at room temperature for 30 min, and the resultant salt was filtered off. The solvent was evaporated under reduced pressure, and the residue was purified by silica gel column chromatography to give the title compound (200 mg).

MS (ESI+): [M+H-Boc]$^+$ 320.0.

C) 2-{[(6RS,7RS)-6-(3,4-dichlorophenyl)-1,4-oxazepan-7-yl]methoxy}ethanol monohydrochloride Using tert-butyl (6SR,7SR)-6-(3,4-dichlorophenyl)-7-[(2-hydroxyethoxy)methyl]-1,4-oxazepane-4-carboxylate (200 mg), and in the same manner as in Example 1, step I, the title compound (142 mg) was obtained.
MS (ESI+): [M+H]$^+$ 320.0.

Example 496

2-{[(6R,7R)-6-(3,4-dichlorophenyl)-1,4-oxazepan-7-yl]methoxy}ethanol monohydrochloride In the same manner as in Example 495, the title compound was obtained.
MS (ESI+): [M+H]$^+$ 320.1.

Example 497

N-(2-{[(6R,7R)-6-(3,4-dichlorophenyl)-1,4-oxazepan-7-yl]methoxy}ethyl)acetamide monohydrochloride A) tert-butyl (6R,7R)-7-[(2-azidoethoxy)methyl]-6-(3,4-dichlorophenyl)-1,4-oxazepane-4-carboxylate Using tert-butyl (6R,7R)-6-(3,4-dichlorophenyl)-7-[(2-hydroxyethoxy)methyl]-1,4-oxazepane-4-carboxylate (440 mg), and in the same manner as in Example 454, step A, the title compound (450 mg) was obtained.
$^1$H NMR (300 MHz, CDCl$_3$) δ 1.31-1.50 (9H, m), 2.89-3.17 (1H, m), 3.21-4.02 (12H, m), 4.12-4.40 (1H, m), 7.07 (1H, dd, J=8.3, 1.9 Hz), 7.32 (1H, d, J=1.9 Hz), 7.39 (1H, d, J=8.3 Hz).
MS (ESI+): [M+H-Boc]$^+$ 345.1.

B) tert-butyl (6R,7R)-7-[(2-aminoethoxy)methyl]-6-(3,4-dichlorophenyl)-1,4-oxazepane-4-carboxylate From tert-butyl (6R,7R)-7-[(2-azidoethoxy)methyl]-6-(3,4-dichlorophenyl)-1,4-oxazepane-4-carboxylate (220 mg) and in the same manner as in Example 62, step I, the title compound was obtained.

C) tert-butyl (6R,7R)-7-{[2-(acetylamino)ethoxy]methyl}-6-(3,4-dichlorophenyl)-1,4-oxazepane-4-carboxylate From tert-butyl (6R,7R)-7-[(2-aminoethoxy)methyl]-6-(3,4-dichlorophenyl)-1,4-oxazepane-4-carboxylate and in the same manner as in Example 6, step C, the title compound (200 mg) was obtained.
$^1$H NMR (300 MHz, CDCl$_3$) δ 1.30-1.53 (9H, m), 1.98 (3H, s), 2.86-4.31 (14H, m), 5.95 (1H, brs), 6.97-7.09 (1H, m), 7.30 (1H, d, J=1.9 Hz), 7.39 (1H, d, J=8.3 Hz).
MS (ESI+): [M+H-Boc]$^+$ 361.3.

D) N-(2-{[(6R,7R)-6-(3,4-dichlorophenyl)-1,4-oxazepan-7-yl]methoxy}ethyl)acetamide monohydrochloride Using tert-butyl (6R,7R)-7-{[2-(acetylamino)ethoxy]methyl}-6-(3,4-dichlorophenyl)-1,4-oxazepane-4-carboxylate (200 mg), and in the same manner as in Example 26, step B, the title compound (89 mg) was obtained.
MS (ESI+): [M+H]$^+$ 361.1.

Example 498

N-(2-{[(6R,7R)-6-(3,4-dichlorophenyl)-1,4-oxazepan-7-yl]methoxy}ethyl)methanesulfonamide monohydrochloride A) tert-butyl (6R,7R)-6-(3,4-dichlorophenyl)-7-({2-[(methylsulfonyl)amino]ethoxy}methyl)-1,4-oxazepane-4-carboxylate From tert-butyl (6R,7R)-7-[(2-aminoethoxy)methyl]-6-(3,4-dichlorophenyl)-1,4-oxazepane-4-carboxylate and in the same manner as in Example 8, step A, the title compound (210 mg) was obtained.
$^1$H NMR (300 MHz, CDCl$_3$) δ 1.30-1.55 (9H, m), 2.89-3.01 (4H, m), 3.16-4.00 (12H, m), 4.17-4.28 (1H, m), 4.92 (1H, brs), 7.04 (1H, dd, J=8.1, 1.7 Hz), 7.29 (1H, d, J=2.3 Hz), 7.40 (1H, d, J=8.3 Hz).
MS (ESI+): [M+H-Boc]$^+$ 397.3.

B) N-(2-{[(6R,7R)-6-(3,4-dichlorophenyl)-1,4-oxazepan-7-yl]methoxy}ethyl)methanesulfonamide monohydrochloride Using tert-butyl (6R,7R)-6-(3,4-dichlorophenyl)-7-({2-[(methylsulfonyl)amino]ethoxy}methyl)-1,4-oxazepane-4-carboxylate (210 mg), and in the same manner as in Example 26, step B, the title compound (155 mg) was obtained.
MS (ESI+): [M+H]$^+$ 397.1.

Example 499

{[(6RS,7RS)-6-(3,4-dichlorophenyl)-1,4-oxazepan-7-yl]methoxy}acetic acid monohydrochloride A) {[(6SR,7SR)-4-(tert-butoxycarbonyl)-6-(3,4-dichlorophenyl)-1,4-oxazepan-7-yl]methoxy}acetic acid From tert-butyl (6SR,7SR)-6-(3,4-dichlorophenyl)-7-[(2-ethoxy-2-oxoethoxy)methyl]-1,4-oxazepane-4-carboxylate (150 mg) and in the same manner as in Example 450, step B, the title compound was obtained.

B) {[(6RS,7RS)-6-(3,4-dichlorophenyl)-1,4-oxazepan-7-yl]methoxy}acetic acid monohydrochloride From {[(6SR,7SR)-4-(tert-butoxycarbonyl)-6-(3,4-dichlorophenyl)-1,4-oxazepan-7-yl]methoxy}acetic acid and in the same manner as in Example 26, step B, the title compound (41 mg) was obtained.
MS (ESI+): [M+H]$^+$ 332.2.

Example 500

Ethyl {[(6RS,7RS)-6-(3,4-dichlorophenyl)-1,4-oxazepan-7-yl]methoxy}acetate monohydrochloride From tert-butyl (6SR,7SR)-6-(3,4-dichlorophenyl)-7-[(2-ethoxy-2-oxoethoxy)methyl]-1,4-oxazepane-4-carboxylate (100 mg) and in the same manner as in Example 26, step B, the title compound (48 mg) was obtained.
MS (ESI+): [M+H]$^+$ 362.0.

Example 501

[(6R,7R)-6-(3,4-dichlorophenyl)-1,4-oxazepan-7-yl] methyl methanesulfonate monohydrochloride From tert-butyl (6R,7R)-6-(3,4-dichlorophenyl)-7-{[(methylsulfonyl)oxy]methyl}-1,4-oxazepane-4-carboxylate (100 mg) and in the same manner as in Example 1, step I, the title compound (49 mg) was obtained.
MS (ESI+): [M+H]$^+$ 354.2.

Example 502

Methyl 2-{[(6S,7S)-6-(3,4-dichlorophenyl)-1,4-oxazepan-7-yl]methoxy}benzoate monohydrochloride Using tert-butyl (6S,7S)-6-(3,4-dichlorophenyl)-7-(hydroxymethyl)-1,4-oxazepane-4-carboxylate, and in the same manner as in Example 451, the title compound (36 mg) was obtained.
MS (ESI+): [M+H]$^+$ 410.0.

Example 503

Methyl 2-{[(6R,7R)-6-(3,4-dichlorophenyl)-1,4-oxazepan-7-yl]methoxy}benzoate monohydrochloride Using tert-butyl (6R,7R)-6-(3,4-dichlorophenyl)-7-(hydroxymethyl)-1,4-oxazepane-4-carboxylate, and in the same manner as in Example 451, the title compound (36 mg) was obtained.
MS (ESI+): [M+H]$^+$ 410.3.

Example 504

Methyl 3-{[(6R,7R)-6-(3,4-dichlorophenyl)-1,4-oxazepan-7-yl]methoxy}benzoate monohydrochloride Using tert-butyl (6R,7R)-6-(3,4-dichlorophenyl)-7-(hydroxymethyl)-1,4-oxazepane-4-carboxylate, and in the same manner as in Example 452, the title compound (33 mg) was obtained.
MS (ESI+): [M+H]$^+$ 410.3.

Example 505

(6RS,7RS)-6-(3,4-dichlorophenyl)-7-[(methylsulfonyl)methyl]-1,4-oxazepane monohydrochloride Using tert-butyl (6RS,7RS)-6-(3,4-dichlorophenyl)-7-(hydroxymethyl)-1,4-oxazepane-4-carboxylate, and in the same manner as in Example 5, the title compound (132 mg) was obtained.
MS (ESI+): [M+H]$^+$ 337.9.

Example 506

N-{[(6RS,7RS)-6-(3,4-dichlorophenyl)-1,4-oxazepan-7-yl]methyl}acetamide monohydrochloride A) tert-butyl (6SR,7SR)-7-[(acetylamino)methyl]-6-(3,4-dichlorophenyl)-1,4-oxazepane-4-carboxylate From tert-butyl (6SR,7SR)-7-(aminomethyl)-6-(3,4-dichlorophenyl)-1,4-oxazepane-4-carboxylate (200 mg) and in the same manner as in Example 6, step C, the title compound (180 mg) was obtained.
$^1$H NMR (300 MHz, CDCl$_3$) δ 1.34-1.52 (9H, m), 1.96 (3H, s), 2.57-4.00 (9H, m), 4.16 (1H, brs), 5.77 (1H, brs), 7.04 (1H, dd, J=8.3, 1.9 Hz), 7.27-7.34 (1H, m), 7.40 (1H, d, J=8.3 Hz).

B) N-{[(6RS,7RS)-6-(3,4-dichlorophenyl)-1,4-oxazepan-7-yl]methyl}acetamide monohydrochloride Using tert-butyl (6SR,7SR)-7-[(acetylamino)methyl]-6-(3,4-dichlorophenyl)-1,4-oxazepane-4-carboxylate (180 mg), and in the same manner as in Example 26, step B, the title compound (120 mg) was obtained.
MS (ESI+): [M+H]$^+$ 317.0.

Example 507

N-{[(6R,7R)-6-(3,4-dichlorophenyl)-1,4-oxazepan-7-yl]methyl}-2-hydroxyacetamide monohydrochloride A) tert-butyl (6R,7R)-6-(3,4-dichlorophenyl)-7-{[(hydroxyacetyl)amino]methyl}-1,4-oxazepane-4-carboxylate To a solution of tert-butyl (6R,7R)-7-(aminomethyl)-6-(3,4-dichlorophenyl)-1,4-oxazepane-4-carboxylate (170 mg) and triethylamine (0.126 mL) in THF (4.0 ml) was added acetoxyacetyl chloride (93 mg), and the mixture was stirred at room temperature overnight. To the reaction solution was added water, and the mixture was extracted with ethyl acetate. The organic layer was washed with water and brine, and dried over anhydrous magnesium sulfate. The solvent was evaporated under reduced pressure. To a solution of the obtained residue in methanol (4.0 mL) was added potassium carbonate (273 mg), and the mixture was stirred at room temperature for 3 hr. The reaction solution was concentrated under reduced pressure, the residue was poured into water, and the mixture was extracted with ethyl acetate. The extract was washed with water and brine, and dried over anhydrous magnesium sulfate. The solvent was evaporated under reduced pressure. The residue was purified by silica gel chromatography (hexane/ethyl acetate) to give the title compound (183 mg).
MS (ESI+): [M+H]$^+$ 433.1.

B) N-{[(6R,7R)-6-(3,4-dichlorophenyl)-1,4-oxazepan-7-yl]methyl}-2-hydroxyacetamide monohydrochloride Using tert-butyl (6R,7R)-6-(3,4-dichlorophenyl)-7-{[(hydroxyacetyl)amino]methyl}-1,4-oxazepane-4-carboxylate, and in the same manner as in Example 10, step H, the title compound (114 mg) was obtained.
MS (ESI+): [M+H]$^+$ 333.4.

Example 508

N-{[(6R,7R)-6-(3,4-dichlorophenyl)-1,4-oxazepan-7-yl]methyl}-2-methoxyacetamide monohydrochloride A) tert-butyl (6R,7R)-6-(3,4-dichlorophenyl)-7-{[(methoxyacetyl)amino]methyl}-1,4-oxazepane-4-carboxylate To a solution of tert-butyl (6R,7R)-7-(aminomethyl)-6-(3,4-dichlorophenyl)-1,4-oxazepane-4-carboxylate (140 mg)

and triethylamine (0.156 mL) in THF (3.0 mL) was added acetoxyacetyl chloride (81 mg), and the mixture was stirred at room temperature overnight. To the reaction solution was added water, and the mixture was extracted with ethyl acetate. The organic layer was washed with water and brine, and dried over anhydrous magnesium sulfate. The solvent was evaporated under reduced pressure. The residue was purified by silica gel chromatography (hexane/ethyl acetate) to give the title compound (168 mg).

$^1$H NMR (300 MHz, CDCl$_3$) δ 1.31-1.55 (9H, m), 2.83 (1H, brs), 2.99 (1H, brs), 3.21-3.39 (2H, m), 3.40 (3H, s), 3.43-3.81 (5H, m), 3.84 (2H, s), 4.20 (1H, brs), 6.78 (1H, brs), 7.04 (1H, dd, J=8.1, 2.1 Hz), 7.30 (1H, d, J=1.9 Hz), 7.40 (1H, d, J=8.3 Hz).

B) N-{[(6R,7R)-6-(3,4-dichlorophenyl)-1,4-oxazepan-7-yl]methyl}-2-methoxyacetamide monohydrochloride Using tert-butyl (6R,7R)-6-(3,4-dichlorophenyl)-7-{[(methoxyacetyl)amino]methyl}-1,4-oxazepane-4-carboxylate, and in the same manner as in Example 10, step H, the title compound (90 mg) was obtained.

MS (ESI+): [M+H]$^+$ 347.3.

Example 509

N-{[(6RS,7RS)-6-(3,4-dichlorophenyl)-1,4-oxazepan-7-yl]methyl}-2-(1H-1,2,4-triazol-1-yl)acetamide monohydrochloride A) tert-butyl (6SR,7SR)-6-(3,4-dichlorophenyl)-7-{[(1H-1,2,4-triazol-1-ylacetyl)amino]methyl}-1,4-oxazepane-4-carboxylate To a solution of tert-butyl (6SR,7SR)-7-(aminomethyl)-6-(3,4-dichlorophenyl)-1,4-oxazepane-4-carboxylate (200 mg) in DMF (5 mL) were added WSC (100 mg), HOBt (90 mg), triethylamine (0.10 mL) and 2-(1H-1,2,4-triazol-1-yl)acetic acid (74 mg), and the mixture was stirred at room temperature overnight. To the reaction mixture was added saturated aqueous sodium hydrogen carbonate, and the mixture was extracted with ethyl acetate. The extract was washed with brine, and dried over anhydrous sodium sulfate. The solvent was evaporated under reduced pressure. The residue was purified by silica gel column chromatography to give the title compound (190 mg).

$^1$H NMR (300 MHz, CDCl$_3$) δ 1.30-1.68 (9H, m), 2.50-3.98 (10H, m), 4.82 (2H, s), 6.55 (1H, brs), 7.00 (1H, dd, J=8.3, 1.5 Hz), 7.39 (1H, d, J=8.3 Hz), 8.05 (1H, s), 8.16 (1H, s), 1H not detected.

B) N-{[(6RS,7RS)-6-(3,4-dichlorophenyl)-1,4-oxazepan-7-yl]methyl}-2-(1H-1,2,4-triazol-1-yl)acetamide monohydrochloride Using tert-butyl (6SR,7SR)-6-(3,4-dichlorophenyl)-7-{[(1H-1,2,4-triazol-1-ylacetyl)amino]methyl}-1,4-oxazepane-4-carboxylate (190 mg), and in the same manner as in Example 26, step B, the title compound (120 mg) was obtained.

MS (ESI+): [M+H]$^+$ 383.9.

Example 510

N-{[(6RS,7RS)-6-(3,4-dichlorophenyl)-1,4-oxazepan-7-yl]methyl}benzamide monohydrochloride From tert-butyl (6SR,7SR)-7-(aminomethyl)-6-(3,4-dichlorophenyl)-1,4-oxazepane-4-carboxylate, and in the same manner as in Example 506, the title compound (150 mg) was obtained.

MS (ESI+): [M+H]$^+$ 379.1.

Example 511

N-{[(6RS,7RS)-6-(3,4-dichlorophenyl)-1,4-oxazepan-7-yl]methyl}methanesulfonamide monohydrochloride From tert-butyl (6SR,7SR)-7-(aminomethyl)-6-(3,4-dichlorophenyl)-1,4-oxazepane-4-carboxylate, and in the same manner as in Example 498, the title compound (48 mg) was obtained.

MS (ESI+): [M+H]$^+$ 353.0.

Example 512

N-(1-{[(6R,7R)-6-(3,4-dichlorophenyl)-1,4-oxazepan-7-yl]methyl}piperidin-4-yl)acetamide dihydrochloride In the same manner as in Example 477, the title compound (160 mg) was obtained.

MS (ESI+): [M+H]$^+$ 400.3.

Example 513

(6RS,7RS)-6-(3,4-dichlorophenyl)-7-[(4-methyl-1H-pyrazol-1-yl)methyl]-1,4-oxazepane monohydrochloride In the same manner as in Example 480, the title compound (120 mg) was obtained.

MS (ESI+): [M+H]$^+$ 340.0.

Example 514

1-{[(6R,7R)-6-(3,4-dichlorophenyl)-1,4-oxazepan-7-yl]methyl}pyridin-2(1H)-one monohydrochloride A) tert-butyl (6R,7R)-6-(3,4-dichlorophenyl)-7-[(2-oxopyridin-1(2H)-yl)methyl]-1,4-oxazepane-4-carboxylate To a solution of tert-butyl (6R,7R)-6-(3,4-dichlorophenyl)-7-(iodomethyl)-1,4-oxazepane-4-carboxylate (370 mg) in DMF (8.0 mL) were added 2(1H)-pyridinone (87 mg) and potassium carbonate (158 mg), and the mixture was heated at 80° C. for 4 hr. The reaction solution was allowed to cool to room temperature, water was added, and the mixture was extracted with ethyl acetate. The organic layer was washed with 0.1 N hydrochloric acid and brine, and dried over anhydrous magnesium sulfate. The solvent was evaporated under reduced pressure. The residue was purified by silica gel chromatography (hexane/ethyl acetate) to give the title compound (44 mg).

¹H NMR (300 MHz, CDCl₃) δ 1.41-1.47 (9H, m), 2.86 (1H, brs), 3.02-4.07 (7H, m), 4.14-4.37 (2H, m), 6.10 (1H, td, J=6.8, 1.1 Hz), 6.50 (1H, d, J=9.0 Hz), 7.22 (1H, dd, J=8.3, 1.9 Hz), 7.27-7.52 (4H, m).

B) 1-{[(6R,7R)-6-(3,4-dichlorophenyl)-1,4-oxazepan-7-yl]methyl}pyridin-2(1H)-one monohydrochloride Using tert-butyl (6R,7R)-6-(3,4-dichlorophenyl)-7-[(2-oxopyridin-1(2H)-yl)methyl]-1,4-oxazepane-4-carboxylate, and in the same manner as in Example 2, step B, the title compound (36 mg) was obtained.
MS (ESI+): [M+H]⁺ 353.0.

Example 515

2-{[(6R,7R)-6-(3,4-dichlorophenyl)-1,4-oxazepan-7-yl]methyl}pyridazin-3(2H)-one monohydrochloride Using tert-butyl (6R,7R)-6-(3,4-dichlorophenyl)-7-(iodomethyl)-1,4-oxazepane-4-carboxylate, and in the same manner as in Example 481, the title compound (46 mg) was obtained.
MS (ESI+): [M+H]⁺ 354.2.

Example 516

[(6RS,7SR)-6-(3,4-dichlorophenyl)-1,4-oxazepan-7-yl]acetonitrile monohydrochloride A) tert-butyl (6SR,7RS)-7-(cyanomethyl)-6-(3,4-dichlorophenyl)-1,4-oxazepane-4-carboxylate To a solution of tert-butyl (6SR,7SR)-6-(3,4-dichlorophenyl)-7-(hydroxymethyl)-1,4-oxazepane-4-carboxylate (900 mg) in THF (5 mL) were successively added dropwise triethylamine (1.0 mL) and methanesulfonyl chloride (0.37 mL), and the mixture was stirred at room temperature overnight. Water was added to the reaction mixture, and the mixture was extracted with ethyl acetate. The obtained extract was washed with brine, and dried over anhydrous sodium sulfate. The solvent was evaporated under reduced pressure.
To a solution of the residue in DMF (4 mL) was added sodium cyanide (230 mg), and the mixture was stirred at 70° C. overnight. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (640 mg).
¹H NMR (300 MHz, CDCl₃) δ 1.35-1.51 (9H, m, J=5.3 Hz), 2.14-2.70 (3H, m), 2.82-3.08 (2H, m), 3.63-3.91 (4H, m), 4.17-4.31 (1H, m, J=17.0 Hz), 7.05 (1H, d, J=8.3 Hz), 7.29 (1H, d, J=1.9 Hz), 7.43 (1H, d, J=8.3 Hz).

B) [(6RS,7SR)-6-(3,4-dichlorophenyl)-1,4-oxazepan-7-yl]acetonitrile monohydrochloride Using tert-butyl (6SR,7RS)-7-(cyanomethyl)-6-(3,4-dichlorophenyl)-1,4-oxazepane-4-carboxylate (100 mg), and in the same manner as in Example 26, step B, the title compound (50 mg) was obtained.
MS (ESI+): [M+H]⁺ 284.9.

Example 517

N-{2-[(6R,7S)-6-(3,4-dichlorophenyl)-1,4-oxazepan-7-yl]ethyl}acetamide monohydrochloride A) tert-butyl (6R,7S)-7-(2-aminoethyl)-6-(3,4-dichlorophenyl)-1,4-oxazepane-4-carboxylate From tert-butyl (6R,7S)-7-(cyanomethyl)-6-(3,4-dichlorophenyl)-1,4-oxazepane-4-carboxylate and in the same manner as in Example 495, step B, the title compound was obtained.
MS (ESI+): [M+H]⁺ 389.3.

B) tert-butyl (6R,7S)-7-[2-(acetylamino)ethyl]-6-(3,4-dichlorophenyl)-1,4-oxazepane-4-carboxylate From tert-butyl (6R,7S)-7-(2-aminoethyl)-6-(3,4-dichlorophenyl)-1,4-oxazepane-4-carboxylate (600 mg), and in the same manner as in Example 6, step C, the title compound (450 mg) was obtained.
¹H NMR (300 MHz, CDCl₃) δ 1.30-1.54 (11H, m), 1.93 (3H, s), 2.80 (1H, brs), 2.99-4.42 (9H, m), 5.61-6.04 (1H, m), 6.99 (1H, d, J=7.9 Hz), 7.24 (1H, d, J=1.5 Hz), 7.38 (1H, d, J=7.9 Hz).

C) N-{2-[(6R,7S)-6-(3,4-dichlorophenyl)-1,4-oxazepan-7-yl]ethyl}acetamide monohydrochloride Using tert-butyl (6R,7S)-7-[2-(acetylamino)ethyl]-6-(3,4-dichlorophenyl)-1,4-oxazepane-4-carboxylate (200 mg), and in the same manner as in Example 26, step B, the title compound (99 mg) was obtained.
MS (ESI+): [M+H]⁺ 331.1.

Example 518

N-{2-[(6R,7S)-6-(3,4-dichlorophenyl)-1,4-oxazepan-7-yl]ethyl}methanesulfonamide monohydrochloride A) tert-butyl (6R,7S)-6-(3,4-dichlorophenyl)-7-{2-[(methylsulfonyl)amino]ethyl}-1,4-oxazepane-4-carboxylate From tert-butyl (6R,7S)-7-(2-aminoethyl)-6-(3,4-dichlorophenyl)-1,4-oxazepane-4-carboxylate (300 mg) and in the same manner as in Example 8, step A, the title compound (300 mg) was obtained.
¹H NMR (300 MHz, CDCl₃) δ 1.33-1.51 (11H, m), 2.80 (1H, brs), 2.90 (3H, s), 3.04-3.56 (4H, m), 3.62-4.33 (5H, m), 4.62 (1H, brs), 7.00 (1H, d, J=8.3 Hz), 7.26-7.34 (1H, m), 7.39 (1H, d, J=8.3 Hz).

B) N-{2-[(6R,7S)-6-(3,4-dichlorophenyl)-1,4-oxazepan-7-yl]ethyl}methanesulfonamide monohydrochloride Using tert-butyl (6R,7S)-6-(3,4-dichlorophenyl)-7-{2-[(methylsulfonyl)amino]ethyl}-1,4-oxazepane-4-carboxylate (300 mg), and in the same manner as in Example 26, step B, the title compound (205 mg) was obtained.
MS (ESI+): [M+H]⁺ 367.1.

Example 519

N-{3-[(6RS,7SR)-6-(3,4-dichlorophenyl)-1,4-oxazepan-7-yl]propyl}acetamide monohydrochloride A) tert-butyl (6SR,7RS)-6-(3,4-dichlorophenyl)-7-[(1E)-3-ethoxy-3-oxoprop-1-en-1-yl]-1,4-oxazepane-4-carboxylate To a solution of triethyl phosphonoacetate (440 mg) in acetonitrile (5 ml) was added dropwise diazabicycloundecene (0.25 mL), and the mixture was stirred at room temperature for 30 min. To the reaction mixture was added a solution of lithium chloride (80 mg) and tert-butyl (6SR,7SR)-6-(3,4-dichlorophenyl)-7-formyl-1,4-oxazepane-4-carboxylate (610 mg) in acetonitrile (10 ml), and the mixture was stirred at room temperature overnight. The solvent was evaporated under reduced pressure, and the residue was purified by silica gel column chromatography to give the title compound (630 mg).

$^1$H NMR (300 MHz, CDCl$_3$) δ 1.26 (3H, t, J=7.0 Hz), 1.33-1.49 (9H, m), 2.71-4.46 (10H, m), 5.96 (1H, d, J=15.9 Hz), 6.61 (1H, dd, J=15.7, 4.0 Hz), 7.02 (1H, d, J=8.3 Hz), 7.29 (1H, d, J=2.3 Hz), 7.40 (1H, d, J=8.0 Hz).

MS (ESI+): [M+H-Boc]$^+$ 344.0.

B) tert-butyl (6SR,7RS)-6-(3,4-dichlorophenyl)-7-(3-ethoxy-3-oxopropyl)-1,4-oxazepane-4-carboxylate To a solution of tert-butyl (6SR,7RS)-6-(3,4-dichlorophenyl)-7-[(1E)-3-ethoxy-3-oxoprop-1-en-1-yl]-1,4-oxazepane-4-carboxylate (630 mg) in ethanol (5 ml) was added 3% Pt/sulfided carbon (100 mg), and the mixture was stirred under a hydrogen atmosphere at room temperature overnight. The catalyst was removed by filtration. The solvent was evaporated under reduced pressure. The residue was purified by silica gel column chromatography to give the title compound (450 mg).

$^1$H NMR (300 MHz, CDCl$_3$) δ 1.22 (3H, t, J=7.2 Hz), 1.33-1.52 (9H, m), 2.23-2.52 (2H, m), 2.78 (1H, brs), 3.11-3.97 (7H, m), 4.00-4.37 (4H, m), 7.02 (1H, d, J=8.3 Hz), 7.28 (1H, brs), 7.38 (1H, d, J=7.9 Hz).

MS (ESI+): [M+H-Boc]$^+$ 346.0.

C) tert-butyl (6SR,7RS)-6-(3,4-dichlorophenyl)-7-(3-hydroxypropyl)-1,4-oxazepane-4-carboxylate Using tert-butyl (6SR,7RS)-6-(3,4-dichlorophenyl)-7-(3-ethoxy-3-oxopropyl)-1,4-oxazepane-4-carboxylate (450 mg), and in the same manner as in Example 495, step B, the title compound (290 mg) was obtained.

$^1$H NMR (300 MHz, CDCl$_3$) δ 1.32-1.50 (9H, m), 1.48-1.87 (4H, m), 2.81 (1H, brs), 3.07-4.42 (10H, m), 7.01 (1H, d, J=7.9 Hz), 7.26-7.32 (1H, m), 7.38 (1H, d, J=8.3 Hz).

D) tert-butyl (6SR,7RS)-7-(3-azidopropyl)-6-(3,4-dichlorophenyl)-1,4-oxazepane-4-carboxylate Using tert-butyl (6SR,7RS)-6-(3,4-dichlorophenyl)-7-(3-hydroxypropyl)-1,4-oxazepane-4-carboxylate (290 mg), and in the same manner as in Example 454, step A, the title compound (300 mg) was obtained.

$^1$H NMR (300 MHz, CDCl$_3$) δ 1.11-1.51 (12H, m), 1.67-1.95 (1H, m), 2.57-4.38 (10H, m), 7.00 (1H, d, J=8.0 Hz), 7.15-7.25 (1H, m), 7.39 (1H, d, J=8.0 Hz).

E) tert-butyl (6SR,7RS)-7-(3-aminopropyl)-6-(3,4-dichlorophenyl)-1,4-oxazepane-4-carboxylate From tert-butyl (6SR,7RS)-7-(3-azidopropyl)-6-(3,4-dichlorophenyl)-1,4-oxazepane-4-carboxylate (300 mg), and in the same manner as in Example 62, step I, the title compound was obtained.

MS (ESI+): [M+H]$^+$ 403.3.

F) tert-butyl (6SR,7RS)-7-[3-(acetylamino)propyl]-6-(3,4-dichlorophenyl)-1,4-oxazepane-4-carboxylate From tert-butyl (6SR,7RS)-7-(3-aminopropyl)-6-(3,4-dichlorophenyl)-1,4-oxazepane-4-carboxylate and in the same manner as in Example 6, step C, the title compound (120 mg) was obtained.

$^1$H NMR (300 MHz, CDCl$_3$) δ 1.13-1.59 (13H, m), 1.92 (3H, s), 2.42-4.32 (10H, m), 5.45 (1H, brs), 7.00 (1H, d, J=8.3 Hz), 7.25 (1H, brs), 7.38 (1H, d, J=7.9 Hz).

MS (ESI+): [M+H-Boc]$^+$ 345.2.

G) N-{3-[(6RS,7SR)-6-(3,4-dichlorophenyl)-1,4-oxazepan-7-yl]propyl}acetamide monohydrochloride Using tert-butyl (6S,7R)-7-[3-(acetylamino)propyl]-6-(3,4-dichlorophenyl)-1,4-oxazepane-4-carboxylate (120 mg), and in the same manner as in Example 26, step B, the title compound (96 mg) was obtained.

MS (ESI+): [M+H]$^+$ 345.2.

Example 520

N-{3-[(6RS,7SR)-6-(3,4-dichlorophenyl)-1,4-oxazepan-7-yl]propyl}methanesulfonamide monohydrochloride A) tert-butyl (6SR,7RS)-6-(3,4-dichlorophenyl)-7-{3-[(methylsulfonyl)amino]propyl}-1,4-oxazepane-4-carboxylate From tert-butyl (6SR,7RS)-7-(3-aminopropyl)-6-(3,4-dichlorophenyl)-1,4-oxazepane-4-carboxylate, and in the same manner as in Example 8, step A, the title compound (60 mg) was obtained.

MS (ESI+): [M–H]$^+$ 479.1.

B) N-{3-[(6RS,7SR)-6-(3,4-dichlorophenyl)-1,4-oxazepan-7-yl]propyl}methanesulfonamide monohydrochloride Using tert-butyl (6SR,7RS)-6-(3,4-dichlorophenyl)-7-{3-[(methylsulfonyl)amino]propyl}-1,4-oxazepane-4-carboxylate (60 mg), and in the same manner as in Example 26, step B, the title compound (15 mg) was obtained.

MS (ESI+): [M+H]$^+$ 381.2.

Example 521

N-{[(6RS,7SR)-7-(3,4-dichlorophenyl)-6-hydroxy-1,4-oxazepan-6-yl]methyl}-1,1-difluoromethanesulfonamide monohydrochloride In the same manner as in Example 100, the title compound was obtained.

MS (ESI+): [M+H]$^+$ 405.1.

Example 522

N-{[(6RS,7SR)-7-(3,4-dichlorophenyl)-6-hydroxy-1,
4-oxazepan-6-yl]methyl}propane-2-sulfonamide
monohydrochloride In the same manner as in Example 100, the title compound was obtained.
MS (ESI+): [M+H]$^+$ 397.1.

Example 523

N-{[(6RS,7SR)-7-(3,4-dichlorophenyl)-6-methoxy-
1,4-oxazepan-6-yl]methyl}methanesulfonamide
monohydrochloride In the same manner as in Example 101, the title compound was obtained.
MS (ESI+): [M+H]$^+$ 383.1.

Example 524

3-(2-{[(6R*,7S*)-7-(3,4-dichlorophenyl)-1,4-ox-
azepan-6-yl]oxy}pyridin-3-yl)-1,2,4-oxadiazol-5
(4H)-one monohydrochloride (retention time short)

tert-Butyl (6RS,7SR)-6-[(3-cyanopyridin-2-yl)oxy]-7-(3, 4-dichlorophenyl)-1,4-oxazepane-4-carboxylate (390 mg) was separated by HPLC (column: CHIRALPAK AD, 50 mmID×500 mL, manufactured by DAICEL CHEMICAL INDUSTRIES, LTD., mobile phase: hexane/2-propanol=90/ 10) to give tert-butyl (6R*,7S*)-6-[(3-cyanopyridin-2-yl) oxy]-7-(3,4-dichlorophenyl)-1,4-oxazepane-4-carboxylate (113 mg, >99.9% ee) having a shorter retention time. In addition, tert-butyl (6R*,7S*)-6-[(3-cyanopyridin-2-yl) oxy]-7-(3,4-dichlorophenyl)-1,4-oxazepane-4-carboxylate (130 mg, >99.9% ee) having a longer retention time was obtained. Using tert-butyl (6R*,7S*)-6-[(3-cyanopyridin-2-yl)oxy]-7-(3,4-dichlorophenyl)-1,4-oxazepane-4-carboxylate (retention time short), and in the same manner as in Example 236, the title compound was obtained.
MS (ESI+): [M+H]$^+$ 423.1.

Example 525

3-(2-{[(6R*,7S*)-7-(3,4-dichlorophenyl)-1,4-ox-
azepan-6-yl]oxy}pyridin-3-yl)-1,2,4-oxadiazol-5
(4H)-one monohydrochloride (retention time long)

Using tert-butyl (6R*,7S*)-6-[(3-cyanopyridin-2-yl)oxy]-7-(3,4-dichlorophenyl)-1,4-oxazepane-4-carboxylate (retention time long) obtained in Example 524, and in the same manner as in Example 236, the title compound was obtained.
MS (ESI+): [M+H]$^+$ 423.1.

Example 526

Methyl 1-{[(6S,7R)-7-(4-chloro-3-fluorophenyl)-1,
4-oxazepan-6-yl]methyl}-2-oxo-1,2-dihydropyri-
dine-3-carboxylate monohydrochloride Using tert-butyl (6S,7R)-7-(4-chloro-3-fluorophenyl)-6-{[(methylsulfonyl)oxy]methyl}-1,4-oxazepane-4-carboxylate and methyl 2-oxo-1,2-dihydropyridine-3-carboxylate, and by a method similar to that in Example 31, steps C and E, the title compound was obtained.
$^1$H NMR (300 MHz, DMSO-d$_6$) δ 2.99-3.29 (5H, m), 3.63-3.87 (5H, m), 3.90-4.06 (2H, m), 4.51 (1H, d, J=9.8 Hz), 6.26 (1H, t, J=7.0 Hz), 7.28 (1H, dd, J=8.3, 1.5 Hz), 7.48 (1H, dd, J=10.6, 1.9 Hz), 7.52-7.60 (1H, m), 7.74 (1H, dd, J=6.6, 2.1 Hz), 7.94 (1H, dd, J=7.2, 1.9 Hz), 8.62-9.34 (2H, m).
MS (ESI+): [M+H]$^+$ 395.3.

Example 527

Methyl 2-{[(6S,7R)-7-(4-chloro-3-fluorophenyl)-1,
4-oxazepan-6-yl]methoxy}pyridine-3-carboxylate
monohydrochloride Using tert-butyl (6S,7R)-7-(4-chloro-3-fluorophenyl)-6-{[(methylsulfonyl)oxy]methyl}-1,4-oxazepane-4-carboxylate and methyl 2-oxo-1,2-dihydropyridine-3-carboxylate, and by a method similar to that in Example 31, steps C and E, the title compound was obtained.
$^1$H NMR (300 MHz, DMSO-d$_6$) δ 2.81-2.97 (1H, m), 3.16-3.53 (3H, m), 3.57-3.69 (1H, m), 3.80-3.93 (4H, m), 3.99 (1H, dd, J=11.3, 6.0 Hz), 4.07-4.18 (1H, m), 4.22-4.32 (1H, m), 4.66 (1H, d, J=9.8 Hz), 7.13 (1H, dd, J=7.6, 4.9 Hz), 7.25 (1H, dd, J=8.3, 1.9 Hz), 7.46 (1H, dd, J=10.6, 1.5 Hz), 7.59 (1H, t, J=8.1 Hz), 8.18 (1H, dd, J=7.6, 1.9 Hz), 8.30 (1H, dd, J=4.9, 1.9 Hz), 9.20-9.65 (2H, m).
MS (ESI+): [M+H]$^+$ 395.3.

Example 528

3-(2-{[(6RS,7SR)-7-(4-chloro-3-fluorophenyl)-1,4-
oxazepan-6-yl]oxy}pyridin-3-yl)-1,2,4-oxadiazol-5
(4H)-one monohydrochloride Using tert-butyl (6RS,7SR)-7-(4-chloro-3-fluorophenyl)-6-hydroxy-1,4-oxazepane-4-carboxylate, and in the same manner as in Example 524, the title compound (127 mg) was obtained.
MS (ESI+): [M+H]$^+$ 407.3.

Example 529

(6RS,7SR)-7-(4-chloro-3-fluorophenyl)-6-{[3-(1H-
tetrazol-5-yl)pyridin-2-yl]oxy}-1,4-oxazepane
monohydrochloride Using tert-butyl (6RS,7SR)-7-(4-chloro-3-fluorophenyl)-6-[(3-cyanopyridin-2-yl)oxy]-1,4-oxazepane-4-carboxylate, and in the same manner as in Example 208, the title compound (34 mg) was obtained.
MS (ESI+): [M+H]$^+$ 391.1.

Example 530

Methyl 2-{[(6RS,7SR)-7-(4-chloro-3-fluorophenyl)-
1,4-oxazepan-6-yl]oxy}pyridine-3-carboxylate
monohydrochloride Using tert-butyl (6RS,7SR)-7-(4-chloro-3-fluorophenyl)-6-hydroxy-1,4-oxazepane-4-carboxylate, and in the same manner as in Example 524, the title compound (127 mg) was obtained.
MS (ESI+): [M+H]$^+$ 381.1.

Example 531

2-{[(6RS,7SR)-7-(4-chloro-3-fluorophenyl)-1,4-oxazepan-6-yl]oxy}pyridine-3-carboxylic acid monohydrochloride Using tert-butyl (6RS,7SR)-7-(4-chloro-3-fluorophenyl)-6-{[3-(methoxycarbonyl)pyridin-2-yl]oxy}-1,4-oxazepane-4-carboxylate, and in the same manner as in Example 58, steps B and C, the title compound (119 mg) was obtained.
MS (ESI+): [M+H]$^+$ 367.3.

Example 532

1-{[(6S,7R)-7-(4-chloro-3-fluorophenyl)-1,4-oxazepan-6-yl]methyl}-3-(5-oxo-4,5-dihydro-1,2,4-oxadiazol-3-yl)tetrahydropyrimidin-2(1H)-one monohydrochloride A) tert-butyl (6R,7R)-7-(4-chloro-3-fluorophenyl)-6-[(3-cyano-2-oxotetrahydropyrimidin-1(2H)-yl)methyl]-1,4-oxazepane-4-carboxylate To a solution of tert-butyl (6R,7R)-7-(4-chloro-3-fluorophenyl)-6-[(2-oxotetrahydropyrimidin-1(2H)-yl)methyl]-1,4-oxazepane-4-carboxylate (260 mg) in DMF (2.9 mL) was added sodium hydride (94.0 mg, 60% in oil) under ice-cooling, and the mixture was stirred at 0° C. for 1 hr, and at room temperature for 1 hr. Then, phenyl cyanate (210 mg) was added, and the mixture was stirred at room temperature for 1 hr. To the reaction mixture was added distilled water, and the mixture was extracted with ethyl acetate. The obtained extract was washed with distilled water and brine, and dried over anhydrous magnesium sulfate, and the solvent was evaporated under reduced pressure. The residue was purified by silica gel chromatography (hexane/ethyl acetate) to give the title compound (147 mg).
$^1$H NMR (300 MHz, CDCl$_3$) δ 1.49 (9H, s), 1.71-2.03 (2H, m), 2.35-2.54 (1H, m), 2.70-3.83 (11H, m), 4.04-4.27 (2H, m), 7.07 (1H, d, J=8.3 Hz), 7.14 (1H, d, J=9.8 Hz), 7.36-7.47 (1H, m).

B) 1-{[(6S,7R)-7-(4-chloro-3-fluorophenyl)-1,4-oxazepan-6-yl]methyl}-3-(5-oxo-4,5-dihydro-1,2,4-oxadiazol-3-yl)tetrahydropyrimidin-2(1H)-one monohydrochloride Using tert-butyl (6R,7R)-7-(4-chloro-3-fluorophenyl)-6-[(3-cyano-2-oxotetrahydropyrimidin-1(2H)-yl)methyl]-1,4-oxazepane-4-carboxylate, and in the same manner as in Example 31, steps D and E, the title compound was obtained.
MS (ESI+): [M−H]$^+$ 426.1.

Example 533

N-{[(6S,7R)-7-(4-chloro-3-fluorophenyl)-1,4-oxazepan-6-yl]methyl}tetrahydro-2H-pyran-2-carboxamide monohydrochloride In the same manner as in Example 311, the title compound was obtained.
MS (ESI+): [M+H]$^+$ 371.2.

Example 534

3-chloro-1-{[(6S,7R)-7-(4-chloro-3-fluorophenyl)-1,4-oxazepan-6-yl]methyl}pyridin-2(1H)-one monohydrochloride Using tert-butyl (6S,7R)-7-(4-chloro-3-fluorophenyl)-6-{[(methylsulfonyl)oxy]methyl}-1,4-oxazepane-4-carboxylate and 3-chloropyridin-2(1H)-one, and by a method similar to that in Example 31, steps C and E, the title compound was obtained.
$^1$H NMR (300 MHz, DMSO-d$_6$) δ 3.07-3.30 (5H, m), 3.70-3.87 (2H, m), 3.93-4.06 (2H, m), 4.52 (1H, d, J=9.5 Hz), 6.20 (1H, t, J=7.0 Hz), 7.24-7.32 (1H, m), 7.44-7.60 (3H, m), 7.62-7.68 (1H, m), 8.82-9.80 (2H, m).
MS (ESI+): [M+H]$^+$ 371.0.

Example 535

1-{[(6S,7R)-7-(3-chloro-4-fluorophenyl)-1,4-oxazepan-6-yl]methyl}-3-(5-oxo-4,5-dihydro-1,2,4-oxadiazol-3-yl)pyridin-2(1H)-one monohydrochloride Using tert-butyl (6S,7R)-7-(3-chloro-4-fluorophenyl)-6-(hydroxymethyl)-1,4-oxazepane-4-carboxylate (200 mg), and in the same manner as in Example 31, step B, Example 44, step A and Example 33, steps D and E, the title compound (5 mg) was obtained.
MS (ESI+): [M+H]$^+$ 421.1.

Example 536

N-{[(6RS,7SR)-7-(4-chloro-3-fluorophenyl)-6-hydroxy-1,4-oxazepan-6-yl]methyl}-N-methylacetamide monohydrochloride In the same manner as in Example 100, the title compound was obtained.
MS (ESI+): [M+H]$^+$ 331.1

Example 537

N-{[(6RS,7SR)-7-(4-chloro-3-fluorophenyl)-6-hydroxy-1,4-oxazepan-6-yl]methyl}-N-methyl-methanesulfonamide monohydrochloride In the same manner as in Example 100, the title compound was obtained.
MS (ESI+): [M+H]$^+$ 367.1

Example 538

(6RS,7RS)-7-(4-chloro-3-fluorophenyl)-6-[(methylsulfonyl)methyl]-1,4-oxazepan-6-ol monohydrochloride Using tert-butyl (3R,4S)-4-(4-chloro-3-fluorophenyl)-1,5-dioxa-8-azaspiro[2.6]nonane-8-carboxylate, and in the same manner as in Example 5, steps B, C and D, the title compound (34 mg) was obtained.
MS (ESI+): [M+H]$^+$ 338.0.

Example 539

3-[(6S,7R)-7-(4-chloro-3-fluorophenyl)-1,4-oxazepan-6-yl]-1,2,4-oxadiazol-5(4H)-one monohydrochloride Using tert-butyl (6S,7R)-7-(4-chloro-3-fluorophenyl)-6-(hydroxymethyl)-1,4-oxazepane-4-carboxylate, and in the same manner as in Example 36, steps A and B, Example 217, steps A and B, Example 43, step A and Example 39, step B, the title compound was obtained.
MS (ESI+): [M+H]$^+$ 314.0.

Example 540

1-{[(6S,7R)-7-(4-chloro-3-fluorophenyl)-1,4-oxazepan-6-yl]methyl}-2-oxo-1,2-dihydropyridine-3-carbonitrile monohydrochloride In the same manner as in Example 43, steps A and C, the title compound was obtained.
MS (ESI+): [M+H]$^+$ 362.2.

Example 541

N-[(6R,7S)-7-(3,4-dichlorophenyl)-1,4-oxazepan-6-yl]-2-oxopropanamide monohydrochloride Using tert-butyl (6R,7S)-6-amino-7-(3,4-dichlorophenyl)-1,4-oxazepane-4-carboxylate, and in the same manner as in Example 39, the title compound was obtained.
MS (ESI+): [M+H]$^+$ 331.0.

Example 542

N-{[(6S,7R)-7-(4-chloro-3-fluorophenyl)-1,4-oxazepan-6-yl]methyl}-2-oxopropanamide monohydrochloride Using tert-butyl (6R,7R)-6-(aminomethyl)-7-(4-chloro-3-fluorophenyl)-1,4-oxazepane-4-carboxylate, and in the same manner as in Example 39, the title compound was obtained.
MS (ESI+): [M+H]$^+$ 329.2.

Example 543

N-[(6R,7S)-7-(3,4-dichlorophenyl)-1,4-oxazepan-6-yl]-N-methylacetamide monohydrochloride Using tert-butyl (6R,7S)-7-(3,4-dichlorophenyl)-6-({[2-(trimethylsilyl)ethoxy]carbonyl}amino)-1,4-oxazepane-4-carboxylate, and in the same manner as in Example 99, step A, Example 36, steps D and E and Example 39, step B, the title compound was obtained.
MS (ESI+): [M+H]$^+$ 317.2.

Example 544

2-{[(6RS,7SR)-7-(4-chloro-3-fluorophenyl)-1,4-oxazepan-6-yl]oxy}-N-methylpyridine-3-carboxamide monohydrochloride In the same manner as in Example 56, the title compound was obtained.
MS (ESI+): [M+H]$^+$ 380.1.

Example 545

1-{[(6R,7S)-6-(3,4-dichlorophenyl)-1,4-oxazepan-7-yl]methyl}tetrahydropyrimidin-2(1H)-one monohydrochloride In the same manner as in Example 532, the title compound was obtained.
MS (ESI+): [M+H]$^+$ 358.1.

Example 546

1-{[(6R,7S)-6-(3,4-dichlorophenyl)-1,4-oxazepan-7-yl]methyl}-3-methyltetrahydropyrimidin-2(1H)-one monohydrochloride A) tert-butyl (6R,7S)-6-(3,4-dichlorophenyl)-7-[(3-methyl-2-oxotetrahydropyrimidin-1(2H)-yl)methyl]-1,4-oxazepane-4-carboxylate To a solution of tert-butyl (6R,7S)-6-(3,4-dichlorophenyl)-7-[(2-oxotetrahydropyrimidin-1(2H)-yl)methyl]-1,4-oxazepane-4-carboxylate (300 mg) in DMF (3 mL) was added sodium hydride (60% in oil, 31 mg), and the mixture was stirred at 0° C. for 30 min. To the reaction mixture was added dropwise methyl iodide (190 mg), and the mixture was stirred at room temperature for 1 hr. Water was added to the reaction mixture, and the mixture was extracted with ethyl acetate. The extract was washed with brine, and dried over anhydrous sodium sulfate. The solvent was evaporated under reduced pressure. The residue was purified by silica gel column chromatography to give the title compound (180 mg).
MS (ESI+): [M+H]$^+$ 472.2.

B) 1-{[(6R,7S)-6-(3,4-dichlorophenyl)-1,4-oxazepan-7-yl]methyl}-3-methyltetrahydropyrimidin-2(1H)-one monohydrochloride Using tert-butyl (6R,7S)-6-(3,4-dichlorophenyl)-7-[(3-methyl-2-oxotetrahydropyrimidin-1(2H)-yl)methyl]-1,4-oxazepane-4-carboxylate (180 mg), and in the same manner as in Example 26, step B, the title compound (120 mg) was obtained.
MS (ESI+): [M+H]$^+$ 372.1.

Example 547

1-{[(6R,7S)-6-(3,4-dichlorophenyl)-1,4-oxazepan-7-yl]methyl}-3-(5-oxo-4,5-dihydro-1,2,4-oxadiazol-3-yl)tetrahydropyrimidin-2(1H)-one monohydrochloride In the same manner as in Example 532, the title compound was obtained.
MS (ESI+): [M+H]$^+$ 442.1.

Example 548

(6S,7R)-7-(4-chloro-3-fluorophenyl)-1,4-oxazepan-6-ol monohydrochloride

A) tert-butyl (6S,7R)-7-(4-chloro-3-fluorophenyl)-6-hydroxy-1,4-oxazepane-4-carboxylate tert-Butyl (6RS,7SR)-7-(4-chloro-3-fluorophenyl)-6-hydroxy-1,4-oxazepane-4-carboxylate (11 g) was separated by HPLC (column: CHIRALPAK IC, 50 mmID×500 mL, manufactured by DAICEL CHEMICAL INDUSTRIES, LTD., mobile phase: hexane/2-propanol=70/30) to give the title compound (5.18 g, >99.9% ee) as a compound having a shorter retention time.

In addition, tert-butyl (6R,7S)-7-(4-chloro-3-fluorophenyl)-6-hydroxy-1,4-oxazepane-4-carboxylate (5.07 g, >99.9% ee) was obtained as a compound having a longer retention time.

$^1$H NMR (300 MHz, CDCl$_3$) δ 1.52 (9H, s), 3.00-3.33 (1H, m), 3.36-4.42 (8H, m), 7.19 (1H, d, J=8.3 Hz), 7.28-7.45 (2H, m).

B) (6S,7R)-7-(4-chloro-3-fluorophenyl)-1,4-oxazepan-6-ol monohydrochloride

Using tert-butyl (6S,7R)-7-(4-chloro-3-fluorophenyl)-6-hydroxy-1,4-oxazepane-4-carboxylate, and in the same manner as in Example 26, step B, the title compound was obtained.
MS (ESI+): [M+H]$^+$ 246.1.

Example 549

N-{[(6S,7R)-7-(4-chloro-3-fluorophenyl)-1,4-oxazepan-6-yl]methyl}-2-(2-methylpropoxy)acetamide monohydrochloride In the same manner as in Example 311, the title compound was obtained.
MS (ESI+): [M+H]$^+$ 373.1.

Example 550

1-{[(6S,7R)-7-(4-chloro-3-fluorophenyl)-1,4-oxazepan-6-yl]methyl}-3-(5-oxo-4,5-dihydro-1,3,4-oxadiazol-2-yl)pyridin-2(1H)-one monohydrochloride A) tert-butyl (6R,7R)-7-(4-chloro-3-fluorophenyl)-6-{[3-(hydrazinocarbonyl)-2-oxopyridin-1(2H)-yl]methyl}-1,4-oxazepane-4-carboxylate To a solution of tert-butyl (6R,7R)-7-(4-chloro-3-fluorophenyl)-6-{[3-(methoxycarbonyl)-2-oxopyridin-1(2H)-yl]methyl}-1,4-oxazepane-4-carboxylate (155.7 mg) in ethanol (1.5 mL) was added hydrazine monohydrate (79 mg) at room temperature, and the mixture was heated under reflux for 2 days. The reaction mixture was allowed to cool to room temperature, and poured into water, and the mixture was partitioned with ethyl acetate. The organic layer was washed with brine, and dried over magnesium sulfate. The solvent was evaporated under reduced pressure to give the title compound (138 mg).
$^1$H NMR (300 MHz, CDCl$_3$) δ 1.52 (9H, brs), 2.75-2.95 (1H, m), 3.07-3.30 (2H, m), 3.56-4.28 (9H, m), 6.31-6.48 (1H, m), 7.05-7.24 (2H, m), 7.35-7.46 (1H, m), 8.14-8.27 (1H, m), 8.38-8.50 (1H, m), 10.51 (1H, brs).

B) 1-{[(6S,7R)-7-(4-chloro-3-fluorophenyl)-1,4-oxazepan-6-yl]methyl}-3-(5-oxo-4,5-dihydro-1,3,4-oxadiazol-2-yl)pyridin-2(1H)-one monohydrochloride Using tert-butyl (6R,7R)-7-(4-chloro-3-fluorophenyl)-6-{[3-(hydrazinocarbonyl)-2-oxopyridin-1(2H)-yl]methyl}-1,4-oxazepane-4-carboxylate, and by a method similar to that in Example 383, steps B and C, the title compound was obtained.
$^1$H NMR (300 MHz, DMSO-d$_6$) δ 3.07-3.29 (5H, m), 3.70-3.87 (2H, m), 3.95-4.07 (2H, m), 4.53 (1H, d, J=9.8 Hz), 6.34 (1H, t, J=7.0 Hz), 7.28 (1H, dd, J=8.3, 1.5 Hz), 7.48 (1H, dd, J=10.4, 1.7 Hz), 7.55 (1H, t, J=8.1 Hz), 7.74 (1H, dd, J=6.6, 2.1 Hz), 7.82 (1H, dd, J=7.2, 2.3 Hz), 8.76-9.16 (1H, m), 9.28-9.66 (1H, m), 12.38-12.59 (1H, m).
MS (ESI+): [M+H]$^+$ 421.1.

Example 551

5-(2-{[(6S,7R)-7-(4-chloro-3-fluorophenyl)-1,4-oxazepan-6-yl]methoxy}pyridin-3-yl)-1,3,4-oxadiazol-2(3H)-one monohydrochloride Using tert-butyl (6S,7R)-7-(4-chloro-3-fluorophenyl)-6-({[3-(methoxycarbonyl)pyridin-2-yl]oxy}methyl)-1,4-oxazepane-4-carboxylate, and by a method similar to that in Example 550, the title compound was obtained.
$^1$H NMR (300 MHz, DMSO-d$_6$) δ 2.84-2.99 (1H, m), 3.17-3.41 (2H, m), 3.46-3.67 (2H, m), 3.83-4.03 (2H, m), 4.16 (1H, dt, J=13.9, 4.2 Hz), 4.40 (1H, dd, J=11.0, 3.0 Hz), 4.77 (1H, d, J=10.2 Hz), 7.15-7.27 (2H, m), 7.47 (1H, dd, J=10.4, 1.7 Hz), 7.56 (1H, t, J=8.1 Hz), 8.12 (1H, dd, J=7.6, 1.9 Hz), 8.27 (1H, dd, J=4.9, 1.9 Hz), 9.71 (2H, brs), 12.89 (1H, s).
MS (ESI+): [M+H]$^+$ 421.1.

Example 552

(6R,7S)-7-(4-chloro-3-fluorophenyl)-1,4-oxazepan-6-ol monohydrochloride

Using tert-butyl (6R,7S)-7-(4-chloro-3-fluorophenyl)-6-hydroxy-1,4-oxazepane-4-carboxylate obtained in Example 548, step A, and in the same manner as in Example 26, step B, the title compound was obtained.
MS (ESI+): [M+H]$^+$ 246.1.

Example 553

N-[(6RS,7SR)-7-(3,4-dichlorophenyl)-1,4-oxazepan-6-yl]acetamide monohydrochloride In the same manner as in Example 36, the title compound was obtained.
MS (ESI+): [M+H]$^+$ 303.1.

Example 554

1-{[(6S,7R)-7-(4-chloro-3-fluorophenyl)-1,4-oxazepan-6-yl]methyl}-2-oxo-1,2-dihydropyridine-3-carboxamide monohydrochloride In the same manner as in Example 44 and Example 39, step A, the title compound was obtained.
MS (ESI+): [M+H]$^+$ 380.0.

Example 555

N-{[(6S,7R)-7-(4-chloro-3-fluorophenyl)-1,4-oxazepan-6-yl]methyl}-2-[($^2$H$_1$) methyloxy]acetamide monohydrochloride A) benzyl [($^2$H$_1$)methyloxy]acetate To a solution of benzyl glycolate (351 mg) in THF (10.6 mL) was added sodium hydride (101 mg, 60% in oil) under ice-cooling, and the mixture was stirred at 0° C. for 10 min.

Methyl iodide-²H₁ (453 mg) was added, and the mixture was stirred at room temperature for 3 hr. To the reaction mixture was added distilled water, and the mixture was extracted with ethyl acetate. The obtained extract was washed with distilled water and brine, and dried over anhydrous magnesium sulfate, and the solvent was evaporated under reduced pressure. The residue was purified by silica gel chromatography (hexane/ethyl acetate) to give the title compound (138 mg).
¹H NMR (300 MHz, CDCl₃) δ 3.44 (2H, s), 4.08 (2H, s), 5.21 (2H, s), 7.30-7.45 (5H, m).

B) sodium [(²H₁) methyloxy]acetate

To a solution of benzyl [(²H₁)methyloxy]acetate (138 mg) in THF (2.5 mL) and methanol (1.3 mL) was added 1.0 M aqueous sodium hydroxide solution (2.29 mL), and the mixture was stirred at room temperature for 2 hr. The reaction mixture was concentrated under reduced pressure. The obtained residue was washed with diisopropyl ether to give the title compound (119 mg).
¹H NMR (300 MHz, DMSO-d₆) δ 3.32 (2H, s), 3.39 (2H, s).

C) N-{[(6S,7R)-7-(4-chloro-3-fluorophenyl)-1,4-oxazepan-6-yl]methyl}-2-[(²H₁)methyloxy]acetamide monohydrochloride Using sodium [(²H₁)methyloxy]acetate, and in the same manner as in Example 311, the title compound was obtained.
MS (ESI+): [M+H]⁺ 332.2.

Example 556

3-(2-{[(6R,7S)-7-(4-chloro-3-fluorophenyl)-1,4-oxazepan-6-yl]oxy}pyridin-3-yl)-1,2,4-oxadiazol-5(4H)-one monohydrochloride Using tert-butyl (6R,7S)-7-(4-chloro-3-fluorophenyl)-6-hydroxy-1,4-oxazepane-4-carboxylate, and in the same manner as in Example 528, the title compound (60 mg) was obtained.
MS (ESI+): [M+H]⁺ 407.2.

Example 557

N-{[(6S,7R)-7-(4-chloro-3-fluorophenyl)-1,4-oxazepan-6-yl]methyl}-2-[(²H₂)methyloxy]acetamide monohydrochloride Using sodium [(²H₂)methyloxy]acetate synthesized in the same manner as in Example 555, steps A and B, and in the same manner as in Example 311, the title compound was obtained.
MS (ESI+): [M+H]⁺ 333.2.

Example 558

5-(2-{[(6R,7S)-7-(4-chloro-3-fluorophenyl)-1,4-oxazepan-6-yl]oxy}pyridin-3-yl)-2,4-dihydro-3H-1,2,4-triazol-3-one monohydrochloride Using tert-butyl (6R,7S)-7-(4-chloro-3-fluorophenyl)-6-[(3-cyanopyridin-2-yl)oxy]-1,4-oxazepane-4-carboxylate, and in the same manner as in Example 378, step A, and Example 379, the title compound (214 mg) was obtained.
MS (ESI+): [M+H]⁺ 406.1.

Example 559

N-{[(6R*,7S*)-7-(4-chloro-3-fluorophenyl)-6-methoxy-1,4-oxazepan-6-yl]methyl}acetamide monohydrochloride (retention time short)

A) tert-butyl (6RS,7RS)-6-(aminomethyl)-7-(4-chloro-3-fluorophenyl)-6-methoxy-1,4-oxazepane-4-carboxylate Using tert-butyl (6RS,7SR)-6-(azidomethyl)-7-(4-chloro-3-fluorophenyl)-6-hydroxy-1,4-oxazepane-4-carboxylate, and in the same manner as in Example 101, steps A and B, the title compound was obtained.
MS (ESI+): [M+H]⁺ 389.2.

B) N-{[(6R*,7S*)-7-(4-chloro-3-fluorophenyl)-6-methoxy-1,4-oxazepan-6-yl]methyl}acetamide monohydrochloride (retention time short)

A racemate (409 mg) of tert-butyl (6RS,7RS)-6-(aminomethyl)-7-(4-chloro-3-fluorophenyl)-6-methoxy-1,4-oxazepane-4-carboxylate was separated by HPLC (CHIRALPAK AD, 50 mmID×500 mL, manufactured by DAICEL CHEMICAL INDUSTRIES, LTD., mobile phase: hexane/2-propanol=950/50), and a compound (135 mg) having a shorter retention time was led to the title compound (89.0 mg) by an operation similar to that in Example 101, step C and Example 13, step I.
MS (ESI+): [M+H]⁺ 331.1.

Example 560

2-{[(6R,7S)-7-(4-chloro-3-fluorophenyl)-1,4-oxazepan-6-yl]oxy}pyridine-3-carboxamide monohydrochloride Using tert-butyl (6R,7S)-7-(4-chloro-3-fluorophenyl)-6-[(3-cyanopyridin-2-yl)oxy]-1,4-oxazepane-4-carboxylate, and in the same manner as in Example 234, the title compound (139 mg) was obtained.
MS (ESI+): [M+H]⁺ 366.1.

Example 561

N-{[(6R*,7S*)-7-(4-chloro-3-fluorophenyl)-6-methoxy-1,4-oxazepan-6-yl]methyl}acetamide monohydrochloride (retention time long)

tert-Butyl (6RS,7SR)-6-(aminomethyl)-7-(4-chloro-3-fluorophenyl)-6-methoxy-1,4-oxazepane-4-carboxylate was separated by an operation similar to that in Example 559, step B, and a compound (165 mg) having a longer retention time was led to the title compound (54.6 mg) by an operation similar to that in Example 101, step C and Example 13, step I.
MS (ESI+): [M+H]⁺ 331.1.

Example 562

3-(2-{[(6S,7R)-7-(4-chloro-3-fluorophenyl)-1,4-oxazepan-6-yl]oxy}pyridin-3-yl)-1,2,4-oxadiazol-5(4H)-one monohydrochloride In the same manner as in Example 528, the title compound was obtained.
MS (ESI+): [M+H]⁺ 407.1.

Example 563

N-{[(6R*,7S*)-7-(4-chloro-3-fluorophenyl)-6-hydroxy-1,4-oxazepan-6-yl]methyl}-N-methylacetamide monohydrochloride (retention time short)

A) tert-butyl (6R*,7R*)-7-(4-chloro-3-fluorophenyl)-6-hydroxy-6-[(methylamino)methyl]-1,4-oxazepane-4-carboxylate (retention time short)

tert-Butyl (6SR,7SR)-7-(4-chloro-3-fluorophenyl)-6-hydroxy-6-[(methylamino)methyl]-1,4-oxazepane-4-carboxylate (1.0 g) was separated by HPLC (column: CHIRALPAK AC, 50 mmID×500 mL, manufactured by DAICEL CHEMICAL INDUSTRIES, LTD., mobile phase: hexane/ethanol=95/5) to give the title compound (459 mg, >99.9% ee) as a compound having a shorter retention time.

In addition, tert-butyl (6R*,7R*)-7-(3,4-dichlorophenyl)-6-hydroxy-6-[(methylamino)methyl]-1,4-oxazepane-4-carboxylate (retention time long) (305 mg, 99.8% ee) was obtained as a compound having a longer retention time.

MS (ESI+): [M+H]$^+$ 489.2.

B) N-{[(6R*,7S*)-7-(4-chloro-3-fluorophenyl)-6-hydroxy-1,4-oxazepan-6-yl]methyl}-N-methylacetamide monohydrochloride (retention time short)

Using tert-butyl (6R*,7R*)-7-(4-chloro-3-fluorophenyl)-6-hydroxy-6-[(methylamino)methyl]-1,4-oxazepane-4-carboxylate (retention time short), and in the same manner as in Example 536, the title compound was obtained.

MS (ESI+): [M+H]$^+$ 331.1.

Example 564

1-{[(6S,7R)-7-(4-chloro-3-fluorophenyl)-1,4-oxazepan-6-yl]methyl}-6-(5-oxo-4,5-dihydro-1,2,4-oxadiazol-3-yl)pyridin-2(1H)-one monohydrochloride Using tert-butyl (6S,7R)-7-(4-chloro-3-fluorophenyl)-6-{[(methylsulfonyl)oxy]methyl}-1,4-oxazepane-4-carboxylate and 6-oxo-1,6-dihydropyridine-2-carbonitrile, and by a method similar to that in Example 31, steps C-E, the title compound was obtained.

$^1$H NMR (300 MHz, DMSO-d$_6$) δ 2.69-3.26 (5H, m), 3.55 (1H, dd, J=14.2, 4.4 Hz), 3.77-3.91 (1H, m), 3.98-4.10 (1H, m), 4.29-4.43 (1H, m), 4.48 (1H, d, J=9.8 Hz), 6.58-6.67 (2H, m), 7.16-7.24 (1H, m), 7.37-7.45 (1H, m), 7.48-7.59 (2H, m), 8.87-9.28 (2H, m), 1H not detected.

MS (ESI+): [M+H]$^+$ 421.1.

Example 565

N-{[(6R*,7S*)-7-(4-chloro-3-fluorophenyl)-6-hydroxy-1,4-oxazepan-6-yl]methyl}-N-methylacetamide monohydrochloride (retention time long)

Using tert-butyl (6R*,7R*)-7-(4-chloro-3-fluorophenyl)-6-hydroxy-6-[(methylamino)methyl]-1,4-oxazepane-4-carboxylate (retention time long) obtained in Example 563, step A, and in the same manner as in Example 536, the title compound was obtained.

MS (ESI+): [M+H]$^+$ 331.1.

Example 566

3-(6-{[(6S,7R)-7-(4-chloro-3-fluorophenyl)-1,4-oxazepan-6-yl]methoxy}pyridin-2-yl)-1,2,4-oxadiazol-5(4H)-one monohydrochloride Using tert-butyl (6S,7R)-7-(4-chloro-3-fluorophenyl)-6-{[(methylsulfonyl)oxy]methyl}-1,4-oxazepane-4-carboxylate and 6-oxo-1,6-dihydropyridine-2-carbonitrile, and by a method similar to that in Example 31, steps C-E, the title compound was obtained.

$^1$H NMR (300 MHz, DMSO-d$_6$) δ 2.93-3.08 (1H, m), 3.12-3.49 (3H, m), 3.51-3.62 (1H, m), 3.79-3.92 (1H, m), 4.00-4.24 (2H, m), 4.27-4.37 (1H, m), 4.64 (1H, d, J=10.2 Hz), 6.96 (1H, d, J=8.0 Hz), 7.26 (1H, dd, J=8.3, 1.5 Hz), 7.46 (1H, dd, J=10.4, 1.7 Hz), 7.52-7.63 (2H, m), 7.86-7.96 (1H, m), 9.14-9.84 (2H, m), 12.62-13.12 (1H, m).

MS (ESI+): [M+H]$^+$ 421.1.

Example 567

N-{[(6R*,7R*)-7-(3,4-dichlorophenyl)-1,4-oxazepan-6-yl]methyl}-2-methoxyacetamide monohydrochloride Using [(6R*,7R*)-7-(3,4-dichlorophenyl)-1,4-oxazepan-6-yl]methanol monohydrochloride (retention time long), and by a method similar to that in Example 3, steps B and C and Example 33, steps A and B, the title compound was obtained.

$^1$H NMR (300 MHz, DMSO-d$_6$) δ 2.57-2.69 (1H, m), 2.85-2.95 (2H, m), 3.23-3.29 (5H, m), 3.35-3.42 (2H, m), 3.75 (2H, s), 3.83-3.95 (1H, m), 4.05-4.16 (1H, m), 5.01 (1H, d, J=3.0 Hz), 7.36 (1H, dd, J=8.3, 1.9 Hz), 7.58-7.68 (2H, m), 7.81-7.90 (1H, m), 8.80-9.39 (2H, m).

MS (ESI+): [M+H]$^+$ 347.1.

Example 568

(6R,7S)-7-(4-chloro-3-fluorophenyl)-6-{[3-(5-methyl-4H-1,2,4-triazol-3-yl)pyridin-2-yl]oxy}-1,4-oxazepane monohydrochloride Using tert-butyl (6R,7S)-7-(4-chloro-3-fluorophenyl)-6-[(3-cyanopyridin-2-yl)oxy]-1,4-oxazepane-4-carboxylate, and in the same manner as in Example 378, the title compound (120 mg) was obtained.

MS (ESI+): [M+H]$^+$ 404.2.

Example 569

N-{[(6R*,7S*)-7-(4-chloro-3-fluorophenyl)-6-hydroxy-1,4-oxazepan-6-yl]methyl}methanesulfonamide monohydrochloride (retention time short)

A) tert-butyl (6RS,7RS)-6-(aminomethyl)-7-(4-chloro-3-fluorophenyl)-6-hydroxy-1,4-oxazepane-4-carboxylate Using tert-butyl (6RS,7SR)-6-(azidomethyl)-7-(4-chloro-3-fluorophenyl)-6-hydroxy-1,4-oxazepane-4-carboxylate, and in the same manner as in Example 101, step B, the title compound was obtained.

$^1$H NMR (300 MHz, CDCl$_3$) δ 1.34-1.62 (9H, m), 2.31-2.64 (1H, m), 2.70-3.05 (4H, m), 3.17-3.41 (2H, m), 3.48-

3.74 (1H, m), 3.82-4.35 (4H, m), 7.01 (1H, dd, J=8.1, 1.7 Hz), 7.20 (1H, dd, J=10.0, 1.7 Hz), 7.33 (1H, t, J=7.9 Hz).

B) tert-butyl (6R*,7S*)-7-(4-chloro-3-fluorophenyl)-6-hydroxy-6-{[(methylsulfonyl)amino]methyl}-1,4-oxazepane-4-carboxylate (retention time short)

tert-Butyl (6RS,7RS)-6-(aminomethyl)-7-(4-chloro-3-fluorophenyl)-6-hydroxy-1,4-oxazepane-4-carboxylate (600 mg) was separated by HPLC (CHIRALPAK AD, 50 mmID× 500 mL, manufactured by DAICEL CHEMICAL INDUSTRIES, LTD., mobile phase: hexane/ethanol=600/400) to give tert-butyl (6R*,7S*)-6-(aminomethyl)-7-(4-chloro-3-fluorophenyl)-6-hydroxy-1,4-oxazepane-4-carboxylate (310 mg, >99.9% ee., recovery rate 100%) having a shorter retention time and tert-butyl (6R*,7S*)-6-(aminomethyl)-7-(4-chloro-3-fluorophenyl)-6-hydroxy-1,4-oxazepane-4-carboxylate (270 mg, >99.9% ee., recovery rate 90%) having a longer retention time were obtained. Using tert-butyl (6R*,7S*)-6-(aminomethyl)-7-(4-chloro-3-fluorophenyl)-6-hydroxy-1,4-oxazepane-4-carboxylate (retention time short), and in the same manner as in Example 486, step A, the title compound (105 mg) was obtained.
$^1$H NMR (300 MHz, CDCl$_3$) δ 1.51 (9H, s), 2.19 (1H, s), 2.83-3.12 (5H, m), 3.23-3.35 (2H, m), 3.54-3.76 (1H, m), 3.92-4.26 (3H, m), 4.42 (1H, s), 6.28 (1H, dd, J=7.3, 5.1 Hz), 7.12 (1H, d, J=7.9 Hz), 7.26-7.30 (1H, m), 7.37 (1H, t, J=7.9 Hz).

C) N-{[(6R*,7S*)-7-(4-chloro-3-fluorophenyl)-6-hydroxy-1,4-oxazepan-6-yl]methyl}methanesulfonamide monohydrochloride (retention time short)

Using tert-butyl (6R*,7S*)-7-(4-chloro-3-fluorophenyl)-6-hydroxy-6-{[(methylsulfonyl)amino]methyl}-1,4-oxazepane-4-carboxylate (retention time short), and in the same manner as in Example 2, step B, the title compound (77 mg) was obtained.
MS (ESI+): [M+H]$^+$ 353.0.

Example 570

N-{[(6R*,7S*)-7-(4-chloro-3-fluorophenyl)-6-hydroxy-1,4-oxazepan-6-yl]methyl}methanesulfonamide monohydrochloride (retention time long)

Using tert-butyl (6R*,7S*)-6-(aminomethyl)-7-(4-chloro-3-fluorophenyl)-6-hydroxy-1,4-oxazepane-4-carboxylate having (retention time long) obtained in Example 569, step B, and in the same manner as in Example 569, step C, the title compound (87 mg) was obtained.
MS (ESI+): [M+H]$^+$ 353.0.

Example 571

7-(4-chloro-3-fluorophenyl)-6-[(methylsulfonyl)methyl]-1,4-oxazepan-6-ol monohydrochloride (retention time short)

A) tert-butyl 7-(4-chloro-3-fluorophenyl)-6-hydroxy-6-[(methylsulfonyl)methyl]-1,4-oxazepane-4-carboxylate (retention time short)

7-(4-Chloro-3-fluorophenyl)-6-(hydroxymethyl)-1,4-oxazepan-6-ol obtained by a method similar to that in Example 74 was led to tert-butyl 7-(4-chloro-3-fluorophenyl)-6-hydroxy-6-(hydroxymethyl)-1,4-oxazepane-4-carboxylate by a method similar to that for tert-butoxycarbonylation in Example 1, step H. Using this compound, and in the same manner as in Example 5, steps A-C, tert-butyl 7-(4-chloro-3-fluorophenyl)-6-hydroxy-6-[(methylsulfonyl)methyl]-1,4-oxazepane-4-carboxylate (320 mg) was obtained. This compound was separated by HPLC (CHIRALPAK AD, 50 mmID×500 mmL, manufactured by DAICEL CHEMICAL INDUSTRIES, LTD., mobile phase: hexane/ethanol=500/500) to give tert-butyl 7-(4-chloro-3-fluorophenyl)-6-hydroxy-6-[(methylsulfonyl)methyl]-1,4-oxazepane-4-carboxylate (ca. 180 mg, >99.6% ee., recovery rate 100%) having a longer retention time and the title compound (190 mg, >99.9% ee., recovery rate 100%) having a shorter retention time.

B) 7-(4-chloro-3-fluorophenyl)-6-[(methylsulfonyl)methyl]-1,4-oxazepan-6-ol monohydrochloride (retention time short)

Using tert-butyl 7-(4-chloro-3-fluorophenyl)-6-hydroxy-6-[(methylsulfonyl)methyl]-1,4-oxazepane-4-carboxylate (retention time short), and in the same manner as in Example 2, step B, the title compound was obtained.
MS (ESI+): [M+H]$^+$ 338.0.

Example 572

7-(4-chloro-3-fluorophenyl)-6-[(methylsulfonyl)methyl]-1,4-oxazepan-6-ol monohydrochloride (retention time long)

Using tert-butyl 7-(4-chloro-3-fluorophenyl)-6-hydroxy-6-[(methylsulfonyl)methyl]-1,4-oxazepane-4-carboxylate (retention time long) obtained in Example 571, step A, and in the same manner as in Example 2, step B, the title compound was obtained.
MS (ESI+): [M+H]$^+$ 338.0.

Example 573

1-{[(6S,7R)-7-(4-chloro-3-fluorophenyl)-1,4-oxazepan-6-yl]methyl}-5-(5-oxo-4,5-dihydro-1,2,4-oxadiazol-3-yl)pyridin-2(1H)-one monohydrochloride Using tert-butyl (6S,7R)-7-(4-chloro-3-fluorophenyl)-6-{[(methylsulfonyl)oxy]methyl}-1,4-oxazepane-4-carboxylate and 6-oxo-1,6-dihydropyridine-3-carbonitrile, and by a method similar to that in Example 31, steps C-E, the title compound was obtained. In the step corresponding to Example 31, step C, a mixture of tert-butyl (6R,7R)-7-(4-chloro-3-fluorophenyl)-6-{[2-oxo-5-(5-oxo-4,5-dihydro-1,2,4-oxadiazol-3-yl)pyridin-1(2H)-yl]methyl}-1,4-oxazepane-4-carboxylate and tert-butyl (6S,7R)-7-(4-chloro-3-fluorophenyl)-6-({[5-(5-oxo-4,5-dihydro-1,2,4-oxadiazol-3-yl)pyridin-2-yl]oxy}methyl)-1,4-oxazepane-4-carboxylate was obtained. The mixture was separated by silica gel column chromatography (eluent; hexane:ethyl acetate) and high-polar tert-butyl (6R,7R)-7-(4-chloro-3-fluorophenyl)-6-{[2-oxo-5-(5-oxo-4,5-dihydro-1,2,4-oxadiazol-3-yl)pyridin-1(2H)-yl]methyl}-1,4-oxazepane-4-carboxylate was used for the next reaction.
$^1$H NMR (300 MHz, DMSO-d$_6$) δ 3.02-3.50 (5H, m), 3.56-3.67 (1H, m), 3.78-3.90 (1H, m), 3.95-4.08 (2H, m), 4.60 (1H, d, J=10.2 Hz), 6.42-6.50 (1H, m), 7.27 (1H, dd, J=8.3, 1.5 Hz), 7.44-7.58 (2H, m), 7.63 (1H, dd, J=9.4, 2.6 Hz), 8.06-8.23 (1H, m), 8.94-9.16 (1H, m), 9.45-9.62 (1H, m), 12.89-13.08 (1H, m)
MS (ESI+): [M+H]+ 421.1.

Example 574

3-(6-{[(6S,7R)-7-(4-chloro-3-fluorophenyl)-1,4-oxazepan-6-yl]methoxy}pyridin-3-yl)-1,2,4-oxadiazol-5(4H)-one monohydrochloride Using tert-butyl (6S,7R)-7-(4-chloro-3-fluorophenyl)-6-{[(methylsulfonyl)oxy]methyl}-1,4-oxazepane-4-carboxylate and 6-oxo-1,6-dihydropyridine-3-carbonitrile, and by a method similar to that in Example 31, steps C-E, the title compound was obtained. In the step corresponding to Example 31, step C, a mixture of tert-butyl (6R,7R)-7-(4-chloro-3-fluorophenyl)-6-{[2-oxo-5-(5-oxo-4,5-dihydro-1,2,4-oxadiazol-3-yl)pyridin-1(2H)-yl]methyl}-1,4-oxazepane-4-carboxylate and tert-butyl (6S,7R)-7-(4-chloro-3-fluorophenyl)-6-({[5-(5-oxo-4,5-dihydro-1,2,4-oxadiazol-3-yl)pyridin-2-yl]oxy}methyl)-1,4-oxazepane-4-carboxylate was obtained. The mixture was separated by silica gel column chromatography (eluent; hexane:ethyl acetate) and low polar tert-butyl (6S,7R)-7-(4-chloro-3-fluorophenyl)-6-({[5-(5-oxo-4,5-dihydro-1,2,4-oxadiazol-3-yl)pyridin-2-yl]oxy}methyl)-1,4-oxazepane-4-carboxylate was used for the next reaction.
1H NMR (300 MHz, DMSO-d6) δ 2.92-3.07 (1H, m), 3.12-3.61 (4H, m), 3.81-3.94 (1H, m), 4.02-4.24 (3H, m), 4.63 (1H, d, J=10.2 Hz), 6.97 (1H, d, J=8.7 Hz), 7.28 (1H, d, J=8.3 Hz), 7.47-7.54 (1H, m), 7.61 (1H, t, J=8.1 Hz), 8.10 (1H, dd, J=8.7, 2.3 Hz), 8.52-8.57 (1H, m), 9.27-9.83 (2H, m), 13.01-13.17 (1H, m).
MS (ESI+): [M+H]+ 421.1.

Example 575

(1S)-1-[(6S,7R)-6-(3,4-dichlorophenyl)-1,4-oxazepan-7-yl]ethane-1,2-diol monohydrochloride A) tert-butyl (6S,7R)-6-(3,4-dichlorophenyl)-7-formyl-1,4-oxazepane-4-carboxylate To a solution of tert-butyl (6S,7R)-6-(3,4-dichlorophenyl)-7-(hydroxymethyl)-1,4-oxazepane-4-carboxylate (3.0 g) in acetonitrile (20 mL) was added Dess-Martin reagent (5.1 g), and the mixture was stirred at 10° C. for 4 hr. To the reaction mixture were added saturated aqueous sodium hydrogen carbonate and aqueous sodium sulfite solution, and the mixture was extracted with ethyl acetate. The extract was washed with brine, and dried over anhydrous magnesium sulfate. The solvent was evaporated under reduced pressure. The residue was purified by silica gel column chromatography to give the title compound (1.3 g).
1H NMR (300 MHz, CDCl3) δ 1.79 (9H, s), 2.86-4.50 (8H, m), 7.16 (1H, d, J=8.3 Hz), 7.35 (1H, d, J=7.9 Hz), 7.44 (1H, d, J=13.6 Hz), 9.45 (1H, d, J=14.7 Hz).
MS (ESI+): [M+H-Boc]+ 274.0.

B) tert-butyl (6S,7S)-6-(3,4-dichlorophenyl)-7-ethenyl-1,4-oxazepane-4-carboxylate To a solution of chlorotris(triphenylphosphine)rhodium (I) (52 mg) and triphenylphosphine (620 mg) in tetrahydrofuran (5 mL) was added 2-propanol (0.18 mL), and tert-butyl (6S,7R)-6-(3,4-dichlorophenyl)-7-formyl-1,4-oxazepane-4-carboxylate (800 mg) was added. To the reaction mixture was added trimethylsilyldiazomethane (2 M diethyl ether solution, 2.1 mL), and the mixture was stirred at room temperature overnight. The solvent was evaporated under reduced pressure, and the residue was purified by silica gel column chromatography to give the title compound (224 mg).
1H NMR (300 MHz, CDCl3) δ 1.47 (9H, d, J=8.7 Hz), 2.91-4.37 (8H, m), 4.84-5.04 (1H, m), 5.09-5.23 (1H, m), 5.34-5.51 (1H, m), 7.07-7.21 (1H, m), 7.33 (1H, dd, J=8.1, 5.1 Hz), 7.40 (1H, d, J=17.0 Hz).

C) (1S)-1-[(6S,7R)-6-(3,4-dichlorophenyl)-1,4-oxazepan-7-yl]ethane-1,2-diol monohydrochloride Using tert-butyl (6S,7S)-6-(3,4-dichlorophenyl)-7-ethenyl-1,4-oxazepane-4-carboxylate, and in the same manner as in Example 46, the title compound was obtained.
MS (ESI+): [M+H]+ 306.0.

Example 576

N-{[(6S,7R)-7-(4-chloro-3-fluorophenyl)-1,4-oxazepan-6-yl]methyl}-N-methylacetamide monohydrochloride Using tert-butyl (6R,7R)-6-[(acetylamino)methyl]-7-(4-chloro-3-fluorophenyl)-1,4-oxazepane-4-carboxylate, and in the same manner as in Example 99, the title compound was obtained.
MS (ESI+): [M+H]+ 315.1.

Example 577

3-(2-{[(6R,7S)-7-(4-chloro-3-fluorophenyl)-1,4-oxazepan-6-yl]oxy}phenyl)-1,2,4-oxadiazol-5(4H)-one monohydrochloride In the same manner as in Example 231 and Example 235, the title compound was obtained.
MS (ESI+): [M+H]+ 406.1.

Example 578

(1S)-1-[(6R,7S)-6-(3,4-dichlorophenyl)-1,4-oxazepan-7-yl]ethane-1,2-diol monohydrochloride A) tert-butyl (6R,7S)-6-(3,4-dichlorophenyl)-7-formyl-1,4-oxazepane-4-carboxylate To a solution of tert-butyl (6R,7S)-6-(3,4-dichlorophenyl)-7-(hydroxymethyl)-1,4-oxazepane-4-carboxylate (3.0 g) in acetonitrile (20 mL) was added Dess-Martin reagent (5.1 g), and the mixture was stirred at 10° C. for 4 hr. To the reaction mixture were added saturated aqueous sodium hydrogen carbonate and aqueous sodium sulfite solution, and the mixture was extracted with ethyl acetate. The extract was washed with brine, and dried over anhydrous magnesium sulfate. The solvent was evaporated, under reduced pressure. The residue was purified by silica gel column chromatography to give the title compound (2.0 g).
1H NMR (300 MHz, CDCl3) δ 1.38-1.50 (9H, m), 2.84-4.59 (8H, m), 7.16 (1H, d, J=7.6 Hz), 7.34 (1H, d, J=7.2 Hz), 7.44 (1H, d, J=14.0 Hz), 9.45 (1H, d, J=14.7 Hz).

B) tert-butyl (6R,7R)-6-(3,4-dichlorophenyl)-7-ethenyl-1,4-oxazepane-4-carboxylate To a solution of chlorotris(triphenylphosphine)rhodium (I) (0.12 g) and triphenylphosphine (1.5 g) in tetrahydrofuran (5 ml) was added 2-propanol (0.44 ml), and tert-butyl (6R,7S)-6-(3,4-dichlorophenyl)-7-formyl-1,4-oxazepane-4-carboxylate (2.0 g) was added. To the reaction mixture was added trimethylsilyldiazomethane (2 M diethyl ether solution, 5.2 ml), and the mixture was stirred at room temperature overnight. The solvent was evaporated under reduced pressure, and the residue was purified by silica gel column chromatography to give the title compound (1.1 g).

$^1$H NMR (300 MHz, CDCl$_3$) δ 1.38-1.51 (9H, m), 2.74-4.38 (8H, m), 4.96 (1H, s), 5.16 (1H, d, J=16.6 Hz), 5.29-5.61 (1H, m), 7.07-7.24 (1H, m), 7.27-7.52 (2H, m).

C) (1S)-1-[(6R,7S)-6-(3,4-dichlorophenyl)-1,4-oxazepan-7-yl]ethane-1,2-diol monohydrochloride Using tert-butyl (6R,7R)-6-(3,4-dichlorophenyl)-7-ethenyl-1,4-oxazepane-4-carboxylate, and in the same manner as in Example 46, the title compound was obtained.
MS (ESI+): [M+H]$^+$ 306.0.

Example 579

(1R)-1-[(6R,7S)-6-(3,4-dichlorophenyl)-1,4-oxazepan-7-yl]ethane-1,2-diol monohydrochloride In the same manner as in Example 45, the title compound was obtained.
MS (ESI+): [M+H]$^+$ 306.0.

Example 580

1-{[(6S,7R)-7-(4-chloro-3-fluorophenyl)-1,4-oxazepan-6-yl]methyl}-4-methyl-3-(5-oxo-4,5-dihydro-1,2,4-oxadiazol-3-yl)pyridin-2(1H)-one monohydrochloride In the same manner as in Example 31, the title compound was obtained.
MS (ESI+): [M+H]$^+$ 435.1.

Example 581

1-{[(6R,7S)-7-(4-chloro-3-fluorophenyl)-1,4-oxazepan-6-yl]methyl}-2-oxo-1,2-dihydropyridine-3-carboxylic acid monohydrochloride Using tert-butyl (6R,7S)-7-(4-chloro-3-fluorophenyl)-6-(hydroxymethyl)-1,4-oxazepane-4-carboxylate, and in the same manner as in Example 34, step A and Example 44, the title compound was obtained.
MS (ESI+): [M+H]$^+$ 381.1.

Example 582

2-{[(6R,7S)-7-(4-chloro-3-fluorophenyl)-1,4-oxazepan-6-yl]oxy}-N-methylpyridine-3-carboxamide monohydrochloride A) 2-((6R,7S)-4-(tert-butoxycarbonyl)-7-(4-chloro-3-fluorophenyl)-1,4-oxazepan-6-yloxy)nicotinic acid Using tert-butyl (6R,7S)-7-(4-chloro-3-fluorophenyl)-6-hydroxy-1,4-oxazepane-4-carboxylate obtained in Example 548, step A, and in the same manner as in Example 231, tert-butyl (6R,7S)-6-[(3-cyanopyridin-2-yl)oxy]-7-(4-chloro-3-fluorophenyl)-1,4-oxazepane-4-carboxylate was obtained. This compound (400 mg) was dissolved in a mixture of ethanol (3 ml) and water (3 mL), lithium hydroxide monohydrate (800 mg) was added, and the mixture was heated under reflux for 18 hr. The reaction solution was adjusted to pH 2-3 with 1 N hydrochloric acid, and the mixture was extracted with ethyl acetate. The organic layer was washed with water and brine, and dried over anhydrous magnesium sulfate. The solvent was evaporated under reduced pressure. The residue was purified by silica gel chromatography (hexane/ethyl acetate) to give the title compound (139 mg).

$^1$H NMR (300 MHz, CDCl$_3$) δ 1.12-1.60 (9H, m), 3.18 (1H, ddd, J=14.3, 12.1, 3.8 Hz), 3.37-3.65 (1H, m), 3.68-3.94 (1H, m), 4.06-4.31 (2H, m), 4.31-4.65 (2H, m), 5.41-5.89 (1H, m), 6.87-7.26 (5H, m), 8.09-8.86 (2H, m).

B) 2-{[(6R,7S)-7-(4-chloro-3-fluorophenyl)-1,4-oxazepan-6-yl]oxy}-N-methylpyridine-3-carboxamide monohydrochloride Using 2-((6R,7S)-4-(tert-butoxycarbonyl)-7-(4-chloro-3-fluorophenyl)-1,4-oxazepan-6-yloxy)nicotinic acid, and in the same manner as in Example 41, the title compound was obtained.
MS (ESI+): [M+H]$^+$ 380.2.

Example 583

3-{[(6R,7S)-7-(4-chloro-3-fluorophenyl)-1,4-oxazepan-6-yl]oxy}pyridine-2-carboxamide monohydrochloride In the same manner as in Example 233 and Example 234, the title compound was obtained.
MS (ESI+): [M+H]$^+$ 366.1.

Example 584

3-(3-{[(6R,7S)-7-(4-chloro-3-fluorophenyl)-1,4-oxazepan-6-yl]oxy}pyridin-2-yl)-1,2,4-oxadiazol-5(4H)-one monohydrochloride In the same manner as in Example 231 and Example 235, the title compound was obtained.
MS (ESI+): [M+H]$^+$ 407.1.

Example 585

2-{[(6R,7S)-7-(4-chloro-3-fluorophenyl)-1,4-oxazepan-6-yl]oxy}-N-(2-hydroxyethyl)pyridine-3-carboxamide monohydrochloride Using 2-((6R,7S)-4-(tert-butoxycarbonyl)-7-(4-chloro-3-fluorophenyl)-1,4-oxazepan-6-yloxy)nicotinic acid obtained in Example 582, step A, and in the same manner as in Example 62, step C and Example 41, the title compound was obtained.
MS (ESI+): [M+H]$^+$ 410.2.

Example 586

3-(3-{[(6R,7S)-7-(4-chloro-3-fluorophenyl)-1,4-oxazepan-6-yl]oxy}pyridin-4-yl)-1,2,4-oxadiazol-5(4H)-one monohydrochloride Using tert-butyl (6R,7S)-7-(4-chloro-3-fluorophenyl)-6-hydroxy-1,4-oxazepane-4-carboxylate obtained in Example 548, step A, and in the same manner as in Example 524, the title compound was obtained.
MS (ESI+): [M+H]$^+$ 407.0.

Example 587

1-{[(6R*,7R*)-7-(3,4-dichlorophenyl)-1,4-oxazepan-6-yl]methyl}-2-oxo-1,2-dihydropyridine-3-carboxylic acid monohydrochloride Using tert-butyl (6R*,7R*)-7-(3,4-dichlorophenyl)-6-(hydroxymethyl)-1,4-oxazepane-4-carboxylate (retention time long) obtained in Example 49, and in the same manner as in Example 531, the title compound was obtained.
MS (ESI+): [M+H]$^+$ 397.1.

Example 588

1-{[(6RS,7SR)-7-(4-chloro-3-fluorophenyl)-1,4-oxazepan-6-yl]methyl}-2-oxo-1,2-dihydropyridine-3-carboxylic acid monohydrochloride Using tert-butyl (6RS,7SR)-7-(4-chloro-3-fluorophenyl)-6-{[3-(methoxycarbonyl)-2-oxopyridin-1(2H)-yl]methyl}-1,4-oxazepane-4-carboxylate, and in the same manner as in Example 531, the title compound was obtained.
MS (ESI+): [M+H]$^+$ 381.1.

Example 589

1-{[(6R*,7R*)-7-(4-chloro-3-fluorophenyl)-1,4-oxazepan-6-yl]methyl}-2-oxo-1,2-dihydropyridine-3-carboxylic acid monohydrochloride (retention time short)

Using tert-butyl (6R*,7R*)-7-(4-chloro-3-fluorophenyl)-6-(hydroxymethyl)-1,4-oxazepane-4-carboxylate (retention time short) obtained in Example 440, and in the same manner as in Example 3, step A and Example 44, the title compound was obtained.
MS (ESI+): [M+H]$^+$ 381.1.

Example 590

1-{[(6R*,7R*)-7-(4-chloro-3-fluorophenyl)-1,4-oxazepan-6-yl]methyl}-2-oxo-1,2-dihydropyridine-3-carboxylic acid monohydrochloride (retention time long)

Using tert-butyl (6R*,7R*)-7-(4-chloro-3-fluorophenyl)-6-(hydroxymethyl)-1,4-oxazepane-4-carboxylate (retention time long) obtained in Example 441, and in the same manner as in Example 3, step A and Example 44, the title compound was obtained.
MS (ESI+): [M+H]$^+$ 381.1.

Example 591

3-{[(6R,7S)-7-(4-chloro-3-fluorophenyl)-1,4-oxazepan-6-yl]oxy}pyridine-4-carboxamide monohydrochloride Using tert-butyl (6R,7S)-6-[(3-cyanopyridin-2-yl)oxy]-7-(4-chloro-3-fluorophenyl)-1,4-oxazepane-4-carboxylate, and in the same manner as in Example 583, the title compound was obtained.
MS (ESI+): [M+H]$^+$ 366.1.

Example 592

N-{[(6S,7R)-7-(4-chloro-3-fluorophenyl)-1,4-oxazepan-6-yl]methyl}propanamide monohydrochloride In the same manner as in Example 311, the title compound was obtained.
MS (ESI+): [M+H]$^+$ 315.1.

Example 593

N-{[(6S,7R)-7-(4-chloro-3-fluorophenyl)-1,4-oxazepan-6-yl]methyl}-2-methylpropanamide monohydrochloride In the same manner as in Example 311, the title compound was obtained.
MS (ESI+): [M+H]$^+$ 329.2.

Example 594

N-{[(6R*,7S*)-7-(4-chloro-3-methylphenyl)-1,4-oxazepan-6-yl]methyl}acetamide monohydrochloride (retention time short)

Using tert-butyl (6R*,7S*)-7-(4-chloro-3-methylphenyl)-6-(hydroxymethyl)-1,4-oxazepane-4-carboxylate (retention time short) obtained in Example 401, step A, and in the same manner as in Example 311, the title compound was obtained.
MS (ESI+): [M+H]$^+$ 297.2.

Example 595

N-{[(6R*,7S*)-7-(3-chloro-4-methylphenyl)-1,4-oxazepan-6-yl]methyl}acetamide monohydrochloride (retention time short)

Using tert-butyl (6R*,7S*)-7-(3-chloro-4-methylphenyl)-6-(hydroxymethyl)-1,4-oxazepane-4-carboxylate (retention time short) obtained in Example 405, step A, and in the same manner as in Example 311, the title compound was obtained.
MS (ESI+): [M+H]$^+$ 297.2.

Example 596

3-(4-{[(6R,7S)-7-(4-chloro-3-fluorophenyl)-1,4-oxazepan-6-yl]oxy}pyridin-3-yl)-1,2,4-oxadiazol-5(4H)-one monohydrochloride In the same manner as in Example 231 and Example 235, the title compound was obtained.
MS (ESI+): [M+H]$^+$ 407.1.

Example 597

2-{[(6S,7R)-7-(4-chloro-3-fluorophenyl)-1,4-oxazepan-6-yl]methyl}-3-oxo-2,3-dihydropyridazine-4-carboxylic acid monohydrochloride In the same manner as in Example 44, the title compound was obtained.
MS (ESI+): [M+H]$^+$ 382.1.

Example 598

N-{[(6S,7R)-7-(4-chloro-3-fluorophenyl)-1,4-oxazepan-6-yl]methyl}benzamide monohydrochloride In the same manner as in Example 311, the title compound was obtained.
MS (ESI+): [M+H]+ 363.2.

Example 599

N-{[(6S,7R)-7-(4-chloro-3-fluorophenyl)-1,4-oxazepan-6-yl]methyl}-2-phenoxyacetamide monohydrochloride In the same manner as in Example 311, the title compound was obtained.
MS (ESI+): [M+H]+ 393.1.

Example 600

(2RS)—N-{[(6S,7R)-7-(4-chloro-3-fluorophenyl)-1,4-oxazepan-6-yl]methyl}-2-fluoropropanamide monohydrochloride In the same manner as in Example 311, the title compound was obtained.
MS (ESI+): [M+H]+ 333.2.

Example 601

N-{[(6S,7R)-7-(4-chloro-3-fluorophenyl)-1,4-oxazepan-6-yl]methyl}-2-fluoro-2-methylpropanamide monohydrochloride In the same manner as in Example 311, the title compound was obtained.
MS (ESI+): [M+H]+ 347.2.

Example 602

3-(2-{[7-(3,4-dichlorophenyl)-7-(hydroxymethyl)-1,4-oxazepan-6-yl]oxy}pyridin-3-yl)-1,2,4-oxadiazol-5(4H)-one monohydrochloride (high-polar diastereomer)

A) tert-butyl 7-(3,4-dichlorophenyl)-6-oxo-1,4-oxazepane-4-carboxylate

To a solution (60 ml) of tert-butyl (6RS,7SR)-7-(3,4-dichlorophenyl)-6-hydroxy-1,4-oxazepane-4-carboxylate (9.18 g) in acetonitrile was added Dess-Martin reagent (15.1 g) under ice-cooling, and the mixture was stirred for 1 hr. The reaction solution was poured into saturated aqueous sodium hydrogen carbonate, and the mixture was extracted with ethyl acetate. The organic layer was washed with brine, and dried over anhydrous magnesium sulfate, and the solvent was evaporated under reduced pressure. The residue was purified by silica gel chromatography (hexane/ethyl acetate) to give the title compound (7.47 g).
$^1$H NMR (300 MHz, CDCl$_3$) δ 1.50 (9H, s), 3.10-3.45 (1H, m), 3.59-5.10 (6H, m), 7.10 (1H, dd, J=8.3, 1.5 Hz), 7.31-7.60 (2H, m).

B) tert-butyl 7-(3,4-dichlorophenyl)-7-(hydroxymethyl)-6-oxo-1,4-oxazepane-4-carboxylate Potassium hydroxide (40 mg) was dissolved in ethanol (1.25 ml), and the solution was diluted with DMSO (25 mL). To this solution were added tert-butyl 7-(3,4-dichlorophenyl)-6-oxo-1,4-oxazepane-4-carboxylate (2.60 g) and paraformaldehyde (267 mg), and the mixture was stirred at room temperature for 30 min. The reaction solution was neutralized with 1 N hydrochloric acid, brine was added, and the mixture was extracted with ethyl acetate. The organic layer was washed twice with brine, and dried over anhydrous magnesium sulfate, and the solvent was evaporated under reduced pressure. The residue was purified by silica gel chromatography (hexane/ethyl acetate) to give the title compound (1.27 g).
$^1$H NMR (300 MHz, CDCl$_3$) δ 1.29-1.46 (9H, m), 2.27 (1H, brs), 3.27 (1H, ddd, J=14.1, 8.9, 3.4 Hz), 3.75-4.06 (6H, m), 4.30-4.71 (1H, m), 7.19 (1H, brs), 7.29-7.53 (2H, m).

C) tert-butyl 7-({[tert-butyl(dimethyl)silyl]oxy}methyl)-7-(3,4-dichlorophenyl)-6-oxo-1,4-oxazepane-4-carboxylate To a solution (20 mL) of tert-butyl 7-(3,4-dichlorophenyl)-7-(hydroxymethyl)-6-oxo-1,4-oxazepane-4-carboxylate (1.27 g) in DMF were added imidazole (266 mg) and tert-butyldimethylchlorosilane (540 mg), and the mixture was stirred at room temperature for 3 hr. The reaction solution was diluted with ethyl acetate, the mixture was washed with water and brine, and dried over anhydrous magnesium sulfate, and the solvent was evaporated under reduced pressure. The residue was purified by silica gel chromatography (hexane/ethyl acetate) to give the title compound (1.35 g).
$^1$H NMR (300 MHz, CDCl$_3$) δ 0.01 (3H, s), 0.03 (3H, s), 0.82-0.88 (9H, m), 1.29-1.50 (9H, m), 3.18-3.35 (1H, m), 3.55-4.07 (6H, m), 4.19-4.53 (1H, m), 7.18-7.26 (1H, m), 7.40 (1H, d, J=8.3 Hz), 7.53 (1H, d, J=1.9 Hz).

D) tert-butyl 7-({[tert-butyl(dimethyl)silyl]oxy}methyl)-7-(3,4-dichlorophenyl)-6-hydroxy-1,4-oxazepane-4-carboxylate (high-polar diastereomer)

To a solution (25 mL) of tert-butyl 7-({[tert-butyl(dimethyl)silyl]oxy}methyl)-7-(3,4-dichlorophenyl)-6-oxo-1,4-oxazepane-4-carboxylate (1.34 g) in methanol was added sodium borohydride (221 mg), and the mixture was stirred at room temperature for 1 hr. To the reaction solution was added saturated aqueous ammonium chloride, and the mixture was extracted with ethyl acetate. The organic layer was washed with water and brine, and dried over anhydrous magnesium sulfate, and the solvent was evaporated under reduced pressure. The residue was purified by silica gel chromatography (hexane/ethyl acetate) to give the title compound (303 mg) as a high-polar diastereomer. In addition, a less polar diastereomer (836 mg) was isolated.

high-polar diastereomer: $^1$H NMR (300 MHz, CDCl$_3$) δ −0.10 (3H, s), 0.00 (3H, d, J=0.8 Hz), 0.78-0.91 (9H, m), 1.43 (9H, s), 3.34-4.01 (9H, m), 4.30 (1H, brs), 7.38-7.49 (2H, m), 7.66 (1H, d, J=1.1 Hz).

less polar diastereomer: $^1$H NMR (300 MHz, CDCl$_3$) δ −0.14 (3H, s), −0.07 (3H, s), 0.76-0.92 (9H, m), 1.42 (9H, s), 2.68 (1H, s), 3.23 (1H, ddd, J=14.0, 9.3, 2.6 Hz), 3.38-3.71 (3H, m), 3.73-4.27 (4H, m), 4.64 (1H, brs), 7.29-7.38 (1H, m), 7.37-7.47 (1H, m), 7.60 (1H, s).

E) 3-(2-{[7-(3,4-dichlorophenyl)-7-(hydroxymethyl)-1,4-oxazepan-6-yl]oxy}pyridin-3-yl)-1,2,4-oxadiazol-5(4H)-one monohydrochloride (high-polar diastereomer)

Using tert-butyl 7-({[tert-butyl(dimethyl)silyl]oxy}methyl)-7-(3,4-dichlorophenyl)-6-hydroxy-1,4-oxazepane-4-carboxylate (high-polar diastereomer), and in the same manner as in Example 556, the title compound was obtained.
MS (ESI+): [M+H]+ 453.1.

Example 603

3-(2-{[7-(3,4-dichlorophenyl)-7-(hydroxymethyl)-1,4-oxazepan-6-yl]oxy}pyridin-3-yl)-1,2,4-oxadiazol-5(4H)-one monohydrochloride (less polar diastereomer)

From tert-butyl 7-({[tert-butyl(dimethyl)silyl]oxy}methyl)-7-(3,4-dichlorophenyl)-6-hydroxy-1,4-oxazepane-4-carboxylate obtained in Example 602, step D, and in the same manner as in Example 602, step E, the title compound was obtained.
MS (ESI+): [M+H]+ 453.1.

Example 604

3-(2-{[(6S,7S)-7-(4-chloro-3-fluorophenyl)-1,4-oxazepan-6-yl]oxy}pyridin-3-yl)-1,2,4-oxadiazol-5(4H)-one monohydrochloride A) tert-butyl (6S,7S)-7-(4-chloro-3-fluorophenyl)-6-[(3-cyanopyridin-2-yl)oxy]-1,4-oxazepane-4-carboxylate Diisopropyl azodicarboxylate (1.9 M in toluene, 0.69 mL) was added dropwise to a solution of tert-butyl (6R,7S)-7-(4-chloro-3-fluorophenyl)-6-hydroxy-1,4-oxazepane-4-carboxylate (300 mg), triphenylphosphine (340 mg) and 2-oxo-1,2-dihydropyridine-3-carbonitrile (160 mg) in tetrahydrofuran (10 mL), and the mixture was stirred at room temperature for 4 hr. Water was added to the reaction mixture, and the mixture was extracted with ethyl acetate. The extract was washed with brine, and dried over anhydrous magnesium sulfate. The solvent was evaporated under reduced pressure. The residue was purified by silica gel column chromatography to give the title compound (250 mg).
$^1$H NMR (300 MHz, CDCl$_3$) δ 1.48 (9H, s), 3.26-4.07 (4H, m), 4.19-4.48 (2H, m), 4.67 (1H, brs), 5.62-5.92 (1H, m, J=16.2 Hz), 6.72-6.98 (1H, m), 7.04-7.26 (3H, m), 7.74 (1H, d, J=7.9 Hz), 8.16 (1H, d, J=4.1 Hz).
MS (ESI+): [M+H-t-Bu]+ 392.1.

B) 3-(2-{[(6S,7S)-7-(4-chloro-3-fluorophenyl)-1,4-oxazepan-6-yl]oxy}pyridin-3-yl)-1,2,4-oxadiazol-5(4H)-one monohydrochloride Using tert-butyl (6S,7S)-7-(4-chloro-3-fluorophenyl)-6-[(3-cyanopyridin-2-yl)oxy]-1,4-oxazepane-4-carboxylate, and in the same manner as in Example 231 and Example 235, the title compound was obtained.
MS (ESI+): [M+H]+ 407.1.

Example 605

(1RS)-1-[(6SR,7SR)-6-(3,4-dichlorophenyl)-1,4-oxazepan-7-yl]ethane-1,2-diol monohydrochloride In the same manner as in Example 45, the title compound was obtained.
MS (ESI+): [M+H]+ 306.1.

Example 606

(1RS)-1-[(6RS,7RS)-6-(3,4-dichlorophenyl)-1,4-oxazepan-7-yl]ethane-1,2-diol monohydrochloride In the same manner as in Example 46, the title compound was obtained.
MS (ESI+): [M+H]+ 306.1.

The compounds of Examples 1-606 are shown in the following Tables.

TABLE 1-1

| Ex. No. | IUPAC name | structure | salt | MS |
|---|---|---|---|---|
| 1 | [(6RS,7RS)-7-(3,4-dichlorophenyl)-1,4-oxazepan-6-yl]methanol | 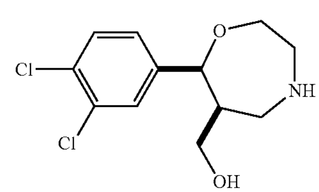 | HCl | 276.1 |
| 2 | (6RS,7RS)-7-(3,4-dichlorophenyl)-6-(methoxymethyl)-1,4-oxazepane | 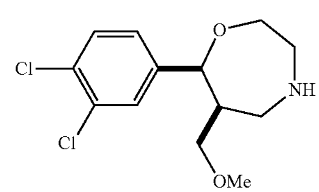 | HCl | 290.0 |

TABLE 1-1-continued

| Ex. No. | IUPAC name | structure | salt | MS |
|---|---|---|---|---|
| 3 | 1-{[(6RS,7RS)-7-(3,4-dichlorophenyl)-1,4-oxazepan-6-yl]methyl}urea | 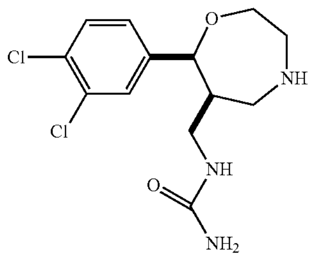 | HCl | 318.1 |
| 4 | [(6RS,7SR)-7-(3,4-dichlorophenyl)-1,4-oxazepan-6-yl]methanol | 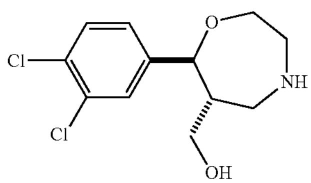 | HCl | 276.1 |
| 5 | (6RS,7RS)-7-(3,4-dichlorophenyl)-6-[(methylsulfonyl)methyl]-1,4-oxazepane | 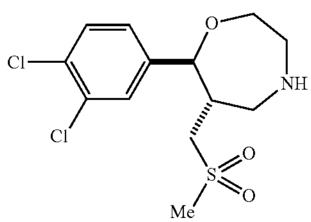 | HCl | 338.2 |
| 6 | N-{[(6RS,7SR)-7-(3,4-dichlorophenyl)-1,4-oxazepan-6-yl]methyl}acetamide | 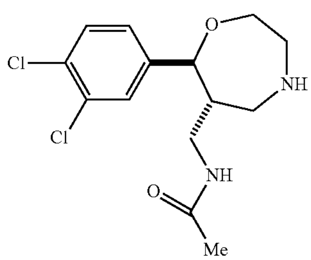 | HCl | 317.2 |

TABLE 1-2

| Ex. No. | IUPAC name | structure | salt | MS |
|---|---|---|---|---|
| 7 | 1-{[(6RS,7SR)-7-(3,4-dichlorophenyl)-1,4-oxazepan-6-yl]methyl}urea | 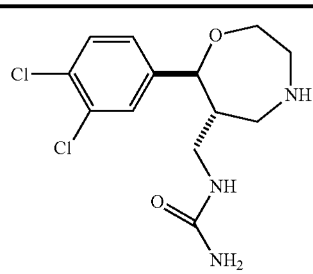 | HCl | 318.1 |

TABLE 1-2-continued

| Ex. No. | IUPAC name | structure | salt | MS |
|---|---|---|---|---|
| 8 | N-{[(6RS,7SR)-7-(3,4-dichlorophenyl)-1,4-oxazepan-6-yl]methyl}-methanesulfonamide | 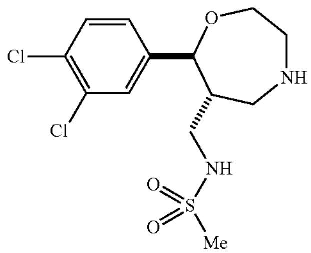 | HCl | 353.0 |
| 9 | N-{[(6RS,7SR)-7-(3,4-dichlorophenyl)-1,4-oxazepan-6-yl]methyl}sulfamide | 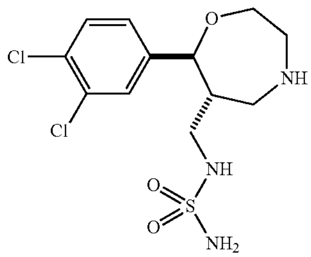 | HCl | 354.1 |
| 10 | [(6RS,7SR)-7-(3-chloro-4-fluorophenyl)-1,4-oxazepan-6-yl]methanol | 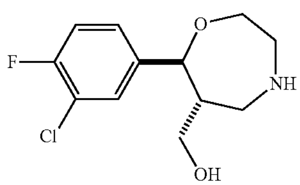 | HCl | 260.0 |
| 11 | 1-{[(6RS,7SR)-7-(3-chloro-4-fluorophenyl)-1,4-oxazepan-6-yl]methyl}urea | 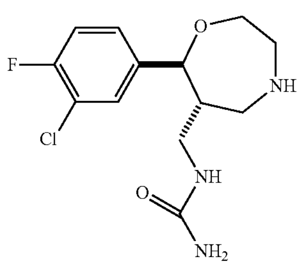 | HCl | 302.3 |
| 12 | (6RS,7SR)-7-(3-chloro-4-fluorophenyl)-6-[(methylsulfonyl)methyl]-1,4-oxazepane | 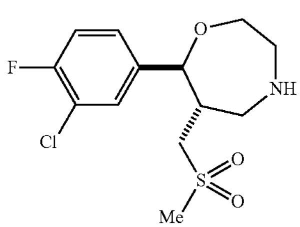 | HCl | 322.3 |

TABLE 1-3

| Ex. No. | IUPAC name | structure | salt | MS |
|---|---|---|---|---|
| 13 | [(6RS,7SR)-7-(4-chloro-3-fluorophenyl)-1,4-oxazepan-6-yl]methanol | 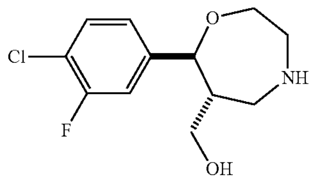 | HCl | 260.0 |
| 14 | [(5RS,6SR)-6-(3,4-dichlorophenyl)-1,4-oxazepan-5-yl]methanol | 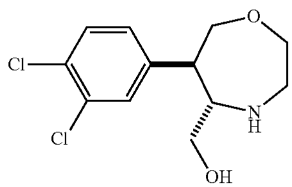 | HCl | 276.2 |
| 15 | (5RS,6SR)-6-(3,4-dichlorophenyl)-5-[(methylsulfonyl)methyl]-1,4-oxazepane | 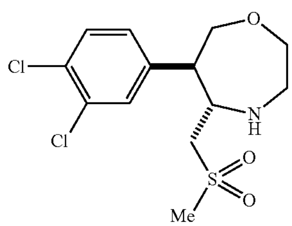 | HCl | 338.0 |
| 16 | (6RS)-6-(3,4-dichlorophenyl)-1,4-oxazepan-6-ol | 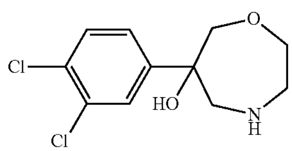 [SMILES: OC1(c2ccc(Cl)c(Cl)c2)CNCCOC1] | HCl | 262.0 |
| 17 | (6RS)-6-(3,4-dichlorophenyl)-6-methoxy-1,4-oxazepane | 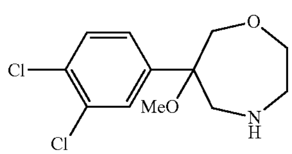 [SMILES: COC1(c2ccc(Cl)c(Cl)c2)CNCCOC1] | HCl | 276.1 |
| 18 | (6RS)-6-(3,4-dichlorophenyl)-6-ethoxy-1,4-oxazepane | 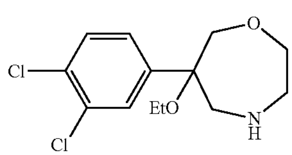 | HCl | 290.0 |

TABLE 1-4

| Ex. No. | IUPAC name | structure | salt | MS |
|---|---|---|---|---|
| 19 | (7RS)-7-(3,4-dichlorophenyl)-7-(methoxymethyl)-1,4-oxazepane | 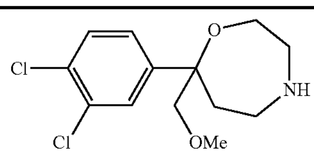 | HCl | 290.0 |
| 20 | [(7RS)-7-(3,4-dichlorophenyl)-1,4-oxazepan-7-yl]methanol | 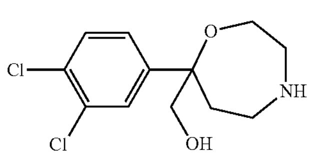 [SMILES: OCC1(c2ccc(Cl)c(Cl)c2)CCNCCO1] | HCl | 276.2 |

TABLE 1-4-continued

| Ex. No. | IUPAC name | structure | salt | MS |
|---|---|---|---|---|
| 21 | N-{[(7RS)-7-(3,4-dichlorophenyl)-1,4-oxazepan-7-yl]methyl}methanesulfonamide | 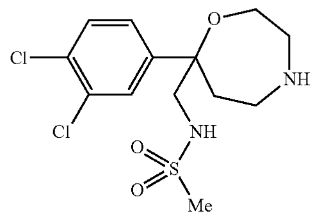 [SMILES: CS(=O)(=O)NCC1(c2ccc(Cl)c(Cl)c2)CCNCCO1] | HCl | 353.2 |
| 22 | N-{[(7RS)-7-(3,4-dichlorophenyl)-1,4-oxazepan-7-yl]methyl}sulfamide | 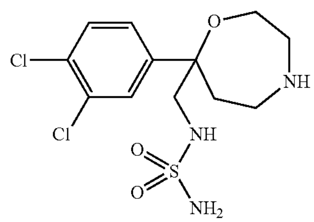 [SMILES: NS(=O)(=O)NCC1(c2ccc(Cl)c(Cl)c2)CCNCCO1] | HCl | 354.2 |
| 23 | [(2RS)-2-(3,4-dichlorophenyl)-1,4-oxazepan-2-yl]methanol | 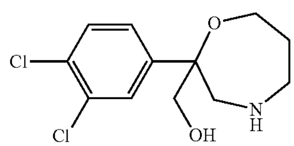 [SMILES: OCC1(c2ccc(Cl)c(Cl)c2)CNCCCO1] | HCl | 276.1 |
| 24 | N-{[(2RS)-2-(3,4-dichlorophenyl)-1,4-oxazepan-2-yl]methyl}methanesulfonamide | 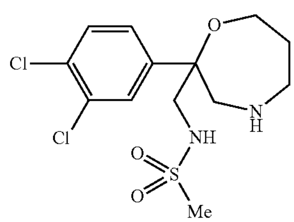 [SMILES: CS(=O)(=O)NCC1(c2ccc(Cl)c(Cl)c2)CNCCCO1] | HCl | 352.9 |

TABLE 1-5

| Ex. No. | IUPAC name | structure | salt | MS |
|---|---|---|---|---|
| 25 | [(6RS,7SR)-6-(3,4-dichlorophenyl)-1,4-oxazepan-7-yl]methanol | 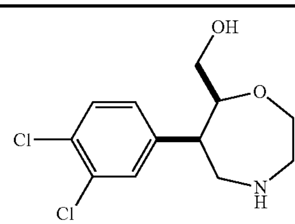 | HCl | 276.2 |
| 26 | (6RS,7SR)-6-(3,4-dichlorophenyl)-7-[(methylsulfonyl)methyl]-1,4-oxazepane | 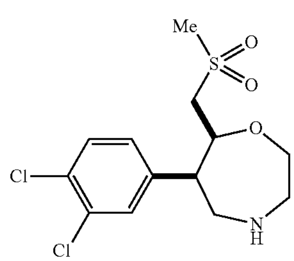 | HCl | 338.2 |

TABLE 1-5-continued

| Ex. No. | IUPAC name | structure | salt | MS |
|---|---|---|---|---|
| 27 | N-{[(6RS,7SR)-6-(3,4-dichlorophenyl)-1,4-oxazepan-7-yl]methyl}acetamide | 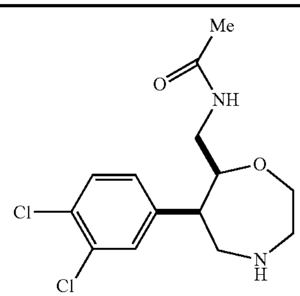 | HCl | 317.3 |
| 28 | 1-{[(6RS,7SR)-6-(3,4-dichlorophenyl)-1,4-oxazepan-7-yl]methyl}urea | 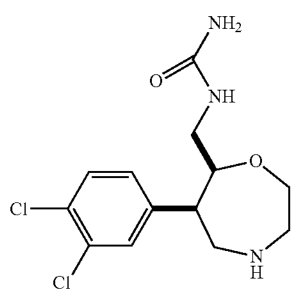 | HCl | 318.2 |
| 29 | N-{[(6RS,7SR)-6-(3,4-dichlorophenyl)-1,4-oxazepan-7-yl]methyl}-methanesulfonamide | 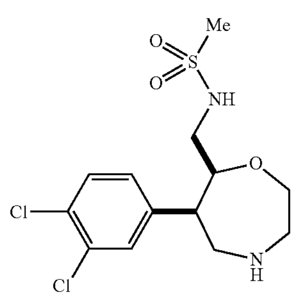 | HCl | 353.2 |
| 30 | N-{[(6RS,7SR)-6-(3,4-dichlorophenyl)-1,4-oxazepan-7-yl]methyl}sulfamide | 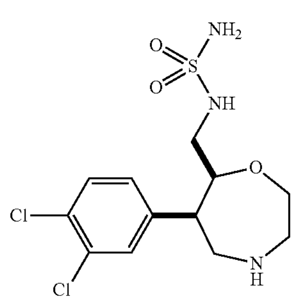 | HCl | 354.2 |

TABLE 1-6

| Ex. No. | IUPAC name | structure | salt | MS |
|---|---|---|---|---|
| 31 | 1-{[(6S,7R)-7-(3,4-dichlorophenyl)-1,4-oxazepan-6-yl]methyl}-3-(5-oxo-4,5-dihydro-1,2,4-oxadiazol-3-yl)pyridin-2(1H)-one | 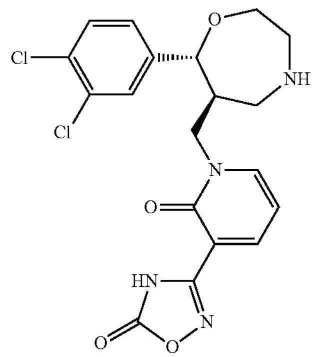 | HCl | 437.0 |
| 32 | N-{[(6S,7R)-7-(3,4-dichlorophenyl)-1,4-oxazepan-6-yl]methyl}acetamide | 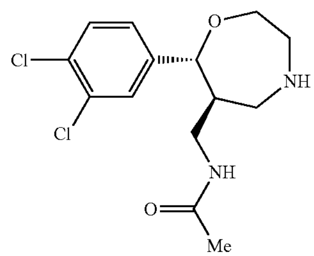 [SMILES: CC(=O)NC[C@@H]1CNCCO[C@H]1c1ccc(Cl)c(Cl)c1] | ½ fumarate | 317.3 |
| 33 | N-{[(6S,7R)-7-(3,4-dichlorophenyl)-1,4-oxazepan-6-yl]methyl}-2-methoxyacetamide | 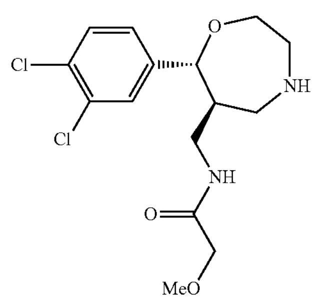 | HCl | 347.0 |
| 34 | N-{[(6S,7R)-7-(3,4-dichlorophenyl)-1,4-oxazepan-6-yl]methyl}-methanesulfonamide | 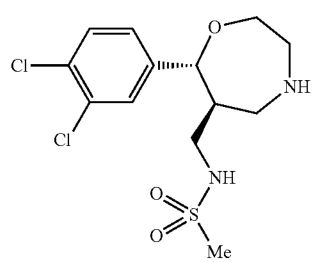 | HCl | 352.9 |
| 35 | N-{[(6S,7R)-7-(3,4-dichlorophenyl)-1,4-oxazepan-6-yl]methyl}sulfamide | 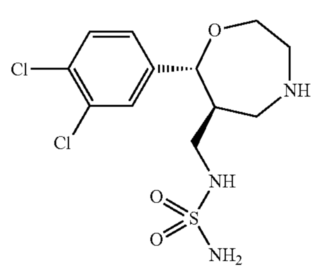 [SMILES: NS(=O)(=O)NC[C@@H]1CNCCO[C@H]1c1ccc(Cl)c(Cl)c1] | HCl | 354.1 |

TABLE 1-7

| Ex. No. | IUPAC name | structure | salt | MS |
|---|---|---|---|---|
| 36 | N-[(6R,7S)-7-(3,4-dichlorophenyl)-1,4-oxazepan-6-yl]acetamide | 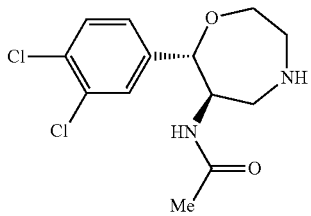 [SMILES: CC(=O)N[C@@H]1CNCCO[C@H]1c1ccc(Cl)c(Cl)c1] | fumarate | 303.2 |
| 37 | N-[(6R,7S)-7-(3,4-dichlorophenyl)-1,4-oxazepan-6-yl]sulfamide | 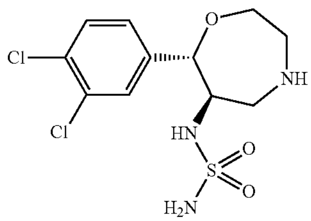 [SMILES: NS(=O)(=O)N[C@@H]1CNCCO[C@H]1c1ccc(Cl)c(Cl)c1] | HCl | 340.0 |
| 38 | N-{[(6S,7R)-7-(4-chloro-3-fluorophenyl)-1,4-oxazepan-6-yl]methyl}-2-methoxyacetamide | 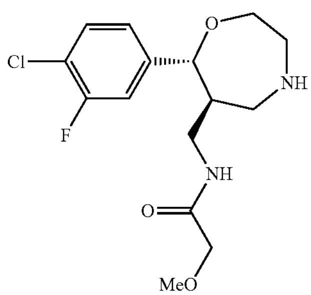 [SMILES: COCC(=O)NC[C@@H]1CNCCO[C@H]1c1ccc(Cl)c(F)c1] | HCl | 331.1 |
| 39 | N-{[(6S,7R)-7-(4-chloro-3-fluorophenyl)-1,4-oxazepan-6-yl]methyl}-2-[($^2$H$_3$)methyloxy]acetamide | 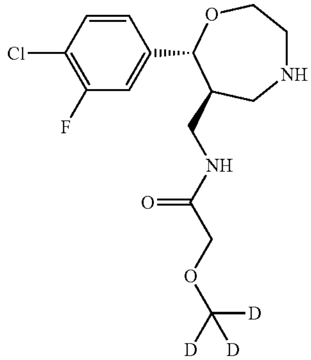 [SMILES: [2H]C([2H])([2H])OCC(=O)NC[C@@H]1CNCCO[C@H]1c1ccc(Cl)c(F)c1] | HCl | — |

TABLE 1-8

| Ex. No. | IUPAC name | structure | salt | MS |
|---|---|---|---|---|
| 40 | N-{[(6S,7R)-7-(4-chloro-3-fluorophenyl)-1,4-oxazepan-6-yl]methyl}-2-ethoxyacetamide | 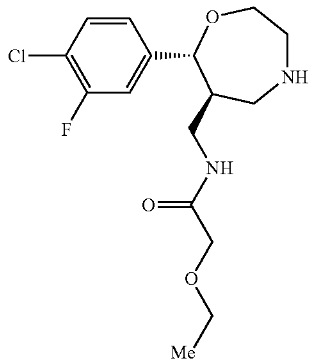 [SMILES: CCOCC(=O)NC[C@@H]1CNCCO[C@H]1c1ccc(Cl)c(F)c1] | HCl | — |
| 41 | N-{[(6S,7R)-7-(4-chloro-3-fluorophenyl)-1,4-oxazepan-6-yl]methyl}-2-(1-methylethoxy)acetamide | 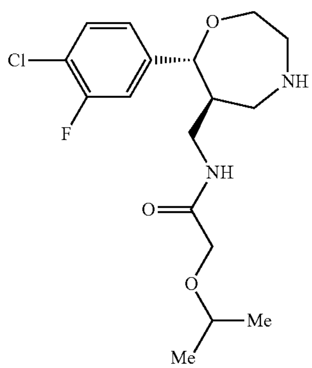 [SMILES: CC(C)OCC(=O)NC[C@@H]1CNCCO[C@H]1c1ccc(Cl)c(F)c1] | HCl | 359.2 |
| 42 | 1-{[(6S,7R)-7-(4-chloro-3-fluorophenyl)-1,4-oxazepan-6-yl]methyl}pyridin-2(1H)-one | 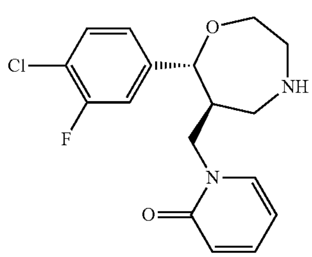 [SMILES: O=c1ccccn1C[C@@H]1CNCCO[C@H]1c1ccc(Cl)c(F)c1] | HCl | 337.1 |
| 43 | 1-{[(6S,7R)-7-(4-chloro-3-fluorophenyl)-1,4-oxazepan-6-yl]methyl}-3-(5-oxo-4,5-dihydro-1,2,4-oxadiazol-3-yl)pyridin-2(1H)-one | 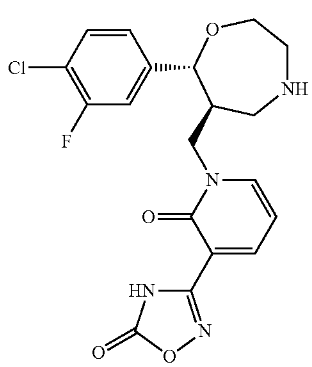 [SMILES: O=c1[nH]c(-c2cccn(C[C@@H]3CNCCO[C@H]3c3ccc(Cl)c(F)c3)c2=O)no1] | HCl | 421.0 |

TABLE 1-9

| Ex. No. | IUPAC name | structure | salt | MS |
|---|---|---|---|---|
| 44 | 1-{[(6S,7R)-7-(4-chloro-3-fluorophenyl)-1,4-oxazepan-6-yl]methyl}-2-oxo-1,2-dihydropyridine-3-carboxylic acid | 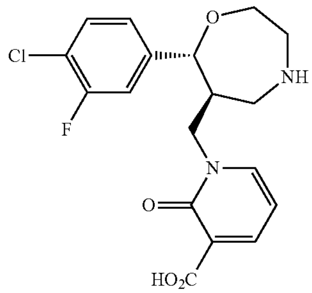 [SMILES: O=C(O)c1cccn(C[C@@H]2CNCCO[C@H]2c2ccc(Cl)c(F)c2)c1=O] | HCl | 381.1 |
| 45 | (1S)-1-[(6R,7R)-6-(3,4-dichlorophenyl)-1,4-oxazepan-7-yl]ethane-1,2-diol | 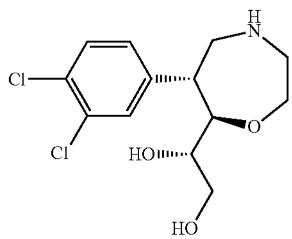 [SMILES: OC[C@H](O)[C@@H]1OCCNC[C@H]1c1ccc(Cl)c(Cl)c1] | HCl | 306.2 |
| 46 | (1R)-1-[(6R,7R)-6-(3,4-dichlorophenyl)-1,4-oxazepan-7-yl]ethane-1,2-diol | 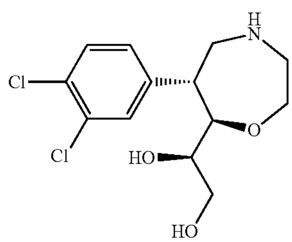 [SMILES: OC[C@@H](O)[C@@H]1OCCNC[C@H]1c1ccc(Cl)c(Cl)c1] | HCl | 306.2 |
| 47 | [(7S)-7-(3,4-dichlorophenyl)-1,4-oxazepan-7-yl]methanol | 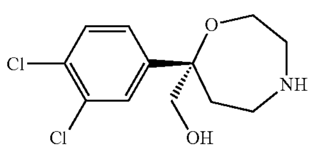 [SMILES: OC[C@@]1(c2ccc(Cl)c(Cl)c2)CCNCCO1] | HCl | 276.1 |

TABLE 1-10

| Ex. No. | IUPAC name | structure | salt | MS |
|---|---|---|---|---|
| 48 | [(6R*,7R*)-7-(3,4-dichlorophenyl)-1,4-oxazepan-6-yl]methanol (retention time short) | 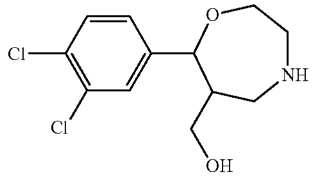 [SMILES: OCC1CNCCOC1c1ccc(Cl)c(Cl)c1] | HCl | 276.1 |
| 49 | [(6R*,7R*)-7-(3,4-dichlorophenyl)-1,4-oxazepan-6-yl]methanol (retention time long) | 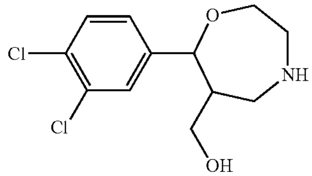 [SMILES: OCC1CNCCOC1c1ccc(Cl)c(Cl)c1] | HCl | 276.1 |

TABLE 1-10-continued

| Ex. No. | IUPAC name | structure | salt | MS |
|---|---|---|---|---|
| 50 | (6RS,7SR)-7-(3,4-dichlorophenyl)-6-[(methylsulfonyl)methyl]-1,4-oxazepane | 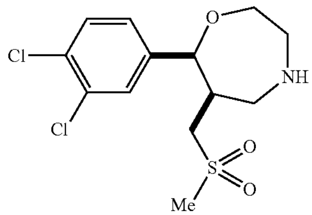 | HCl | 338.0 |
| 51 | N-{[(6RS,7RS)-7-(3,4-dichlorophenyl)-1,4-oxazepan-6-yl]methyl}acetamide | 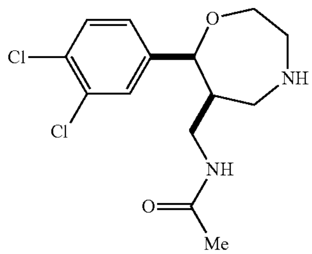 | HCl | 317.0 |
| 52 | 1-{[(6RS,7RS)-7-(3,4-dichlorophenyl)-1,4-oxazepan-6-yl]methyl}-3-ethylurea | 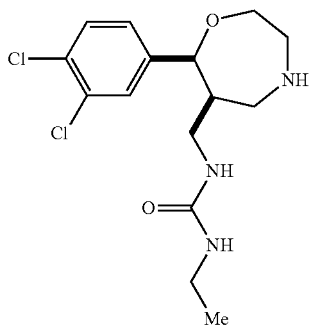 | HCl | 346.1 |

TABLE 1-11

| Ex. No. | IUPAC name | structure | salt | MS |
|---|---|---|---|---|
| 53 | N-{[(6RS,7RS)-7-(3,4-dichlorophenyl)-1,4-oxazepan-6-yl]methyl}methanesulfonamide | 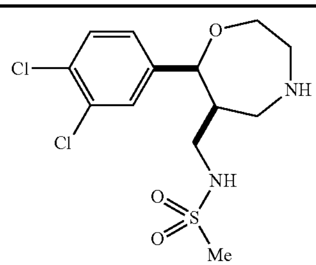 | HCl | 353.0 |
| 54 | N-{[(6RS,7RS)-7-(3,4-dichlorophenyl)-1,4-oxazepan-6-yl]methyl}sulfamide | 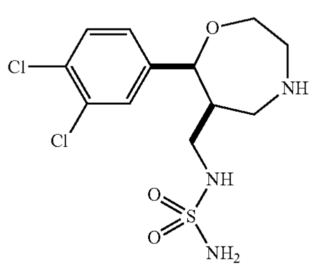 | HCl | 354.1 |

TABLE 1-11-continued

| Ex. No. | IUPAC name | structure | salt | MS |
|---|---|---|---|---|
| 55 | {[(6R*,7R*)-7-(3,4-dichlorophenyl)-1,4-oxazepan-6-yl]methoxy}acetic acid (derived from compound of Example 49) | 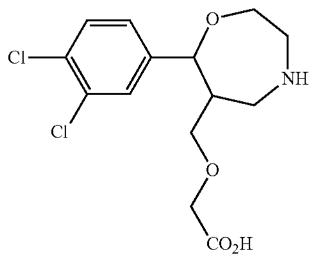 [SMILES: O=C(O)COCC1CNCCOC1c1ccc(Cl)c(Cl)c1] | HCl | 334.0 |
| 56 | 1-({[(6R*,7R*)-7-(3,4-dichlorophenyl)-1,4-oxazepan-6-yl]methoxy}-acetyl)azetidin-3-ol (derived from compound of Example 49) | 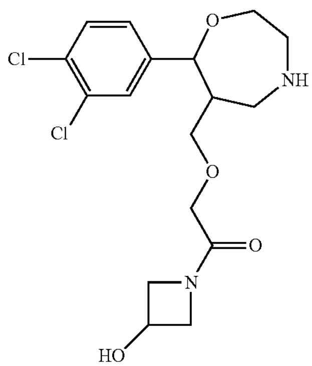 [SMILES: O=C(COCC1CNCCOC1c1ccc(Cl)c(Cl)c1)N1CC(O)C1] | HCl | 389.3 |
| 57 | (6R*,7R*)-7-(3,4-dichlorophenyl)-6-{[2-(1,1-dioxidothiomorpholin-4-yl)-2-oxoethoxy]methyl}-1,4-oxazepane (derived from compound of Example 49) | 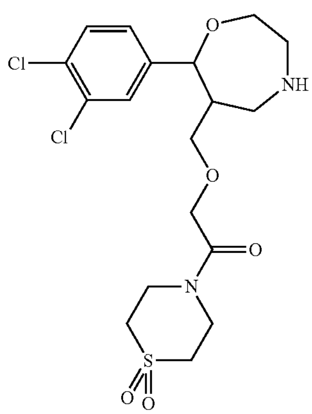 [SMILES: O=C(COCC1CNCCOC1c1ccc(Cl)c(Cl)c1)N1CCS(=O)(=O)CC1] | HCl | 451.3 |

TABLE 1-12

| Ex. No. | IUPAC name | structure | salt | MS |
|---|---|---|---|---|
| 58 | 2-{[(6R*,7R*)-7-(3,4-dichlorophenyl)-1,4-oxazepan-6-yl]methoxy}benzoic acid (derived from compound of Example 49) | 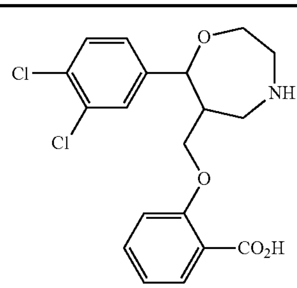 | HCl | 396.1 |
| 59 | 3-{[(6R*,7R*)-7-(3,4-dichlorophenyl)-1,4-oxazepan-6-yl]methoxy}benzoic acid (derived from compound of Example 49) | | HCl | 396.2 |

TABLE 1-12-continued

| Ex. No. | IUPAC name | structure | salt | MS |
|---|---|---|---|---|
| 60 | 4-{[(6R*,7R*)-7-(3,4-dichlorophenyl)-1,4-oxazepan-6-yl]methoxy}benzoic acid (derived from compound of Example 49) | 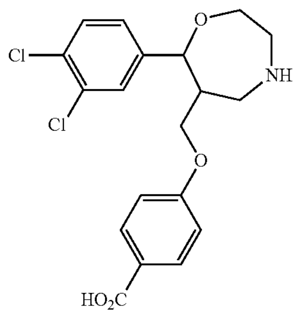 [SMILES: O=C(O)c1ccc(OCC2CNCCOC2c2ccc(Cl)c(Cl)c2)cc1] | HCl | 395.9 |
| 61 | 1-[(2-{[(6R*,7R*)-7-(3,4-dichlorophenyl)-1,4-oxazepan-6-yl]methoxy}phenyl)-carbonyl]azetidin-3-ol (derived from compound of Example 49) | 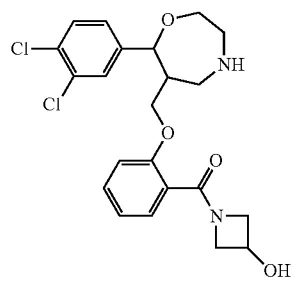 [SMILES: O=C(c1ccccc1OCC1CNCCOC1c1ccc(Cl)c(Cl)c1)N1CC(O)C1] | HCl | 451.0 |

TABLE 1-13

| Ex. No. | IUPAC name | structure | salt | MS |
|---|---|---|---|---|
| 62 | N-[(6RS,7RS)-7-(3,4-dichlorophenyl)-1,4-oxazepan-6-yl]acetamide | 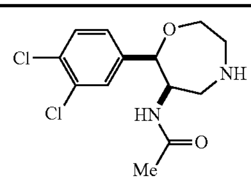 | HCl | 303.1 |
| 63 | N-[(6RS,7RS)-7-(3,4-dichlorophenyl)-1,4-oxazepan-6-yl]methanesulfonamide | 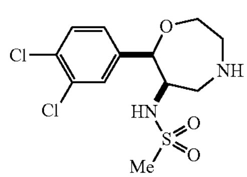 | HCl | 339.1 |
| 64 | 1-[(6RS,7SR)-7-(3,4-dichlorophenyl)-1,4-oxazepan-6-yl]-3-(5-oxo-4,5-dihydro-1,2,4-oxadiazol-3-yl)pyridin-2(1H)-one | 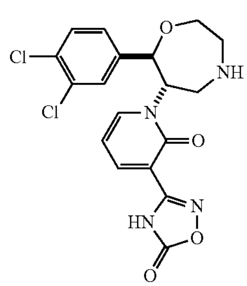 | HCl | 423.1 |
| 65 | [(6RS,7RS)-7-(3,4-dichlorophenyl)-1,4-oxazepan-6-yl]acetonitrile | 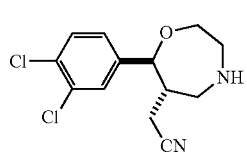 | HCl | 285.1 |

TABLE 1-13-continued

| Ex. No. | IUPAC name | structure | salt | MS |
|---|---|---|---|---|
| 66 | [(6R,7R)-7-(3,4-dichlorophenyl)-1,4-oxazepan-6-yl]acetic acid | 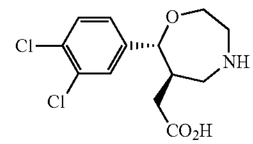 [SMILES: O=C(O)C[C@@H]1CNCCO[C@H]1c1ccc(Cl)c(Cl)c1] | HCl | 304.0 |

TABLE 1-14

| Ex. No. | IUPAC name | structure | salt | MS |
|---|---|---|---|---|
| 67 | 3-[(6R,7R)-7-(3,4-dichlorophenyl)-1,4-oxazepan-6-yl]propanoic acid | 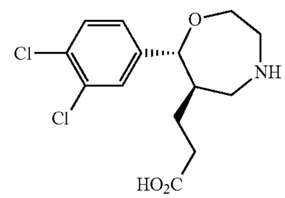 [SMILES: O=C(O)CC[C@@H]1CNCCO[C@H]1c1ccc(Cl)c(Cl)c1] | HCl | 318.2 |
| 68 | 2-[(6RS,7RS)-7-(3,4-dichlorophenyl)-1,4-oxazepan-6-yl]acetamide | 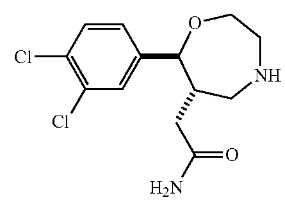 | HCl | 302.9 |
| 69 | N-{[(6R,7R)-7-(3,4-dichlorophenyl)-1,4-oxazepan-6-yl]acetyl}-2-methylalanine | 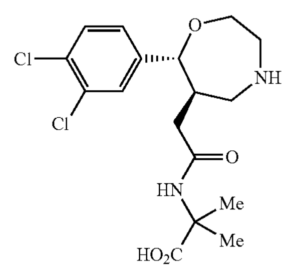 [SMILES: CC(C)(NC(=O)C[C@@H]1CNCCO[C@H]1c1ccc(Cl)c(Cl)c1)C(=O)O] | HCl | 389.0 |
| 70 | 3-({[(6R,7R)-7-(3,4-dichlorophenyl)-1,4-oxazepan-6-yl]acetyl}amino)benzoic acid | 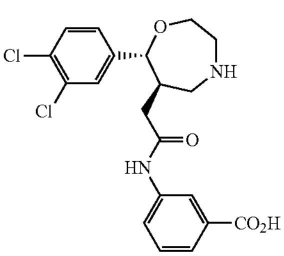 [SMILES: O=C(C[C@@H]1CNCCO[C@H]1c1ccc(Cl)c(Cl)c1)Nc1cccc(C(=O)O)c1] | HCl | 423.1 |
| 71 | [(6RS,7SR)-7-(3,4-dichlorophenyl)-1,4-oxazepan-6-yl]methyl acetate | 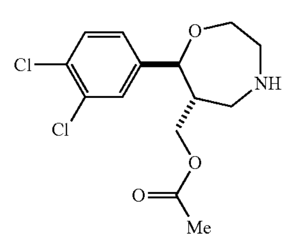 | HCl | 318.2 |

TABLE 1-15

| Ex. No. | IUPAC name | structure | salt | MS |
|---|---|---|---|---|
| 72 | [(6S,7R)-7-(3,4-dichlorophenyl)-1,4-oxazepan-6-yl]methanol | 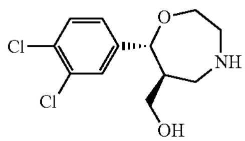 [SMILES: OC[C@@H]1CNCCO[C@H]1c1ccc(Cl)c(Cl)c1] | HCl | 276.1 |
| 73 | [(6R,7S)-7-(3,4-dichlorophenyl)-1,4-oxazepan-6-yl]methanol | 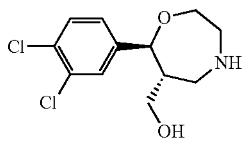 [SMILES: OC[C@H]1CNCCO[C@@H]1c1ccc(Cl)c(Cl)c1] | HCl | 275.9 |
| 74 | 7-(3,4-dichlorophenyl)-6-(hydroxymethyl)-1,4-oxazepan-6-ol | 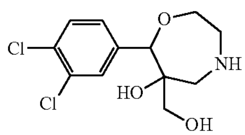 [SMILES: OCC1(O)CNCCOC1c1ccc(Cl)c(Cl)c1] | HCl | 292.1 |
| 75 | 2-[(6R,7R)-7-(3,4-dichlorophenyl)-1,4-oxazepan-6-yl]propan-2-ol | 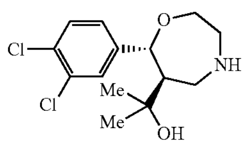 [SMILES: CC(C)(O)[C@@H]1CNCCO[C@H]1c1ccc(Cl)c(Cl)c1] | HCl | 304.1 |
| 76 | 2-{[(6S,7R)-7-(3,4-dichlorophenyl)-1,4-oxazepan-6-yl]methoxy}benzonitrile | 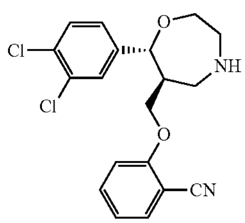 [SMILES: N#Cc1ccccc1OC[C@@H]1CNCCO[C@H]1c1ccc(Cl)c(Cl)c1] | HCl | 377.0 |

TABLE 1-16

| Ex. No. | IUPAC name | structure | salt | MS |
|---|---|---|---|---|
| 77 | 2-{[(6S,7R)-7-(3,4-dichlorophenyl)-1,4-oxazepan-6-yl]methoxy}benzoic acid | 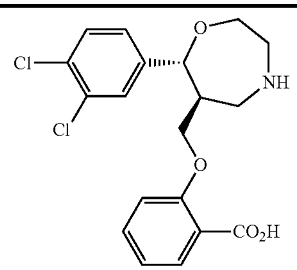 | HCl | 395.9 |
| 78 | 2-{[(6S,7R)-7-(3,4-dichlorophenyl)-1,4-oxazepan-6-yl]methoxy}-6-fluorobenzoic acid | 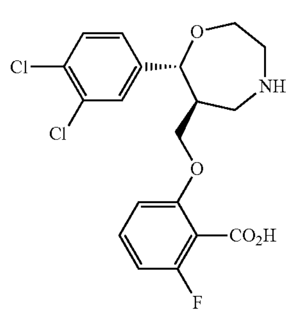 [SMILES: O=C(O)c1c(F)cccc1OC[C@@H]1CNCCO[C@H]1c1ccc(Cl)c(Cl)c1] | HCl | 414.1 |

TABLE 1-16-continued

| Ex. No. | IUPAC name | structure | salt | MS |
|---|---|---|---|---|
| 79 | methyl 2-{[(6S,7R)-7-(3,4-dichlorophenyl)-1,4-oxazepan-6-yl]methoxy}benzoate | 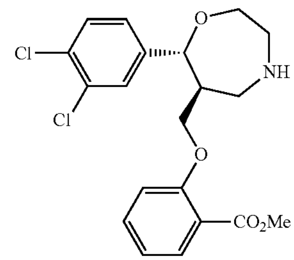 [SMILES: COC(=O)c1ccccc1OC[C@@H]1CNCCO[C@H]1c1ccc(Cl)c(Cl)c1] | HCl | 410.0 |
| 80 | 2-{[(6S,7R)-7-(3,4-dichlorophenyl)-1,4-oxazepan-6-yl]methoxy}-N-(methylsulfonyl)benzamide | 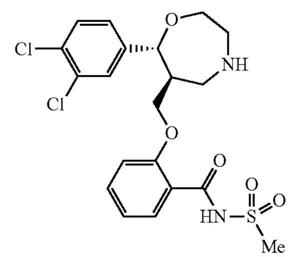 [SMILES: CS(=O)(=O)NC(=O)c1ccccc1OC[C@@H]1CNCCO[C@H]1c1ccc(Cl)c(Cl)c1] | HCl | 473.2 |

TABLE 1-17

| Ex. No. | IUPAC name | structure | salt | MS |
|---|---|---|---|---|
| 81 | 3-{[(6S,7R)-7-(3,4-dichlorophenyl)-1,4-oxazepan-6-yl]methoxy}-N-(methylsulfonyl)benzamide | 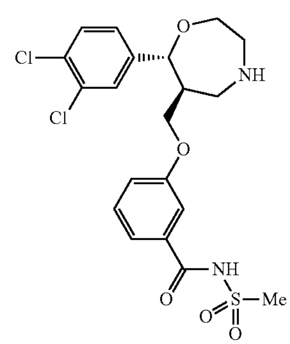 [SMILES: CS(=O)(=O)NC(=O)c1cccc(OC[C@@H]2CNCCO[C@H]2c2ccc(Cl)c(Cl)c2)c1] | HCl | 473.0 |
| 82 | (6S,7R)-7-(3,4-dichlorophenyl)-6-{[2-(methylsulfonyl)phenoxy]methyl}-1,4-oxazepane | 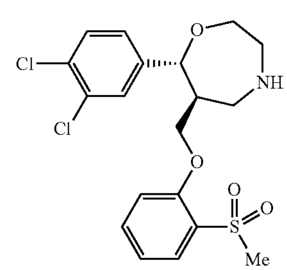 [SMILES: CS(=O)(=O)c1ccccc1OC[C@@H]1CNCCO[C@H]1c1ccc(Cl)c(Cl)c1] | free amine | 430.3 |

TABLE 1-17-continued

| Ex. No. | IUPAC name | structure | salt | MS |
|---|---|---|---|---|
| 83 | 3-(2-{[(6S,7R)-7-(3,4-dichlorophenyl)-1,4-yl]methoxy}phenyl)-1,2,4-oxadiazol-5(4H)-one | 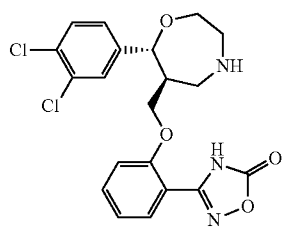 [SMILES: O=c1[nH]c(-c2ccccc2OC[C@@H]2CNCCO[C@H]2c2ccc(Cl)c(Cl)c2)no1] | HCl | 436.0 |
| 84 | 3-(3-{[(6S,7R)-7-(3,4-dichlorophenyl)-1,4-oxazepan-6-yl]methoxy}phenyl)-1,2,4-oxadiazol-5(4H)-one | | HCl | 436.0 |

TABLE 1-18

| Ex. No. | IUPAC name | structure | salt | MS |
|---|---|---|---|---|
| 85 | 3-(3-{[(6S,7R)-7-(3,4-dichlorophenyl)-1,4-oxazepan-6-yl]methoxy}phenyl)-1,2,4-oxadiazole-5(4H)-thione | 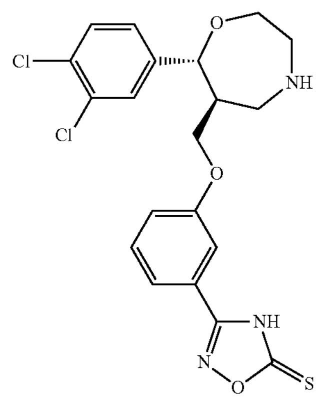 [SMILES: S=c1[nH]c(-c2cccc(OC[C@@H]3CNCCO[C@H]3c3ccc(Cl)c(Cl)c3)c2)no1] | HCl | 452.0 |
| 86 | 3-(2-{[(6S,7R)-7-(3,4-dichlorophenyl)-1,4-oxazepan-6-yl]methoxy}pyridin-3-yl)-1,2,4-oxadiazol-5(4H)-one | 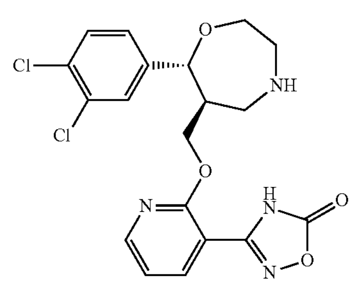 [SMILES: O=c1[nH]c(-c2cccnc2OC[C@@H]2CNCCO[C@H]2c2ccc(Cl)c(Cl)c2)no1] | HCl | 436.9 |

TABLE 1-18-continued

| Ex. No. | IUPAC name | structure | salt | MS |
|---|---|---|---|---|
| 87 | 3-(6-{[(6S,7R)-7-(3,4-dichlorophenyl)-1,4-oxazepan-6-yl]methoxy}pyridin-3-yl)-1,2,4-oxadiazol-5(4H)-one | 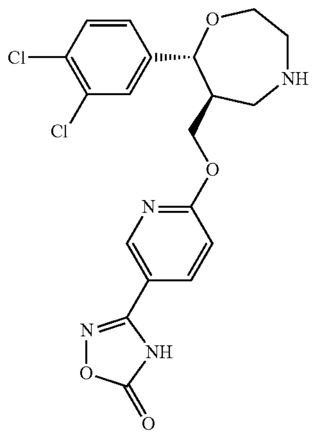 [SMILES: O=c1[nH]c(-c2ccc(OC[C@@H]3CNCCO[C@H]3c3ccc(Cl)c(Cl)c3)nc2)no1] | HCl | 437.0 |
| 88 | 3-[3-({[(6S,7R)-7-(3,4-dichlorophenyl)-1,4-oxazepan-6-yl]methoxy}methyl)-phenyl]-1,2,4-oxadiazol-5(4H)-one | 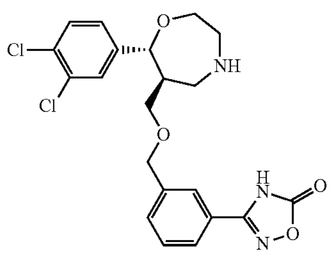 [SMILES: O=c1[nH]c(-c2cccc(COC[C@@H]3CNCCO[C@H]3c3ccc(Cl)c(Cl)c3)c2)no1] | HCl | 450.1 |

TABLE 1-19

| Ex. No. | IUPAC name | structure | salt | MS |
|---|---|---|---|---|
| 89 | 3-(2-{[(6S,7R)-7-(3,4-dichlorophenyl)-1,4-oxazepan-6-yl]methoxy}pyridin-4-yl)-1,2,4-oxadiazol-5(4H)-one | 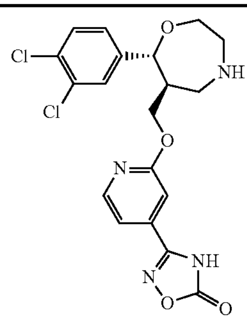 | HCl | 436.9 |
| 90 | (6R,7R)-7-(3,4-dichlorophenyl)-6-[(methylsulfanyl)-methyl]-1,4-oxazepane | 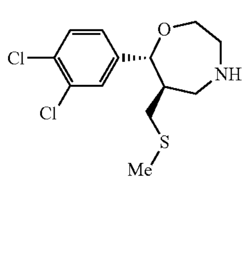 [SMILES: CSC[C@@H]1CNCCO[C@H]1c1ccc(Cl)c(Cl)c1] | HCl | 306.1 |
| 91 | (6R,7R)-7-(3,4-dichlorophenyl)-6-[(methylsulfinyl)-methyl]-1,4-oxazepane | 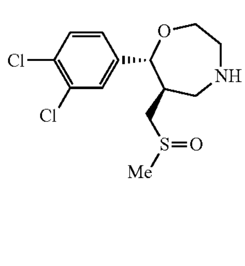 [SMILES: CS(=O)C[C@@H]1CNCCO[C@H]1c1ccc(Cl)c(Cl)c1] | HCl | 322.0 |
| 92 | (6R,7R)-7-(3,4-dichlorophenyl)-6-[(methylsulfonyl)-methyl]-1,4-oxazepane | | HCl | 338.3 |
| 93 | (6S,7S)-7-(3,4-dichlorophenyl)-6-[(methylsulfonyl)-methyl]-1,4-oxazepane | | HCl | 338.2 |

TABLE 1-20

| Ex. No. | IUPAC name | structure | salt | MS |
|---|---|---|---|---|
| 94 | 2-({[(6R,7R)-7-(3,4-dichlorophenyl)-1,4-oxazepan-6-yl]methyl}sulfanyl)-benzoic acid | 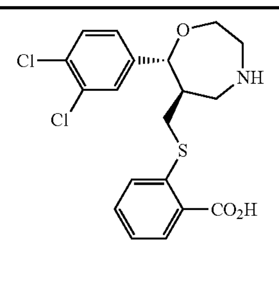 | HCl | 412.0 |

TABLE 1-20-continued

| Ex. No. | IUPAC name | salt | MS |
|---|---|---|---|
| 95 | 2-({[(6R,7R)-7-(3,4-dichlorophenyl)-1,4-oxazepan-6-yl]methyl}sulfonyl)benzoic acid | HCl | 443.9 |
| 96 | 3-[3-({[(6R,7R)-7-(3,4-dichlorophenyl)-1,4-yl]methyl}sulfonyl)phenyl]-1,2,4-oxadiazol-5(4H)-one | HCl | 484.1 |
| 97 | 1-({[(6S,7R)-7-(3,4-dichlorophenyl)-1,4-oxazepan-6-yl]methyl}azetidine-3-carboxylic acid | HCl | 359.1 |
| 98 | N-{[(6R,7S)-7-(3,4-dichlorophenyl)-1,4-oxazepan-6-yl]methyl}acetamide | fumarate | 317.0 |

TABLE 1-21

| Ex. No. | IUPAC name | salt | MS |
|---|---|---|---|
| 99 | N-{[(6S,7R)-7-(3,4-dichlorophenyl)-1,4-oxazepan-6-yl]methyl}-N-methylacetamide | HCl | 331.3 |
| 100 | N-{[(6RS,7SR)-7-(3,4-dichlorophenyl)-6-hydroxy-1,4-oxazepan-6-yl]methyl}acetamide | HCl | 333.1 |
| 101 | N-{[(6RS,7SR)-7-(3,4-dichlorophenyl)-6-methoxy-1,4-oxazepan-6-yl]methyl}propanamide | HCl | 347.1 |
| 102 | N-{[(6S,7R)-7-(3,4-dichlorophenyl)-1,4-oxazepan-6-yl]methyl}propanamide | HCl | 331.3 |
| 103 | N-{[(6S,7R)-7-(3,4-dichlorophenyl)-1,4-oxazepan-6-yl]methyl}butanamide | HCl | 345.4 |

TABLE 1-22

| Ex. No. | IUPAC name | salt | MS |
|---|---|---|---|
| 104 | 2-cyano-N-{[(6S,7R)-7-(3,4-dichlorophenyl)-1,4-oxazepan-6-yl]methyl}acetamide | HCl | 342.1 |
| 105 | 2-({[(6S,7R)-7-(3,4-dichlorophenyl)-1,4-oxazepan-6-yl]methyl}amino)-2-oxoethyl acetate | fumarate | 375.1 |
| 106 | N-{[(6S,7R)-7-(3,4-dichlorophenyl)-1,4-oxazepan-6-yl]methyl}-2-hydroxyacetamide | 1/2 fumarate | 333.1 |

TABLE 1-22-continued

| Ex. No. | IUPAC name | structure | salt | MS |
|---|---|---|---|---|
| 107 | N-{[(6RS,7SR)-7-(3,4-dichlorophenyl)-6-hydroxy-1,4-oxazepan-6-yl]methyl}-2-methoxy-acetamide | 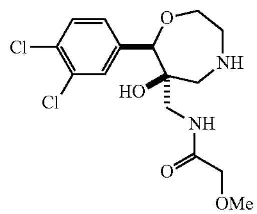 | HCl | 363.1 |

TABLE 1-23

| Ex. No. | IUPAC name | structure | salt | MS |
|---|---|---|---|---|
| 108 | N-{[(6S,7R)-7-(3,4-dichlorophenyl)-1,4-oxazepan-6-yl]methyl}-2-phenoxy-acetamide | 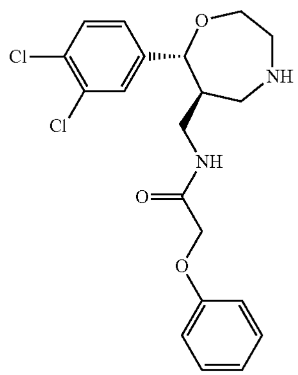 [SMILES: O=C(COc1ccccc1)NC[C@@H]1CNCCO[C@H]1c1ccc(Cl)c(Cl)c1] | HCl | 409.1 |
| 109 | 2-[2-({[(6S,7R)-7-(3,4-dichlorophenyl)-1,4-oxazepan-6-yl]methyl}amino)-2-oxoethoxy]benzoic acid | 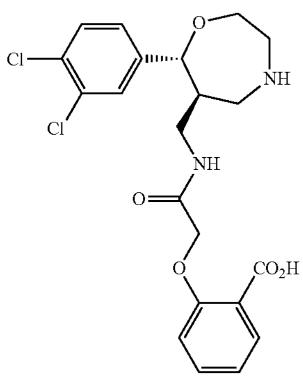 [SMILES: O=C(COc1ccccc1C(=O)O)NC[C@@H]1CNCCO[C@H]1c1ccc(Cl)c(Cl)c1] | HCl | 453.1 |
| 110 | N-{[(6S,7R)-7-(3,4-dichlorophenyl)-1,4-oxazepan-6-yl]methyl}-2-[2-(5-oxo-4,5-dihydro-1,2,4-oxadiazol-3-yl)phenoxy]acetamide | 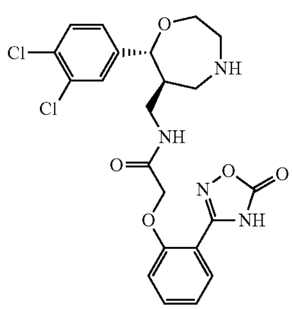 [SMILES: O=C(COc1ccccc1-c1noc(=O)[nH]1)NC[C@@H]1CNCCO[C@H]1c1ccc(Cl)c(Cl)c1] | HCl | 493.0 |

TABLE 1-23-continued

| Ex. No. | IUPAC name | structure | salt | MS |
|---|---|---|---|---|
| 111 | N-{[(6S,7R)-7-(3,4-dichlorophenyl)-1,4-oxazepan-6-yl]methyl}-N-(2-hydroxyethyl)-2-pyrrolidin-1-ylacetamide | 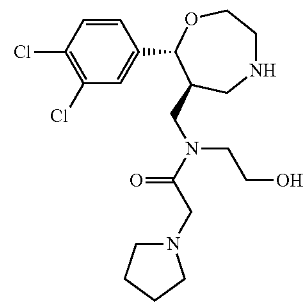 [SMILES: O=C(CN1CCCC1)N(CCO)C[C@@H]1CNCCO[C@H]1c1ccc(Cl)c(Cl)c1] | 2HCl | 430.4 |

TABLE 1-24

| Ex. No. | IUPAC name | structure | salt | MS |
|---|---|---|---|---|
| 112 | N-{[(6S,7R)-7-(3,4-dichlorophenyl)-1,4-oxazepan-6-yl]methyl}-2-(methylsulfanyl)-acetamide | 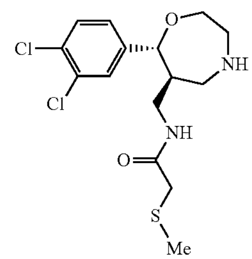 [SMILES: CSCC(=O)NC[C@@H]1CNCCO[C@H]1c1ccc(Cl)c(Cl)c1] | fumarate | 362.9 |
| 113 | N-{[(6R,7S)-7-(3,4-dichlorophenyl)-1,4-oxazepan-6-yl]methyl}-2-(methylsulfanyl)-acetamide | 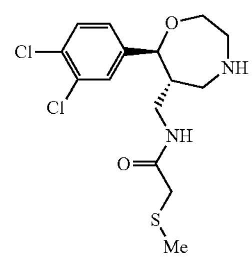 [SMILES: CSCC(=O)NC[C@H]1CNCCO[C@@H]1c1ccc(Cl)c(Cl)c1] | HCl | 362.9 |
| 114 | N-{[(6S,7R)-7-(3,4-dichlorophenyl)-1,4-oxazepan-6-yl]methyl}-2-(methylsulfonyl)-acetamide | 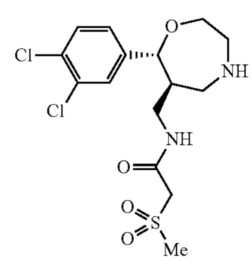 [SMILES: CS(=O)(=O)CC(=O)NC[C@@H]1CNCCO[C@H]1c1ccc(Cl)c(Cl)c1] | HCl | 395.0 |
| 115 | N-{[(6R,7S)-7-(3,4-dichlorophenyl)-1,4-oxazepan-6-yl]methyl}-2-(methylsulfonyl)-acetamide | 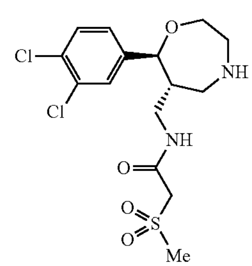 [SMILES: CS(=O)(=O)CC(=O)NC[C@H]1CNCCO[C@@H]1c1ccc(Cl)c(Cl)c1] | HCl | 395.0 |

TABLE 1-25

| Ex. No. | IUPAC name | structure | salt | MS |
|---|---|---|---|---|
| 116 | N-{[(6S,7R)-7-(3,4-dichlorophenyl)-1,4-oxazepan-6-yl]methyl}-2-phenylacetamide | 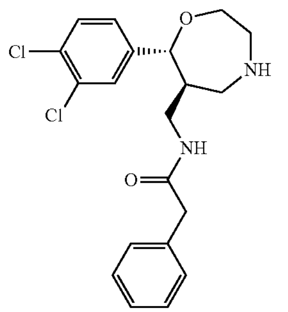 [SMILES: O=C(Cc1ccccc1)NC[C@@H]1CNCCO[C@H]1c1ccc(Cl)c(Cl)c1] | HCl | 393.1 |
| 117 | N-{[(6S,7R)-7-(3,4-dichlorophenyl)-1,4-oxazepan-6-yl]methyl}-2-[3-(5-oxo-4,5-dihydro-1,2,4-oxadiazol-3-yl)phenyl]acetamide | 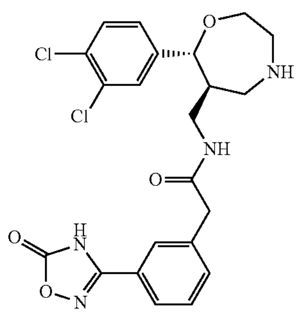 [SMILES: O=C(Cc1cccc(-c2noc(=O)[nH]2)c1)NC[C@@H]1CNCCO[C@H]1c1ccc(Cl)c(Cl)c1] | fumarate | 477.1 |
| 118 | N-{[(6S,7R)-7-(3,4-dichlorophenyl)-1,4-oxazepan-6-yl]methyl}-4-(5-oxo-4,5-dihydro-1,2,4-oxadiazol-3-yl)benzamide | 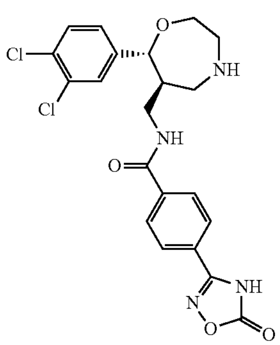 [SMILES: O=C(NC[C@@H]1CNCCO[C@H]1c1ccc(Cl)c(Cl)c1)c1ccc(-c2noc(=O)[nH]2)cc1] | HCl | 463.0 |
| 119 | N-{[(6S,7R)-7-(3,4-dichlorophenyl)-1,4-oxazepan-6-yl]methyl}-2-(1H-1,2,4-triazol-1-yl)acetamide | 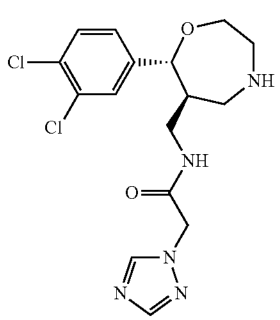 [SMILES: O=C(Cn1cncn1)NC[C@@H]1CNCCO[C@H]1c1ccc(Cl)c(Cl)c1] | HCl | 384.1 |

TABLE 1-26

| Ex. No. | IUPAC name | structure | salt | MS |
|---|---|---|---|---|
| 120 | N-{[(6S,7R)-7-(3,4-dichlorophenyl)-1,4-oxazepan-6-yl]methyl}-2-(1H-tetrazol-1-yl)acetamide | 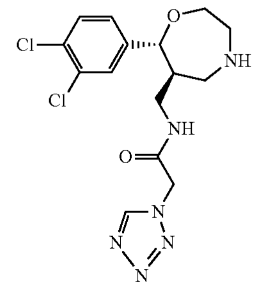 [SMILES: O=C(Cn1cnnn1)NC[C@@H]1CNCCO[C@H]1c1ccc(Cl)c(Cl)c1] | HCl | 385.0 |
| 121 | 1-[2-({[(6S,7R)-7-(3,4-dichlorophenyl)-1,4-oxazepan-6-yl]methyl}amino)-2-oxoethyl]-3-methyl-1H-pyrazole-5-carboxylic acid | 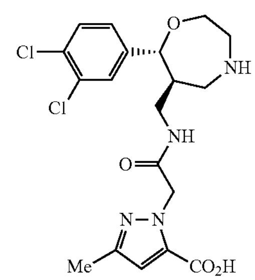 [SMILES: Cc1cc(C(=O)O)n(CC(=O)NC[C@@H]2CNCCO[C@H]2c2ccc(Cl)c(Cl)c2)n1] | HCl | 440.9 |
| 122 | N-{[(6S,7R)-7-(3,4-dichlorophenyl)-1,4-oxazepan-6-yl]methyl}-2-(2-oxopyrrolidin-1-yl)acetamide | 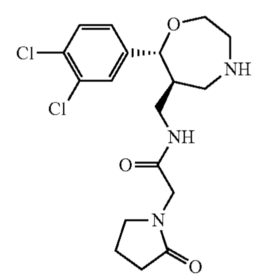 [SMILES: O=C(CN1CCCC1=O)NC[C@@H]1CNCCO[C@H]1c1ccc(Cl)c(Cl)c1] | HCl | 400.0 |
| 123 | N-{[(6S,7R)-7-(3,4-dichlorophenyl)-1,4-oxazepan-6-yl]methyl}-2-(5-oxo-4,5-dihydro-1,2,4-oxadiazol-3-yl)acetamide | 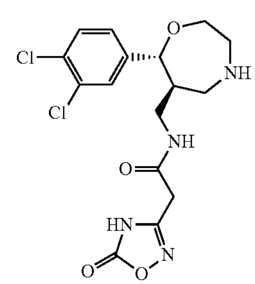 [SMILES: O=C(Cc1noc(=O)[nH]1)NC[C@@H]1CNCCO[C@H]1c1ccc(Cl)c(Cl)c1] | HCl | 401.0 |

TABLE 1-27

| Ex. No. | IUPAC name | structure | salt | MS |
|---|---|---|---|---|
| 124 | N-{[(6S,7R)-7-(3,4-dichlorophenyl)-1,4-oxazepan-6-yl]methyl}-2-(2,4-dioxoimidazolidin-1-yl)acetamide | 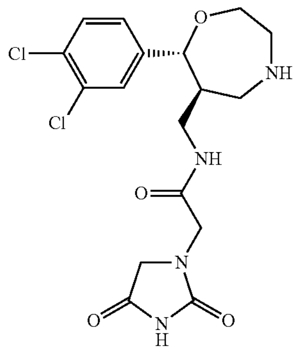 [SMILES: O=C(CN1CC(=O)NC1=O)NC[C@@H]1CNCCO[C@H]1c1ccc(Cl)c(Cl)c1] | HCl | 415.0 |
| 125 | 1-[2-({[(6S,7R)-7-(3,4-dichlorophenyl)-1,4-oxazepan-6-yl]methyl}amino)-2-oxoethyl]-5-methyl-1H-pyrazole-3-carboxylic acid | 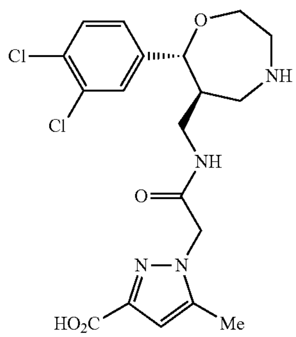 [SMILES: Cc1cc(C(=O)O)nn1CC(=O)NC[C@@H]1CNCCO[C@H]1c1ccc(Cl)c(Cl)c1] | HCl | 441.4 |
| 126 | N-{[(6S,7R)-7-(3,4-dichlorophenyl)-1,4-oxazepan-6-yl]methyl}benzamide | | HCl | 379.0 |
| 127 | 3,5-di-tert-butyl-N-{[(6S,7R)-7-(3,4-dichlorophenyl)-1,4-oxazepan-6-yl]methyl}benzamide | | HCl | 491.0 |

TABLE 1-28

| Ex. No. | IUPAC name | structure | salt | MS |
|---|---|---|---|---|
| 128 | N-{[(6S,7R)-7-(3,4-dichlorophenyl)-1,4-oxazepan-6-yl]methyl}biphenyl-2-carboxamide | 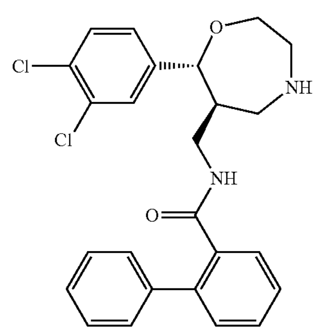 [SMILES: O=C(NC[C@@H]1CNCCO[C@H]1c1ccc(Cl)c(Cl)c1)c1ccccc1-c1ccccc1] | HCl | 455.0 |
| 129 | N-{[(6S,7R)-7-(3,4-dichlorophenyl)-1,4-oxazepan-6-yl]methyl}biphenyl-3-carboxamide | 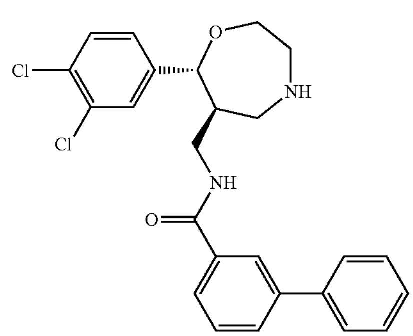 [SMILES: O=C(NC[C@@H]1CNCCO[C@H]1c1ccc(Cl)c(Cl)c1)c1cccc(-c2ccccc2)c1] | HCl | 455.0 |

TABLE 1-28-continued

| Ex. No. | IUPAC name | structure | salt | MS |
|---|---|---|---|---|
| 130 | N-{[(6S,7R)-7-(3,4-dichlorophenyl)-1,4-oxazepan-6-yl]methyl}-2-hydroxybiphenyl-3-carboxamide | 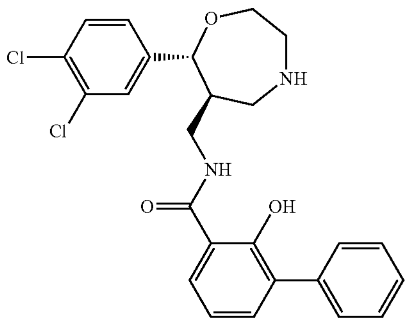 [SMILES: O=C(NC[C@@H]1CNCCO[C@H]1c1ccc(Cl)c(Cl)c1)c1cccc(-c2ccccc2)c1O] | HCl | 471.2 |
| 131 | 2-({[(6S,7R)-7-(3,4-dichlorophenyl)-1,4-oxazepan-6-yl]methyl}carbamoyl)-benzoic acid | 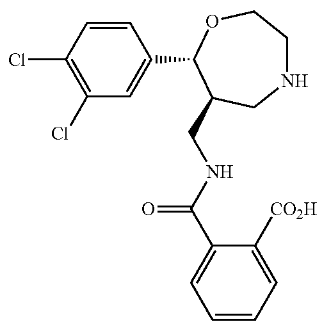 [SMILES: O=C(O)c1ccccc1C(=O)NC[C@@H]1CNCCO[C@H]1c1ccc(Cl)c(Cl)c1] | HCl | 423.1 |
| 132 | N-{[(6R*,7S*)-7-(4-chloro-3-methylphenyl)-1,4-oxazepan-6-yl]methyl}-methanesulfonamide | 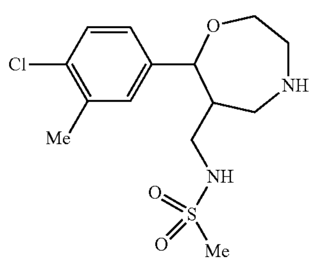 [SMILES: Cc1cc(C2OCCNCC2CNS(C)(=O)=O)ccc1Cl] | HCl | 333.2 |

TABLE 1-29

| Ex. No. | IUPAC name | structure | salt | MS |
|---|---|---|---|---|
| 133 | 2-({[(6S,7R)-7-(3,4-dichlorophenyl)-1,4-oxazepan-6-yl]methyl}carbamoyl)-4,5-difluorobenzoic acid | 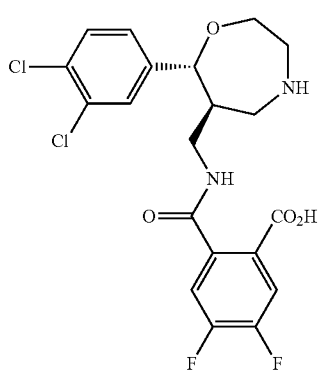 [SMILES: O=C(O)c1cc(F)c(F)cc1C(=O)NC[C@@H]1CNCCO[C@H]1c1ccc(Cl)c(Cl)c1] | HCl | 459.1 |

TABLE 1-29-continued

| Ex. No. | IUPAC name | structure | salt | MS |
|---|---|---|---|---|
| 134 | N-{[(6S,7R)-7-(3,4-dichlorophenyl)-1,4-oxazepan-6-yl]methyl}-2-[(5-oxo-4,5-dihydro-1,2,4-oxadiazol-3-yl)methyl]benzamide | 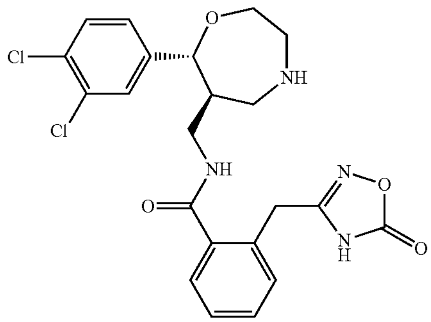 [SMILES: O=C(NC[C@@H]1CNCCO[C@H]1c1ccc(Cl)c(Cl)c1)c1ccccc1Cc1noc(=O)[nH]1] | HCl | 477.1 |
| 135 | 3-({[(6S,7R)-7-(3,4-dichlorophenyl)-1,4-oxazepan-6-yl]methyl}carbamoyl)-benzoic acid | 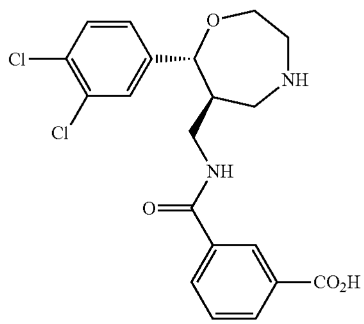 [SMILES: O=C(O)c1cccc(C(=O)NC[C@@H]2CNCCO[C@H]2c2ccc(Cl)c(Cl)c2)c1] | HCl | 423.1 |
| 136 | 4-({[(6S,7R)-7-(3,4-dichlorophenyl)-1,4-oxazepan-6-yl]methyl}carbamoyl)-benzoic acid | 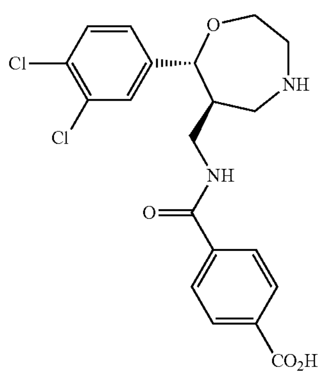 [SMILES: O=C(O)c1ccc(C(=O)NC[C@@H]2CNCCO[C@H]2c2ccc(Cl)c(Cl)c2)cc1] | HCl | 423.1 |

TABLE 1-30

| Ex. No. | IUPAC name | structure | salt | MS |
|---|---|---|---|---|
| 137 | 3-cyano-N-{[(6S,7R)-7-(3,4-dichlorophenyl)-1,4-oxazepan-6-yl]methyl}benzamide | 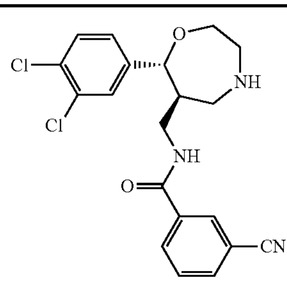 | HCl | 404.0 |
| 138 | 3-cyano-N-{[(6S,7R)-7-(3,4-dichlorophenyl)-1,4-oxazepan-6-yl]methyl}-N-methylbenzamide | | HCl | 418.3 |

TABLE 1-30-continued

| Ex. No. | IUPAC name | structure | salt | MS |
|---|---|---|---|---|
| 139 | N-{[(6S,7R)-7-(3,4-dichlorophenyl)-1,4-oxazepan-6-yl]methyl}-2-(5-oxo-4,5-dihydro-1,2,4-oxadiazol-3-yl)benzamide | 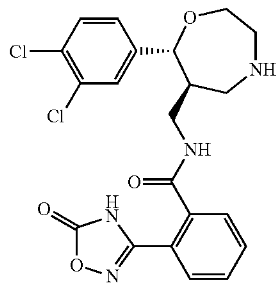 [SMILES: O=C(NC[C@@H]1CNCCO[C@H]1c1ccc(Cl)c(Cl)c1)c1ccccc1-c1noc(=O)[nH]1] | HCl | 463.3 |
| 140 | 3-(2-{[(6S,7R)-7-(3,4-dichlorophenyl)-1,4-oxazepan-6-yl]methoxy}-6-fluorophenyl)-1,2,4-oxadiazol-5(4H)-one | | HCl | 454.0 |

TABLE 1-31

| Ex. No. | IUPAC name | structure | salt | MS |
|---|---|---|---|---|
| 141 | 3-(2-chloro-6-{[(6S,7R)-7-(3,4-dichlorophenyl)-1,4-oxazepan-6-yl]methoxy}phenyl)-1,2,4-oxadiazol-5(4H)-one | 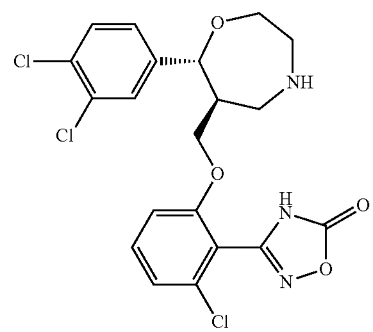 [SMILES: O=c1[nH]c(-c2c(Cl)cccc2OC[C@@H]2CNCCO[C@H]2c2ccc(Cl)c(Cl)c2)no1] | HCl | 469.9 |
| 142 | N-{[(6S,7R)-7-(3,4-dichlorophenyl)-1,4-oxazepan-6-yl]methyl}-3-(5-oxo-4,5-dihydro-1,2,4-oxadiazol-3-yl)benzamide | 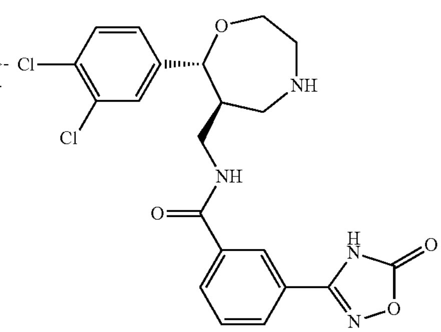 | HCl | 463.0 |
| 143 | N-{[(6S,7R)-7-(3,4-dichlorophenyl)-1,4-oxazepan-6-yl]methyl}-N-methyl-3-(5-oxo-4,5-dihydro-1,2,4-oxadiazol-3-yl)benzamide | 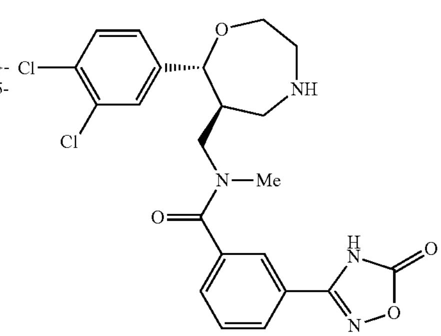 | HCl | 477.4 |

TABLE 1-31-continued

| Ex. No. | IUPAC name | structure | salt | MS |
|---|---|---|---|---|
| 144 | N-{[(6S,7R)-7-(3,4-dichlorophenyl)-1,4-oxazepan-6-yl]methyl}-3-(1H-tetrazol-5-yl)benzamide | 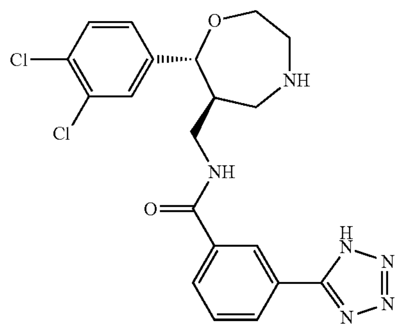 [SMILES: O=C(NC[C@@H]1CNCCO[C@H]1c1ccc(Cl)c(Cl)c1)c1cccc(-c2nnn[nH]2)c1] | HCl | 447.2 |

TABLE 1-32

| Ex. No. | IUPAC name | structure | salt | MS |
|---|---|---|---|---|
| 145 | N-{[(6S,7R)-7-(3,4-dichlorophenyl)-1,4-oxazepan-6-yl]methyl}pyridine-2-carboxamide | 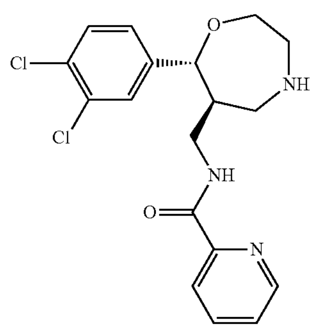 [SMILES: O=C(NC[C@@H]1CNCCO[C@H]1c1ccc(Cl)c(Cl)c1)c1ccccn1] | 2HCl | 380.0 |
| 146 | N-{[(6S,7R)-7-(3,4-dichlorophenyl)-1,4-oxazepan-6-yl]methyl}-4-(5-oxo-4,5-dihydro-1,2,4-oxadiazol-3-yl)pyridine-2-carboxamide | 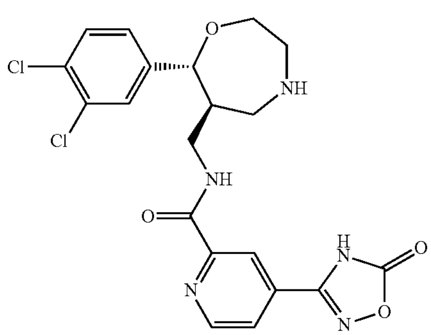 [SMILES: O=C(NC[C@@H]1CNCCO[C@H]1c1ccc(Cl)c(Cl)c1)c1cc(-c2noc(=O)[nH]2)ccn1] | HCl | 464.1 |
| 147 | N-{[(6S,7R)-7-(3,4-dichlorophenyl)-1,4-oxazepan-6-yl]methyl}-6-(5-oxo-4,5-dihydro-1,2,4-oxadiazol-3-yl)pyridine-2-carboxamide | 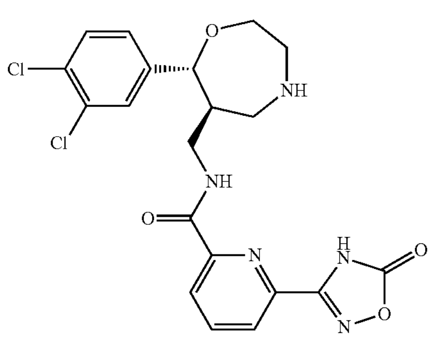 [SMILES: O=C(NC[C@@H]1CNCCO[C@H]1c1ccc(Cl)c(Cl)c1)c1cccc(-c2noc(=O)[nH]2)n1] | HCl | 464.0 |

TABLE 1-32-continued

| Ex. No. | IUPAC name | structure | salt | MS |
|---|---|---|---|---|
| 148 | N-{[(6S,7R)-7-(3,4-dichlorophenyl)-1,4-oxazepan-6-yl]methyl}-4-methyl-1,3-thiazole-5-carboxamide | 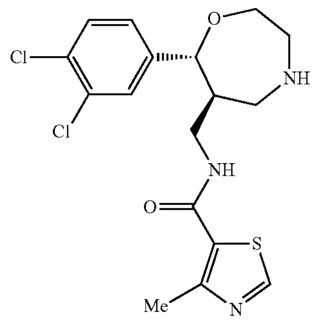 [SMILES: Cc1ncsc1C(=O)NC[C@@H]1CNCCO[C@H]1c1ccc(Cl)c(Cl)c1] | HCl | 400.0 |

TABLE 1-33

| Ex. No. | IUPAC name | structure | salt | MS |
|---|---|---|---|---|
| 149 | N-{[(6S,7R)-7-(3,4-dichlorophenyl)-1,4-oxazepan-6-yl]methyl}-2-oxobutanamide | 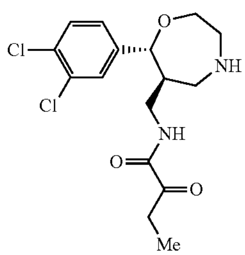 [SMILES: CCC(=O)C(=O)NC[C@@H]1CNCCO[C@H]1c1ccc(Cl)c(Cl)c1] | HCl | 359.0 |
| 150 | methyl {[(6S,7R)-7-(3,4-dichlorophenyl)-1,4-oxazepan-6-yl]methyl}carbamate | 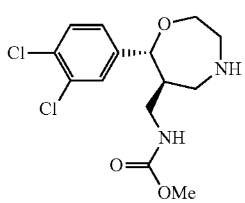 [SMILES: COC(=O)NC[C@@H]1CNCCO[C@H]1c1ccc(Cl)c(Cl)c1] | HCl | 333.4 |
| 151 | 1-methylethyl {[(6S,7R)-7-(3,4-dichlorophenyl)-1,4-oxazepan-6-yl]methyl}carbamate | 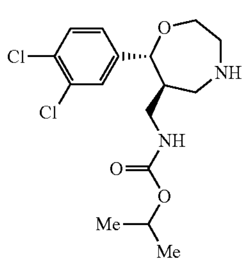 [SMILES: CC(C)OC(=O)NC[C@@H]1CNCCO[C@H]1c1ccc(Cl)c(Cl)c1] | HCl | 361.1 |
| 152 | 1-{[(6S,7R)-7-(3,4-dichlorophenyl)-1,4-oxazepan-6-yl]methyl}urea | 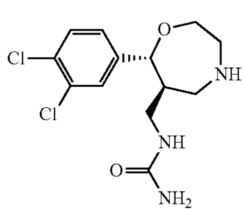 [SMILES: NC(=O)NC[C@@H]1CNCCO[C@H]1c1ccc(Cl)c(Cl)c1] | fumarate | 318.1 |

TABLE 1-33-continued

| Ex. No. | IUPAC name | structure | salt | MS |
|---|---|---|---|---|
| 153 | 1-{[(6R,7S)-7-(3,4-dichlorophenyl)-1,4-oxazepan-6-yl]methyl}urea | 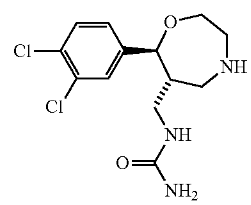 [SMILES: NC(=O)NC[C@H]1CNCCO[C@@H]1c1ccc(Cl)c(Cl)c1] | fumarate | 318.1 |

TABLE 1-34

| Ex. No. | IUPAC name | structure | salt | MS |
|---|---|---|---|---|
| 154 | 1-{[(6RS,7SR)-7-(3,4-dichlorophenyl)-1,4-oxazepan-6-yl]methyl}-3-ethylurea | 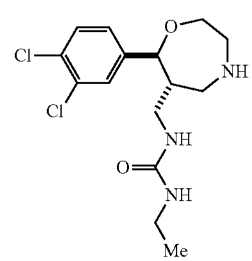 [SMILES: CCNC(=O)NC[C@H]1CNCCO[C@@H]1c1ccc(Cl)c(Cl)c1] | HCl | 346.1 |
| 155 | 1-{[(6S,7R)-7-(3,4-dichlorophenyl)-1,4-oxazepan-6-yl]methyl}-3-ethylurea | 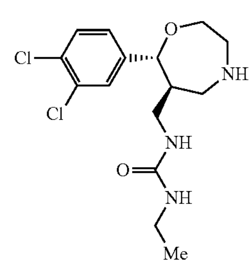 [SMILES: CCNC(=O)NC[C@@H]1CNCCO[C@H]1c1ccc(Cl)c(Cl)c1] | fumarate | 346.3 |

TABLE 1-34-continued

| Ex. No. | IUPAC name | structure | salt | MS |
|---|---|---|---|---|
| 156 | 1-{[(6R,7S)-7-(3,4-dichlorophenyl)-1,4-oxazepan-6-yl]methyl}-3-ethylurea | 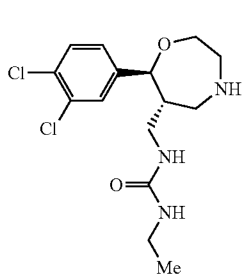 [SMILES: CCNC(=O)NC[C@H]1CNCCO[C@@H]1c1ccc(Cl)c(Cl)c1] | HCl | 346.1 |
| 157 | 1-tert-butyl-3-{[(6S,7R)-7-(3,4-dichlorophenyl)-1,4-oxazepan-6-yl]methyl}urea | 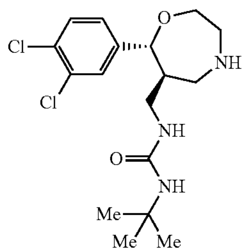 [SMILES: CC(C)(C)NC(=O)NC[C@@H]1CNCCO[C@H]1c1ccc(Cl)c(Cl)c1] | HCl | 374.2 |

TABLE 1-35

| Ex. No. | IUPAC name | structure | salt | MS |
|---|---|---|---|---|
| 158 | N-{[(6S,7R)-7-(3,4-dichlorophenyl)-1,4-oxazepan-6-yl]methyl}pyrrolidine-1-carboxamide | 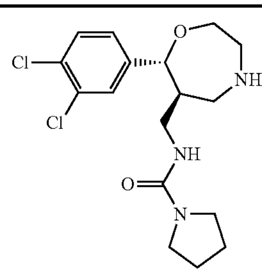 | HCl | 372.1 |
| 159 | N-{[(6S,7R)-7-(3,4-dichlorophenyl)-1,4-oxazepan-6-yl]methyl}morpholine-4-carboxamide | 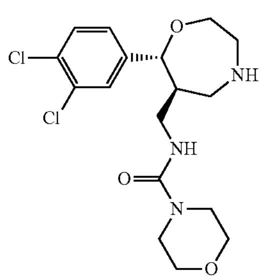 | HCl | 388.0 |
| 160 | 1-{[(6S,7R)-7-(3,4-dichlorophenyl)-1,4-oxazepan-6-yl]methyl}-1-(2-hydroxyethyl)-3-methylurea | 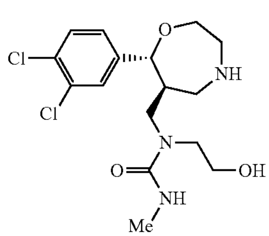 [SMILES: CNC(=O)N(CCO)C[C@@H]1CNCCO[C@H]1c1ccc(Cl)c(Cl)c1] | HCl | 376.1 |

TABLE 1-35-continued

| Ex. No. | IUPAC name | structure | salt | MS |
|---|---|---|---|---|
| 161 | N-{[(6R,7S)-7-(3,4-dichlorophenyl)-1,4-oxazepan-6-yl]methyl}methanesulfonamide | 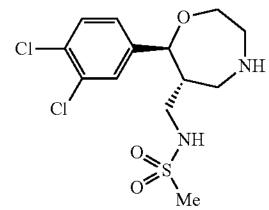 [SMILES: CS(=O)(=O)NC[C@H]1CNCCO[C@@H]1c1ccc(Cl)c(Cl)c1] | HCl | 353.0 |
| 162 | N-{[(6RS,7SR)-7-(3,4-dichlorophenyl)-6-hydroxy-1,4-oxazepan-6-yl]methyl}methanesulfonamide | 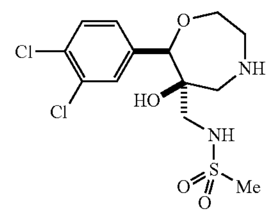 [SMILES: CS(=O)(=O)NC[C@@]1(O)CNCCO[C@@H]1c1ccc(Cl)c(Cl)c1] | HCl | 369.1 |

TABLE 1-36

| Ex. No. | IUPAC name | structure | salt | MS |
|---|---|---|---|---|
| 163 | N-{[(6S,7R)-7-(3,4-dichlorophenyl)-1,4-oxazepan-6-yl]methyl}-2-methoxyethanesulfonamide | 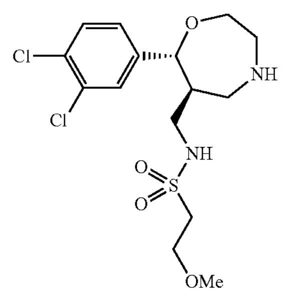 [SMILES: COCCS(=O)(=O)NC[C@@H]1CNCCO[C@H]1c1ccc(Cl)c(Cl)c1] | HCl | 397.0 |
| 164 | N-{[(6S,7R)-7-(3,4-dichlorophenyl)-1,4-oxazepan-6-yl]methyl}-2-(morpholin-4-yl)ethanesulfonamide | 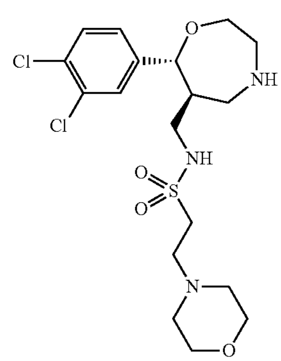 [SMILES: O=S(=O)(CCN1CCOCC1)NC[C@@H]1CNCCO[C@H]1c1ccc(Cl)c(Cl)c1] | 2HCl | 452.3 |

TABLE 1-36-continued

| Ex. No. | IUPAC name | structure | salt | MS |
|---|---|---|---|---|
| 165 | N-{[(6S,7R)-7-(3,4-dichloro-phenyl)-1,4-oxazepan-6-yl]methyl}-1,1,1-trifluoro-methane-sulfonamide | 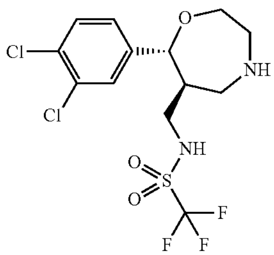 [SMILES: O=S(=O)(NC[C@@H]1CNCCO[C@H]1c1ccc(Cl)c(Cl)c1)C(F)(F)F] | HCl | 406.9 |
| 166 | 3-({[(6S,7R)-7-(3,4-dichloro-phenyl)-1,4-oxazepan-6-yl]methyl}sulfamoyl)-benzoic acid | 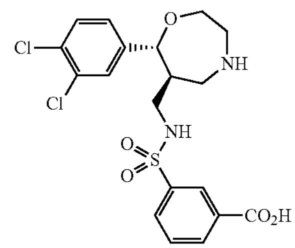 [SMILES: O=C(O)c1cccc(S(=O)(=O)NC[C@@H]2CNCCO[C@H]2c2ccc(Cl)c(Cl)c2)c1] | HCl | 458.9 |

TABLE 1-37

| Ex. No. | IUPAC name | structure | salt | MS |
|---|---|---|---|---|
| 167 | 3-[2-({[(6R,7R)-7-(3,4-dichlorophenyl)-1,4-oxazepan-6-yl]methyl}sulfonyl)-phenyl]-1,2,4-oxadiazol-5(2H)-one | 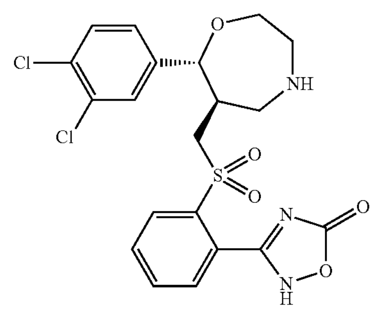 [SMILES: O=c1nc(-c2ccccc2S(=O)(=O)C[C@@H]2CNCCO[C@H]2c2ccc(Cl)c(Cl)c2)[nH]o1] | HCl | 484.1 |
| 168 | N-{[(6S,7R)-7-(3,4-dichlorophenyl)-1,4-oxazepan-6-yl]methyl}-3-(5-oxo-4,5-dihydro-1,2,4-oxadiazol-3-yl)benzenesulfonamide | 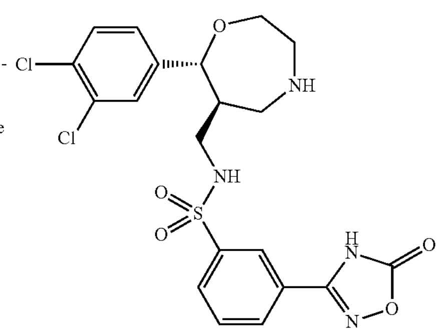 | HCl | 499.3 |
| 169 | N-{[(6S,7R)-7-(3,4-dichlorophenyl)-1,4-oxazepan-6-yl]methyl}pyridine-3-sulfonamide | 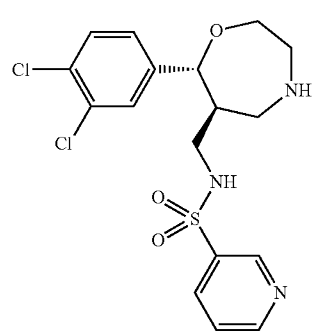 [SMILES: O=S(=O)(NC[C@@H]1CNCCO[C@H]1c1ccc(Cl)c(Cl)c1)c1cccnc1] | HCl | 416.0 |

TABLE 1-37-continued

| Ex. No. | IUPAC name | structure | salt | MS |
|---|---|---|---|---|
| 170 | 6-({[(6S,7R)-7-(3,4-dichlorophenyl)-1,4-oxazepan-6-yl]methyl}-sulfamoyl)pyridine-2-carboxylic acid | 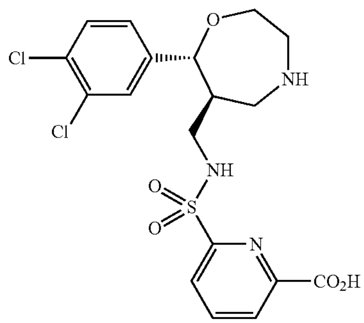 [SMILES: O=C(O)c1cccc(S(=O)(=O)NC[C@@H]2CNCCO[C@H]2c2ccc(Cl)c(Cl)c2)n1] | HCl | 460.0 |
| 171 | 5-({[(6S,7R)-7-(3,4-dichlorophenyl)-1,4-oxazepan-6-yl]methyl}-sulfamoyl)pyridine-3-carboxylic acid | 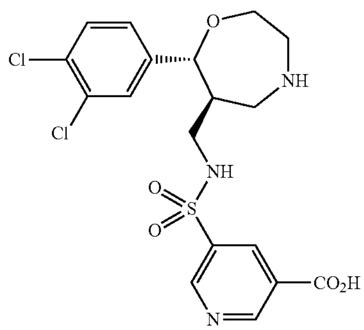 [SMILES: O=C(O)c1cncc(S(=O)(=O)NC[C@@H]2CNCCO[C@H]2c2ccc(Cl)c(Cl)c2)c1] | HCl | 460.3 |

TABLE 1-38

| Ex. No. | IUPAC name | structure | salt | MS |
|---|---|---|---|---|
| 172 | 5-({[(6S,7R)-7-(3,4-dichlorophenyl)-1,4-oxazepan-6-yl]-methyl}sulfamoyl)-pyridine-2-carboxylic acid | 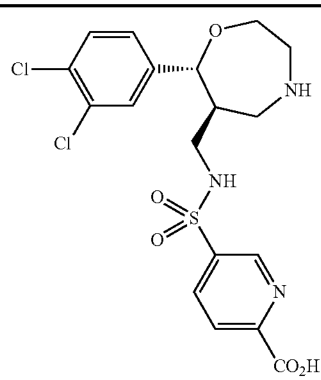 | HCl | 460.0 |
| 173 | N-{[(6S,7R)-7-(3,4-dichlorophenyl)-1,4-oxazepan-6-yl]methyl}-5-(5-oxo-4,5-dihydro-1,2,4-oxadiazol-3-yl)pyridine-3-sulfonamide | 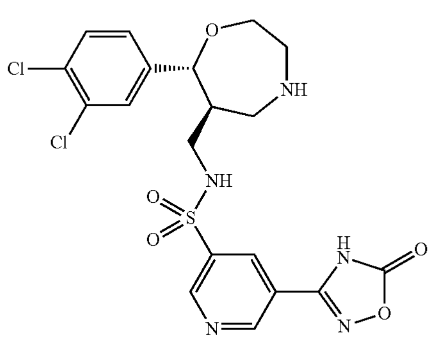 [SMILES: O=c1[nH]c(-c2cncc(S(=O)(=O)NC[C@@H]3CNCCO[C@H]3c3ccc(Cl)c(Cl)c3)c2)no1] | HCl | 500.2 |

TABLE 1-38-continued

| Ex. No. | IUPAC name | structure | salt | MS |
|---|---|---|---|---|
| 174 | N-{[(6R,7S)-7-(3,4-dichlorophenyl)-1,4-oxazepan-6-yl]methyl}sulfamide | 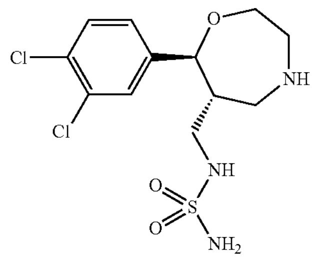 [SMILES: NS(=O)(=O)NC[C@H]1CNCCO[C@@H]1c1ccc(Cl)c(Cl)c1] | HCl | 354.2 |
| 175 | N-{[(6S,7R)-7-(3,4-dichlorophenyl)-1,4-oxazepan-6-yl]methyl}-N'-methoxysulfamide | 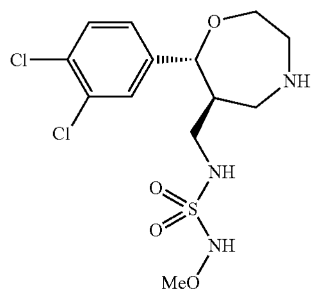 [SMILES: CONS(=O)(=O)NC[C@@H]1CNCCO[C@H]1c1ccc(Cl)c(Cl)c1] | HCl | 383.9 |

TABLE 1-39

| Ex. No. | IUPAC name | structure | salt | MS |
|---|---|---|---|---|
| 176 | 2-({[(6S,7R)-7-(3,4-dichlorophenyl)-1,4-oxazepan-6-yl]methyl}amino)pyridine-3-carboxylic acid | 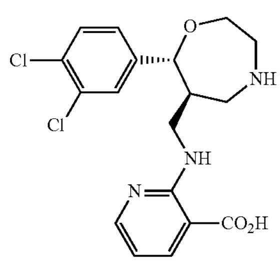 [SMILES: O=C(O)c1cccnc1NC[C@@H]1CNCCO[C@H]1c1ccc(Cl)c(Cl)c1] | HCl | 396.1 |
| 177 | N-{2-[(6R,7R)-7-(3,4-dichlorophenyl)-1,4-oxazepan-6-yl]ethyl}acetamide | 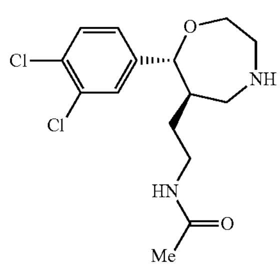 [SMILES: CC(=O)NCC[C@@H]1CNCCO[C@H]1c1ccc(Cl)c(Cl)c1] | HCl | 331.1 |
| 178 | (6S,7R)-7-(3,4-dichlorophenyl)-6-[(4-methyl-1H-pyrazol-1-yl)methyl]-1,4-oxazepane | 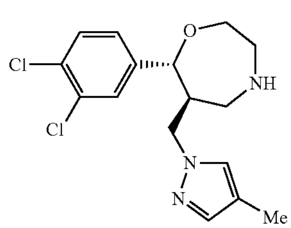 [SMILES: Cc1cnn(C[C@@H]2CNCCO[C@H]2c2ccc(Cl)c(Cl)c2)c1] | HCl | 340.0 |
| 179 | 1-{[(6S,7R)-7-(3,4-dichlorophenyl)-1,4-oxazepan-6-yl]methyl}-1H-pyrazole-3-carboxylic acid | | HCl | 370.3 |
| 180 | 1-{[(6S,7R)-7-(3,4-dichlorophenyl)-1,4-oxazepan-6-yl]methyl}-1H-pyrazole-4-carboxylic acid | | HCl | 370.0 |

TABLE 1-40

| Ex. No. | IUPAC name | structure | salt | MS |
|---|---|---|---|---|
| 181 | 1-{[(6S,7R)-7-(3,4-dichlorophenyl)-1,4-oxazepan-6-yl]methyl}-1H-pyrazole-5-carboxylic acid | 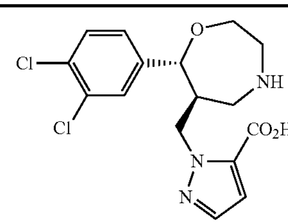 | HCl | 370.3 |

TABLE 1-40-continued

| Ex. No. | IUPAC name | structure | salt | MS |
|---|---|---|---|---|
| 182 | 1-{[(6S,7R)-7-(3,4-dichlorophenyl)-1,4-oxazepan-6-yl]methyl}-3-(trifluoromethyl)-1H-pyrazole-4-carboxylic acid | 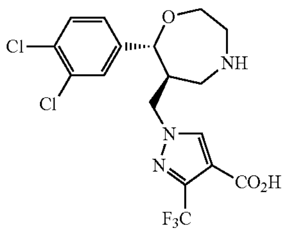 [SMILES: O=C(O)c1cn(C[C@@H]2CNCCO[C@H]2c2ccc(Cl)c(Cl)c2)nc1C(F)(F)F] | HCl | 437.9 |
| 183 | [1-{[(6S,7R)-7-(3,4-dichlorophenyl)-1,4-oxazepan-6-yl]methyl}-3-(trifluoromethyl)-1H-pyrazol-4-yl]methanol | 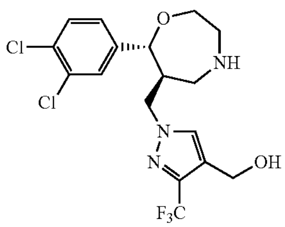 [SMILES: OCc1cn(C[C@@H]2CNCCO[C@H]2c2ccc(Cl)c(Cl)c2)nc1C(F)(F)F] | free amine | 424.0 |
| 184 | 1-{[(6S,7R)-7-(3,4-dichlorophenyl)-1,4-oxazepan-6-yl]methyl}-3-methyl-1H-pyrazole-5-carboxylic acid | 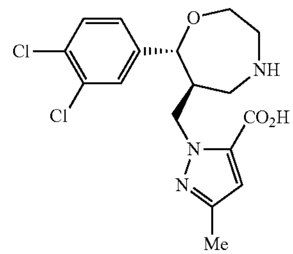 [SMILES: Cc1cc(C(=O)O)n(C[C@@H]2CNCCO[C@H]2c2ccc(Cl)c(Cl)c2)n1] | HCl | 384.2 |
| 185 | 5-cyclopropyl-1-{[(6S,7R)-7-(3,4-dichlorophenyl)-1,4-oxazepan-6-yl]methyl}-1H-pyrazole-3-carboxylic acid | 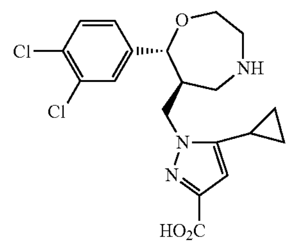 [SMILES: O=C(O)c1cc(C2CC2)n(C[C@@H]2CNCCO[C@H]2c2ccc(Cl)c(Cl)c2)n1] | HCl | 410.3 |

TABLE 1-41

| Ex. No. | IUPAC name | structure | salt | MS |
|---|---|---|---|---|
| 186 | 1-{[(6S,7R)-7-(3,4-dichlorophenyl)-1,4-oxazepan-6-yl]methyl}-5-(2-methoxyethoxy)-1H-pyrazole-3-carboxylic acid | 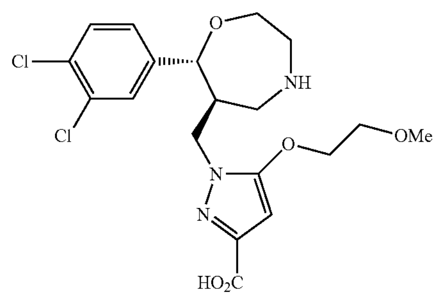 [SMILES: COCCOc1cc(C(=O)O)nn1C[C@@H]1CNCCO[C@H]1c1ccc(Cl)c(Cl)c1] | HCl | 444.2 |
| 187 | 1-{[(6S,7R)-7-(3,4-dichlorophenyl)-1,4-oxazepan-6-yl]methyl}-5-methyl-1H-pyrazole-3-carboxylic acid | 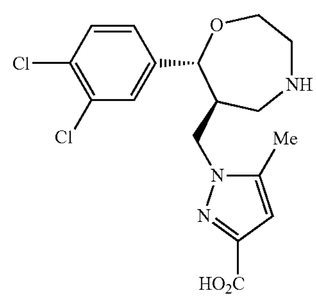 [SMILES: Cc1cc(C(=O)O)nn1C[C@@H]1CNCCO[C@H]1c1ccc(Cl)c(Cl)c1] | HCl | 384.2 |
| 188 | 3-tert-butyl-1-{[(6S,7R)-7-(3,4-dichlorophenyl)-1,4-oxazepan-6-yl]methyl}-1H-pyrazole-5-carboxylic acid | 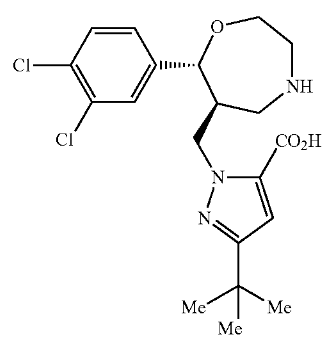 [SMILES: CC(C)(C)c1cc(C(=O)O)n(C[C@@H]2CNCCO[C@H]2c2ccc(Cl)c(Cl)c2)n1] | HCl | 426.2 |

TABLE 1-41-continued

| Ex. No. | IUPAC name | structure | salt | MS |
|---|---|---|---|---|
| 189 | 3-cyclopropyl-1-{[(6S,7R)-7-(3,4-dichlorophenyl)-1,4-oxazepan-6-yl]methyl}-1H-pyrazole-5-carboxylic acid | 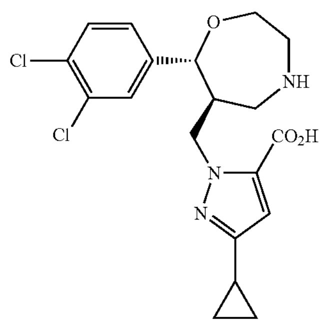 [SMILES: O=C(O)c1cc(C2CC2)nn1C[C@@H]1CNCCO[C@H]1c1ccc(Cl)c(Cl)c1] | HCl | 410.3 |

TABLE 1-42

| Ex. No. | IUPAC name | structure | salt | MS |
|---|---|---|---|---|
| 190 | 1-{[(6S,7R)-7-(3,4-dichlorophenyl)-1,4-oxazepan-6-yl]methyl}-3-(2-methoxyethoxy)-1H-pyrazole-5-carboxylic acid | 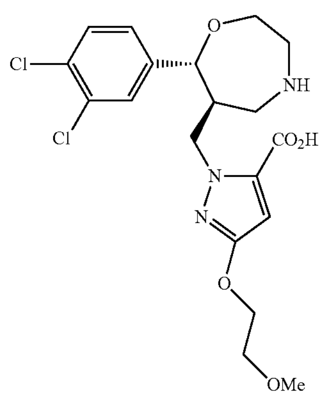 [SMILES: COCCOc1cc(C(=O)O)n(C[C@@H]2CNCCO[C@H]2c2ccc(Cl)c(Cl)c2)n1] | HCl | 444.2 |
| 191 | 3-{[(6R,7R)-7-(3,4-dichlorophenyl)-1,4-oxazepan-6-yl]methyl}-1-methyl-1H-pyrazole-4-carboxylic acid | 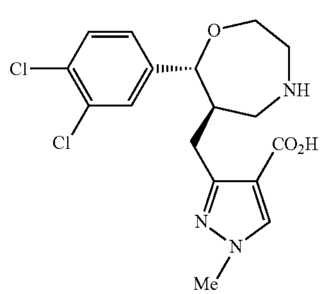 [SMILES: Cn1cc(C(=O)O)c(C[C@@H]2CNCCO[C@H]2c2ccc(Cl)c(Cl)c2)n1] | HCl | 384.2 |
| 192 | (6R,7R)-7-(3,4-dichlorophenyl)-6-[(5-methyl-1,2,4-oxadiazol-3-yl)methyl]-1,4-oxazepane | 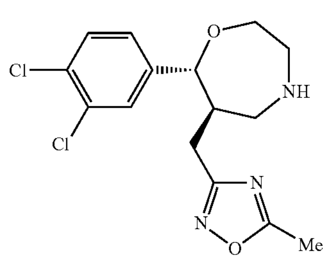 [SMILES: Cc1nc(C[C@@H]2CNCCO[C@H]2c2ccc(Cl)c(Cl)c2)no1] | HCl | 342.1 |

TABLE 1-42-continued

| Ex. No. | IUPAC name | structure | salt | MS |
|---|---|---|---|---|
| 193 | 3-{[(6R,7R)-7-(3,4-dichlorophenyl)-1,4-oxazepan-6-yl]methyl}-1,2,4-oxadiazol-5(4H)-one | 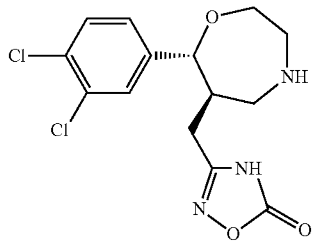 [SMILES: O=c1[nH]c(C[C@@H]2CNCCO[C@H]2c2ccc(Cl)c(Cl)c2)no1] | HCl | 344.0 |
| 194 | 2-{[(6R,7R)-7-(3,4-dichlorophenyl)-1,4-oxazepan-6-yl]methyl}-1,3-thiazole-4-carboxylic acid | 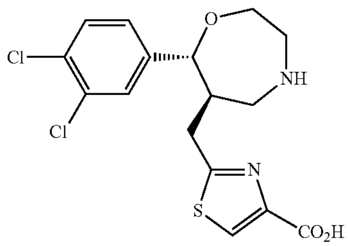 [SMILES: O=C(O)c1csc(C[C@@H]2CNCCO[C@H]2c2ccc(Cl)c(Cl)c2)n1] | HCl | 386.9 |

TABLE 1-43

| Ex. No. | IUPAC name | structure | salt | MS |
|---|---|---|---|---|
| 195 | 2-{[(6R,7R)-7-(3,4-dichlorophenyl)-1,4-oxazepan-6-yl]methyl}-1,3-thiazole-5-carboxylic acid | 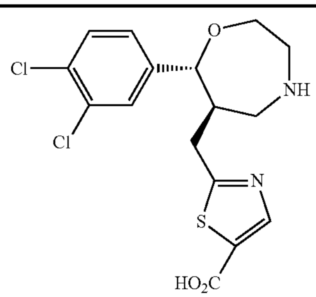 | HCl | 386.9 |
| 196 | 4-{[(6R,7R)-7-(3,4-dichlorophenyl)-1,4-oxazepan-6-yl]methyl}-2-methyl-1,3-thiazole-5-carboxylic acid | 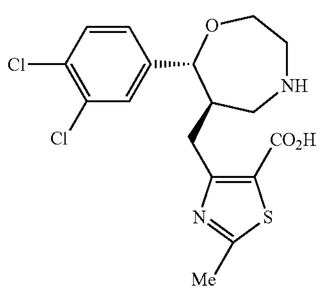 [SMILES: Cc1nc(C[C@@H]2CNCCO[C@H]2c2ccc(Cl)c(Cl)c2)c(C(=O)O)s1] | HCl | 401.2 |
| 197 | 2-{[(6R,7R)-7-(3,4-dichlorophenyl)-1,4-oxazepan-6-yl]methyl}-4-methyl-1,3-thiazole-5-carboxylic acid | 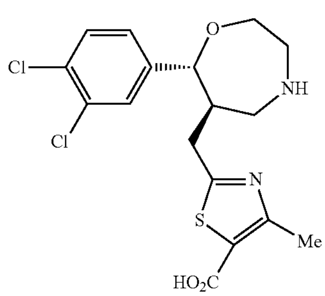 [SMILES: Cc1nc(C[C@@H]2CNCCO[C@H]2c2ccc(Cl)c(Cl)c2)sc1C(=O)O] | HCl | 401.0 |

TABLE 1-43-continued

| Ex. No. | IUPAC name | structure | salt | MS |
|---|---|---|---|---|
| 198 | (2-{[(6R,7R)-7-(3,4-dichlorophenyl)-1,4-oxazepan-6-yl]methyl}-1,3-thiazol-4-yl) acetic acid | 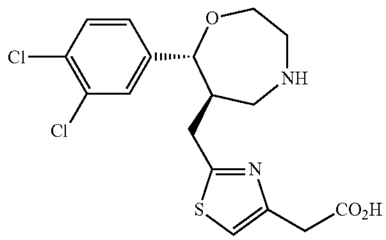 [SMILES: O=C(O)Cc1csc(C[C@@H]2CNCCO[C@H]2c2ccc(Cl)c(Cl)c2)n1] | HCl | 401.0 |
| 199 | 3-(2-{[(6R,7R)-7-(3,4-dichlorophenyl)-1,4-oxazepan-6-yl]methyl}-1,3-thiazol-4-yl)-1,2,4-oxadiazol-5(4H)-one | 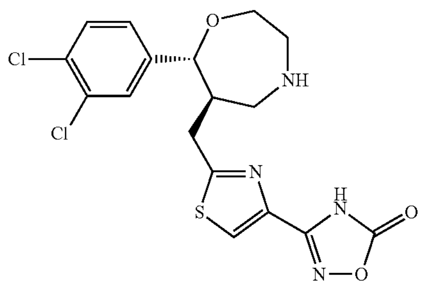 [SMILES: O=c1[nH]c(-c2csc(C[C@@H]3CNCCO[C@H]3c3ccc(Cl)c(Cl)c3)n2)no1] | HCl | 427.0 |

TABLE 1-44

| Ex. No. | IUPAC name | structure | salt | MS |
|---|---|---|---|---|
| 200 | (6R,7R)-7-(3,4-dichlorophenyl)-6-[(5-methyl-4H-1,2,4-triazol-3-yl)methyl]-1,4-oxazepane | 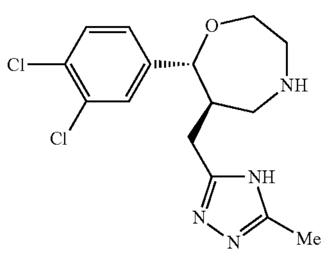 [SMILES: Cc1nnc(C[C@@H]2CNCCO[C@H]2c2ccc(Cl)c(Cl)c2)[nH]1] | HCl | 341.3 |
| 201 | 1-{[(6S,7R)-7-(3,4-dichlorophenyl)-1,4-oxazepan-6-yl]methyl}-5-methyl-1H-1,2,3-triazole-4-carboxylic acid | 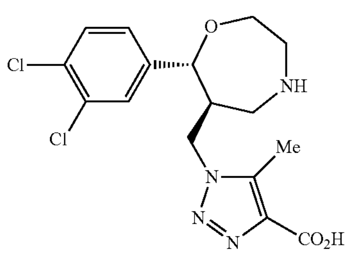 [SMILES: Cc1c(C(=O)O)nnn1C[C@@H]1CNCCO[C@H]1c1ccc(Cl)c(Cl)c1] | HCl | 385.3 |
| 202 | 1-{[(6S,7R)-7-(3,4-dichlorophenyl)-1,4-oxazepan-6-yl]methyl}-1H-indazole-3-carboxylic acid | 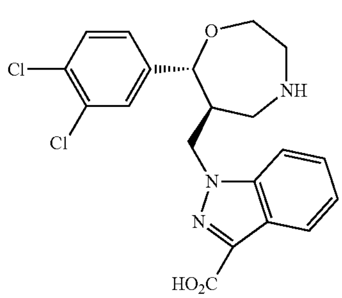 [SMILES: O=C(O)c1nn(C[C@@H]2CNCCO[C@H]2c2ccc(Cl)c(Cl)c2)c2ccccc12] | HCl | 420.1 |

TABLE 1-44-continued

| Ex. No. | IUPAC name | structure | salt | MS |
|---|---|---|---|---|
| 203 | 1-{[(6S,7R)-7-(3,4-dichlorophenyl)-1,4-oxazepan-6-yl]methyl}imidazolidine-2,4-dione | 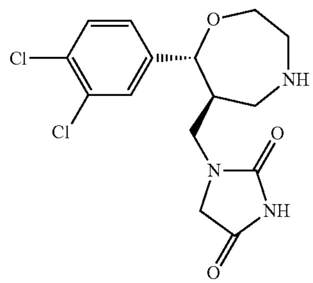 [SMILES: O=C1CN(C[C@@H]2CNCCO[C@H]2c2ccc(Cl)c(Cl)c2)C(=O)N1] | HCl | 358.0 |
| 204 | 1-{[(6S,7R)-7-(3,4-dichlorophenyl)-1,4-oxazepan-6-yl]methyl}-2-oxo-1,2-dihydropyridine-3-carbonitrile | 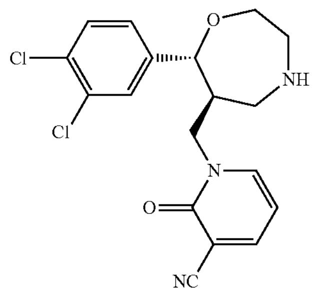 [SMILES: N#Cc1cccn(C[C@@H]2CNCCO[C@H]2c2ccc(Cl)c(Cl)c2)c1=O] | HCl | 378.1 |

TABLE 1-45

| Ex. No. | IUPAC name | structure | salt | MS |
|---|---|---|---|---|
| 205 | 1-{[(6S,7R)-7-(3,4-dichlorophenyl)-1,4-oxazepan-6-yl]methyl}-2-oxo-1,2-dihydropyridine-3-carboxylic acid | 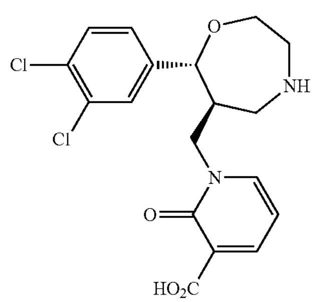 [SMILES: O=C(O)c1cccn(C[C@@H]2CNCCO[C@H]2c2ccc(Cl)c(Cl)c2)c1=O] | HCl | 397.1 |
| 206 | 1-{[(6S,7R)-7-(3,4-dichlorophenyl)-1,4-oxazepan-6-yl]methyl}-5-(5-oxo-4,5-dihydro-1,2,4-oxadiazol-3-yl)pyridin-2(1H)-one | 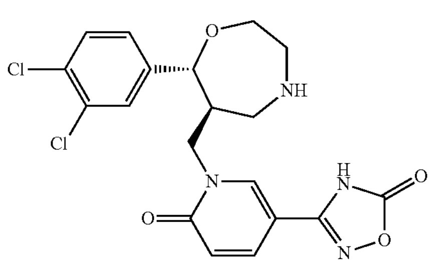 | HCl | 437.0 |

TABLE 1-45-continued

| Ex. No. | IUPAC name | structure | salt | MS |
|---|---|---|---|---|
| 207 | 1-{[(6S,7R)-7-(3,4-dichlorophenyl)-1,4-oxazepan-6-yl]methyl}-4-(5-oxo-4,5-dihydro-1,2,4-oxadiazol-3-yl)pyridin-2(1H)-one | 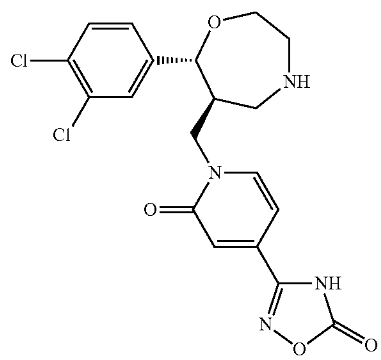 | HCl | 436.9 |
| 208 | 1-{[(6S,7R)-7-(3,4-dichlorophenyl)-1,4-oxazepan-6-yl]methyl}-3-(1H-tetrazol-5-yl)pyridin-2(1H)-one | 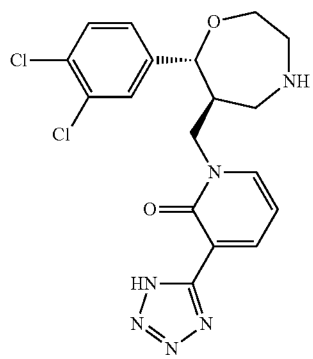 [SMILES: O=c1c(-c2nnn[nH]2)cccn1C[C@@H]1CNCCO[C@H]1c1ccc(Cl)c(Cl)c1] | HCl | 421.0 |

TABLE 1-46

| Ex. No. | IUPAC name | structure | salt | MS |
|---|---|---|---|---|
| 209 | 2-{[(6S,7R)-7-(3,4-dichlorophenyl)-1,4-oxazepan-6-yl]methyl}-4-(5-oxo-4,5-dihydro-1,2,4-oxadiazol-3-yl)pyridazin-3(2H)-one | 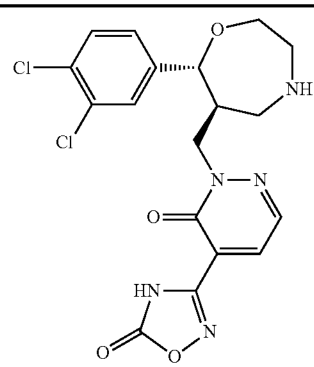 | HCl | 438.1 |
| 210 | 2-{[(6S,7R)-7-(3,4-dichlorophenyl)-1,4-oxazepan-6-yl]methyl}-5,6-dimethyl-3-oxo-2,3-dihydropyridazine-4-carbonitrile | 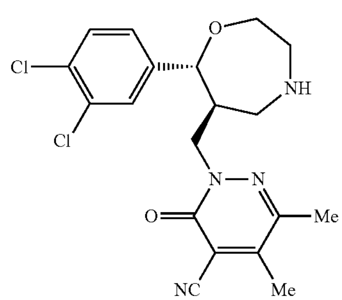 [SMILES: Cc1nn(C[C@@H]2CNCCO[C@H]2c2ccc(Cl)c(Cl)c2)c(=O)c(C#N)c1C] | HCl | 407.3 |

TABLE 1-46-continued

| Ex. No. | IUPAC name | structure | salt | MS |
|---|---|---|---|---|
| 211 | 2-{[(6S,7R)-7-(3,4-dichlorophenyl)-1,4-oxazepan-6-yl]methyl}-5,6-dimethyl-4-(5-oxo-4,5-dihydro-1,2,4-oxadiazol-3-yl)pyridazin-3(2H)-one | 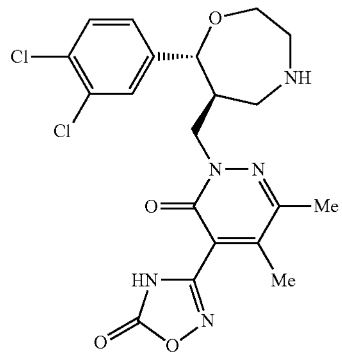 [SMILES: Cc1nn(C[C@@H]2CNCCO[C@H]2c2ccc(Cl)c(Cl)c2)c(=O)c(-c2noc(=O)[nH]2)c1C] | HCl | 464.2 |
| 212 | 3-[(6R,7R)-7-(3,4-dichlorophenyl)-1,4-oxazepan-6-yl]propan-1-ol | 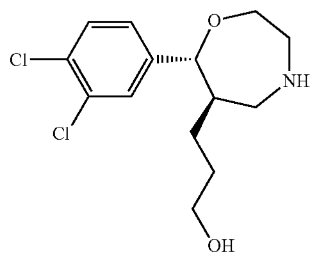 [SMILES: OCCC[C@@H]1CNCCO[C@H]1c1ccc(Cl)c(Cl)c1] | HCl | 304.3 |

TABLE 1-47

| Ex. No. | IUPAC name | structure | salt | MS |
|---|---|---|---|---|
| 213 | 1-{3-[(6R,7R)-7-(3,4-dichlorophenyl)-1,4-oxazepan-6-yl]propyl}-3-methyl-1H-pyrazole-5-carboxylic acid | 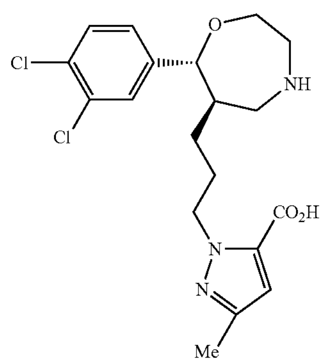 [SMILES: Cc1cc(C(=O)O)n(CCC[C@@H]2CNCCO[C@H]2c2ccc(Cl)c(Cl)c2)n1] | HCl | 412.3 |
| 214 | 1-{3-[(6R,7R)-7-(3,4-dichlorophenyl)-1,4-oxazepan-6-yl]propyl}-5-methyl-1H-pyrazole-3-carboxylic acid | 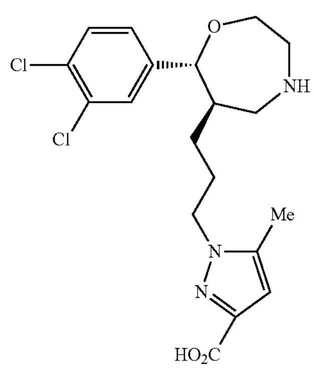 [SMILES: Cc1cc(C(=O)O)nn1CCC[C@@H]1CNCCO[C@H]1c1ccc(Cl)c(Cl)c1] | HCl | 412.3 |

TABLE 1-47-continued

| Ex. No. | IUPAC name | structure | salt | MS |
|---|---|---|---|---|
| 215 | 1-[(6S,7R)-7-(3,4-dichlorophenyl)-1,4-oxazepan-6-yl]-2,2,2-trifluoroethanol | 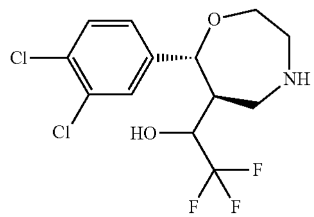 [SMILES: OC([C@@H]1CNCCO[C@H]1c1ccc(Cl)c(Cl)c1)C(F)(F)F] | HCl | 344.0 |
| 216 | 1-[(6R,7R)-7-(3,4-dichlorophenyl)-1,4-oxazepan-6-yl]ethanone | 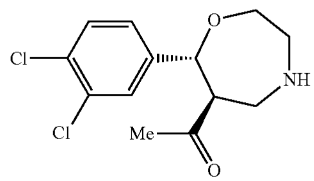 [SMILES: CC(=O)[C@@H]1CNCCO[C@H]1c1ccc(Cl)c(Cl)c1] | HCl | 288.2 |
| 217 | (6S,7R)-7-(3,4-dichlorophenyl)-1,4-oxazepane-6-carbonitrile | 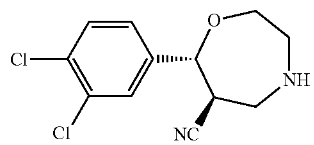 [SMILES: N#C[C@@H]1CNCCO[C@H]1c1ccc(Cl)c(Cl)c1] | HCl | 271.0 |

TABLE 1-48

| Ex. No. | IUPAC name | structure | salt | MS |
|---|---|---|---|---|
| 218 | (6R,7R)-7-(3,4-dichlorophenyl)-1,4-oxazepane-6-carboxylic acid | 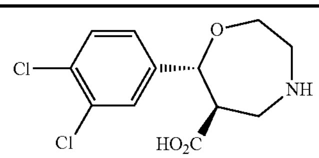 | HCl | 290.0 |
| 219 | (6R,7R)-7-(3,4-dichlorophenyl)-1,4-oxazepane-6-carboxamide | 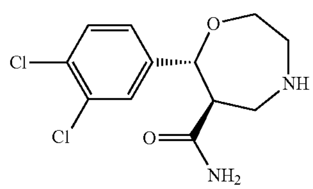 [SMILES: NC(=O)[C@@H]1CNCCO[C@H]1c1ccc(Cl)c(Cl)c1] | HCl | 289.0 |
| 220 | (6R,7R)-7-(3,4-dichlorophenyl)-N-methyl-1,4-oxazepane-6-carboxamide | 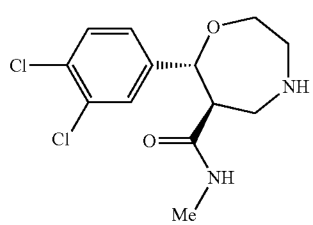 [SMILES: CNC(=O)[C@@H]1CNCCO[C@H]1c1ccc(Cl)c(Cl)c1] | HCl | 303.0 |
| 221 | (6R,7R)-7-(3,4-dichlorophenyl)-N,N-dimethyl-1,4-oxazepane-6-carboxamide | 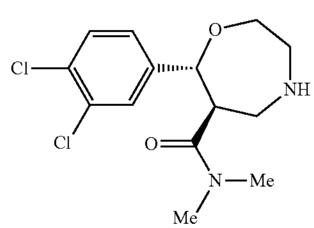 [SMILES: CN(C)C(=O)[C@@H]1CNCCO[C@H]1c1ccc(Cl)c(Cl)c1] | HCl | 317.3 |

TABLE 1-48-continued

| Ex. No. | IUPAC name | structure | salt | MS |
|---|---|---|---|---|
| 222 | (6R,7R)-7-(3,4-dichlorophenyl)-N-(2-hydroxy-2-methylpropyl)-1,4-oxazepane-6-carboxamide | 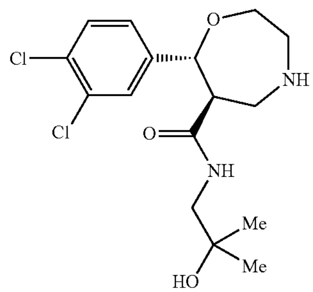 [SMILES: CC(C)(O)CNC(=O)[C@@H]1CNCCO[C@H]1c1ccc(Cl)c(Cl)c1] | HCl | 361.0 |

TABLE 1-49

| Ex. No. | IUPAC name | structure | salt | MS |
|---|---|---|---|---|
| 223 | (6R,7R)-7-(3,4-dichlorophenyl)-N-[2-(methylsulfonyl)ethyl]-1,4-oxazepane-6-carboxamide | 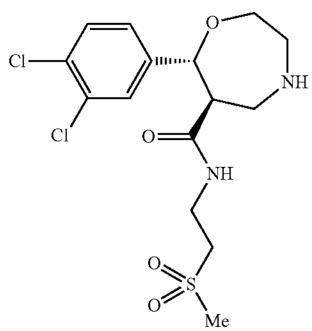 [SMILES: CS(=O)(=O)CCNC(=O)[C@@H]1CNCCO[C@H]1c1ccc(Cl)c(Cl)c1] | HCl | 395.0 |
| 224 | 3-({[(6R,7R)-7-(3,4-dichlorophenyl)-1,4-oxazepan-6-yl]carbonyl}amino)benzoic acid | 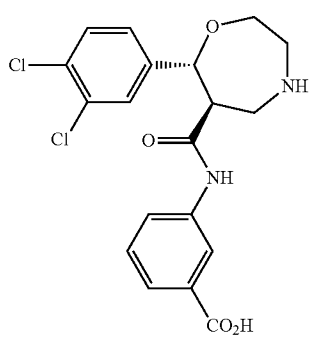 [SMILES: O=C(O)c1cccc(NC(=O)[C@@H]2CNCCO[C@H]2c2ccc(Cl)c(Cl)c2)c1] | HCl | 409.0 |
| 225 | (6R,7R)-7-(3,4-dichlorophenyl)-N-(methylsulfonyl)-1,4-oxazepane-6-carboxamide | 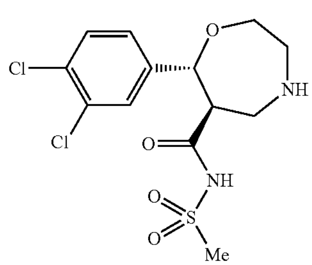 [SMILES: CS(=O)(=O)NC(=O)[C@@H]1CNCCO[C@H]1c1ccc(Cl)c(Cl)c1] | HCl | 367.0 |

TABLE 1-49-continued

| Ex. No. | IUPAC name | structure | salt | MS |
|---|---|---|---|---|
| 226 | (6R,7R)-7-(3,4-dichlorophenyl)-N-methyl-N-(methylsulfonyl)-1,4-oxazepane-6-carboxamide | 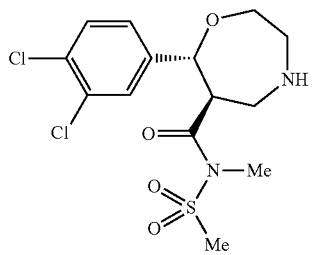 [SMILES: CN(C(=O)[C@@H]1CNCCO[C@H]1c1ccc(Cl)c(Cl)c1)S(C)(=O)=O] | HCl | 381.1 |

TABLE 1-50

| Ex. No. | IUPAC name | structure | salt | MS |
|---|---|---|---|---|
| 227 | (6R,7R)-7-(3,4-dichlorophenyl)-N-{[4-(difluoromethoxy)-phenyl]sulfonyl}-1,4-oxazepane-6-carboxamide | 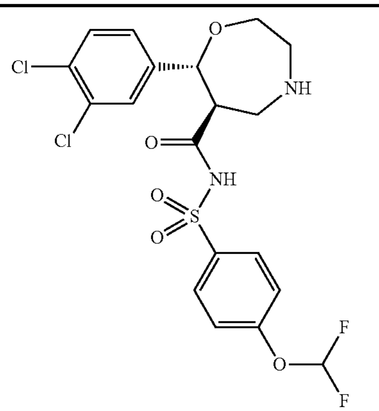 | HCl | 495.2 |
| 228 | (6R,7R)-7-(3,4-dichlorophenyl)-N-{[4-(trifluoromethyl)-phenyl]sulfonyl}-1,4-oxazepane-6-carboxamide | 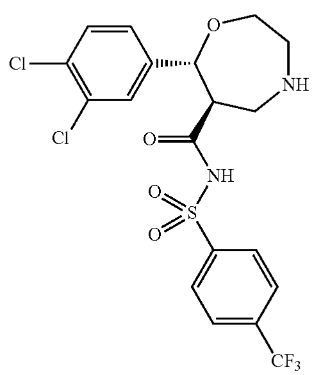 [SMILES: O=C(NS(=O)(=O)c1ccc(C(F)(F)F)cc1)[C@@H]1CNCCO[C@H]1c1ccc(Cl)c(Cl)c1] | HCl | 496.9 |
| 229 | 2-[(6R,7R)-7-(3,4-dichlorophenyl)-1,4-oxazepan-6-yl]-1,3-thiazole-4-carboxylic acid | 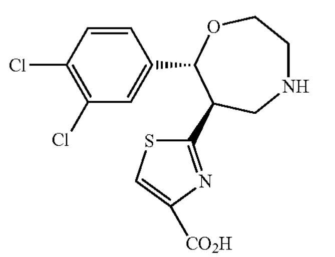 [SMILES: O=C(O)c1csc([C@@H]2CNCCO[C@H]2c2ccc(Cl)c(Cl)c2)n1] | HCl | 373.0 |
| 230 | (6RS,7SR)-7-(3,4-dichlorophenyl)-1,4-oxazepan-6-ol | 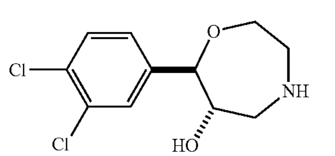 | HCl | 262.1 |

TABLE 1-50-continued

| Ex. No. | IUPAC name | structure | salt | MS |
|---|---|---|---|---|
| 231 | 6-{[(6RS,7SR)-7-(3,4-dichlorophenyl)-1,4-oxazepan-6-yl)oxy)pyridine-2-carboxylic acid | 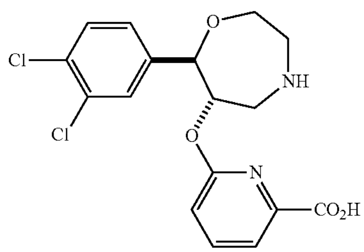 | HCl | 383.1 |

TABLE 1-51

| Ex. No. | IUPAC name | structure | salt | MS |
|---|---|---|---|---|
| 232 | 6-{[(6RS,7SR)-7-(3,4-dichlorophenyl)-1,4-oxazepan-6-yl]oxy}pyridine-2-carbonitrile | 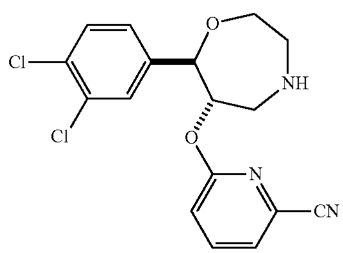 | HCl | 364.1 |
| 233 | 2-{[(6RS,7SR)-7-(3,4-dichlorophenyl)-1,4-oxazepan-6-yl]oxy}pyridine-3-carbonitrile | 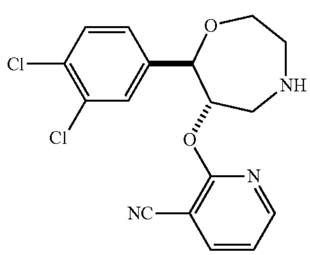 | HCl | 364.1 |
| 234 | 2-{[(6RS,7SR)-7-(3,4-dichlorophenyl)-1,4-oxazepan-6-yl]oxy}pyridine-3-carboxamide | 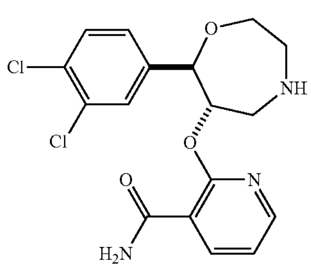 | HCl | 382.2 |
| 235 | 3-(6-{[(6RS,7SR)-7-(3,4-dichlorophenyl)-1,4-oxazepan-6-yl]oxy}pyridin-2-yl)1,2,4-oxadiazol-5(4H)-one | 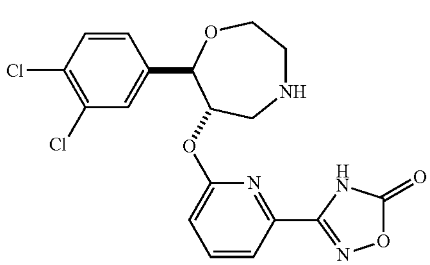 | HCl | 423.1 |

TABLE 1-51-continued

| Ex. No. | IUPAC name | structure | salt | MS |
|---|---|---|---|---|
| 236 | 3-(2-{[(6RS,7SR)-7-(3,4-dichlorophenyl)-1,4-oxazepan-6-yl]oxy}pyridin-3-yl)-1,2,4-oxadiazol-5(4H)-one | 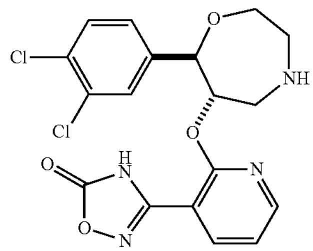 | HCl | 423.1 |
| 237 | (6R,7S)-7-(3,4-dichlorophenyl)-1,4-oxazepan-6-amine | 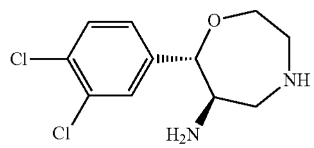 [SMILES: N[C@@H]1CNCCO[C@H]1c1ccc(Cl)c(Cl)c1] | 2HCl | 261.2 |

TABLE 1-52

| Ex. No. | IUPAC name | structure | salt | MS |
|---|---|---|---|---|
| 238 | (6R,7S)-7-(3,4-dichlorophenyl)-N,N-dimethyl-1,4-oxazepan-6-amine | 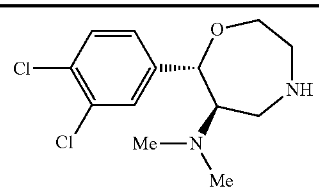 | 2HCl | 289.0 |
| 239 | (6R,7S)-N-benzyl-7-(3,4-dichlorophenyl)-1,4-oxazepan-6-amine | 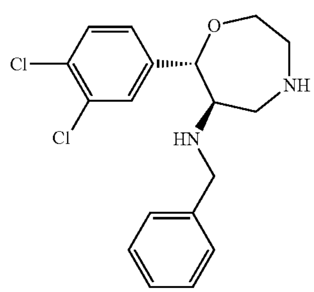 [SMILES: Clc1ccc([C@@H]2OCCNC[C@H]2NCc2ccccc2)cc1Cl] | HCl | 351.1 |
| 240 | N-[(6S,7R)-7-(3,4-dichlorophenyl)-1,4-oxazepan-6-yl]acetamide | 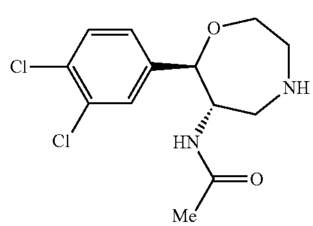 [SMILES: CC(=O)N[C@H]1CNCCO[C@@H]1c1ccc(Cl)c(Cl)c1] | HCl | 303.2 |
| 241 | N-[(6R,7S)-7-(3,4-dichlorophenyl)-1,4-oxazepan-6-yl]propanamide | 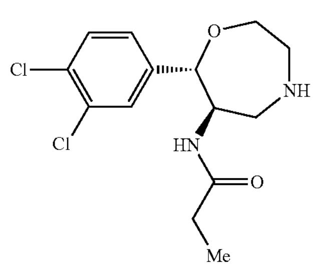 [SMILES: CCC(=O)N[C@@H]1CNCCO[C@H]1c1ccc(Cl)c(Cl)c1] | HCl | 317.0 |

TABLE 1-52-continued

| Ex. No. | IUPAC name | structure | salt | MS |
| --- | --- | --- | --- | --- |
| 242 | N-[(6R,7S)-7-(3,4-dichlorophenyl)-1,4-oxazepan-6-yl]-cyclopropanecarboxamide | 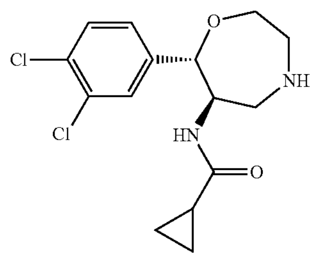 [SMILES: O=C(N[C@@H]1CNCCO[C@H]1c1ccc(Cl)c(Cl)c1)C1CC1] | HCl | 329.1 |

TABLE 1-53

| Ex. No. | IUPAC name | structure | salt | MS |
| --- | --- | --- | --- | --- |
| 243 | N-[(6R,7S)-7-(3,4-dichlorophenyl)-1,4-oxazepan-6-yl]-2,2-difluoroacetamide | 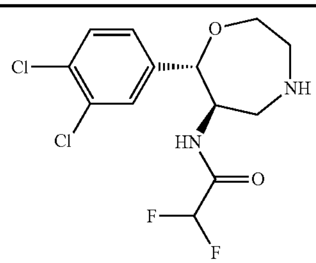 | free amine | 339.2 |
| 244 | N-[(6R,7S)-7-(3,4-dichlorophenyl)-1,4-oxazepan-6-yl]-2-hydroxyacetamide | 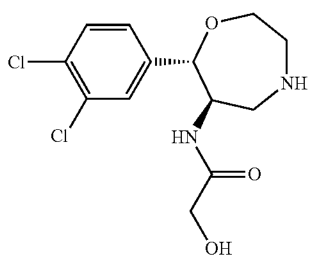 [SMILES: O=C(CO)N[C@@H]1CNCCO[C@H]1c1ccc(Cl)c(Cl)c1] | HCl | 319.1 |
| 245 | N-[(6R,7S)-7-(3,4-dichlorophenyl)-1,4-oxazepan-6-yl]-2-methoxyacetamide | 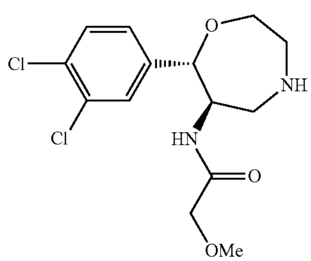 | HCl | 333.1 |
| 246 | 3-[2-({[(6S,7R)-7-(3,4-dichlorophenyl)-1,4-oxazepan-6-yl]methyl}amino)-2-oxoethoxy]benzoic acid | 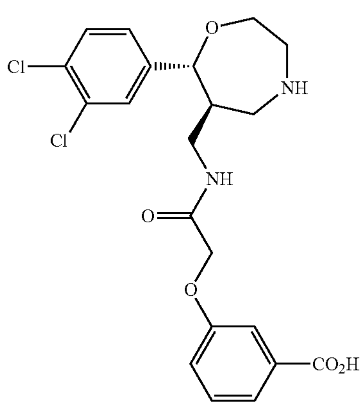 [SMILES: O=C(COc1cccc(C(=O)O)c1)NC[C@@H]1CNCCO[C@H]1c1ccc(Cl)c(Cl)c1] | HCl | 453.1 |

TABLE 1-53-continued

| Ex. No. | IUPAC name | structure | salt | MS |
|---|---|---|---|---|
| 247 | N-[(6R,7S)-7-(3,4-dichlorophenyl)-1,4-oxazepan-6-yl]-2-phenylacetamide | 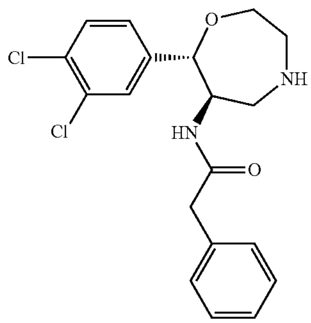 [SMILES: O=C(Cc1ccccc1)N[C@@H]1CNCCO[C@H]1c1ccc(Cl)c(Cl)c1] | HCl | 379.1 |

TABLE 1-54

| Ex. No. | IUPAC name | structure | salt | MS |
|---|---|---|---|---|
| 248 | N-[(6R,7S)-7-(3,4-dichlorophenyl)-1,4-oxazepan-6-yl]-2-[3-(5-oxo-4,5-dihydro-1,2,4-oxadiazol-3-yl)phenyl]acetamide | 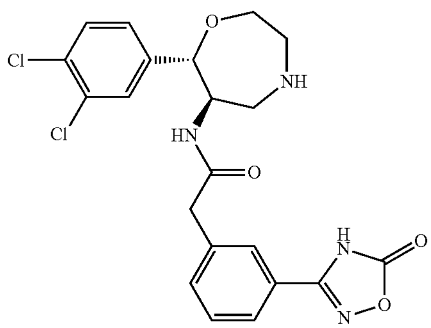 [SMILES: O=C(Cc1cccc(-c2noc(=O)[nH]2)c1)N[C@@H]1CNCCO[C@H]1c1ccc(Cl)c(Cl)c1] | HCl | 463.1 |
| 249 | N-[(6R,7S)-7-(3,4-dichlorophenyl)-1,4-oxazepan-6-yl]-2-[4-(5-oxo-4,5-dihydro-1,2,4-oxadiazol-3-yl)phenyl]acetamide | 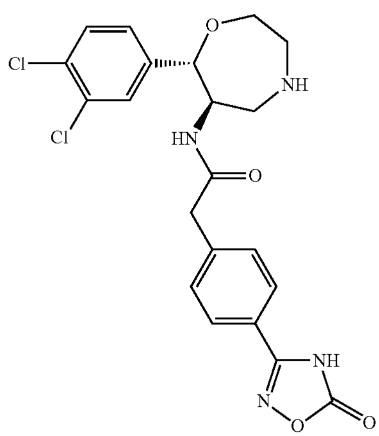 [SMILES: O=C(Cc1ccc(-c2noc(=O)[nH]2)cc1)N[C@@H]1CNCCO[C@H]1c1ccc(Cl)c(Cl)c1] | HCl | 463.1 |
| 250 | N-[(6R,7S)-7-(3,4-dichlorophenyl)-1,4-oxazepan-6-yl]-2-(1H-1,2,4-triazol-1-yl)acetamide | 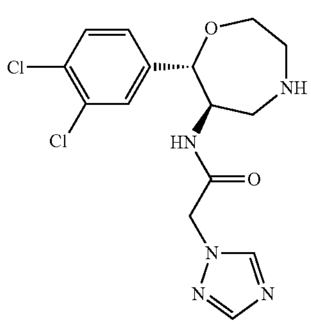 [SMILES: O=C(Cn1cncn1)N[C@@H]1CNCCO[C@H]1c1ccc(Cl)c(Cl)c1] | 3HCl | 370.0 |

TABLE 1-54-continued

| Ex. No. | IUPAC name | structure | salt | MS |
|---|---|---|---|---|
| 251 | N-[(6R,7S)-7-(3,4-dichlorophenyl)-1,4-oxazepan-6-yl]-2-(5-oxo-4,5-dihydro-1,2,4-oxadiazol-3-yl)acetamide | 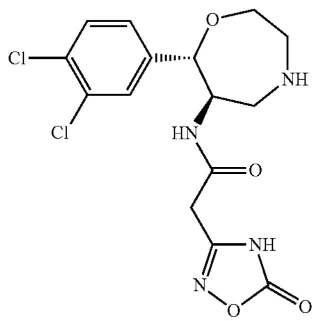 [SMILES: O=C(Cc1noc(=O)[nH]1)N[C@@H]1CNCCO[C@H]1c1ccc(Cl)c(Cl)c1] | HCl | 386.9 |

TABLE 1-55

| Ex. No. | IUPAC name | structure | salt | MS |
|---|---|---|---|---|
| 252 | N-[(6R,7S)-7-(3,4-dichlorophenyl)-1,4-oxazepan-6-yl]benzamide | 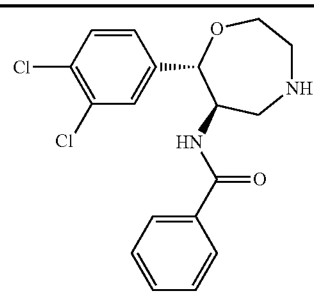 | HCl | 365.0 |
| 253 | N-[(6R,7S)-7-(3,4-dichlorophenyl)-1,4-oxazepan-6-yl]-N-methylbenzamide | 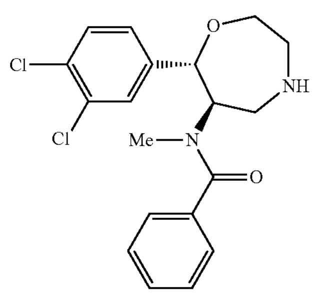 [SMILES: CN(C(=O)c1ccccc1)[C@@H]1CNCCO[C@H]1c1ccc(Cl)c(Cl)c1] | HCl | 379.3 |
| 254 | 2-{[(6R,7S)-7-(3,4-dichlorophenyl)-1,4-oxazepan-6-yl]carbamoyl}benzoic acid | 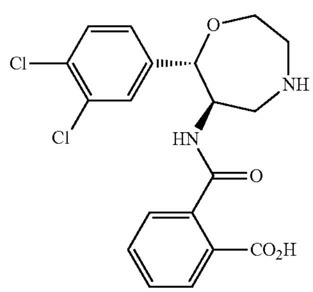 [SMILES: O=C(O)c1ccccc1C(=O)N[C@@H]1CNCCO[C@H]1c1ccc(Cl)c(Cl)c1] | HCl | 409.1 |

TABLE 1-55-continued

| Ex. No. | IUPAC name | structure | salt | MS |
|---|---|---|---|---|
| 255 | 3-{[(6R,7S)-7-(3,4-dichlorophenyl)-1,4-oxazepan-6-yl]carbamoyl}benzoic acid | 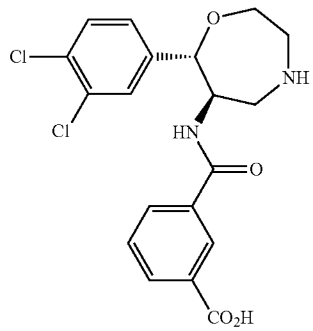 [SMILES: O=C(O)c1cccc(C(=O)N[C@@H]2CNCCO[C@H]2c2ccc(Cl)c(Cl)c2)c1] | HCl | 409.0 |

TABLE 1-56

| Ex. No. | IUPAC name | structure | salt | MS |
|---|---|---|---|---|
| 256 | 4-{[(6R,7S)-7-(3,4-dichlorophenyl)-1,4-oxazepan-6-yl]carbamoyl}benzoic acid | 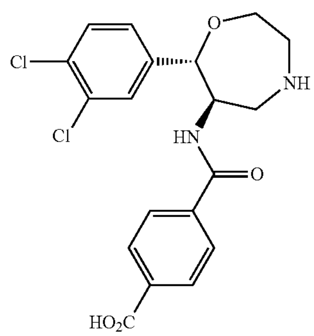 [SMILES: O=C(O)c1ccc(C(=O)N[C@@H]2CNCCO[C@H]2c2ccc(Cl)c(Cl)c2)cc1] | HCl | 409.1 |
| 257 | ethyl 2-{[(6R,7S)-7-(3,4-dichlorophenyl)-1,4-oxazepan-6-yl]carbamoyl}benzoate | 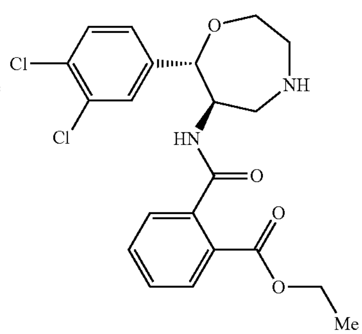 [SMILES: CCOC(=O)c1ccccc1C(=O)N[C@@H]1CNCCO[C@H]1c1ccc(Cl)c(Cl)c1] | HCl | 437.3 |
| 258 | 2-cyano-N-[(6R,7S)-(3,4-dichlorophenyl)-1,4-oxazepan-6-yl]benzamide | 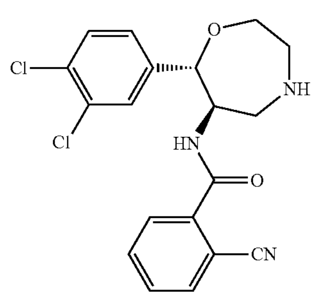 [SMILES: N#Cc1ccccc1C(=O)N[C@@H]1CNCCO[C@H]1c1ccc(Cl)c(Cl)c1] | HCl | 390.1 |

TABLE 1-56-continued

| Ex. No. | IUPAC name | structure | salt | MS |
|---|---|---|---|---|
| 259 | N-[(6R,7S)-7-(3,4-dichlorophenyl)-1,4-oxazepan-6-yl]-2-[(methylsulfonyl)amino]benzamide | 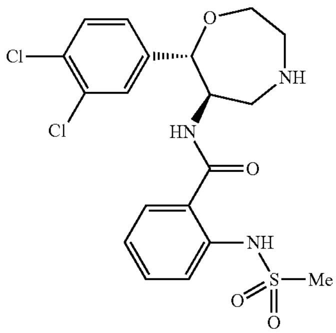 [SMILES: CS(=O)(=O)Nc1ccccc1C(=O)N[C@@H]1CNCCO[C@H]1c1ccc(Cl)c(Cl)c1] | HCl | 458.0 |

TABLE 1-57

| Ex. No. | IUPAC name | structure | salt | MS |
|---|---|---|---|---|
| 260 | N-[(6R,7S)-7-(3,4-dichlorophenyl)-1,4-oxazepan-6-yl]-2-(5-oxo-4,5-dihydro-1,2,4-oxadiazol-3-yl)benzamide | 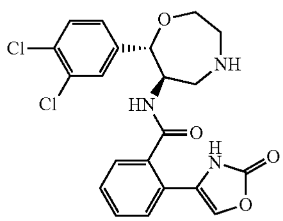 [SMILES: O=C(N[C@@H]1CNCCO[C@H]1c1ccc(Cl)c(Cl)c1)c1ccccc1-c1coc(=O)[nH]1] | HCl | 449.0 |
| 261 | N-[(6R,7S)-7-(3,4-dichlorophenyl)-1,4-oxazepan-6-yl]-1,3-oxazole-5-carboxamide | 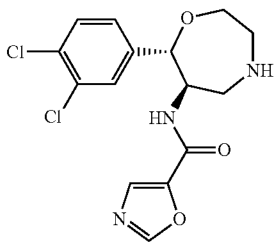 [SMILES: O=C(N[C@@H]1CNCCO[C@H]1c1ccc(Cl)c(Cl)c1)c1cnco1] | HCl | 356.0 |
| 262 | 1-[(6R,7S)-7-(3,4-dichlorophenyl)-1,4-oxazepan-6-yl]urea | 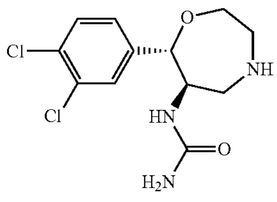 [SMILES: NC(=O)N[C@@H]1CNCCO[C@H]1c1ccc(Cl)c(Cl)c1] | HCl | 304.0 |
| 263 | 1-[(6R,7S)-7-(3,4-dichlorophenyl)-1,4-oxazepan-6-yl]-3-methylurea | 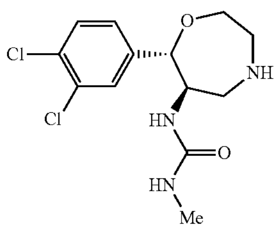 [SMILES: CNC(=O)N[C@@H]1CNCCO[C@H]1c1ccc(Cl)c(Cl)c1] | HCl | 318.1 |
| 264 | N-[(6R,7S)-7-(3,4-dichlorophenyl)-1,4-oxazepan-6-yl]morpholine-4-carboxamide | | HCl | 374.0 |

TABLE 1-58

| Ex. No. | IUPAC name | structure | salt | MS |
|---|---|---|---|---|
| 265 | N-[(6R,7S)-7-(3,4-dichlorophenyl)-1,4-oxazepan-6-yl]methanesulfonamide | 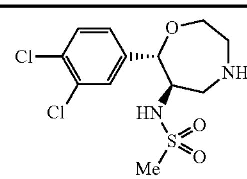 | HCl | 339.1 |
| 266 | N-[(6S,7R)-7-(3,4-dichlorophenyl)-1,4-oxazepan-6-yl]methanesulfonamide | 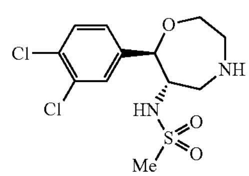 [SMILES: CS(=O)(=O)N[C@H]1CNCCO[C@@H]1c1ccc(Cl)c(Cl)c1] | HCl | 339.2 |
| 267 | N-[(6R,7S)-7-(3,4-dichlorophenyl)-1,4-oxazepan-6-yl]ethanesulfonamide | 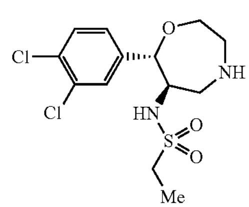 [SMILES: CCS(=O)(=O)N[C@@H]1CNCCO[C@H]1c1ccc(Cl)c(Cl)c1] | HCl | 353.0 |

TABLE 1-58-continued

| Ex. No. | IUPAC name | structure | salt | MS |
|---|---|---|---|---|
| 268 | N-[(6R,7S)-7-(3,4-dichlorophenyl)-1,4-oxazepan-6-yl]-cyclopropane-sulfonamide | 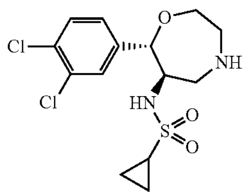 [SMILES: O=S(=O)(N[C@@H]1CNCCO[C@H]1c1ccc(Cl)c(Cl)c1)C1CC1] | HCl | 365.0 |
| 269 | N-[(6R,7S)-7-(3,4-dichlorophenyl)-1,4-oxazepan-6-yl]benzenesulfonamide | 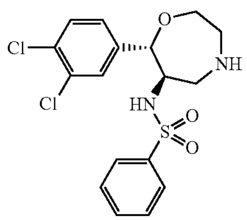 [SMILES: O=S(=O)(N[C@@H]1CNCCO[C@H]1c1ccc(Cl)c(Cl)c1)c1ccccc1] | HCl | 401.0 |

TABLE 1-59

| Ex. No. | IUPAC name | structure | salt | MS |
|---|---|---|---|---|
| 270 | N-[(6R,7S)-7-(3,4-dichlorophenyl)-1,4-oxazepan-6-yl]pyridine-3-sulfonamide | 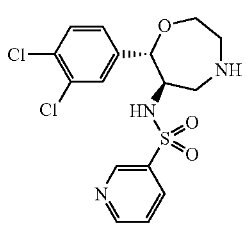 [SMILES: O=S(=O)(N[C@@H]1CNCCO[C@H]1c1ccc(Cl)c(Cl)c1)c1cccnc1] | 3HCl | 402.1 |
| 271 | N-[(6S,7R)-7-(3,4-dichlorophenyl)-1,4-oxazepan-6-yl]sulfamide | 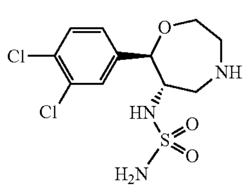 [SMILES: NS(=O)(=O)N[C@H]1CNCCO[C@@H]1c1ccc(Cl)c(Cl)c1] | HCl | 340.1 |
| 272 | N-[(6R,7S)-7-(3,4-dichlorophenyl)-1,4-oxazepan-6-yl]-N-methylsulfamide | 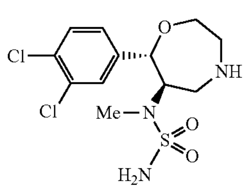 [SMILES: CN([C@@H]1CNCCO[C@H]1c1ccc(Cl)c(Cl)c1)S(N)(=O)=O] | HCl | 354.2 |
| 273 | N-[(6R,7S)-7-(3,4-dichlorophenyl)-1,4-oxazepan-6-yl]-N'-methylsulfamide | 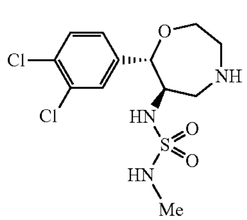 [SMILES: CNS(=O)(=O)N[C@@H]1CNCCO[C@H]1c1ccc(Cl)c(Cl)c1] | HCl | 354.1 |

TABLE 1-59-continued

| Ex. No. | IUPAC name | structure | salt | MS |
|---|---|---|---|---|
| 274 | N-[(6R,7S)-7-(3,4-dichlorophenyl)-1,4-oxazepan-6-yl]-N'-ethylsulfamide | 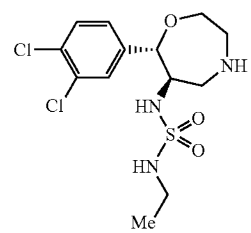 [SMILES: CCNS(=O)(=O)N[C@@H]1CNCCO[C@H]1c1ccc(Cl)c(Cl)c1] | HCl | 368.0 |

TABLE 1-60

| Ex. No. | IUPAC name | structure | salt | MS |
|---|---|---|---|---|
| 275 | N-cyclopropyl-N'-[(6R,7S)-7-(3,4-dichlorophenyl)-1,4-oxazepan-6-yl]sulfamide | 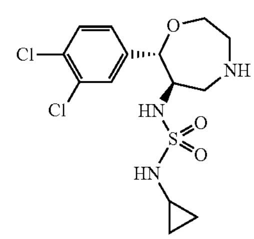 [SMILES: O=S(=O)(NC1CC1)N[C@@H]1CNCCO[C@H]1c1ccc(Cl)c(Cl)c1] | HCl | 380.0 |
| 276 | 1-[(6R,7S)-7-(3,4-dichlorophenyl)-1,4-oxazepan-6-yl]imidazolidine-2,4-dione | 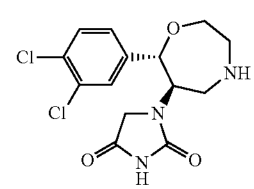 [SMILES: O=C1CN([C@@H]2CNCCO[C@H]2c2ccc(Cl)c(Cl)c2)C(=O)N1] | HCl | 344.3 |
| 277 | 3-[(6R,7S)-7-(3,4-dichlorophenyl)-1,4-oxazepan-6-yl]imidazolidine-2,4-dione | 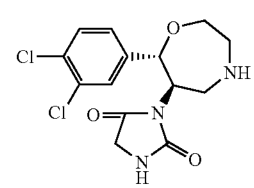 [SMILES: O=C1CNC(=O)N1[C@@H]1CNCCO[C@H]1c1ccc(Cl)c(Cl)c1] | HCl | 344.3 |
| 278 | [(6R,7RS)-7-(3-chloro-4-fluorophenyl)-1,4-oxazepan-6-yl]methanol | 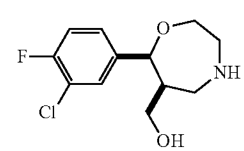 | HCl | 260.3 |
| 279 | N-{[(6RS,7RS)-7-(3-chloro-4-fluorophenyl)-1,4-oxazepan-6-yl]methyl}acetamide | 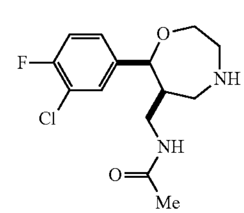 | HCl | 301.3 |

TABLE 1-61

| Ex. No. | IUPAC name | structure | salt | MS |
|---|---|---|---|---|
| 280 | 1-{[(6RS,7RS)-7-(3-chloro-4-fluoro-phenyl)-1,4-oxazepan-6-yl]methyl}urea | 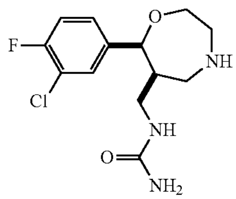 | HCl | 302.3 |
| 281 | (6RS,7SR)-7-(3-chloro-4-fluorophenyl)-6-[(methylsulfonyl)-methyl]-1,4-oxazepane | 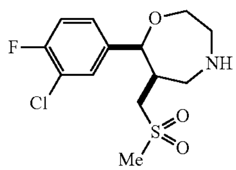 | HCl | 322.3 |
| 282 | N-{[(6RS,7RS)-7-(3-chloro-4-fluoro-phenyl)-1,4-oxazepan-6-yl]methyl}-methanesulfonamide | 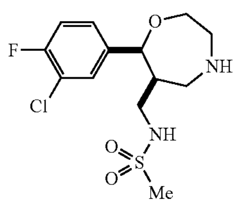 | HCl | 337.3 |
| 283 | N-{[(6RS,7RS)-7-(3-chloro-4-fluorophenyl)-1,4-oxazepan-6-yl]methyl}sulfonamide | 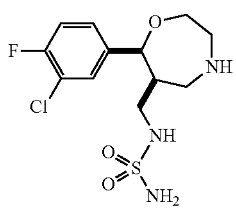 | HCl | 338.3 |
| 284 | [(6S,7R)-7-(3-chloro-4-fluorophenyl)-1,4-oxazepan-6-yl]methanol | 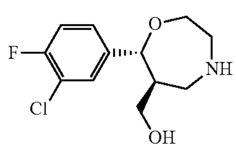 [SMILES: OC[C@@H]1CNCCO[C@H]1c1ccc(F)c(Cl)c1] | fumarate | 260.3 |
| 285 | [(6R,7S)-7-(3-chloro-4-fluorophenyl)-1,4-oxazepan-6-yl]methanol | 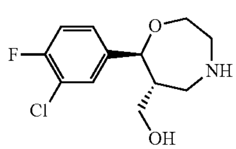 [SMILES: OC[C@H]1CNCCO[C@@H]1c1ccc(F)c(Cl)c1] | 1/2 fumarate | 260.3 |

TABLE 1-62

| Ex. No. | IUPAC name | structure | salt | MS |
|---|---|---|---|---|
| 286 | N-{[(6RS,7SR)-7-(3-chloro-4-fluorophenyl)-1,4-oxazepan-6-yl]methyl}acetamide | | HCl | 301.4 |
| 287 | N-{[(6S,7R)-7-(3-chloro-4-fluorophenyl)-1,4-oxazepan-6-yl]methyl}acetamide | 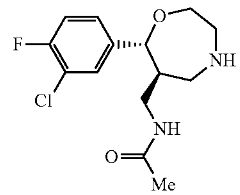 [SMILES: CC(=O)NC[C@@H]1CNCCO[C@H]1c1ccc(F)c(Cl)c1] | 1/2 fumarate | 301.1 |
| 288 | N-{[(6R,7S)-7-(3-chloro-4-fluorophenyl)-1,4-oxazepan-6-yl]methyl}acetamide | 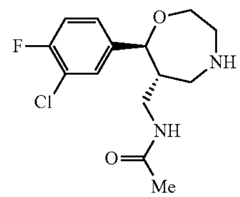 [SMILES: CC(=O)NC[C@H]1CNCCO[C@@H]1c1ccc(F)c(Cl)c1] | 1/2 fumarate | 301.0 |
| 289 | 1-{[(6S,7R)-7-(3-chloro-4-fluorophenyl)-1,4-oxazepan-6-yl]methyl}urea | 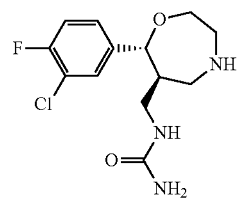 [SMILES: NC(=O)NC[C@@H]1CNCCO[C@H]1c1ccc(F)c(Cl)c1] | fumarate | 302.0 |
| 290 | 1-{[(6R,7S)-7-(3-chloro-4-fluorophenyl)-1,4-oxazepan-6-yl]methyl}urea | 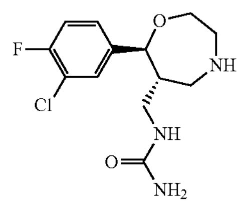 [SMILES: NC(=O)NC[C@H]1CNCCO[C@@H]1c1ccc(F)c(Cl)c1] | fumarate | 302.0 |
| 291 | (6R,7R)-7-(3-chloro-4-fluorophenyl)-6-[(methylsulfonyl)-methyl]-1,4-oxazepan | 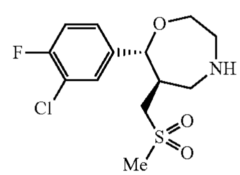 [SMILES: CS(=O)(=O)C[C@@H]1CNCCO[C@H]1c1ccc(F)c(Cl)c1] | HCl | 322.0 |

TABLE 1-63

| Ex. No. | IUPAC name | structure | salt | MS |
|---|---|---|---|---|
| 292 | (6S,7S)-7-(3-chloro-4-fluorophenyl)-6-[(methylsulfonyl)-methyl]-1,4-oxazepane | 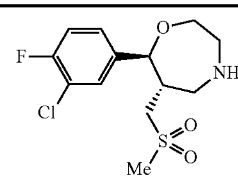 | HCl | 322.0 |
| 293 | N-{[(6R,7SR)-7-(3-chloro-4-fluorophenyl)-1,4-oxazepan-6-yl]methyl}-methanesulfonamide | 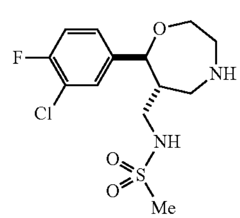 | HCl | 337.3 |

TABLE 1-63-continued

| Ex. No. | IUPAC name | structure | salt | MS |
|---|---|---|---|---|
| 294 | N-{[(6S,7R)-7-(3-chloro-4-fluorophenyl)-1,4-oxazepan-6-yl]methyl}-methanesulfonamide | 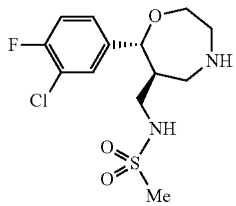 [SMILES: CS(=O)(=O)NC[C@@H]1CNCCO[C@H]1c1ccc(F)c(Cl)c1] | HCl | 337.0 |
| 295 | N-{[(6R,7S)-7-(3-chloro-4-fluorophenyl)-1,4-oxazepan-6-yl]methyl}-methansesulfonamide | 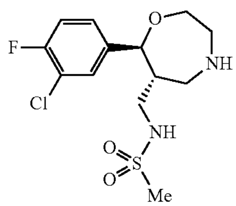 [SMILES: CS(=O)(=O)NC[C@H]1CNCCO[C@@H]1c1ccc(F)c(Cl)c1] | HCl | 337.1 |
| 296 | N-{[(6RS,7SR)-7-(3-chloro-4-fluorophenyl)-1,4-oxazepan-6-yl]methyl}sulfonamide | 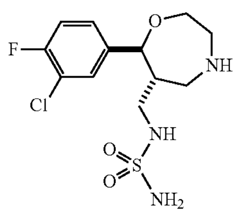 | HCl | 338.3 |
| 297 | N-{[(6S,7R)-7-(3-chloro-4-fluorophenyl)-1,4-oxazepan-6-yl]methyl}sulfamide | 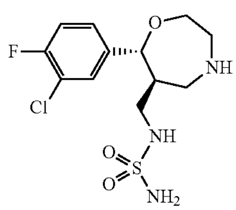 [SMILES: NS(=O)(=O)NC[C@@H]1CNCCO[C@H]1c1ccc(F)c(Cl)c1] | HCl | 338.0 |

TABLE 1-64

| Ex. No. | IUPAC name | structure | salt | MS |
|---|---|---|---|---|
| 298 | N-{[(6R,7S)-7-(3-chloro-4-fluorophenyl)-1,4-oxazepan-6-yl]methyl}sulfamide | 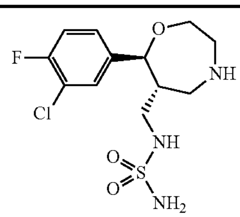 | HCl | 338.0 |
| 299 | N-{[(6S,7R)-7-(3-chloro-4-fluorophenyl)-1,4-oxazepan-6-yl]methyl}-N'-methylsulfamide | 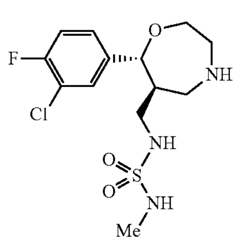 [SMILES: CNS(=O)(=O)NC[C@@H]1CNCCO[C@H]1c1ccc(F)c(Cl)c1] | HCl | 352.0 |

TABLE 1-64-continued

| Ex. No. | IUPAC name | structure | salt | MS |
|---|---|---|---|---|
| 300 | N-{[(6R,7S)-7-(3-chloro-4-fluorophenyl)-1,4-oxazepan-6-yl]methyl}-N'-methylsulfamide | 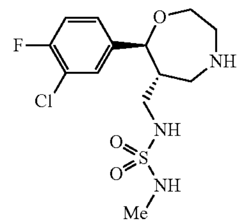 [SMILES: CNS(=O)(=O)NC[C@H]1CNCCO[C@@H]1c1ccc(F)c(Cl)c1] | HCl | 352.0 |
| 301 | [(6S,7R)-7-(4-chloro-3-fluorophenyl)-1,4-oxazepan-6-yl]methanol | 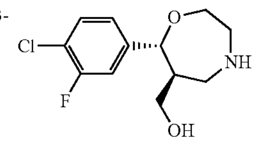 | HCl | 260.3 |
| 302 | [(6R,7S)-7-(4-chloro-3-fluorophenyl)-1,4-oxazepan-6-yl]methanol | 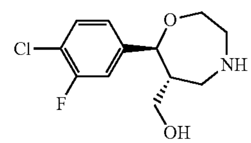 | HCl | 260.3 |

TABLE 1-65

| Ex. No. | IUPAC name | structure | salt | MS |
|---|---|---|---|---|
| 303 | 1-[(6S,7R)-7-(4-chloro-3-fluorophenyl)-1,4-oxazepan-6-yl]ethane-1,2-diol (retention time short) | 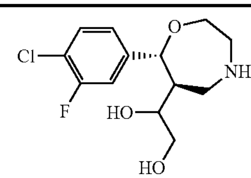 | HCl | 290.3 |
| 304 | 1-[(6S,7R)-7-(4-chloro-3-fluorophenyl)-1,4-oxazepan-6-yl]ethane-1,2-diol (retention time long) | 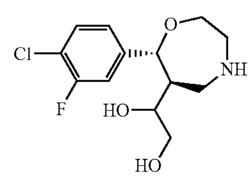 [SMILES: OCC(O)[C@@H]1CNCCO[C@H]1c1ccc(Cl)c(F)c1] | HCl | 290.3 |
| 305 | (6S,7R)-7-(4-chloro-3-fluorophenyl)-6-[(pyridin-2-yloxy)methyl]-1,4-oxazepane | 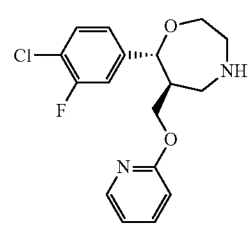 [SMILES: Fc1cc([C@@H]2OCCNC[C@H]2COc2ccccn2)ccc1Cl] | HCl | 337.1 |
| 306 | 2-{[(6S,7R)-7-(4-chloro-3-fluorophenyl)-1,4-oxazepan-6-yl]methoxy}pyridine-3-carboxylic acid | 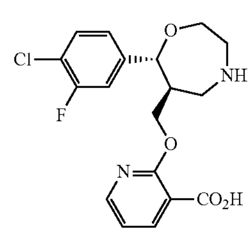 [SMILES: O=C(O)c1cccnc1OC[C@@H]1CNCCO[C@H]1c1ccc(Cl)c(F)c1] | HCl | 381.1 |

TABLE 1-65-continued

| Ex. No. | IUPAC name | structure | salt | MS |
|---|---|---|---|---|
| 307 | 1-[(6R,7R)-7-(4-chloro-3-fluorophenyl)-1,4-oxazepan-6-yl]methanamine | 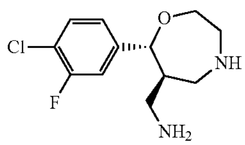 [SMILES: NC[C@@H]1CNCCO[C@H]1c1ccc(Cl)c(F)c1] | 2HCl | 259.0 |

TABLE 1-66

| Ex. No. | IUPAC name | structure | salt | MS |
|---|---|---|---|---|
| 308 | N-{[(6S,7R)-7-(4-chloro-3-fluorophenyl)-1,4-oxazepan-6-yl]methyl}acetamide | 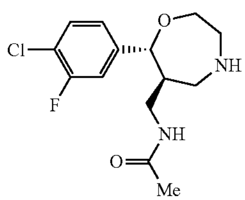 [SMILES: CC(=O)NC[C@@H]1CNCCO[C@H]1c1ccc(Cl)c(F)c1] | HCl | 301.3 |
| 309 | N-{[(6S,7R)-7-(4-chloro-3-fluorophenyl)-1,4-oxazepan-6-yl]methyl}butanamide | 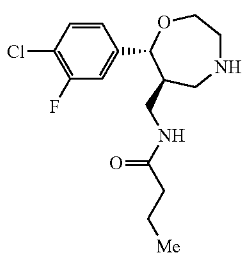 [SMILES: CCCC(=O)NC[C@@H]1CNCCO[C@H]1c1ccc(Cl)c(F)c1] | HCl | 329.2 |
| 310 | N-{[(6S,7R)-7-(4-chloro-3-fluorophenyl)-1,4-oxazepan-6-yl]methyl}cyclopropane-carboxamide | 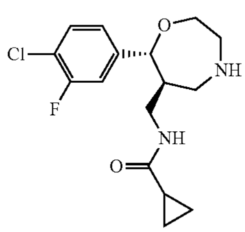 [SMILES: O=C(NC[C@@H]1CNCCO[C@H]1c1ccc(Cl)c(F)c1)C1CC1] | HCl | 327.2 |
| 311 | N-{[(6S,7R)-7-(4-chloro-3-fluorophenyl)-1,4-oxazepan-6-yl]methyl}-2,2-difluoroacetamide | 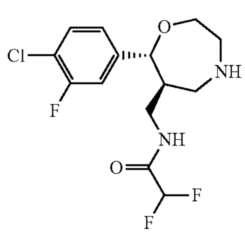 [SMILES: O=C(NC[C@@H]1CNCCO[C@H]1c1ccc(Cl)c(F)c1)C(F)F] | HCl | 337.3 |
| 312 | N-{[(6S,7R)-7-(4-chloro-3-fluorophenyl)-1,4-oxazepan-6-yl]methyl}-2,2-difluoropropanamide | 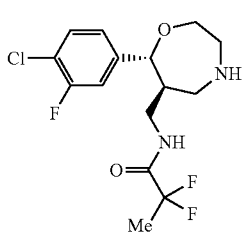 [SMILES: CC(F)(F)C(=O)NC[C@@H]1CNCCO[C@H]1c1ccc(Cl)c(F)c1] | free amine | 351.2 |

TABLE 1-67

| Ex. No. | IUPAC name | structure | salt | MS |
|---|---|---|---|---|
| 313 | N-{[(6S,7R)-7-(4-chloro-3-fluorophenyl)-1,4-oxazepan-6-yl]methyl}-2,2-difluorobutanamide | 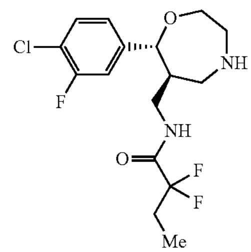 [SMILES: CCC(F)(F)C(=O)NC[C@@H]1CNCCO[C@H]1c1ccc(Cl)c(F)c1] | HCl | 365.2 |
| 314 | N-{[(6S,7R)-7-(4-chloro-3-fluorophenyl)-1,4-oxazepan-6-yl]methyl}-3,3,3-trifluoropropanamide | 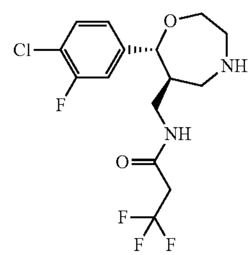 [SMILES: O=C(CC(F)(F)F)NC[C@@H]1CNCCO[C@H]1c1ccc(Cl)c(F)c1] | HCl | 369.2 |
| 315 | N-{[(6S,7R)-7-(4-chloro-3-fluorophenyl)-1,4-oxazepan-6-yl]methyl}-2-hydroxyacetamide | 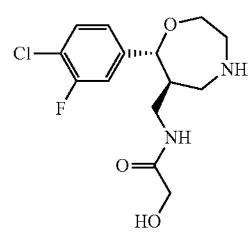 [SMILES: O=C(CO)NC[C@@H]1CNCCO[C@H]1c1ccc(Cl)c(F)c1] | HCl | 318.2 |
| 316 | N-{[(6S,7R)-7-(4-chloro-3-fluorophenyl)-1,4-oxazepan-6-yl]methyl}-2-methoxy-N-methylacetamide | 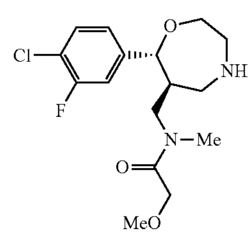 [SMILES: COCC(=O)N(C)C[C@@H]1CNCCO[C@H]1c1ccc(Cl)c(F)c1] | HCl | 345.2 |

TABLE 1-68

| Ex. No. | IUPAC name | structure | salt | MS |
|---|---|---|---|---|
| 317 | N-{[(6S,7R)-7-(4-chloro-3-fluorophenyl)-1,4-oxazepan-6-yl]methyl}-2-methoxypropanamide | 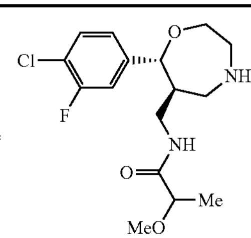 | HCl | 345.2 |

TABLE 1-68-continued

| Ex. No. | IUPAC name | structure | salt | MS |
|---|---|---|---|---|
| 318 | N-{[(6S,7R)-7-(4-chloro-3-fluorophenyl)-1,4-oxazepan-6-yl]methyl}-3-methoxypropanamide | 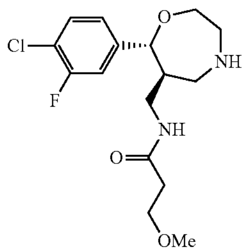 [SMILES: COCCC(=O)NC[C@@H]1CNCCO[C@H]1c1ccc(Cl)c(F)c1] | HCl | 345.4 |
| 319 | N-{[(6S,7R)-7-(4-chloro-3-fluorophenyl)-1,4-oxazepan-6-yl]methyl}-2-(cyclopropyloxy)-acetamide | 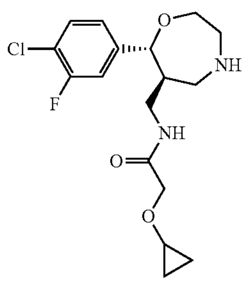 [SMILES: O=C(COC1CC1)NC[C@@H]1CNCCO[C@H]1c1ccc(Cl)c(F)c1] | HCl | 357.2 |
| 320 | N-{[(6S,7R)-7-(4-chloro-3-fluorophenyl)-1,4-oxazepan-6-yl]methyl}-2-(cyclopropyl-methoxy)-acetamide | 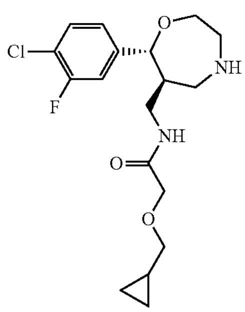 [SMILES: O=C(COCC1CC1)NC[C@@H]1CNCCO[C@H]1c1ccc(Cl)c(F)c1] | HCl | 371.0 |

TABLE 1-69

| Ex. No. | IUPAC name | structure | salt | MS |
|---|---|---|---|---|
| 321 | N-{[(6S,7R)-7-(4-chloro-3-fluorophenyl)-1,4-oxazepan-6-yl]methyl}-2-(difluoromethoxy)-acetamide | 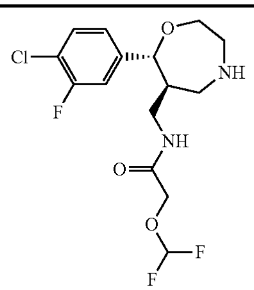 | HCl | 367.1 |
| 322 | N-{[(6S,7R)-7-(4-chloro-3-fluorophenyl)-1,4-oxazepan-6-yl]methyl}-2-(2,2,2-trifluoroethoxy)-acetamide | 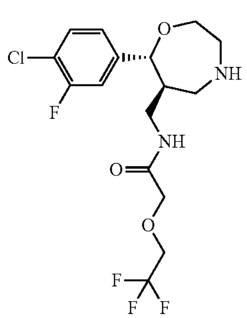 [SMILES: O=C(COCC(F)(F)F)NC[C@@H]1CNCCO[C@H]1c1ccc(Cl)c(F)c1] | HCl | 399.2 |

TABLE 1-69-continued

| Ex. No. | IUPAC name | structure | salt | MS |
|---|---|---|---|---|
| 323 | N-{[(6S,7R)-7-(4-chloro-3-fluorophenyl)-1,4-oxazepan-6-yl]methyl}-2-(2-methoxyethoxy)acetamide | 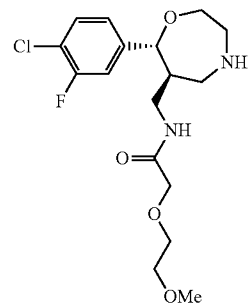 [SMILES: COCCOCC(=O)NC[C@@H]1CNCCO[C@H]1c1ccc(Cl)c(F)c1] | HCl | 375.1 |
| 324 | N-{[(6S,7R)-7-(4-chloro-3-fluorophenyl)-1,4-oxazepan-6-yl]methyl}-2-hydroxy-2-methylpropanamide | 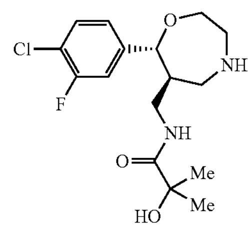 [SMILES: CC(C)(O)C(=O)NC[C@@H]1CNCCO[C@H]1c1ccc(Cl)c(F)c1] | HCl | 345.1 |

TABLE 1-70

| Ex. No. | IUPAC name | structure | salt | MS |
|---|---|---|---|---|
| 325 | N-{[(6S,7R)-7-(4-chloro-3-fluorophenyl)-1,4-oxazepan-6-yl]methyl}-2-methoxy-2-methylpropanamide | 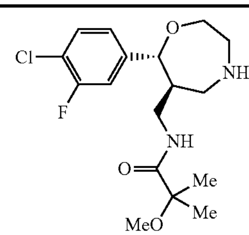 | HCl | 359.2 |
| 326 | N-{[(6S,7R)-7-(4-chloro-3-fluorophenyl)-1,4-oxazepan-6-yl]methyl}-2-(pyridin-2-yloxy)acetamide | 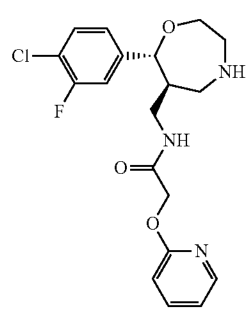 [SMILES: O=C(COc1ccccn1)NC[C@@H]1CNCCO[C@H]1c1ccc(Cl)c(F)c1] | HCl | 394.2 |
| 327 | N-{[(6S,7R)-7-(4-chloro-3-fluorophenyl)-1,4-oxazepan-6-yl]methyl}-2-[(3-chloropyridin-2-yl)oxy]acetamide | 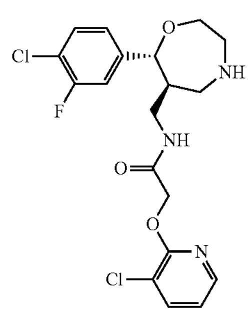 [SMILES: O=C(COc1ncccc1Cl)NC[C@@H]1CNCCO[C@H]1c1ccc(Cl)c(F)c1] | HCl | 428.0 |

TABLE 1-70-continued

| Ex. No. | IUPAC name | structure | salt | MS |
|---|---|---|---|---|
| 328 | N-{[(6S,7R)-7-(4-chloro-3-fluorophenyl)-1,4-oxazepan-6-yl]methyl}-2-(pyrimidin-2-yloxy)acetamide | 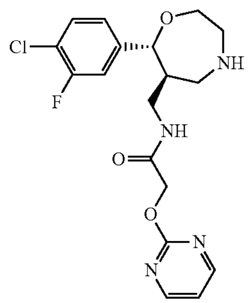 [SMILES: O=C(COc1ncccn1)NC[C@@H]1CNCCO[C@H]1c1ccc(Cl)c(F)c1] | HCl | 395.2 |

TABLE 1-71

| Ex. No. | IUPAC name | structure | salt | MS |
|---|---|---|---|---|
| 329 | N-{[(6S,7R)-7-(4-chloro-3-fluorophenyl)-1,4-oxazepan-6-yl]methyl}tetrahydrofuran-2-carboxamide | 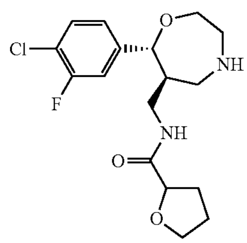 [SMILES: O=C(NC[C@@H]1CNCCO[C@H]1c1ccc(Cl)c(F)c1)C1CCCO1] | HCl | 357.4 |

TABLE 1-71-continued

| Ex. No. | IUPAC name | structure | salt | MS |
|---|---|---|---|---|
| 330 | N-{[(6S,7R)-7-(4-chloro-3-fluorophenyl)-1,4-oxazepan-6-yl]methyl}tetrahydrofuran-3-carboxamide | 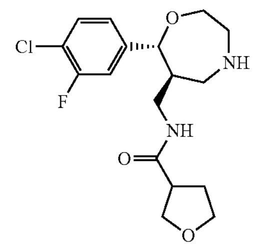 [SMILES: O=C(NC[C@@H]1CNCCO[C@H]1c1ccc(Cl)c(F)c1)C1CCOC1] | HCl | 357.1 |
| 331 | N-{[(6S,7R)-7-(4-chloro-3-fluorophenyl)-1,4-oxazepan-6-yl]methyl}tetrahydro-2H-pyran-4-carboxamide | 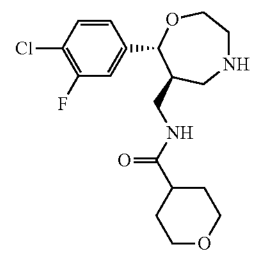 [SMILES: O=C(NC[C@@H]1CNCCO[C@H]1c1ccc(Cl)c(F)c1)C1CCOCC1] | HCl | 371.3 |
| 332 | N-{[(6S,7R)-7-(4-chloro-3-fluorophenyl)-1,4-oxazepan-6-yl]methyl}-1,4-dioxane-2-carboxamide | 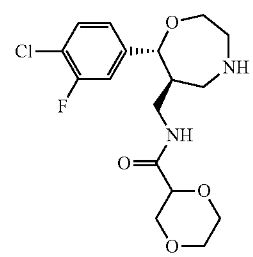 [SMILES: O=C(NC[C@@H]1CNCCO[C@H]1c1ccc(Cl)c(F)c1)C1COCCO1] | HCl | 373.0 |

TABLE 1-72

| Ex. No. | IUPAC name | structure | salt | MS |
|---|---|---|---|---|
| 333 | N-{[(6S,7R)-7-(4-chloro-3-fluorophenyl)-1,4-oxazepan-6-yl]methyl}-2-(methylamino)acetamide | 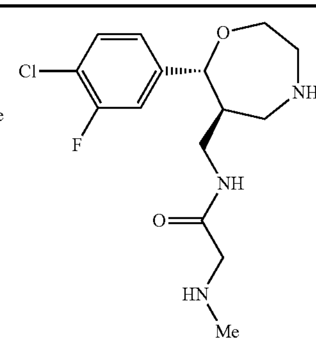 | 2HCl | 330.1 |
| 334 | N-{[(6S,7R)-7-(4-chloro-3-fluorophenyl)-1,4-oxazepan-6-yl]methyl}-2-(dimethylamino)acetamide | 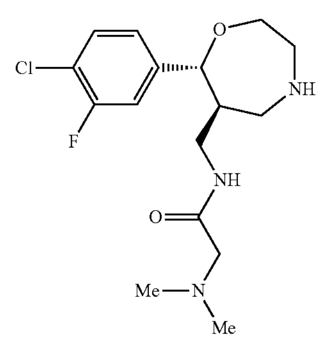 [SMILES: CN(C)CC(=O)NC[C@@H]1CNCCO[C@H]1c1ccc(Cl)c(F)c1] | 2HCl | 344.1 |

TABLE 1-72-continued

| Ex. No. | IUPAC name | structure | salt | MS |
|---|---|---|---|---|
| 335 | N-{[(6S,7R)-7-(4-chloro-3-fluorophenyl)-1,4-oxazepan-6-yl]methyl}-2-(pyrrolidin-1-yl)acetamide | 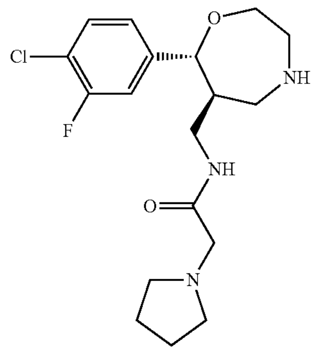 [SMILES: O=C(CN1CCCC1)NC[C@@H]1CNCCO[C@H]1c1ccc(Cl)c(F)c1] | 2HCl | 370.1 |
| 336 | N-{[(6S,7R)-7-(4-chloro-3-fluorophenyl)-1,4-oxazepan-6-yl]methyl}-2-(4,4-difluoropiperidin-1-yl)acetamide | 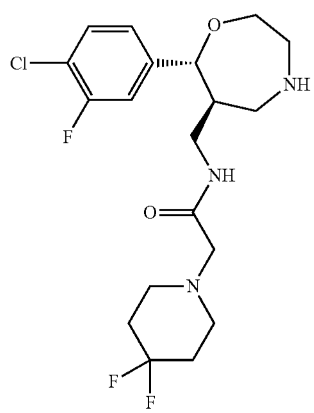 [SMILES: O=C(CN1CCC(F)(F)CC1)NC[C@@H]1CNCCO[C@H]1c1ccc(Cl)c(F)c1] | 2HCl | 420.2 |

TABLE 1-73

| Ex. No. | IUPAC name | structure | salt | MS |
|---|---|---|---|---|
| 337 | N-{[(6S,7R)-7-(4-chloro-3-fluoropbenyl)-1,4-oxazepan-6-yl]methyl}-2-(morpholin-4-yl)acetamide | 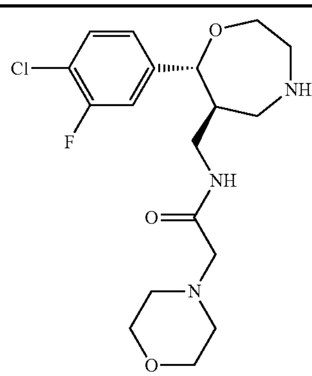 | 2HCl | 386.3 |

TABLE 1-73-continued

| Ex. No. | IUPAC name | structure | salt | MS |
|---|---|---|---|---|
| 338 | N-{[(6S,7R)-7-(4-chloro-3-fluorophenyl)-1,4-oxazepan-6-yl]methyl}-2-(8-oxa-3-azabicyclo[3.2.1]oct-3-yl)acetamide | 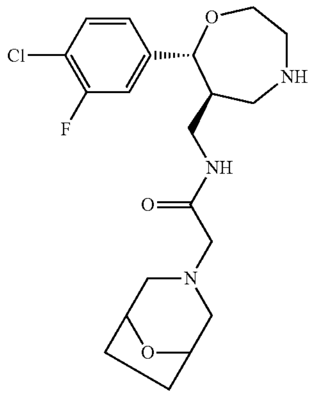 [SMILES: O=C(CN1CC2CCC(C1)O2)NC[C@@H]1CNCCO[C@H]1c1ccc(Cl)c(F)c1] | 2HCl | 412.1 |
| 339 | N-[2-({[(6S,7R)-7-(4-chloro-3-fluorophenyl)-1,4-oxazepan-6-yl]methyl}amino)-2-oxoethyl]-N-methylacetamide | 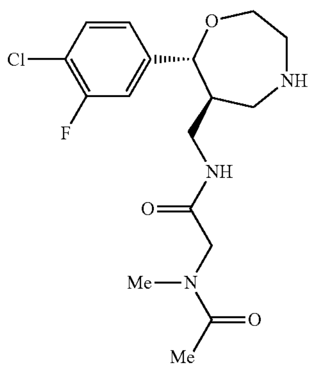 [SMILES: CC(=O)N(C)CC(=O)NC[C@@H]1CNCCO[C@H]1c1ccc(Cl)c(F)c1] | HCl | 372.1 |
| 340 | N-[2-({[(6S,7R)-7-(4-chloro-3-fluorophenyl)-1,4-oxazepan-6-yl]methyl}amino)-2-oxoethyl]benzamide | 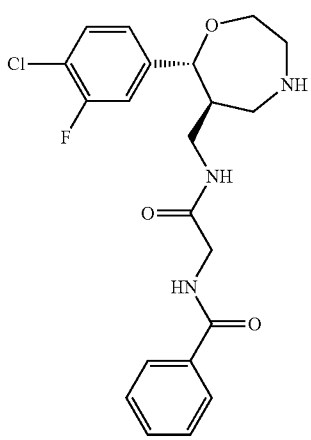 [SMILES: O=C(CNC(=O)c1ccccc1)NC[C@@H]1CNCCO[C@H]1c1ccc(Cl)c(F)c1] | HCl | 420.2 |

TABLE 1-74

| Ex. No. | IUPAC name | structure | salt | MS |
| --- | --- | --- | --- | --- |
| 341 | N-[2-({[(6S,7R)-7-(4-chloro-3-fluorophenyl)-1,4-oxazepan-6-yl]methyl}amino)-2-oxoethyl]pyridine-2-carboxamide | 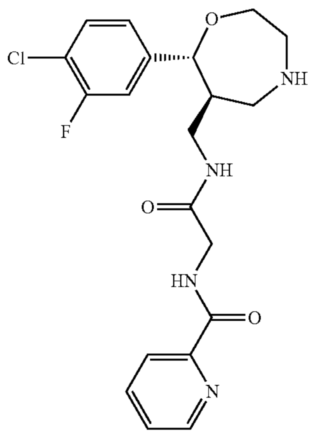 [SMILES: O=C(CNC(=O)c1ccccn1)NC[C@@H]1CNCCO[C@H]1c1ccc(Cl)c(F)c1] | HCl | 421.2 |
| 342 | N-[2-({[(6S,7R)-7-(4-chloro-3-fluorophenyl)-1,4-oxazepan-6-yl]methyl}amino)-2-oxoethyl]-N-methylpyridine-2-carboxamide | 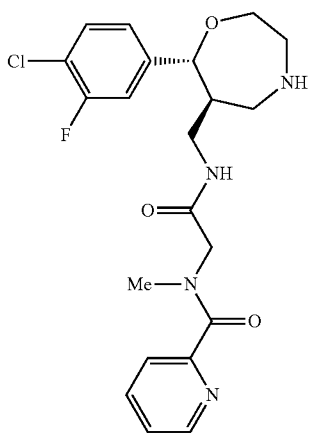 [SMILES: CN(CC(=O)NC[C@@H]1CNCCO[C@H]1c1ccc(Cl)c(F)c1)C(=O)c1ccccn1] | HCl | 435.2 |
| 343 | N-{[(6S,7R)-7-(4-chloro-3-fluorophenyl)-1,4-oxazepan-6-yl]methyl}-2-[(phenylsulfonyl)amino]acetamide | 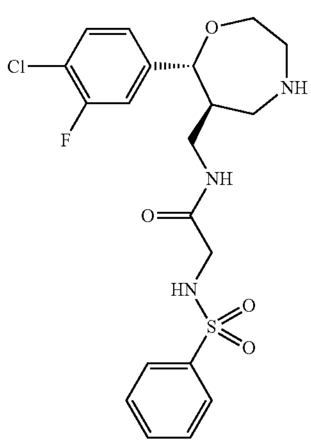 [SMILES: O=C(CNS(=O)(=O)c1ccccc1)NC[C@@H]1CNCCO[C@H]1c1ccc(Cl)c(F)c1] | HCl | 456.1 |

TABLE 1-75

| Ex. No. | IUPAC name | structure | salt | MS |
|---|---|---|---|---|
| 344 | N-{[(6S,7R)-7-(4-chloro-3-fluorophenyl)-1,4-oxazepan-6-yl]methyl}-2-(pyridin-2-yl)acetamide | 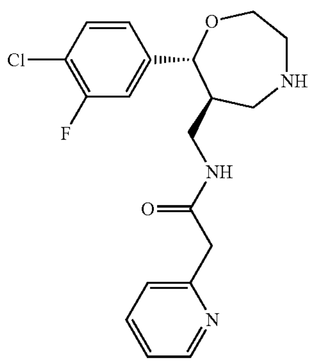 [SMILES: O=C(Cc1ccccn1)NC[C@@H]1CNCCO[C@H]1c1ccc(Cl)c(F)c1] | HCl | 378.4 |
| 345 | N-{[(6S,7R)-7-(4-chloro-3-fluorophenyl)-1,4-oxazepan-6-yl]methyl}-3-(pyridin-2-yl)propanamide | 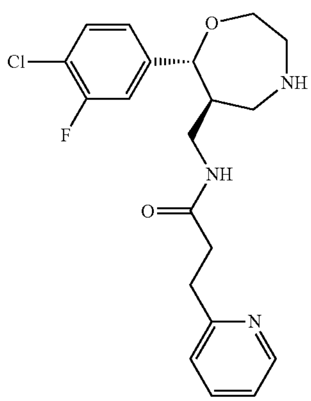 [SMILES: O=C(CCc1ccccn1)NC[C@@H]1CNCCO[C@H]1c1ccc(Cl)c(F)c1] | HCl | 392.2 |
| 346 | N-{[(6S,7R)-7-(4-chloro-3-fluorophenyl)-1,4-oxazepan-6-yl]methyl}-2-(2-oxopyridin-1(2H)-yl)acetamide | 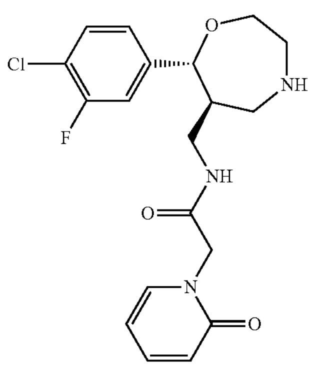 [SMILES: O=C(Cn1ccccc1=O)NC[C@@H]1CNCCO[C@H]1c1ccc(Cl)c(F)c1] | HCl | 394.1 |
| 347 | N-{[(6S,7R)-7-(4-chloro-3-fluorophenyl)-1,4-oxazepan-6-yl]methyl}-2-(3-chloro-2-oxopyridin-1(2H)-yl)acetamide | 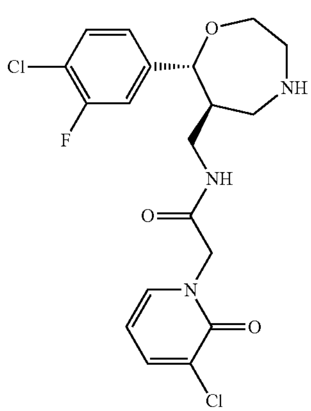 [SMILES: O=C(Cn1cccc(Cl)c1=O)NC[C@@H]1CNCCO[C@H]1c1ccc(Cl)c(F)c1] | HCl | 428.0 |

TABLE 1-76

| Ex. No. | IUPAC name | structure | salt | MS |
|---|---|---|---|---|
| 348 | N-{[(6S,7R)-7-(4-chloro-3-fluorophenyl)-1,4-oxazepan-6-yl]methyl}-2-[(3-fluoropyridin-2-yl)oxy]acetamide | 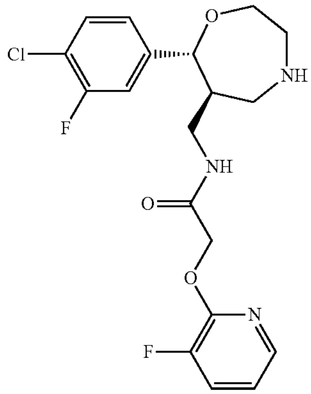 [SMILES: O=C(COc1ncccc1F)NC[C@@H]1CNCCO[C@H]1c1ccc(Cl)c(F)c1] | free amine | 412.2 |
| 349 | N-{[(6S,7R)-7-(4-chloro-3-fluorophenyl)-1,4-oxazepan-6-yl]methyl}-2-[(3-cyanopyridin-2-yl)oxy]acetamide | 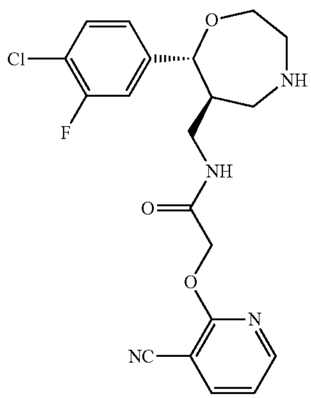 [SMILES: N#Cc1cccnc1OCC(=O)NC[C@@H]1CNCCO[C@H]1c1ccc(Cl)c(F)c1] | free amine | 419.0 |
| 350 | N-{[(6S,7R)-7-(4-chloro-3-fluorophenyl)-1,4-oxazepan-6-yl]methyl}-2-methyl-2-(pyridin-2-yloxy)propanamide | 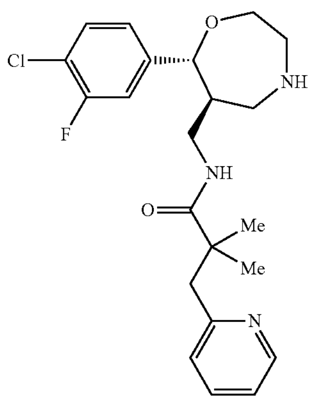 [SMILES: CC(C)(Cc1ccccn1)C(=O)NC[C@@H]1CNCCO[C@H]1c1ccc(Cl)c(F)c1] | free amine | 422.2 |
| 351 | N-{[(6S,7R)-7-(4-chloro-3-fluorophenyl)-1,4-oxazepan-6-yl]methyl}-2-(3-methylisoxazol-5-yl)acetamide | 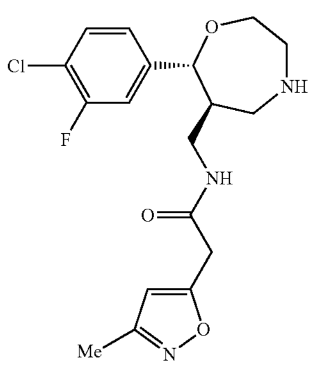 [SMILES: Cc1cc(CC(=O)NC[C@@H]2CNCCO[C@H]2c2ccc(Cl)c(F)c2)on1] | HCl | 382.0 |

TABLE 1-77

| Ex. No. | IUPAC name | structure | salt | MS |
|---|---|---|---|---|
| 352 | N-{[(6S,7R)-7-(4-chloro-3-fluorophenyl)-1,4-oxazepan-6-yl]methyl}-2-(1H-1,2,4-triazol-1-yl)acetamide | 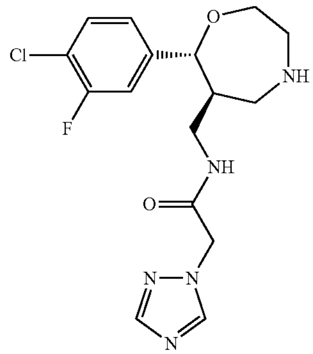 [SMILES: O=C(Cn1cncn1)NC[C@@H]1CNCCO[C@H]1c1ccc(Cl)c(F)c1] | 3HCl | 368.0 |
| 353 | N-{[(6S,7R)-7-(4-chloro-3-fluorophenyl)-1,4-oxazepan-6-yl]methyl}-3-(5-oxo-4,5-dihydro-1,2,4-oxadiazol-3-yl)benzamide | 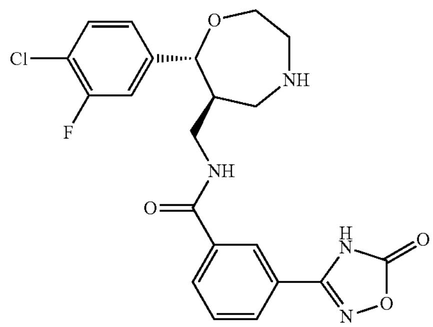 [SMILES: O=C(NC[C@@H]1CNCCO[C@H]1c1ccc(Cl)c(F)c1)c1cccc(-c2noc(=O)[nH]2)c1] | HCl | 447.1 |
| 354 | N-{[(6S,7R)-7-(4-chloro-3-fluorophenyl)-1,4-oxazepan-6-yl]methyl}-2-methoxy-3-(5-oxo-4,5-dihydro-1,2,4-oxadiazol-3-yl)benzamide | 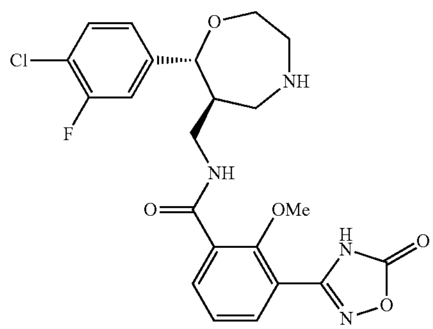 [SMILES: COc1c(C(=O)NC[C@@H]2CNCCO[C@H]2c2ccc(Cl)c(F)c2)cccc1-c1noc(=O)[nH]1] | HCl | 476.9 |
| 355 | N-{[(6S,7R)-7-(4-chloro-3-fluorophenyl)-1,4-oxazepan-6-yl]methyl}-4-ethoxy-3-(5-oxo-4,5-dihydro-1,2,4-oxadiazol-3-yl)benzamide | 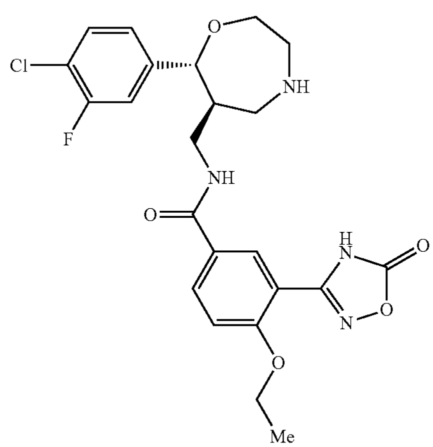 [SMILES: CCOc1ccc(C(=O)NC[C@@H]2CNCCO[C@H]2c2ccc(Cl)c(F)c2)cc1-c1noc(=O)[nH]1] | HCl | 491.0 |

TABLE 1-78

| Ex. No. | IUPAC name | structure | salt | MS |
|---|---|---|---|---|
| 356 | N-{([(6S,7R)-7-(4-chloro-3-fluorophenyl)-1,4-oxazepan-6-yl]methyl}-2-fluoro-3-(5-oxo-4,5-dihydro-1,2,4-oxadiazol-3-yl)benzamide | 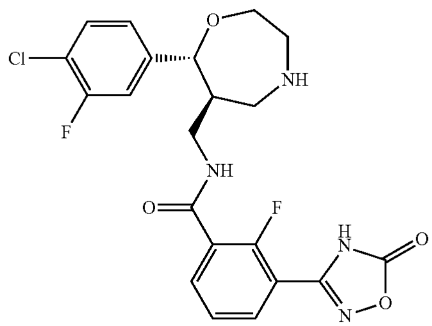 [SMILES: O=C(NC[C@@H]1CNCCO[C@H]1c1ccc(Cl)c(F)c1)c1cccc(-c2noc(=O)[nH]2)c1F] | HCl | 465.1 |
| 357 | N-{[(6S,7R)-7-(4-chloro-3-fluorophenyl)-1,4-oxazepan-6-yl]methyl}-2-fluoro-5-(5-oxo-4,5-dihydro-1,2,4-oxadiazol-3-yl)benzamide | 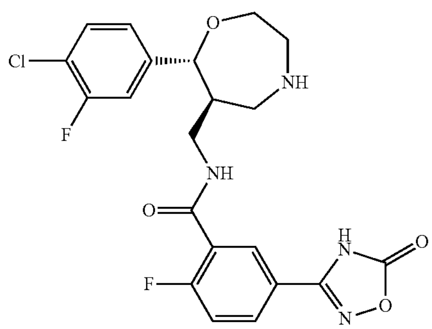 [SMILES: O=C(NC[C@@H]1CNCCO[C@H]1c1ccc(Cl)c(F)c1)c1cc(-c2noc(=O)[nH]2)ccc1F] | HCl | 465.1 |
| 358 | N-{[(6S,7R)-7-(4-chloro-3-fluorophenyl)-1,4-oxazepan-6-yl]methyl}-4-fluoro-3-(5-oxo-4,5-dihydro-1,2,4-oxadiazol-3-yl)benzanmide | 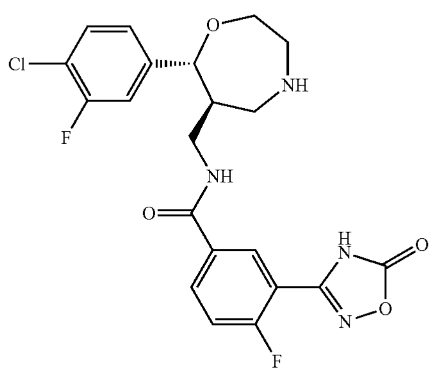 [SMILES: O=C(NC[C@@H]1CNCCO[C@H]1c1ccc(Cl)c(F)c1)c1ccc(F)c(-c2noc(=O)[nH]2)c1] | HCl | 465.1 |
| 359 | N-{[(6S,7R)-7-(4-chloro-3-fluorophenyl)-1,4-oxazepan-6-yl]methyl}-3-fluoro-5-(5-oxo-4,5-dihydro-1,2,4-oxadiazol-3-yl)benzamide | 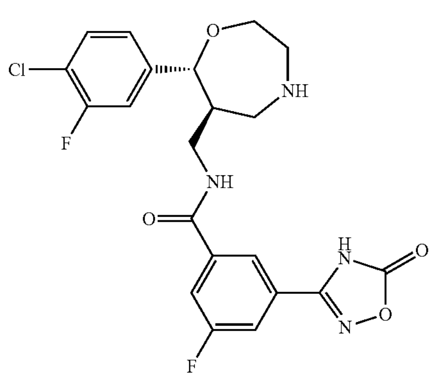 [SMILES: O=C(NC[C@@H]1CNCCO[C@H]1c1ccc(Cl)c(F)c1)c1cc(F)cc(-c2noc(=O)[nH]2)c1] | HCl | 464.9 |

TABLE 1-79

| Ex. No. | IUPAC name | structure | salt | MS |
|---|---|---|---|---|
| 360 | N-{[(6S,7R)-7-(4-chloro-3-fluorophenyl)-1,4-oxazepan-6-yl]methyl}-2-methyl-5-(5-oxo-4,5-dihydro-1,2,4-oxadiazol-3-yl)benzamide | 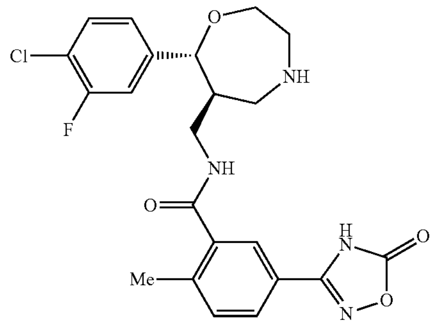 [SMILES: Cc1ccc(-c2noc(=O)[nH]2)cc1C(=O)NC[C@@H]1CNCCO[C@H]1c1ccc(Cl)c(F)c1] | HCl | 461.2 |
| 361 | N-{[(6S,7R)-7-(4-chloro-3-fluorophenyl)-1,4-oxazepan-6-yl]methyl}-2-(5-methyl-1,2,4-oxadiazol-3-yl)benzamide | 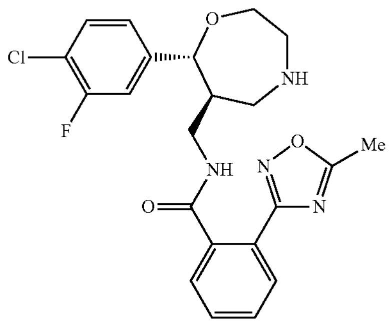 [SMILES: Cc1nc(-c2ccccc2C(=O)NC[C@@H]2CNCCO[C@H]2c2ccc(Cl)c(F)c2)no1] | HCl | 445.2 |
| 362 | N-{[(6S,7R)-7-(4-chloro-3-fluorophenyl)-1,4-oxazepan-6-yl]methyl}-2-(methylsulfonyl)-benzamide | 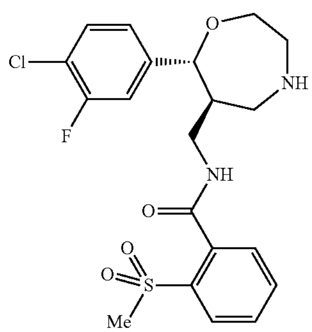 [SMILES: CS(=O)(=O)c1ccccc1C(=O)NC[C@@H]1CNCCO[C@H]1c1ccc(Cl)c(F)c1] | HCl | 441.2 |
| 363 | N-{[(6S,7R)-7-(4-chloro-3-fluorophenyl)-1,4-oxazepan-6-yl]methyl}-2-(2-oxopyrrolidin-1-yl)benzamide | 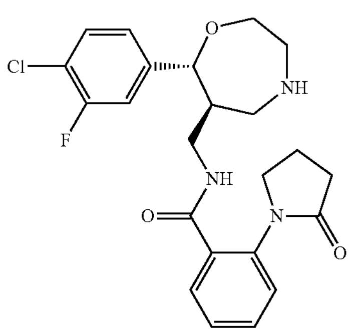 [SMILES: O=C(NC[C@@H]1CNCCO[C@H]1c1ccc(Cl)c(F)c1)c1ccccc1N1CCCC1=O] | HCl | 446.2 |

TABLE 1-80

| Ex. No. | IUPAC name | structure | salt | MS |
|---|---|---|---|---|
| 364 | N-{[(6S,7R)-7-(4-chloro-3-fluorophenyl)-1,4-oxazepan-6-yl]methyl}-2-[(methylsulfonyl)-amino]benzamide | 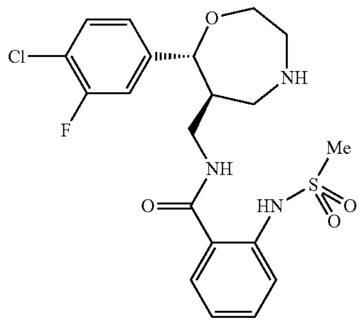 [SMILES: CS(=O)(=O)Nc1ccccc1C(=O)NC[C@@H]1CNCCO[C@H]1c1ccc(Cl)c(F)c1] | HCl | 456.2 |
| 365 | N-{[(6S,7R)-7-(4-chloro-3-fluorophenyl)-1,4-oxazepan-6-yl]methyl}pyridine-2-carboxamide | 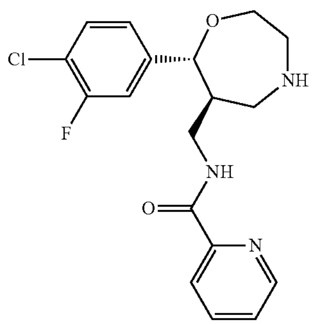 [SMILES: O=C(NC[C@@H]1CNCCO[C@H]1c1ccc(Cl)c(F)c1)c1ccccn1] | HCl | 364.3 |
| 366 | N-{[(6S,7R)-7-(4-chloro-3-fluorophenyl)-1,4-oxazepan-6-yl]methyl}pyridine-3-carboxamide | 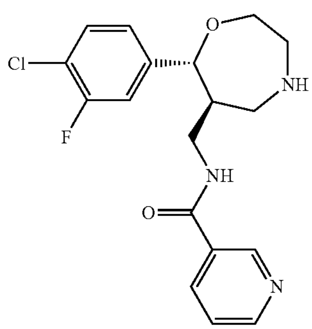 [SMILES: O=C(NC[C@@H]1CNCCO[C@H]1c1ccc(Cl)c(F)c1)c1cccnc1] | HCl | 364.3 |
| 367 | N-{[(6S,7R)-7-(4-chloro-3-fluorophenyl)-1,4-oxazepan-6-yl]methyl}-2-oxo-1,2-dihyopyridine-3-carboxamide | 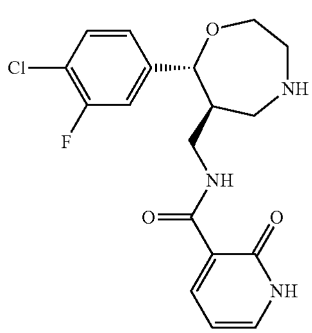 [SMILES: O=C(NC[C@@H]1CNCCO[C@H]1c1ccc(Cl)c(F)c1)c1ccc[nH]c1=O] | HCl | 380.2 |

TABLE 1-80-continued

| Ex. No. | IUPAC name | structure | salt | MS |
|---|---|---|---|---|
| 368 | N-{[(6S,7R)-7-(4-chloro-3-fluorophenyl)-1,4-oxazepan-6-yl]methyl}-3-[(methylsulfonyl)amino]pyridine-2-carboxamide | 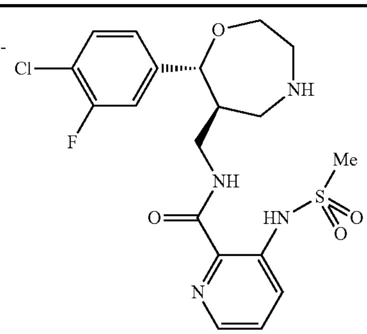 | HCl | 457.3 |

TABLE 1-81

| Ex. No. | IUPAC name | structure | salt | MS |
|---|---|---|---|---|
| 369 | N-{[(6S,7R)-7-(4-chloro-3-fluorophenyl)-1,4-oxazepan-6-yl]methyl}-2-oxo-2-(pyrrolidin-1-yl)acetamide | 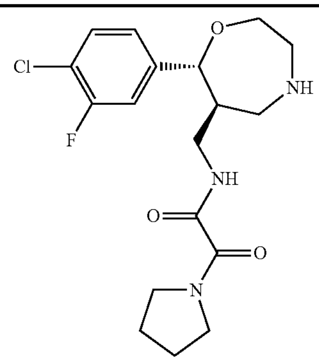 | HCl | 384.4 |
| 370 | N-{[(6S,7R)-7-(4-chloro-3-fluorophenyl)-1,4-oxazepan-6-yl]methyl}-methanesulfonamide | 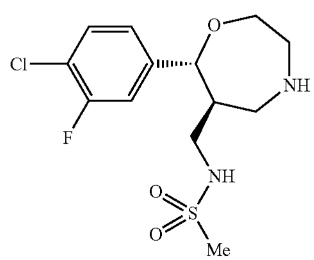 [SMILES: CS(=O)(=O)NC[C@@H]1CNCCO[C@H]1c1ccc(Cl)c(F)c1] | HCl | 337.3 |
| 371 | N-{[(6S,7R)-7-(4-chloro-3-fluorophenyl)-1,4-oxazepan-6-yl]methyl}-1,1-difluoromethanesulfonamide | 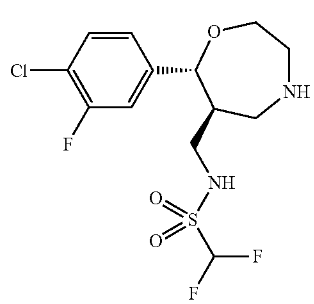 [SMILES: O=S(=O)(NC[C@@H]1CNCCO[C@H]1c1ccc(Cl)c(F)c1)C(F)F] | HCl | 373.0 |

TABLE 1-81-continued

| Ex. No. | IUPAC name | structure | salt | MS |
|---|---|---|---|---|
| 372 | 1-{[(6S,7R)-7-(4-chloro-3-fluorophenyl)-1,4-oxazepan-6-yl]methyl}tetrahydro-pyrimidin-2(1H)-one | 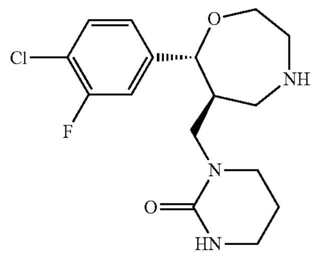 [SMILES: O=C1NCCCN1C[C@@H]1CNCCO[C@H]1c1ccc(Cl)c(F)c1] | HCl | 342.2 |
| 373 | 1-{[(6S,7R)-7-(4-chloro-3-fluorophenyl)-1,4-oxazepan-6-yl]methyl}-3-methyl-1H-pyrazole-5-carboxylic acid | 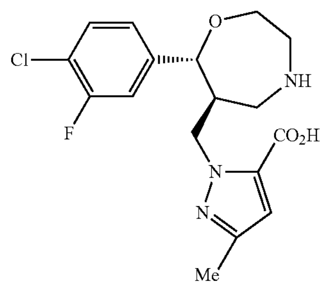 [SMILES: Cc1cc(C(=O)O)n(C[C@@H]2CNCCO[C@H]2c2ccc(Cl)c(F)c2)n1] | HCl | 368.3 |

TABLE 1-82

| Ex. No. | IUPAC name | structure | salt | MS |
|---|---|---|---|---|
| 374 | 1-{[(6S,7R)-7-(4-chloro-3-fluorophenyl)-1,4-oxazepan-6-yl]methyl}-5-methyl-1H-pyrazole-3-carboxylic acid | 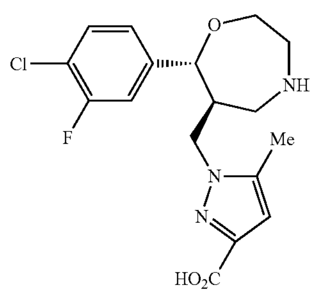 [SMILES: Cc1cc(C(=O)O)nn1C[C@@H]1CNCCO[C@H]1c1ccc(Cl)c(F)c1] | HCl | 368.3 |
| 375 | 1-{[(6S,7R)-7-(4-chloro-3-fluorophenyl)-1,4-oxazepan-6-yl]methyl}pyrrolidin-2-one | 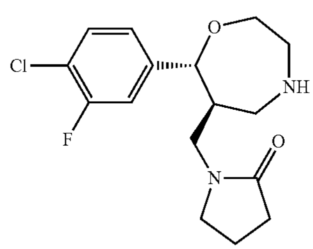 [SMILES: O=C1CCCN1C[C@@H]1CNCCO[C@H]1c1ccc(Cl)c(F)c1] | HCl | 327.2 |
| 376 | 1-{[(6S,7R)-7-(4-chloro-3-fluorophenyl)-1,4-oxazepan-6-yl]methyl}piperidin-2-one | 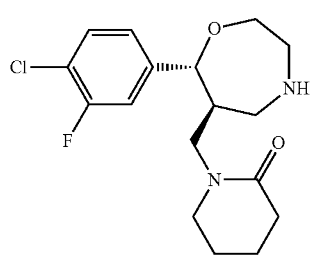 [SMILES: O=C1CCCCN1C[C@@H]1CNCCO[C@H]1c1ccc(Cl)c(F)c1] | HCl | 341.1 |

TABLE 1-82-continued

| Ex. No. | IUPAC name | structure | salt | MS |
|---|---|---|---|---|
| 377 | 1-{[(6S,7R)-7-(4-chloro-3-fluorophenyl)-1,4-oxazepan-6-yl]methyl}-4-(5-oxo-4,5-dihydro-1,2,4-oxadiazol-3-yl)pyridin-2(1H)-one | 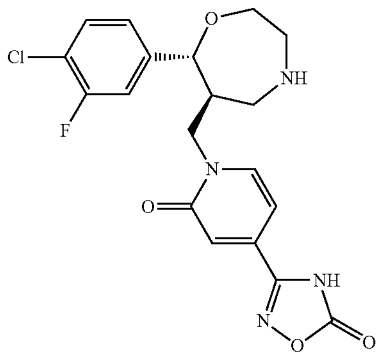 [SMILES: O=c1[nH]c(-c2ccn(C[C@@H]3CNCCO[C@H]3c3ccc(Cl)c(F)c3)c(=O)c2)no1] | HCl | 421.3 |
| 378 | 1-{[(6S,7R)-7-(4-chloro-3-fluorophenyl)-1,4-oxazepan-6-yl]methyl}-3-(5-methyl-4H-1,2,4-triazol-3-yl)pyridin-2(1H)-one | 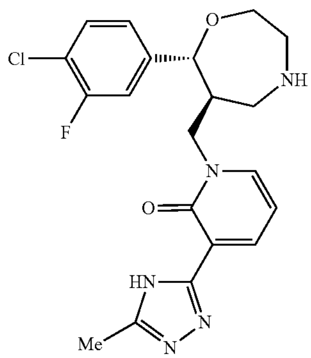 [SMILES: Cc1nnc(-c2cccn(C[C@@H]3CNCCO[C@H]3c3ccc(Cl)c(F)c3)c2=O)[nH]1] | HCl | 418.1 |

TABLE 1-83

| Ex. No. | IUPAC name | structure | salt | MS |
|---|---|---|---|---|
| 379 | 1-{[(6S,7R)-7-(4-chloro-3-fluorophenyl)-1,4-oxazepan-6-yl]methyl}-3-(5-oxo-4,5-dihydro-1H-1,2,4-triazol-3-yl)pyridin-2(1H)-one | 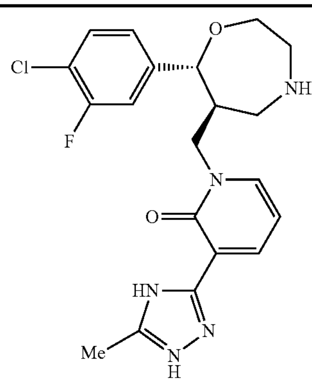 | HCl | 420.1 |
| 380 | 1-{[(6S,7R)-7-(4-chloro-3-fluorophenyl)-1,4-oxazepan-6-yl]methyl}-3-(1H-tetrazol-5-yl)pyridin-2(1H)-one | 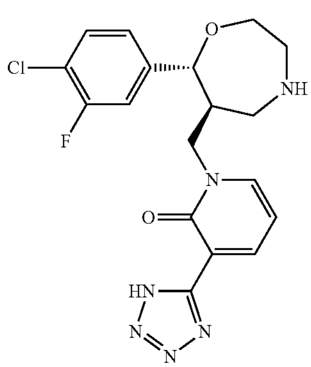 [SMILES: O=c1c(-c2nnn[nH]2)cccn1C[C@@H]1CNCCO[C@H]1c1ccc(Cl)c(F)c1] | free amine | 405.1 |

TABLE 1-83-continued

| Ex. No. | IUPAC name | structure | salt | MS |
|---|---|---|---|---|
| 381 | 2-{[(6S,7R)-7-(4-chloro-3-fluorophenyl)-1,4-oxazepan-6-yl]methyl}pyridazin-3(2H)-one | 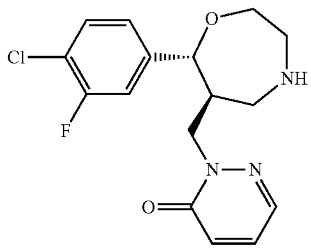 [SMILES: O=c1cccnn1C[C@@H]1CNCCO[C@H]1c1ccc(Cl)c(F)c1] | HCl | 338.2 |
| 382 | 2-{[(6S,7R)-7-(4-chloro-3-fluorophenyl)-1,4-oxazepan-6-yl]methyl}-4-(5-oxo-4,5-dihydro-1,2,4-oxadiazol-3-yl)pyridazin-3(2H)-one | 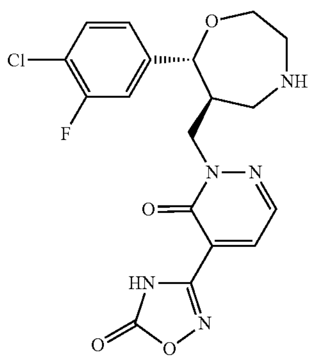 | HCl | 422.3 |

TABLE 1-84

| Ex. No. | IUPAC name | structure | salt | MS |
|---|---|---|---|---|
| 383 | 3-{[(6S,7R)-7-(4-chloro-3-fluorophenyl)-1,4-oxazepan-6-yl]methyl}quinazoline-2,4(1H,3H)-dione | 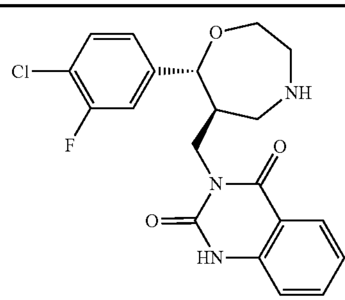 | HCl | 404.3 |
| 384 | 3-{[(6S,7R)-7-(4-chloro-3-fluorophenyl)-1,4-oxazepan-6-yl]methyl}-1-methylquinazoline-2,4(1H,3H)-dione | 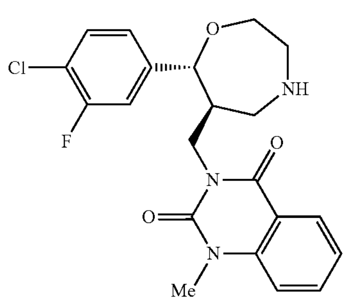 [SMILES: Cn1c(=O)n(C[C@@H]2CNCCO[C@H]2c2ccc(Cl)c(F)c2)c(=O)c2ccccc21] | HCl | 418.3 |

TABLE 1-84-continued

| Ex. No. | IUPAC name | structure | salt | MS |
|---|---|---|---|---|
| 385 | 3-{[(6S,7R)-7-(4-chloro-3-fluorophenyl)-1,4-oxazepan-6-yl]methyl}pyrido[3,2-d]pyrimidine-2,4(1H,3H)-dione | 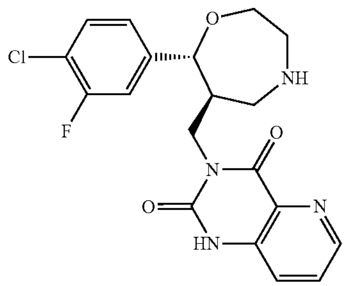 [SMILES: O=c1[nH]c2cccnc2c(=O)n1C[C@@H]1CNCCO[C@H]1c1ccc(Cl)c(F)c1] | HCl | 405.2 |
| 386 | 3-{[(6S,7R)-7-(4-chloro-3-fluorophenyl)-1,4-oxazepan-6-yl]methyl}pteridine-2,4(1H,3H)-dione | 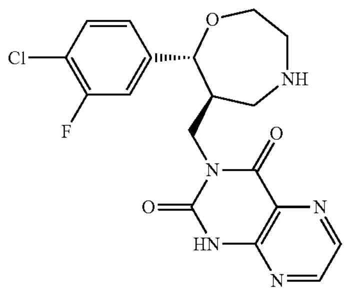 [SMILES: O=c1[nH]c2nccnc2c(=O)n1C[C@@H]1CNCCO[C@H]1c1ccc(Cl)c(F)c1] | HCl | 406.3 |
| 387 | 3-{[(6S,7R)-7-(4-chloro-3-fluorophenyl)-1,4-oxazepan-6-yl]methyl}-1-methylpteridine-2,4(1H,3H)-dione | 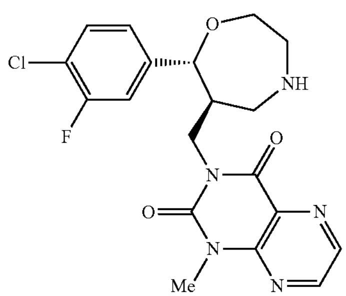 [SMILES: Cn1c(=O)n(C[C@@H]2CNCCO[C@H]2c2ccc(Cl)c(F)c2)c(=O)c2nccnc21] | HCl | 420.4 |

TABLE 1-85

| Ex. No. | IUPAC name | structure | salt | MS |
|---|---|---|---|---|
| 388 | 2-{[(6R,7R)-7-(4-chloro-3-fluorophenyl)-1,4-oxazepan-6-yl]methyl}-1H-benzimidazole | 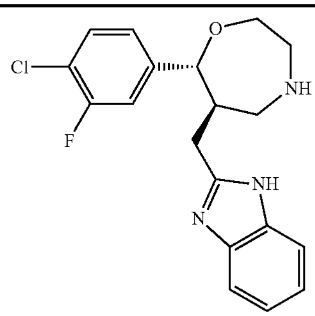 | HCl | 360.1 |

TABLE 1-85-continued

| Ex. No. | IUPAC name | structure | salt | MS |
|---|---|---|---|---|
| 389 | N-{[(6S,7R)-7-(4-chloro-3-fluorophenyl)-1,4-oxazepan-6-yl]methyl}pyridin-2-amine | 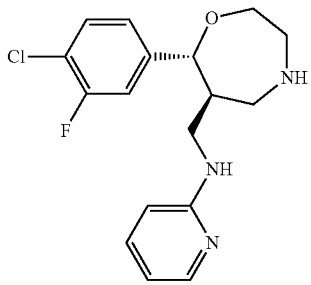 [SMILES: Fc1cc([C@@H]2OCCNC[C@H]2CNc2ccccn2)ccc1Cl] | 2HCl | 336.1 |
| 390 | N-{[(6S,7R)-7-(4-chloro-3-fluorophenyl)-1,4-oxazepan-6-yl]methyl}pyrimidin-2-amine | 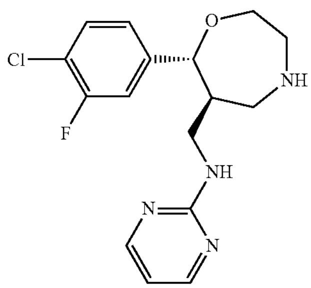 [SMILES: Fc1cc([C@@H]2OCCNC[C@H]2CNc2ncccn2)ccc1Cl] | HCl | 337.1 |
| 391 | N-{[(6S,7R)-7-(4-chloro-3-fluorophenyl)-1,4-oxazepan-6-yl]methyl}-1,3-benzoxazol-2-amine | 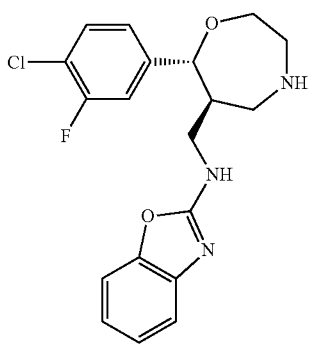 [SMILES: Fc1cc([C@@H]2OCCNC[C@H]2CNc2nc3ccccc3o2)ccc1Cl] | HCl | 376.3 |

TABLE 1-86

| Ex. No. | IUPAC name | structure | salt | MS |
|---|---|---|---|---|
| 392 | 3-[2-({[(6S,7R)-7-(4-chloro-3-fluorophenyl)-1,4-oxazepan-6-yl]methyl}amino)-1,3-benzoxazol-4-yl]-1,2,4-oxadiazol-5(4H)-one | 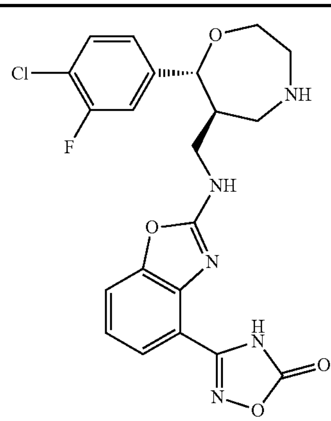 | HCl | 460.3 |

TABLE 1-86-continued

| Ex. No. | IUPAC name | structure | salt | MS |
|---|---|---|---|---|
| 393 | 3-{[(6S,7R)-7-(4-chloro-3-fluorophenyl)-1,4-oxazepan-6-yl]methyl}-2-methylquinazolin-4(3H)-one | 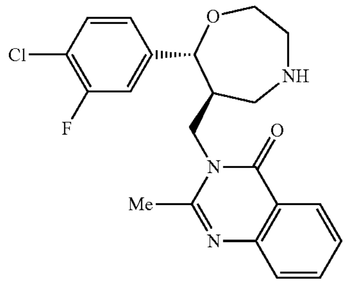 [SMILES: Cc1nc2ccccc2c(=O)n1C[C@@H]1CNCCO[C@H]1c1ccc(Cl)c(F)c1] | HCl | 402.1 |
| 394 | N-(2-[(6R,7R)-7-(4-chloro-3-fluorophenyl)-1,4-oxazepan-6-yl]ethyl}-2-methoxyacetamide | 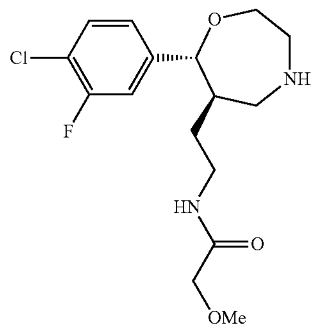 [SMILES: COCC(=O)NCC[C@@H]1CNCCO[C@H]1c1ccc(Cl)c(F)c1] | HCl | 345.2 |
| 395 | (6R,7R)-7-(4-chloro-3-fluorophenyl)-N-(2-methoxyethyl)-1,4-oxazepane-6-carboxamide | 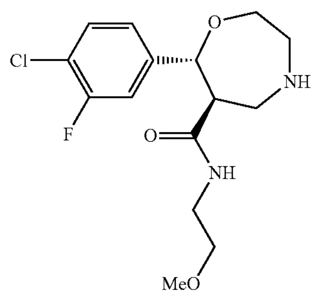 [SMILES: COCCNC(=O)[C@@H]1CNCCO[C@H]1c1ccc(Cl)c(F)c1] | HCl | 331.0 |

TABLE 1-87

| Ex. No. | IUPAC name | structure | salt | MS |
|---|---|---|---|---|
| 396 | (6R,7R)-7-(4-chloro-3-fluorophenyl)-N-methoxy-N-methyl-1,4-oxazepane-6-carboxamide | 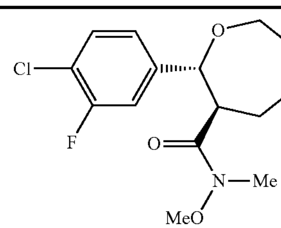 | HCl | 317.3 |
| 397 | N-[(6R,7S)-7-(4-chloro-3-fluoro-phenyl)-1,4-oxazepan-6-yl]acetamide | 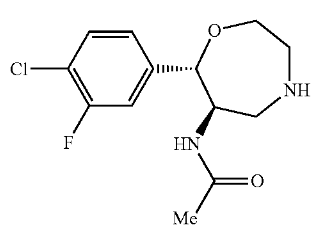 | free amine | 287.2 |

TABLE 1-87-continued

| Ex. No. | IUPAC name | structure | salt | MS |
|---|---|---|---|---|
| 398 | N-[(6R,7S)-7-(4-chloro-3-fluorophenyl)-1,4-oxazepan-6-yl]methanesulfonamide | 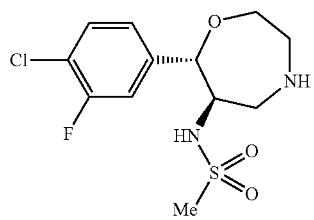 [SMILES: CS(=O)(=O)N[C@@H]1CNCCO[C@H]1c1ccc(Cl)c(F)c1] | HCl | 323.3 |
| 399 | N-[(6R,7S)-7-(4-chloro-3-fluorophenyl)-1,4-oxazepan-6-yl]ethanesulfonamide | 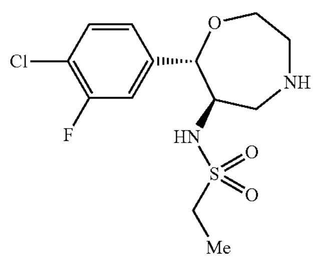 [SMILES: CCS(=O)(=O)N[C@@H]1CNCCO[C@H]1c1ccc(Cl)c(F)c1] | HCl | 337.0 |
| 400 | N-[(6R,7S)-7-(4-chloro-3-fluorophenyl)-1,4-oxazepan-6-yl]-N'-methylsulfamide | 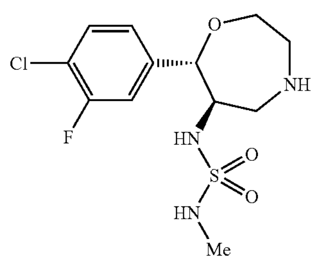 [SMILES: CNS(=O)(=O)N[C@@H]1CNCCO[C@H]1c1ccc(Cl)c(F)c1] | HCl | 337.9 |
| 401 | [(6R*,7S*)-7-(4-chloro-3-methylphenyl)-1,4-oxazepan-6-yl]methanol (retention time short) | 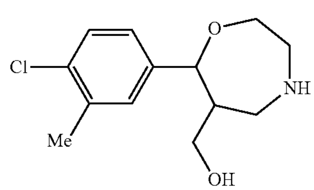 [SMILES: Cc1cc(C2OCCNCC2CO)ccc1Cl] | HCl | 256.0 |

TABLE 1-88

| Ex. No. | IUPAC name | structure | salt | MS |
|---|---|---|---|---|
| 402 | [(6R*,7S*)-7-(4-chloro-3-methylphenyl)-1,4-oxazepan-6-yl]methanol (retention time long) | 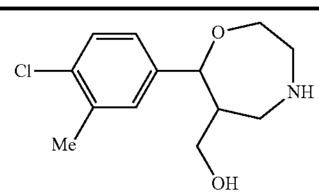 | HCl | 256.0 |
| 403 | N-{[(6R*,7S*)-7-(4-chloro-3-methylphenyl)-1,4-oxazepan-6-yl]methyl}-2-methoxyacetamide (derived from compound of Example 401) | 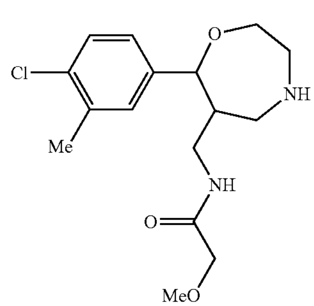 [SMILES: COCC(=O)NCC1CNCCOC1c1ccc(Cl)c(C)c1] | HCl | 327.4 |

TABLE 1-88-continued

| Ex. No. | IUPAC name | structure | salt | MS |
|---|---|---|---|---|
| 404 | 1-{[(6R*,7S*)-7-(4-chloro-3-methylphenyl)-1,4-oxazepan-6-yl]methyl}-3-(5-oxo-4,5-dihydro-1,2,4-oxadiazol-3-yl)pyridin-2(1H)-one (derived from compound of Example 401) | 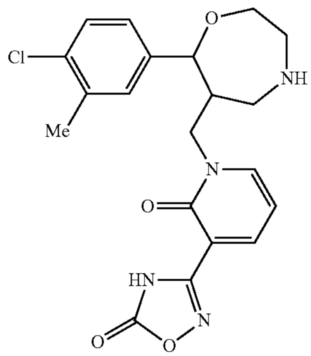 [SMILES: Cc1cc(C2OCCNCC2Cn2cccc(-c3noc(=O)[nH]3)c2=O)ccc1Cl] | HCl | 417.2 |
| 405 | [(6R*,7S*)-7-(3-chloro-4-methylphenyl)-1,4-oxazepan-6-yl]methanol (retention time short) | 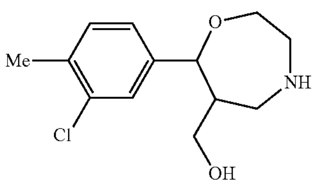 [SMILES: Cc1ccc(C2OCCNCC2CO)cc1Cl] | HCl | 256.3 |
| 406 | [(6R*,7S*)-7-(3-chloro-4-methylphenyl)-1,4-oxazepan-6-yl]methanol (retention time long) | 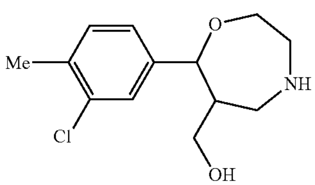 [SMILES: Cc1ccc(C2OCCNCC2CO)cc1Cl] | HCl | 256.0 |

TABLE 1-89

| Ex. No. | IUPAC name | structure | salt | MS |
|---|---|---|---|---|
| 407 | N-{[(6R*,7S*)-7-(3-chloro-4-methylphenyl)-1,4-oxazepan-6-yl]methyl}-2-methoxyacetamide (derived from compound of Example 405) | 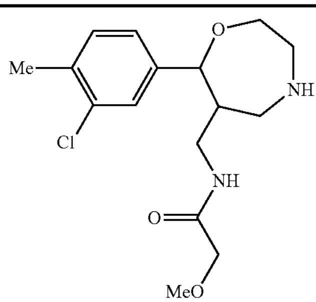 | HCl | 327.4 |
| 408 | 1-{[(6R*,7S*)-7-(3-chloro-4-methylphenyl)-1,4-oxazepan-6-yl]methyl}-3-(5-oxo-4,5-dihydro-1,2,4-oxadiazol-3-yl)pyridin-2(1H)-one (derived from compound of Example 405) | 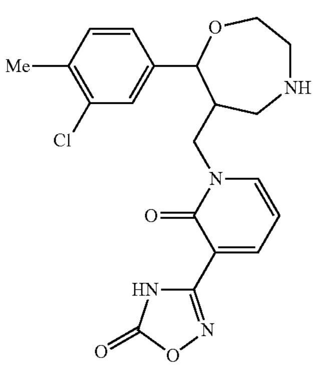 [SMILES: Cc1ccc(C2OCCNCC2Cn2cccc(-c3noc(=O)[nH]3)c2=O)cc1Cl] | HCl | 417.2 |

TABLE 1-89-continued

| Ex. No. | IUPAC name | structure | salt | MS |
|---|---|---|---|---|
| 409 | N-{[(6R*,7S*)-7-(3-chloro-4-methylphenyl)-1,4-oxazepan-6-yl]methyl}methane-sulfonamide (derived from compound of Example 405) | 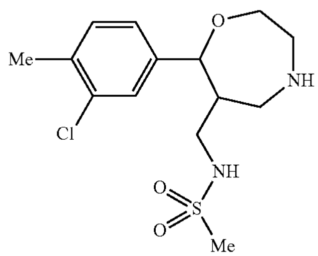 [SMILES: Cc1ccc(C2OCCNCC2CNS(C)(=O)=O)cc1Cl] | HCl | 333.2 |
| 410 | [(6RS,7SR)-7-(1-benzothiophen-2-yl)-1,4-oxazepan-6-yl]methanol | 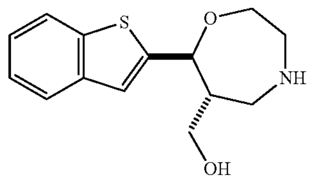 | HCl | 264.2 |
| 411 | ethyl (5RS,6RS)-6-(3,4-dichlorophenyl)-1,4-oxazepane-5-carboxylate | 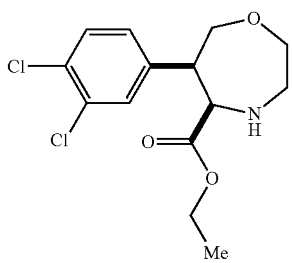 | HCl | 318.1 |

TABLE 1-90

| Ex. No. | IUPAC name | structure | salt | MS |
|---|---|---|---|---|
| 412 | ethyl (5RS,6RS)-6-(3,4-dichlorophenyl)-1,4-oxazepane-5-carboxylate | 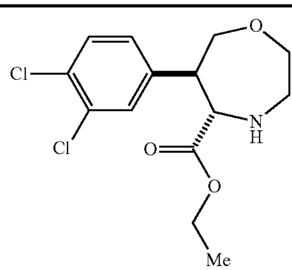 | HCl | 318.2 |
| 413 | (7RS)-7-(3,4-dichlorophenyl)-7-[(4-methoxyphenoxy)methyl]-1,4-oxazepane | 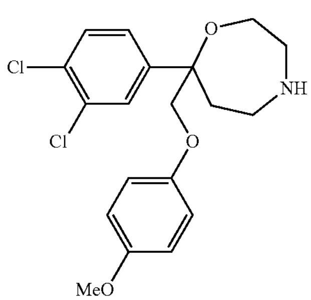 [SMILES: COc1ccc(OCC2(c3ccc(Cl)c(Cl)c3)CCNCCO2)cc1] | HCl | 382.1 |
| 414 | [(7R)-7-(3,4-dichlorophenyl)-1,4-oxazepan-7-yl]methanol | 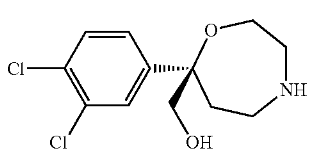 [SMILES: OC[C@]1(c2ccc(Cl)c(Cl)c2)CCNCCO1] | HCl | 276.1 |

TABLE 1-90-continued

| Ex. No. | IUPAC name | structure | salt | MS |
|---|---|---|---|---|
| 415 | 2-{[(7R)-7-(3,4-dichlorophenyl)-1,4-oxazepan-7-yl]methoxy}ethanol | 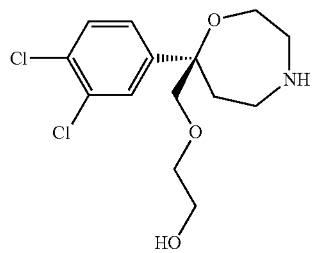 [SMILES: OCCOC[C@]1(c2ccc(Cl)c(Cl)c2)CCNCCO1] | HCl | 320.1 |
| 416 | 2-{[(7S)-7-(3,4-dichlorophenyl)-1,4-oxazepan-7-yl]methoxy}ethanol | 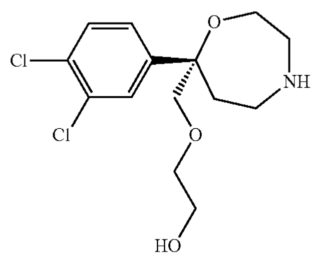 [SMILES: OCCOC[C@@]1(c2ccc(Cl)c(Cl)c2)CCNCCO1] | HCl | 320.1 |

TABLE 1-91

| Ex. No. | IUPAC name | structure | salt | MS |
|---|---|---|---|---|
| 417 | 3-{[(7S)-7-(3,4-dichlorophenyl)-1,4-oxazepan-7-yl]methoxy}propane-1,2-diol | 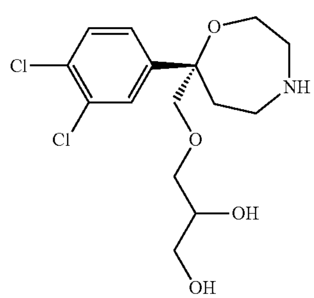 [SMILES: OCC(O)COC[C@@]1(c2ccc(Cl)c(Cl)c2)CCNCCO1] | HCl | 350.1 |
| 418 | 2-{[(7R)-7-(3,4-dichlorophenyl)-1,4-oxazepan-7-yl]methoxy}acetamide | 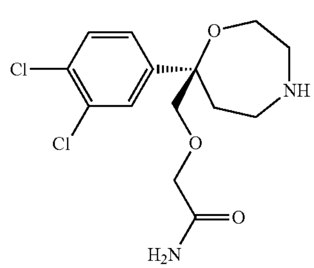 [SMILES: NC(=O)COC[C@]1(c2ccc(Cl)c(Cl)c2)CCNCCO1] | HCl | 333.1 |
| 419 | (7RS)-7-(3,4-dichlorophenyl)-7-[(methylsulfonyl)methyl]-1,4-oxazepane | 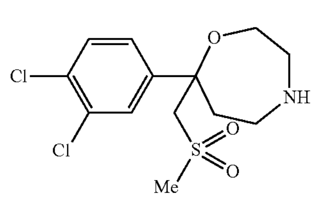 [SMILES: CS(=O)(=O)CC1(c2ccc(Cl)c(Cl)c2)CCNCCO1] | HCl | 338.2 |

TABLE 1-91-continued

| Ex. No. | IUPAC name | structure | salt | MS |
|---|---|---|---|---|
| 420 | 2-{[(7RS)-7-(3,4-dichlorophenyl)-1,4-oxazepan-7-yl]methyl}-1H-isoindole-1,3(2H)-dione | 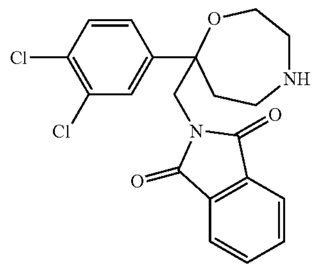 [SMILES: O=C1c2ccccc2C(=O)N1CC1(c2ccc(Cl)c(Cl)c2)CCNCCO1] | HCl | 405.1 |
| 421 | 1-[(7RS)-7-(3,4-dichlorophenyl)-1,4-oxazepan-7-yl]methanamine | 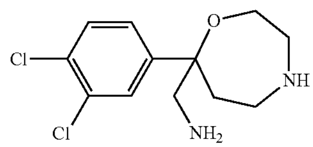 [SMILES: NCC1(c2ccc(Cl)c(Cl)c2)CCNCCO1] | HCl | 275.2 |

TABLE 1-92

| Ex. No. | IUPAC name | structure | salt | MS |
|---|---|---|---|---|
| 422 | N-{[(7RS)-7-(3,4-dichlorophenyl)-1,4-oxazepan-7-yl]methyl}acetamide | 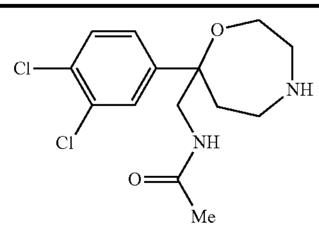 | HCl | 317.2 |
| 423 | N-{[(7S)-7-(3,4-dichlorophenyl)-1,4-oxazepan-7-yl]methyl}acetamide | 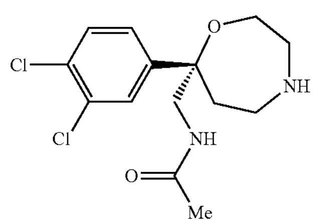 [SMILES: CC(=O)NC[C@@]1(c2ccc(Cl)c(Cl)c2)CCNCCO1] | fumarate | 317.0 |
| 424 | N-{[(7R)-7-(3,4-dichlorophenyl)-1,4-oxazepan-7-yl]methyl}acetamide | 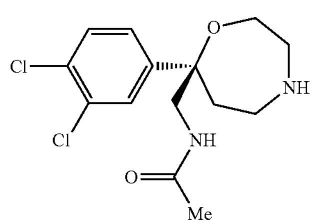 [SMILES: CC(=O)NC[C@]1(c2ccc(Cl)c(Cl)c2)CCNCCO1] | fumarate | 317.0 |
| 425 | N-{[(7S)-7-(3,4-dichlorophenyl)-1,4-oxazepan-7-yl]methyl}-3-(5-oxo-4,5-dihydro-1,2,4-oxadiazol-3-yl)benzamide | 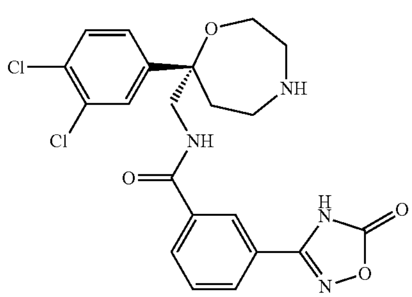 [SMILES: O=C(NC[C@@]1(c2ccc(Cl)c(Cl)c2)CCNCCO1)c1cccc(-c2noc(=O)[nH]2)c1] | HCl | 463.0 |

TABLE 1-92-continued

| Ex. No. | IUPAC name | structure | salt | MS |
|---|---|---|---|---|
| 426 | 1-{[(7RS)-7-(3,4-dichlorophenyl)-1,4-oxazepan-7-yl]methyl}urea | 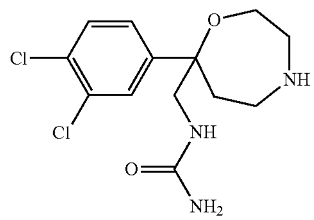 [SMILES: NC(=O)NCC1(c2ccc(Cl)c(Cl)c2)CCNCCO1] | HCl | 318.2 |

TABLE 1-93

| Ex. No. | IUPAC name | structure | salt | MS |
|---|---|---|---|---|
| 427 | 1-{[(7R)-7-(3,4-dichlorophenyl)-1,4-oxazepan-7-yl]methyl}urea | 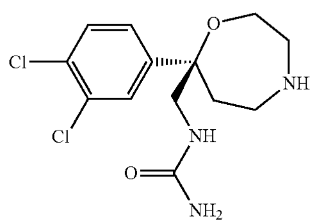 [SMILES: NC(=O)NC[C@]1(c2ccc(Cl)c(Cl)c2)CCNCCO1] | HCl | 318.1 |
| 428 | 1-{[(7S)-7-(3,4-dichlorophenyl)-1,4-oxazepan-7-yl]methyl}urea | 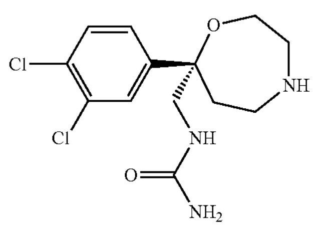 [SMILES: NC(=O)NC[C@@]1(c2ccc(Cl)c(Cl)c2)CCNCCO1] | HCl | 318.1 |
| 429 | 1-{[(7RS)-7-(3,4-dichlorophenyl)-1,4-oxazepan-7-yl]methyl}-3-ethylurea | 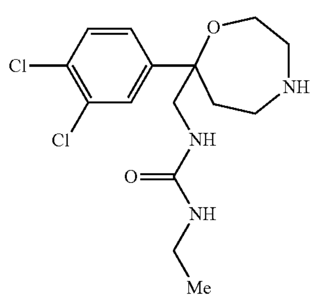 [SMILES: CCNC(=O)NCC1(c2ccc(Cl)c(Cl)c2)CCNCCO1] | HCl | 346.3 |
| 430 | N-{[(7S)-7-(3,4-dichlorophenyl)-1,4-oxazepan-7-yl]methyl}thiomorpholine-4-carboxamide 1,1-dioxide | 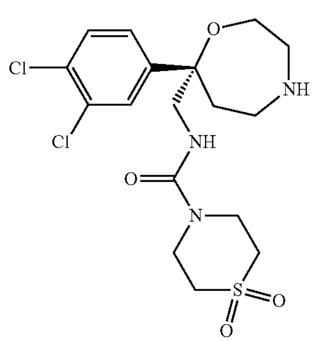 [SMILES: O=C(NC[C@@]1(c2ccc(Cl)c(Cl)c2)CCNCCO1)N1CCS(=O)(=O)CC1] | HCl | 436.2 |

TABLE 1-93-continued

| Ex. No. | IUPAC name | structure | salt | MS |
|---|---|---|---|---|
| 431 | N-{[(7R)-7-(3,4-dichlorophenyl)-1,4-oxazepan-7-yl]methyl}-methanesulfonamide | 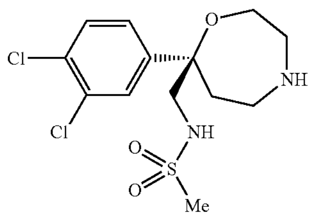 [SMILES: CS(=O)(=O)NC[C@]1(c2ccc(Cl)c(Cl)c2)CCNCCO1] | HCl | 353.0 |

TABLE 1-94

| Ex. No. | IUPAC name | structure | salt | MS |
|---|---|---|---|---|
| 432 | N-{[(7S)-7-(3,4-dichlorophenyl)-1,4-oxazepan-7-yl]methyl}-methanesulfonamide | 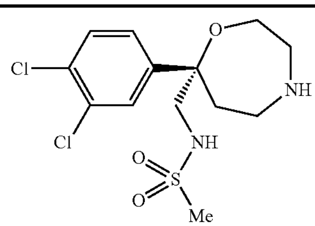 | HCl | 353.0 |
| 433 | N-{[(7R)-7-(3,4-dichlorophenyl)-1,4-oxazepan-7-yl]methyl}sulfamide | 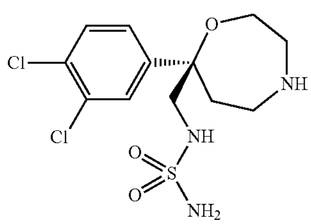 [SMILES: NS(=O)(=O)NC[C@]1(c2ccc(Cl)c(Cl)c2)CCNCCO1] | free amine | 353.9 |
| 434 | N-{[(7S)-7-(3,4-dichlorophenyl)-1,4-oxazepan-7-yl]methyl}sulfamide | 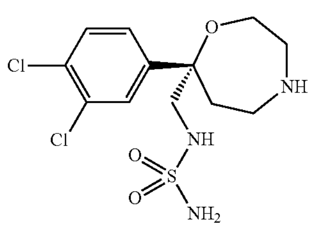 [SMILES: NS(=O)(=O)NC[C@@]1(c2ccc(Cl)c(Cl)c2)CCNCCO1] | free amine | 354.1 |
| 435 | N-{[(7R)-7-(3,4-dichlorophenyl)-1,4-oxazepan-7-yl]methyl}-N'-methylsulfamide | 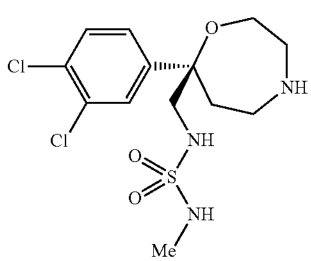 [SMILES: CNS(=O)(=O)NC[C@]1(c2ccc(Cl)c(Cl)c2)CCNCCO1] | HCl | 368.0 |
| 436 | N-{[(7S)-7-(3,4-dichlorophenyl)-1,4-oxazepan-7-yl]methyl}-N'-methylsulfamide | 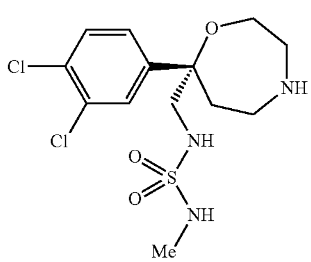 [SMILES: CNS(=O)(=O)NC[C@@]1(c2ccc(Cl)c(Cl)c2)CCNCCO1] | free amine | 368.0 |

TABLE 1-94-continued

| Ex. No. | IUPAC name | structure | salt | MS |
|---|---|---|---|---|
| 437 | N-{[(7S)-7-(3,4-dichlorophenyl)-1,4-oxazepan-7-yl]methyl}-N-methylsulfamide | 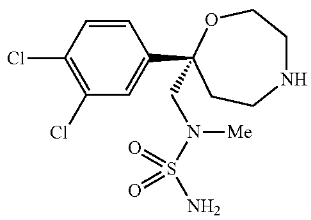 [SMILES: CN(C[C@@]1(c2ccc(Cl)c(Cl)c2)CCNCCO1)S(N)(=O)=O] | free amine | 368.0 |

TABLE 1-95

| Ex. No. | IUPAC name | structure | salt | MS |
|---|---|---|---|---|
| 438 | 3-{[(7R)-7-(3,4-dichlorophenyl)-1,4-oxazepan-7-yl]methyl}imidazolidine-2,4-dione | 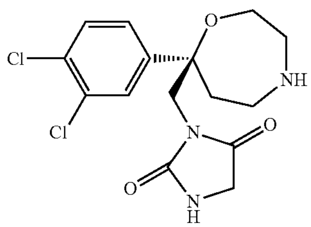 [SMILES: O=C1CNC(=O)N1C[C@]1(c2ccc(Cl)c(Cl)c2)CCNCCO1] | HCl | 358.3 |
| 439 | 3-{[(7S)-7-(3,4-dichlorophenyl)-1,4-oxazepan-7-yl]methyl}imidazolidine-2,4-dione | 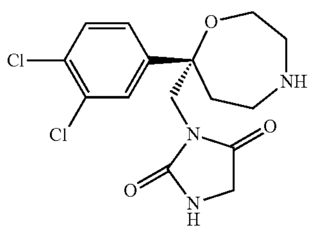 [SMILES: O=C1CNC(=O)N1C[C@@]1(c2ccc(Cl)c(Cl)c2)CCNCCO1] | HCl | 358.1 |
| 440 | [(6R*,7R*)-7-(4-chloro-3-fluorophenyl)-1,4-oxazepan-6-yl]methanol (retention time short) | 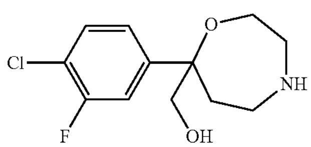 [SMILES: OCC1(c2ccc(Cl)c(F)c2)CCNCCO1] | HCl | 260.2 |
| 441 | [(6R*,7R*)-7-(4-chloro-3-fluorophenyl)-1,4-oxazepan-6-yl]methanol (retention time long) | 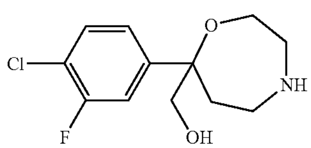 [SMILES: OCC1(c2ccc(Cl)c(F)c2)CCNCCO1] | HCl | 260.2 |
| 442 | (2RS)-2-(3,4-dichlorophenyl)-2-[(4-methoxyphenoxy)methyl]-1,4-oxazepane | 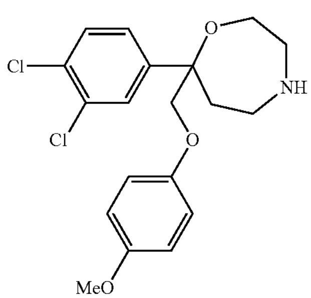 [SMILES: COc1ccc(OCC2(c3ccc(Cl)c(Cl)c3)CCNCCO2)cc1] | HCl | 382.3 |

TABLE 1-96

| Ex. No. | IUPAC name | structure | salt | MS |
|---|---|---|---|---|
| 443 | 2-{[(2RS)-2-(3,4-dichlorophenyl)-1,4-oxazepan-2-yl]methyl}-1H-isoindole-1,3(2H)-dione | 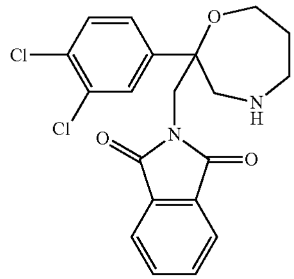 [SMILES: O=C1c2ccccc2C(=O)N1CC1(c2ccc(Cl)c(Cl)c2)CNCCCO1] | HCl | 405.1 |
| 444 | N-{[(2RS)-2-(3,4-dichlorophenyl)-1,4-oxazepan-2-yl]methyl}acetamide | 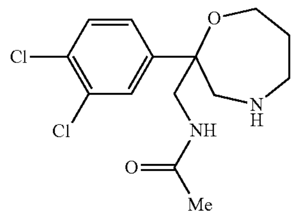 [SMILES: CC(=O)NCC1(c2ccc(Cl)c(Cl)c2)CNCCCO1] | HCl | 316.9 |
| 445 | 1-{[(2RS)-2-(3,4-dichlorophenyl)-1,4-oxazepan-2-yl]methyl}urea | 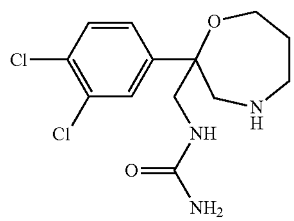 [SMILES: NC(=O)NCC1(c2ccc(Cl)c(Cl)c2)CNCCCO1] | HCl | 318.1 |
| 446 | N-{[(2RS)-2-(3,4-dichlorophenyl)-1,4-oxazepan-2-yl]methyl}sulfamide | 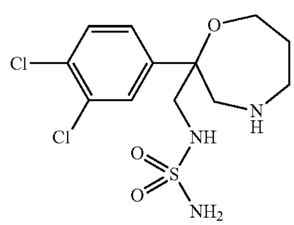 [SMILES: NS(=O)(=O)NCC1(c2ccc(Cl)c(Cl)c2)CNCCCO1] | HCl | 353.9 |
| 447 | [(6R,7S)-6-(3,4-dichlorophenyl)-1,4-oxazepan-7-yl]methanol | 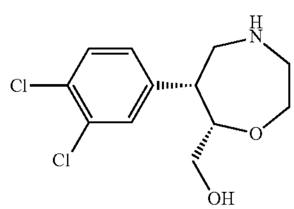 [SMILES: OC[C@H]1OCCNC[C@H]1c1ccc(Cl)c(Cl)c1] | HCl | 276.2 |

TABLE 1-97

| Ex. No. | IUPAC name | structure | salt | MS |
|---|---|---|---|---|
| 448 | [(6S,7R)-6-(3,4-dichlorophenyl)-1,4-oxazepan-7-yl]methanol | 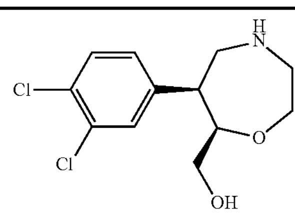 | HCl | 276.2 |

TABLE 1-97-continued

| Ex. No. | IUPAC name | structure | salt | MS |
|---|---|---|---|---|
| 449 | (6RS,7SR)-6-(3,4-dichlorophenyl)-7-(methoxymethyl)-1,4-oxazepane | 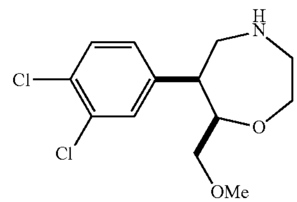 | HCl | 290.0 |
| 450 | {[(6RS,7SR)-6-(3,4-dichlorophenyl)-1,4-oxazepan-7-yl]methoxy}acetic acid | 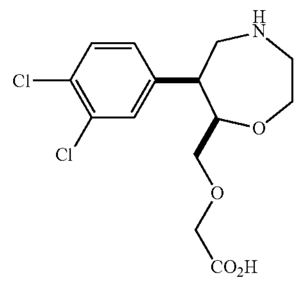 | HCl | 334.3 |
| 451 | methyl 2-{[(6RS,7SR)-6-(3,4-dichlorophenyl)-1,4-oxazepan-7-yl]methoxy}benzoate | 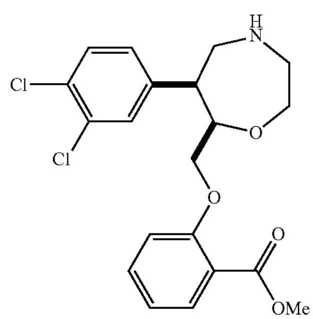 | HCl | 410.0 |
| 452 | methyl 3-{[(6RS,7SR)-6-(3,4-dichlorophenyl)-1,4-oxazepan-7-yl]methoxy}benzoate | 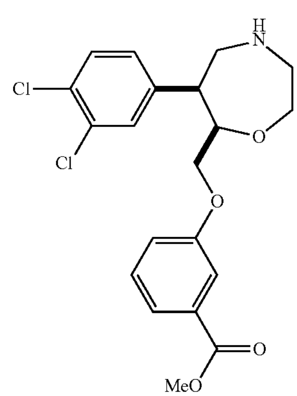 | HCl | 410.2 |

TABLE 1-98

| Ex. No. | IUPAC name | structure | salt | MS |
|---|---|---|---|---|
| 453 | N-{[(6R,7S)-6-(3,4-dichlorophenyl)-1,4-oxazepan-7-yl]methyl}acetamide | 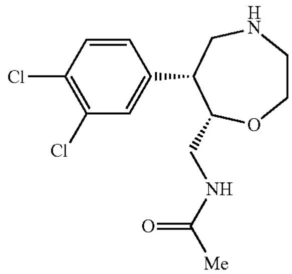 [SMILES: CC(=O)NC[C@H]1OCCNC[C@H]1c1ccc(Cl)c(Cl)c1] | HCl | 317.0 |
| 454 | N-{[(6R,7S)-6-(3,4-dichlorophenyl)-1,4-oxazepan-7-yl]methyl}-2-methoxyacetamide | 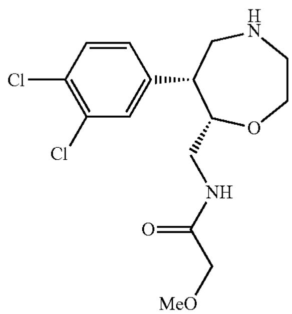 [SMILES: COCC(=O)NC[C@H]1OCCNC[C@H]1c1ccc(Cl)c(Cl)c1] | HCl | 347.3 |
| 455 | N-{[(6R,7S)-6-(3,4-dichlorophenyl)-1,4-oxazepan-7-yl]methyl}-2-methoxy-N-methylacetamide | 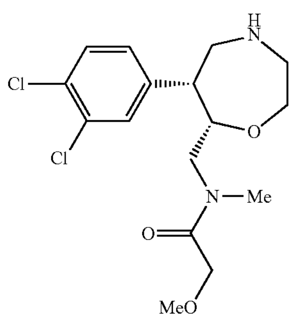 [SMILES: COCC(=O)N(C)C[C@H]1OCCNC[C@H]1c1ccc(Cl)c(Cl)c1] | HCl | 361.3 |
| 456 | N-{[(6RS,7SR)-6-(3,4-dichlorophenyl)-1,4-oxazepan-7-yl]methyl}-2-hydroxy-2-methylpropanamide | 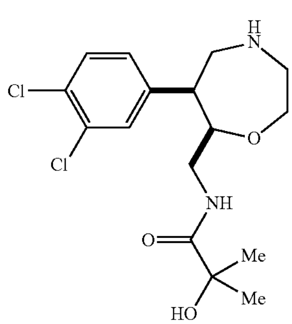 | HCl | 361.1 |

TABLE 1-99

| Ex. No. | IUPAC name | structure | salt | MS |
|---|---|---|---|---|
| 457 | N-{[(6RS,7SR)-6-(3,4-dichlorophenyl)-1,4-oxazepan-7-yl]methyl}-2-(1H-1,2,4-triazol-1-yl)acetamide | 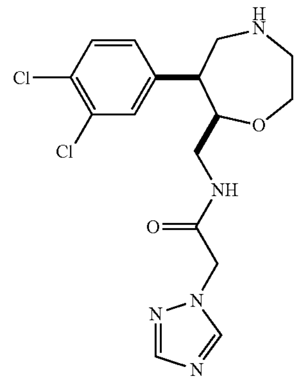 | HCl | 384.2 |
| 458 | N-{[(6RS,7SR)-6-(3,4-dichlorophenyl)-1,4-oxazepan-7-yl]methyl}benzamide | 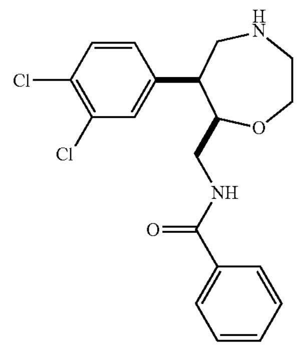 | HCl | 379.3 |
| 459 | N-{[(6RS,7SR)-6-(3,4-dichlorophenyl)-1,4-oxazepan-7-yl]methyl}-N-methylbenzamide | 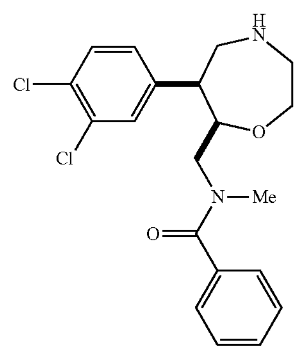 | HCl | 393.1 |
| 460 | N-{[(6R,7S)-6-(3,4-dichlorophenyl)-1,4-oxazepan-7-yl]methyl}pyridine-2-carboxamide | 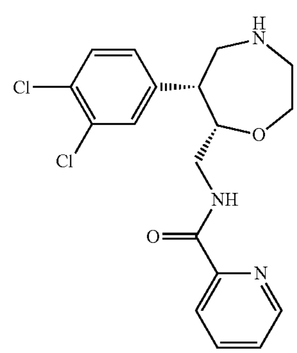 [SMILES: O=C(NC[C@H]1OCCNC[C@H]1c1ccc(Cl)c(Cl)c1)c1ccccn1] | HCl | 380.0 |

TABLE 1-100

| Ex. No. | IUPAC name | structure | salt | MS |
|---|---|---|---|---|
| 461 | N-{[(6R,7S)-6-(3,4-dichlorophenyl)-1,4-oxazepan-7-yl]methyl}-N-methylpyridine-2-carboxamide | 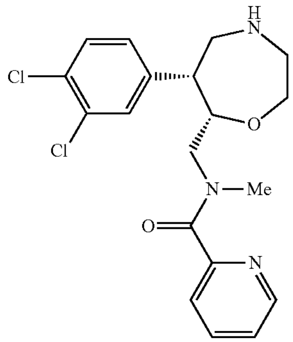 [SMILES: CN(C[C@H]1OCCNC[C@H]1c1ccc(Cl)c(Cl)c1)C(=O)c1ccccn1] | HCl | 394.1 |
| 462 | 1-{[(6RS,7SR)-6-(3,4-dichlorophenyl)-1,4-oxazepan-7-yl]methyl}-3-ethylurea | 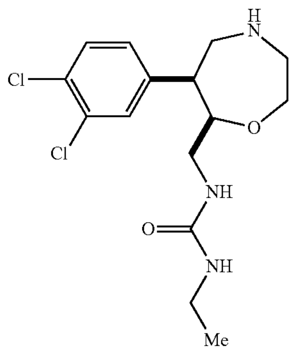 | HCl | 346.0 |
| 463 | 3-{[(6RS,7SR)-6-(3,4-dichlorophenyl)-1,4-oxazepan-7-yl]methyl}-1,1-dimethylurea | 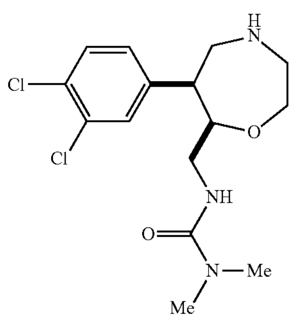 | HCl | 346.1 |
| 464 | 1-{[(6RS,7SR)-6-(3,4-dichlorophenyl)-1,4-oxazepan-7-yl]methyl}-3-(2-hydroxyethyl)urea | 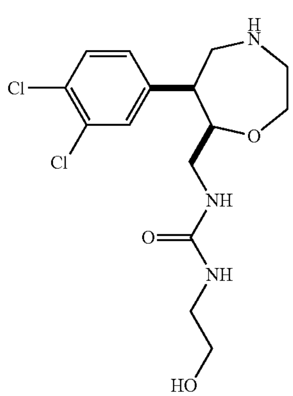 | HCl | 362.3 |

TABLE 1-101

| Ex. No. | IUPAC name | structure | salt | MS |
|---|---|---|---|---|
| 465 | 3-{[(6R,7S)-6-(3,4-dichlorophenyl)-1,4-oxazepan-7-yl]methyl}-1-(2-hydroxyethyl)-1-methylurea | 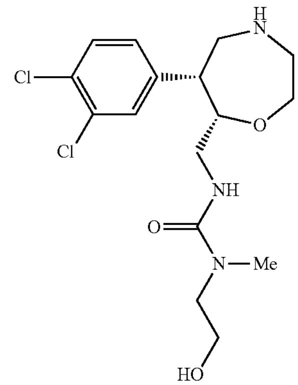 [SMILES: CN(CCO)C(=O)NC[C@H]1OCCNC[C@H]1c1ccc(Cl)c(Cl)c1] | HCl | 376.1 |
| 466 | 1-{[(6RS,7SR)-6-(3,4-dichlorophenyl)-1,4-oxazepan-7-yl]methyl}-3-(2-methoxyethyl)urea | 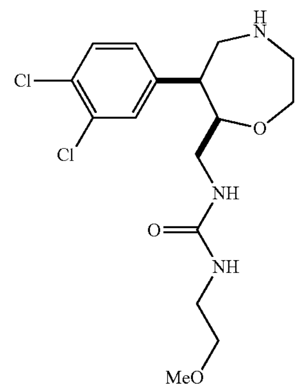 | HCl | 376.3 |
| 467 | N-{[(6R,7S)-6-(3,4-dichlorophenyl)-1,4-oxazepan-7-yl]methyl}-methanesulfonamide | 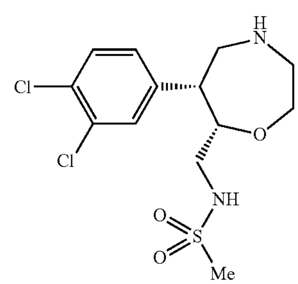 [SMILES: CS(=O)(=O)NC[C@H]1OCCNC[C@H]1c1ccc(Cl)c(Cl)c1] | HCl | 353.0 |
| 468 | N-{[(6R,7S)-6-(3,4-dichlorophenyl)-1,4-oxazepan-7-yl]methyl}propane-2-sulfonamide | 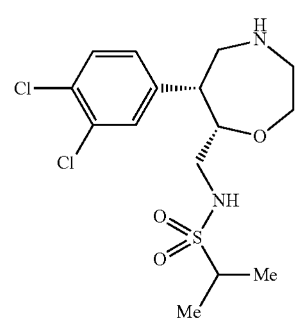 [SMILES: CC(C)S(=O)(=O)NC[C@H]1OCCNC[C@H]1c1ccc(Cl)c(Cl)c1] | HCl | 381.2 |

TABLE 1-102

| Ex. No. | IUPAC name | structure | salt | MS |
|---|---|---|---|---|
| 469 | N-{[(6R,7S)-6-(3,4-dichlorophenyl)-1,4-oxazepan-7-yl]methyl}-2-methoxyethane-sulfonamide | 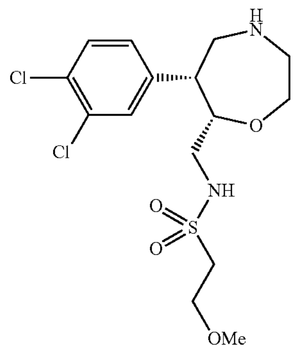 [SMILES: COCCS(=O)(=O)NC[C@H]1OCCNC[C@H]1c1ccc(Cl)c(Cl)c1] | HCl | 397.1 |
| 470 | N-{[(6R,7S)-6-(3,4-dichlorophenyl)-1,4-oxazepan-7-yl]methyl}-1,1-difluoromethane-sulfonamide | 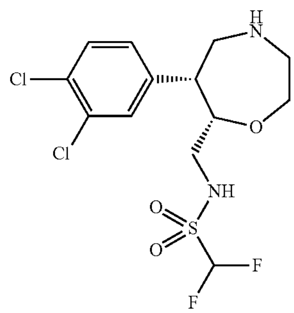 [SMILES: O=S(=O)(NC[C@H]1OCCNC[C@H]1c1ccc(Cl)c(Cl)c1)C(F)F] | HCl | 389.0 |
| 471 | N-{[(6R,7S)-6-(3,4-dichlorophenyl)-1,4-oxazepan-7-yl]methyl}-2,2,2-trifluoroethane-sulfonamide | | HCl | 421.3 |
| 472 | N-{[(6RS,7SR)-6-(3,4-dichlorophenyl)-1,4-oxazepan-7-yl]methyl}-N-methylmethane-sulfonamide | | HCl | 367.3 |

TABLE 1-103

| Ex. No. | IUPAC name | structure | salt | MS |
|---|---|---|---|---|
| 473 | N-{[(6RS,7SR)-6-(3,4-dichlorophenyl)-1,4-oxazepan-7-yl]methyl}-N-(4-methoxybenzyl)-methanesulfonamide | 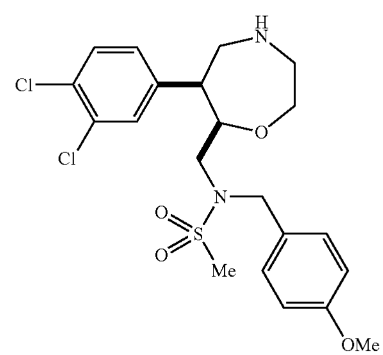 | HCl | 473.2 |
| 474 | N-{[(6RS,7SR)-6-(3,4-dichlorophenyl)-1,4-oxazepan-7-yl]methyl}-benzenesulfonamide | 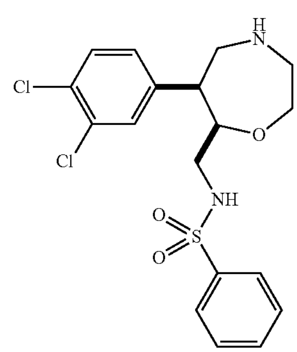 | HCl | 415.1 |

TABLE 1-103-continued

| Ex. No. | IUPAC name | structure | salt | MS |
|---|---|---|---|---|
| 475 | N-{[(6R,7S)-6-(3,4-dichlorophenyl)-1,4-oxazepan-7-yl]methyl}furan-2-sulfonamide | 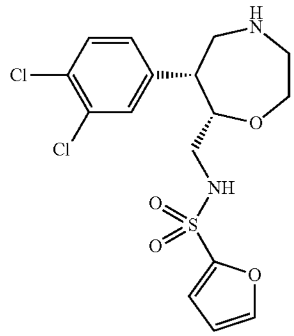 [SMILES: O=S(=O)(NC[C@H]1OCCNC[C@H]1c1ccc(Cl)c(Cl)c1)c1ccco1] | HCl | 405.2 |
| 476 | 1-[(6R,7S)-6-(3,4-dichlorophenyl)-1,4-oxazepan-7-yl]-N-(1-methylethyl)-methanesulfonamide | 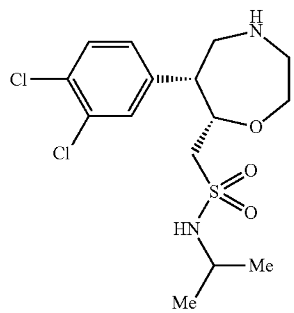 [SMILES: CC(C)NS(=O)(=O)C[C@H]1OCCNC[C@H]1c1ccc(Cl)c(Cl)c1] | HCl | 381.2 |

TABLE 1-104

| Ex. No. | IUPAC name | structure | salt | MS |
|---|---|---|---|---|
| 477 | N-(1-{[(6RS,7SR)-6-(3,4-dichlorophenyl)-1,4-oxazepan-7-yl]methyl}piperidin-4-yl)acetamide | 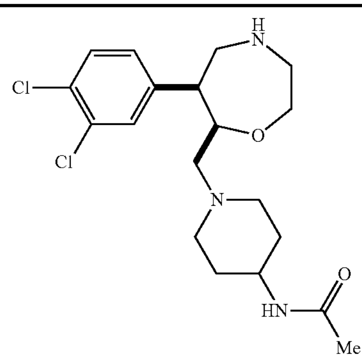 | 2HCl | 400.2 |
| 478 | ethyl 1-{[(6R,7S)-6-(3,4-dichlorophenyl)-1,4-oxazepan-7-yl]methyl}piperidine-4-carboxylate | 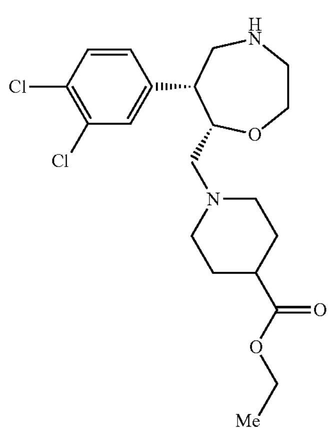 [SMILES: CCOC(=O)C1CCN(C[C@H]2OCCNC[C@H]2c2ccc(Cl)c(Cl)c2)CC1] | 2HCl | 415.2 |

TABLE 1-104-continued

| Ex. No. | IUPAC name | structure | salt | MS |
|---|---|---|---|---|
| 479 | 1-{[(6R,7S)-6-(3,4-dichlorophenyl)-1,4-oxazepan-7-yl]methyl}piperidine-4-carboxylic acid | 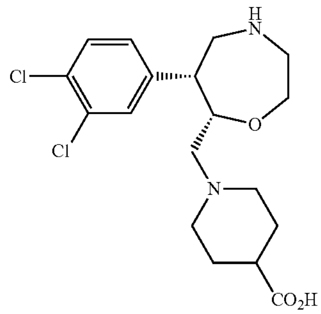 [SMILES: O=C(O)C1CCN(C[C@H]2OCCNC[C@H]2c2ccc(Cl)c(Cl)c2)CC1] | 2HCl | 387.2 |
| 480 | (6RS,7SR)-6-(3,4-dichlorophenyl)-7-[(4-methyl-1H-pyrazol-1-yl)methyl]-1,4-oxazepane | 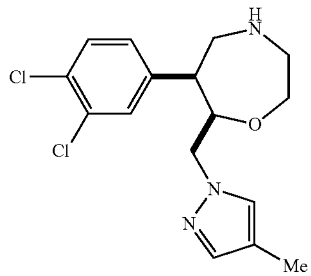 | HCl | 340.1 |

TABLE 1-105

| Ex. No. | IUPAC name | structure | salt | MS |
|---|---|---|---|---|
| 481 | 2-{[(6R,7S)-6-(3,4-dichlorophenyl)-1,4-oxazepan-7-yl]methyl}pyridazin-3(2H)-one | 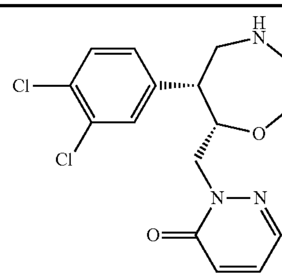 | HCl | 354.2 |
| 482 | 3-{[(6RS,7SR)-6-(3,4-dichlorophenyl)-1,4-oxazepan-7-yl]methyl}quinazoline-2,4(1H,3H)-dione | 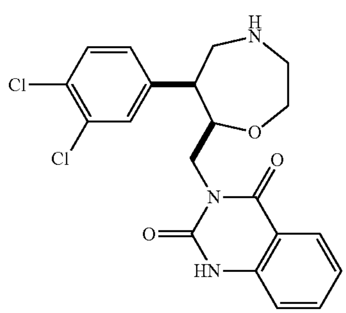 | HCl | 420.1 |
| 483 | [(6RS,7RS)-6-(3,4-dichlorophenyl)-1,4-oxazepan-7-yl]acetonitrile | 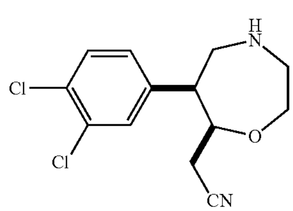 | HCl | 285.2 |

TABLE 1-105-continued

| Ex. No. | IUPAC name | structure | salt | MS |
|---|---|---|---|---|
| 484 | N-{2-[(6RS,7RS)-6-(3,4-dichlorophenyl)-1,4-oxazepan-7-yl]methyl}acetamide | 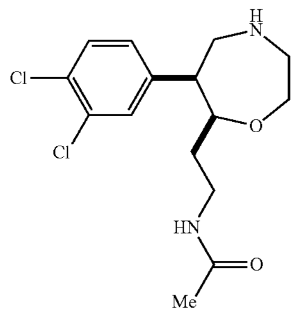 | HCl | 331.1 |
| 485 | N-{2-[(6RS,7RS)-6-(3,4-dichlorophenyl)-1,4-oxazepan-7-yl]ethyl}-2-methoxyacetamide | 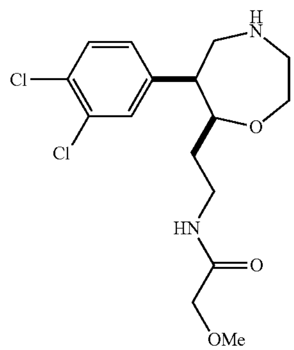 | HCl | 361.1 |

TABLE 1-106

| Ex. No. | IUPAC name | structure | salt | MS |
|---|---|---|---|---|
| 486 | N-{2-[(6RS,7RS)-6-(3,4-dichlorophenyl)-1,4-oxazepan-7-yl]ethyl}-methanesulfonamide | 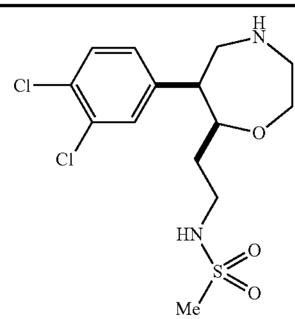 | HCl | 367.1 |
| 487 | [(6S,7S)-6-(3,4-dichlorophenyl)-1,4-oxazepan-7-yl]methanol | 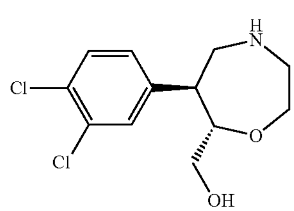 [SMILES: OC[C@H]1OCCNC[C@@H]1c1ccc(Cl)c(Cl)c1] | HCl | 276.1 |
| 488 | [(6R,7R)-6-(3,4-dichlorophenyl)-1,4-oxazepan-7-yl]methanol | 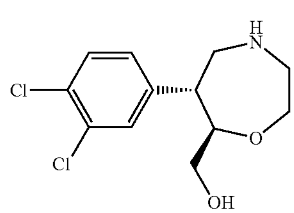 [SMILES: OC[C@@H]1OCCNC[C@H]1c1ccc(Cl)c(Cl)c1] | HCl | 276.1 |

TABLE 1-106-continued

| Ex. No. | IUPAC name | structure | salt | MS |
|---|---|---|---|---|
| 489 | (1R)-1-[(6S,7S)-6-(3,4-dichlorophenyl)-1,4-oxazepan-7-yl]ethane-1,2-diol | 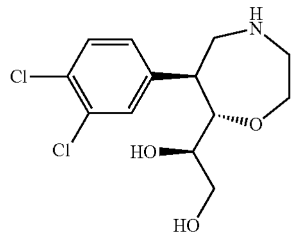 [SMILES: OC[C@@H](O)[C@H]1OCCNC[C@@H]1c1ccc(Cl)c(Cl)c1] | HCl | 306.0 |
| 490 | (1S)-1-[(6S,7S)-6-(3,4-dichlorophenyl)-1,4-oxazepan-7-yl]ethane-1,2-diol | 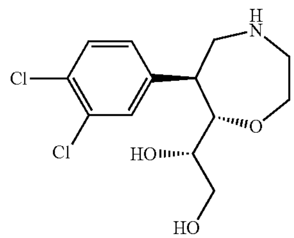 [SMILES: OC[C@H](O)[C@H]1OCCNC[C@@H]1c1ccc(Cl)c(Cl)c1] | HCl | 306.1 |

TABLE 1-107

| Ex. No. | IUPAC name | structure | salt | MS |
|---|---|---|---|---|
| 491 | 2-[(6R,7R)-6-(3,4-dichlorophenyl)-1,4-oxazepan-7-yl]propane-1,2,3-triol | 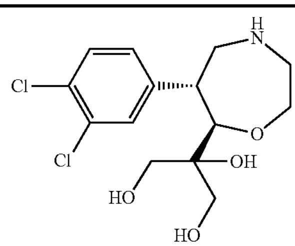 | HCl | 336.0 |
| 492 | 2-[(6S,7S)-6-(3,4-dichlorophenyl)-1,4-oxazepan-7-yl]propane-1,2,3-triol | 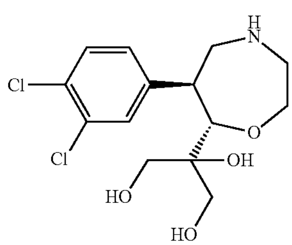 [SMILES: OCC(O)(CO)[C@H]1OCCNC[C@@H]1c1ccc(Cl)c(Cl)c1] | HCl | 335.9 |
| 493 | (1RS)-1-[(6SR,7SR)-6-(3,4-dichlorophenyl)-1,4-oxazepan-7-yl]-2-(methylsulfonyl)ethanol | 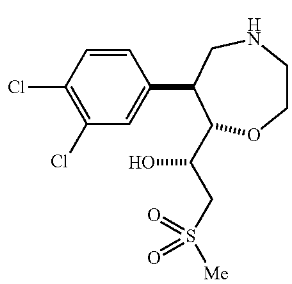 | HCl | 367.9 |

TABLE 1-107-continued

| Ex. No. | IUPAC name | structure | salt | MS |
|---|---|---|---|---|
| 494 | (1RS)-1-[(6RS,7RS)-6-(3,4-dichlorophenyl)-1,4-oxazepan-7-yl]-2-(methylsulfonyl)ethanol | 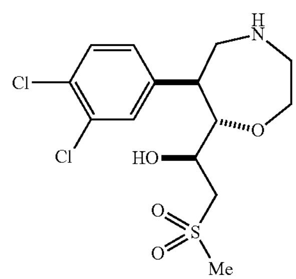 | HCl | 367.9 |
| 495 | 2-{[(6RS,7RS)-6-(3,4-dichlorophenyl)-1,4-oxazepan-7-yl]methoxy}ethanol | 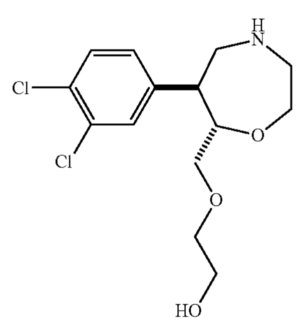 | HCl | 320.0 |

TABLE 1-108

| Ex. No. | IUPAC name | structure | salt | MS |
|---|---|---|---|---|
| 496 | 2-{[(6R,7R)-6-(3,4-dichlorophenyl)-1,4-oxazepan-7-yl]methoxy}ethanol | 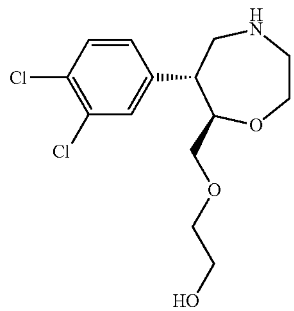 [SMILES: OCCOC[C@@H]1OCCNC[C@H]1c1ccc(Cl)c(Cl)c1] | HCl | 320.1 |
| 497 | N-(2-{[(6R,7R)-6-(3,4-dichlorophenyl)-1,4-oxazepan-7-yl]methoxy}ethyl)-acetamide | 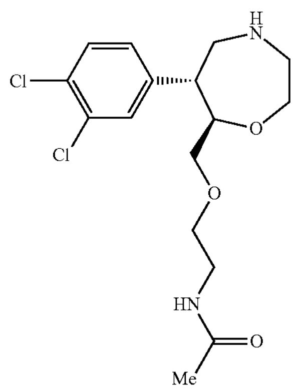 [SMILES: CC(=O)NCCOC[C@@H]1OCCNC[C@H]1c1ccc(Cl)c(Cl)c1] | HCl | 361.1 |

TABLE 1-108-continued

| Ex. No. | IUPAC name | structure | salt | MS |
|---|---|---|---|---|
| 498 | N-(2-{[(6R,7R)-6-(3,4-dichlorophenyl)-1,4-oxazepan-7-yl]methoxy}ethyl)-methanesulfonamide | 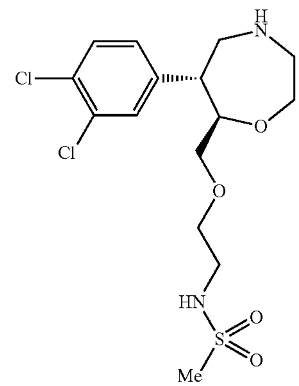 [SMILES: CS(=O)(=O)NCCOC[C@@H]1OCCNC[C@H]1c1ccc(Cl)c(Cl)c1] | HCl | 397.1 |
| 499 | {[(6RS,7RS)-6-(3,4-dichlorophenyl)-1,4-oxazepan-7-yl]methoxy}acetic acid | 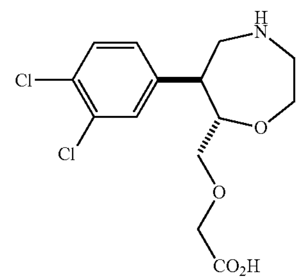 | HCl | 332.2 |

TABLE 1-109

| Ex. No. | IUPAC name | structure | salt | MS |
|---|---|---|---|---|
| 500 | ethyl {[(6RS,7RS)-6-(3,4-dichlorophenyl)-1,4-oxazepan-7-yl]methoxy}acetate | 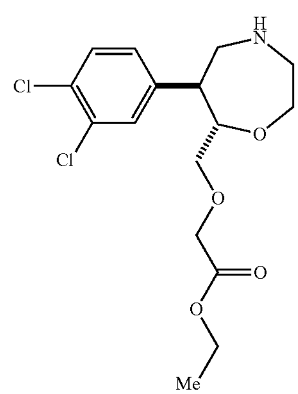 | HCl | 362.0 |
| 501 | [(6R,7R)-6-(3,4-dichlorophenyl)-1,4-oxazepan-7-yl]methyl methanesulfonate | 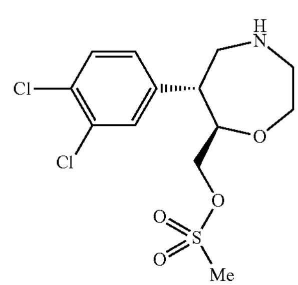 [SMILES: CS(=O)(=O)OC[C@@H]1OCCNC[C@H]1c1ccc(Cl)c(Cl)c1] | HCl | 354.2 |

TABLE 1-109-continued

| Ex. No. | IUPAC name | structure | salt | MS |
|---|---|---|---|---|
| 502 | methyl 2-{[(6S,7S)-6-(3,4-dichlorophenyl)-1,4-oxazepan-7-yl]methoxy}benzoate | 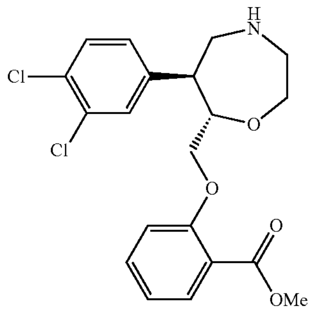 [SMILES: COC(=O)c1ccccc1OC[C@H]1OCCNC[C@@H]1c1ccc(Cl)c(Cl)c1] | HCl | 410.0 |
| 503 | methyl 2-{[(6R,7R)-6-(3,4-dichlorophenyl)-1,4-oxazepan-7-yl]methoxy}benzoate | 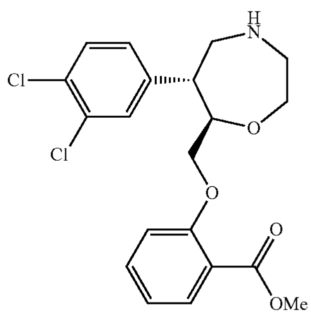 [SMILES: COC(=O)c1ccccc1OC[C@@H]1OCCNC[C@H]1c1ccc(Cl)c(Cl)c1] | HCl | 410.3 |

TABLE 1-110

| Ex. No. | IUPAC name | structure | salt | MS |
|---|---|---|---|---|
| 504 | methyl 3-{[(6R,7R)-6-(3,4-dichlorophenyl)-1,4-oxazepan-7-yl]methoxy}benzoate | 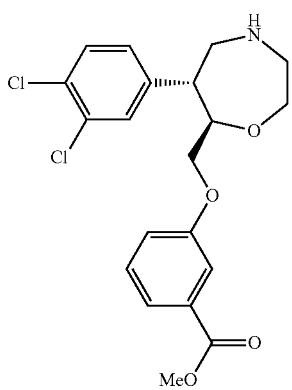 [SMILES: COC(=O)c1cccc(OC[C@@H]2OCCNC[C@H]2c2ccc(Cl)c(Cl)c2)c1] | HCl | 410.3 |
| 505 | ((6RS,7RS)-6-(3,4-dichlorophenyl)-7-[(methylsulfonyl)methyl]-1,4-oxazepane | 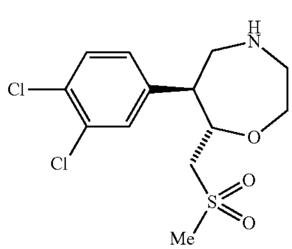 [SMILES: CS(=O)(=O)C[C@H]1OCCNC[C@@H]1c1ccc(Cl)c(Cl)c1] | HCl | 337.9 |

TABLE 1-110-continued

| Ex. No. | IUPAC name | structure | salt | MS |
|---|---|---|---|---|
| 506 | N-{[(6RS,7RS)-6-(3,4-dichlorophenyl)-1,4-oxazepan-7-yl]methyl}acetamide | 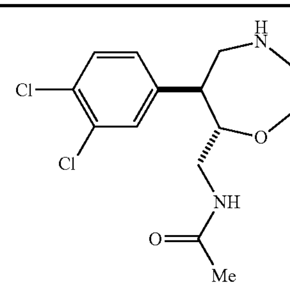 | HCl | 317.0 |
| 507 | N-{[(6R,7R)-6-(3,4-dichlorophenyl)-1,4-oxazepan-7-yl]methyl}-2-hydroxyacetamide | 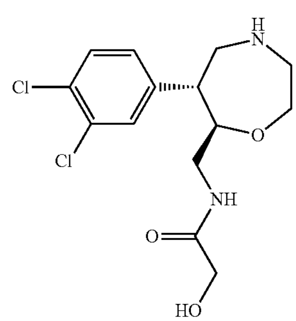 [SMILES: O=C(CO)NC[C@@H]1OCCNC[C@H]1c1ccc(Cl)c(Cl)c1] | HCl | 333.4 |

TABLE 1-111

| Ex. No. | IUPAC name | structure | salt | MS |
|---|---|---|---|---|
| 508 | N-{[(6R,7R)-6-(3,4-dichlorophenyl)-1,4-oxazepan-7-yl]methyl}-2-methoxy-acetamide | 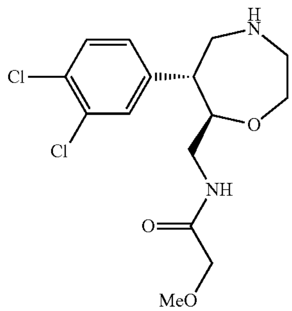 [SMILES: COCC(=O)NC[C@@H]1OCCNC[C@H]1c1ccc(Cl)c(Cl)c1] | HCl | 347.3 |
| 509 | N-{[(6RS,7RS)-6-(3,4-dichloro-phenyl)-1,4-oxazepan-7-yl]methyl}-2-(1H-1,2,4-triazol-1-yl)acetamide | 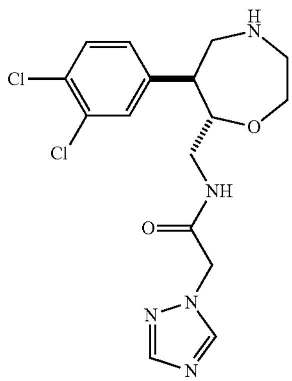 | HCl | 383.9 |

TABLE 1-111-continued

| Ex. No. | IUPAC name | structure | salt | MS |
|---|---|---|---|---|
| 510 | N-{[(6RS,7RS)-6-(3,4-dichloro-phenyl)-1,4-oxazepan-7-yl]methyl}benzamide | 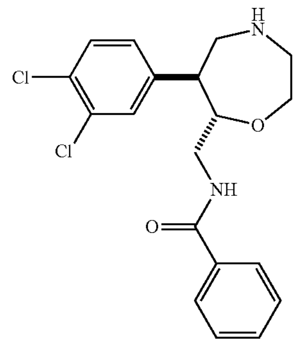 | HCl | 379.1 |
| 511 | N-{[(6RS,7RS)-6-(3,4-dichloro-phenyl)-1,4-oxazepan-7-yl]methyl}-methane-sulfonamide | 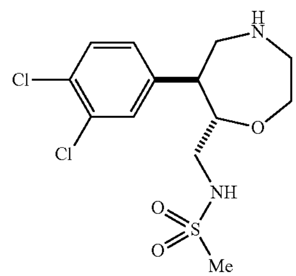 | HCl | 353.0 |

TABLE 1-112

| Ex. No. | IUPAC name | structure | salt | MS |
|---|---|---|---|---|
| 512 | N-(1-{[(6R,7R)-6-(3,4-dichlorophenyl)-1,4-oxazepan-7-yl]methyl}piperidin-4-yl)acetamide | 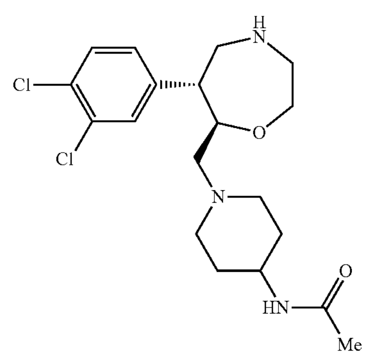 [SMILES: CC(=O)NC1CCN(C[C@@H]2OCCNC[C@H]2c2ccc(Cl)c(Cl)c2)CC1] | 2HCl | 400.3 |
| 513 | (6RS,7RS)-6-(3,4-dichlorophenyl)-7-[(4-methyl-1H-pyrazol-1-yl)methyl]-1,4-oxazepane | 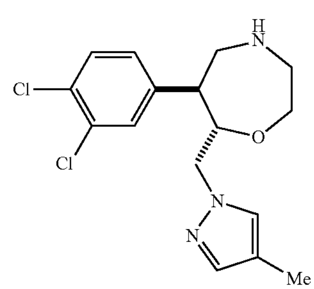 | HCl | 340.0 |

TABLE 1-112-continued

| Ex. No. | IUPAC name | structure | salt | MS |
|---|---|---|---|---|
| 514 | 1-{[(6R,7R)-6-(3,4-dichlorophenyl)-1,4-oxazepan-7-yl]methyl}pyridin-2(1H)-one | 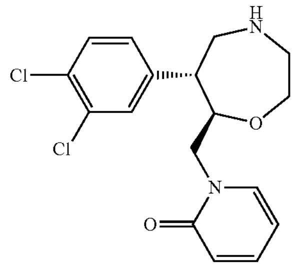 [SMILES: O=c1ccccn1C[C@@H]1OCCNC[C@H]1c1ccc(Cl)c(Cl)c1] | HCl | 353.0 |
| 515 | 2-{[(6R,7R)-6-(3,4-dichlorophenyl)-1,4-oxazepan-7-yl]methyl}pyridazin-3(2H)-one | 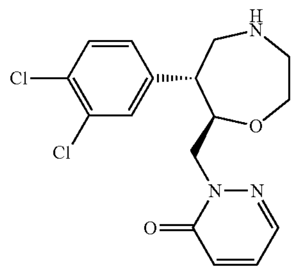 [SMILES: O=c1cccnn1C[C@@H]1OCCNC[C@H]1c1ccc(Cl)c(Cl)c1] | HCl | 354.2 |
| 516 | [(6RS,7SR)-6-(3,4-dichlorophenyl)-1,4-oxazepan-7-yl]acetonitrile | 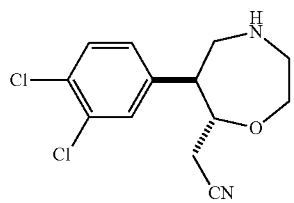 | HCl | 284.9 |

TABLE 1-113

| Ex. No. | IUPAC name | structure | salt | MS |
|---|---|---|---|---|
| 517 | N-{2-[(6R,7S)-6-(3,4-dihclorophenyl)-1,4-oxazepan-7-yl]ethyl}acetamide | 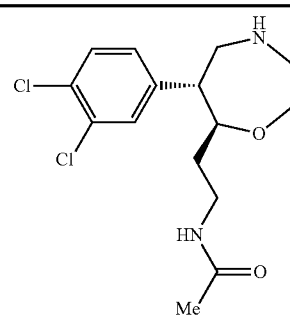 | HCl | 331.1 |
| 518 | N-{2-[(6R,7S)-6-(3,4-dichlorophenyl)-1,4-oxazepan-7-yl]ethyl}-methanesulfonamide | 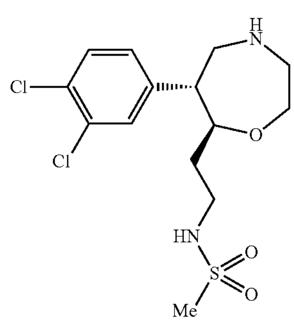 [SMILES: CS(=O)(=O)NCC[C@@H]1OCCNC[C@H]1c1ccc(Cl)c(Cl)c1] | HCl | 367.1 |

TABLE 1-113-continued

| Ex. No. | IUPAC name | structure | salt | MS |
|---|---|---|---|---|
| 519 | N-{3-[(6RS,7SR)-6-(3,4-dichlorophenyl)-1,4-oxazepan-7-yl]propyl}acetamide | 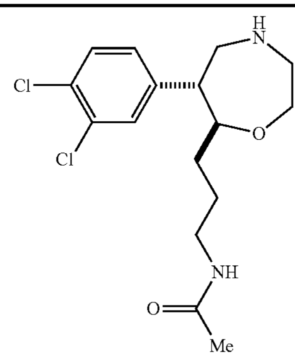 | HCl | 345.2 |
| 520 | N-{3-[(6RS,7SR)-6-(3,4-dichlorophenyl)-1,4-oxazepan-7-yl]propyl}-methanesulfonamide | 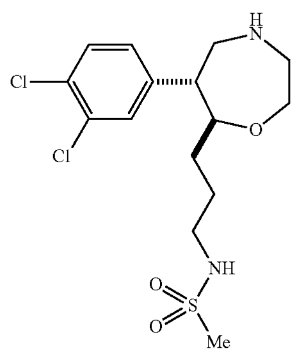 | HCl | 381.2 |

TABLE 1-114

| Ex. No. | IUPAC name | structure | salt | MS |
|---|---|---|---|---|
| 521 | N-{[(6RS,7SR)-7-(3,4-dichlorophenyl)-6-hydroxy-1,4-oxazepan-6-yl]methyl}-1,1-difluoromethane-sulfonamide | 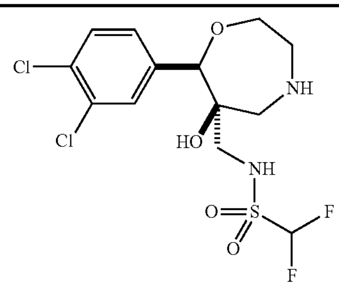 | HCl | 405.1 |
| 522 | N-{[(6RS,7SR)-7-(3,4-dichlorophenyl)-6-hydroxy-1,4-oxazepan-6-yl]methyl}propane-2-sulfonamide | 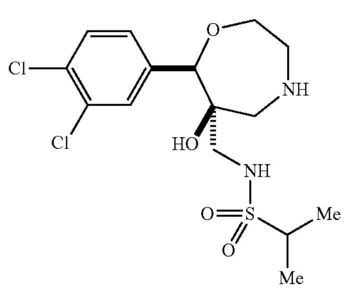 | HCl | 397.1 |

TABLE 1-114-continued

| Ex. No. | IUPAC name | structure | salt | MS |
|---|---|---|---|---|
| 523 | N-{[(6RS,7SR)-7-(3,4-dichlorophenyl)-6-methoxy-1,4-oxazepan-6-yl]methyl}methanesulfonamide | 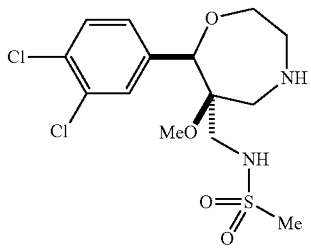 | HCl | 383.1 |
| 524 | 3-(2-{[(6R*,7S*)-7-(3,4-dichlorophenyl)-1,4-oxazepan-6-yl]oxy}pyridin-3-yl)-1,2,4-oxadiazol-5(4H)-one (retention time short) | 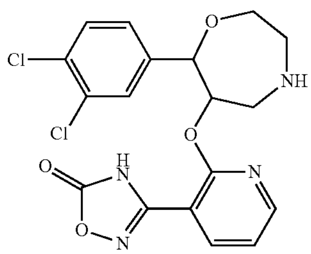 [SMILES: O=c1[nH]c(-c2cccnc2OC2CNCCOC2c2ccc(Cl)c(Cl)c2)no1] | HCl | 423.1 |

TABLE 1-115

| Ex. No. | IUPAC name | structure | salt | MS |
|---|---|---|---|---|
| 525 | 3-(2-{[(6R*,7S*)-7-(3,4-dichlorophenyl)-1,4-oxazepan-6-yl]oxy}pyridin-3-yl)-1,2,4-oxadiazol-5(4H)-one (retention time long) | 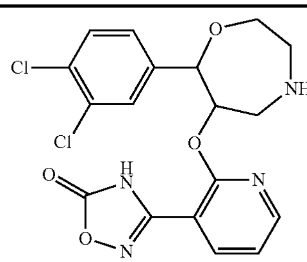 | HCl | 423.1 |
| 526 | methyl 1-{[(6S,7R)-7-(4-chloro-3-fluorophenyl)-1,4-oxazepan-6-yl]methyl}-2-oxo-1,2-dihydropyridine-3-carboxylate | 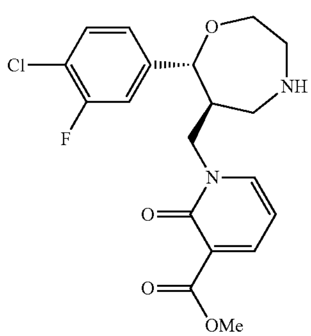 [SMILES: COC(=O)c1cccn(C[C@@H]2CNCCO[C@H]2c2ccc(Cl)c(F)c2)c1=O] | HCl | 395.3 |
| 527 | methyl 2-{[(6S,7R)-7-(4-chloro-3-fluorophenyl)-1,4-oxazepan-6-yl]methoxy}pyridine-3-carboxylate | 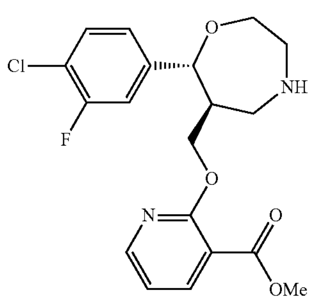 [SMILES: COC(=O)c1cccnc1OC[C@@H]1CNCCO[C@H]1c1ccc(Cl)c(F)c1] | HCl | 395.3 |

TABLE 1-115-continued

| Ex. No. | IUPAC name | structure | salt | MS |
|---|---|---|---|---|
| 528 | 3-(2-{[(6RS,7SR)-7-(4-chloro-3-fluorophenyl)-1,4-oxazepan-6-yl]oxy}pyridin-3-yl)-1,2,4-oxadiazol-5(4H)-one | 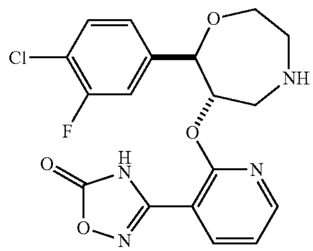 | HCl | 407.3 |
| 529 | (6RS,7SR)-7-(4-chloro-3-fluorophenyl)-6-{[3-(1H-tetrazol-5-yl)pyridin-2-yl]oxy}-1,4-oxazepane | 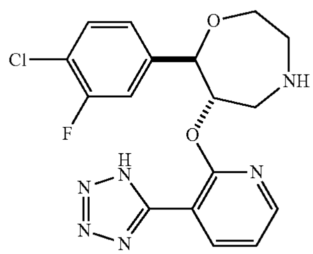 | HCl | 391.1 |

TABLE 1-116

| Ex. No. | IUPAC name | structure | salt | MS |
|---|---|---|---|---|
| 530 | methyl 2-{[(6RS,7SR)-7-(4-chloro-3-fluorophenyl)-1,4-oxazepan-6-yl]oxy}pyridine-3-carboxylate | 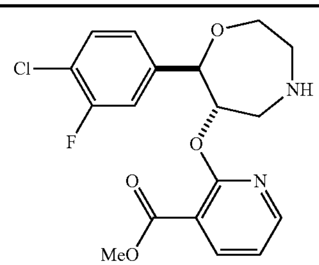 | HCl | 381.1 |
| 531 | 2-{[(6RS,7SR)-7-(4-chloro-3-fluorophenyl)-1,4-oxazepan-6-yl]oxy}pyridine-3-carboxylic acid | 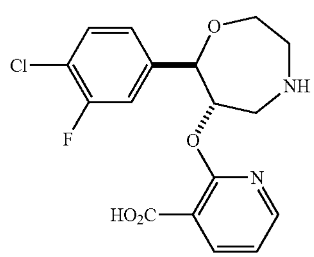 | HCl | 367.3 |
| 532 | 1-{[(6S,7R)-7-(4-chloro-3-fluorophenyl)-1,4-oxazepan-6-yl]methyl}-3-(5-oxo-4,5-dihydro-1,2,4-oxadiazol-3-yl)tetrahydropyrimidin-2(1H)-one | 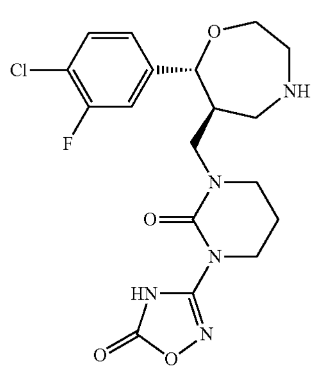 [SMILES: O=C1N(C[C@@H]2CNCCO[C@H]2c2ccc(Cl)c(F)c2)CCCN1c1noc(=O)[nH]1] | HCl | 426.1 |

TABLE 1-116-continued

| Ex. No. | IUPAC name | structure | salt | MS |
|---|---|---|---|---|
| 533 | N-{[(6S,7R)-7-(4-chloro-3-fluorophenyl)-1,4-oxazepan-6-yl]methyl}tetrahydro-2H-pyran-2-carboxamide | 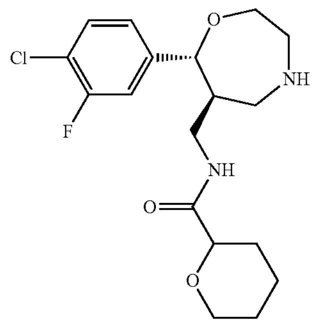 [SMILES: O=C(NC[C@@H]1CNCCO[C@H]1c1ccc(Cl)c(F)c1)C1CCCCO1] | HCl | 371.2 |

TABLE 1-117

| Ex. No. | IUPAC name | structure | salt | MS |
|---|---|---|---|---|
| 534 | 3-chloro-1-{[(6S,7R)-7-(4-chloro-3-fluorophenyl)-1,4-oxazepan-6-yl]methyl}pyridin-2(1H)-one | 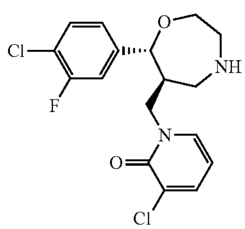 [SMILES: O=c1c(Cl)cccn1C[C@@H]1CNCCO[C@H]1c1ccc(Cl)c(F)c1] | HCl | 371.0 |
| 535 | 1-{[(6S,7R)-7-(3-chloro-4-fluorophenyl)-1,4-oxazepan-6-yl]methyl}-3-(5-oxo-4,5-dihydro-1,2,4-oxadiazol-3-yl)pyridin-2(1H)-one | 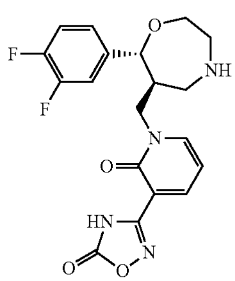 [SMILES: O=c1[nH]c(-c2cccn(C[C@@H]3CNCCO[C@H]3c3ccc(F)c(F)c3)c2=O)no1] | HCl | 421.1 |
| 536 | N-{[(6RS,7SR)-7-(4-chloro-3-fluorophenyl)-6-hydroxy-1,4-oxazepan-6-yl]methyl}-N-methylacetamide | 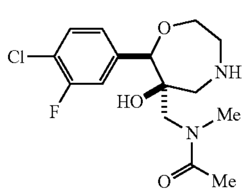 | HCl | 331.1 |
| 537 | N-{[(6RS,7SR)-7-(4-chloro-3-fluorophenyl)-6-hydroxy-1,4-oxazepan-6-yl]methyl}-N-methylmethanesulfonamide | 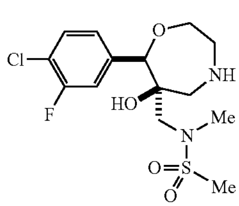 | HCl | 367.1 |

TABLE 1-118

| Ex. No. | IUPAC name | structure | salt | MS |
|---|---|---|---|---|
| 538 | (6RS,7RS)-7-(4-chloro-3-fluorophenyl)-6-[(methylsulfonyl)methyl]-1,4-oxazepan-6-ol | 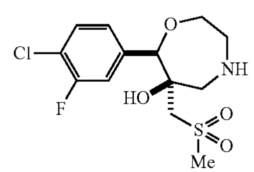 | HCl | 338.0 |
| 539 | 3-[(6S,7R)-7-(4-chloro-3-fluorophenyl)-1,4-oxazepan-6-yl]-1,2,4-oxadiazol-5(4H)-one | 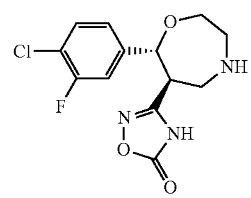 [SMILES: O=c1[nH]c([C@@H]2CNCCO[C@H]2c2ccc(Cl)c(F)c2)no1] | HCl | 314.0 |
| 540 | 1-{[(6S,7R)-7-(4-chloro-3-fluorophenyl)-1,4-oxazepan-6-yl]methyl}-2-oxo-1,2-dihydropyridine-3-carbonitrile | 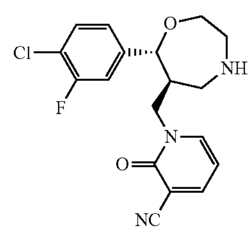 [SMILES: N#Cc1cccn(C[C@@H]2CNCCO[C@H]2c2ccc(Cl)c(F)c2)c1=O] | HCl | 362.2 |
| 541 | N-[(6R,7S)-7-(3,4-dichlorophenyl)-1,4-oxazepan-6-yl]-2-oxopropanamide | 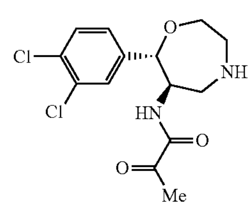 [SMILES: CC(=O)C(=O)N[C@@H]1CNCCO[C@H]1c1ccc(Cl)c(Cl)c1] | HCl | 331.0 |
| 542 | N-{[(6S,7R)-7-(4-chloro-3-fluorophenyl)-1,4-oxazepan-6-yl]methyl}-2-oxopropanamide | 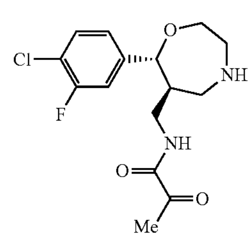 [SMILES: CC(=O)C(=O)NC[C@@H]1CNCCO[C@H]1c1ccc(Cl)c(F)c1] | HCl | 329.2 |

TABLE 1-119

| Ex. No. | IUPAC name | salt | MS |
|---|---|---|---|
| 543 | N-[(6R,7S)-7-(3,4-dichlorophenyl)-1,4-oxazepan-6-yl]-N-methylacetamide | HCl | 317.2 |
| 544 | 2-{[(6RS,7SR)-7-(4-chloro-3-fluorophenyl)-1,4-oxazepan-6-yl]oxy}-N-methylpyridine-3-carboxamide | HCl | 380.1 |
| 545 | 1-{[(6R,7S)-6-(3,4-dichlorophenyl)-1,4-oxazepan-7-yl]methyl}-tetrahydropyrimidin-2(1H)-one | HCl | 358.1 |
| 546 | 1-{[(6R,7S)-6-(3,4-dichlorophenyl)-1,4-oxazepan-7-yl]methyl}-3-methyl-tetrahydropyrimidin-2(1H)-one | HCl | 372.1 |
| 547 | 1-{[(6R,7S)-6-(3,4-dichlorophenyl)-1,4-oxazepan-7-yl]methyl}-3-(5-oxo-4,5-dihydro-1,2,4-oxadiazol-3-yl)tetrahydropyrimidin-2(1H)-one | HCl | 442.1 |

TABLE 1-120

| Ex. No. | IUPAC name | salt | MS |
|---|---|---|---|
| 548 | (6S,7R)-7-(4-chloro-3-fluorophenyl)-1,4-oxazepan-6-ol | HCl | 246.1 |
| 549 | N-{[(6S,7R)-7-(4-chloro-3-fluorophenyl)-1,4-oxazepan-6-yl]methyl}-2-(2-methylpropoxy)acetamide | HCl | 373.1 |
| 550 | 1-{[(6S,7R)-7-(4-chloro-3-fluorophenyl)-1,4-oxazepan-6-yl]methyl}-3-(5-oxo-4,5-dihydro-1,3,4-oxadiazol-2-yl)pyridin-2(1H)-one | HCl | 421.1 |
| 551 | 5-(2-{[(6S,7R)-7-(4-chloro-3-fluorophenyl)-1,4-oxazepan-6-yl]methoxy}pyridin-3-yl)-1,3,4-oxadiazol-2(3H)-one | HCl | 421.1 |

TABLE 1-121

| Ex. No. | IUPAC name | salt | MS |
|---|---|---|---|
| 552 | (6R,7S)-7-(4-chloro-3-fluorophenyl)-1,4-oxazepan-6-ol | HCl | 246.1 |
| 553 | N-[(6RS,7SR)-7-(3,4-dichlorophenyl)-1,4-oxazepan-6-yl]acetamide | HCl | 303.1 |

TABLE 1-121-continued

| Ex. No. | IUPAC name | structure | salt | MS |
|---|---|---|---|---|
| 554 | 1-{[(6S,7R)-7-(4-chloro-3-fluorophenyl)-1,4-oxazepan-6-yl]methyl}-2-oxo-1,2-dihydropyridine-3-carboxamide | 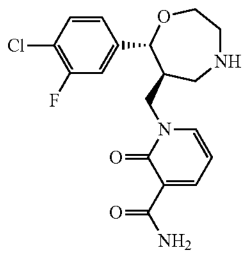 [SMILES: NC(=O)c1cccn(C[C@@H]2CNCCO[C@H]2c2ccc(Cl)c(F)c2)c1=O] | HCl | 380.0 |
| 555 | N-{[(6S,7R)-7-(4-chloro-3-fluorophenyl)-1,4-oxazepan-6-yl]methyl}-2-[(²H₁)methyloxy]-acetamide | 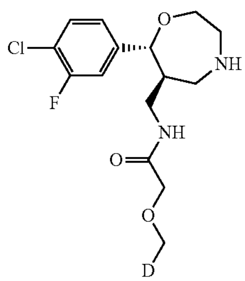 [SMILES: [2H]COCC(=O)NC[C@@H]1CNCCO[C@H]1c1ccc(Cl)c(F)c1] | HCl | 332.2 |
| 556 | 3-(2-{[(6R,7S)-7-(4-chloro-3-fluorophenyl)-1,4-oxazepan-6-yl]oxy}pyridin-3-yl)-1,2,4-oxadiazol-5(4H)-one | 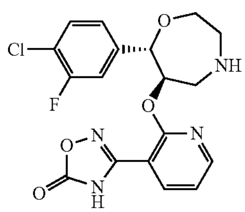 [SMILES: O=c1[nH]c(-c2cccnc2O[C@@H]2CNCCO[C@H]2c2ccc(Cl)c(F)c2)no1] | HCl | 407.2 |

TABLE 1-122

| Ex. No. | IUPAC name | structure | salt | MS |
|---|---|---|---|---|
| 557 | N-{[(6S,7R)-7-(4-chloro-3-fluorophenyl)-1,4-oxazepan-6-yl]methyl}-2-[(²H₂)methyloxy]-acetamide | 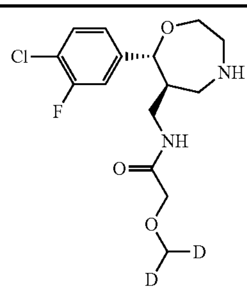 | HCl | 333.2 |
| 558 | 5-(2-{[(6R,7S)-7-(4-chloro-3-fluorophenyl)-1,4-oxazepan-6-yl]oxy}pyridin-3-yl)-2,4-dihydro-3H-1,2,4-triazol-3-one | 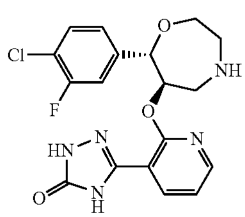 [SMILES: O=c1[nH]nc(-c2cccnc2O[C@@H]2CNCCO[C@H]2c2ccc(Cl)c(F)c2)[nH]1] | HCl | 406.1 |
| 559 | N-{[(6R*,7S*)-7-(4-chloro-3-fluorophenyl)-6-methoxy-1,4-oxazepan-6-yl]methyl}acetamide (retention time short) | 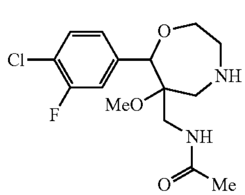 [SMILES: COC1(CNC(C)=O)CNCCOC1c1ccc(Cl)c(F)c1] | HCl | 331.1 |

TABLE 1-122-continued

| Ex. No. | IUPAC name | structure | salt | MS |
|---|---|---|---|---|
| 560 | 2-{[(6R,7S)-7-(4-chloro-4-fluorophenyl)-1,4-oxazepan-6-yl]oxy}pyridine-3-carboxamide | 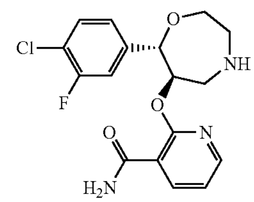 [SMILES: NC(=O)c1cccnc1O[C@@H]1CNCCO[C@H]1c1ccc(Cl)c(F)c1] | HCl | 366.1 |
| 561 | N-{[(6R*,7S*)-7-(4-chloro-3-fluorophenyl)-6-methoxy-1,4-oxazepan-6-yl]methyl}acetamide (retention time long) | 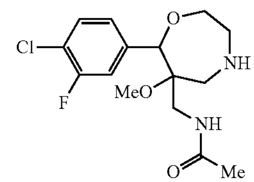 [SMILES: COC1(CNC(C)=O)CNCCOC1c1ccc(Cl)c(F)c1] | HCl | 331.1 |

TABLE 1-123

| Ex. No. | IUPAC name | structure | salt | MS |
|---|---|---|---|---|
| 562 | 3-(2-{[(6S,7R)-7-(4-chloro-3-fluorophenyl)-1,4-oxazepan-6-yl]oxy}pyridin-3-yl)-1,2,4-oxadiazol-5(4H)-one | 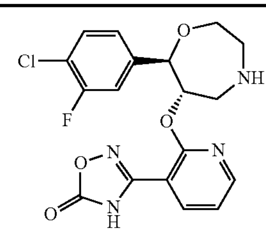 | HCl | 407.1 |
| 563 | N-{[(6R*,7S*)-7-(4-chloro-3-fluorophenyl)-6-hydroxy-1,4-oxazepan-6-yl]methyl}-N-methylacetamide (retention time short) | 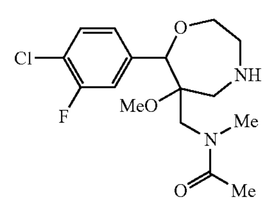 [SMILES: COC1(CN(C)C(C)=O)CNCCOC1c1ccc(Cl)c(F)c1] | HCl | 331.1 |
| 564 | 1-{[(6S,7R)-7-(4-chloro-3-fluorophenyl)-1,4-oxazepan-6-yl]methyl}-6-(5-oxo-4,5-dihydro-1,2,4-oxadiazol-3-yl)pyridin-2(1H)-one | 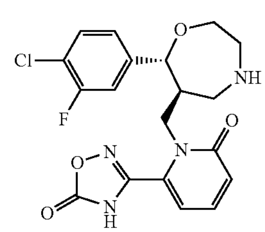 [SMILES: O=c1[nH]c(-c2cccc(=O)n2C[C@@H]2CNCCO[C@H]2c2ccc(Cl)c(F)c2)no1] | HCl | 421.1 |
| 565 | N-{[(6R*,7S*)-7-(4-chloro-3-fluorophenyl)-6-hydroxy-1,4-oxazepan-6-yl]methyl}-N-methylacetamide (retention time long) | 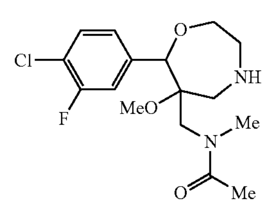 [SMILES: COC1(CN(C)C(C)=O)CNCCOC1c1ccc(Cl)c(F)c1] | HCl | 331.1 |

TABLE 1-123-continued

| Ex. No. | IUPAC name | structure | salt | MS |
|---|---|---|---|---|
| 566 | 3-(6-{[(6S,7R)-7-(4-chloro-3-fluorophenyl)-1,4-oxazepan-6-yl]methoxy}pyridin-2-yl)-1,2,4-oxadiazol-5(4H)-one | 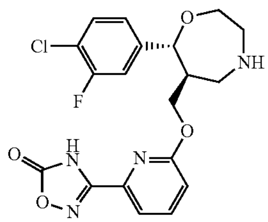 [SMILES: O=c1[nH]c(-c2cccc(OC[C@@H]3CNCCO[C@H]3c3ccc(Cl)c(F)c3)n2)no1] | HCl | 421.1 |

TABLE 1-124

| Ex. No. | IUPAC name | structure | salt | MS |
|---|---|---|---|---|
| 567 | N-{[(6R*,7R*)-7-(3,4-dichlorophenyl)-1,4-oxazepan-6-yl]methyl}-2-methoxyacetamide (derived from compound of Example 49) | 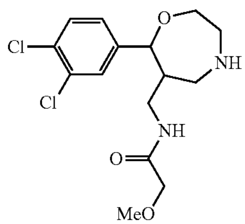 [SMILES: COCC(=O)NCC1CNCCOC1c1ccc(Cl)c(Cl)c1] | HCl | 347.1 |
| 568 | (6R,7S)-7-(4-chloro-3-fluorophenyl)-6-{[3-(5-methy-4H-1,2,4-triazol-3-yl)pyridin-2-yl]oxy}-1,4-oxazepane | 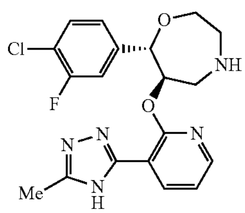 [SMILES: Cc1nnc(-c2cccnc2O[C@@H]2CNCCO[C@H]2c2ccc(Cl)c(F)c2)[nH]1] | HCl | 404.2 |

TABLE 1-124-continued

| Ex. No. | IUPAC name | structure | salt | MS |
|---|---|---|---|---|
| 569 | N-{[(6R*,7S*)-7-(4-chloro-3-fluorophenyl)-6-hydroxy-1,4-oxazepan-6-yl]methyl}-methanesulfonamide (retention time short) | 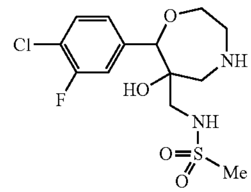 [SMILES: CS(=O)(=O)NCC1(O)CNCCOC1c1ccc(Cl)c(F)c1] | HCl | 353.0 |
| 570 | N-{[(6R*,7S*)-7-(4-chloro-3-fluorophenyl)-6-hydroxy-1,4-oxazepan-6-yl]methyl}-methanesulfonamide (retention time long) | 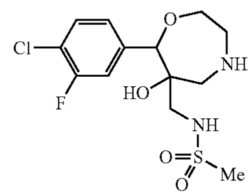 [SMILES: CS(=O)(=O)NCC1(O)CNCCOC1c1ccc(Cl)c(F)c1] | HCl | 353.0 |
| 571 | 7-(4-chloro-3-fluorophenyl)-6-[(methylsulfonyl)methyl]-1,4-oxazepan-6-ol (retention time short) | 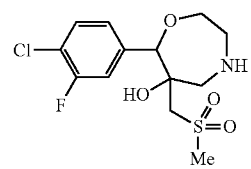 [SMILES: CS(=O)(=O)CC1(O)CNCCOC1c1ccc(Cl)c(F)c1] | HCl | 338.0 |

TABLE 1-125

| Ex. No. | IUPAC name | structure | salt | MS |
|---|---|---|---|---|
| 572 | 7-(4-chloro-3-fluorophenyl)-6-[(methylsulfonyl)methyl]-1,4-oxazepan-6-ol (retention time long) | 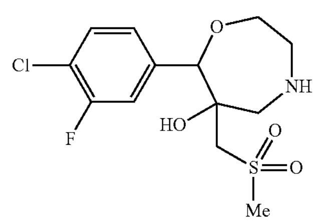 [SMILES: CS(=O)(=O)CC1(O)CNCCOC1c1ccc(Cl)c(F)c1] | HCl | 338.0 |
| 573 | 1-{[(6S,7R)-7-(4-chloro-3-fluorophenyl)-1,4-oxazepan-6-yl]methyl}-5-(5-oxo-4,5-dihydro-1,2,4-oxadiazol-3-yl)pyridin-2(1H)-one | 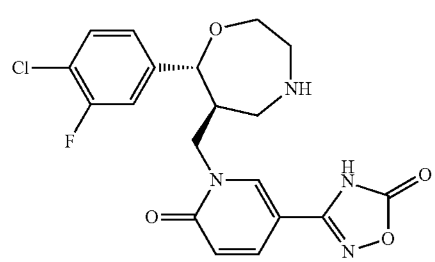 [SMILES: O=c1[nH]c(-c2ccc(=O)n(C[C@@H]3CNCCO[C@H]3c3ccc(Cl)c(F)c3)c2)no1] | HCl | 421.1 |

TABLE 1-125-continued

| Ex. No. | IUPAC name | structure | salt | MS |
|---|---|---|---|---|
| 574 | 3-(6-{[(6S,7R)-7-(4-chloro-3-fluorophenyl)-1,4-oxazepan-6-yl]methoxy}pyridin-3-yl)-1,2,4-oxadiazol-5(4H)-one | 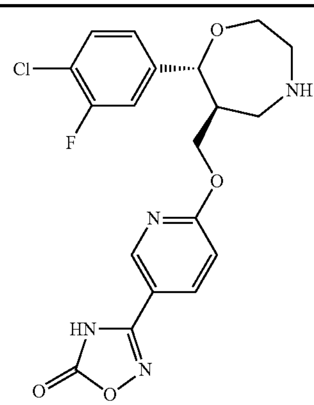 | HCl | 421.1 |
| 575 | (1S)-1-[(6S,7R)-6-(3,4-dichlorophenyl)-1,4-oxazepan-7-yl]ethane-1,2-diol | 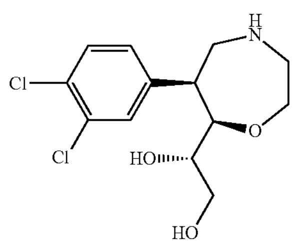 [SMILES: OC[C@H](O)[C@@H]1OCCNC[C@@H]1c1ccc(Cl)c(Cl)c1] | HCl | 306.0 |
| 576 | N-{[(6S,7R)-7-(4-chloro-3-fluorophenyl)-1,4-oxazepan-6-yl]methyl}-N-methylacetamide | 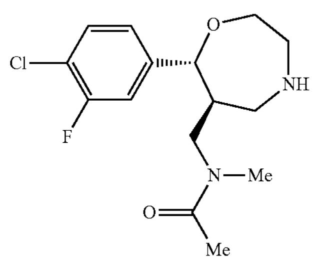 [SMILES: CC(=O)N(C)C[C@@H]1CNCCO[C@H]1c1ccc(Cl)c(F)c1] | HCl | 315.1 |

TABLE 1-126

| Ex. No. | IUPAC name | structure | salt | MS |
|---|---|---|---|---|
| 577 | 3-(2-{[(6R,7S)-7-(4-chloro-3-fluorophenyl)-1,4-oxazepan-6-yl]oxy}phenyl)-1,2,4-oxadiazol-5(4H)-one | 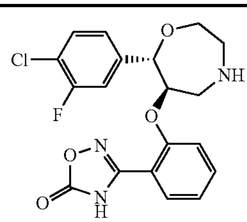 | HCl | 406.1 |
| 578 | (1S)-1-[(6R,7S)-6-(3,4-dichlorophenyl)-1,4-oxazepan-7-yl]ethane-1,2-diol | 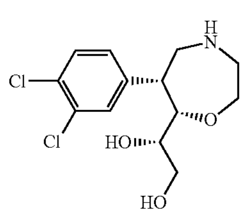 [SMILES: OC[C@H](O)[C@H]1OCCNC[C@H]1c1ccc(Cl)c(Cl)c1] | HCl | 306.0 |
| 579 | (1R)-1-[(6R,7S)-6-(3,4-dichlorophenyl)-1,4-oxazepan-7-yl]ethane-1,2-diol | | HCl | 306.0 |
| 580 | 1-{[(6S,7R)-7-(4-chloro-3-fluorophenyl)-1,4-oxazepan-6-yl]methyl}-4-methyl-3-(5-oxo-4,5-dihydro-1,2,4-oxadiazol-3-yl)pyridin-2(1H)-one | | HCl | 435.1 |

TABLE 1-126-continued

| Ex. No. | IUPAC name | salt | MS |
|---|---|---|---|
| 581 | 1-{[(6R,7S)-7-(4-chloro-3-fluorophenyl)-1,4-oxazepan-6-yl]methyl}-2-oxo-1,2-dihydropyridine-3-carboxylic acid | HCl | 381.1 |

TABLE 1-127

| Ex. No. | IUPAC name | salt | MS |
|---|---|---|---|
| 582 | 2-{[(6R,7S)-7-(4-chloro-3-fluorophenyl)-1,4-oxazepan-6-yl]oxy}-N-methylpyridine-3-carboxamide | HCl | 380.2 |
| 583 | 3-{[(6R,7S)-7-(4-chloro-3-fluorophenyl)-1,4-oxazepan-6-yl]oxy}pyridine-2-carboxamide | HCl | 366.1 |
| 584 | 3-(3-{[(6R,7S)-7-(4-chloro-3-fluorophenyl)-1,4-oxazepan-6-yl]oxy}pyridin-2-yl)-1,2,4-oxadiazol-5(4H)-one | HCl | 407.1 |
| 585 | 2-{[(6R,7S)-7-(4-chloro-3-fluorophenyl)-1,4-oxazepan-6-yl]oxy}-N-(2-hydroxyethyl)pyridine-3-carboxamide | HCl | 410.2 |
| 586 | 3-(3-{[(6R,7S)-7-(4-chloro-3-fluorophenyl)-1,4-oxazepan-6-yl]oxy}pyridin-4-yl)-1,2,4-oxadiazol-5(4H)-one | HCl | 407.0 |

TABLE 1-128

| Ex. No. | IUPAC name | salt | MS |
|---|---|---|---|
| 587 | 1-{[(6R*,7R*)-7-(3,4-dichlorophenyl)-1,4-oxazepan-6-yl]methyl}-2-oxo-1,2-dihydropyridine-3-carboxylic acid (derived from compound of Example 49) | HCl | 397.1 |
| 588 | 1-{[(6RS,7SR)-7-(4-chloro-3-fluorophenyl)-1,4-oxazepan-6-yl]methyl}-2-oxo-1,2-dihydropyridine-3-carboxylic acid | HCl | 381.1 |
| 589 | 1-{[(6R*,7R*)-7-(4-chloro-3-fluorophenyl)-1,4-oxazepan-6-yl]methyl}-2-oxo-1,2-dihydropyridine-3-carboxylic acid (retention time short) | HCl | 381.1 |
| 590 | 1-{[(6R*,7R*)-7-(4-chloro-3-fluorophenyl)-1,4-oxazepan-6-yl]methyl}-2-oxo-1,2-dihydropyridine-3-carboxylic acid (retention time long) | HCl | 381.1 |
| 591 | 3-{[(6R,7S)-7-(4-chloro-3-fluorophenyl)-1,4-oxazepan-6-yl]oxy}pyridine-4-carboxamide | HCl | 366.1 |

TABLE 1-129

| Ex. No. | IUPAC name | salt | MS |
|---|---|---|---|
| 592 | N-{[(6S,7R)-7-(4-chloro-3-fluorophenyl)-1,4-oxazepan-6-yl]methyl}propanamide | HCl | 315.1 |

TABLE 1-129-continued

| Ex. No. | IUPAC name | salt | MS |
|---|---|---|---|
| 593 | N-{[(6S,7R)-7-(4-chloro-3-fluorophenyl)-1,4-oxazepan-6-yl]methyl}-2-methylpropanamide | HCl | 329.2 |
| 594 | N-{[(6R*,7S*)-7-(4-chloro-3-methylphenyl)-1,4-oxazepan-6-yl]methyl}acetamide (retention time short) | HCl | 297.2 |
| 595 | N-{[(6R*,7S*)-7-(3-chloro-4-methyl-phenyl)-1,4-oxazepan-6-yl]methyl}acetamide (retention time short) | HCl | 297.2 |
| 596 | 3-(4-{[(6R,7S)-7-(4-chloro-3-fluorophenyl)-1,4-oxazepan-6-yl]oxy}pyridin-3-yl)-1,2,4-oxadiazol-5(4H)-one | HCl | 407.1 |

TABLE 1-130

| Ex. No. | IUPAC name | salt | MS |
|---|---|---|---|
| 597 | 2-{[(6S,7R)-7-(4-chloro-3-fluorophenyl)-1,4-oxazepan-6-yl]methyl}-3-oxo-2,3-dihydropyridazine-4-carboxylic acid | HCl | 382.1 |
| 598 | N-{[(6S,7R)-7-(4-chloro-3-fluorophenyl)-1,4-oxazepan-6-yl]methyl}benzamide | HCl | 363.1 |

TABLE 1-130-continued

| Ex. No. | IUPAC name | salt | MS |
|---|---|---|---|
| 599 | N-{[(6S,7R)-7-(4-chloro-3-fluorophenyl)-1,4-oxazepan-6-yl]methyl}-2-phenoxyacetamide | HCl | 393.1 |
| 600 | (2RS)-N-{[(6S,7R)-7-(4-chloro-3-fluorophenyl)-1,4-oxazepan-6-yl]methyl}-2-fluoropropanamide | HCl | 333.2 |
| 601 | N-{[(6S,7R)-7-(4-chloro-3-fluorophenyl)-1,4-oxazepan-6-yl]methyl}-2-fluoro-2-methylpropanamide | HCl | 347.2 |

TABLE 1-131

| Ex. No. | IUPAC name | salt | MS |
|---|---|---|---|
| 602 | 3-(2-{[7-(3,4-dichlorophenyl)-7-(hydroxymethyl)-1,4-oxazepan-6-yl]oxy}pyridin-3-yl)-1,2,4-oxadiazol-5(4H)-one (high-polar diastereomer) | HCl | 453.1 |
| 603 | 3-(2-{[7-(3,4-dichlorophenyl)-7-(hydroxymethyl)-1,4-oxazepan-6-yl]oxy}pyridin-3-yl)-1,2,4-oxadiazol-5(4H)-one (less polar diastereomer) | HCl | 453.1 |

TABLE 1-131-continued

| Ex. No. | IUPAC name | structure | salt | MS |
|---|---|---|---|---|
| 604 | 3-(2-{[(6S,7S)-7-(4-chloro-3-fluorophenyl)-1,4-oxazepan-6-yl]oxy}pyridin-3-yl)-1,2,4-oxadiazol-5(4H)-one | 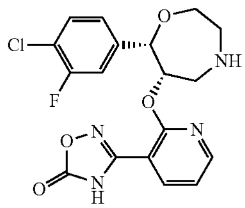 [SMILES: O=c1[nH]c(-c2cccnc2O[C@H]2CNCCO[C@H]2c2ccc(Cl)c(F)c2)no1] | HCl | 407.1 |
| 605 | (1RS)-1-[(6SR,7SR)-6-(3,4-dichlorophenyl)-1,4-oxazepan-7-yl]ethane-1,2-diol | 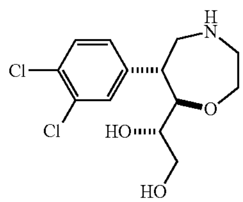 | HCl | 306.1 |
| 606 | (1RS)-1-[(6RS,7RS)-6-(3,4-dichlorophenyl)-1,4-oxazepan-7-yl]ethane-1,2-diol | 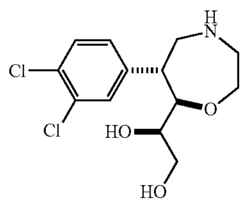 | HCl | 306.1 |

Experimental Example 1

(1) Construction of Human Dopamine Transporter Expression Plasmid

SRα promoter contained in pTB1411 described in JP-A-H5-076385 was cleaved with restriction enzyme HindIII (manufactured by TAKARA BIO INC.), blunt-ended, further cleaved with restriction enzyme EcoRI (manufactured by TAKARA BIO INC.), and fragmented. On the other hand, pCI vector was cleaved with restriction enzyme BglII (manufactured by TAKARA BIO INC.), blunt-ended with T4 DNA polymerase, and further cleaved with restriction enzyme EcoRI (manufactured by TAKARA BIO INC.). Into this site was inserted an SRα promoter fragment to give pCI-SRa. Then, pCI-SRa was cleaved with restriction enzyme ClaI (manufactured by TAKARA BIO INC.) and blunt-ended. Into this site was inserted a 1.63 Kb fragment obtained by cleaving pGFP-C1 (manufactured by TOYOBO) with restriction enzyme Bsu36I (manufactured by Daiichi Pure Chemicals Co., Ltd.) followed by blunt-ending, whereby pMSRα neo was prepared. Human dopamine transporter cDNA was amplified from human substantia nigra cDNA library by PCR, and inserted into the pCRII vector (manufactured by Invitrogen). The base sequence was confirmed, modified and subcloned to pMSRα neo, whereby a human dopamine transporter expression plasmid was constructed.

(2) Preparation of Human Monoamine Expressing Cell

Human serotonin transporter cDNA was amplified from human brain cDNA library by PCR, and inserted into pCRII-TOPO vector (manufactured by Invitrogen). The base sequence was confirmed and modified, and subcloned to pcDNA3.1 vector (manufactured by Invitrogen), whereby a human serotonin transporter expression plasmid was constructed. Human norepinephrine transporter cDNA was purchased from Invitrogen, and the base sequence was confirm and modified, and subcloned to pcDNA3.1 vector, whereby a human norepinephrine transporter expression plasmid was constructed.

The monoamine transporter expression plasmids thus prepared were introduced into CHO-K1 cells using FuGENE6 (manufactured by Roche Diagnostics) and according to the attached protocol, whereby each expressing cell was established.

(3) Inhibitory Action on Human Serotonin Transporter

CHO cells stably expressing a human serotonin transporter were used for the measurement of human serotonin transporter inhibitory activity. Unless particularly indicated, these CHO cells were cultured in a Ham/F12 medium (Invitrogen) containing 10% fetal bovine serum (MOREGATE).

The cultured cells that reached almost confluent were rinsed with PBS (Invitrogen), detached with Trypsin/EDTA (Invitrogen), and collected by a centrifugal operation. The obtained cells were counted, and diluted to $3\times10^5$ cells per 1 mL medium, the mixture was dispensed to a 96 well white plate (Corning) at 100 µL per well, and cultured overnight in a $CO_2$ incubator.

Then, an assay buffer (126 mM NaCl, 4.95 mM KCl, 1.26 mM $KH_2PO_4$, 1.26 mM $MgSO_4$, 10 mM HEPES, 2.32 mM $CaCl_2$, 5.52 mM Glucose, 0.5% BSA) was prepared, the medium in the cell plate was removed and the assay buffer was added by 80 µL. A test compound was diluted with the assay buffer to a 10-fold concentration of the final concentration, and the mixture was dispensed to a 96 well polypropylene plate. The diluted test compound was dispensed to the cell plate by 10 µL. [3H]-5-Hydroxytryptamine (GE Healthcare) was diluted with the assay buffer to 200 nM, and the mixture was dispensed to the cell plate by 10 µL. At 20 min from [3H]-5-hydroxytryptamine addition, the assay buffer was removed by suction, and the plate was washed twice with 150 µL of PBS (Invitrogen) per well. Microscinti20 (PerkinElmer) was dispensed to each well by 100 µL, and the mixture was stirred for about 30 min. The radioactivity was measured by TopCount (PerkinElmer).

The inhibitory activity of each compound (10 µM) was calculated as a relative activity value based on the inhibitory activity of 10 µM Paroxetine (serotonin transporter inhibitor) as 100%. The results are shown in the following Table 2.

TABLE 2

| Example No. | inhibitory rate (%) |
|---|---|
| 6 | 98 |
| 12 | 97 |
| 14 | 79 |
| 17 | 96 |
| 22 | 98 |
| 24 | 99 |
| 25 | 65 |

In addition, the inhibitory activity of each compound (1 µM) was calculated as a relative activity value based on the inhibitory activity of 10 µM Paroxetine (serotonin transporter inhibitor) as 100%. The results are shown in the following Table 3.

TABLE 3

| Example No. | inhibitory rate (%) |
|---|---|
| 6 | 84 |
| 12 | 87 |
| 14 | 31 |

TABLE 3-continued

| Example No. | inhibitory rate (%) |
|---|---|
| 17 | 70 |
| 22 | 82 |
| 24 | 87 |
| 25 | 29 |
| 31 | 95 |
| 32 | 84 |
| 33 | 92 |
| 34 | 84 |
| 35 | 86 |
| 36 | 69 |
| 37 | 71 |
| 38 | 69 |
| 39 | 58 |
| 40 | 80 |
| 41 | 70 |
| 42 | 87 |
| 43 | 72 |
| 44 | 40 |
| 45 | 36 |
| 46 | 70 |
| 47 | 82 |
| 48 | 98 |
| 49 | 87 |
| 50 | 100 |
| 52 | 99 |
| 62 | 98 |
| 63 | 93 |
| 72 | 90 |
| 73 | 97 |
| 87 | 96 |
| 92 | 97 |
| 93 | 97 |
| 99 | 99 |
| 114 | 94 |
| 115 | 99 |
| 126 | 97 |
| 142 | 95 |
| 146 | 100 |
| 152 | 89 |
| 153 | 93 |
| 160 | 99 |
| 162 | 65 |
| 167 | 93 |
| 176 | 80 |
| 181 | 87 |
| 187 | 86 |
| 199 | 100 |
| 209 | 97 |
| 212 | 98 |
| 216 | 42 |
| 230 | 59 |
| 236 | 92 |
| 240 | 94 |
| 262 | 71 |
| 265 | 79 |
| 266 | 82 |
| 276 | 87 |
| 278 | 87 |
| 281 | 95 |
| 284 | 34 |
| 285 | 79 |
| 293 | 65 |
| 301 | 52 |
| 302 | 73 |
| 314 | 49 |
| 315 | 43 |
| 357 | 102 |
| 367 | 99 |
| 372 | 98 |
| 376 | 98 |
| 379 | 95 |
| 401 | 75 |
| 402 | 91 |
| 405 | 71 |
| 406 | 82 |
| 409 | 56 |
| 410 | 91 |

TABLE 3-continued

| Example No. | inhibitory rate (%) |
|---|---|
| 412 | 8 |
| 416 | 85 |
| 417 | 92 |
| 432 | 84 |
| 438 | 81 |
| 439 | 74 |
| 440 | 93 |
| 441 | 51 |
| 447 | 42 |
| 448 | 28 |
| 449 | 53 |
| 453 | 41 |
| 457 | 27 |
| 467 | 38 |
| 470 | 66 |
| 481 | 76 |
| 487 | 15 |
| 488 | 61 |
| 491 | 77 |
| 495 | 59 |
| 496 | 62 |
| 507 | 46 |
| 515 | 82 |
| 520 | 84 |
| 521 | 84 |
| 523 | 64 |
| 525 | 97 |
| 538 | 91 |
| 545 | 94 |
| 550 | 97 |
| 552 | 14 |
| 556 | 77 |
| 558 | 81 |
| 561 | 46 |
| 563 | 87 |
| 568 | 94 |
| 572 | 95 |
| 577 | 53 |
| 578 | 28 |
| 579 | 61 |
| 584 | 41 |
| 588 | 43 |
| 597 | 78 |

Experimental Example 2 Inhibitory Action on Human Norepinephrine Transporter

CHO cells stably expressing human norepinephrine transporter were used for the measurement of human norepinephrine transporter inhibitory activity. Unless otherwise indicated, these CHO cells were cultured in Ham/F12 medium (Invitrogen) containing 10% fetal bovine serum (MOREGATE).

The cultured cells that reached almost confluent were rinsed with PBS (Invitrogen), detached with Trypsin/EDTA (Invitrogen), and collected by a centrifugal operation. The obtained cells were counted, and diluted to $3 \times 10^5$ cells per 1 mL medium, and the mixture was dispensed to a 96 well white plate (Corning) at 100 μL per well, and cultured overnight in a $CO_2$ incubator.

Then, an assay buffer (126 mM NaCl, 4.95 mM KCl, 1.26 mM $KH_2PO_4$, 1.26 mM $MgSO_4$, 10 mM HEPES, 2.32 mM $CaCl_2$, 5.52 mM Glucose, 0.5% BSA) was prepared, the medium in the cell plate was removed and the assay buffer was added by 80 μL. A test compound was diluted with the assay buffer to a 10-fold concentration of the final concentration, and the mixture was dispensed to a 96 well polypropylene plate. The diluted test compound was dispensed to the cell plate by 10 μL. [3H]-Norepinephrine (GE Healthcare) was diluted with the assay buffer to 200 nM, and the mixture was dispensed to the cell plate by 10 μL. At 45 min from [3H]-norepinephrine addition, the assay buffer was removed by suction, and the plate was washed twice with 150 μL of PBS (Invitrogen) per well. Microscinti20 (PerkinElmer) was dispensed to each well by 100 μL, and the mixture was stirred for about 30 min. The radioactivity was measured by Top-Count (PerkinElmer).

The inhibitory activity of each compound (10 μM) was calculated as a relative activity value based on the inhibitory activity of 10 μM DMI (norepinephrine transporter inhibitor) as 100%. The results are shown in the following Table 4.

TABLE 4

| Example No. | inhibitory rate (%) |
| --- | --- |
| 6 | 97 |
| 12 | 100 |
| 14 | 100 |
| 17 | 97 |
| 22 | 99 |
| 24 | 99 |
| 25 | 100 |

The inhibitory activity of each compound (1 μM) was calculated as a relative activity value based on the inhibitory activity of 10 μM DMI (norepinephrine transporter inhibitor) as 100%. The results are shown in the following Table 5.

TABLE 5

| Example No. | inhibitory rate (%) |
| --- | --- |
| 6 | 95 |
| 12 | 97 |
| 14 | 98 |
| 17 | 75 |
| 22 | 97 |
| 24 | 94 |
| 25 | 99 |
| 31 | 108 |
| 32 | 93 |
| 33 | 100 |
| 34 | 96 |
| 35 | 99 |
| 36 | 101 |
| 37 | 102 |
| 38 | 102 |
| 39 | 102 |
| 40 | 104 |
| 41 | 101 |
| 42 | 102 |
| 43 | 102 |
| 44 | 102 |
| 45 | 105 |
| 46 | 104 |
| 47 | 99 |
| 48 | 99 |
| 49 | 98 |
| 50 | 98 |
| 52 | 97 |
| 62 | 100 |
| 63 | 100 |
| 72 | 95 |
| 73 | 98 |
| 87 | 108 |
| 92 | 96 |
| 93 | 96 |
| 99 | 98 |
| 114 | 99 |
| 115 | 98 |
| 126 | 103 |
| 142 | 100 |
| 146 | 101 |
| 152 | 95 |
| 153 | 95 |
| 160 | 101 |
| 162 | 105 |
| 167 | 103 |
| 176 | 101 |
| 181 | 100 |
| 187 | 101 |
| 199 | 99 |
| 209 | 101 |
| 212 | 103 |
| 216 | 94 |
| 230 | 100 |
| 236 | 105 |
| 240 | 105 |
| 262 | 98 |
| 265 | 102 |
| 266 | 103 |
| 276 | 103 |
| 278 | 91 |
| 281 | 95 |
| 284 | 96 |
| 285 | 94 |
| 293 | 95 |
| 301 | 100 |
| 302 | 98 |
| 314 | 104 |
| 315 | 105 |
| 357 | 103 |
| 367 | 103 |
| 372 | 103 |
| 376 | 102 |
| 379 | 102 |
| 401 | 100 |
| 402 | 98 |
| 405 | 100 |
| 406 | 98 |
| 409 | 105 |
| 410 | 103 |
| 412 | 86 |
| 416 | 100 |
| 417 | 102 |
| 432 | 97 |
| 438 | 97 |
| 439 | 98 |
| 440 | 105 |
| 441 | 103 |
| 447 | 99 |
| 448 | 88 |
| 449 | 100 |
| 453 | 104 |
| 457 | 101 |
| 467 | 102 |
| 470 | 103 |
| 481 | 100 |
| 487 | 70 |
| 488 | 102 |
| 491 | 100 |
| 495 | 105 |
| 496 | 105 |
| 507 | 104 |
| 515 | 104 |
| 520 | 105 |
| 521 | 104 |
| 523 | 91 |
| 525 | 104 |
| 538 | 102 |
| 545 | 108 |
| 550 | 109 |
| 552 | 107 |
| 556 | 101 |
| 558 | 106 |
| 561 | 98 |
| 563 | 103 |
| 568 | 103 |
| 572 | 103 |
| 577 | 97 |
| 578 | 99 |
| 579 | 96 |

TABLE 5-continued

| Example No. | inhibitory rate (%) |
|---|---|
| 584 | 107 |
| 588 | 104 |
| 597 | 104 |

Experimental Example 3 Inhibitory Action on Human Dopamine Transporter

CHO cells stably expressing human dopamine transporter were used for the measurement of human dopamine transporter inhibitory activity. Unless otherwise indicated, these CHO cells were cultured in Ham/F12 medium (Invitrogen) containing 10% fetal bovine serum (MOREGATE).

One day before the assay, the cultured cells that reached almost confluent were rinsed with PBS (Invitrogen), detached with Trypsin/EDTA (Invitrogen), and collected by a centrifugal operation. The obtained cells were counted, and diluted to $3 \times 10^5$ cells per 1 mL medium, and the mixture was dispensed to a 96 well white plate (Corning) at 100 μL per well, and cultured overnight in a $CO_2$ incubator.

On the day of the test, an assay buffer (126 mM NaCl, 4.95 mM KCl, 1.26 mM $KH_2PO_4$, 1.26 mM $MgSO_4$, 10 mM HEPES, 2.32 mM $CaCl_2$, 5.52 mM Glucose, 0.5% BSA) was prepared, the medium in the cell plate was removed and the assay buffer was added by 80 μL. A test compound was diluted with the assay buffer to a 10-fold concentration of the final concentration, and the mixture was dispensed to a 96 well polypropylene plate. The diluted test compound was dispensed to the cell plate by 10 μL. [3H]-Dopamine (GE Healthcare) was diluted with the assay buffer to 200 nM, cold dopamine was diluted to 10 μM, and the mixture was dispensed to the cell plate by 10 μL. At 60 min from [3H]-dopamine addition, the assay buffer was removed by suction, and the plate was washed twice with 150 μL of PBS (Invitrogen) per well. Microscinti20 (PerkinElmer) was dispensed to each well by 100 μL, and the mixture was stirred for about 30 min. The radioactivity was measured by TopCount (PerkinElmer).

The inhibitory activity of each compound (10 μM) was calculated as a relative activity value based on the inhibitory activity of 100 μM Nomifensine (dopamine transporter inhibitor) as 100%. The results are shown in the following Table 6.

TABLE 6

| Example No. | inhibitory rate (%) |
|---|---|
| 6 | 84 |
| 12 | 90 |
| 14 | 99 |
| 17 | 53 |
| 22 | 63 |
| 24 | 50 |
| 25 | 94 |

The inhibitory activity of each compound (1 μM) was calculated as a relative activity value based on the inhibitory activity of 100 μM Nomifensine (dopamine transporter inhibitor) as 100%. The results are shown in the following Table 7.

TABLE 7

| Example No. | inhibitory rate (%) |
|---|---|
| 6 | 33 |
| 12 | 39 |
| 14 | 87 |
| 17 | 19 |
| 22 | 25 |
| 24 | 20 |
| 25 | 46 |
| 31 | 33 |
| 32 | 34 |
| 33 | 35 |
| 34 | 75 |
| 35 | 63 |
| 36 | 53 |
| 37 | 51 |
| 38 | 11 |
| 39 | 17 |
| 40 | 9 |
| 41 | 11 |
| 42 | 47 |
| 43 | 15 |
| 44 | 8 |
| 45 | 52 |
| 46 | 27 |
| 47 | 9 |
| 48 | 22 |
| 49 | 41 |
| 50 | 64 |
| 52 | 29 |
| 62 | 64 |
| 63 | 82 |
| 72 | 41 |
| 73 | 64 |
| 87 | 20 |
| 92 | 86 |
| 93 | 96 |
| 99 | 94 |
| 114 | 59 |
| 115 | 66 |
| 126 | 27 |
| 142 | 4 |
| 146 | 47 |
| 152 | 59 |
| 153 | 49 |
| 160 | 99 |
| 162 | 40 |
| 167 | 88 |
| 176 | 20 |
| 181 | 39 |
| 187 | 53 |
| 199 | 66 |
| 209 | 71 |
| 212 | 94 |
| 216 | 3 |
| 230 | 25 |
| 236 | 93 |
| 240 | 60 |
| 262 | 52 |
| 265 | 72 |
| 266 | 76 |
| 276 | 94 |
| 278 | 13 |
| 281 | 22 |
| 284 | 11 |
| 285 | 19 |
| 293 | 31 |
| 301 | 10 |
| 302 | 12 |
| 314 | 11 |
| 315 | 13 |
| 357 | 19 |
| 367 | 57 |
| 372 | 97 |
| 376 | 89 |
| 379 | 64 |
| 401 | 17 |
| 402 | 19 |
| 405 | 12 |

TABLE 7-continued

| Example No. | inhibitory rate (%) |
|---|---|
| 406 | 22 |
| 409 | 24 |
| 410 | 32 |
| 412 | 83 |
| 416 | 18 |
| 417 | 17 |
| 432 | 10 |
| 438 | 6 |
| 439 | 7 |
| 440 | 10 |
| 441 | 6 |
| 447 | 51 |
| 448 | 7 |
| 449 | 58 |
| 453 | 99 |
| 457 | 47 |
| 467 | 60 |
| 470 | 91 |
| 481 | 61 |
| 487 | 14 |
| 488 | 37 |
| 491 | 77 |
| 495 | 42 |
| 496 | 57 |
| 507 | 25 |
| 515 | 53 |
| 520 | 36 |
| 521 | 76 |
| 523 | 2 |
| 525 | 98 |
| 538 | 38 |
| 545 | 81 |
| 550 | 46 |
| 552 | 1 |
| 556 | 71 |
| 558 | 100 |
| 561 | 1 |
| 563 | 2 |
| 568 | 100 |
| 572 | 62 |
| 577 | 53 |
| 578 | 68 |
| 579 | 49 |
| 584 | 57 |
| 588 | 12 |
| 597 | 38 |

Experimental Example 4 Measurement of Urethral Resistance Increasing Effect

The urethral resistance increasing effect in rat was measured by a modified method of Matsumoto et al. (WO2009/063992) as follows. That is, SD female rats (CLEA Japan, Inc.) were anesthetized with isoflurane (1.0%; Abbott), and the spinal cord was transected at Th8-9 to avoid the voiding reflex. After laparotomy, an intravesical pressure measurement catheter and a saline infusion catheter (PE-100; Clay Adams) were inserted into the bladder. Thereafter, the abdomen of the rat was closed with aronalpha A "Sankyo" (Daiichi Sankyo). The rat with an inserted catheter was placed in a Bollman cage (KN-326 Bollman cage TYPE III; Natsume). The intravesical pressure measurement catheter was connected to a computer via a pressure transducer (REF685640; Nihon Koden), an amplifier (RPM-6008M; Nihon Koden), and a multi-channel data analyzer (MP150; Biopack), and changes in the intravesical pressure were recorded on a hard disc at a frequency of 100 samples/sec. The saline infusion catheter was connected to a 50 mL syringe (Terumo) filled with saline colored with Evans Blue (Wako). The saline was infused into the bladder from the 50 mL syringe filled with saline at a rate of 0.1 mL/sec by using an infusion pump (Kds100; KD Scientific). When the saline leaked from the urethral orifice, infusion was discontinued, and the saline in the bladder was released. The maximum pressure observed during infusion of saline into the bladder and leakage thereof was taken as an LPP (Leak point pressure) value. The measurement was repeated until the LPP value was stabilized, and an average of continuous three stable LPP values was taken as the result. In addition, the measurement of drug effect was started 1 hr after the animal was placed in the Bollman cage. The LPP value (Pre value) was measured, a drug was intravenously administered, and the measurement of LPP value (Post value) was again started 10 min after administration. The urethral resistance increasing effect by the drug was shown by the difference between the LPP value (Post value) and LPP value (Pre value). The drug was intravenously administered at 1.0 mL/kg, using saline as a vehicle. For detection of a significant difference in the urethral resistance increasing effect by the drug as compared to the vehicle, the Williams' test was used.

The compound of Example 6 (0.3 mg/kg), the compound of Example 6 (1.0 mg/kg) and the vehicle were administered to the rats, and the urethral resistance increasing effect was measured by the aforementioned method. As shown in the following Table 8, the rats administered with the compound of Example 6 showed a dose-dependent and significant urethral resistance increasing effect as compared to the vehicle administration.

TABLE 8

| dose (mg/kg) | n | urethral resistance increasing effect (cmH$_2$O) | significant difference |
|---|---|---|---|
| vehicle | 10 | 0.6 ± 0.5 cmH$_2$O | |
| 0.3 | 4 | 12.8 ± 1.1 cmH$_2$O | # |
| 1.0 | 4 | 19.1 ± 1.8 cmH$_2$O | # |

Williams' test, # P < 0.025

Experimental Example 5 Measurement of Urethral Resistance Increasing Effect

Oral Administration

The urethral resistance increasing effect in rat was measured by a modified method of Matsumoto et al. (WO2009/063992) as follows. That is, SD female rats (CLEA Japan, Inc.) were anesthetized with isoflurane (1.0%; Abbott), and the spinal cord was transected at Th8-9 to avoid the voiding reflex. After laparotomy, an intravesical pressure measurement catheter and a saline infusion catheter (PE-100; Clay Adams) were inserted into the bladder. Thereafter, the abdomen of the rat was closed with aronalpha A "Sankyo" (Daiichi Sankyo). The rat with an inserted catheter was placed in a Bollman cage (KN-326 Bollman cage TYPE III; Natsume). The intravesical pressure measurement catheter was connected to a computer via a pressure transducer (DX-100; Nihon Koden), an amplifier (RPM-6008M; Nihon Koden/303638; SAN-EI), and a multi-channel data analyzer (MP150/MP100; Biopack), and changes in the intravesical pressure were recorded on a hard disc at a frequency of 100 samples/sec. The saline infusion catheter was connected to a 50 mL syringe (Terumo) filled with saline colored with Evans Blue (Wako). The saline was infused into the bladder from the 50 mL syringe filled with saline at a rate of 0.1 mL/sec by using an infusion pump (Kds100; KD Scientific). When the saline leaked from the urethral orifice, infusion was discontinued, and the saline in the bladder was released. The maximum pressure observed during infusion of saline into the bladder and leakage thereof was taken as an LPP (Leak point pressure) value. The measurement was repeated until the LPP value was stabilized, and an average of continuous three stable LPP values was taken as the result. In addition, the measurement of drug effect was started 1 hr after the animal was placed in the Bollman cage. The LPP value (Pre value) was measured, a drug was orally administered, and the measurement of LPP value (Post value) was again started 15 min, 30 min, 1 hr, 2 hr and 4 hr after administration. The urethral resistance increasing effect by the drug was shown by the difference between the LPP value (Post value) and LPP value (Pre value). The drug was orally administered at 2.0 mL/kg, using 0.5% methylcellulose as a vehicle. For detection of a significant difference in the urethral resistance increasing effect by the drug as compared to the vehicle, the following method was used. For comparison of 3 or more groups, the Williams' test was used for a parametric test, and the Shirley-Williams' test was used for a non-parametric test. For comparison of 2 groups, the Student's t-test was used for a parametric test, and the Aspin-Welch test was used for a non-parametric test.

The results of the compound of Examples 31-33, 36-41, 43-45, 556, 577 and 584 are shown below. As shown below, all compounds showed a significant urethral resistance increasing effect by oral administration to rats, as compared to the vehicle administration. The compounds tested in multiple doses showed a dose-dependent urethral resistance increasing effect.

TABLE 9 compound of Example 31

| dose (mg/kg) (oral) | n | urethral resistance increasing effect (cmH$_2$O) | | | |
|---|---|---|---|---|---|
| | | 15 min later | | 30 min later | |
| vehicle | 10 | −0.3 ± 0.9 | significant difference | −1.2 ± 1.0 | significant difference |
| 1.0 | 6 | 6.7 ± 2.5 | $ | 9.0 ± 3.8 | |
| 3.0 | 6 | 13.2 ± 3.8 | $ | 14.5 ± 3.6 | $ |
| 10.0 | 6 | 16.2 ± 2.1 | $ | 14.3 ± 2.2 | $ |

Shirley-Williams' test, $ P ≤ 0.025

TABLE 10 compound of Example 32

| dose (mg/kg) (oral) | n | urethral resistance increasing effect (cmH$_2$O) | | | |
|---|---|---|---|---|---|
| | | 15 min later | | 30 min later | |
| vehicle | 6 | −1.1 ± 1.2 | significant difference | −0.8 ± 0.8 | significant difference |
| 10.0 | 6 | 18.3 ± 2.1 | *** | 17.1 ± 3.2 | ++ |

Student's t-test, *** P ≤ 0.001,
Aspin-Welch test, ++ P ≤ 0.01

TABLE 11 compound of Example 33

| dose (mg/kg) (oral) | n | urethral resistance increasing effect (cmH$_2$O) | | | |
|---|---|---|---|---|---|
| | | 15 min later | | 30 min later | |
| vehicle | 6 | −1.1 ± 1.2 | significant difference | −0.8 ± 0.8 | significant difference |
| 10.0 | 5 | 21.8 ± 3.3 | ++ | 20.9 ± 3.4 | ++ |

Aspin-Welch test, ++ P ≤ 0.01

TABLE 12 compound of Example 36

| dose (mg/kg) (oral) | n | urethral resistance increasing effect (cmH$_2$O) | | | |
|---|---|---|---|---|---|
| | | 15 min later | | 30 min later | |
| vehicle | 8 | −1.3 ± 1.2 | significant difference | −1.2 ± 1.2 | significant difference |
| 10.0 | 7 | 15.0 ± 1.8 | *** | 14.3 ± 1.8 | *** |

Student's t-test, *** P ≤ 0.001

TABLE 13 compound of Example 37

| dose (mg/kg) (oral) | n | urethral resistance increasing effect (cmH$_2$O) | | | |
|---|---|---|---|---|---|
| | | 15 min later | | 30 min later | |
| vehicle | 10 | −0.3 ± 0.9 | significant difference | −1.2 ± 1.0 | significant difference |
| 3.0 | 6 | 8.5 ± 1.4 | # | 7.6 ± 1.6 | # |
| 10.0 | 6 | 16.3 ± 1.2 | # | 17.2 ± 1.9 | # |

Williams' test, # P ≤ 0.025

TABLE 14 compound of Example 38

| dose (mg/kg) (oral) | n | urethral resistance increasing effect (cmH$_2$O) | | | |
|---|---|---|---|---|---|
| | | 15 min later | | 30 min later | |
| vehicle | 8 | −1.3 ± 1.2 | significant difference | −1.2 ± 1.2 | significant difference |
| 0.3 | 8 | 4.2 ± 1.7 | | 5.1 ± 1.7 | |
| 1.0 | 8 | 12.9 ± 3.3 | # | 9.3 ± 1.6 | # |
| 3.0 | 8 | 18.0 ± 2.5 | # | 17.4 ± 2.4 | # |
| 10.0 | 8 | 21.6 ± 2.9 | # | 21.3 ± 3.3 | # |

Williams' test, # P ≤ 0.025

TABLE 15

| compound of Example 39 | | | |
|---|---|---|---|
| dose (mg/kg) | | urethral resistance increasing effect ($cmH_2O$) | |
| (oral) | n | 15 min later | 30 min later |
| vehicle | 10 | −0.3 ± 0.9 significant difference | −1.2 ± 1.0 significant difference |
| 1.0 | 5 | 12.3 ± 2.2 # | 8.7 ± 2.6 # |
| 3.0 | 11 | 15.8 ± 1.7 # | 14.1 ± 1.5 # |
| 10.0 | 11 | 17.9 ± 1.8 # | 17.1 ± 2.3 # |

Williams' test, # $P \leq 0.025$

TABLE 16

| compound of Example 40 | | | |
|---|---|---|---|
| dose (mg/kg) | | urethral resistance increasing effect ($cmH_2O$) | |
| (oral) | n | 15 min later | 30 min later |
| vehicle | 10 | −0.3 ± 0.9 significant difference | −1.2 ± 1.0 significant difference |
| 1.0 | 4 | 8.5 ± 1.9 # | 8.6 ± 2.6 # |
| 3.0 | 5 | 11.4 ± 1.9 # | 12.8 ± 1.6 # |
| 10.0 | 6 | 16.6 ± 2.0 # | 17.2 ± 2.2 # |

Williams' test, # $P \leq 0.025$

TABLE 17

| compound of Example 41 | | | |
|---|---|---|---|
| dose (mg/kg) | | urethral resistance increasing effect ($cmH_2O$) | |
| (oral) | n | 15 min later | 30 min later |
| vehicle | 10 | −0.3 ± 0.9 significant difference | −1.2 ± 1.0 significant difference |
| 3.0 | 6 | 9.8 ± 3.8 $ | 9.6 ± 2.3 # |
| 10.0 | 5 | 17.8 ± 1.6 $ | 16.1 ± 1.5 # |

Williams' test, # $P \leq 0.025$,
Shirley-Williams' test, $ $P \leq 0.025$

TABLE 18

| compound of Example 43 | | | |
|---|---|---|---|
| dose (mg/kg) | | urethral resistance increasing effect ($cmH_2O$) | |
| (oral) | n | 15 min later | 30 min later |
| vehicle | 10 | −0.3 ± 0.9 significant difference | −1.2 ± 1.0 significant difference |
| 3.0 | 6 | 8.4 ± 3.0 # | 11.8 ± 2.8 $ |
| 10.0 | 8 | 13.9 ± 2.1 # | 14.8 ± 0.9 $ |

Williams' test, # $P \leq 0.025$,
Shirley-Williams' test, $ $P \leq 0.025$

TABLE 19

| compound of Example 44 | | | |
|---|---|---|---|
| dose (mg/kg) | | urethral resistance increasing effect ($cmH_2O$) | |
| (oral) | n | 15 min later | 30 min later |
| vehicle | 10 | −0.3 ± 0.9 significant difference | −1.2 ± 1.0 significant difference |
| 0.3 | 4 | 0.1 ± 2.5 | 2.2 ± 2.6 |
| 1.0 | 6 | 8.6 ± 2.6 # | 9.8 ± 2.6 # |
| 3.0 | 6 | 15.5 ± 3.7 # | 13.7 ± 3.3 # |
| 10.0 | 10 | 18.8 ± 1.5 # | 16.4 ± 1.5 # |

Williams' test, # $P \leq 0.025$

TABLE 20

| compound of Example 45 | | | |
|---|---|---|---|
| dose (mg/kg) | | urethral resistance increasing effect ($cmH_2O$) | |
| (oral) | n | 15 min later | 30 min later |
| vehicle | 10 | −0.3 ± 0.9 significant difference | −1.2 ± 1.0 significant difference |
| 0.3 | 6 | 6.4 ± 1.3 # | 9.3 ± 3.3 # |
| 1.0 | 6 | 10.0 ± 2.6 # | 13.4 ± 1.2 # |
| 3.0 | 6 | 16.9 ± 1.4 # | 17.5 ± 2.8 # |
| 10.0 | 6 | 21.0 ± 2.0 # | 22.1 ± 2.0 # |

Williams' test, # $P \leq 0.025$

TABLE 21

| compound of Example 556 | | | |
|---|---|---|---|
| dose (mg/kg) | | urethral resistance increasing effect ($cmH_2O$) | |
| (oral) | n | 15 min later | 30 min later |
| vehicle | 10 | −0.3 ± 0.9 significant difference | −1.2 ± 1.0 significant difference |
| 3.0 | 5 | 6.0 ± 2.0 # | 5.0 ± 2.9 # |
| 10.0 | 6 | 13.4 ± 1.7 # | 10.6 ± 1.8 # |
| 30.0 | 6 | 17.8 ± 3.4 # | 17.5 ± 2.3 # |

Williams' test, # $P \leq 0.025$

TABLE 22

| compound of Example 577 | | | |
|---|---|---|---|
| dose (mg/kg) | | urethral resistance increasing effect ($cmH_2O$) | |
| (oral) | n | 15 min later | 30 min later |
| vehicle | 10 | −0.3 ± 0.9 significant difference | −1.2 ± 1.0 significant difference |
| 3.0 | 6 | 14.3 ± 3.0 # | 13.1 ± 3.1 # |
| 10.0 | 6 | 18.7 ± 1.8 # | 15.4 ± 1.5 # |

Williams' test, # $P \leq 0.025$

TABLE 23 compound of Example 584

| dose (mg/kg) | | urethral resistance increasing effect (cmH$_2$O) | | | |
|---|---|---|---|---|---|
| (oral) | n | 15 min later | | 30 min later | |
| vehicle | 10 | −0.3 ± 0.9 | significant difference | −1.2 ± 1.0 | significant difference |
| 3.0 | 6 | 9.5 ± 3.5 | $ | 7.2 ± 2.6 | # |
| 10.0 | 6 | 18.4 ± 3.4 | $ | 16.2 ± 3.3 | # |

Williams' test, # P ≤ 0.025,
Shirley-Williams' test, $ P ≤ 0.025

Formulation Example 1

A medicament containing compound (I') can be produced, for example, by the following formulation.

1. Capsule

| | |
|---|---|
| (1) compound obtained in Example 1 | 40 mg |
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. Thereto is added the rest of (4) and the whole mixture is sealed in a gelatin capsule.

2. Tablet

| | |
|---|---|
| (1) compound obtained in Example 1 | 40 mg |
| (2) lactose | 58 mg |
| (3) cornstarch | 18 mg |
| (4) microcrystalline cellulose | 3.5 mg |
| (4) magnesium stearate | 0.5 mg |
| 1 tablet | 120 mg |

(1), (2), (3), ⅔ of (4) and ½ of (5) are blended and granulated. Thereto is added the rest of (4) and (5) and the mixture is compression formed to give a tablet.

Formulation Example 2

The compound (50 mg) obtained in Example 1 is dissolved in the Japanese Pharmacopoeia distilled water for injection (50 mL), and the Japanese Pharmacopoeia distilled water for injection is added to 100 mL. This solution is filtered under sterile conditions, 1 mL of this solution is taken and, under sterile conditions, filled in an injection vial, freeze-dried and sealed.

INDUSTRIAL APPLICABILITY

Since the compound of the present invention and a prodrug thereof have a superior monoamine (serotonin, norepinephrine, dopamine etc.) reuptake inhibitory activity, it is useful, for example, as a safe drug for the prophylaxis or treatment of depression, anxiety, attention deficit hyperactivity disorder, climacteric disorder, pain, stress urinary incontinence, mixed urinary incontinence and the like.

This application is based on patent application Nos. 2010-227864 and 2011-175336 filed in Japan, the contents of which are incorporated in full herein.

The invention claimed is:

1. A compound represented by formula (I)

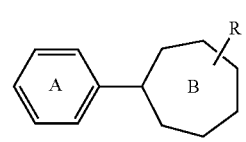

(I)

wherein
ring A is an optionally substituted 6-membered aromatic ring, and the group represented by

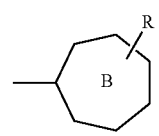

is

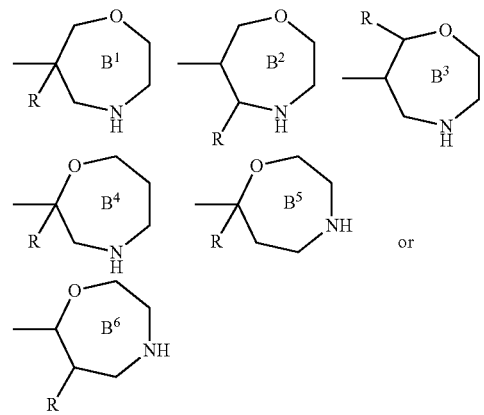

or wherein ring B$^1$-B$^6$ are optionally further substituted, provided a hydrogen atom bonded to a nitrogen atom constituting rings B$^1$-B$^6$ is not substituted, and R is a cyano group, an optionally substituted carboxy group, an optionally substituted amino group, an optionally substituted C$_{1-6}$ alkyl group, an optionally substituted C$_{1-6}$ alkoxy group, an optionally substituted C$_{1-6}$ alkyl-carbonyl group, an optionally substituted carbamoyl group, an optionally substituted C$_{6-12}$ aryloxy group, an optionally substituted aromatic heterocyclyloxy group, an optionally substituted aromatic heterocyclic group, or an optionally substituted nonaromatic heterocyclic group,
wherein
the "optionally substituted carboxy group" is selected from the group consisting of
(1) a carboxy group,
(2) a C$_{1-6}$ alkoxy-carbonyl group,
(3) a C$_{6-12}$ aryloxy-carbonyl group, and
(4) a C$_{7-12}$ aralkyloxy-carbonyl group;
the "optionally substituted amino group" is selected from the group consisting of
(1) an amino group,
(2) a mono- or di-C$_{1-6}$ alkylamino group,
(3) a mono- or di-C$_{3-6}$ cycloalkylamino group,
(4) a mono- or di-C$_{6-12}$ arylamino group, (5) a mono- or di-$C_{7-12}$ aralkylamino group,
(6) a hydrazino group,
(7) a mono- or di-($C_{1-6}$ alkylsulfonyl)amino group,
(8) a mono- or di-($C_{3-6}$ cycloalkylsulfonyl)amino group,
(9) a mono- or di-($C_{6-12}$ arylsulfonyl)amino group,
(10) a mono- or di-(aromatic heterocyclyl-sulfonyl)amino group,
(11) —$NR^A$—CO—$R^B$, wherein
$R^A$ is
(a) a hydrogen atom,
(b) a $C_{1-6}$ alkyl group, or
(c) a $C_{1-6}$ alkyl-carbonyl group, and
$R^B$ is
(a) a $C_{1-6}$ alkyl group optionally substituted by 1 to 3 substituents selected from the group consisting of
(i) a halogen atom,
(ii) a hydroxy group,
(iii) a $C_{1-6}$ alkoxy group,
(iv) an aromatic heterocyclic group, and
(v) a nonaromatic heterocyclic group optionally substituted by an oxo group,
(b) a $C_{1-6}$ alkoxy group,
(c) a $C_{3-6}$ cycloalkyl group,
(d) a $C_{1-6}$ alkyl-carbonyl group,
(e) an amino group,
(f) a mono- or di-$C_{1-6}$ alkylamino group,
(g) a cyclic amino group,
(h) a $C_{6-12}$ aryl group optionally substituted by 1 to 3 substituents selected from the group consisting of
(i) a cyano group,
(ii) a carboxy group,
(iii) a $C_{1-6}$ alkoxy-carbonyl group,
(iv) a $C_{1-6}$ alkylsulfonylamino group, and
(v) a nonaromatic heterocyclic group optionally substituted by an oxo group,
(i) a $C_{7-12}$ aralkyl group optionally substituted by a heterocyclic group optionally substituted by an oxo group, or
(j) an aromatic heterocyclic group,
(12) —$NR^C$—$SO_2$—$N(R^D)(R^E)$, wherein
$R^C$ is
(a) a hydrogen atom, or
(b) a $C_{1-6}$ alkyl group, and
$R^D$ and $R^E$ are each independently,
(a) a hydrogen atom,
(b) a $C_{1-6}$ alkyl group, or
(c) a $C_{3-6}$ cycloalkyl group, and
(13) an optionally substituted cyclic amino group;
the "optionally substituted carbamoyl group" is —CO—$NR^PR^Q$,
wherein
$R^P$ and $R^Q$ are each independently,
(a) a hydrogen atom,
(b) a $C_{1-6}$ alkyl group optionally substituted by 1 to 3 substituents selected from the group consisting of
(i) a hydroxy group,
(ii) a $C_{1-6}$ alkylsulfonyl group, and
(iii) a $C_{1-6}$ alkoxy group,
(c) a $C_{1-6}$ alkoxy group,
(d) a $C_{6-12}$ aryl group optionally substituted by a carboxy group,
(e) a $C_{7-12}$ aralkyl group,
(f) a $C_{1-6}$ alkylsulfonyl group, or
(g) a $C_{6-12}$ arylsulfonyl group optionally substituted by 1 to 3 substituents selected from the group consisting of
(i) a $C_{1-6}$ alkyl group optionally substituted by 1 to 3 halogen atoms, and
(ii) a $C_{1-6}$ alkoxy group optionally substituted by 1 to 3 halogen atoms;
wherein substituents on ring A are optionally bonded to form, together with ring A, an optionally substituted 9- or 10-membered aromatic fused ring,
provided that
(1) a compound, wherein a partial structure of the formula (I):

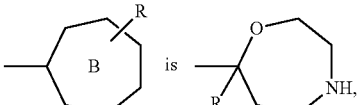

ring A is a benzene ring, and
R is $R^x$—$CH_2$— ($R^x$ is a phenoxy group optionally substituted by substituent(s) selected from the group consisting of a halogen atom and a methoxy group),
(2) 2-methyl-2-phenyl-1,4-oxazepane,
(3) 6-methyl-6-phenyl-1,4-oxazepane,
(4) (2R)-2-phenyl-2-(trifluoromethyl)-1,4-oxazepane, and
(5) 7-methyl-7-phenyl-1,4-oxazepane are excluded, or a salt thereof.

2. A compound represented by formula (I')

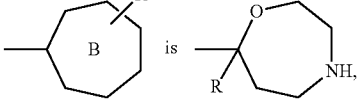

wherein
ring A is an optionally substituted 6-membered aromatic ring, and the group represented by

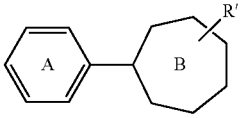

is

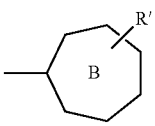

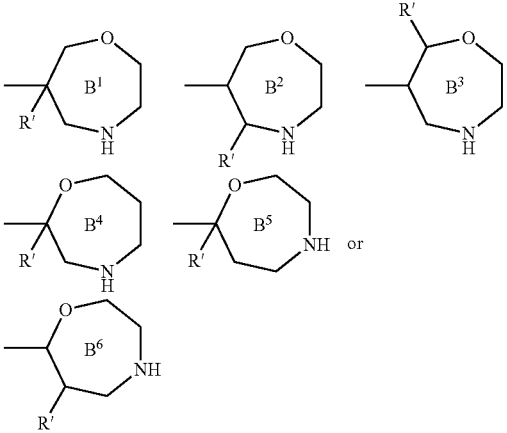

wherein ring $B^1$-$B^6$ are optionally further substituted, provided a hydrogen atom bonded to a nitrogen atom constituting rings $B^1$-$B^6$ is not substituted, and R' is a cyano group, an optionally substituted carboxy group, an optionally substituted amino group, an optionally substituted $C_{1-6}$ alkyl group, an optionally substituted $C_{1-6}$ alkoxy group, or an optionally substituted carbamoyl group,
wherein
the "optionally substituted carboxy group" is selected from the group consisting of
(1) a carboxy group,
(2) a $C_{1-6}$ alkoxy-carbonyl group,
(3) a $C_{6-12}$ aryloxy-carbonyl group, and
(4) a $C_{7-12}$ aralkyloxy-carbonyl group;
the "optionally substituted amino group" is selected from the group consisting of
(1) an amino group,
(2) a mono- or di-$C_{1-6}$ alkylamino group,
(3) a mono- or di-$C_{3-6}$ cycloalkylamino group,
(4) a mono- or di-$C_{6-12}$ arylamino group,
(5) a mono- or di-$C_{7-12}$ aralkylamino group,
(6) a hydrazino group,
(7) a mono- or di-($C_{1-6}$ alkylsulfonyl)amino group,
(8) a mono- or di-($C_{3-6}$ cycloalkylsulfonyl)amino group,
(9) a mono- or di-($C_{6-12}$ arylsulfonyl)amino group,
(10) a mono- or di-(aromatic heterocyclyl-sulfonyl)amino group,
(11) —$NR^A$—CO—$R^B$, wherein
$R^A$ is
(a) a hydrogen atom,
(b) a $C_{1-6}$ alkyl group, or
(c) a $C_{1-6}$ alkyl-carbonyl group, and
$R^B$ is
(a) a $C_{1-6}$ alkyl group optionally substituted by 1 to 3 substituents selected from the group consisting of
(i) a halogen atom,
(ii) a hydroxy group,
(iii) a $C_{1-6}$ alkoxy group,
(iv) an aromatic heterocyclic group, and
(v) a nonaromatic heterocyclic group optionally substituted by an oxo group,
(b) a $C_{1-6}$ alkoxy group,
(c) a $C_{3-6}$ cycloalkyl group,
(d) a $C_{1-6}$ alkyl-carbonyl group,
(e) an amino group,
(f) a mono- or di-$C_{1-6}$ alkylamino group,
(g) a cyclic amino group,
(h) a $C_{6-12}$ aryl group optionally substituted by 1 to 3 substituents selected from the group consisting of
(i) a cyano group,
(ii) a carboxy group,
(iii) a $C_{1-6}$ alkoxy-carbonyl group,
(iv) a $C_{1-6}$ alkylsulfonylamino group, and
(v) a nonaromatic heterocyclic group optionally substituted by an oxo group,
(i) a $C_{7-12}$ aralkyl group optionally substituted by a heterocyclic group optionally substituted by an oxo group, or
(j) an aromatic heterocyclic group,
(12) —$NR^C$—$SO_2$—$N(R^D)(R^E)$, wherein
$R^C$ is
(a) a hydrogen atom, or
(b) a $C_{1-6}$ alkyl group, and
$R^D$ and $R^E$ are each independently,
(a) a hydrogen atom,
(b) a $C_{1-6}$ alkyl group, or
(c) a $C_{3-6}$ cycloalkyl group, and

(13) an optionally substituted cyclic amino group;
the "optionally substituted carbamoyl group" is —CO—$NR^PR^Q$,
wherein
$R^P$ and $R^Q$ are each independently,
(a) a hydrogen atom,
(b) a $C_{1-6}$ alkyl group optionally substituted by 1 to 3 substituents selected from the group consisting of
(i) a hydroxy group,
(ii) a $C_{1-6}$ alkylsulfonyl group, and
(iii) a $C_{1-6}$ alkoxy group,
(c) a $C_{1-6}$ alkoxy group,
(d) a $C_{6-12}$ aryl group optionally substituted by a carboxy group,
(e) a $C_{7-12}$ aralkyl group,
(f) a $C_{1-6}$ alkylsulfonyl group, or
(g) a $C_{6-12}$ arylsulfonyl group optionally substituted by 1 to 3 substituents selected from the group consisting of
(i) a $C_{1-6}$ alkyl group optionally substituted by 1 to 3 halogen atoms, and
(ii) a $C_{1-6}$ alkoxy group optionally substituted by 1 to 3 halogen atoms;
wherein substituents on ring A are optionally bonded to form, together with ring A, an optionally substituted 9- or 10-membered aromatic fused ring,
provided that
(1) a compound, wherein a partial structure of the formula (I'):

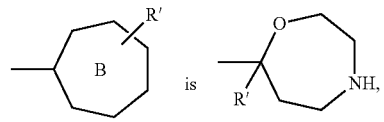

ring A is a benzene ring, and
R' is $R^x$—$CH_2$— ($R^x$ is a phenoxy group optionally substituted by substituent(s) selected from the group consisting of a halogen atom and a methoxy group),
(2) 2-methyl-2-phenyl-1,4-oxazepane,
(3) 6-methyl-6-phenyl-1,4-oxazepane,
(4) (2R)-2-phenyl-2-(trifluoromethyl)-1,4-oxazepane, and
(5) 7-methyl-7-phenyl-1,4-oxazepane are excluded, or a salt thereof.

3. The compound according to claim 2, wherein ring A is an optionally substituted benzene ring, or a salt thereof.

4. The compound according to claim 2 or 3, wherein R' is
(1) a mono- or di-($C_{1-6}$ alkyl-carbonyl)amino group,
(2) a sulfamoylamino group, or
(3) a $C_{1-6}$ alkyl group optionally substituted by 1 to 3 substituents selected from the group consisting of
(a) a hydroxy group,
(b) a mono- or di-($C_{1-6}$ alkyl-carbonyl)amino group,
(c) a sulfamoylamino group,
(d) a $C_{1-6}$ alkoxy-$C_{1-6}$ alkyl-carbonylamino group,
(e) a $C_{1-6}$ alkylsulfonylamino group, and
(f) 2-oxopyridin-1(2H)-yl optionally substituted by 1 to 3 substituents selected from the group consisting of a carboxy group and 5-oxo-4,5-dihydro-1,2,4-oxadiazolyl, or a salt thereof.

5. The compound according to claim 2, wherein the group represented by

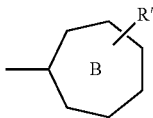

is

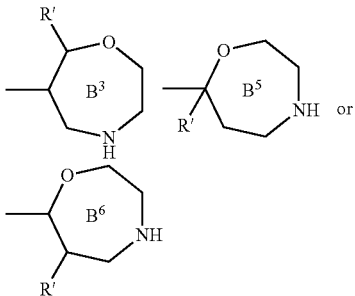

wherein R', $B^3$, $B^5$ and $B^6$ are each as defined in claim 2, or a salt thereof.

6. The compound according to claim 2, wherein the ring A is a benzene ring substituted by 2 substituents selected from the group consisting of a fluorine atom and a chlorine atom, the group represented by

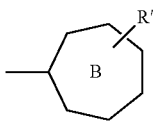

is

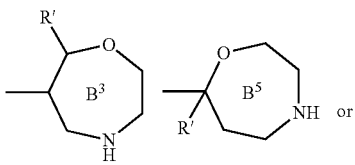

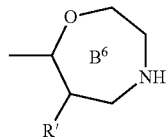

wherein
R' is
(1) a mono- or di-($C_{1-6}$ alkyl-carbonyl)amino group,
(2) a sulfamoylamino group, or
(3) a $C_{1-6}$ alkyl group optionally substituted by 1 to 3 substituents selected from the group consisting of
    (a) a hydroxy group,
    (b) a mono- or di-($C_{1-6}$ alkyl-carbonyl)amino group,
    (c) a sulfamoylamino group,
    (d) a $C_{1-6}$ alkoxy-$C_{1-6}$ alkyl-carbonylamino group,
    (e) a $C_{1-6}$ alkylsulfonylamino group, and
    (f) 2-oxopyridin-1(2H)-yl optionally substituted by 1 to 3 substituents selected from the group consisting of a carboxy group and 5-oxo-4,5-dihydro-1,2,4-oxadiazolyl,
and $B^3$, $B^5$ and $B^6$ are each as defined in claim 2, or a salt thereof.

7. N-{[(6S,7R)-7-(3,4-Dichlorophenyl)-1,4-oxazepan-6-yl]methyl}-2-methoxyacetamide, or a salt thereof.

8. N-[(6R,7S)-7-(3,4-Dichlorophenyl)-1,4-oxazepan-6-yl]acetamide, or a salt thereof.

9. N-{[(6S,7R)-7-(4-Chloro-3-fluorophenyl)-1,4-oxazepan-6-yl]methyl}-2-[($^2H_3$)methyloxy]acetamide, or a salt thereof.

10. 1-{[(6S,7R)-7-(4-Chloro-3-fluorophenyl)-1,4-oxazepan-6-yl]methyl}-2-oxo-1,2-dihydropyridine-3-carboxylic acid, or a salt thereof.

11. (1S)-1-[(6R,7R)-6-(3,4-Dichlorophenyl)-1,4-oxazepan-7-yl]ethane-1,2-diol, or a salt thereof.

12. [(7S)-7-(3,4-Dichlorophenyl)-1,4-oxazepan-7-yl]methanol, or a salt thereof.

13. A pharmaceutical composition comprising the compound according to claim 1 or 2, or a salt thereof, and a pharmacologically acceptable carrier.

14. A method for the treatment of depression, anxiety, attention deficit hyperactivity disorder, climacteric disorder, pain, stress urinary incontinence or mixed urinary incontinence in a mammal, comprising administering an effective amount of the compound according to claim 1 or 2, or a salt thereof to said mammal.

\* \* \* \* \*